(12) United States Patent
Sheppard et al.

(10) Patent No.: US 7,772,231 B2
(45) Date of Patent: Aug. 10, 2010

(54) SUBSTITUTED PYRAZOLO[3,4-D]PYRIMIDINES AS PROTEIN KINASE INHIBITORS

(75) Inventors: George S. Sheppard, Wilmette, IL (US); Gary T. Wang, Libertyville, IL (US); Fabio Palazzo, Libertyville, IL (US); Randy L Bell, Lindenhurst, IL (US); Robert A. Mantei, Franklin, WI (US); Jieyi Wang, Lake Bluff, IL (US); Robert D. Hubbard, Lindenhurst, IL (US); Megumi Kawai, Libertyville, IL (US); Scott A. Erickson, Zion, IL (US); Nwe BaMaung, Niles, IL (US); Steve D. Fidanze, Grayslake, IL (US)

(73) Assignee: Abbott Laboratories, Abbott Park, IL (US)

( * ) Notice: Subject to any disclaimer, the term of this patent is extended or adjusted under 35 U.S.C. 154(b) by 684 days.

(21) Appl. No.: 11/617,398

(22) Filed: Dec. 28, 2006

(65) Prior Publication Data

US 2007/0203143 A1    Aug. 30, 2007

Related U.S. Application Data

(60) Provisional application No. 60/754,685, filed on Dec. 29, 2005.

(51) Int. Cl.
*C07D 487/04* (2006.01)
*A61K 31/497* (2006.01)
*A61K 31/4985* (2006.01)
*A61K 31/519* (2006.01)
*A61K 31/5377* (2006.01)
*C07D 413/08* (2006.01)
*A61P 35/00* (2006.01)

(52) U.S. Cl. ............... 514/234.2; 514/252.16; 514/252.11; 514/262.1; 544/118; 544/262

(58) Field of Classification Search ................. 544/262; 514/262.1
See application file for complete search history.

(56) References Cited

FOREIGN PATENT DOCUMENTS

| WO | 9723161 | 8/1997 |
|---|---|---|
| WO | 9732879 | 9/1997 |
| WO | 9734895 | 9/1997 |
| WO | 0042042 | 7/2000 |
| WO | 2005010009 | 2/2005 |
| WO | 2005037836 | 4/2005 |
| WO | 2005097800 | 10/2005 |
| WO | 2007041130 | 4/2007 |

*Primary Examiner*—Susanna Moore
(74) *Attorney, Agent, or Firm*—Glen J. Gesicki

(57) ABSTRACT

Compounds of formula (25) that inhibit protein kinases, compositions containing the compounds and methods of treating diseases using the compounds are disclosed.

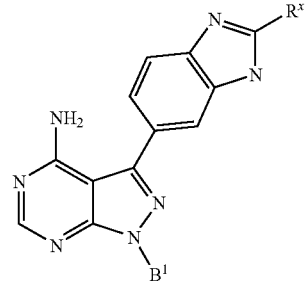

(25)

20 Claims, No Drawings

SUBSTITUTED PYRAZOLO[3,4-D]PYRIMIDINES AS PROTEIN KINASE INHIBITORS

This application claims priority to U.S. Provisional Application Ser. No. 60/754,685, filed Dec. 29, 2005.

FIELD OF THE INVENTION

This invention pertains to compounds that inhibit protein kinases, compositions containing the compounds and methods of treating diseases using the compounds.

BACKGROUND OF THE INVENTION

Numerous human diseases are characterized by increased and uncontrolled cell growth. This biology is driven, in many cases, by increased growth factor signaling. In addition, these pathologies often require an expanding blood supply and new vessel growth. Protein kinases are key components of both cell proliferation and endothelial cell expansion. Kinases are thus important targets for therapeutic intervention in pathologies characterized by uncontrolled cell growth.

SUMMARY OF THE INVENTION

One embodiment of this invention, therefore, pertains to compounds that inhibit protein kinases and have Formula I

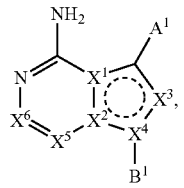

and salts, prodrugs, salts of prodrugs and metabolites thereof, wherein one of $X^1$ or $X^2$ is C and the other is C or N;

$X^3$ is C(H), C($C_1$-$C_4$-alkyl), or N; $X^4$ is N or C; $X^5$ is C(H) or N; X is C(H) or N;

$A^1$ is $R^1$ or $R^2$;

$R^1$ is phenyl which is fused with benzene, heteroarene or heterocycloalkane which is unfused or fused with benzene;

$R^2$ is heteroaryl which is fused with benzene or heteroarene;

$B^1$ is $R^3$, $R^4$, $R^5$ or $W^1$;

$R^3$ is phenyl which is unfused or fused with benzene, heteroarene or $R^{3A}$; $R^{3A}$ is cycloalkane, cycloalkene, heterocycloalkane or heterocycloalkene;

$R^4$ is heteroaryl which is unfused or fused with benzene, heteroarene or $R^{4A}$; $R^{4A}$ is cycloalkane, cycloalkene, heterocycloalkane or heterocycloalkene;

$R^5$ is cycloalkyl, cycloalkenyl, heterocycloalkyl or heterocycloalkenyl, each of which is unfused or fused with benzene, heteroarene or $R^{5A}$; $R^{5A}$ is cycloalkane, cycloalkene, heterocycloalkane or heterocycloalkene;

$W^1$ is alkyl, alkenyl or alkynyl, each of which is unsubstituted or substituted with one or two of independently selected $W^2$, $W^3$, $W^4$, OH, $OW^5$, $SW^5$, $S(O)W^5$, $SO_2W^5$, $NH_2$, $NHW^5$, $N(W^5)_2$, $C(O)NH_2$, $C(O)NHW^5$, $C(O)N(W^5)_2$, NHC(O)$W^5$ or $NW^5C(O)W^5$;

$W^2$ is phenyl which is unfused or fused with benzene, heteroarene or $W^{2A}$; $W^{2A}$ is cycloalkane, cycloalkene, heterocycloalkane or heterocycloalkene;

$W^3$ is heteroaryl which is unfused or fused with benzene, heteroarene or $W^{3A}$; $W^{3A}$ is cycloalkane, cycloalkene, heterocycloalkane or heterocycloalkene;

$W^4$ is cycloalkyl, cycloalkenyl, heterocycloalkyl or heterocycloalkenyl, each of which is unfused or fused with benzene, heteroarene or $W^{5A}$; $W^{5A}$ is cycloalkane, cycloalkene, heterocycloalkane or heterocycloalkene;

$W^5$ is alkyl, alkenyl or alkynyl;

wherein the moieties represented by $A^1$, $B^1$, $W^2$, $W^3$ and $W^4$ are independently unsubstituted or substituted with one or two or three or four of independently selected $R^6$, $OR^6$, $SR^6$, $S(O)R^6$, $SO_2R^6$, $NH_2$, $NHR^6$, $N(R^6)_2$, $C(O)R^6$, $C(O)OR^6$, $C(O)NH_2$, $C(O)NHR^6$, $C(O)N(R^6)_2$, $NHC(O)R^6$, $NR^6C(O)R^6$, $NHSO_2R^6$, $NR^6SO_2R^6$, $NHC(O)OR^6$, $NR^6C(O)OR^6$, $SO_2NH_2$, $SO_2NHR^6$, $SO_2N(R^6)_2$, $NHC(O)NH_2$, $NHC(O)NHR^6$, $NHC(O)N(R^6)_2$, $NR^6C(O)N(R^6)_2$, $C(N)NH_2$, $C(N)NHR^6$, $C(N)N(R^6)_2$, $NHC(N)NH_2$, $NHC(N)NHR^6$, $NHC(N)N(R^6)_2$, OH, (O), C(O)H, C(O)OH, $NO_2$, CN, $CF_3$, $OCF_3$, $CF_2CF_3$, F, Cl, Br or I;

$R^6$ is $R^7$, $R^8$, $R^9$ or $R^{10}$;

$R^7$ is phenyl which is unfused or fused with benzene, heteroarene or $R^{7A}$; $R^{7A}$ is cycloalkane, cycloalkene, heterocycloalkane or heterocycloalkene;

$R^8$ is heteroaryl which is unfused or fused with benzene, heteroarene or $R^{8A}$; $R^{8A}$ is cycloalkane, cycloalkene, heterocycloalkane or heterocycloalkene;

$R^9$ is cycloalkyl, cycloalkenyl, heterocycloalkyl or heterocycloalkenyl, each of which is unfused or fused with benzene, heteroarene or $R^{9A}$; $R^{9A}$ is cycloalkane, cycloalkene, heterocycloalkane or heterocycloalkene;

$R^{10}$ is alkyl, alkenyl or alkynyl, each of which is unsubstituted or substituted with one or two of independently selected $R^{11}$, $OR^{11}$ $SR^{11}$ $S(O)R^{11}$, $SO_2R^{11}$, $NH_2$, $NHR^{11}$, $N(R^{11})_2$, $C(O)R^{11}$, C(O)NH, $C(O)NHR^{11}$, $C(O)N(R^{11})$, $NHC(O)R^{11}$, $NR^{11}C(O)R^{11}$, $NHSO_2R^{11}$, $NR^{11}SO_2R^{11}$, $NHC(O)OR^{11}$, $NR^{11}C(O)OR^{11}$, $SO_2NH_2$, $SO_2NHR^{11}$, $SO_2N(R^{11})_2$, $NHC(O)NH_2$, $NHC(O)NHR^{11}$, $NHC(O)N(R^{11})_2$, $NR^{11}C(O)N(R^{11})_2$, OH, (O), C(O)OH, CN, $CF_3$, $OCF_3$, $CF_2CF_3$, F, Cl, Br or I;

$R^{11}$ is alkyl, alkenyl, alkynyl, $R^{12}$, $R^{13}$, $R^{14}$ or $T^1$;

$R^{12}$ is phenyl which is unfused or fused with benzene, heteroarene or $R^{12A}$; $R^{12A}$ is cycloalkane, cycloalkene, heterocycloalkane or heterocycloalkene;

$R^{13}$ is heteroaryl which is unfused or fused with benzene, heteroarene or $R^{13A}$; $R^{13A}$ is cycloalkane, cycloalkene, heterocycloalkane or heterocycloalkene; and $R^{14}$ is cycloalkyl, cycloalkenyl, heterocycloalkyl or heterocycloalkenyl, each of which is unfused or fused with benzene, heteroarene or $R^{14A}$; $R^{14A}$ is cycloalkane, cycloalkene, heterocycloalkane or heterocycloalkene;

$T^1$ is alkyl, alkenyl or alkynyl, each of which is substituted with one or two of independently selected OH, $OT^2$, $ST^2$, $S(O)T^2$, $NH_2$, $NHT^2$ or $N(T^2)_2$;

$T^2$ is alkyl, alkenyl or alkynyl;

wherein the moieties represented by $R^7$, $R^8$, $R^9$ and $R^{11}$ are independently unsubstituted or substituted with one or two or three of four of independently selected $R^{15}$, $OR^{15}$, $SR^{15}$, $S(O)R^{15}$, $SO_2R^{15}$, $C(O)R^{15}$, $C(O)(O)R^{15}$, $C(O)NH_2$, $C(O)NHR^{15}$, $C(O)N(R^{15})_2$, OH, (O), C(O)OH, CN, $CF_3$, $OCF_3$, $CF_2CF_3$, F, Cl, Br or I, wherein $R^{15}$ is alkyl, alkenyl, alkynyl, each of which is unsubstituted or substituted with phenyl, heteroaryl, cycloalkyl, heterocycloalkyl, OH, $OR^{16}$, $C(O)NH_2$, $C(O)NHR^{16}$, C(O)N$(R^{16})_2$; wherein $R^{16}$ is alkyl, alkenyl or alkynyl; and wherein
the phenyl, heteroaryl, cycloalkyl and heterocycloalkyl of $R^{15}$ are unsubstituted or substituted with O(alkyl).

Another embodiment pertains to compounds having Formula I, wherein
one of $X^1$ or $X^2$ is C and the other is C or N;
$X^3$ is C(H) or N; $X^4$ is N or C; $X^5$N; $X^6$ is C(H);
$A^1$ is $R^1$ or $R^2$;
$R^1$ is phenyl which is fused with benzene, heteroarene or heterocycloalkane which is unfused or fused with benzene;
$R^2$ is heteroaryl which is fused with benzene or heteroarene;
$B^1$ is $R^3$, $R^4$, $R^5$ or $W^1$;
$R^3$ is phenyl which is unfused or fused with benzene or heteroarene;
$R^4$ is heteroaryl which is unfused or fused with benzene or heteroarene;
$R^5$ is cycloalkyl, cycloalkenyl, heterocycloalkyl or heterocycloalkenyl, each of which is unfused or fused with benzene or heteroarene;
$W^1$ is alkyl, alkenyl or alkynyl, each of which is unsubstituted or substituted with $W^2$, $W^3$, $W^4$, OH, $OW^5$, $SW^5$, $S(O)W^5$, $SO_2W^5$, $NH_2$, $NHW^5$, $N(W^5)_2$, $C(O)NH_2$, $C(O)NHW^5$, $C(O)N(W^5)_2$, $NHC(O)W^5$ or $NW^5C(O)W^5$;
$W^2$ is phenyl which is unfused or fused with benzene or heteroarene;
$W^3$ is heteroaryl which is unfused or fused with benzene or heteroarene;
$W^4$ is cycloalkyl, cycloalkenyl, heterocycloalkyl or heterocycloalkenyl, each of which is unfused or fused with benzene or heteroarene;
$W^5$ is alkyl, alkenyl or alkynyl;
wherein the moieties represented by $A^1$, $B^1$, $W^2$, $W^3$ and $W^4$ are independently unsubstituted or substituted with one or two or three or four of independently selected $R^6$, $OR^6$, $SR^6$, $S(O)R^6$, $SO_2R^6$, $NH_2$, $NHR^6$, $N(R^6)_2$, $C(O)R^6$, $C(O)OR^6$, $C(O)NH_2$, $C(O)NHR^6$, $C(O)N(R^6)_2$, $NHC(O)R^6$, $NR^6C(O)R^6$, $NHSO_2R^6$, $NR^6SO_2R^6$, $NHC(O)OR^6$, $NR^6C(O)OR^6$, $SO_2NH_2$, $SO_2NHR^6$, $SO_2N(R^6)_2$, OH, (O), C(O)H, C(O)OH, $NO_2$, CN, $CF_3$, $OCF_3$, $CF_2CF_3$, F, Cl, Br or I;
$R^6$ is $R^7$, $R^8$, $R^9$ or $R^{10}$;
$R^7$ is phenyl which is unfused or fused with benzene or heteroarene;
$R^8$ is heteroaryl which is unfused or fused with benzene or heteroarene;
$R^9$ is cycloalkyl, cycloalkenyl, heterocycloalkyl or heterocycloalkenyl, each of which is unfused or fused with benzene or heteroarene;
$R^{10}$ is alkyl, alkenyl or alkynyl, each of which is unsubstituted or substituted with one or two of independently selected $R^{11}$, $OR^{11}SR^{11}S(O)R^{11}$, $SO_2R^{11}$, $NH_2$, $NHR^{11}$, $N(R^{11})_2$, $C(O)R^{11}$, $C(O)NH_2$, $C(O)NHR^{11}$, $C(O)N(R^{11})_2$, $NHC(O)R^{11}$, $NR^{11}C(O)R^{11}$, $NHSO_2R^{11}$, $NR^{11}SO_2R^{11}$, $NHC(O)OR^{11}$, $NR^{11}C(O)OR^{11}$, $SO_2NH_2$, $SO_2NHR^{11}$, $SO_2N(R^{11})_2$, OH, (O), C(O)OH, CN, $CF_3$, $OCF_3$, $CF_2CF_3$, F, Cl, Br or I;
$R^{11}$ is alkyl, alkenyl, alkynyl, $R^{12}$, $R^{13}$, $R^{14}$ or $T^1$;
$R^{12}$ is phenyl which is unfused or fused with benzene or heteroarene;
$R^{13}$ is heteroaryl which is unfused or fused with benzene or heteroarene;
$R^{14}$ is cycloalkyl, cycloalkenyl, heterocycloalkyl or heterocycloalkenyl, each of which is unfused or fused with benzene or heteroarene;
$T^1$ is alkyl, alkenyl or alkynyl, each of which is substituted with one or two of independently selected OH, $OT^2$, $ST^2$, $S(O)T^2$, $NH_2$, $NHT^2$ or $N(T^2)_2$;
$T^2$ is alkyl, alkenyl or alkynyl;

wherein the moieties represented by $R^7$, $R^8$, $R^9$ and $R^{11}$ are independently unsubstituted or substituted with one or two or three of four of independently selected $R^{15}$, $OR^{15}$, $SR^{15}$, $S(O)R^{15}$, $SO^2R^{15}$, $C(O)R^{15}$, $C(O)(O)R^{15}$, $C(O)NH_2$, $C(O)NHR^{15}$, $C(O)N(R^{15})_2$, OH, (O), C(O)OH, CN, $CF_3$, $OCF_3$, $CF_2CF_3$, F, Cl, Br or I; wherein
$R^{15}$ is alkyl, alkenyl, alkynyl, each of which is unsubstituted or substituted with phenyl, heteroaryl, cycloalkyl, heterocycloalkyl, OH, $OR^{16}$, $C(O)NH_2$, $C(O)NHR^{16}$, $C(O)N(R^{16})_2$; wherein
$R^{16}$ is alkyl, alkenyl or alkynyl; and wherein
the phenyl, heteroaryl, cycloalkyl and heterocycloalkyl of $R^{15}$ are unsubstituted or substituted with O(alkyl).

Still another embodiment pertains to compositions comprising an excipient and a therapeutically effective amount of a compound having Formula I.

Still another embodiment pertains to compositions comprising an excipient and therapeutically effective amounts of a compound having Formula I and one or more than one additional therapeutic agents.

Still another embodiment pertains to methods of treating a mammal having a disease involving overexpression or unregulation of a protein kinase comprising administering thereto a therapeutically effective amount of a compound having Formula I.

Still another embodiment pertains to methods of treating a mammal having a disease involving overexpression or unregulation of a protein kinase comprising administering thereto radiotherapy and a therapeutically effective amount of a compound having Formula I.

Still another embodiment pertains to methods of treating a mammal having cervical cancer, colon cancer, endometrial cancer, esophageal cancer, lung cancer comprising administering thereto a therapeutically effective amount of a compound having Formula I.

Still another embodiment pertains to methods of treating a mammal having cervical cancer, colon cancer, endometrial cancer, esophageal cancer, lung cancer comprising administering thereto radiotherapy and a therapeutically effective amount of a compound having Formula I.

Still another embodiment pertains to methods of treating diseases involving overexpression or unregulation of a protein kinase in a mammal comprising administering thereto therapeutically effective amounts of a compound having Formula I and one or more than one additional therapeutic agents.

Still another embodiment pertains to methods of treating diseases involving overexpression or unregulation of a protein kinase in a mammal comprising administering thereto radiotherapy and therapeutically effective amounts of a compound having Formula I and one or more than one additional therapeutic agents.

Still another embodiment pertains to methods of treating cervical cancer, colon cancer, endometrial cancer, esophageal cancer, lung cancer in a mammal comprising administering thereto a therapeutically effective amount of a compound having Formula I and one or more than one additional therapeutic agents.

Still another embodiment pertains to methods of treating cervical cancer, colon cancer, endometrial cancer, esophageal cancer, lung cancer in a mammal comprising administering thereto radiotherapy a therapeutically effective amount of a compound having Formula I and one or more than one additional therapeutic agents.

Still another embodiment pertains to the compounds cis-4-(4-(4-amino-3-(2-phenyl-1H-benzimidazol-6-yl)-1H-pyrazolo[3,4-d]pyrimidin-1-yl)cyclohexyl)-1-methylpiperazin-2-one;

cis-4-(4-(4-amino-3-(2-(4-fluorophenyl)-1H-benzimidazol-6-yl)-1H-pyrazolo[3,4-d]pyrimidin-1-yl)cyclohexyl)-1-methylpiperazin-2-one;

cis-4-(4-(4-amino-3-(2-cyclopropyl-1H-benzimidazol-6-yl)-1H-pyrazolo[3,4-d]pyrimidin-1-yl)cyclohexyl)-1-methylpiperazin-2-one;

cis-4-(4-(4-amino-3-(2-pyridin-2-yl-1H-benzimidazol-6-yl)-1H-pyrazolo[3,4-d]pyrimidin-1-yl)cyclohexyl)-1-methylpiperazin-2-one;

trans-1-(4-(2-methoxyethoxy)cyclohexyl)-3-(2-phenyl-1H-benzimidazol-5-yl)-1H-pyrazolo[3,4-d]pyrimidin-4-amine;

cis-1-(4-(4-methylpiperazin-1-yl)cyclohexyl)-3-(2-phenyl-1H-benzimidazol-5-yl)-1H-pyrazolo[3,4-d]pyrimidin-4-amine;

trans-1-(4-morpholin-4-ylcyclohexyl)-3-(2-phenyl-1H-benzimidazol-5-yl)-1H-pyrazolo[3,4-d]pyrimidin-4-amine;

trans-3-(2-(4-methylphenyl)-1H-benzimidazol-6-yl)-1-(4-morpholin-4-ylcyclohexyl)-1H-pyrazolo[3,4-d]pyrimidin-4-amine;

trans-3-(2-(4-chlorophenyl)-1H-benzimidazol-6-yl)-1-(4-morpholin-4-ylcyclohexyl)-1H-pyrazolo[3,4-d]pyrimidin-4-amine;

trans-3-(2-(4-methoxyphenyl)-1H-benzimidazol-6-yl)-1-(4-morpholin-4-ylcyclohexyl)-1H-pyrazolo[3,4-d]pyrimidin-4-amine;

trans-3-(2-(3,4-dichlorophenyl)-1H-benzimidazol-6-yl)-1-(4-morpholin-4-ylcyclohexyl)-1H-pyrazolo[3,4-d]pyrimidin-4-amine;

trans-3-(2-benzyl-1H-benzimidazol-6-yl)-1-(4-morpholin-4-ylcyclohexyl)-1H-pyrazolo[3,4-d]pyrimidin-4-amine;

trans-1-(4-morpholin-4-ylcyclohexyl)-3-(2-(2-phenylethyl)-1H-benzimidazol-6-yl)-1H-pyrazolo[3,4-d]pyrimidin-4-amine;

trans-1-(4-morpholin-4-ylcyclohexyl)-3-(2-(thien-2-ylmethyl)-1H-benzimidazol-6-yl)-1H-pyrazolo[3,4-d]pyrimidin-4-amine;

trans-3-(2-(3-chlorobenzyl)-1H-benzimidazol-6-yl)-1-(4-morpholin-4-ylcyclohexyl)-1H-pyrazolo[3,4-d]pyrimidin-4-amine;

trans-3-(2-(4-chlorobenzyl)-1H-benzimidazol-6-yl)-1-(4-morpholin-4-ylcyclohexyl)-1H-pyrazolo[3,4-d]pyrimidin-4-amine;

trans-1-(4-morpholin-4-ylcyclohexyl)-3-(2-(1-phenylethyl)-1H-benzimidazol-6-yl)-1H-pyrazolo[3,4-d]pyrimidin-4-amine;

trans-3-(2-(2-chlorobenzyl)-1H-benzimidazol-6-yl)-1-(4-morpholin-4-ylcyclohexyl)-1H-pyrazolo[3,4-d]pyrimidin-4-amine;

trans-3-(2-(2-fluorobenzyl)-1H-benzimidazol-6-yl)-1-(4-morpholin-4-ylcyclohexyl)-1H-pyrazolo[3,4-d]pyrimidin-4-amine;

trans-3-(2-(2-methylbenzyl)-1H-benzimidazol-6-yl)-1-(4-morpholin-4-ylcyclohexyl)-1H-pyrazolo[3,4-d]pyrimidin-4-amine;

trans-3-(2-(3-fluorobenzyl)-1H-benzimidazol-6-yl)-1-(4-morpholin-4-ylcyclohexyl)-1H-pyrazolo[3,4-d]pyrimidin-4-amine;

trans-3-(2-(3-methylbenzyl)-1H-benzimidazol-6-yl)-1-(4-morpholin-4-ylcyclohexyl)-1H-pyrazolo[3,4-d]pyrimidin-4-amine;

trans-3-(2-(4-fluorobenzyl)-1H-benzimidazol-6-yl)-1-(4-morpholin-4-ylcyclohexyl)-1H-pyrazolo[3,4-d]pyrimidin-4-amine;

trans-3-(2-(4-methylbenzyl)-1H-benzimidazol-6-yl)-1-(4-morpholin-4-ylcyclohexyl)-1H-pyrazolo[3,4-d]pyrimidin-4-amine;

trans-3-(2-(3,4-dichlorobenzyl)-1H-benzimidazol-6-yl)-1-(4-morpholin-4-ylcyclohexyl)-1H-pyrazolo[3,4-d]pyrimidin-4-amine;

trans-3-(2-(2,6-dichlorobenzyl)-1H-benzimidazol-5-yl)-1-(4-morpholin-4-ylcyclohexyl)-1H-pyrazolo[3,4-d]pyrimidin-4-amine;

trans-3-(2-(2,3-dichlorobenzyl)-1H-benzimidazol-5-yl)-1-(4-morpholin-4-ylcyclohexyl)-1H-pyrazolo[3,4-d]pyrimidin-4-amine;

trans-3-(2-((3-fluorophenyl)amino)-1H-benzimidazol-6-yl)-1-(4-morpholin-4-ylcyclohexyl)-1H-pyrazolo[3,4-d]pyrimidin-4-amine;

trans-3-(2-benzyl-4-methyl-1H-benzimidazol-6-yl)-1-(4-morpholin-4-ylcyclohexyl)-1H-pyrazolo[3,4-d]pyrimidin-4-amine;

trans-3-(2-benzyl-1-methyl-1H-benzimidazol-5-yl)-1-(4-morpholin-4-ylcyclohexyl)-1H-pyrazolo[3,4-d]pyrimidin-4-amine;

trans-1-(4-(4-amino-3-(2-benzyl-1H-benzimidazol-5-yl)-1H-pyrazolo[3,4-d]pyrimidin-1-yl)cyclohexyl)pyrrolidin-3-ol;

cis-1-(4-(4-amino-3-(2-benzyl-1H-benzimidazol-5-yl)-1H-pyrazolo[3,4-d]pyrimidin-1-yl)cyclohexyl)pyrrolidin-3-ol;

trans-3-(2-benzyl-1H-benzimidazol-5-yl)-1-(4-(4-(ethylsulfonyl)piperazin-1-yl)cyclohexyl)-1H-pyrazolo[3,4-d]pyrimidin-4-amine;

cis-3-(2-benzyl-1H-benzimidazol-5-yl)-1-(4-(4-(ethylsulfonyl)piperazin-1-yl)cyclohexyl)-1H-pyrazolo[3,4-d]pyrimidin-4-amine;

trans-3-(2-benzyl-1H-benzimidazol-5-yl)-1-(4-(4-(2-methoxyethyl)piperazin-1-yl)cyclohexyl)-1H-pyrazolo[3,4-d]pyrimidin-4-amine;

cis-3-(2-benzyl-1H-benzimidazol-5-yl)-1-(4-(4-(2-methoxyethyl)piperazin-1-yl)cyclohexyl)-1H-pyrazolo[3,4-d]pyrimidin-4-amine;

trans-3-(2-benzyl-1H-benzimidazol-5-yl)-1-(4-((3R,5S)-3,5-dimethylpiperazin-1-yl)cyclohexyl)-1H-pyrazolo[3,4-d]pyrimidin-4-amine;

cis-3-(2-benzyl-1H-benzimidazol-5-yl)-1-(4-((3R,5S)-3,5-dimethylpiperazin-1-yl)cyclohexyl)-1H-pyrazolo[3,4-d]pyrimidin-4-amine;

trans-1-(4-(4-acetylpiperazin-1-yl)cyclohexyl)-3-(2-benzyl-1H-benzimidazol-5-yl)-1H-pyrazolo[3,4-d]pyrimidin-4-amine;

cis-1-(4-(4-acetylpiperazin-1-yl)cyclohexyl)-3-(2-benzyl-1H-benzimidazol-5-yl)-1H-pyrazolo[3,4-d]pyrimidin-4-amine;

trans-3-(2-benzyl-1H-benzimidazol-5-yl)-1-(4-(3-(trifluoromethyl)-5,6-dihydro[1,2,4]triazolo[4,3-a]pyrazin-7(8H)-yl)cyclohexyl)-1H-pyrazolo[3,4-d]pyrimidin-4-amine;

cis-3-(2-benzyl-1H-benzimidazol-5-yl)-1-(4-(3-(trifluoromethyl)-5,6-dihydro[1,2,4]triazolo[4,3-a]pyrazin-7(8H)-yl)cyclohexyl)-1H-pyrazolo[3,4-d]pyrimidin-4-amine;

2-(4-(4-amino-3-(2-benzyl-1H-benzimidazol-5-yl)-1H-pyrazolo[3,4-d]pyrimidin-1-yl)piperidin-1-yl)acetamide;

trans-1-(4-(4-amino-3-(2-benzyl-1H-benzimidazol-5-yl)-1H-pyrazolo[3,4-d]pyrimidin-1-yl)cyclohexyl)piperidine-3-carboxamide;

cis-1-(4-(4-amino-3-(2-benzyl-1H-benzimidazol-5-yl)-1H-pyrazolo[3,4-d]pyrimidin-1-yl)cyclohexyl)piperidine-3-carboxamide;

trans-1-(4-(4-amino-3-(2-benzyl-1H-benzimidazol-5-yl)-1H-pyrazolo[3,4-d]pyrimidin-1-yl)cyclohexyl)piperidine-4-carboxamide;

cis-1-(4-(4-amino-3-(2-benzyl-1H-benzimidazol-5-yl)-1H-pyrazolo[3,4-d]pyrimidin-1-yl)cyclohexyl)piperidine-4-carboxamide;

3-(2-benzyl-1H-benzimidazol-5-yl)-1-(4-(morpholin-4-ylmethyl)phenyl)-1H-pyrazolo[3,4-d]pyrimidin-4-amine;

trans-3-(2-benzyl-1H-benzimidazol-5-yl)-1-(4-(4-(methylsulfonyl)piperazin-1-yl)cyclohexyl)-1H-pyrazolo[3,4-d]pyrimidin-4-amine;

cis-3-(2-benzyl-1H-benzimidazol-5-yl)-1-(4-(4-(methylsulfonyl)piperazin-1-yl)cyclohexyl)-1H-pyrazolo[3,4-d]pyrimidin-4-amine;

3-(2-benzyl-1H-benzimidazol-5-yl)-1-(1-(morpholin-4-ylcarbonyl)piperidin-4-yl)-1H-pyrazolo[3,4-d]pyrimidin-4-amine;

2-(3-(4-amino-3-(2-benzyl-1H-benzimidazol-5-yl)-1H-pyrazolo[3,4-d]pyrimidin-1-yl)pyrrolidin-1-yl)acetamide;

trans-2-(4-(4-(4-amino-3-(2-benzyl-1H-benzimidazol-5-yl)-1H-pyrazolo[3,4-d]pyrimidin-1-yl)cyclohexyl)piperazin-1-yl)ethanol;

cis-2-(4-(4-(4-amino-3-(2-benzyl-1H-benzimidazol-5-yl)-1H-pyrazolo[3,4-d]pyrimidin-1-yl)cyclohexyl)piperazin-1-yl)ethanol;

4-(4-amino-3-(2-benzyl-1H-benzimidazol-5-yl)-1H-pyrazolo[3,4-d]pyrimidin-1-yl)cyclohexanol;

cis-7-(4-(4-methylpiperazin-1-yl)cyclohexyl)-5-(2-phenyl-1H-benzimidazol-5-yl)-7H-pyrrolo[2,3-d]pyrimidin-4-amine;

cis-7-(4-(4-methylpiperazin-1-yl)cyclohexyl)-5-(2-(2-phenylethyl)-1H-benzimidazol-5-yl)-7H-pyrrolo[2,3-d]pyrimidin-4-amine;

cis-3-(2-anilino-1,3-benzoxazol-6-yl)-1-(4-(4-methylpiperazin-1-yl)cyclohexyl)-1H-pyrazolo[3,4-d]pyrimidin-4-amine;

trans-3-(2-anilino-1,3-benzoxazol-6-yl)-1-(4-(4-methylpiperazin-1-yl)cyclohexyl)-1H-pyrazolo[3,4-d]pyrimidin-4-amine;

trans-3-(2-anilino-1,3-benzoxazol-6-yl)-1-(4-(4-morpholin-4-ylcyclohexyl)-1H-pyrazolo[3,4-d]pyrimidin-4-amine;

trans-3-(2-anilino-1,3-benzoxazol-6-yl)-1-(4-(2-methoxyethoxy)cyclohexyl)-1H-pyrazolo[3,4-d]pyrimidin-4-amine;

trans-3-(2-(2-chloro-6-fluorobenzyl)-1H-benzimidazol-5-yl)-1-(4-morpholin-4-ylcyclohexyl)-1H-pyrazolo[3,4-d]pyrimidin-4-amine;

trans-3-(1-(2-chlorobenzyl)-1H-indol-4-yl)-1-(4-morpholin-4-ylcyclohexyl)-1H-pyrazolo[3,4-d]pyrimidin-4-amine;

trans-3-(1-(2-chlorobenzyl)-1H-indol-6-yl)-1-(4-morpholin-4-ylcyclohexyl)-1H-pyrazolo[3,4-d]pyrimidin-4-amine;

trans-3-(1-(2-chlorobenzyl)-1H-indol-5-yl)-1-(4-morpholin-4-ylcyclohexyl)-1H-pyrazolo[3,4-d]pyrimidin-4-amine;

trans-3-(1-(3-chlorobenzyl)-1H-indol-5-yl)-1-(4-morpholin-4-ylcyclohexyl)-1H-pyrazolo[3,4-d]pyrimidin-4-amine;

trans-3-(2-benzyl-1,3-benzoxazol-5-yl)-1-(4-morpholin-4-ylcyclohexyl)-1H-pyrazolo[3,4-d]pyrimidin-4-amine;

trans-3-(1-(2-chlorobenzyl)-1H-indazol-6-yl)-1-(4-morpholin-4-ylcyclohexyl)-1H-pyrazolo[3,4-d]pyrimidin-4-amine;

trans-3-(1-(3-chlorobenzyl)-1H-indazol-6-yl)-1-(4-morpholin-4-ylcyclohexyl)-1H-pyrazolo[3,4-d]pyrimidin-4-amine;

trans-3-(2-benzyl-1,3-benzoxazol-6-yl)-1-(4-morpholin-4-ylcyclohexyl)-1H-pyrazolo[3,4-d]pyrimidin-4-amine;

trans-3-(1-(3-fluorobenzyl)-1H-indazol-6-yl)-1-(4-morpholin-4-ylcyclohexyl)-1H-pyrazolo[3,4-d]pyrimidin-4-amine;

3-(2-benzyl-1H-benzimidazol-5-yl)-1-(1-(methylsulfonyl)piperidin-4-yl)-1H-pyrazolo[3,4-d]pyrimidin-4-amine;

(2S)-1-(4-amino-3-(2-benzyl-1H-benzimidazol-5-yl)-1H-pyrazolo[3,4-d]pyrimidin-1-yl)-3-morpholin-4-ylpropan-2-ol;

trans-3-(2-(2,6-difluorobenzyl)-1H-benzimidazol-6-yl)-1-(4-morpholin-4-ylcyclohexyl)-1H-pyrazolo[3,4-d]pyrimidin-4-amine;

trans-3-(2-(3-trifluorobenzyl)-1H-benzimidazol-6-yl-1-4-morpholin-4-ylcyclohexyl)-1H-pyrazolo[3,4-d]pyrimidin-4-amine;

trans-3-(3-((2,4-dimethylphenyl)amino)-1H-indazol-6-yl)-1-(4-morpholin-4-ylcyclohexyl)-1H-pyrazolo[3,4-d]pyrimidin-4-amine;

trans-3-(3-((2-chlorophenyl)amino)-1H-indazol-5-yl)-1-(4-morpholin-4-ylcyclohexyl)-1H-pyrazolo[3,4-d]pyrimidin-4-amine;

trans-3-(3-((3-chlorophenyl)amino)-1H-indazol-5-yl)-1-(4-morpholin-4-ylcyclohexyl)-1H-pyrazolo[3,4-d]pyrimidin-4-amine;

trans-3-(3-((3-fluorophenyl)amino)-1H-indazol-5-yl)-1-(4-morpholin-4-ylcyclohexyl)-1H-pyrazolo[3,4-d]pyrimidin-4-amine;

trans-1-(4-morpholin-4-ylcyclohexyl)-3-(3-((3-nitrophenyl)amino)-1H-indazol-5-yl)-1H-pyrazolo[3,4-d]pyrimidin-4-amine;

trans-3-(3-((2-methoxyphenyl)amino)-1H-indazol-5-yl)-1-(4-morpholin-4-ylcyclohexyl)-1H-pyrazolo[3,4-d]pyrimidin-4-amine;

trans-1-(4-morpholin-4-ylcyclohexyl)-3-(3-((6-(trifluoromethyl)pyridin-3-yl)amino)-1H-indazol-5-yl)-1H-pyrazolo[3,4-d]pyrimidin-4-amine;

trans-3-(3-(benzylamino)-1H-indazol-6-yl)-1-(4-morpholin-4-ylcyclohexyl)-1H-pyrazolo[3,4-d]pyrimidin-4-amine;

trans-1-(4-morpholin-4-ylcyclohexyl)-3-(3-((4-(trifluoromethyl)phenyl)amino)-1H-indazol-5-yl)-1H-pyrazolo[3,4-d]pyrimidin-4-amine;

trans-3-(3-((4-tert-butylphenyl)amino)-1H-indazol-5-yl)-1-(4-morpholin-4-ylcyclohexyl)-1H-pyrazolo[3,4-d]pyrimidin-4-amine;

trans-3-((5-(4-amino-1-(4-morpholin-4-ylcyclohexyl)-1H-pyrazolo[3,4-d]pyrimidin-3-yl)-1H-indazol-3-yl)amino)phenol;

trans-3-(3-((2-fluoro-5-methylphenyl)amino)-1H-indazol-6-yl)-1-(4-morpholin-4-ylcyclohexyl)-1H-pyrazolo[3,4-d]pyrimidin-4-amine;

trans-3-(3-((2,5-dimethylphenyl)amino)-1H-indazol-6-yl)-1-(4-morpholin-4-ylcyclohexyl)-1H-pyrazolo[3,4-d]pyrimidin-4-amine;

trans-3-(3-((2,5-difluorophenyl)amino)-1H-indazol-6-yl)-1-(4-morpholin-4-ylcyclohexyl)-1H-pyrazolo[3,4-d]pyrimidin-4-amine;

trans-3-(3-[(4-fluoro-2-methylphenyl)amino]-1H-indazol-6-yl)-1-(4-morpholin-4-ylcyclohexyl)-1H-pyrazolo[3,4-d]pyrimidin-4-amine and trans-1-(4-morpholin-4-ylcyclohexyl)-3-(2-phenoxy-1H-benzimidazol-5-yl)-1H-pyrazolo[3,4-d]pyrimidin-4-amine 3-(2-benzyl-1H-benzimidazol-5-yl)-1-(1-(methylsulfonyl)piperidin-4-yl)-1H-pyrazolo[3,4-d]pyrimidin-4-amine;

(trans)-3-(1-(2-chlorobenzyl)-1H-indol-5-yl)-1-(4-morpholin-4-ylcyclohexyl)-1H-pyrazolo[3,4-d]pyrimidin-4-amine;

(trans)-3-(1-(2-chlorobenzyl)-1H-indazol-6-yl)-1-(4-morpholin-4-ylcyclohexyl)-1H-pyrazolo[3,4-d]pyrimidin-4-amine;

3-(2-benzyl-1H-benzimidazol-6-yl)-1-(2-morpholin-4-yl-ethyl)-1H-pyrazolo[3,4-d]pyrimidin-4-amine;

3-(2-benzyl-1H-benzimidazol-6-yl)-1-(1-pyrimidin-2-ylpiperidin-4-yl)-1H-pyrazolo[3,4-d]pyrimidin-4-amine;

(trans)-3-(2-(2,3-difluorobenzyl)-1H-benzimidazol-6-yl)-1-(4-morpholin-4-ylcyclohexyl)-1H-pyrazolo[3,4-d]pyrimidin-4-amine;

(trans)-3-(2-(3,4-difluorobenzyl)-1H-benzimidazol-6-yl)-1-(4-morpholin-4-ylcyclohexyl)-1H-pyrazolo[3,4-d]pyrimidin-4-amine;

(trans)-3-(2-(3,5-difluorobenzyl)-1H-benzimidazol-6-yl)-1-(4-morpholin-4-ylcyclohexyl)-1H-pyrazolo[3,4-d]pyrimidin-4-amine;

(trans)-3-(2-benzyl-1H-benzimidazol-5-yl)-1-(4-((2-(methylsulfonyl)ethyl)amino)cyclohexyl)-1H-pyrazolo[3,4-d]pyrimidin-4-amine;

(cis)-3-(2-benzyl-1H-benzimidazol-5-yl)-1-(4-((2-(methylsulfonyl)ethyl)amino)cyclohexyl)-1H-pyrazolo[3,4-d]pyrimidin-4-amine;

3-(2-benzyl-1H-benzimidazol-5-yl)-1-(4-(1,1-dioxidothiomorpholin-4-yl)cyclohexyl)-1H-pyrazolo[3,4-d]pyrimidin-4-amine;

3-(2-benzyl-1H-benzimidazol-5-yl)-1-(4-(((2-(methylsulfonyl)ethyl)amino)methyl)phenyl)-1H-pyrazolo[3,4-d]pyrimidin-4-amine;

(trans)-2-(4-(4-(4-amino-3-(2-(2-fluorobenzyl)-1H-benzimidazol-5-yl)-1H-pyrazolo[3,4-d]pyrimidin-1-yl)cyclohexyl)piperazin-1-yl)ethanol;

(cis)-2-(4-(4-(4-amino-3-(2-(2-fluorobenzyl)-1H-benzimidazol-5-yl)-1H-pyrazolo[3,4-d]pyrimidin-1-yl)cyclohexyl)piperazin-1-yl)ethanol;

(trans)-3-(2-(2-chloro-3-fluorophenyl)-1H-benzimidazol-6-yl)-1-(4-morpholin-4-ylcyclohexyl)-1H-pyrazolo[3,4-d]pyrimidin-4-amine;

(trans)-1-(4-morpholin-4-ylcyclohexyl)-3-(2-(3-(trifluoromethyl)benzyl)-1H-benzimidazol-6-yl)-1H-pyrazolo[3,4-d]pyrimidin-4-amine;

N-(4-(4-amino-3-(2-benzyl-1H-benzimidazol-5-yl)-1H-pyrazolo[3,4-d]pyrimidin-1-yl)cyclohexyl)methanesulfonamide;

ethyl 4-(4-amino-3-(2-benzyl-1H-benzimidazol-5-yl)-1H-pyrazolo[3,4-d]pyrimidin-1-yl)cyclohexylcarbamate;

3-(2-benzyl-1H-benzimidazol-5-yl)-1-(1-(2-(methylsulfonyl)ethyl)pyrrolidin-3-yl)-1H-pyrazolo[3,4-d]pyrimidin-4-amine;

3-(2-(2-fluorobenzyl)-1H-benzimidazol-5-yl)-1-(1-(2-(methylsulfonyl)ethyl)pyrrolidin-3-yl)-1H-pyrazolo[3,4-d]pyrimidin-4-amine;

(trans)-3-(2-benzyl-1H-benzimidazol-5-yl)-1-(4-(4-(3-methoxypropyl)piperazin-1-yl)cyclohexyl)-1H-pyrazolo[3,4-d]pyrimidin-4-amine;

(cis)-3-(2-benzyl-1H-benzimidazol-5-yl)-1-(4-(4-(3-methoxypropyl)piperazin-1-yl)cyclohexyl)-1H-pyrazolo[3,4-d]pyrimidin-4-amine;

(trans)-3-(1-benzyl-1H-indol-5-yl)-1-(4-morpholin-4-ylcyclohexyl)-1H-pyrazolo[3,4-d]pyrimidin-4-amine;

(trans)-3-(1-(2-methylbenzyl)-1H-indol-5-yl)-1-(4-morpholin-4-ylcyclohexyl)-1H-pyrazolo[3,4-d]pyrimidin-4-amine;

(trans)-3-(1-(3-methylbenzyl)-1H-indol-5-yl)-1-(4-morpholin-4-ylcyclohexyl)-1H-pyrazolo[3,4-d]pyrimidin-4-amine;

(trans)-3-(1-(2-fluorobenzyl)-1H-indol-5-yl)-1-(4-morpholin-4-ylcyclohexyl)-1H-pyrazolo[3,4-d]pyrimidin-4-amine;

(trans)-3-(1-(3-fluorobenzyl)-1H-indol-5-yl)-1-(4-morpholin-4-ylcyclohexyl)-1H-pyrazolo[3,4-d]pyrimidin-4-amine;

(trans)-1-(4-morpholin-4-ylcyclohexyl)-3-(1-(2-(trifluoromethyl)benzyl)-1H-indol-5-yl)-1H-pyrazolo[3,4-d]pyrimidin-4-amine;

(trans)-3-(1-(2-fluorobenzyl)-1H-indazol-5-yl)-1-(4-morpholin-4-ylcyclohexyl)-1H-pyrazolo[3,4-d]pyrimidin-4-amine;

(trans)-3-(1-(2-chlorobenzyl)-1H-indazol-5-yl)-1-(4-morpholin-4-ylcyclohexyl)-1H-pyrazolo[3,4-d]pyrimidin-4-amine;

(trans)-3-(1-(3-chlorobenzyl)-1H-indazol-5-yl)-1-(4-morpholin-4-ylcyclohexyl)-1H-pyrazolo[3,4-d]pyrimidin-4-amine;

(trans)-3-(1-benzyl-1H-indazol-5-yl)-1-(4-morpholin-4-ylcyclohexyl)-1H-pyrazolo[3,4-d]pyrimidin-4-amine;

3-(2-benzyl-1H-benzimidazol-5-yl)-1-(1-(2-(methylsulfonyl)ethyl)piperidin-4-yl)-1H-pyrazolo[3,4-d]pyrimidin-4-amine;

3-(2-(2-fluorobenzyl)-1H-benzimidazol-5-yl)-1-(1-(2-(methylsulfonyl)ethyl)piperidin-4-yl)-1H-pyrazolo[3,4-d]pyrimidin-4-amine;

(trans)-3-(1-(cyclohexylmethyl)-1H-indol-5-yl)-1-(4-morpholin-4-ylcyclohexyl)-1H-pyrazolo[3,4-d]pyrimidin-4-amine;

(trans)-3-(1-cyclopentyl-1H-indol-5-yl)-1-(4-morpholin-4-ylcyclohexyl)-1H-pyrazolo[3,4-d]pyrimidin-4-amine;

(trans)-3-(1-(2,3-difluorobenzyl)-1H-indol-5-yl)-1-(4-morpholin-4-ylcyclohexyl)-1H-pyrazolo[3,4-d]pyrimidin-4-amine;

(trans)-3-(1-(2,5-difluorobenzyl)-1H-indol-5-yl)-1-(4-morpholin-4-ylcyclohexyl)-1H-pyrazolo[3,4-d]pyrimidin-4-amine;

(trans)-3-(1-(2,6-difluorobenzyl)-1H-indol-5-yl)-1-(4-morpholin-4-ylcyclohexyl)-1H-pyrazolo[3,4-d]pyrimidin-4-amine;

(trans)-3-(1-(2,5-dichlorobenzyl)-1H-indol-5-yl)-1-(4-morpholin-4-ylcyclohexyl)-1H-pyrazolo[3,4-d]pyrimidin-4-amine;

(trans)-3-(1-(2,6-dichlorobenzyl)-1H-indol-5-yl)-1-(4-morpholin-4-ylcyclohexyl)-1H-pyrazolo[3,4-d]pyrimidin-4-amine;

(trans)-1-(4-morpholin-4-ylcyclohexyl)-3-(2-(phenylsulfonyl)-1H-benzimidazol-5-yl)-1H-pyrazolo[3,4-d]pyrimidin-4-amine;

(trans)-2-(4-(4-(4-amino-3-(1-(2-chlorobenzyl)-1H-indol-5-yl)-1H-pyrazolo[3,4-d]pyrimidin-1-yl)cyclohexyl)piperazin-1-yl)ethanol;

(trans)-3-(1-(2-fluorobenzyl)-1H-indazol-6-yl)-1-(4-morpholin-4-ylcyclohexyl)-1H-pyrazolo[3,4-d]pyrimidin-4-amine;

3-(1-(2-chlorobenzyl)-1H-indol-5-yl)-1-(4-(4-(2-ethoxyethyl)piperazin-1-yl)cyclohexyl)-1H-pyrazolo[3,4-d]pyrimidin-4-amine;

(cis)-2-(4-(4-(4-amino-3-(1-(2-chlorobenzyl)-1H-indol-5-yl)-1H-pyrazolo[3,4-d]pyrimidin-1-yl)cyclohexyl)piperazin-1-yl)ethanol;

4-(4-amino-3-(1-(2-chlorobenzyl)-1H-indol-5-yl)-1H-pyrazolo[3,4-d]pyrimidin-1-yl)cyclohexanol;

3-(2-benzyl-1H-benzimidazol-6-yl)-1-(3-pyridin-3-ylpropyl)-1H-pyrazolo[3,4-d]pyrimidin-4-amine;

3-(2-benzyl-1H-benzimidazol-6-yl)-1-(1-benzylpiperidin-4-yl)-1H-pyrazolo[3,4-d]pyrimidin-4-amine;

3-(2-benzyl-1H-benzimidazol-6-yl)-1-(2-(4-methyl-1,3-thiazol-5-yl)ethyl)-1H-pyrazolo[3,4-d]pyrimidin-4-amine;

3-(2-benzyl-1H-benzimidazol-6-yl)-1-(1-(6-chloropyridazin-3-yl)piperidin-4-yl)-1H-pyrazolo[3,4-d]pyrimidin-4-amine;

3-(2-benzyl-1H-benzimidazol-6-yl)-1-(4-morpholin-4-ylbut-2-ynyl)-1H-pyrazolo[3,4-d]pyrimidin-4-amine;

3-(2-benzyl-1H-benzimidazol-6-yl)-1-(4-(4-(ethylsulfonyl)piperazin-1-yl)but-2-ynyl)-1H-pyrazolo[3,4-d]pyrimidin-4-amine;

(cis)-5-(2-(2-chlorobenzyl)-1H-benzimidazol-6-yl)-7-(4-(4-methylpiperazin-1-yl)cyclohexyl)-7H-pyrrolo[2,3-d]pyrimidin-4-amine;

(trans)-3-(4-(4-(4-amino-3-(2-benzyl-1H-benzimidazol-5-yl)-1H-pyrazolo[3,4-d]pyrimidin-1-yl)cyclohexyl)piperazin-1-yl)propan-1-ol;

(cis)-3-(4-(4-(4-amino-3-(2-benzyl-1H-benzimidazol-5-yl)-1H-pyrazolo[3,4-d]pyrimidin-1-yl)cyclohexyl)piperazin-1-yl)propan-1-ol;

(cis)-3-(4-(4-(4-amino-3-(1-(2-chlorobenzyl)-1H-indol-5-yl)-1H-pyrazolo[3,4-d]pyrimidin-1-yl)cyclohexyl)piperazin-1-yl)propan-1-ol;

(trans)-3-(4-(4-(4-amino-3-(1-(2-chlorobenzyl)-1H-indol-5-yl)-1H-pyrazolo[3,4-d]pyrimidin-1-yl)cyclohexyl)piperazin-1-yl)propan-1-ol;

2-(1-(4-(4-amino-3-(1-(2-chlorobenzyl)-1H-indol-5-yl)-1H-pyrazolo[3,4-d]pyrimidin-1-yl)cyclohexyl)piperidin-4-yl)ethanol;

(trans)-2-(1-(4-(4-amino-3-(1-(2-chlorobenzyl)-1H-indol-5-yl)-1H-pyrazolo[3,4-d]pyrimidin-1-yl)cyclohexyl)piperidin-4-yl)ethanol;

(cis)-(1-(4-(4-amino-3-(1-(2-chlorobenzyl)-1H-indol-5-yl)-1H-pyrazolo[3,4-d]pyrimidin-1-yl)cyclohexyl)piperidin-4-yl)methanol;

(trans)-(1-(4-(4-amino-3-(1-(2-chlorobenzyl)-1H-indol-5-yl)-1H-pyrazolo[3,4-d]pyrimidin-1-yl)cyclohexyl)piperidin-4-yl)methanol;

(cis)-3-(1-(2-chlorobenzyl)-1H-indol-5-yl)-1-(4-(4-(3-methoxypropyl)piperazin-1-yl)cyclohexyl)-1H-pyrazolo[3,4-d]pyrimidin-4-amine;

(trans)-3-(1-(2-chlorobenzyl)-1H-indol-5-yl)-1-(4-(4-(3-methoxypropyl)piperazin-1-yl)cyclohexyl)-1H-pyrazolo[3,4-d]pyrimidin-4-amine;

3-(1-(2-chlorobenzyl)-1H-indol-5-yl)-1-(4-pyrrolidin-1-ylcyclohexyl)-1H-pyrazolo[3,4-d]pyrimidin-4-amine;

3-(4-(4-(4-amino-3-(1-(2-chlorobenzyl)-1H-indol-5-yl)-1H-pyrazolo[3,4-d]pyrimidin-1-yl)cyclohexyl)piperazin-1-yl)propanenitrile;

3-(1-(2-fluorobenzyl)-1H-indol-5-yl)-1-(4-(4-(3-methoxypropyl)piperazin-1-yl)cyclohexyl)-1H-pyrazolo[3,4-d]pyrimidin-4-amine;

1-(4-(4-(2-ethoxyethyl)piperazin-1-yl)cyclohexyl)-3-(1-(2-fluorobenzyl)-1H-indol-5-yl)-1H-pyrazolo[3,4-d]pyrimidin-4-amine;

(cis)-2-(4-(4-(4-amino-3-(1-(2-fluorobenzyl)-1H-indol-5-yl)-1H-pyrazolo[3,4-d]pyrimidin-1-yl)cyclohexyl)piperazin-1-yl)ethanol;

(trans)-2-(4-(4-(4-amino-3-(1-(2-fluorobenzyl)-1H-indol-5-yl)-1H-pyrazolo[3,4-d]pyrimidin-1-yl)cyclohexyl)piperazin-1-yl)ethanol;

(cis)-3-(4-(4-(4-amino-3-(1-(2-fluorobenzyl)-1H-indol-5-yl)-1H-pyrazolo[3,4-d]pyrimidin-1-yl)cyclohexyl)piperazin-1-yl)propan-1-ol;

(trans)-3-(4-(4-(4-amino-3-(1-(2-fluorobenzyl)-1H-indol-5-yl)-1H-pyrazolo[3,4-d]pyrimidin-1-yl)cyclohexyl)piperazin-1-yl)propan-1-ol;

3-(4-(4-(4-amino-3-(1-(2-fluorobenzyl)-1H-indol-5-yl)-1H-pyrazolo[3,4-d]pyrimidin-1-yl)cyclohexyl)piperazin-1-yl)propanenitrile;

3-(2-benzyl-1H-benzimidazol-6-yl)-1-((2-pyridin-3-yl-1,3-thiazol-4-yl)methyl)-1H-pyrazolo[3,4-d]pyrimidin-4-amine;

3-(2-benzyl-1H-benzimidazol-6-yl)-1-((4-benzylmorpholin-2-yl)methyl)-1H-pyrazolo[3,4-d]pyrimidin-4-amine;

3-(1-(2-chlorobenzyl)-1H-indol-5-yl)-1-(3-(1,1-dioxidothiomorpholin-4-yl)propyl)-1H-pyrazolo[3,4-d]pyrimidin-4-amine;

1-(4-(4-acetylpiperazin-1-yl)but-2-ynyl)-3-(2-benzyl-1H-benzimidazol-6-yl)-1H-pyrazolo[3,4-d]pyrimidin-4-amine;

3-(2-benzyl-1H-benzimidazol-6-yl)-1-(4-(4-(2-methoxyethyl)piperazin-1-yl)but-2-ynyl)-1H-pyrazolo[3,4-d]pyrimidin-4-amine;

3-(1-(2-chlorobenzyl)-1H-indol-5-yl)-1-(4-(1,1-dioxidothiomorpholin-4-yl)but-2-ynyl)-1H-pyrazolo[3,4-d]pyrimidin-4-amine;

1-(4-(4-acetylpiperazin-1-yl)but-2-ynyl)-3-(1-(2-chlorobenzyl)-1H-indol-5-yl)-1H-pyrazolo[3,4-d]pyrimidin-4-amine;

3-(1-(2-chlorobenzyl)-1H-indol-5-yl)-1-(4-(4-(2-methoxyethyl)piperazin-1-yl)but-2-ynyl)-1H-pyrazolo[3,4-d]pyrimidin-4-amine;

1-((4-benzylmorpholin-2-yl)methyl)-3-(1-(2-chlorobenzyl)-1H-indol-5-yl)-1H-pyrazolo[3,4-d]pyrimidin-4-amine;

(trans)-3-(2-(2-chlorobenzyl)-1H-benzimidazol-6-yl)-1-(4-(4-(3-methoxypropyl)piperazin-1-yl)cyclohexyl)-1H-pyrazolo[3,4-d]pyrimidin-4-amine;

3-(2-benzyl-1H-benzimidazol-5-yl)-1-(1-(3-methoxypropyl)pyrrolidin-3-yl)-1H-pyrazolo[3,4-d]pyrimidin-4-amine;

(trans)-3-(2-benzyl-1H-benzimidazol-5-yl)-1-(4-(4-(2-(1,3-dioxolan-2-yl)ethyl)piperazin-1-yl)cyclohexyl)-1H-pyrazolo[3,4-d]pyrimidin-4-amine;

(cis)-3-(2-benzyl-1H-benzimidazol-5-yl)-1-(4-(4-(2-(1,3-dioxolan-2-yl)ethyl)piperazin-1-yl)cyclohexyl)-1H-pyrazolo[3,4-d]pyrimidin-4-amine;

(trans)-1-(4-morpholin-4-ylcyclohexyl)-3-(1-(tetrahydro-2H-pyran-2-ylmethyl)-1H-indol-5-yl)-1H-pyrazolo[3,4-d]pyrimidin-4-amine;

(trans)-1-(4-morpholin-4-ylcyclohexyl)-3-(1-(pyridin-3-ylmethyl)-1H-indol-5-yl)-1H-pyrazolo[3,4-d]pyrimidin-4-amine;

(trans)-1-(4-morpholin-4-ylcyclohexyl)-3-(1-(pyridin-2-ylmethyl)-1H-indol-5-yl)-1H-pyrazolo[3,4-d]pyrimidin-4-amine;

3-(2-benzyl-1H-benzimidazol-5-yl)-1-tert-butyl-1H-pyrazolo[3,4-d]pyrimidin-4-amine;

5-(2-benzyl-1H-benzimidazol-5-yl)-7-tert-butyl-7H-pyrrolo[2,3-d]pyrimidin-4-amine;

5-(2-benzyl-1H-benzimidazol-5-yl)-7-(4-(4-methylpiperazin-1-yl)cyclohexyl)-7H-pyrrolo[2,3-d]pyrimidin-4-amine;

(trans)-3-(1-benzyl-1H-benzimidazol-5-yl)-1-(4-morpholin-4-ylcyclohexyl)-1H-pyrazolo[3,4-d]pyrimidin-4-amine;

(trans)-3-(1-(2-chlorobenzyl)-1H-benzimidazol-5-yl)-1-(4-morpholin-4-ylcyclohexyl)-1H-pyrazolo[3,4-d]pyrimidin-4-amine;

(trans)-3-(1-(2-fluorobenzyl)-1H-benzimidazol-5-yl)-1-(4-morpholin-4-ylcyclohexyl)-1H-pyrazolo[3,4-d]pyrimidin-4-amine;

3-(1-(2-chlorobenzyl)-1H-indol-5-yl)-1-tetrahydro-2H-pyran-4-yl-1H-pyrazolo[3,4-d]pyrimidin-4-amine;

3-(2-benzyl-1H-benzimidazol-5-yl)-1-(3-methoxypropyl)-1H-pyrazolo[3,4-d]pyrimidin-4-amine;

3-(1-(2-chlorobenzyl)-1H-indol-5-yl)-1-(3-methoxypropyl)-1H-pyrazolo[3,4-d]pyrimidin-4-amine;

3-(2-benzyl-1H-benzimidazol-5-yl)-1-tetrahydro-2H-pyran-4-yl-1H-pyrazolo[3,4-d]pyrimidin-4-amine;

3-(2-benzyl-1H-benzimidazol-5-yl)-1-(1-methylpiperidin-4-yl)-1H-pyrazolo[3,4-d]pyrimidin-4-amine;

3-(1-(2-chlorobenzyl)-1H-indol-5-yl)-1-(1-methylpiperidin-4-yl)-1H-pyrazolo[3,4-d]pyrimidin-4-amine;

3-(2-benzyl-1H-benzimidazol-5-yl)-1-(3-(dimethylamino)propyl)-1H-pyrazolo[3,4-d]pyrimidin-4-amine;

3-(1-(2-chlorobenzyl)-1H-indol-5-yl)-1-(3-(dimethylamino)propyl)-1H-pyrazolo[3,4-d]pyrimidin-4-amine;

(trans)-3-(2-(2-bromobenzyl)-1H-benzimidazol-5-yl)-1-(4-morpholin-4-ylcyclohexyl)-1H-pyrazolo[3,4-d]pyrimidin-4-amine;

(trans)-3-(2-(2-methoxybenzyl)-1H-benzimidazol-5-yl)-1-(4-morpholin-4-ylcyclohexyl)-1H-pyrazolo[3,4-d]pyrimidin-4-amine;

(cis)-3-(2-(2-methoxybenzyl)-1H-benzimidazol-5-yl)-1-(4-(4-(3-methoxypropyl)piperazin-1-yl)cyclohexyl)-1H-pyrazolo[3,4-d]pyrimidin-4-amine;

(trans)-3-(2-(2-methoxybenzyl)-1H-benzimidazol-5-yl)-1-(4-(4-(3-methoxypropyl)piperazin-1-yl)cyclohexyl)-1H-pyrazolo[3,4-d]pyrimidin-4-amine;

(trans)-3-(2-(2-bromobenzyl)-1H-benzimidazol-5-yl)-1-(4-(4-(3-methoxypropyl)piperazin-1-yl)cyclohexyl)-1H-pyrazolo[3,4-d]pyrimidin-4-amine;

(cis)-3-(2-(2-bromobenzyl)-1H-benzimidazol-5-yl)-1-(4-(4-(3-methoxypropyl)piperazin-1-yl)cyclohexyl)-1H-pyrazolo[3,4-d]pyrimidin-4-amine;

3-(1-(2-chlorobenzyl)-1H-indol-5-yl)-1-(1'-methyl-1,4'-bipiperidin-4-yl)-1H-pyrazolo[3,4-d]pyrimidin-4-amine;

3-(1-(2-chlorobenzyl)-1H-indol-5-yl)-1-(1'-ethyl-1,4'-bipiperidin-4-yl)-1H-pyrazolo[3,4-d]pyrimidin-4-amine;

3-(1-(2-chlorobenzyl)-1H-indol-5-yl)-1-(1'-propyl-1,4'-bipiperidin-4-yl)-1H-pyrazolo[3,4-d]pyrimidin-4-amine;

3-(1-(2-chlorobenzyl)-1H-indol-5-yl)-1-(1'-isopropyl-1,4'-bipiperidin-4-yl)-1H-pyrazolo[3,4-d]pyrimidin-4-amine;

3-(1-(2-chlorobenzyl)-1H-indol-5-yl)-1-(1'-isobutyl-1,4'-bipiperidin-4-yl)-1H-pyrazolo[3,4-d]pyrimidin-4-amine;

(trans)-3-(2-benzyl-1H-indol-5-yl)-1-(4-morpholin-4-ylcyclohexyl)-1H-pyrazolo[3,4-d]pyrimidin-4-amine;

(trans)-3-(2-benzyl-1H-indol-6-yl)-1-(4-morpholin-4-ylcyclohexyl)-1H-pyrazolo[3,4-d]pyrimidin-4-amine;

3-(1-(2-chlorobenzyl)-1H-indol-5-yl)-1-(4-((4-(3-methoxypropyl)piperazin-1-yl)methyl)phenyl)-1H-pyrazolo[3,4-d]pyrimidin-4-amine;

(trans)-3-(2-(2-chlorobenzyl)-1H-indol-6-yl)-1-(4-morpholin-4-ylcyclohexyl)-1H-pyrazolo[3,4-d]pyrimidin-4-amine;

(3-((4-(4-amino-3-(1-(2-fluorobenzyl)-1H-indol-5-yl)-1H-pyrazolo[3,4-d]pyrimidin-1-yl)cyclohexyl)amino)phenyl)methanol;

4-((4-(4-amino-3-(1-(2-fluorobenzyl)-1H-indol-5-yl)-1H-pyrazolo[3,4-d]pyrimidin-1-yl)cyclohexyl)amino)-3-methylphenol;

3-((4-(4-amino-3-(1-(2-fluorobenzyl)-1H-indol-5-yl)-1H-pyrazolo[3,4-d]pyrimidin-1-yl)cyclohexyl)amino)phenol;

ethyl 4-((4-(4-amino-3-(1-(2-fluorobenzyl)-1H-indol-5-yl)-1H-pyrazolo[3,4-d]pyrimidin-1-yl)cyclohexyl)amino)benzoate;

(trans)-3-((4-(4-amino-3-(1-(2-fluorobenzyl)-1H-indol-5-yl)-1H-pyrazolo[3,4-d]pyrimidin-1-yl)cyclohexyl)amino)benzoic acid;

(cis)-3-((4-(4-amino-3-(1-(2-fluorobenzyl)-1H-indol-5-yl)-1H-pyrazolo[3,4-d]pyrimidin-1-yl)cyclohexyl)amino)benzoic acid;

(trans)-3-(2-(2-chlorobenzyl)-1H-indol-5-yl)-1-(4-morpholin-4-ylcyclohexyl)-1H-pyrazolo[3,4-d]pyrimidin-4-amine;

(trans)-3-(2-(2-fluorobenzyl)-1H-indol-5-yl)-1-(4-morpholin-4-ylcyclohexyl)-1H-pyrazolo[3,4-d]pyrimidin-4-amine;

3-((4-(4-amino-3-(1-(2-fluorobenzyl)-1H-indol-5-yl)-1H-pyrazolo[3,4-d]pyrimidin-1-yl)cyclohexyl)amino)-4-chlorobenzoic acid;

(trans)-3-(2-(4-methylphenoxy)-1H-benzimidazol-6-yl)-1-(4-morpholin-4-ylcyclohexyl)-1H-pyrazolo[3,4-d]pyrimidin-4-amine;

(trans)-3-(2-(3-methylphenoxy)-1H-benzimidazol-6-yl)-1-(4-morpholin-4-ylcyclohexyl)-1H-pyrazolo[3,4-d]pyrimidin-4-amine;

3-(4-(4-(4-amino-3-(3-(2-fluorobenzyl)-1H-indol-5-yl)-1H-pyrazolo[3,4-d]pyrimidin-1-yl)cyclohexyl)piperazin-1-yl)propan-1-ol;

(cis)-3-(4-(4-(4-amino-3-(2-(2-fluorobenzyl)-1H-indol-5-yl)-1H-pyrazolo[3,4-d]pyrimidin-1-yl)cyclohexyl)piperazin-1-yl)propan-1-ol;

(trans)-3-(4-(4-(4-amino-3-(2-(2-fluorobenzyl)-1H-indol-5-yl)-1H-pyrazolo[3,4-d]pyrimidin-1-yl)cyclohexyl)piperazin-1-yl)propan-1-ol;

3-(3-(2-fluorobenzyl)-1H-indol-5-yl)-1-(4-(4-(3-methoxypropyl)piperazin-1-yl)cyclohexyl)-1H-pyrazolo[3,4-d]pyrimidin-4-amine;

3-(2-(2-fluorobenzyl)-1H-indol-5-yl)-1-(4-(4-(3-methoxypropyl)piperazin-1-yl)cyclohexyl)-1H-pyrazolo[3,4-d]pyrimidin-4-amine;

2-(4-(4-(4-amino-3-(3-(2-fluorobenzyl)-1H-indol-5-yl)-1H-pyrazolo[3,4-d]pyrimidin-1-yl)cyclohexyl)piperazin-1-yl)ethanol;

(cis)-2-(4-(4-(4-amino-3-(2-(2-fluorobenzyl)-1H-indol-5-yl)-1H-pyrazolo[3,4-d]pyrimidin-1-yl)cyclohexyl)piperazin-1-yl)ethanol;

(trans)-2-(4-(4-(4-amino-3-(2-(2-fluorobenzyl)-1H-indol-5-yl)-1H-pyrazolo[3,4-d]pyrimidin-1-yl)cyclohexyl)piperazin-1-yl)ethanol;

(cis)-3-(4-(4-(4-amino-3-(2-benzyl-1H-indol-5-yl)-1H-pyrazolo[3,4-d]pyrimidin-1-yl)cyclohexyl)piperazin-1-yl)propan-1-ol;

(trans)-3-(4-(4-(4-amino-3-(2-benzyl-1H-indol-5-yl)-1H-pyrazolo[3,4-d]pyrimidin-1-yl)cyclohexyl)piperazin-1-yl)propan-1-ol;

3-(2-benzyl-1H-indol-5-yl)-1-(4-(4-(3-methoxypropyl)piperazin-1-yl)cyclohexyl)-1H-pyrazolo[3,4-d]pyrimidin-4-amine;

(cis)-2-(4-(4-(4-amino-3-(2-benzyl-1H-indol-5-yl)-1H-pyrazolo[3,4-d]pyrimidin-1-yl)cyclohexyl)piperazin-1-yl)ethanol;

(trans)-2-(4-(4-(4-amino-3-(2-benzyl-1H-indol-5-yl)-1H-pyrazolo[3,4-d]pyrimidin-1-yl)cyclohexyl)piperazin-1-yl)ethanol;

(cis)-4-(4-(4-amino-5-(1-(2-fluorobenzyl)-1H-indol-5-yl)-7H-pyrrolo[2,3-d]pyrimidin-7-yl)cyclohexyl)-1-isopropylpiperazin-2-one;

(cis)-4-(4-(4-amino-5-(1-(2-chlorobenzyl)-1H-indol-5-yl)-7H-pyrrolo[2,3-d]pyrimidin-7-yl)cyclohexyl)-1-isopropylpiperazin-2-one;

(cis)-4-(4-(4-amino-5-(1-(2-fluorobenzyl)-1H-indol-5-yl)-7H-pyrrolo[2,3-d]pyrimidin-7-yl)cyclohexyl)-1-ethylpiperazin-2-one;

(cis)-4-(4-(4-amino-5-(1-(2-chlorobenzyl)-1H-indol-5-yl)-7H-pyrrolo[2,3-d]pyrimidin-7-yl)cyclohexyl)-1-ethylpiperazin-2-one;

5-(1-(2-fluorobenzyl)-1H-indol-5-yl)-7-(4-(4-methylpiperazin-1-yl)cyclohexyl)-7H-pyrrolo[2,3-d]pyrimidin-4-amine;

5-(1-(2-chlorobenzyl)-1H-indol-5-yl)-7-(4-(4-methylpiperazin-1-yl)cyclohexyl)-7H-pyrrolo[2,3-d]pyrimidin-4-amine;

7-tert-butyl-5-(1-(2-fluorobenzyl)-1H-indol-5-yl)-7H-pyrrolo[2,3-d]pyrimidin-4-amine;

7-tert-butyl-5-(1-(2-chlorobenzyl)-1H-indol-5-yl)-7H-pyrrolo[2,3-d]pyrimidin-4-amine;

3-(1-(2-fluorobenzyl)-1H-indol-5-yl)-1-(4-(morpholin-4-ylmethyl)phenyl)-1H-pyrazolo[3,4-d]pyrimidin-4-amine;

(trans)-4-((4-(4-amino-3-(1-(2-fluorobenzyl)-1H-indol-5-yl)-1H-pyrazolo[3,4-d]pyrimidin-1-yl)cyclohexyl)amino)benzoic acid;

(cis)-4-((4-(4-amino-3-(1-(2-fluorobenzyl)-1H-indol-5-yl)-1H-pyrazolo[3,4-d]pyrimidin-1-yl)cyclohexyl)amino)benzoic acid;

3-(2-(2-chlorobenzyl)-1H-benzimidazol-5-yl)-1-(4-(morpholin-4-ylmethyl)phenyl)-1H-pyrazolo[3,4-d]pyrimidin-4-amine;

3-(2-(3-methylbenzyl)-1H-benzimidazol-5-yl)-1-(4-(morpholin-4-ylmethyl)phenyl)-1H-pyrazolo[3,4-d]pyrimidin-4-amine;

3-(2-(2-bromobenzyl)-1H-benzimidazol-5-yl)-1-(4-(morpholin-4-ylmethyl)phenyl)-1H-pyrazolo[3,4-d]pyrimidin-4-amine;

3-(2-(2-methoxybenzyl)-1H-benzimidazol-5-yl)-1-(4-(morpholin-4-ylmethyl)phenyl)-1H-pyrazolo[3,4-d]pyrimidin-4-amine;

(trans)-4-(4-(4-amino-3-(2-benzyl-1H-benzimidazol-5-yl)-1H-pyrazolo[3,4-d]pyrimidin-1-yl)cyclohexyl)piperazin-1-yl)-2-methylbutan-2-ol;

(cis)-4-(4-(4-amino-3-(2-benzyl-1H-benzimidazol-5-yl)-1H-pyrazolo[3,4-d]pyrimidin-1-yl)cyclohexyl)piperazin-1-yl)-2-methylbutan-2-ol;

(cis)-3-((4-(4-amino-3-(1-(2-fluorobenzyl)-1H-indol-5-yl)-1H-pyrazolo[3,4-d]pyrimidin-1-yl)cyclohexyl)amino)propan-1-ol;

(trans)-3-((4-(4-amino-3-(1-(2-fluorobenzyl)-1H-indol-5-yl)-1H-pyrazolo[3,4-d]pyrimidin-1-yl)cyclohexyl)amino)propan-1-ol;

2-((4-(4-amino-3-(1-(2-fluorobenzyl)-1H-indol-5-yl)-1H-pyrazolo[3,4-d]pyrimidin-1-yl)cyclohexyl)amino)ethanol;

2-(2-((4-(4-amino-3-(1-(2-fluorobenzyl)-1H-indol-5-yl)-1H-pyrazolo[3,4-d]pyrimidin-1-yl)cyclohexyl)amino)ethoxy)ethanol;

(cis)-(2S)-3-((4-(4-amino-3-(1-(2-fluorobenzyl)-1H-indol-5-yl)-1H-pyrazolo[3,4-d]pyrimidin-1-yl)cyclohexyl)amino)propane-1,2-diol;

(trans)-(2S)-3-((4-(4-amino-3-(1-(2-fluorobenzyl)-1H-indol-5-yl)-1H-pyrazolo[3,4-d]pyrimidin-1-yl)cyclohexyl)amino)propane-1,2-diol;

2,2'-(4-(4-amino-3-(1-(2-fluorobenzyl)-1H-indol-5-yl)-1H-pyrazolo[3,4-d]pyrimidin-1-yl)cyclohexylazanediyl)diethanol;

(cis)-N-(4-(4-amino-3-(1-(2-fluorobenzyl)-1H-indol-5-yl)-1H-pyrazolo[3,4-d]pyrimidin-1-yl)cyclohexyl)-beta-alanine;

(trans)-N-(4-(4-amino-3-(1-(2-fluorobenzyl)-1H-indol-5-yl)-1H-pyrazolo[3,4-d]pyrimidin-1-yl)cyclohexyl)-beta-alanine;

(trans)-4-(4-amino-3-(2-(2-methoxybenzyl)-1H-benzimidazol-5-yl)-1H-pyrazolo[3,4-d]pyrimidin-1-yl)cyclohexanol;

N-(4-(4-amino-3-(1-(2-fluorobenzyl)-1H-indol-5-yl)-1H-pyrazolo[3,4-d]pyrimidin-1-yl)cyclohexyl)-L-alanine;

(cis)-N-(4-(4-amino-3-(1-(2-fluorobenzyl)-1H-indol-5-yl)-1H-pyrazolo[3,4-d]pyrimidin-1-yl)cyclohexyl)-D-alanine;

(trans)-N-(4-(4-amino-3-(1-(2-fluorobenzyl)-1H-indol-5-yl)-1H-pyrazolo[3,4-d]pyrimidin-1-yl)cyclohexyl)-D-alanine;

N-(4-(4-amino-3-(1-(2-fluorobenzyl)-1H-indol-5-yl)-1H-pyrazolo[3,4-d]pyrimidin-1-yl)cyclohexyl)-N-methylglycine;

(trans)-1-(4-(4-(3-methoxypropyl)piperazin-1-yl)cyclohexyl)-3-(2-(thien-2-ylmethyl)-1H-benzimidazol-6-yl)-1H-pyrazolo[3,4-d]pyrimidin-4-amine;

3-(2-benzyl-1H-benzimidazol-6-yl)-1-(1'-(3-methoxypropyl)-1,4'-bipiperidin-4-yl)-1H-pyrazolo[3,4-d]pyrimidin-4-amine;

(cis)-2-(4-(4-(4-amino-3-(1-(2-(difluoromethoxy)benzyl)-1H-indol-5-yl)-1H-pyrazolo[3,4-d]pyrimidin-1-yl)cyclohexyl)piperazin-1-yl)ethanol;

(trans)-2-(4-(4-(4-amino-3-(1-(2-(difluoromethoxy)benzyl)-1H-indol-5-yl)-1H-pyrazolo[3,4-d]pyrimidin-1-yl)cyclohexyl)piperazin-1-yl)ethanol;

(cis)-3-(4-(4-(4-amino-3-(1-(2-(difluoromethoxy)benzyl)-1H-indol-5-yl)-1H-pyrazolo[3,4-d]pyrimidin-1-yl)cyclohexyl)piperazin-1-yl)propan-1-ol;

(trans)-3-(4-(4-(4-amino-3-(1-(2-(difluoromethoxy)benzyl)-1H-indol-5-yl)-1H-pyrazolo[3,4-d]pyrimidin-1-yl)cyclohexyl)piperazin-1-yl)propan-1-ol;

3-(2-(2,6-difluorobenzyl)-1H-benzimidazol-5-yl)-1-(4-(morpholin-4-ylmethyl)phenyl)-1H-pyrazolo[3,4-d]pyrimidin-4-amine;

2-(4-(4-amino-3-(2-benzyl-1H-benzimidazol-6-yl)-1H-pyrazolo[3,4-d]pyrimidin-1-yl)-1,4'-bipiperidin-1'-yl)ethanol;

3-(4-(4-amino-3-(2-benzyl-1H-benzimidazol-6-yl)-1H-pyrazolo[3,4-d]pyrimidin-1-yl)-1,4'-bipiperidin-1'-yl)propan-1-ol;

3-(2-benzyl-1H-benzimidazol-6-yl)-1-(1'-(2-methoxyethyl)-1,4'-bipiperidin-4-yl)-1H-pyrazolo[3,4-d]pyrimidin-4-amine;

2-(4-(4-amino-3-(1-(2-chlorobenzyl)-1H-indol-5-yl)-1H-pyrazolo[3,4-d]pyrimidin-1-yl)-1,4'-bipiperidin-1'-yl)ethanol;

3-(1-(2-chlorobenzyl)-1H-indol-5-yl)-1-(1'-(2-methoxyethyl)-1,4'-bipiperidin-4-yl)-1H-pyrazolo[3,4-d]pyrimidin-4-amine;

3-(1-(2-fluorobenzyl)-1H-indol-5-yl)-1-(4-(4-pyridin-2-ylpiperazin-1-yl)cyclohexyl)-1H-pyrazolo[3,4-d]pyrimidin-4-amine;

(trans)-3-(2-benzyl-1H-benzimidazol-5-yl)-1-(4-(4-pyridin-2-ylpiperazin-1-yl)cyclohexyl)-1H-pyrazolo[3,4-d]pyrimidin-4-amine;

(cis)-3-(2-benzyl-1H-benzimidazol-5-yl)-1-(4-(4-pyridin-2-ylpiperazin-1-yl)cyclohexyl)-1H-pyrazolo[3,4-d]pyrimidin-4-amine;

(trans)-1-(4-morpholin-4-ylcyclohexyl)-3-(2-(pyridin-2-ylmethyl)-1H-benzimidazol-6-yl)-1H-pyrazolo[3,4-d]pyrimidin-4-amine;

3-(2-benzyl-1H-benzimidazol-6-yl)-1-(1'-isobutyl-1,4'-bipiperidin-4-yl)-1H-pyrazolo[3,4-d]pyrimidin-4-amine;

(trans)-1-(4-morpholin-4-ylcyclohexyl)-3-(2-(pyridin-3-ylmethyl)-1H-benzimidazol-6-yl)-1H-pyrazolo[3,4-d]pyrimidin-4-amine;

(cis)-1-(1-(2-chlorobenzyl)-1H-indol-5-yl)-3-(3-(4-methylpiperazin-1-yl)cyclobutyl)imidazo[1,5-a]pyrazin-8-amine;

(cis)-1-(2-benzyl-1H-indol-5-yl)-3-(3-(4-methylpiperazin-1-yl)cyclobutyl)imidazo[1,5-a]pyrazin-8-amine;

(cis)-1-(2-benzyl-1H-benzimidazol-5-yl)-3-(3-(4-methylpiperazin-1-yl)cyclobutyl)imidazo[1,5-a]pyrazin-8-amine;

(trans)-1-(4-morpholin-4-ylcyclohexyl)-3-(2-(thien-3-ylmethyl)-1H-benzimidazol-6-yl)-1H-pyrazolo[3,4-d]pyrimidin-4-amine;

(trans)-3-(2-(1,3-benzodioxol-5-ylmethyl)-1H-benzimidazol-6-yl)-1-(4-morpholin-4-ylcyclohexyl)-1H-pyrazolo[3,4-d]pyrimidin-4-amine;

(trans)-3-(2-(2-fluorobenzyl)-1H-indol-5-yl)-1-(4-(4-(3-methoxypropyl)piperazin-1-yl)cyclohexyl)-1H-pyrazolo[3,4-d]pyrimidin-4-amine;

(cis)-3-(2-(2-fluorobenzyl)-1H-indol-5-yl)-1-(4-(4-(3-methoxypropyl)piperazin-1-yl)cyclohexyl)-1H-pyrazolo[3,4-d]pyrimidin-4-amine;

(trans)-4-(4-amino-3-(2-(trifluoromethoxy)benzyl)-1H-benzimidazol-5-yl)-1H-pyrazolo[3,4-d]pyrimidin-1-yl)cyclohexanol;

(trans)-1-(4-(4-(3-methoxypropyl)piperazin-1-yl)cyclohexyl)-3-(2-(2-(trifluoromethoxy)benzyl)-1H-benzimidazol-5-yl)-1H-pyrazolo[3,4-d]pyrimidin-4-amine;

(cis)-1-(4-(4-(3-methoxypropyl)piperazin-1-yl)cyclohexyl)-3-(2-(2-(trifluoromethoxy)benzyl)-1H-benzimidazol-5-yl)-1H-pyrazolo[3,4-d]pyrimidin-4-amine;

(trans)-1-(4-morpholin-4-ylcyclohexyl)-3-(2-(2-naphthylmethyl)-1H-benzimidazol-6-yl)-1H-pyrazolo[3,4-d]pyrimidin-4-amine;

(trans)-3-(2-(2,6-difluorobenzyl)-1H-benzimidazol-5-yl)-1-(4-(4-(3-methoxypropyl)piperazin-1-yl)cyclohexyl)-1H-pyrazolo[3,4-d]pyrimidin-4-amine;

(cis)-3-(2-(2,6-difluorobenzyl)-1H-benzimidazol-5-yl)-1-(4-(4-(3-methoxypropyl)piperazin-1-yl)cyclohexyl)-1H-pyrazolo[3,4-d]pyrimidin-4-amine;

(trans)-2-((6-(4-amino-1-(4-morpholin-4-ylcyclohexyl)-1H-pyrazolo[3,4-d]pyrimidin-3-yl)-1H-benzimidazol-2-yl)methyl)phenol;

3-(2-(2-methoxybenzyl)-1H-benzimidazol-5-yl)-1-(4-((4-(3-methoxypropyl)piperazin-1-yl)methyl)phenyl)-1H-pyrazolo[3,4-d]pyrimidin-4-amine;

1-(4-((4-(2-(1,3-dioxolan-2-yl)ethyl)piperazin-1-yl)methyl)phenyl)-3-(2-(2-methoxybenzyl)-1H-benzimidazol-5-yl)-1H-pyrazolo[3,4-d]pyrimidin-4-amine;

(trans)-3-(2-((2-methyl-1,3-thiazol-4-yl)methyl)-1H-benzimidazol-6-yl)-1-(4-morpholin-4-ylcyclohexyl)-1H-pyrazolo[3,4-d]pyrimidin-4-amine;

3-(2-(2-methoxybenzyl)-1H-benzimidazol-5-yl)-1-(4-((4-(methylsulfonyl)piperazin-1-yl)methyl)phenyl)-1H-pyrazolo[3,4-d]pyrimidin-4-amine;

2-(4-(4-amino-3-(2-(2-fluorobenzyl)-1H-indol-5-yl)-1H-pyrazolo[3,4-d]pyrimidin-1-yl)-1,4'-bipiperidin-1'-yl)ethanol;

3-(4-(4-amino-3-(2-(2-fluorobenzyl)-1H-indol-5-yl)-1H-pyrazolo[3,4-d]pyrimidin-1-yl)-1,4'-bipiperidin-1'-yl)propan-1-ol;

3-(2-(2-fluorobenzyl)-1H-indol-5-yl)-1-(1'-(2-methoxyethyl)-1,4'-bipiperidin-4-yl)-1H-pyrazolo[3,4-d]pyrimidin-4-amine;

3-(2-(2-fluorobenzyl)-1H-indol-5-yl)-1-(1'-(3-methoxypropyl)-1,4'-bipiperidin-4-yl)-1H-pyrazolo[3,4-d]pyrimidin-4-amine;

3-(2-(2-fluorobenzyl)-1H-indol-5-yl)-1-(1'-isobutyl-1,4'-bipiperidin-4-yl)-1H-pyrazolo[3,4-d]pyrimidin-4-amine;

2-(4-(4-(4-amino-3-(2-(2,5-difluorobenzyl)-1H-indol-5-yl)-1H-pyrazolo[3,4-d]pyrimidin-1-yl)cyclohexyl)piperazin-1-yl)ethanol;

3-(4-(4-amino-3-(2-(2-fluorobenzyl)-1H-indol-5-yl)-1H-pyrazolo[3,4-d]pyrimidin-1-yl)cyclohexyl)piperazin-1-yl)propan-1-ol;

(cis)-1-(4-((2-(2-(2-aminoethoxy)ethoxy)ethyl)amino)cyclohexyl)-3-(2-(2-fluorobenzyl)-1H-indol-5-yl)-1H-pyrazolo[3,4-d]pyrimidin-4-amine;

1-(4-((2-(2-(2-aminoethoxy)ethoxy)ethyl)amino)cyclohexyl)-3-(2-(2-fluorobenzyl)-1H-indol-5-yl)-1H-pyrazolo[3,4-d]pyrimidin-4-amine;

(trans)-1-(4-((2-(2-(2-aminoethoxy)ethoxy)ethyl)amino)cyclohexyl)-3-(2-(2-fluorobenzyl)-1H-indol-5-yl)-1H-pyrazolo[3,4-d]pyrimidin-4-amine;

2-(2-((4-(4-amino-3-(2-(2-fluorobenzyl)-1H-indol-5-yl)-1H-pyrazolo[3,4-d]pyrimidin-1-yl)cyclohexyl)amino)ethoxy)ethanol;

2-(1-(4-(4-amino-3-(2-(2-fluorobenzyl)-1H-indol-5-yl)-1H-pyrazolo[3,4-d]pyrimidin-1-yl)cyclohexyl)piperidin-4-yl)ethanol;

(1-(4-(4-amino-3-(2-(2-fluorobenzyl)-1H-indol-5-yl)-1H-pyrazolo[3,4-d]pyrimidin-1-yl)cyclohexyl)piperidin-4-yl)methanol;

(trans)-3-(2-(2-fluorobenzyl)-1H-indol-5-yl)-1-(4-(4-(2-(2-methoxyethoxy)ethyl)piperazin-1-yl)cyclohexyl)-1H-pyrazolo[3,4-d]pyrimidin-4-amine;

(trans)-3-(2-(2-fluorobenzyl)-1H-indol-5-yl)-1-(4-(4-(2-(methoxymethoxy)ethyl)piperazin-1-yl)cyclohexyl)-1H-pyrazolo[3,4-d]pyrimidin-4-amine;

3-(4-(4-(4-amino-3-(2-(2,5-difluorobenzyl)-1H-indol-5-yl)-1H-pyrazolo[3,4-d]pyrimidin-1-yl)cyclohexyl)piperazin-1-yl)propan-1-ol;

2-(4-(4-(4-amino-3-(2-(2-fluorobenzyl)-1H-indol-5-yl)-1H-pyrazolo[3,4-d]pyrimidin-1-yl)cyclohexyl)piperazin-1-yl)ethanol;

(trans)-1-(4-(4-(2-(2-ethoxyethoxy)ethyl)piperazin-1-yl)cyclohexyl)-3-(2-(2-fluorobenzyl)-1H-indol-5-yl)-1H-pyrazolo[3,4-d]pyrimidin-4-amine;

1-(4-(4-amino-3-(2-(2-methoxybenzyl)-1H-benzimidazol-5-yl)-1H-pyrazolo[3,4-d]pyrimidin-1-yl)cyclohexyl)piperidin-4-ol;

(trans)-3-(2-(2-methoxybenzyl)-1H-benzimidazol-5-yl)-1-(4-(4-(4-methoxyphenyl)piperazin-1-yl)cyclohexyl)-1H-pyrazolo[3,4-d]pyrimidin-4-amine;

(cis)-3-(2-(2-methoxybenzyl)-1H-benzimidazol-5-yl)-1-(4-(4-(4-methoxyphenyl)piperazin-1-yl)cyclohexyl)-1H-pyrazolo[3,4-d]pyrimidin-4-amine;

(trans)-4-(4-(4-amino-3-(2-(2-methoxybenzyl)-1H-benzimidazol-5-yl)-1H-pyrazolo[3,4-d]pyrimidin-1-yl)cyclohexyl)piperazin-2-one;

(cis)-4-(4-(4-amino-3-(2-(2-methoxybenzyl)-1H-benzimidazol-5-yl)-1H-pyrazolo[3,4-d]pyrimidin-1-yl)cyclohexyl)piperazin-2-one;

(trans)-5-(2-(2-methoxybenzyl)-1H-benzimidazol-5-yl)-7-(4-(4-(3-methoxypropyl)piperazin-1-yl)cyclohexyl)-7H-pyrrolo[2,3-d]pyrimidin-4-amine;

(cis)-5-(2-(2-methoxybenzyl)-1H-benzimidazol-5-yl)-7-(4-(4-(3-methoxypropyl)piperazin-1-yl)cyclohexyl)-7H-pyrrolo[2,3-d]pyrimidin-4-amine;

(trans)-3-(2-(2-methoxybenzyl)-1H-benzimidazol-5-yl)-1-(4-(4-(tetrahydrofuran-2-ylmethyl)piperazin-1-yl)cyclohexyl)-1H-pyrazolo[3,4-d]pyrimidin-4-amine;

(cis)-3-(2-(2-methoxybenzyl)-1H-benzimidazol-5-yl)-1-(4-(4-(tetrahydrofuran-2-ylmethyl)piperazin-1-yl)cyclohexyl)-1H-pyrazolo[3,4-d]pyrimidin-4-amine;

(trans)-3-(2-(2-methoxybenzyl)-1H-benzimidazol-5-yl)-1-(4-(4-(tetrahydrofuran-2-ylcarbonyl)piperazin-1-yl)cyclohexyl)-1H-pyrazolo[3,4-d]pyrimidin-4-amine;

(cis)-3-(2-(2-methoxybenzyl)-1H-benzimidazol-5-yl)-1-(4-(4-(tetrahydrofuran-2-ylcarbonyl)piperazin-1-yl)cyclohexyl)-1H-pyrazolo[3,4-d]pyrimidin-4-amine;

(cis)-2-(2-((4-(4-amino-3-(1-(2-fluorobenzyl)-1H-indol-5-yl)-1H-pyrazolo[3,4-d]pyrimidin-1-yl)cyclohexyl)amino)ethoxy)ethanol;

(trans)-2-(2-((4-(4-amino-3-(1-(2-fluorobenzyl)-1H-indol-5-yl)-1H-pyrazolo[3,4-d]pyrimidin-1-yl)cyclohexyl)amino)ethoxy)ethanol;

(trans)-3-(4-(4-(4-amino-3-(2-(2-fluorobenzyl)-1H-indol-6-yl)-1H-pyrazolo[3,4-d]pyrimidin-1-yl)cyclohexyl)piperazin-1-yl)propan-1-ol;

(trans)-3-(2-(2-fluorobenzyl)-1H-indol-6-yl)-1-(4-(4-(3-methoxypropyl)piperazin-1-yl)cyclohexyl)-1H-pyrazolo[3,4-d]pyrimidin-4-amine;

(trans)-2-(4-(4-(4-amino-3-(2-(2-fluorobenzyl)-1H-indol-6-yl)-1H-pyrazolo[3,4-d]pyrimidin-1-yl)cyclohexyl)piperazin-1-yl)ethanol;

(trans)-1-(4-(4-amino-3-(2-(2-fluorobenzyl)-1H-indol-5-yl)-1H-pyrazolo[3,4-d]pyrimidin-1-yl)cyclohexyl)piperidin-4-ol;

(trans)-1-(4-(4-(2-(1,3-dioxolan-2-yl)ethyl)piperazin-1-yl)cyclohexyl)-3-(2-(2-methoxybenzyl)-1H-benzimidazol-5-yl)-1H-pyrazolo[3,4-d]pyrimidin-4-amine;

(cis)-1-(4-(4-(2-(1,3-dioxolan-2-yl)ethyl)piperazin-1-yl)cyclohexyl)-3-(2-(2-methoxybenzyl)-1H-benzimidazol-5-yl)-1H-pyrazolo[3,4-d]pyrimidin-4-amine;

(trans)-3-(2-(2-methoxybenzyl)-1H-benzimidazol-6-yl)-1-(4-(2-(trifluoromethyl)-5,6-dihydroimidazo[1,2-a]pyrazin-7(8H)-yl)cyclohexyl)-1H-pyrazolo[3,4-d]pyrimidin-4-amine;

4-(4-amino-3-(2-(2-methoxybenzyl)-1H-benzimidazol-6-yl)-1H-pyrazolo[3,4-d]pyrimidin-1-yl)cyclohexanone;

(cis)-3-(2-(2-methoxybenzyl)-1H-benzimidazol-6-yl)-1-(4-(2-(trifluoromethyl)-5,6-dihydroimidazo[1,2-a]pyrazin-7(8H)-yl)cyclohexyl)-1H-pyrazolo[3,4-d]pyrimidin-4-amine;

(trans)-2-(4-(4-(4-amino-3-(2-(2-methoxybenzyl)-1H-indol-5-yl)-1H-pyrazolo[3,4-d]pyrimidin-1-yl)cyclohexyl)piperazin-1-yl)ethanol;

(trans)-3-(4-(4-(4-amino-3-(2-(2-methoxybenzyl)-1H-indol-5-yl)-1H-pyrazolo[3,4-d]pyrimidin-1-yl)cyclohexyl)piperazin-1-yl)propan-1-ol;

(trans)-3-(2-(2-methoxybenzyl)-1H-indol-5-yl)-1-(4-(4-(3-methoxypropyl)piperazin-1-yl)cyclohexyl)-1H-pyrazolo[3,4-d]pyrimidin-4-amine;

(trans)-2-(4-(4-(4-amino-3-(2-(2-methoxybenzyl)-1H-indol-6-yl)-1H-pyrazolo[3,4-d]pyrimidin-1-yl)cyclohexyl)piperazin-1-yl)ethanol;

(trans)-3-(4-(4-(4-amino-3-(2-(2-methoxybenzyl)-1H-indol-6-yl)-1H-pyrazolo[3,4-d]pyrimidin-1-yl)cyclohexyl)piperazin-1-yl)propan-1-ol;

(trans)-3-(2-(2-methoxybenzyl)-1H-indol-6-yl)-1-(4-(4-(3-methoxypropyl)piperazin-1-yl)cyclohexyl)-1H-pyrazolo[3,4-d]pyrimidin-4-amine;

(trans)-3-(2-(2-methoxybenzyl)-1H-benzimidazol-5-yl)-1-(4-piperazin-1-ylcyclohexyl)-1H-pyrazolo[3,4-d]pyrimidin-4-amine;

(trans)-3-(2-(2-methoxybenzyl)-1H-benzimidazol-5-yl)-1-(4-(4-methylpiperazin-1-yl)cyclohexyl)-1H-pyrazolo[3,4-d]pyrimidin-4-amine;

(trans)-(5-(4-amino-1-(4-morpholin-4-ylcyclohexyl)-1H-pyrazolo[3,4-d]pyrimidin-3-yl)-1-benzofuran-2-yl)(phenyl)methanone;

(trans)-3-(2-benzyl-1,3-benzothiazol-5-yl)-1-(4-morpholin-4-ylcyclohexyl)-1H-pyrazolo[3,4-d]pyrimidin-4-amine;

(trans)-3-dibenzo(b,d)thien-3-yl-1-(4-morpholin-4-ylcyclohexyl)-1H-pyrazolo[3,4-d]pyrimidin-4-amine;

(trans)-1-(4-(4-ethylpiperazin-1-yl)cyclohexyl)-3-(2-(2-methoxybenzyl)-1H-benzimidazol-6-yl)-1H-pyrazolo[3,4-d]pyrimidin-4-amine;

(cis)-1-(4-(4-ethylpiperazin-1-yl)cyclohexyl)-3-(2-(2-methoxybenzyl)-1H-benzimidazol-6-yl)-1H-pyrazolo[3,4-d]pyrimidin-4-amine;

(trans)-5-(2-(2-methoxybenzyl)-1H-benzimidazol-5-yl)-7-(4-(2-methoxyethoxy)cyclohexyl)-7H-pyrrolo[2,3-d]pyrimidin-4-amine;

(trans)-1-(4-(4-acetylpiperazin-1-yl)cyclohexyl)-3-(2-(3-methoxybenzyl)-1H-benzimidazol-6-yl)-1H-pyrazolo[3,4-d]pyrimidin-4-amine;

(trans)-4-(4-(4-(4-amino-3-(2-(2-methoxybenzyl)-1H-benzimidazol-6-yl)-1H-pyrazolo[3,4-d]pyrimidin-1-yl)cyclohexyl)piperazin-1-yl)-2-methylbutan-2-ol;

(cis)-4-(4-(4-(4-amino-3-(2-(3-methoxybenzyl)-1H-benzimidazol-6-yl)-1H-pyrazolo[3,4-d]pyrimidin-1-yl)cyclohexyl)piperazin-1-yl)-2-methylbutan-2-ol;

(cis)-3-(2-(2-methoxybenzyl)-1H-benzimidazol-6-yl)-1-(4-(4-pyrazin-2-ylpiperazin-1-yl)cyclohexyl)-1H-pyrazolo[3,4-d]pyrimidin-4-amine;

(cis)-2-(4-(4-(4-amino-3-(2-(2-methoxybenzyl)-1H-benzimidazol-6-yl)-1H-pyrazolo[3,4-d]pyrimidin-1-yl)cyclohexyl)piperazin-1-yl)ethanol;

(trans)-2-(4-(4-(4-amino-3-(2-(2-methoxybenzyl)-1H-benzimidazol-6-yl)-1H-pyrazolo[3,4-d]pyrimidin-1-yl)cyclohexyl)piperazin-1-yl)ethanol;

(trans)-4-(4-(4-amino-3-(2-(2-methoxybenzyl)-1H-benzimidazol-6-yl)-1H-pyrazolo[3,4-d]pyrimidin-1-yl)cyclohexyl)-N,N-dimethylpiperazine-1-carboxamide;

(cis)-4-(4-(4-amino-3-(2-(2-methoxybenzyl)-1H-benzimidazol-6-yl)-1H-pyrazolo[3,4-d]pyrimidin-1-yl)cyclohexyl)-N,N-dimethylpiperazine-1-carboxamide;

(trans)-ethyl 4-(4-(4-amino-3-(2-(2-methoxybenzyl)-1H-benzimidazol-6-yl)-1H-pyrazolo[3,4-d]pyrimidin-1-yl)cyclohexyl)piperazine-1-carboxylate;

(cis)-ethyl 4-(4-(4-amino-3-(2-(2-methoxybenzyl)-1H-benzimidazol-6-yl)-1H-pyrazolo[3,4-d]pyrimidin-1-yl)cyclohexyl)piperazine-1-carboxylate;

(cis)-3-(7-chloro-2-(2-methoxybenzyl)-1H-benzimidazol-5-yl)-1-(4-(4-(3-methoxypropyl)piperazin-1-yl)cyclohexyl)-1H-pyrazolo[3,4-d]pyrimidin-4-amine;

(trans)-1-(4-(4-(ethylsulfonyl)piperazin-1-yl)cyclohexyl)-3-(2-(2-methoxybenzyl)-1H-benzimidazol-6-yl)-1H-pyrazolo[3,4-d]pyrimidin-4-amine;

(cis)-1-(4-(4-(ethylsulfonyl)piperazin-1-yl)cyclohexyl)-3-(2-(2-methoxybenzyl)-1H-benzimidazol-6-yl)-1H-pyrazolo[3,4-d]pyrimidin-4-amine;

(trans)-3-(7-chloro-2-(2-methoxybenzyl)-1H-benzimidazol-5-yl)-1-(4-(4-(3-methoxypropyl)piperazin-1-yl)cyclohexyl)-1H-pyrazolo[3,4-d]pyrimidin-4-amine;

(trans)-1-(4-(4-(2-(2-(2-aminoethoxy)ethoxy)ethyl)piperazin-1-yl)cyclohexyl)-3-(2-(2-methoxybenzyl)-1H-benzimidazol-6-yl)-1H-pyrazolo[3,4-d]pyrimidin-4-amine;

(trans)-1-(4-(4-(cyclopropylmethyl)piperazin-1-yl)cyclohexyl)-3-(2-(2-methoxybenzyl)-1H-benzimidazol-6-yl)-1H-pyrazolo[3,4-d]pyrimidin-4-amine;

(cis)-1-(4-(4-(cyclopropylmethyl)piperazin-1-yl)cyclohexyl)-3-(2-(2-methoxybenzyl)-1H-benzimidazol-6-yl)-1H-pyrazolo[3,4-d]pyrimidin-4-amine;

(trans)-4-(4-(4-amino-3-(2-(2,6-difluorobenzyl)-1H-benzimidazol-5-yl)-1H-pyrazolo[3,4-d]pyrimidin-1-yl)cyclohexyl)piperazin-1-yl)-2-methylbutan-2-ol;

(cis)-4-(4-(4-(4-amino-3-(2-(2,6-difluorobenzyl)-1H-benzimidazol-5-yl)-1H-pyrazolo[3,4-d]pyrimidin-1-yl)cyclohexyl)piperazin-1-yl)-2-methylbutan-2-ol;

(trans)-2-(4-(4-(4-amino-3-(2-(2,6-difluorobenzyl)-1H-benzimidazol-5-yl)-1H-pyrazolo[3,4-d]pyrimidin-1-yl)cyclohexyl)piperazin-1-yl)ethanol;

(cis)-2-(4-(4-(4-amino-3-(2-(2,6-difluorobenzyl)-1H-benzimidazol-5-yl)-1H-pyrazolo[3,4-d]pyrimidin-1-yl)cyclohexyl)piperazin-1-yl)ethanol;

(trans)-3-(2-(2,6-difluorobenzyl)-1H-benzimidazol-5-yl)-1-(4-(4-ethylpiperazin-1-yl)cyclohexyl)-1H-pyrazolo[3,4-d]pyrimidin-4-amine;

(cis)-3-(2-(2,6-difluorobenzyl)-1H-benzimidazol-5-yl)-1-(4-(4-ethylpiperazin-1-yl)cyclohexyl)-1H-pyrazolo[3,4-d]pyrimidin-4-amine;

(trans)-3-(2-(2-methoxybenzyl)-1H-benzimidazol-6-yl)-1-(4-(4-(2-methoxyethyl)piperazin-1-yl)cyclohexyl)-1H-pyrazolo[3,4-d]pyrimidin-4-amine;

(cis)-3-(2-(2-methoxybenzyl)-1H-benzimidazol-6-yl)-1-(4-(4-(2-methoxyethyl)piperazin-1-yl)cyclohexyl)-1H-pyrazolo[3,4-d]pyrimidin-4-amine;

(trans)-1-(4-(4-isopropylpiperazin-1-yl)cyclohexyl)-3-(2-(2-methoxybenzyl)-1H-benzimidazol-6-yl)-1H-pyrazolo[3,4-d]pyrimidin-4-amine;

(cis)-1-(4-(4-isopropylpiperazin-1-yl)cyclohexyl)-3-(2-(2-methoxybenzyl)-1H-benzimidazol-6-yl)-1H-pyrazolo[3,4-d]pyrimidin-4-amine;

(trans)-3-(2-(cyclohexylmethyl)-1H-benzimidazol-6-yl)-1-(4-(4-(3-methoxypropyl)piperazin-1-yl)cyclohexyl)-1H-pyrazolo[3,4-d]pyrimidin-4-amine;

(trans)-3-(2-(cyclopentylmethyl)-1H-benzimidazol-6-yl)-1-(4-(4-(3-methoxypropyl)piperazin-1-yl)cyclohexyl)-1H-pyrazolo[3,4-d]pyrimidin-4-amine;

(trans)-3-(1-(3-fluorobenzyl)-1H-indazol-5-yl)-1-(4-morpholin-4-ylcyclohexyl)-1H-pyrazolo[3,4-d]pyrimidin-4-amine;

(trans)-3-(1-(2-methylbenzyl)-1H-indazol-5-yl)-1-(4-morpholin-4-ylcyclohexyl)-1H-pyrazolo[3,4-d]pyrimidin-4-amine;

(trans)-3-(1-(3-methylbenzyl)-1H-indazol-5-yl)-1-(4-morpholin-4-ylcyclohexyl)-1H-pyrazolo[3,4-d]pyrimidin-4-amine;

(trans)-3-(2-(2-methoxybenzyl)-1H-benzimidazol-6-yl)-1-(4-(4-phenylpiperazin-1-yl)cyclohexyl)-1H-pyrazolo[3,4-d]pyrimidin-4-amine;

(cis)-3-(2-(2-methoxybenzyl)-1H-benzimidazol-6-yl)-1-(4-(4-phenylpiperazin-1-yl)cyclohexyl)-1H-pyrazolo[3,4-d]pyrimidin-4-amine;

(trans)-3-(2-(2-chlorobenzyl)-1H-benzimidazol-6-yl)-1-(4-(4-ethylpiperazin-1-yl)cyclohexyl)-1H-pyrazolo[3,4-d]pyrimidin-4-amine;

(cis)-3-(2-(2-chlorobenzyl)-1H-benzimidazol-6-yl)-1-(4-(4-ethylpiperazin-1-yl)cyclohexyl)-1H-pyrazolo[3,4-d]pyrimidin-4-amine;

(trans)-2-(4-(4-(4-amino-3-(2-(2-chlorobenzyl)-1H-benzimidazol-6-yl)-1H-pyrazolo[3,4-d]pyrimidin-1-yl)cyclohexyl)piperazin-1-yl)ethanol;

(cis)-2-(4-(4-(4-amino-3-(2-(2-chlorobenzyl)-1H-benzimidazol-6-yl)-1H-pyrazolo[3,4-d]pyrimidin-1-yl)cyclohexyl)piperazin-1-yl)ethanol; and salts, esters, amides, prodrugs and salts of esters, amides and prodrugs thereof

DETAILED DESCRIPTION OF THE INVENTION

Variable moieties of compounds herein are represented by identifiers (capital letters with numerical and/or alphabetical superscripts) and may be specifically embodied.

It is meant to be understood that proper valences are maintained for all moieties and combinations thereof, that monovalent moieties having more than one atom are attached through their left ends.

It is also meant to be understood that a specific embodiment of a variable moiety may be the same or different as another specific embodiment having the same identifier.

The term "cyclic moiety," as used herein, means benzene, cycloalkane, cycloalkyl, cycloalkene, cycloalkenyl, heteroarene, heteroaryl, heterocycloalkane, heterocycloalkyl, heterocycloalkene, heterocycloalkenyl, phenyl, spiroalkyl, spiroalkenyl, spiroheteroalkyl and spiroheteroalkenyl.

The term "cycloalkane," as used herein, means $C_3$-cycloalkane, $C_4$-cycloalkane, $C_5$-cycloalkane and $C_6$-cycloalkane.

The term "cycloalkyl," as used herein, means $C_3$-cycloalkyl, $C_4$-cycloalkyl, $C_5$-cycloalkyl and $C_6$-cycloalkyl.

The term "cycloalkene," as used herein, means $C_4$-cycloalkene, $C_5$-cycloalkene and $C_6$-cycloalkene.

The term "cycloalkenyl," as used herein, means $C_4$-cycloalkenyl, $C_5$-cycloalkenyl and $C_6$-cycloalkenyl.

The term "heteroarene," as used herein, means furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine and 1,2,3-triazole.

The term "heteroaryl," as used herein, means furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl and 1,2,3-triazolyl.

The term "heterocycloalkane," as used herein, means cycloalkane having one or two or three $CH_2$ moieties replaced with independently selected O, S, S(O), $SO_2$ or NH and one or two CH moieties unreplaced or replaced with N and also means cycloalkane having one or two or three $CH_2$ moieties unreplaced or replaced with independently selected O, S, S(O), $SO_2$ or NH and one or two CH moieties replaced with N.

The term "heterocycloalkyl," as used herein, means cycloalkyl having one or two or three $CH_2$ moieties replaced with independently selected O, S, S(O), $SO_2$ or NH and one or two CH moieties unreplaced or replaced with N and also means cycloalkyl having one or two or three $CH_2$ moieties unreplaced or replaced with independently selected O, S, S(O), $SO_2$ or NH and one or two CH moieties replaced with N.

The term "heterocycloalkene," as used herein, means cycloalkene having one or two or three $CH_2$ moieties replaced with independently selected O, S, S(O), $SO_2$ or NH and one or two CH moieties unreplaced or replaced with N and also means cycloalkene having one or two or three $CH_2$ moieties unreplaced or replaced with independently selected O, S, S(O), $SO_2$ or NH and one or two CH moieties replaced with N.

The term "heterocycloalkenyl," as used herein, means cycloalkenyl having one or two or three $CH_2$ moieties replaced with independently selected O, S, S(O), $SO_2$ or NH and one or two CH moieties unreplaced or replaced with N and also means cycloalkenyl having one or two or three $CH_2$ moieties unreplaced or replaced with independently selected O, S, S(O), $SO_2$ or NH and one or two CH moieties replaced with N.

The term "alkenyl," as used herein, means $C_2$-alkenyl, $C_3$-alkenyl, $C_4$-alkenyl, $C_5$-alkenyl and $C_6$-alkenyl.

The term "alkyl," as used herein, means $C_1$-alkyl, $C_2$-alkyl, $C_3$-alkyl, $C_4$-alkyl, $C_5$-alkyl and $C_6$-alkyl.

The term "alkynyl," as used herein, means $C_2$-alkynyl, $C_3$-alkynyl, $C_4$-alkynyl, $C_5$-alkynyl and $C_6$-alkynyl.

The term "$C_2$-alkenyl," as used herein, means ethenyl (vinyl).

The term "$C_3$-alkenyl," as used herein, means 1-propen-1-yl, 1-propen-2-yl (isopropenyl) and 1-propen-3-yl (allyl).

The term "$C_4$-alkenyl," as used herein, means 1-buten-1-yl, 1-buten-2-yl, 1,3-butadien-1-yl, 1,3-butadien-2-yl, 2-buten-1-yl, 2-buten-2-yl, 3-buten-1-yl, 3-buten-2-yl, 2-methyl-1-propen-1-yl and 2-methyl-2-propen-1-yl.

The term "$C_5$-alkenyl," as used herein, means 2-methylene-3-buten-1-yl, 2-methylenebut-1-yl, 2-methyl-1-buten-1-yl, 2-methyl-1,3-butadien-1-yl, 2-methyl-2-buten-1-yl, 2-methyl-3-buten-1-yl, 2-methyl-3-buten-2-yl, 3-methyl-1-buten-1-yl, 3-methyl-1-buten-2-yl, 3-methyl-1,3-butadien-1-yl, 3-methyl-1,3-butadien-2-yl, 3-methyl-2-buten-1-yl, 3-methyl-2-buten-2-yl, 3-methyl-3-buten-1-yl, 3-methyl-3-buten-2-yl, 1-penten-1-yl, 1-penten-2-yl, 1-penten-3-yl, 1,3-pentadien-1-yl, 1,3-penta-dien-2-yl, 1,3-pentadien-3-yl, 1,4-pentadien-1-yl, 1,4-pentadien-2-yl, 1,4-pentadien-3-yl, 2-penten-1-yl, 2-penten-2-yl, 2-penten-3-yl, 2,4-pentadien-1-yl, 2,4-pentadien-2-yl, 3-penten-1-yl, 3-penten-2-yl, 4-penten-1-yl and 4-penten-2-yl.

The term "$C_6$-alkenyl," as used herein, means 2,2-dimethyl-3-buten-1-yl, 2,3-dimethyl-1-buten-1-yl, 2,3-dimethyl-1,3-butadien-1-yl, 2,3-dimethyl-2-buten-1-yl, 2,3-dimethyl-3-buten-1-yl, 2,3-dimethyl-3-buten-2-yl, 3,3-dimethyl-1-buten-1-yl, 3,3-dimethyl-1-buten-2-yl, 2-ethenyl-1,3-butadien-1-yl, 2-ethenyl-2-buten-1-yl, 2-ethyl-1-buten-1-yl, 2-ethyl-1,3-butadien-1-yl, 2-ethyl-2-buten-1-yl, 2-ethyl-3-buten-1-yl, 1-hexen-1-yl, 1-hexen-2-yl, 1-hexen-3-yl, 1,3-hexadien-1-yl, 1,3-hexadien-2-yl, 1,3-hexadien-3-yl, 1,3,5-hexatrien-1-yl, 1,3,5-hexatrien-2-yl, 1,3,5-hexatrien-3-yl, 1,4-hexadien-1-yl, 1,4-hexadien-2-yl, 1,4-hexadien-3-yl, 1,5-hexadien-1-yl, 1,5-hexadien-2-yl, 1,5-hexadien-3-yl, 2-hexen-1-yl, 2-hexen-2-yl, 2-hexen-3-yl, 2,4-hexadien-1-yl, 2,4-hexadien-2-yl, 2,4-hexadien-3-yl, 2,5-hexadien-1-yl, 2,5-hexadien-2-yl, 2,5-hexadien-3-yl, 3-hexen-1-yl, 3-hexen-2-yl, 3-hexen-3-yl, 3,5-hexadien-1-yl, 3,5-hexadien-2-yl, 3,5-hexadien-3-yl, 4-hexen-1-yl, 4-hexen-2-yl, 4-hexen-3-yl, 5-hexen-1-yl, 5-hexen-2-yl, 5-hexen-3-yl, 2-methylene-3-methyl-3-buten-1-yl, 2-methylene-3-methylbut-1-yl, 2-methylene-3-penten-1-yl, 2-methylene-4-penten-1-yl, 2-methylenepent-1-yl, 2-methylenepent-3-yl, 3-methylene-1-penten-1-yl, 3-methylene-1-penten-2-yl, 3-methylenepent-1-yl, 3-methylene-1,4-pentadien-1-yl, 3-methylene-1,4-pentadien-2-yl, 3-methylene-pent-2-yl, 2-methyl-1-penten-1-yl, 2-methyl-1-penten-3-yl, 2-methyl-1,3-pentadien-1-yl, 2-methyl-1,3-pentadien-3-yl, 2-methyl-1,4-pentadien-1-yl, 2-methyl-1,4-pentadien-3-yl, 2-methyl-2-penten-1-yl, 2-methyl-2-penten-3-yl, 2-methyl-2,4-pentadien-1-yl, 2-methyl-2,4-pentadien-3-yl, 2-methyl-3-penten-1-yl, 2-methyl-3-penten-2-yl, 2-methyl-3-penten-3-yl, 2-methyl-4-penten-1-yl, 2-methyl-4-penten-2-yl, 2-methyl-4-penten-3-yl, 3-methyl-1-penten-1-yl, 3-methyl-1-penten-2-yl, 3-methyl-1,3-pentadien-1-yl, 3-methyl-1,3-pentadien-2-yl, 3-methyl-1,4-pentadien-1-yl, 3-methyl-1,4-pentadien-2-yl, 3-methyl-2-penten-1-yl, 3-methyl-2-penten-2-yl, 3-methyl-2,4-pentadien-1-yl, 3-methyl-3-penten-1-yl, 3-methyl-3-penten-2-yl, 3-methyl-4-penten-1-yl, 3-methyl-4-penten-2-yl, 3-methyl-4-penten-3-yl, 4-methyl-1-penten-1-yl, 4-methyl-1-penten-2-yl, 4-methyl-1-penten-3-yl, 4-methyl-1,3-pentadien-1-yl, 4-methyl-1,3-pentadien-2-yl, 4-methyl-1,3-pentadien-3-yl, 4-methyl-1,4-pentadien-1-yl, 4-methyl-1,4-pentadien-2-yl, 4-methyl-1,4-pentadien-3-yl, 4-methylene-2-penten-3-yl, 4-methyl-2-penten-1-yl, 4-methyl-2-penten-2-yl, 4-methyl-2-penten-3-yl, 4-methyl-2,4-pentadien-1-yl, 4-methyl-2,4-pentadien-2-yl, 4-methyl-3-penten-1-yl, 4-methyl-3-penten-2-yl, 4-methyl-3-penten-3-yl, 4-methyl-4-penten-1-yl and 4-methyl-4-penten-2-yl.

The term "$C_1$-alkyl," as used herein, means methyl.

The term "$C_2$-alkyl," as used herein, means ethyl.

The term "$C_3$-alkyl," as used herein, means prop-1-yl and prop-2-yl (isopropyl).

The term "$C_4$-alkyl," as used herein, means but-1-yl, but-2-yl, 2-methylprop-1-yl and 2-methylprop-2-yl (tert-butyl).

The term "$C_5$-alkyl," as used herein, means 2,2-dimethylprop-1-yl (neo-pentyl), 2-methylbut-1-yl, 2-methylbut-2-yl, 3-methylbut-1-yl, 3-methylbut-2-yl, pent-1-yl, pent-2-yl and pent-3-yl.

The term "$C_6$-alkyl," as used herein, means 2,2-dimethylbut-1-yl, 2,3-dimethylbut-1-yl, 2,3-dimethylbut-2-yl, 3,3-dimethylbut-1-yl, 3,3-dimethylbut-2-yl, 2-ethylbut-1-yl, hex-1-yl, hex-2-yl, hex-3-yl, 2-methylpent-1-yl, 2-methylpent-2-yl, 2-methylpent-3-yl, 3-methylpent-1-yl, 3-methylpent-2-yl, 3-methylpent-3-yl, 4-methylpent-1-yl and 4-methylpent-2-yl.

The term "$C_2$-alkynyl," as used herein, means ethynyl (acetylenyl).

The term "$C_3$-alkynyl," as used herein, means 1-propyn-1-yl and 2-propyn-1-yl (propargyl).

The term "$C_4$-alkynyl," as used herein, means 1-butyn-1-yl, 1,3-butadiyn-1-yl, 2-butyn-1-yl, 3-butyn-1-yl and 3-butyn-2-yl.

The term "$C_5$-alkynyl," as used herein, means 2-methyl-3-butyn-1-yl, 2-methyl-3-butyn-2-yl, 3-methyl-1-butyn-1-yl, 1,3-pentadiyn-1-yl, 1,4-pentadiyn-1-yl, 1,4-pentadiyn-3-yl, 2,4-pentadiyn-1-yl, 1-pentyn-1-yl, 1-pentyn-3-yl, 2-pentyn-1-yl, 3-pentyn-1-yl, 3-pentyn-2-yl, 4-pentyn-1-yl and 4-pentyn-2-yl.

The term "$C_6$-alkynyl," as used herein, means 2,2-dimethyl-3-butyn-1-yl, 3,3-dimethyl-1-butyn-1-yl, 2-ethyl-3-butyn-1-yl, 2-ethynyl-3-butyn-1-yl, 1-hexyn-1-yl, 1-hexyn-3-yl, 1,3-hexadiyn-1-yl, 1,3,5-hexatriyn-1-yl, 1,4-hexadiyn-1-yl, 1,4-hexadiyn-3-yl, 1,5-hexadiyn-1-yl, 1,5-hexadiyn-3-yl, 2-hexyn-1-yl, 2,5-hexadiyn-1-yl, 3-hexyn-1-yl, 3-hexyn-2-yl, 3,5-hexadiyn-2-yl, 4-hexyn-1-yl, 4-hexyn-2-yl, 4-hexyn-3-yl, 5-hexyn-1-yl, 5-hexyn-2-yl, 5-hexyn-3-yl, 2-methyl-3-pentyn-1-yl, 2-methyl-3-pentyn-2-yl, 2-methyl-4-pentyn-1-yl, 2-methyl-4-pentyn-2-yl, 2-methyl-4-pentyn-3-yl, 3-methyl-1-pentyn-1-yl, 3-methyl-4-pentyn-1-yl, 3-methyl-4-pentyn-2-yl, 3-methyl-1,4-pentadiyn-1-yl, 3-methyl-1,4-pentadiyn-3-yl, 3-methyl-4-pentyn-1-yl, 3-methyl-4-pentyn-3-yl, 4-methyl-1-pentyn-1-yl and 4-methyl-2-pentyn-1-yl.

The term "$C_4$-cycloalkane," as used herein, means cyclobutane.

The term "$C_5$-cycloalkane," as used herein, means cyclopentane.

The term "$C_6$-cycloalkane," as used herein, means cyclohexane.

The term "$C_4$-cycloalkene," as used herein, means cyclobutene and 1,3-cyclobutadiene.

The term "$C_5$-cycloalkene," as used herein, means cyclopentene and 1,3-cyclopentadiene.

The term "$C_6$-cycloalkene," as used herein, means cyclohexene, 1,3-cyclohexadiene and 1,4-cyclohexadiene.

The term "$C_3$-cycloalkenyl," as used herein, means cycloprop-1-en-1-yl and cycloprop-2-en-1-yl.

The term "$C_4$-cycloalkenyl," as used herein, means cyclobut-1-en-1-yl and cyclobut-2-en-1-yl.

The term "$C_5$-cycloalkenyl," as used herein, means cyclopent-1-en-1-yl, cyclopent-2-en-1-yl, cyclopent-3-en-1-yl and cyclopenta-1,3-dien-1-yl.

The term "C$_6$-cycloalkenyl," as used herein, means cyclohex-1-en-1-yl, cyclohex-2-en-1-yl, cyclohex-3-en-1-yl, cyclohexa-1,3-dien-1-yl, cyclohexa-1,4-dien-1-yl, cyclohexa-1,5-dien-1-yl, cyclohexa-2,4-dien-1-yl and cyclohexa-2,5-dien-1-yl.

The term "C$_3$-cycloalkyl," as used herein, means cycloprop-1-yl.

The term "C$_4$-cycloalkyl," as used herein, means cyclobut-1-yl.

The term "C$_5$-cycloalkyl," as used herein, means cyclopent-1-yl.

The term "C$_6$-cycloalkyl," as used herein, means cyclohex-1-yl.

Compounds of this invention may contain asymmetrically substituted carbon atoms in the R or S configuration, wherein the terms "R" and "S" are as defined in Pure Appl. Chem. (1976) 45, 13-10. Compounds having asymmetrically substituted carbon atoms with equal amounts of R and S configurations are racemic at those atoms. Atoms having excess of one configuration over the other are assigned the configuration in excess, preferably an excess of about 85%-90%, more preferably an excess of about 95%-99%, and still more preferably an excess greater than about 99%. Accordingly, this invention is meant to embrace racemic mixtures and relative and absolute diastereoisomers of the compounds thereof.

Compounds of this invention may also contain carbon-carbon double bonds or carbon-nitrogen double bonds in the Z or E configuration, in which the term "Z" represents the larger two substitutents on the same side of a carbon-carbon or carbon-nitrogen double bond and the term "E" represents the larger two substitutents on opposite sides of a carbon-carbon or carbon-nitrogen double bond. The compounds of this invention may also exist as a mixture of "Z" and "E" isomers.

Compounds of this invention may also exist as tautomers or equilibrium mixtures thereof wherein a proton of a compound shifts from one atom to another. Examples of tautomers include, but are not limited to, keto-enol, phenol-keto, oxime-nitroso, nitro-aci, imine-enamine and the like.

Compounds of this invention containing NH, C(O)OH, OH or SH moieties may have attached thereto prodrug-forming moieties. The prodrug-forming moieties are removed by metabolic processes and release the compounds having the freed NH, C(O)OH, OH or SH in vivo. Prodrugs are useful for adjusting such pharmacokinetic properties of the compounds as solubility and/or hydrophobicity, absorption in the gastrointestinal tract, bioavailability, tissue penetration, and rate of clearance.

Metabolites of compounds having Formula I produced by in vitro or in vivo metabolic processes, may also have utility for treating diseases associated with overexpression or unregulation of a kinase.

Certain precursor compounds which may be metabolized in vitro or in vivo to form compounds having Formula I may also have utility for treating diseases associated with overexpression or unregulation of a kinase.

Compounds having Formula I may exist as acid addition salts, basic addition salts or zwitterions. Salts of compounds having Formula I are prepared during their isolation or following their purification. Acid addition salts are those derived from the reaction of a compound having Formula I with acid. Accordingly, salts including the acetate, adipate, alginate, bicarbonate, citrate, aspartate, benzoate, benzenesulfonate (besylate), bisulfate, butyrate, camphorate, camphorsulfonate, digluconate, formate, fumarate, glycerophosphate, glutamate, hemisulfate, heptanoate, hexanoate, hydrochloride, hydrobromide, hydroiodide, lactobionate, lactate, maleate, mesitylenesulfonate, methanesulfonate, naphthylenesulfonate, nicotinate, oxalate, pamoate, pectinate, persulfate, phosphate, picrate, propionate, succinate, tartrate, thiocyanate, trichloroacetic, trifluoroacetic, para-toluenesulfonate and undecanoate salts of the compounds having Formula I are meant to be embraced by this invention. Basic addition salts of compounds are those derived from the reaction of the compounds having Formula I with the bicarbonate, carbonate, hydroxide or phosphate of cations such as lithium, sodium, potassium, calcium and magnesium.

Compounds having Formula I may be administered, for example, bucally, ophthalmically, orally, osmotically, parenterally (intramuscularly, intraperitoneally intrasternally, intravenously, subcutaneously), rectally, topically, transdermally, vaginally and intraarterially as well as by intraarticular injection, infusion, and placement in the body, such as, for example, the vasculature.

Therapeutically effective amounts of a compound having Formula I depend on recipient of treatment, disease treated and severity thereof, composition comprising it, time of administration, route of administration, duration of treatment, potency, rate of clearance and whether or not another drug is co-administered. The amount of a compound having Formula I used to make a composition to be administered daily to a mammal in a single dose or in divided doses is from about 0.001 to about 200 mg/kg body weight. Single dose compositions contain these amounts or a combination of submultiples thereof.

Compounds having Formula I may be administered with or without an excipient. Excipients include, but are not limited to, encapsulators and additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents, mixtures thereof and the like.

Excipients for preparation of compositions comprising a compound having Formula I to be administered orally include, but are not limited to, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl cellulose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, mixtures thereof and the like. Excipients for preparation of compositions comprising a compound having Formula I to be administered ophthalmically or orally include, but are not limited to, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water, mixtures thereof and the like. Excipients for preparation of compositions comprising a compound having Formula I to be administered osmotically include, but are not limited to, chlorofluorohydrocarbons, ethanol, water, mixtures thereof and the like. Excipients for preparation of compositions comprising a compound having Formula I to be administered parenterally include, but are not limited to, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water, mixtures thereof and the like. Excipients for preparation of compositions comprising a compound having Formula I to be administered rectally or vaginally include, but are not limited to, cocoa butter, polyethylene glycol, wax, mixtures thereof and the like.

Compounds having Formula I are also expected to be useful as chemotherapeutic agents in combination with actinomycins, alkylating agents, anthracyclines, antifolates, antiestrogen agents, anti-metabolites, anti-androgens, antimicrotubule agents, aromatase inhibitors, bleomycins, $Ca^{2+}$ adenosine triphosphate (ATP)ase inhibitors, cytosine analogs, deltoids/retinoids, dihydrofolate reductase inhibitors, deoxyribonucleic acid (DNA) topoisomerase inhibitors, dopaminergic neurotoxins, glucocorticoids, histone deacetylase (HDAC) inhibitors, hormonal therapies, immunotherapeutic agents, inosine monophosphate (IMP) dehydrogenase inhibitors, isoprenylation inhibitors, luteinizing hormone-releasing hormone agonists, mammalian target of rapamycin (mtor) inhibitors, multi-drug resistance (MDR) inhibitors, mitomycins, photodyamic therapies, proteasome inhibitors, platinum containing compounds, radiation, receptor tyrosine kinase inhibitors, ribonucleotide reductase inhibitors, thrombospondin mimetics, uracil analogs, vinca alkaloids, and vitamin D3 analogs such as, but not limited to, γ-radiation or an additional chemotherapeutic agent or additional chemotherapeutic agents such as N-Ac-Sar-Gly-Val-D-alloIle-Thr-Nva-Ile-Arg-Pro-NHCH$_2$CH$_3$ or a salt thereof, actinomycin D, AG13736, 17-allylamino-17-demethoxygeldanamycin, 9-aminocamptothecin, N-(4-(3-amino-1H-indazol-4-yl)phenyl)-N'-(2-fluoro-5-methylphenyl)urea or a salt thereof, N-(4-(4-aminothieno[2,3-d]pyrimidin-5-yl)phenyl)-N'-(2-fluoro-5-(trifluoromethyl)phenyl)urea or a salt thereof, anastozole, AP-23573, asparaginase, azacitidine, bevacizumab, bicalutamide, bleomycin a2, bleomycin b2, bortezamib, busulfan, campathecins, carboplatin, carmustine (BCNU), CB1093, cetuximab, CHOP (C: Cytoxan® (cyclophosphamide); H: Adriamycin® (hydroxydoxorubicin); O: Vincristine (Oncovin®); P: prednisone), chlorambucil, CHIR258, cisplatin, CNF-101, CNF-1001, CNF-2024, CP547632, crisnatol, cytarabine, cyclophosphamide, cytosine arabinoside, daunorubicin, dacarbazine, dactinomycin, dasatinib, daunorubicin, deferoxamine, demethoxyhypocrellin A, depsipeptide, dexamethasone, 17-dimethylaminoethylamino-17-demethoxygeldanamycin, docetaxel, doxifluridine, doxorubicin, EB1089, epothilone D, epirubicin, 5-ethynyl-1-β-D-ribofuranosylimidazole-4-carboxamide (EICAR), erlotinib, etoposide, everolimus, 5-fluorouracil (5-FU), floxuridine, fludarabine, flutamide, gefitinib, geldanamycin, gemcitabine, goserelin, N-(2-(4-hydroxyanilino)-3-pyridinyl)-4-methoxybenzenesulfonamide or a salt thereof, hydroxyurea, idarubicin, ifosfamide, imatinab, interferon-α, interferon-γ, IPI-504, irinotecan, KH 1060, lapatanib, leucovorin calcium, LAQ824, leuprolide acetate, letrozole, lomustine (CCNU), lovastatin, megestrol, melphalan, mercaptopurine, methotrexate, 1-methyl-4-phyenylpyridinium, MG132, mitomycin, mitoxantrone, MLN-518, MS-275, mycophenolic acid, mitomycin C, nitrosoureas, oprelvekin, oxaliplatin, paclitaxel, PD98059, peplomycin, photosensitizer Pc4, phtalocyanine, pirarubicin, plicamycin, prednisone, procarbizine, PTK787, PU24FC1, PU3, radicicol, raloxifene, rapamycin, ratitrexed, retinoids such as pheuretinide, ribavirin, rituximab (Rituxin®), sorafenib, staurosporine, steroids such as dexamethasone and prednisone, suberoylanilide hydroxamic acid, sunitinib, tamoxifen, taxol, temozolamide, temsirolimus, teniposide, thapsigargin, thioguanine, thrombospondin-1, tiazofurin, topotecan, trapoxin, trastuzumab, treosulfan, trichostatin A, trimetrexate, trofosfamide, tumor necrosis factor, valproic acid, VER49009, verapamil, vertoporfin, vinblastine, vincristine, vindesine, vinorelbine vitamin D3, VX-680, zactima, ZK-EPO, zorubicin or combinations thereof.

To determine the binding of compounds having Formula I to a representative protein kinase, protein tyrosine kinase, the following assay was used:

Homogenous time-resolved fluorescence (HTRF) in vitro kinase assays were used to detect and measure the inhibition of kinase activity. The HTRF assays were conducted as described in Mathis, G., HTRF(R) Technology. J Biomol. Screen, 1999. 4(6): pp. 309-314). The protocol was adapted for determining activity with respect to a specific protein tyrosine kinase (PTK). A preferred protocol for conducting the HTRF experiments is described hereinbelow. Adaptation of these protocols for determining a compound's activity for other kinases are well within the abilities of the skilled practitioner.

In a representative experiment, 10 μL of KDR, prepared as described herein, was mixed with 10 μL of inhibitor (various concentrations, 2% final DMSO) and 10 μL of ATP (125 μM final concentration) in reaction buffer (50 mM HEPES, pH 7.5, 10 mM MgCl$_2$, 2 mM MnCl$_2$, 0.1% BSA and 1 mM DTT, 40 μL final volume). The reaction was initiated by addition of Bio-fgfr peptide (Genemed Biotechnologies, Inc., San Francisco, Calif.), 0.5 μM final concentration) in a black 96-well plate (Packard). After 45 minutes incubation at room temperature, the reaction was quenched by adding 60 μL of stop/revelation buffer to give 30 mM EDTA, 1 μg/mL streptavidin-APC (Prozyme), 50 ng/mL anti-phosphotyrosine mAb PT66-K Europium Cryptate, 30 mM HEPES, pH 7.5, 120 mM KF, 0.005% Tween-20, 0.05% BSA). The quenched reaction stood at room temperature for 1 hour and then read in a time-resolved fluorescence detector (Envision, Perkin Elmer) at 615 nm and 665 nm, simultaneously. The ratio between the signal of 615 nm and 665 nm was used in the calculation of the $IC_{50}$'s. $K_i$ values were calculated as described in Biochem. Pharmacol. 1973, 22, 3099-3108.

The coding sequence for the human KDR intra-cellular domain (aa789-1354) was generated through PCR using cDNAs isolated from HUVEC cells. A poly-His6 sequence was also introduced at the N-terminus of this protein. This fragment was cloned into transfection vector pVL1393 at the Xba 1 and Not 1 site. Recombinant baculovirus (BV) was generated through co-transfection using the BaculoGold Transfection reagent (PharMingen). Recombinant BV was plaque purified and verified through Western analysis. For protein production, SF-9 cells were grown in SF-900-II medium at 2×106/mL, and were infected at 0.5 plaque forming units per cell (MOI). Cells were harvested at 48 hours post infection.

SF-9 cells expressing (His)$_6$ KDR(aa789-1354) were lysed by adding 50 mL of Triton X-100 lysis buffer (20 mM Tris, pH 8.0, 137 mM NaCl, 10% glycerol, 1% Triton X-100, 1 mM PMSF, 10 μg/mL aprotinin, 1 μg/mL leupeptin) to the cell pellet from IL of cell culture. The lysate was centrifuged at 19,000 rpm in a Sorval SS-34 rotor for 30 min at 4° C. The cell lysate was applied to a 5 ml NiCl$_2$ chelating sepharose column, equilibrated with 50 mM HEPES, pH7.5, 0.3 M NaCl. KDR was eluted using the same buffer containing 0.25 M imidazole. Column fractions were analyzed using SDS-PAGE and an ELISA assay (below) which measures kinase activity. The purified KDR was exchanged into 25 mM HEPES, pH7.5, 25 mM NaCl, 5 mM DTT buffer and stored at −80° C. Results are shown in TABLES 1 and 2.

TABLE 1

KDR inhibition (nM)

| | | | | | |
|---|---|---|---|---|---|
| 5.73 nM | 5.73 nM, | 6.46 nM | 25.9 nM | 37.6 nM | 40.4 nM |
| 42.1 nM | 42.3 nM | 47.6 nM | 51.7 nM | 61.3 nM | 76 nM |
| 90.3 nM | 92.7 nM | 104 nM | 105 nM | 108 nM | 116 nM |
| 118 nM | 138 nM | 141 nM | 145 nM | 146 nM | 155 nM |
| 164 nM | 187 nM | 191 nM | 227 nM | 271 nM | 287 nM |
| 299 nM | 303 nM | 323 nM | 332 nM | 342 nM | 354 nM |
| 384 nM | 393 nM | 438 nM | 489 nM | 503 nM | 506 nM |
| 546 nM | 551 nM | 569 nM | 894 nM | 937 nM | 938 nM |
| 1060 nM | 1130 nM | 1210 nM | 1540 nM | 1570 nM | 1870 nM |
| 3540 nM | | | | | |

TABLE 2

KDR inhibition (μM)

| | | | | |
|---|---|---|---|---|
| 0.00174 | 0.00207 | 0.00274 | 0.00293 | 0.00311 |
| 0.00319 | 0.00431 | 0.00445 | 0.00452 | 0.00463 |
| 0.00476 | 0.00625 | 0.00665 | 0.00691 | 0.00695 |
| 0.00718 | 0.00725 | 0.00737 | 0.00743 | 0.00806 |
| 0.00815 | 0.00821 | 0.00833 | 0.00905 | 0.0095 |
| 0.0095 | 0.00986 | 0.00988 | 0.0103 | 0.0103 |
| 0.0105 | 0.0115 | 0.0122 | 0.0124 | 0.0126 |
| 0.0127 | 0.0128 | 0.013 | 0.013 | 0.0146 |
| 0.0146 | 0.0149 | 0.0149 | 0.0152 | 0.0154 |
| 0.0155 | 0.0158 | 0.0159 | 0.0163 | 0.0165 |
| 0.0168 | 0.017 | 0.0178 | 0.0179 | 0.0181 |
| 0.0181 | 0.0182 | 0.0182 | 0.0193 | 0.0193 |
| 0.0194 | 0.0197 | 0.021 | 0.021 | 0.0217 |
| 0.0225 | 0.0229 | 0.0233 | 0.0238 | 0.0241 |
| 0.0242 | 0.0247 | 0.0255 | 0.0276 | 0.0277 |
| 0.0288 | 0.0289 | 0.0293 | 0.0311 | 0.0314 |
| 0.0317 | 0.0318 | 0.032 | 0.0322 | 0.0322 |
| 0.0349 | 0.0354 | 0.0362 | 0.0364 | 0.0365 |
| 0.0374 | 0.0395 | 0.0399 | 0.0399 | 0.04 |
| 0.0402 | 0.0411 | 0.0411 | 0.0413 | 0.0415 |
| 0.0429 | 0.0429 | 0.043 | 0.0436 | 0.0467 |
| 0.0488 | 0.051 | 0.053 | 0.0536 | 0.0538 |
| 0.0555 | 0.0607 | 0.0662 | 0.0705 | 0.0711 |
| 0.0712 | 0.0763 | 0.0821 | 0.0824 | 0.0861 |
| 0.0863 | 0.0879 | 0.0899 | 0.0917 | 0.0926 |
| 0.0928 | 0.0932 | 0.0941 | 0.0954 | 0.096 |
| 0.096 | 0.0967 | 0.0977 | 0.0997 | 0.101 |
| 0.105 | 0.108 | 0.109 | 0.113 | 0.117 |
| 0.118 | 0.123 | 0.127 | 0.132 | 0.134 |
| 0.134 | 0.136 | 0.137 | 0.141 | 0.143 |
| 0.149 | 0.149 | 0.152 | 0.153 | 0.156 |
| 0.159 | 0.167 | 0.171 | 0.176 | 0.181 |
| 0.183 | 0.183 | 0.19 | 0.191 | 0.194 |
| 0.202 | 0.206 | 0.208 | 0.209 | 0.213 |
| 0.22 | 0.222 | 0.225 | 0.228 | 0.229 |
| 0.232 | 0.233 | 0.245 | 0.246 | 0.248 |
| 0.251 | 0.254 | 0.257 | 0.261 | 0.268 |
| 0.271 | 0.272 | 0.278 | 0.281 | 0.289 |
| 0.293 | 0.294 | 0.305 | 0.31 | 0.311 |
| 0.312 | 0.316 | 0.331 | 0.332 | 0.336 |
| 0.337 | 0.339 | 0.341 | 0.344 | 0.349 |
| 0.359 | 0.361 | 0.382 | 0.394 | 0.403 |
| 0.406 | 0.409 | 0.42 | 0.429 | 0.451 |
| 0.457 | 0.462 | 0.469 | 0.472 | 0.477 |
| 0.48 | 0.491 | 0.494 | 0.496 | 0.509 |
| 0.516 | 0.517 | 0.521 | 0.522 | 0.537 |
| 0.553 | 0.557 | 0.558 | 0.576 | 0.579 |
| 0.585 | 0.608 | 0.617 | 0.619 | 0.64 |
| 0.64 | 0.662 | 0.683 | 0.7 | 0.71 |
| 0.895 | 0.926 | 1.03 | 1.06 | 1.1 |
| 1.13 | 1.22 | 1.3 | 1.36 | 1.36 |
| 1.76 | 1.77 | 1.82 | 1.87 | 1.87 |
| 1.87 | 1.87 | 1.87 | 1.87 | 1.87 |
| 1.87 | 1.87 | 1.87 | 1.87 | 1.87 |
| 1.87 | 1.87 | 1.87 | 1.87 | 1.87 |
| 1.87 | 1.87 | 1.87 | 1.87 | 1.87 |

TABLE 2-continued

KDR inhibition (μM)

| | | | | |
|---|---|---|---|---|
| 1.87 | 1.87 | 1.87 | 1.87 | 1.87 |
| 1.87 | 1.87 | 1.87 | 1.87 | 0.0111 |
| 0.0466 | 0.0194 | 0.75 | 0.192 | |

SCHEME 1

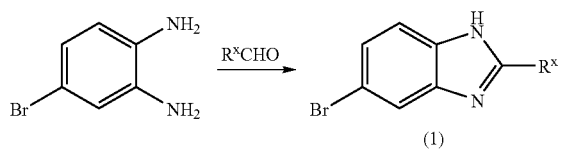

4-Bromo-benzene-1,2-diamine can be converted to compounds having Formula 1 by reacting the former, $R^xCHO$, oxone, and a base. Bases include potassium carbonate and the like. The reaction is typically conducted in DMF/water at ambient temperature.

SCHEME 2

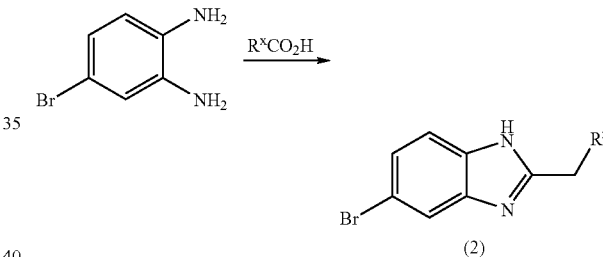

4-Bromo-benzene-1,2-diamine can be converted to compounds having Formula 2 by reacting the former, $R^xCO_2H$, and an aqueous acid. Acids include HCl and the like. The reaction is typically conducted at reflux.

SCHEME 3

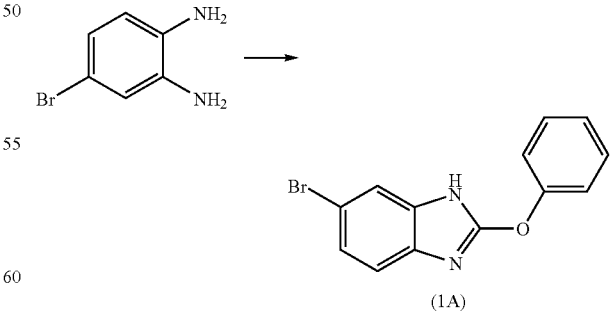

4-Bromo-benzene-1,2-diamine can be converted to 6-bromo-2-phenoxy-1H-benzimidazole by reacting the former, 1,1-dichloro-1,1-diphenoxymethane, and a base. Bases include sodium carbonate and the like. The reaction is

SCHEME 4

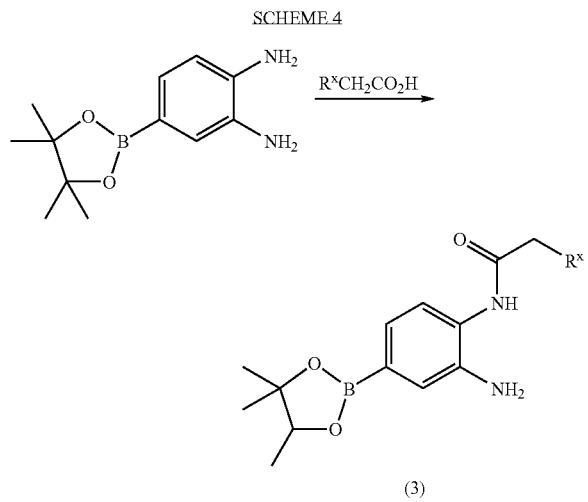

4-(4,4,5,5-tetramethyl-1,3,2-dioxaborolan-2-yl)benzene-1,2-diamine (Example 280A) can be converted to compounds having Formula 3 by reacting the former, $R^xCH_2CO_2H$, and a coupling agent. Coupling agents include 1,1'-carbonyldiimidazole and the like. The reaction is typically conducted at 50° C. in solvents such as THF and the like.

SCHEME 5

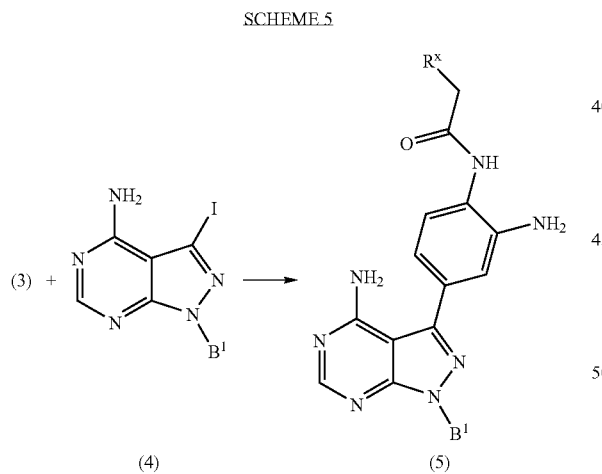

Compounds of Formula 3 can be converted to compounds of Formula 5 by reacting the former with compounds of Formula 4 (prepared as described in WO 2005/074603 and A. F. Burchat et al. Bioorg Med. Chem. Lett. 2002, 12, 1687-1690), a base, and a catalyst. Bases include sodium carbonate and the like. Catalysts include dichloro[1,1'-bis(diphenylphosphino)ferrocene]palladium (II) dichloromethane adduct and the like. The reaction is typically conducted in mixture of DME and water and the like at about 130° C. in a microwave reactor.

SCHEME 6

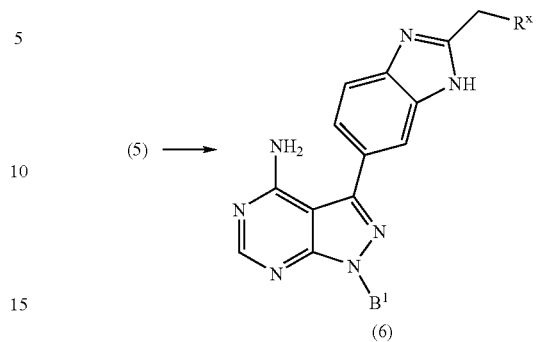

Compounds of Formula 5 can be converted to compounds of Formula 6 by reacting the former and acetic acid. The reaction is typically conducted at about 100° C.

SCHEME 7

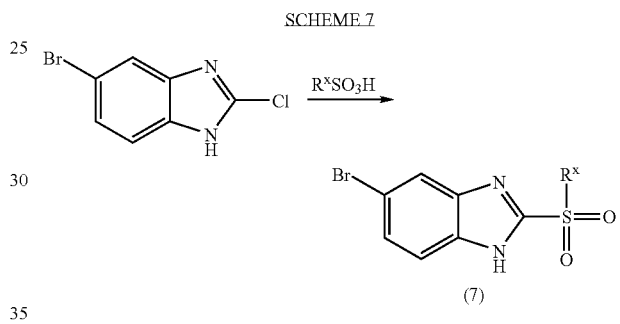

5-Bromo-2-chloro-1H-benzimidazole (Example 133A) can be converted to compounds of Formula 7 by reacting the former and $R^xSO_3H$. The reaction is typically conducted in solvents such as DMF in a microwave reactor at about 170° C.

SCHEME 8

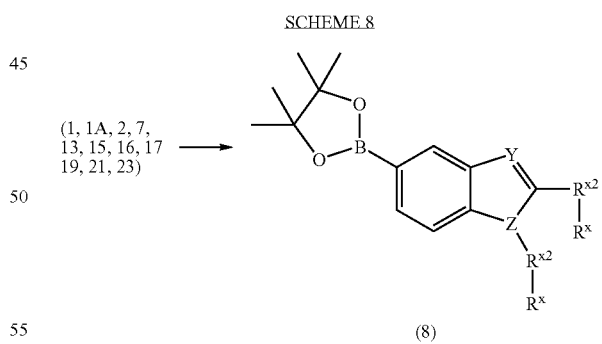

Y = CH, N,
Z = NH, O, S, $CH_2$
$R^{x2}$ = (($CH_2$)n, O, NH, H)

Compounds of Formula 1, 1A, 2, 7, 13, 15, 17, 19, 21, and 23 can be converted to compounds of Formula 8 by reacting one of the former with bis(pinacolato)diboron, potassium acetate, and a catalyst. Catalysts include dichloro[1,1'-bis(diphenylphosphino)ferrocene]palladium (II) dichloromethane adduct and the like. Solvents include DMF and the like. The reaction is typically conducted at about 100° C.

SCHEME 9

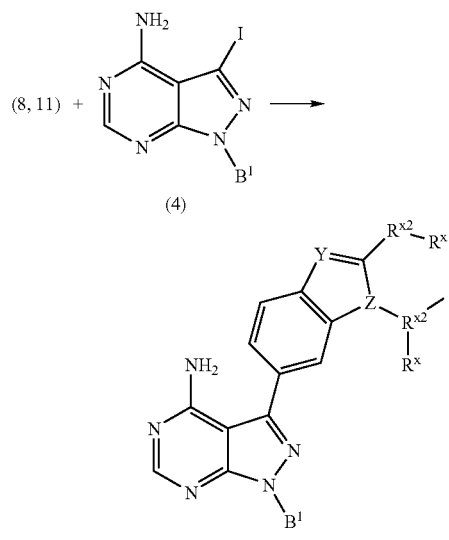

Y = CH, N,
Z = NH, O, S, CH$_2$
R$^{x2}$ = ((CH$_2$)n, O, NH, H)

Compounds of Formula 8 and Formula 11 can be converted to compounds of Formula 9 by reacting one of the former with compounds of Formula 4, base, and a catalyst. Bases include sodium carbonate and the like. Catalysts include dichlorobis(triphenylphosphine)palladium(II) and the like. The reaction is typically conducted in solvents such as DME, DMF, water, or mixtures thereof in a microwave reactor at about 130° C.

SCHEME 10

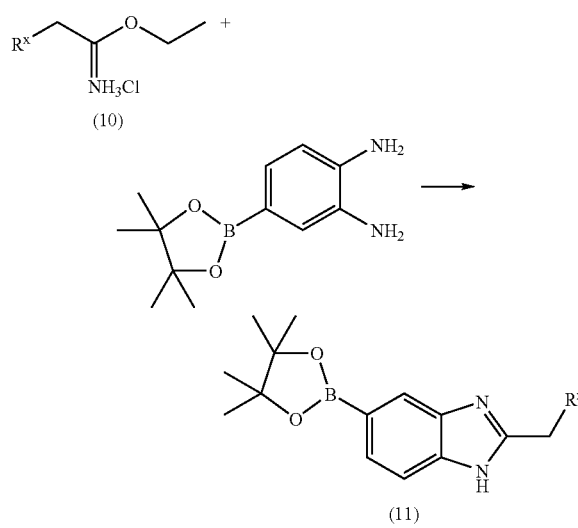

Compounds of Formula 10 (prepared as described in Example 188B) and 4-(4,4,5,5-tetramethyl-1,3,2-dioxaborolan-2-yl)benzene-1,2-diamine (Example 280A) can be converted to compounds of Formula 11. The reaction is typically conducted at room temperature in solvents such as methanol and the like.

SCHEME 11

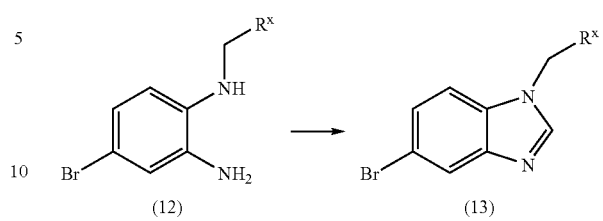

Compounds of Formula 12 (prepared as described in Example 185C) can be converted to compounds of Formula 13 by reacting the former, triethylorthoformate, and an acid. Acids include trifluoroacetic acid and the like. The reaction is typically conducted at room temperature in solvents such as methylene chloride and the like.

SCHEME 12

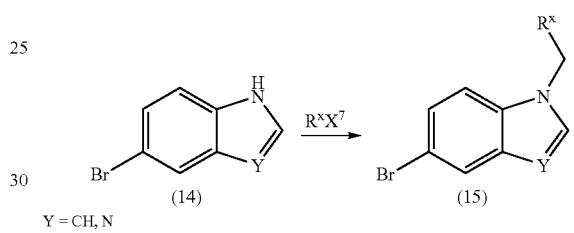

Y = CH, N

Compounds of Formula 14 can be converted to compounds of Formula 15 by reacting the former, R$^x$X$^7$ (wherein X$^7$ is a halide), and a base. Bases include sodium hydride and the like. The reaction is typically conducted in solvents such as DMF and the like between 0° C. and ambient temperature.

SCHEME 13

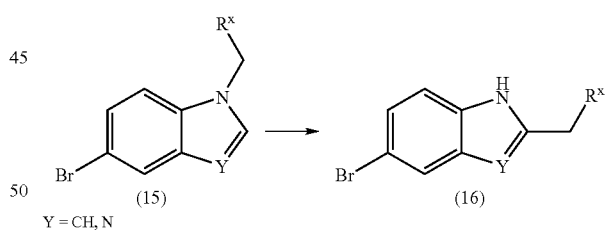

Y = CH, N

Compounds of Formula 15 can be converted to compounds of Formula 16 by reacting the former with an acid. Acids include polyphosphoric acid and the like. The reaction is typically conducted in at about 90-100° C.

SCHEME 14

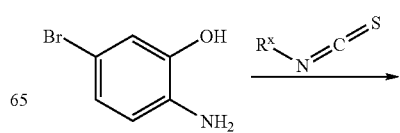

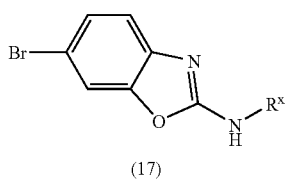

(17)

2-Amino-5-bromophenol (prepared as described in Example 58B) can be converted to compounds of Formula 17 by reacting the former, $R^xNCS$, copper sulfate, and a base. Bases include triethylamine and the like. The reaction is typically conducted in solvents such as THF and the like with silica gel at ambient temperature.

SCHEME 14

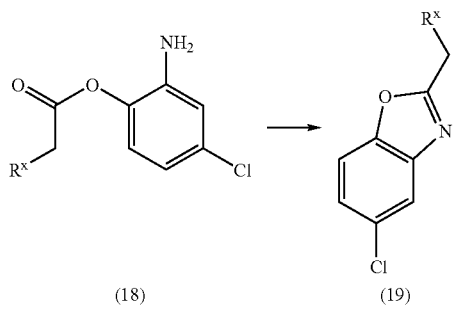

(18) (19)

Compounds of Formula 18 (prepared as described in Example 57A) can be converted to compounds of Formula 19 by reacting the former, diethylazodicarboxylate, and triphenylphosphine. The reaction is typically conducted in solvents such as THF at ambient temperature.

SCHEME 15

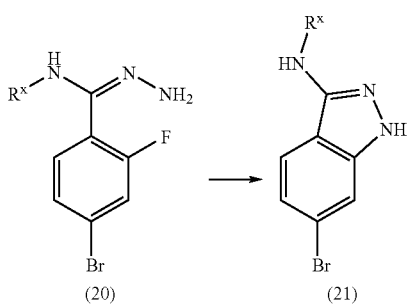

(20) (21)

Compounds of Formula 20 (prepared as described in Example 76B) can be converted to compounds of Formula 21 by reacting the former and a base in a microwave reactor. Bases include triethylamine and the like. The reaction is typically conducted in solvents such as acetonitrile at about 170° C.

SCHEME 16

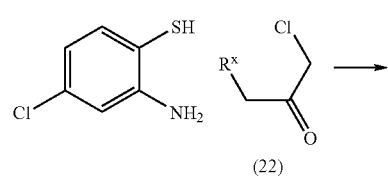

(22)

(23)

Compounds of Formula 22 can be converted to compounds of Formula 23 by reacting the former with 4-chloro-2-aminobenzenethiol. The reaction is typically conducted in solvents such as benzene at about 80° C.

SCHEME 17

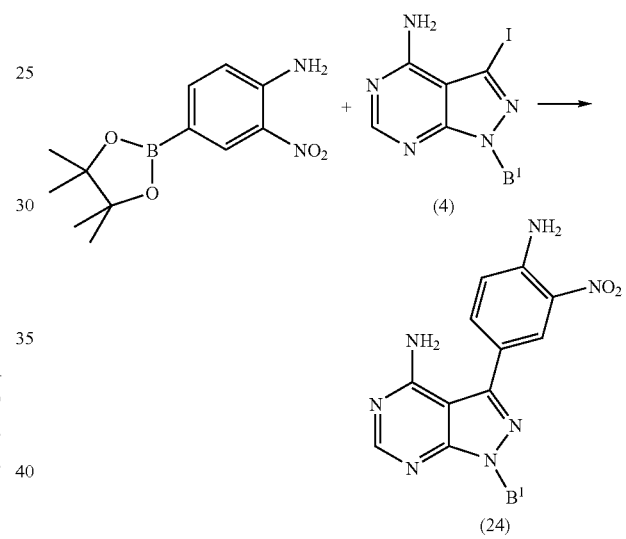

(4)

(24)

2-nitro-4-(4,4,5,5-tetramethyl-1,3,2-dioxaborolan-2-yl) aniline can be converted to compounds having Formula 24 by reacting the former, compounds having Formula 4, $(Ph_3P)_2PdCl_2PdCl_2$ and a base. Bases include sodium carbonate and the like. The reaction is typically conducted in DME/Water at about 80° C.

SCHEME 18

(24) + $R^xCHO$ →

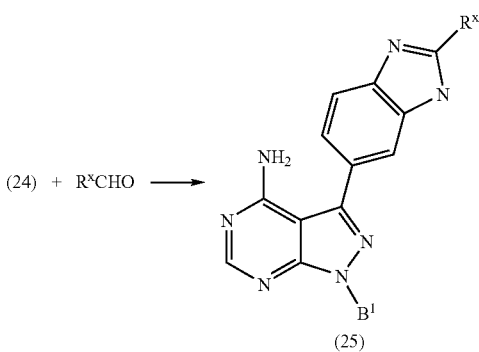

(25)

Compounds having Formula 24 can be converted to compounds having Formula 25 by reacting the former, R$^x$CHO and Na$_2$S$_2$O$_4$. The reaction is typically conducted in methanol, ethanol or mixtures thereof at about 130° C.

SCHEME 19

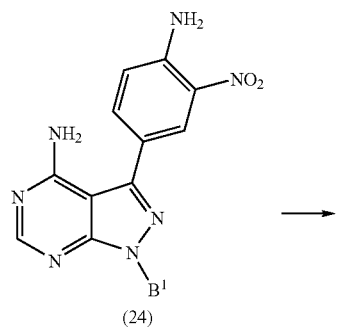

(24)

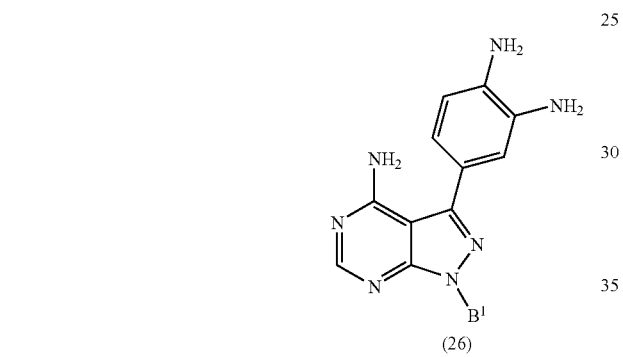

(26)

Compounds having Formula 24 can be converted to compounds having Formula 26 by reacting the former, hydrogen and a catalyst. Catalysts include palladium on carbon, Raney nickel and the like. The reaction is typically conducted in methanol, ethanol, tert-butanol, THF, ethyl acetate or mixtures thereof at about 40° C. to about 100° C.

Compounds having Formula 26 can be converted to compounds having Formula 25 by reacting the former and CH$_3$CH$_2$OC(NH)R$^x$.HCl. The reaction is typically conducted in methanol, ethanol, tert-butanol or mixtures thereof at about 25° C.

Compounds having Formula 26 can be converted to compounds having Formula 25 by reacting the former and compounds having formula (CH$_3$CH$_2$O)$_3$CR$^x$. The reaction is typically conducted in methanol, ethanol, tert-butanol or mixtures thereof at about 80° C.

Compounds having Formula 26 can be converted to compounds having Formula 25 by reacting the former and R$^x$NCS and reacting the product therefrom and a coupling agent. Coupling agents include DCC, EDCI and the like. The reactions are typically conducted continuously in THF at about 25° C. to about 50° C. for the first step and at about 50° C. for the second step.

SCHEME 20

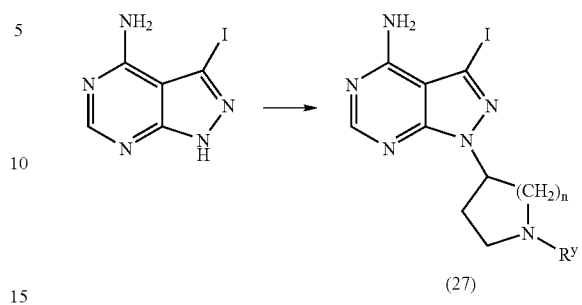

(27)

3-Iodo-1H-pyrazolo[3,4-d]pyrimidin-4-ylamine (prepared as described in A. F. Burchat et al. Bioorg Med. Chem. Lett. 2002, 12, 1687-1690) can be converted to compounds of Formula 27 by reacting the former with an alcohol under Mitsunobu conditions followed by an alkylation or reductive amination.

SCHEME 21

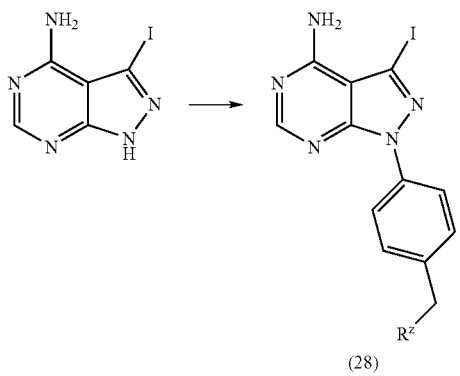

(28)

3-Iodo-1H-pyrazolo[3,4-d]pyrimidin-4-ylamine (prepared as described in A. F. Burchat et al. Bioorg Med. Chem. Lett. 2002, 12, 1687-1690) can be converted to compounds of Formula 28 by reacting the former with 4-fluorobenzaldehyde using standard alkylation conditions, followed by standard reductive amination conditions using an amine.

SCHEME 22

(27, 28) → 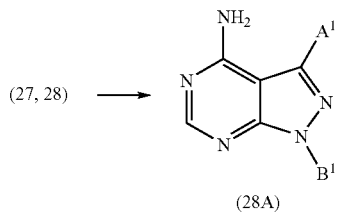

(28A)

Compounds of Formula 27 and 28 can be converted to compounds of Formula 28A by typical methods such as those described in Palladium Reagents And Catalysts: New Perspectives For The 21st Century, By J. Tsuji, John Wiley & Sons, Ltd., Chichester, 2004, 1-670.

Scheme 23

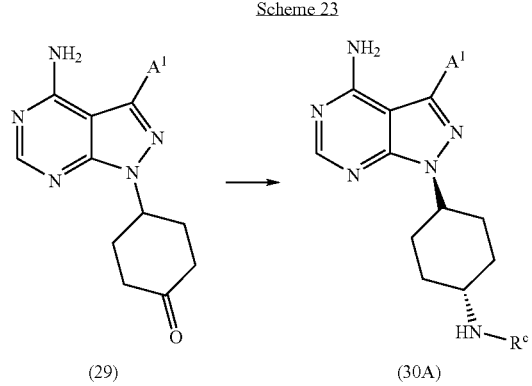

Compounds of Formula 29 (prepared as described in Example 31B) can be converted to compounds of Formula 30A and Formula 30B by reacting the former, $R^cNH_2$ and a reducing agent. Reducing agents include sodium cyanoborohydride and the like. The reaction is typically conducted in solvents such as methanol and the like with a few drops of acetic acid. The reaction is typically conducted at about 70° C.

SCHEME 24

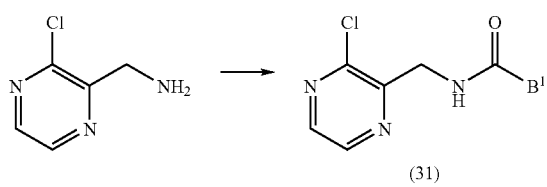

(3-Chloropyrazin-2-yl)methylamine (Example 283A) can be converted to compounds having Formula 31 by reacting the former, $B^1CO_2H$, a catalyst, and a coupling agent. Catalysts include DMAP and the like. Coupling agents include DCC, EDCI, and the like. The reactions are typically run in solvents such as DMF, dichloromethane, DME and the like or mixtures thereof, at or above room temperature.

SCHEME 25

Compounds having Formula 32 can be converted to compounds having Formula 33 by reacting the former with $POCl_3$. The reaction is typically conducted in solvents such as acetonitrile at about 55° C.

SCHEME 26

Compounds having Formula 33 can be converted to compounds having Formula 34 by reacting the former with N-iodosuccinimide. The reaction is typically conducted in solvents such as DMF at about 25° C.

SCHEME 27

Compounds having Formula 34 can be converted to compounds having Formula 35 by reacting the former with ammonia. The reaction is typically conducted at in solvents such as isopropanol, dioxane and the like or mixtures thereof at about 25° C.

SCHEME 28

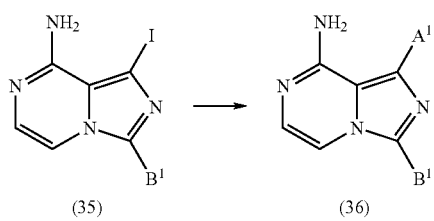

Compounds having Formula 35 can be converted to compounds having Formula 36 by typical methods such as those described in Palladium Reagents And Catalysts: New Perspectives For The 21st Century, By J. Tsuji, John Wiley & Sons, Ltd., Chichester, 2004, 1-670.

SCHEME 29

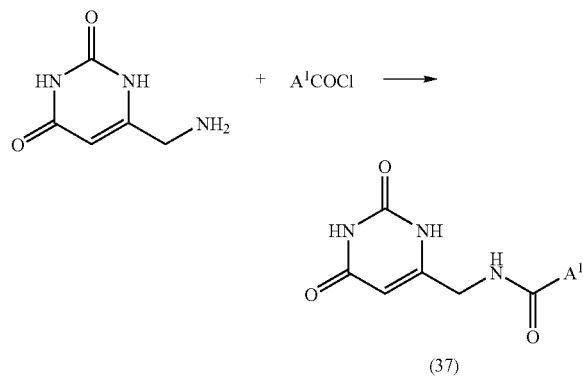

The compound 6-(aminomethyl)pyrimidine-2,4(1H,3H)-dione can be converted to compounds having Formula 37 by reacting the former, A¹COCl, and a base. Bases include triethylamine and the like. The reaction is typically conducted in solvents such as DMF at about 50° C.

SCHEME 30

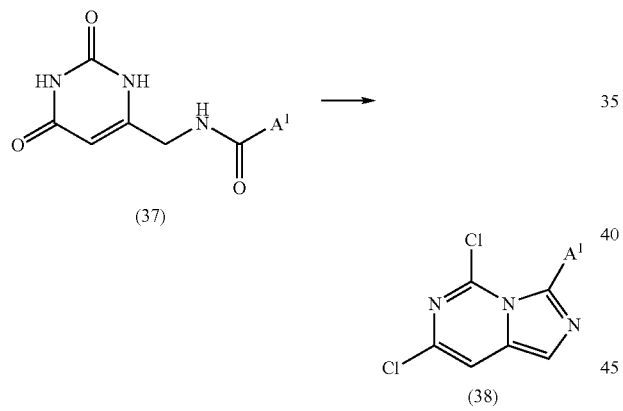

Compounds having Formula 37 can be converted to compounds having Formula 38 by reacting the former with POCl₃. The reaction is typically conducted in solvents such as toluene and the like or mixtures thereof at about 100° C.

SCHEME 31

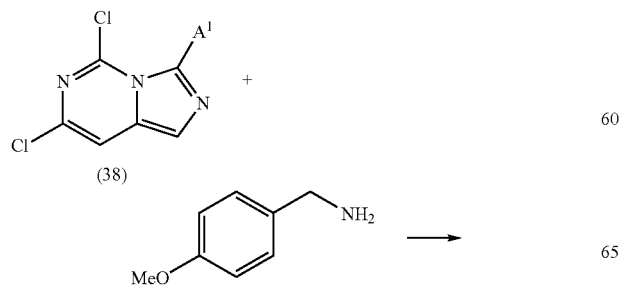

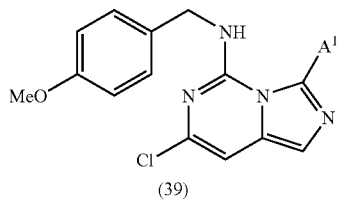

Compounds having Formula 38 can be converted to compounds having Formula 39 by reacting the former with 1-(4-methoxyphenyl)methanamine. The reaction is typically conducted in solvents such as dioxane and the like at about 80° C.

SCHEME 32

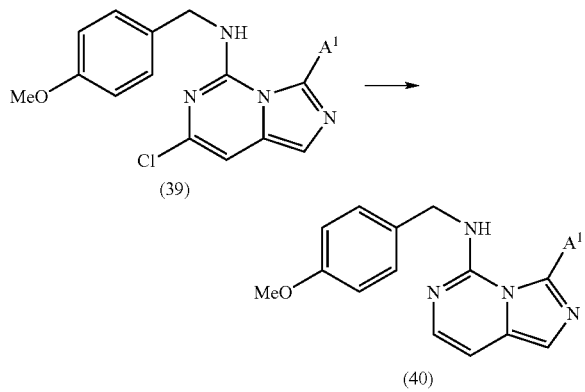

Compounds having Formula 39 can be converted to compounds having Formula 40 by reacting the former, hydrogen and a catalyst. Catalysts include palladium on carbon and the like. The reaction is typically conducted in methanol, ethanol, tert-butanol, THF, ethyl acetate or mixtures thereof at about 25° C. to about 100° C.

SCHEME 33

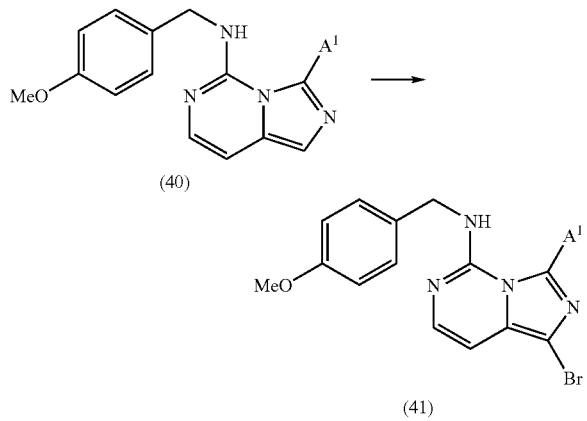

Compounds having Formula 40 can be converted to compounds having Formula 41 by reacting the former with N-bromosuccinimide. The reaction is typically conducted in solvents such as DMF and the like at about 25° C.

SCHEME 34

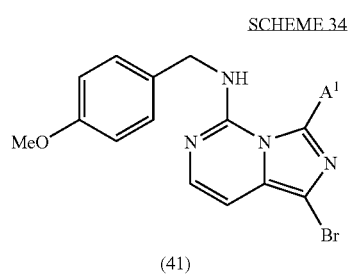

Compounds having Formula 41 can be converted to compounds having Formula 42 by typical methods such as those described in Palladium Reagents And Catalysts: New Perspectives For The 21st Century, By J. Tsuji, John Wiley & Sons, Ltd., Chichester, 2004, 1-670.

SCHEME 35

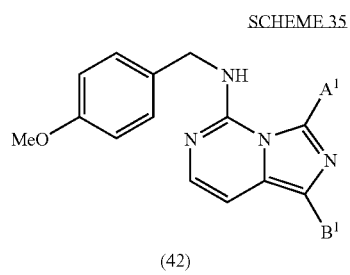

Compounds having Formula 42 can be converted to compounds having Formula 42A by reacting the former with trifluoroacetic acid. The reaction is typically conducted in a microwave reactor in solvents such as dichloromethane and the like at about 100° C.

SCHEME 36

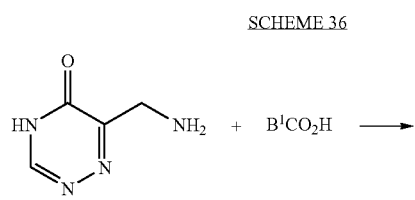

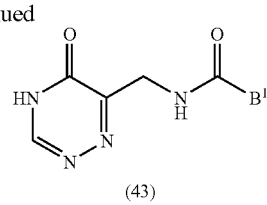

The compound 6-(aminomethyl)-1,2,4-triazin-5(4H)-one can be converted to compounds having Formula 43 by reacting the former, $B^1CO_2H$, a catalyst, and a coupling agent. Catalysts include DMAP and the like. Coupling agents include DCC, EDCI, and the like. The reactions are typically run in solvents such as DMF, dichloromethane, DME and the like or mixtures thereof, at or above room temperature.

SCHEME 37

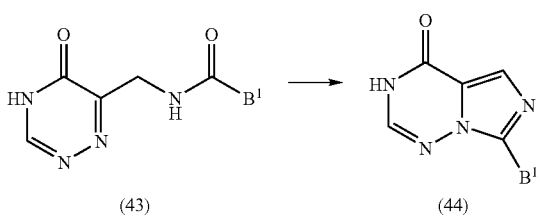

Compounds having Formula 43 can be converted to compounds having Formula 44 by reacting the former with $POCl_3$. The reaction is typically conducted in solvents such as acetonitrile at about 80° C.

SCHEME 38

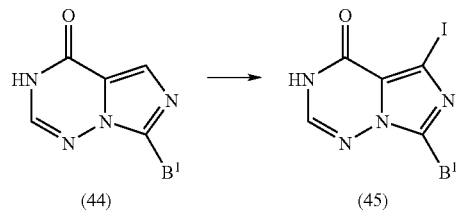

Compounds having Formula 44 can be converted to compounds having Formula 45 by reacting the former with N-iodosuccinimide. The reaction is typically conducted in solvents such as DMF at about 25° C.

SCHEME 39

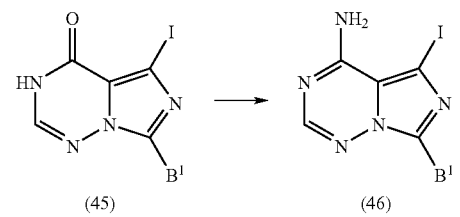

Compounds of Formula 45 can be converted to compounds of Formula 46 by reacting the former with $POCl_3$, 1,2,4- triazole and pyridine, followed by ammonia. The reaction is typically conducted in solvents such as isopropanol and the like.

SCHEME 40

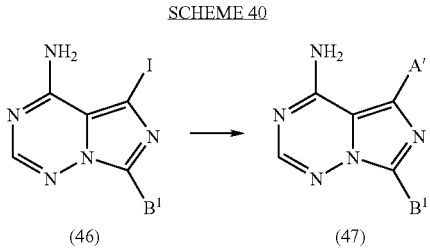

(46)    (47)

Compounds of Formula 46 can be converted to compounds of Formula 47 by typical methods such as those described in Palladium Reagents And Catalysts: New Perspectives For The 21st Century, By J. Tsuji, John Wiley & Sons, Ltd., Chichester, 2004, 1-670.

SCHEME 41

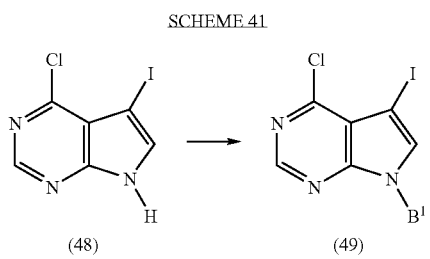

(48)    (49)

Compounds of Formula 48 (J. Med. Chem. 1990, 33, 1984) can be converted to compounds of Formula 49 by reacting the former with $B^1X^7$ (wherein $X^7$ is a halide), base, and a phase transfer catalyst. Bases include potassium carbonate and the like. Phase transfer catalysts include 1,4,7,10,13,16-hexaoxacyclooctadecane (18-crown-6) and the like. The reaction is typically conducted in solvents such as DMF at 25° C. or higher Compounds of Formula 48 (J. Med. Chem. 1990, 33, 1984) can be converted to compounds of Formula 49 by reacting the former with $B^{10}H$, DIAD, and $PPh_3$. The reaction is typically conducted in solvents such as THF at 25° C. or higher.

SCHEME 42

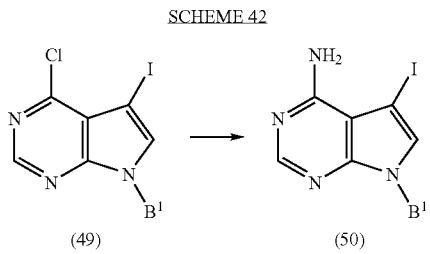

(49)    (50)

Compounds of Formula 49 can be converted to compounds of Formula 50 by reacting the former with ammonia. The reaction is typically conducted in solvents such as isopropanol, dioxane and the like or mixtures thereof at about 25° C.

SCHEME 43

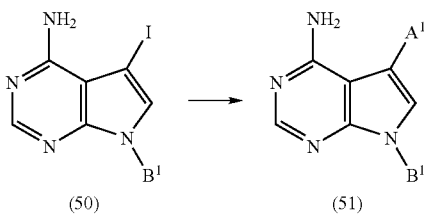

(50)    (51)

Compounds of Formula 50 can be converted to compounds of Formula 51 by typical methods such as those described in Palladium Reagents And Catalysts: New Perspectives For The 21st Century, By J. Tsuji, John Wiley & Sons, Ltd., Chichester, 2004, 1-670.

Homogenous time-resolved fluorescence (HTRF) in vitro kinase assays were also sed to measure inhibition of kinase activity. The HTRF assays were conducted according to known protocols (Technology. J. Biomol. Screen, 1999, 4(6): pp 309-314).

The protocol was adapted for determining activity with respect to a specific PTK. For example, a preferred protocol for conducting the HTRF experiments is provided below. Adaptation of these protocols for determination of a compound's activity for other kinases are well within the abilities of the skilled practioner.

In a representative experiment, 10 μL KDR, prepared as described herein, was mixed with 10 μL inhibitor (various concentrations, 2% final DMSO) and 10 μL of ATP (125 μM final concentration) in reaction buffer (50 mM HEPES, pH 7.5, 10 mM $MgCl_2$, 2 mM $MnCl_2$, 0.1% BSA and 1 mM DTT; final volume: 40 μL). The reaction was initiated by adding Bio-fgfr peptide (purchased from Genemed Biotechnologies Inc., San Francisco, Calif., 0.5 M final concentration) in a black 96-well plate (Packard). After 45 minutes incubation at room temperature, the reaction was quenched by adding 60 μL stop/revelation buffer to give 30 mM EDTA, 1 μg/mL Streptavidin-APC (Prozyme), 50 ng/mL anti-phosphotyrosine mAb PT66-K Europium Cryptate, 30 mM HEPES, pH 7.5, 120 mM KF, 0.005% Tween-20, 0.05% BSA). The quenched reaction stood at room temperature for 1 hour and was read in a time-resolved fluorescence detector (Envision, Perkin Elmer) at 615 nm and 665 nm to calculate the $IC_{50}$. $K_i$ values were calculated as described in Biochem. Pharmacol. 1973, 22, 3099-3108.

Related procedures were used to assay the inhibitory effect of compounds of this invention on c-Kit, IGF-IR, EGFR, Src and ErbB2 tyrosine kinase activity.

The coding sequence for human KDR intra-cellular domain (aa789-1354) was generated through PCR using cDNAs isolated from HUVEC cells. A poly-His6 sequence was introduced at the N-terminus of this protein, as well. This fragment was cloned into transfection vector pVL1393 at the Xba 1 and Not 1 site. Recombinant baculovirus (BV) was generated through co-transfection using the BaculoGold Transfection reagent (PharMingen). Recombinant BV was plaque purified and verified through western analysis. For protein production, SF-9 cells were grown in SF-900-II medium at 2×106/mL, and were infected at 0.5 plaque forming units per cell (MOI). Cells were harvested at 48 hours post infection.

SF-9 cells expressing $(His)_6$ KDR (aa789-1354) were lysed by adding 50 ml of Triton X-100 lysis buffer (20 mM Tris, pH 8.0, 137 mM NaCl, 10% glycerol, 1% Triton X-100, 1 mM PMSF, 10 μ/mL aprotinin, 1 μg/mL leupeptin) to the cell pellet from 1L of cell culture. The lysate was centrifuged at 19,000 rpm in a Sorval SS-34 rotor for 30 minutes a 4° C. The cell lysate was applied to a 5 mL $NiCl_2$ chelating sepharose column equilibrated with 50 mM HEPES, pH 7.5 and 0.3 M NaCl. KDR was eluted using the same buffer containing 0.25 M imidazole. Column fractions were analyzed using SDS-PAGE and ELISA assay, which measures kinase activity. The purified KDR was exchanged into 25 mM HEPES, pH 7.5, 25 mM NaCl and 5 mM DTT buffer and stored at −80° C.

The data from these assays demonstrate the utility of compounds having Formula I as protein kinase inhibitors and are therefore expected to have utility in treatment of diseases during which any kinase family member is expressed.

Diseases involving overexpression or unregulation of a protein kinase family member include, but are not limited to, acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myleogeneous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, heavy chain disease, hemangioblastoma, hepatoma, hepatocellular cancer, hormone insensitive prostate cancer, leiomyosarcoma, liposarcoma, lung cancer, lymphagioendothelio-sarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

It is also expected that compounds having Formula I would inhibit the growth of cells derived from a cancer or neoplasm such as breast cancer (including estrogen-receptor positive breast cancer), colorectal cancer, endometrial cancer, lung cancer (including small cell lung cancer), lymphoma (including follicular or Diffuse Large B-cell), lymphoma (including non-Hodgkin's lymphoma), neuroblastoma, ovarian cancer, prostate cancer (including hormone-insensitive prostate cancer) and testicular cancer (including germ cell testicular cancer).

It is also expected that compounds having Formula I would inhibit the growth of cells derived from a pediatric cancer or neoplasm such as embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoid/rhabdoid tumor of the central nervous system, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric psteosarcoma, pediatric rhabdoid kidney tumor, pediatric rhabdomyosarcoma, and pediatric T-cell cancers such as lymphoma and skin cancer.

For example, involvement of protein kinases in bladder cancer, breast cancer, cervical cancer, colon cancer, endometrial cancer, esophageal cancer, lung cancer, ovarian cancer, pancreatic cancer, prostate cancer, rectal cancer, skin cancer, stomach cancer and thyroid cancer are reported in Endocrine Rev. 21, 215 (2000), Br. J. Cancer 92, 1467 (2005), Cytokine Growth Factor Rev. 7, 133 (1996) and Biochem. Pharm. 51, 1101 (1996) (IGF1R-1); Biochem. Biophys. Acta 1198, 165 (1994), New Eng. J. Med. 344, 783 (2001) (ErbB2); Cancer Metastasis Rev. 22, 337 (2003), J. Clin. Invest. 91, 53 (1993) and BBRC 243,503 (1998) (SRC-1); Science 279, 577 (1998) and NELM 344, 1038 (2001).

Still another embodiment comprises methods of treating a mammal having a disease characterized by unregulated protein kinase activity comprising administering thereto therapeutically effective amounts of a compound having formula (I) and one or more than one additional therapeutic agents, with or without administering radiation.

Compounds having formula (I) are also expected to be useful when used with alkylating agents, angiogenesis inhibitors, antibodies, antimetabolites, antimitotics, antiproliferatives, aurora kinase inhibitors, Bcr-Abl kinase inhibitors, biologic response modifiers, cyclin-dependent kinase inhibitors, cell cycle inhibitors, cyclooxygenase-2 inhibitors, leukemia viral oncogene homolog (ErbB2) receptor inhibitors, growth factor inhibitors, heat shock protein (HSP)-90 inhibitors, histone deacetylase (HDAC) inhibitors inhibitors, hormonal therapies, immunologicals, intercalating antibiotics, kinase inhibitors, mammalian target of rapomycin inhibitors, mitogen-activated extracellular signal-regulated kinase inhibitors, non-steroidal anti-inflammatory drugs (NSAID's), platinum chemotherapeutics, polo-like kinase inhibitors, proteasome inhibitors, purine analogs, pyrimidine analogs, receptor tyrosine kinase inhibitors, retinoids/deltoids plant alkaloids, topoisomerase inhibitors and the like.

Alkylating agents include altretamine, AMD-473, AP-5280, apaziquone, bendamustine, brostallicin, busulfan, carboquone, carmustine (BCNU), chlorambucil, Cloretazine™ (VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, treosulfan, trofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9)

inhibitors, platelet-derived growth factor receptor (PDGFR) inhibitors, thrombospondin analogs vascular endothelial growth factor receptor tyrosine kinase (VEGFR) inhibitors and the like.

Aurora kinase inhibitors include AZD-1152, MLN-8054, VX-680 and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX™ (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole),
MK-663 (etoricoxib), NS-398, parecoxib, RS-57067, SC-58125, SD-8381, SVT-2016, S-2474, T-614, VIOXX® (rofecoxib) and the like.

EGFR inhibitors include ABX-EGF, anti-EGFr immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), Herceptin® (trastuzumab), TYKERB® (lapatinib), OMNITARG® (2C4, petuzumab), TAK-165, GW-572016 (ionafamib), GW-282974, EKB-569, PI-166, dHER2 (HER2 vaccine), APC-8024 (HER-2 vaccine), anti-HER/2neu bispecific antibody, B7.her21gG3, AS HER2 trifunctional bispecific antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB®, NCS-683664, PU24FC1, PU-3, radicicol, SNX-2112, STA-9090 VER49009 and the like.

MEK inhibitors include ARRAY-142886, ARRAY-438162 PD-325901, PD-98059 and the like.

mTOR inhibitors include AP-23573, CCI-779, everolimus, RAD-001, rapamycin, temsirolimus and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam) ibuprofin cream, ALEVE® and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin and the like.

Polo-like kinase inhibitors include BI-2536 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™, axitinib (AG-13736), AZD-2171, CP-547,632, IM-862, Macugen (pegaptamib), NEXAVAR® (sorafenib, BAY43-9006), pazopanib (GW-786034), (PTK-787, ZK-222584), SUTENT® (sunitinib, SU-11248), VEGF trap, vatalanib, ZACTIMA™ (vandetanib, ZD-6474) and the like.

Antimetabolites include ALIMTA® (premetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR, enocitabine, ethnylcytidine, fludarabine, hydroxyurea, 5-fluorouracil (5-FU) alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosate, pelitrexol, pentostatin, raltitrexed, Ribavirin, triapine, trimetrexate, S-1, tiazofurin, tegafur, TS-1, vidarabine, UFT and the like.

Antibiotics include intercalating antibiotics aclarubicin, actinomycin D, amrubicin, annamycin, adriamycin, BLENOXANE® (bleomycin), daunorubicin, CAELYX® or MYOCET® (doxorubicin), elsamitrucin, epirbucin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL®, (flutamide), EVISTA® (raloxifene), fadrozole, FARESTON® (toremifene), FASLODEX® (fulvestrant), FEMARA®, (letrozole), formestane, glucocorticoids, HECTOROL® or RENAGEL® (doxercalciferol), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), predisone, PROPECIA® (finasteride), rilostane, SUPREFACT® (buserelin), TRELSTAR® (luteinizing hormone releasing hormone (LHRH)), vantas, VETORYL®, (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN® (aliretinoin), ATRAGEN® (liposomal tretinoin), TARGRETIN® (bexarotene), LGD-1550 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b), or interferon gamma-n1, combinations thereof and the like. Other agents include ALFAFERONE®, BAM-002, BEROMUN® (tasonermin), BEXXAR® (tositumomab), CamPath (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010, melanoma vaccine, mitumomab, molgramostim, MYLOTARG™ (gemtuzumab ozogamicin), NEUPOGEN® (filgrastim), OncoVAC-CL, OvaRex® (oregovomab), pemtumomab (Y-muHMFG1), PROVENGE®, sargaramostim, sizofilan, teceleukin, TheraCys®, ubenimex, VIRULIZIN®, Z 100, WF-10, PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth, or differentiation of tissue cells to direct them to have anti-tumor activity and include krestin, lentinan, sizofuran, picibanil PF-3512676 (CpG-8954), ubenimex and the like.

Pyrimidine analogs include cytarabine (ara C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881, vinflunine, ZK-EPO and the like.

Compounds of this invention are also intended to be used as a radiosensitizer that enhances the efficacy of radiotherapy. Examples of radiotherapy include, but are not limited to, external beam radiotherapy, teletherapy, brachtherapy and sealed and unsealed source radiotherapy.

Additionally, compounds having formula (I) may be combined with other chemptherapeutic agents such as ABRAXANE™ (ABI-007), ABT-100 (farnesyl transferase inhibitor), ADVEXIN®, ALTOCOR® or MEVACOR® (lovastatin), AMPLIGEN® (poly I:poly C12U, a synthetic RNA), APTOSYN™ (exisulind), AREDIA® (pamidronic acid), arglabin, L-asparaginase, atamestane (1-methyl-3,17-dione-androsta-1,4-diene), AVAGE® (tazarotne), AVE-8062, BEC2 (mitumomab), cachectin or cachexin (tumor necrosis factor), canvaxin (vaccine), CeaVac™ (cancer vaccine), CELEUK (celmoleukin), CEPLENE® (histamine dihydrochloride), CERVARIX™ (human papillomavirus vaccine), CHOP® (C: CYTOXAN® (cyclophosphamide); H: ADRIAMYCIN® (hydroxydoxorubicin); O: Vincristine (ONCOVIN®); P: prednisone), CyPat™, combrestatin A4P, DAB(389)EGF or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE™ (T4N5 liposome lotion), discodermolide, DX-8951f (exatecanmesylate), enzastaurin, EP0906, GARDASIL® (quadrivalent human papillomavirus (Types 6, 11, 16, 18) recombinant vaccine), gastrimmune, genasense, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT® (AE-941), NEUTREXIN® (trimetrexate glucuronate), NIPENT® (pentostatin), ONCONASE® (a ribonuclease enzyme), ONCOPHAGE® (melanoma vaccine treatment), OncoVAX (IL-2 Vaccine), ORATHECIN™ (rubitecan), OSIDEM® (antibody-based cell drug), OvaRex® MAb (murine monoclonal antibody), paditaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (*Streptomyces staurospores*), talabostat (PT100), TARGRETIN® (bexarotene), Taxoprexin (DHA-paclitaxel), TELCYTA™ (TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFerade™ (adenovector: DNA carrier containing the gene for tumor necrosis factor-α) TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS™ (trabectedin), ZD-6126, ZINECARD® (dexrazoxane), zometa (zolendronic acid), zorubicin and the like.

It is also expected that compounds having formula (I) would inhibit growth of cells derived from a pediatric cancer or neoplasm including embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoid/rhabdoid tumor of the central nervous system, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer and the like.

Compounds having Formula I may be made by synthetic chemical processes, examples of which are shown hereinbelow. It is meant to be understood that the order of the steps in the processes may be varied, that reagents, solvents and reaction conditions may be substituted for those specifically mentioned, and that vulnerable moieties may be protected and deprotected, as necessary.

Protecting groups for C(O)OH moieties include, but are not limited to, acetoxymethyl, allyl, benzoylmethyl, benzyl, benzyloxymethyl, tert-butyl, tert-butyldiphenylsilyl, diphenylmethyl, cyclobutyl, cyclohexyl, cyclopentyl, cyclopropyl, diphenylmethylsilyl, ethyl, para-methoxybenzyl, methoxymethyl, methoxyethoxymethyl, methyl, methylthiomethyl, naphthyl, para-nitrobenzyl, phenyl, n-propyl, 2,2,2-trichloroethyl, triethylsilyl, 2-(trimethylsilyl)ethyl, 2-(trimethylsilyl)ethoxymethyl, triphenylmethyl and the like.

Protecting groups for C(O) and C(O)H moieties include, but are not limited to, 1,3-dioxylketal, diethylketal, dimethylketal, 1,3-dithianylketal, O-methyloxime, O-phenyloxime and the like.

Protecting groups for NH moieties include, but are not limited to, acetyl, alanyl, benzoyl, benzyl (phenylmethyl), benzylidene, benzyloxycarbonyl (Cbz), tert-butoxycarbonyl (Boc), 3,4-dimethoxybenzyloxycarbonyl, diphenylmethyl, diphenylphosphoryl, formyl, methanesulfonyl, para-methoxybenzyloxycarbonyl, phenylacetyl, phthaloyl, succinyl, trichloroethoxycarbonyl, triethylsilyl, trifluoroacetyl, trimethylsilyl, triphenylmethyl, triphenylsilyl, para-toluenesulfonyl and the like.

Protecting groups for OH and SH moieties include, but are not limited to, acetyl, allyl, allyloxycarbonyl, benzyloxycarbonyl (Cbz), benzoyl, benzyl, tert-butyl, tert-butyldimethylsilyl, tert-butyldiphenylsilyl, 3,4-dimethoxybenzyl, 3,4-dimethoxybenzyloxycarbonyl, 1,1-dimethyl-2-propenyl, diphenylmethyl, formyl, methanesulfonyl, methoxyacetyl, 4-methoxybenzyloxycarbonyl, para-methoxybenzyl, methoxycarbonyl, methyl, para-toluenesulfonyl, 2,2,2-trichloroethoxycarbonyl, 2,2,2-trichloroethyl, triethylsilyl, trifluoroacetyl, 2-(trimethylsilyl)ethoxycarbonyl, 2-trimethylsilylethyl, triphenylmethyl, 2-(triphenylphosphonio)ethoxycarbonyl and the like.

The following abbreviations have the meanings indicated.
ADDP means 1,1'-(azodicarbonyl)dipiperidine;
AD-mix-β means a mixture of (DHQD)$_2$PHAL, K$_3$Fe(CN)$_6$, K$_2$CO$_3$ and K$_2$SO$_4$);
AIBN means 2,2'-azobis(2-methylpropionitrile);
9-BBN means 9-borabicyclo[3.3.1]nonane;
Cp means cyclopentadiene;
(DHQD)$_2$PHAL means hydroquinidine 1,4-phthalazinediyl diethyl ether;
DBU means 1,8-diazabicyclo[5.4.0]undec-7-ene;
DCC means dicyclohexylcarbodiimide;
DIBAL means diisobutylaluminum hydride;
DIEA means diisopropylethylamine;
DMAP means N,N-dimethylaminopyridine;
DME means 1,2-dimethoxyethane;
DMF means N,N-dimethylformamide;
dmpe means 1,2-bis(dimethylphosphino)ethane;
DMSO means dimethylsulfoxide;
dppa means diphenylphosphoryl azide;
dppb means 1,4-bis(diphenylphosphino)butane;
dppe means 1,2-bis(diphenylphosphino)ethane;
dppf means 1,1'-bis(diphenylphosphino)ferrocene;
dppm means 1,1-bis(diphenylphosphino)methane;
EDAC means 1-(3-dimethylaminopropyl)-3-ethylcarbodiimide;
Fmoc means fluorenylmethoxycarbonyl;
HATU means O-(7-azabenzotriazol-1-yl)-N,N'N'N'-tetramethyluronium hexafluorophosphate;
HMPA means hexamethylphosphoramide;
IPA means isopropyl alcohol;
LDA means lithium diisopropylamide;
LHMDS means lithium bis(hexamethyldisilylamide);
MP-BH$_3$ means macroporus triethylammonium methylpolystyrene cyanoborohydride;
LAH means lithium aluminum hydride;
NCS means N-chlorosuccinimide;
PyBOP means benzotriazol-1-yloxytripyrrolidinophosphonium hexafluorophosphate;
TDA-1 means tris(2-(2-methoxyethoxy)ethyl)amine;
TEA means triethylamine;
TFA means trifluoroacetic acid;
THF means tetrahydrofuran;
NCS means N-chlorosuccinimide;
NMM means N-methylmorpholine;
NMP means N-methylpyrrolidine;
PPh$_3$ means triphenylphosphine.
R$^x$ and the group to which it is attached combine to form a substituent defined by A$^1$.

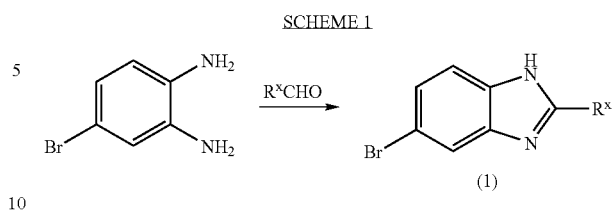

4-Bromo-benzene-1,2-diamine can be converted to compounds having Formula 1 by reacting the former, R$^x$CHO, oxone, and a base. Bases include potassium carbonate and the like. The reaction is typically conducted in DMF/water at ambient temperature.

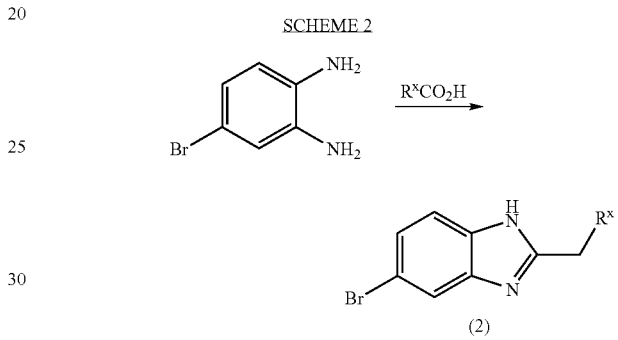

4-Bromo-benzene-1,2-diamine can be converted to compounds having Formula 2 by reacting the former, R$^x$CO$_2$H, and an aqueous acid. Acids include HCl and the like. The reaction is typically conducted at reflux.

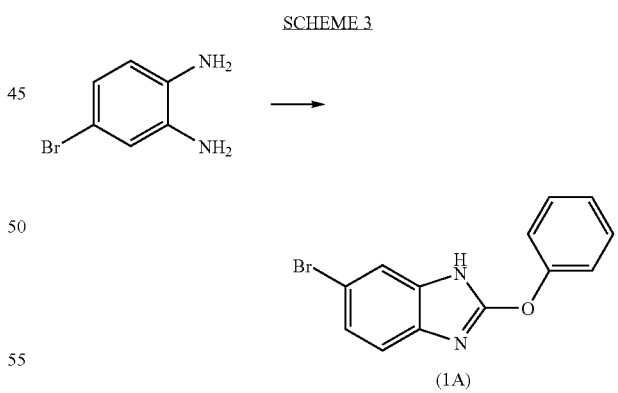

4-Bromo-benzene-1,2-diamine can be converted to 6-bromo-2-phenoxy-1H-benzimidazole by reacting the former, 1,1-dichloro-1,1-diphenoxymethane, and a base. Bases include sodium carbonate and the like. The reaction is typically conducted in solvents such as ethyl acetate at ambient temperature. The compound of Formula 1A is another example of a precursor compound that can be used to make A$^1$.

SCHEME 4

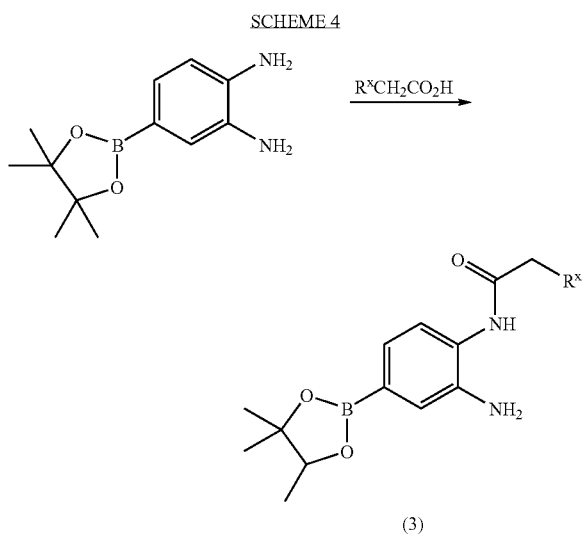

4-(4,4,5,5-tetramethyl-1,3,2-dioxaborolan-2-yl)benzene-1,2-diamine (Example 280A) can be converted to compounds having Formula 3 by reacting the former, R$^x$CH$_2$CO$_2$H, and a coupling agent. Coupling agents include 1,1'-carbonyldiimidazole and the like. The reaction is typically conducted at 50° C. in solvents such as THF and the like.

SCHEME 5

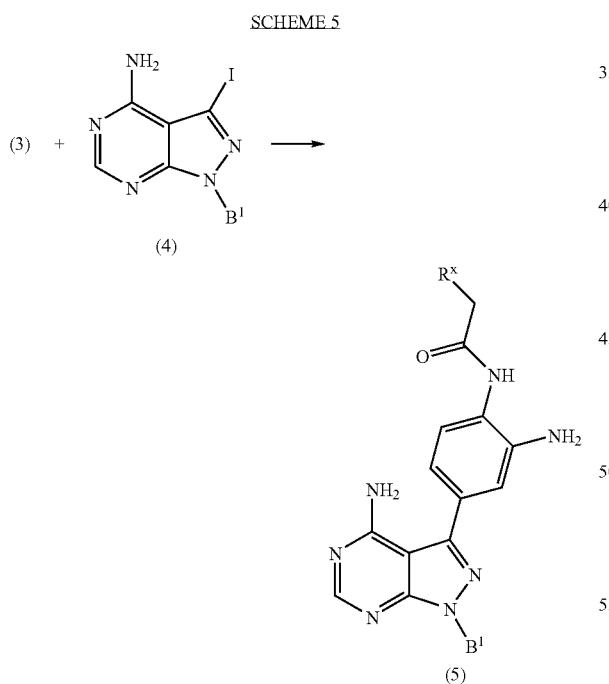

Compounds of Formula 3 can be converted to compounds of Formula 5 by reacting the former with compounds of Formula 4 (prepared as described in WO 2005/074603 and A. F. Burchat et al. Bioorg Med. Chem. Lett. 2002, 12, 1687-1690), a base, and a catalyst. Bases include sodium carbonate and the like. Catalysts include dichloro[1,1'-bis(diphenylphosphino)ferrocene]palladium (II) dichloromethane adduct and the like. The reaction is typically conducted in mixture of DME and water and the like at about 130° C. in a microwave reactor.

SCHEME 6

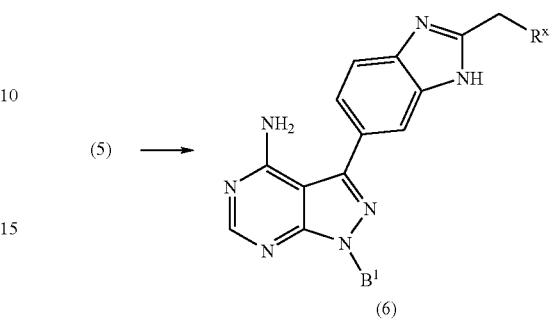

Compounds of Formula 5 can be converted to compounds of Formula 6 by reacting the former and acetic acid. The reaction is typically conducted at about 100° C.

SCHEME 7

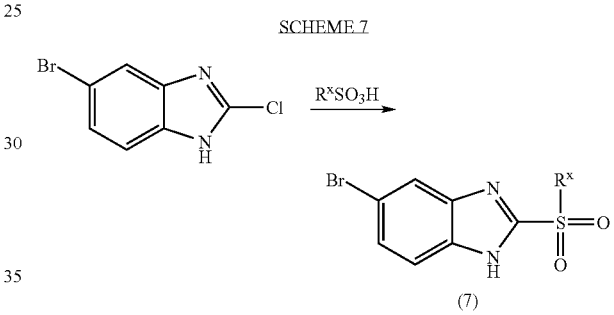

5-Bromo-2-chloro-1H-benzimidazole (Example 133A) can be converted to compounds of Formula 7 by reacting the former and R$^x$SO$_3$H. The reaction is typically conducted in solvents such as DMF in a microwave reactor at about 170° C.

SCHEME 8

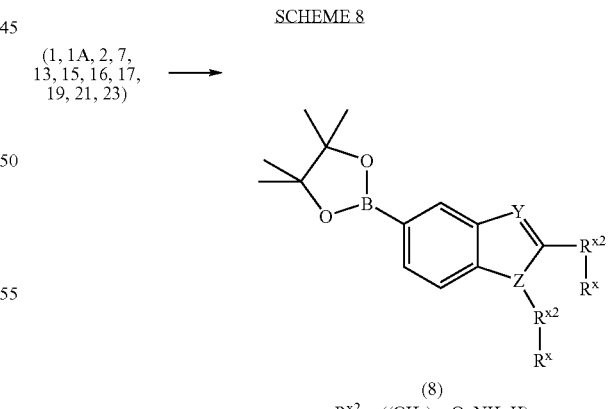

R$^{x2}$ = ((CH$_2$)n, O, NH, H)
Y = CH, N,
Z = NH, O, S, CH$_2$

Compounds of Formula 1, 1A, 2, 7, 13, 15, 17, 19, 21, and 23 can be converted to compounds of Formula 8 by reacting one of the former with bis(pinacolato)diboron, potassium acetate, and a catalyst. Catalysts include dichloro[1,1'-bis (diphenylphosphino)ferrocene]palladium (II) dichloromethane adduct and the like. Solvents include DMF and the like. The reaction is typically conducted at about 100° C.

Compounds of Formula 10 (prepared as described in Example 188B) and 4-(4,4,5,5-tetramethyl-1,3,2-dioxaborolan-2-yl)benzene-1,2-diamine (Example 280A) can be converted to compounds of Formula 11. The reaction is typically conducted at room temperature in solvents such as methanol and the like.

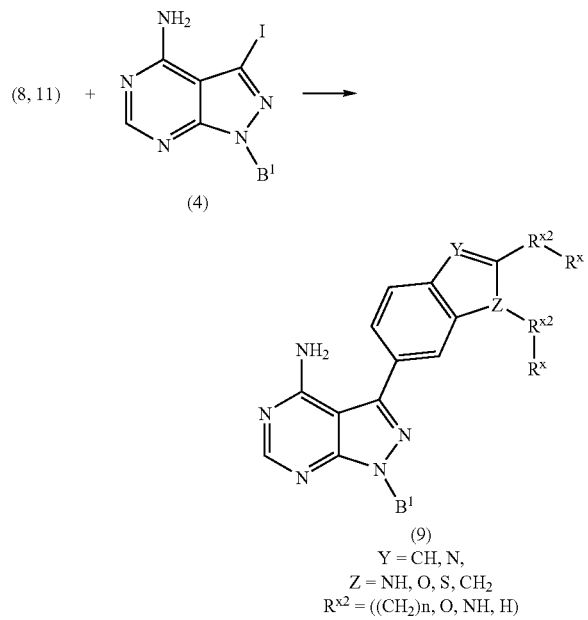

Compounds of Formula 8 and Formula 11 can be converted to compounds of Formula 9 by reacting one of the former with compounds of Formula 4, base, and a catalyst. Bases include sodium carbonate and the like. Catalysts include dichlorobis(triphenylphosphine)palladium(II) and the like. The reaction is typically conducted in solvents such as DME, DMF, water, or mixtures thereof in a microwave reactor at about 130° C.

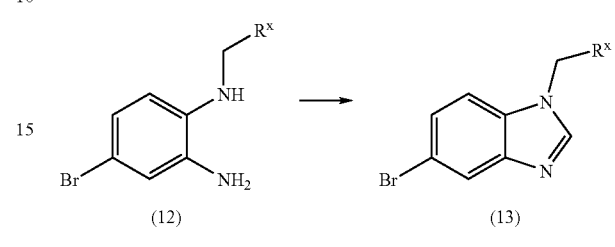

Compounds of Formula 12 (prepared as described in Example 185C) can be converted to compounds of Formula 13 by reacting the former, triethylorthoformate, and an acid. Acids include trifluoroacetic acid and the like. The reaction is typically conducted at room temperature in solvents such as methylene chloride and the like.

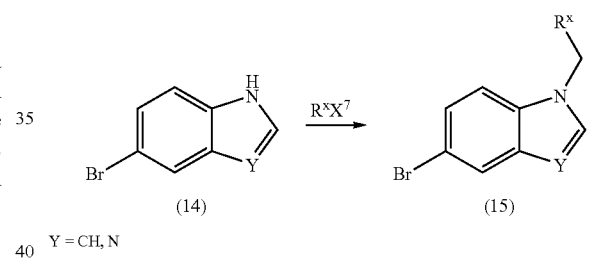

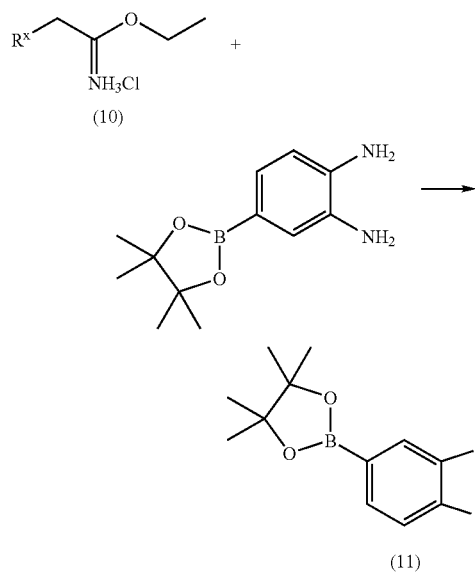

Compounds of Formula 14 can be converted to compounds of Formula 15 by reacting the former, $R^xX^7$ (wherein $X^7$ is a halide), and a base. Bases include sodium hydride and the like. The reaction is typically conducted in solvents such as DMF and the like between 0° C. and ambient temperature.

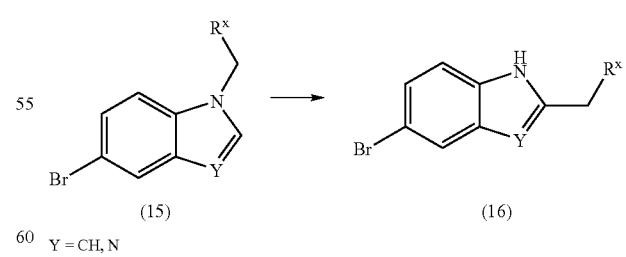

Compounds of Formula 15 can be converted to compounds of Formula 16 by reacting the former with an acid. Acids include polyphosphoric acid and the like. The reaction is typically conducted in at about 90-100° C.

SCHEME 14

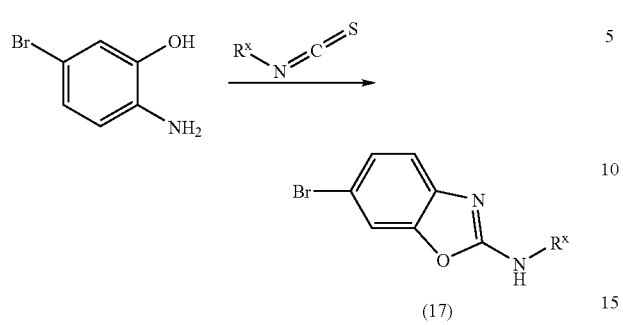

2-Amino-5-bromophenol (prepared as described in Example 58B) can be converted to compounds of Formula 17 by reacting the former, R$^x$NCS, copper sulfate, and a base. Bases include triethylamine and the like. The reaction is typically conducted in solvents such as THF and the like with silica gel at ambient temperature.

SCHEME 14

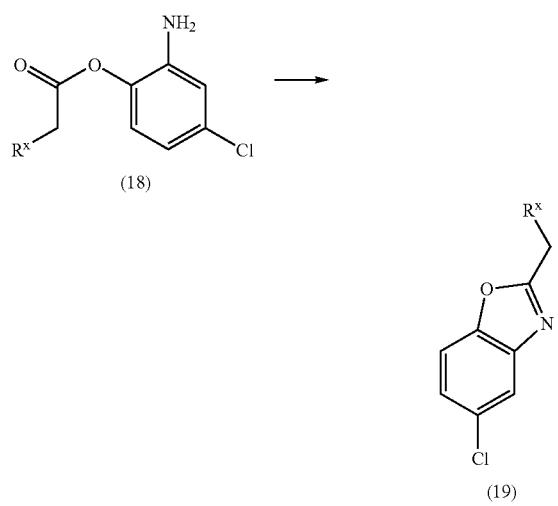

Compounds of Formula 18 (prepared as described in Example 57A) can be converted to compounds of Formula 19 by reacting the former, diethylazodicarboxylate, and triphenylphosphine. The reaction is typically conducted in solvents such as THF at ambient temperature.

SCHEME 15

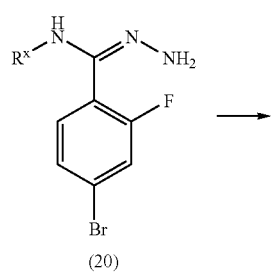

Compounds of Formula 20 (prepared as described in Example 76B) can be converted to compounds of Formula 21 by reacting the former and a base in a microwave reactor. Bases include triethylamine and the like. The reaction is typically conducted in solvents such as acetonitrile at about 170° C.

SCHEME 16

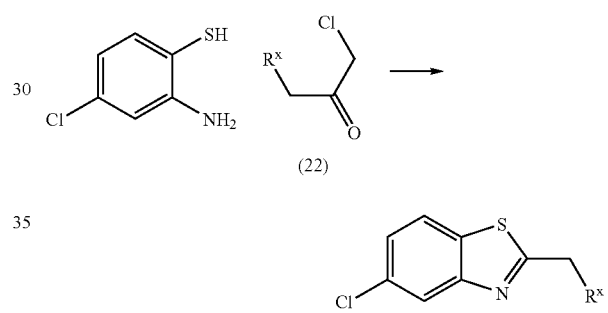

Compounds of Formula 22 can be converted to compounds of Formula 23 by reacting the former with 4-chloro-2-aminobenzenethiol. The reaction is typically conducted in solvents such as benzene at about 80° C.

SCHEME 17

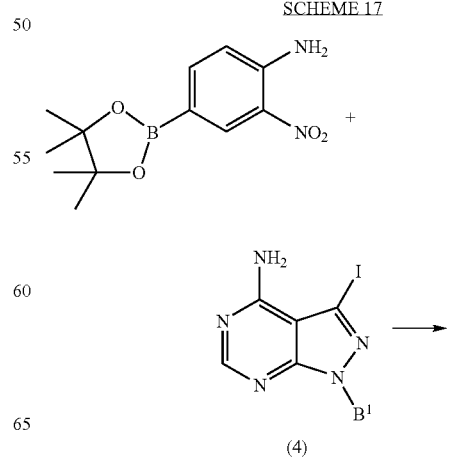

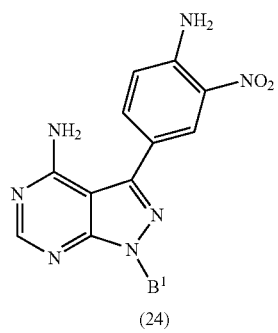

(24)

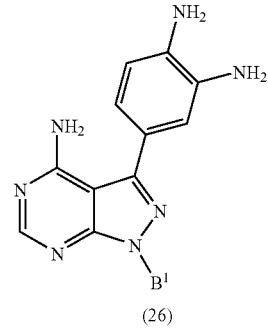

(26)

2-nitro-4-(4,4,5,5-tetramethyl-1,3,2-dioxaborolan-2-yl) aniline can be converted to compounds having Formula 24 by reacting the former, compounds having Formula 4, $(Ph_3P)_2PdCl_2PdCl_2$ and a base. Bases include sodium carbonate and the like. The reaction is typically conducted in DME/Water at about 80° C.

Compounds having Formula 24 can be converted to compounds having Formula 26 by reacting the former, hydrogen and a catalyst. Catalysts include palladium on carbon, Raney nickel and the like. The reaction is typically conducted in methanol, ethanol, tert-butanol, THF, ethyl acetate or mixtures thereof at about 40° C. to about 100° C.

Compounds having Formula 26 can be converted to compounds having Formula 25 by reacting the former and $CH_3CH_2OC(NH)R^x \cdot HCl$. The reaction is typically conducted in methanol, ethanol, tert-butanol or mixtures thereof at about 25° C.

Compounds having Formula 26 can be converted to compounds having Formula 25 by reacting the former and compounds having formula $(CH_3CH_2O)_3CR^x$. The reaction is typically conducted in methanol, ethanol, tert-butanol or mixtures thereof at about 80° C.

Compounds having Formula 26 can be converted to compounds having Formula 25 by reacting the former and $R^xNCS$ and reacting the product therefrom and a coupling agent. Coupling agents include DCC, EDCI and the like. The reactions are typically conducted continuously in THF at about 25° C. to about 50° C. for the first step and at about 50° C. for the second step.

SCHEME 18

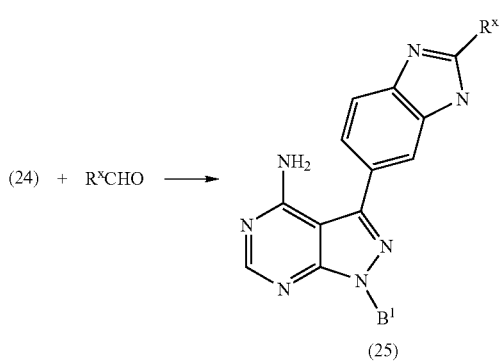

(24) + $R^xCHO$ ⟶

(25)

Compounds having Formula 24 can be converted to compounds having Formula 25 by reacting the former, $R^xCHO$ and $Na_2S_2O_4$. The reaction is typically conducted in methanol, ethanol or mixtures thereof at about 130° C.

SCHEME 19

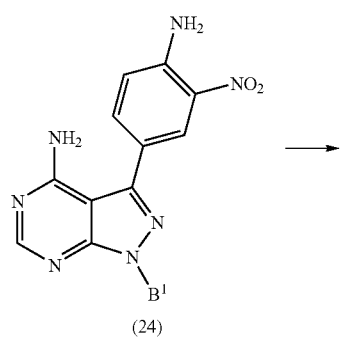

(24)

SCHEME 20

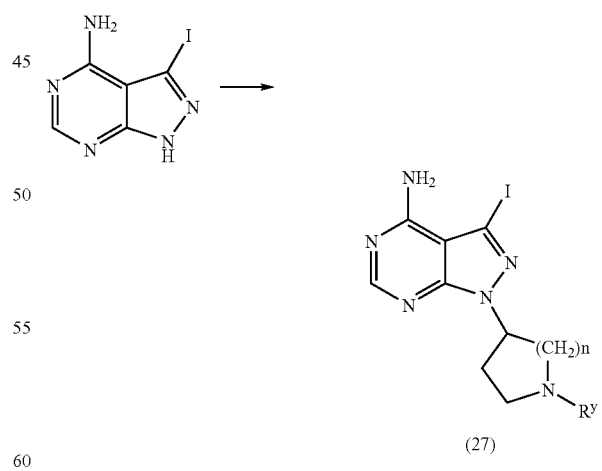

(27)

3-Iodo-1H-pyrazolo[3,4-d]pyrimidin-4-ylamine (prepared as described in A. F. Burchat et al. Bioorg Med. Chem. Lett. 2002, 12, 1687-1690) can be converted to compounds of Formula 27 by reacting the former with an alcohol under Mitsunobu conditions followed by an alkylation or reductive amination.

SCHEME 21

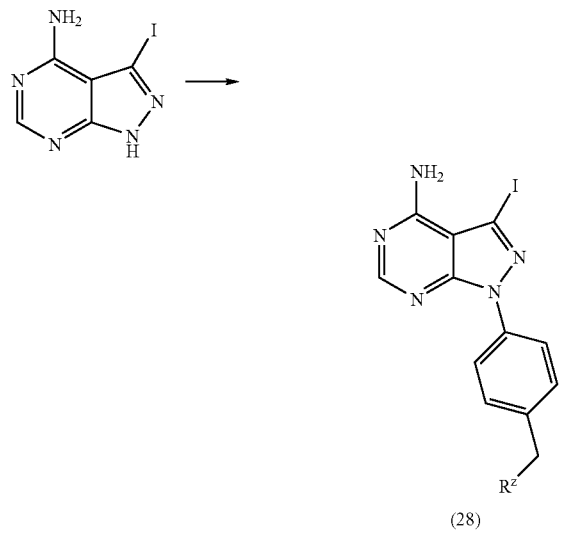

3-Iodo-1H-pyrazolo[3,4-d]pyrimidin-4-ylamine (prepared as described in A. F. Burchat et al. Bioorg Med. Chem. Lett. 2002, 12, 1687-1690) can be converted to compounds of Formula 28 by reacting the former with 4-fluorobenzaldehyde using standard alkylation conditions, followed by standard reductive amination conditions using an amine.

SCHEME 22

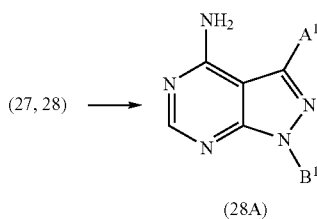

Compounds of Formula 27 and 28 can be converted to compounds of Formula 28A by typical methods such as those described in Palladium Reagents And Catalysts: New Perspectives For The 21st Century, By J. Tsuji, John Wiley & Sons, Ltd., Chichester, 2004, 1-670.

Scheme 23

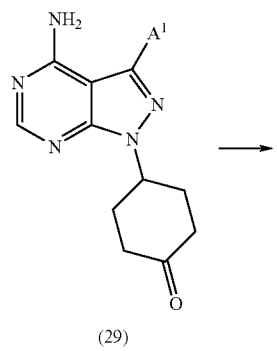

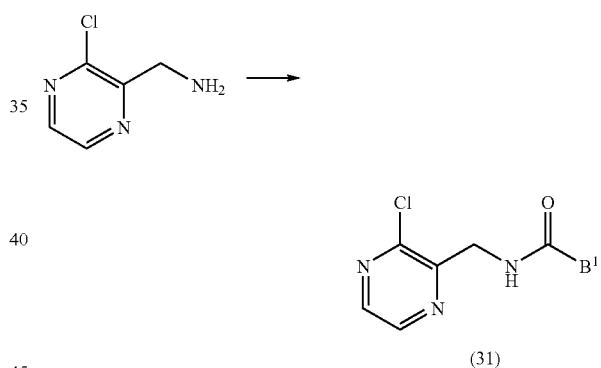

Compounds of Formula 29 (prepared as described in Example 31B) can be converted to compounds of Formula 30A and Formula 30B by reacting the former, $R^cNH_2$ and a reducing agent. Reducing agents include sodium cyanoborohydride and the like. The reaction is typically conducted in solvents such as methanol and the like with a few drops of acetic acid. The reaction is typically conducted at about 70° C.

SCHEME 24

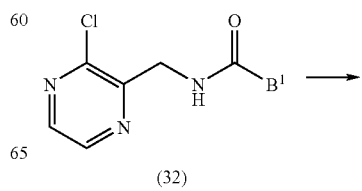

(3-Chloropyrazin-2-yl)methylamine (Example 283A) can be converted to compounds having Formula 31 by reacting the former, $B^1CO_2H$, a catalyst, and a coupling agent. Catalysts include DMAP and the like. Coupling agents include DCC, EDCI, and the like. The reactions are typically run in solvents such as DMF, dichloromethane, DME and the like or mixtures thereof, at or above room temperature.

SCHEME 25

-continued

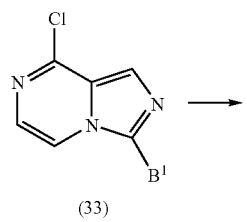

(33)

Compounds having Formula 32 can be converted to compounds having Formula 33 by reacting the former with POCl₃. The reaction is typically conducted in solvents such as acetonitrile at about 55° C.

SCHEME 26

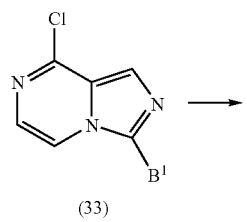

(33)

(34)

Compounds having Formula 33 can be converted to compounds having Formula 34 by reacting the former with N-iodosuccinimide. The reaction is typically conducted in solvents such as DMF at about 25° C.

SCHEME 27

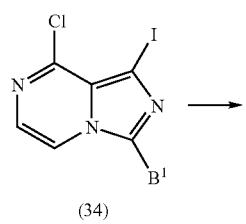

(34)

(35)

Compounds having Formula 34 can be converted to compounds having Formula 35 by reacting the former with ammonia. The reaction is typically conducted at in solvents such as isopropanol, dioxane and the like or mixtures thereof at about 25° C.

SCHEME 28

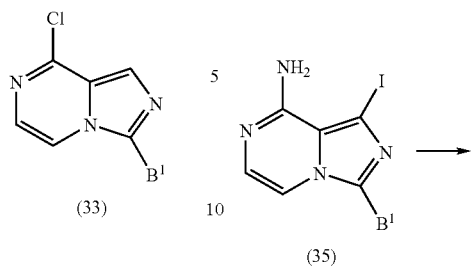

(35)

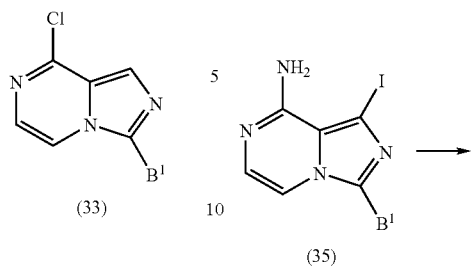

(36)

Compounds having Formula 35 can be converted to compounds having Formula 36 by typical methods such as those described in Palladium Reagents And Catalysts: New Perspectives For The 21st Century, By J. Tsuji, John Wiley & Sons, Ltd., Chichester, 2004, 1-670.

SCHEME 29

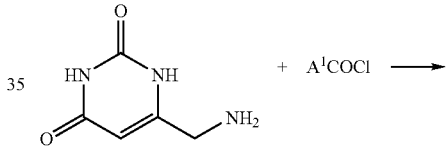

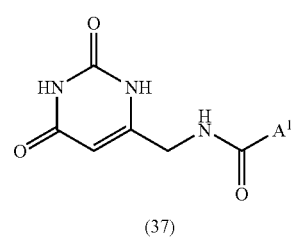

(37)

The compound 6-(aminomethyl)pyrimidine-2,4(1H,3H)-dione can be converted to compounds having Formula 37 by reacting the former, A¹COCl, and a base. Bases include triethylamine and the like. The reaction is typically conducted in solvents such as DMF at about 50° C.

SCHEME 30

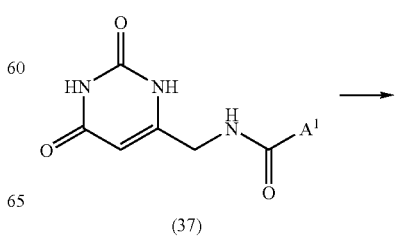

(37)

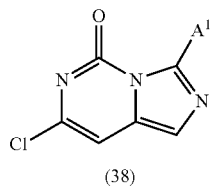

(38)

Compounds having Formula 37 can be converted to compounds having Formula 38 by reacting the former with POCl₃. The reaction is typically conducted in solvents such as toluene and the like or mixtures thereof at about 100° C.

SCHEME 31

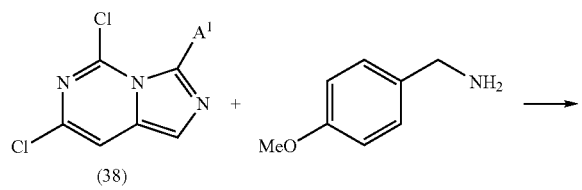

Compounds having Formula 38 can be converted to compounds having Formula 39 by reacting the former with 1-(4-methoxyphenyl)methanamine. The reaction is typically conducted in solvents such as dioxane and the like at about 80° C.

SCHEME 32

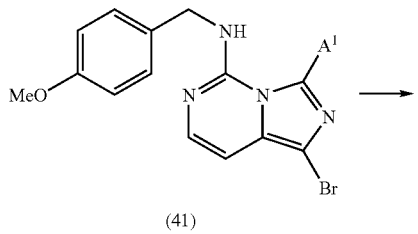

Compounds having Formula 39 can be converted to compounds having Formula 40 by reacting the former, hydrogen and a catalyst. Catalysts include palladium on carbon and the like. The reaction is typically conducted in methanol, ethanol, tert-butanol, THF, ethyl acetate or mixtures thereof at about 25° C. to about 100° C.

SCHEME 33

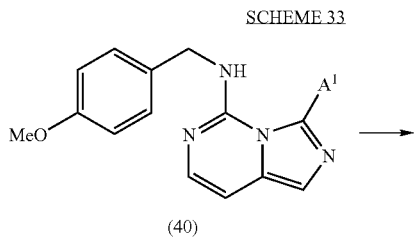

Compounds having Formula 40 can be converted to compounds having Formula 41 by reacting the former with N-bromosuccinimide. The reaction is typically conducted in solvents such as DMF and the like at about 25° C.

SCHEME 34

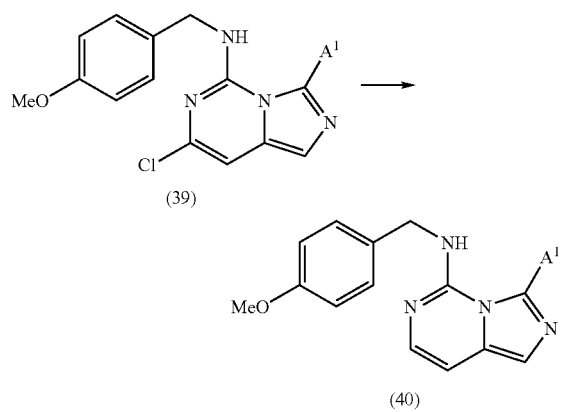

Compounds having Formula 41 can be converted to compounds having Formula 42 by typical methods such as those described in Palladium Reagents And Catalysts: New Perspectives For The 21st Century, By J. Tsuji, John Wiley & Sons, Ltd., Chichester, 2004, 1-670.

SCHEME 35

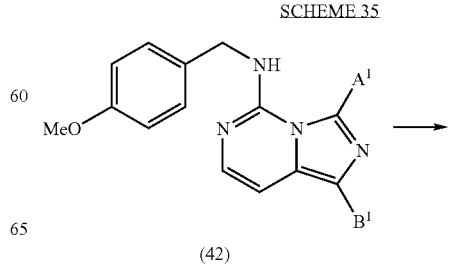

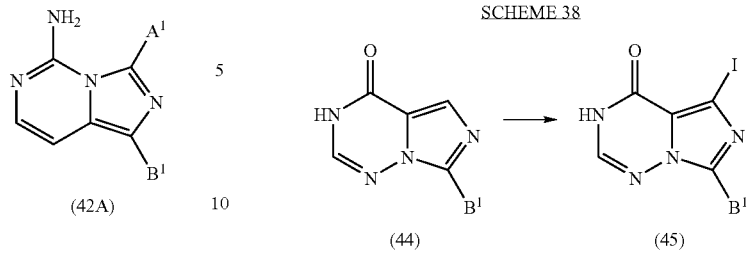

(42A)

Compounds having Formula 42 can be converted to compounds having Formula 42A by reacting the former with trifluoroacetic acid. The reaction is typically conducted in a microwave reactor in solvents such as dichloromethane and the like at about 100° C.

SCHEME 36

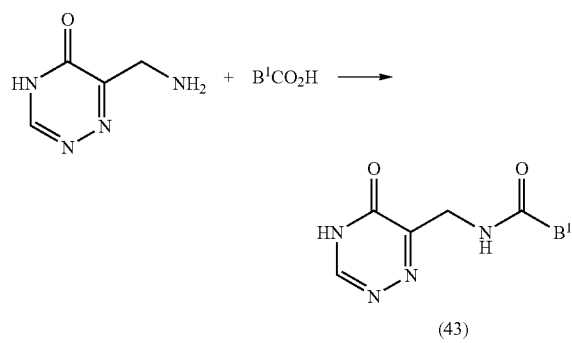

(43)

The compound 6-(aminomethyl)-1,2,4-triazin-5(4H)-one can be converted to compounds having Formula 43 by reacting the former, $B^1CO_2H$, a catalyst, and a coupling agent. Catalysts include DMAP and the like. Coupling agents include DCC, EDCI, and the like. The reactions are typically run in solvents such as DMF, dichloromethane, DME and the like or mixtures thereof, at or above room temperature.

SCHEME 37

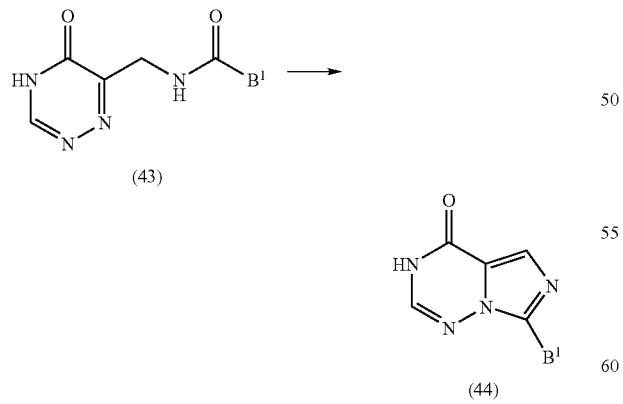

Compounds having Formula 43 can be converted to compounds having Formula 44 by reacting the former with $POCl_3$. The reaction is typically conducted in solvents such as acetonitrile at about 80° C.

SCHEME 38

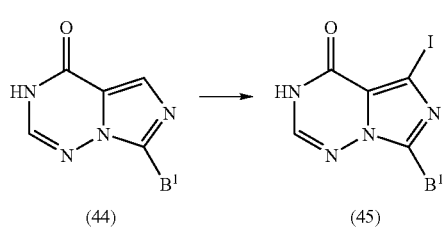

(44)      (45)

Compounds having Formula 44 can be converted to compounds having Formula 45 by reacting the former with N-iodosuccinimide. The reaction is typically conducted in solvents such as DMF at about 25° C.

SCHEME 39

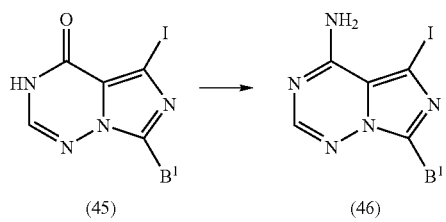

(45)      (46)

Compounds of Formula 45 can be converted to compounds of Formula 46 by reacting the former with $POCl_3$, 1,2,4-triazole and pyridine, followed by ammonia. The reaction is typically conducted in solvents such as isopropanol and the like.

SCHEME 40

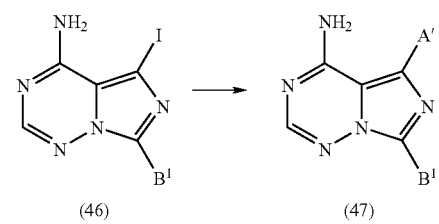

(46)      (47)

Compounds of Formula 46 can be converted to compounds of Formula 47 by typical methods such as those described in Palladium Reagents And Catalysts: New Perspectives For The 21st Century, By J. Tsuji, John Wiley & Sons, Ltd., Chichester, 2004, 1-670.

SCHEME 41

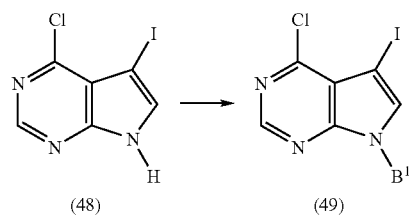

(48)      (49)

Compounds of Formula 48 (J. Med. Chem. 1990, 33, 1984) can be converted to compounds of Formula 49 by reacting the former with $B^1X^7$ (wherein $X^7$ is a halide), base, and a phase transfer catalyst. Bases include potassium carbonate and the like. Phase transfer catalysts include 1,4,7,10,13,16-hexaoxacyclooctadecane (18-crown-6) and the like. The reaction is typically conducted in solvents such as DMF at 25° C. or higher Compounds of Formula 48 (J. Med. Chem. 1990, 33, 1984) can be converted to compounds of Formula 49 by reacting the former with $B^1OH$, DIAD, and $PPh_3$. The reaction is typically conducted in solvents such as THF at 25° C. or higher.

SCHEME 42

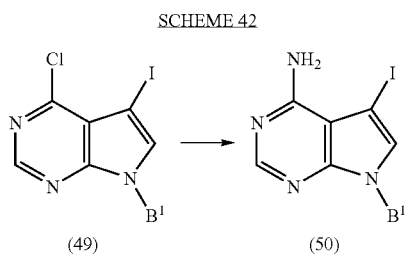

(49)  (50)

Compounds of Formula 49 can be converted to compounds of Formula 50 by reacting the former with ammonia. The reaction is typically conducted in solvents such as isopropanol, dioxane and the like or mixtures thereof at about 25° C.

SCHEME 43

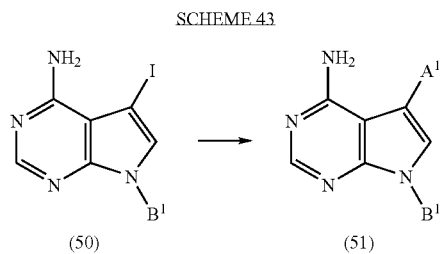

(50)  (51)

Compounds of Formula 50 can be converted to compounds of Formula 51 by typical methods such as those described in Palladium Reagents And Catalysts: New Perspectives For The 21st Century, By J. Tsuji, John Wiley & Sons, Ltd., Chichester, 2004, 1-670.

The following examples are presented to provide what is believed to be the most useful and readily understood description of procedures and conceptual aspects of this invention.

EXAMPLE 1A

To a mixture of 4-bromobenzene-1,2-diamine (0.2 g) in DMF/water (2 mL/50 µL) was added oxone (0.4 g) and benzaldehyde (0.12 g) in DMF (2 mL). After 1 hour, the mixture was diluted with water, treated with $K_2CO_3$ and filtered. The filtrate was dissolved in dichloromethane, and this mixture was dried ($Na_2SO_4$), filtered and concentrated. The concentrate was chromatographed on silica with an Intelliflash-280 purification system with ethyl acetate/hexanes.

EXAMPLE 1B

A mixture of EXAMPLE 1A (0.095 g), bis(pinacolato) diboron (0.17 g), potassium acetate (0.10 g) and dichloro(1,1'-bis(diphenylphosphino)ferrocene)-palladium(II).dichloromethane (0.007 g) in DMF (2.5 mL) was stirred at 160° C. for 15 minutes in a microwave reactor. Fresh bis(pinacolato) diboron (2 equivalents), potassium acetate (3 equivalents), and dichloro(1,1'-bis(diphenylphosphino)ferrocene) palladium(II).dichloromethane (0.03 equivalents) were added, and the mixture was stirred at 180° C. for another 20 minutes, cooled, filtered through diatomaceous earth (Celite®) and concentrated. The concentrate was purified on silica gel with an Intelliflash-280 purification system with ethyl acetate/hexanes. To the product was added cis-4-(4-(4-amino-3-iodopyrazolo[3,4-d]pyrimidin-1-yl)cyclohexyl)-1-methylpiperazin-2-one, prepared as described in WO 05/074603, (0.11 g), 2M $Na_2CO_3$ (0.23 mL) and dichlorobis(triphenyl-phosphine) palladium(II) (8 mg) in ethanol/water (2 mL/1 mL). The mixture was stirred at 120° C. for 20 minutes in a microwave reactor, cooled, filtered through diatomaceous earth (Celite®) and dried ($Na_2SO_4$) filtered and concentrated. The concentrate was purified by reverse phase HPLC with $CH_3CN$/water/0.1% TFA. $^1H$ NMR (300 MHz, DMSO-$d_6$) δ 13.09 (d, 1H), 8.25-8.20 (m, 3H), 7.89-7.68 (m, 2H), 7.61-7.50 (m, 4H), 4.88-4.78 (m, 1H), 3.07 (bs, 2H), 2.83 (s, 3H), 2.74-2.71 (m, 2H), 2.36-2.22 (m, 3H), 2.16-2.04 (m, 2H), 1.76-1.60 (m, 4H).

EXAMPLE 2A

A mixture of 4-bromo-2-nitrophenylamine (1 g), bis(pinacolato)diboron (2.35 g), potassium acetate (2.3 g) and dichloro(1,1'-bis(diphenylphosphino)ferrocene) palladium (II).dichloromethane (0.10 g) in DMF (9.2 mL) was stirred at 100° C. for 45 minutes. The reaction was filtered through diatomaceous earth (Celite®). The filtrate washed with water and brine and dried ($Na_2SO_4$) filtered and concentrated. The concentrate was purified on silica with an Intelliflash-280 purification system with ethyl acetate/hexanes.

EXAMPLE 2B

A mixture of EXAMPLE 2A (0.21 g), cis-4-(4-(4-amino-3-iodopyrazolo[3,4-d]pyrimidin-1-yl)cyclohexyl)-1-methylpiperazin-2-one, prepared as described in WO 05/074603, (0.18 g) 2M $Na_2CO_3$ (0.38 mL), and dichlorobis(triphenylphosphine) palladium(II) (0.014 g) in DME/water (3 mL/1 mL) in microwave reactor was stirred at 130° C. for 15 minutes. The mixture was filtered through diatomaceous earth (Celite®) and dried ($Na_2SO_4$), filtered and concentrated. The concentrate was purified on silica gel with an Intelliflash-280 purification system with dichloromethane/methanol.

EXAMPLE 2C

A mixture of EXAMPLE 2B (0.11 g), 4-fluorobenzaldehyde (0.029 g), and 1M $Na_2S_2O_4$ (0.71 mL) in ethanol (1 mL) was stirred at 130° C. for 20 minutes in a microwave reactor, cooled, treated with 5M $NH_4OH$ (2 mL) and filtered. $^1H$ NMR (300 MHz, DMSO-$d_6$) 13.10 (d, 1H), 8.28-8.24 (m, 3H), 7.88-7.68 (m, 2H), 7.64-7.60 (m, 1H), 7.46-7.40 (m, 2H), 4.89-4.78 (m, 1H), 3.07 (bs, 2H), 2.83 (s, 3H), 2.74-2.71 (m, 2H), 2.33-2.22 (m, 3H), 2.15-2.08 (m, 2H), 1.79-1.61 (m, 4H).

EXAMPLE 3

This example was prepared by substituting cyclopropanecarboxyaldehyde for 4-fluorobenzaldehyde in EXAMPLE 2C. $^1H$ NMR (300 MHz, DMSO-$d_6$) 12.39 (s, 1H), 8.27-8.18

(m, 1H), 7.68-7.52 (m, 2H), 7.40 (d, 1H), 4.87-4.75 (m, 1H), 3.07 (bs, 2H), 2.85-2.83 (m, 3H), 2.76-2.76 (m, 2H), 2.32-2.07 (m, 6H), 1.73-1.61 (m, 4H).

EXAMPLE 4

This example was prepared by substituting pyridine-2-carboxaldehyde for 4-fluoro-benzaldehyde in EXAMPLE 2C. $^1$H NMR (300 MHz, DMSO-$d_6$) 13.24 (d, 1H), 8.7 (d, 1H), 8.38 (d, 1H), 8.25 (s, 1H), 8.06-8.00 (m, 1H), 7.92-7.80 (m, 2H), 7.57-7.53 (m, 2H), 4.89-4.78 (m, 1H), 3.07 (s, 3H), 2.83 (s, 4H), 2.74-2.71 (m, 3H), 2.33-2,25 (m, 4H), 2.12-2.08 (m, 3H), 1.75-1.60 (m, 5H).

EXAMPLE 5A

This example was prepared by substituting trans-3-iodo-1-(4-(2-methoxy-ethoxy)cyclohexyl)-1H-pyrazolo[3,4-d]pyrimidin-4-ylamine, prepared as described in WO 05/074603, for cis-4-(4-(4-amino-3-iodopyrazolo[3,4-d]pyrimidin-1-yl)cyclohexyl)-1-methylpiperazin-2-one in EXAMPLE 2B.

EXAMPLE 5B

A mixture of EXAMPLE 5A (0.10 g), benzaldehyde (0.029 g), and 1M $Na_2S_2O_4$ (0.70 mL) in ethanol (1.1 mL) was stirred at 130° C. for 20 minutes in a microwave reactor. The reaction was treated with 5M $NH_4OH$ (2 mL), and the precipitate was dissolved into dichloromethane/IPA. The mixture was dried ($Na_2SO_4$) filtered and concentrated. The concentrate was purified on silica gel with an Intelliflash-280 purification system with ethyl acetate/methanol. $^1$H NMR (300 MHz, DMSO-$d_6$) 12.25 (s, 1H), 7.39-7.34 (m, 3H), 6.99-6.82 (m, 2H), 6.72-6.64 (m, 4H), 3.90-3.81 (m, 1H), 2.73-2.70 (m, 2H), 2.61-2.58 (m, 2H), 2.40 (s, 3H), 1.30-1.11 (m, 5H).

EXAMPLE 6A

This example was prepared by substituting cis-3-iodo-1-(4-(4-methylpiperazin-1-yl)cyclohexyl)-1H-pyrazolo[3,4-d]pyrimidin-4-ylamine, prepared as described in Bioorg. Med. Chem. Lett. 2002, 12, 1687-1690, for cis-4-(4-(4-amino-3-iodopyrazolo[3,4-d]pyrimidin-1-yl)cyclohexyl)-1-methylpiperazin-2-one in EXAMPLE 2B.

EXAMPLE 6B

A mixture of EXAMPLE 6A (0.12 g), benzaldehyde (0.028 g), and 1M $Na_2S_2O_4$ (0.68 mL) in ethanol (1 mL) was stirred at 130° C. for 20 minutes in a microwave reactor. The reaction was treated with 5M $NH_4OH$ (2 mL), and the precipitate was dissolved in dichloromethane/IPA. The mixture was dried ($MgSO_4$), filtered and concentrated. The concentrate was purified on silica gel with an Intelliflash-280 purification system with ethyl acetate/methanol/$NH_4OH$).

$^1$H NMR (300 MHz, DMSO-$d_6$) 13.10 (bs, 1H), 8.24-8.20 (m, 3H), 7.89-7.69 (m, 2H), 7.61-7.50 (m, 4H), 4.86-4.79 (m, 1H), 2.48-2.20 (m, 7H), 2.14 (s, 3H), 2.09-2.04 (m, 1H), 1.76-1.56 (m, 4H).

EXAMPLE 7A

This example was prepared by substituting trans-3-iodo-1-(4-morpholin-4-yl-cyclohexyl)-1H-pyrazolo[3,4-d]pyrimidin-4-ylamine, prepared as described in WO 05/074603, for cis-4-(4-(4-amino-3-iodopyrazolo[3,4-d]pyrimidin-1-yl)cyclohexyl)-1-methylpiperazin-2-one in EXAMPLE 2B.

EXAMPLE 7B

A mixture of EXAMPLE 7A (0.14 g), benzaldehyde (35 mg), and 1M $Na_2S_2O_4$ (0.95 mL) in ethanol (1.5 mL) was stirred at 130° C. for 20 minutes in a microwave reactor. The reaction was treated with 5M $NH_4OH$ (2 mL), and the precipitate was dissolved methyl acetate/IPA. The mixture was dried ($Na_2SO_4$) filtered and concentrated. The concentrate was purified on silica gel with an Intelliflash-280 purification system with ethyl acetate/methanol/$NH_4OH$. $^1$H NMR (300 MHz, DMSO-$d_6$) 13.09 (bs, 1H), 8.25-8.20 (m, 3H), 7.83 (bs, 2H), 7.61-7.50 (m, 4H), 4.72-4.64 (m, 1H), 3.58 (bs, 4H), 2.42-2.32 (m, 1H), 2.09-1.94 (m, 6H), 1.52-1.43 (m, 2H).

EXAMPLE 8

This example was prepared by substituting 4-methylbenzaldehyde for benzaldehyde in EXAMPLE 7B. $^1$H NMR (300 MHz, DMSO-$d_6$) 13.00 (bs, 1H), 8.24 (s, 1H), 8.10 (d, 2H), 7.87-7.65 (m, 2H), 7.52-7.49 (m, 1H), 7.39 (d, 2H), 4.69-4.63 (m, 1H), 3.58 (bs, 4H), 2.40 (bs, 4H), 2.08-1.97 (m, 6H), 1.48-1.46 (m, 2H).

EXAMPLE 9

This example was prepared by substituting 4-chlorobenzaldehyde for benzaldehyde in EXAMPLE 7B. $^1$H NMR (300 MHz, DMSO-$d_6$) 13.18 (bs, 1H), 8.24-8.21 (m, 3H), 7.89-7.71 (m, 2H), 7.68-7.65 (d, 2H), 7.56-7.51 (m, 1H), 4.68 (bs, 1H), 3.60-3.57 (m, 4H), 2.44-2.27 (m, 1H), 2.10-1.97 (m, 5H), 1.54-1.45 (m, 1H).

EXAMPLE 10

This example was prepared by substituting 4-methoxybenzaldehyde for benzaldehyde in EXAMPLE 7B. $^1$H NMR (300 MHz, DMSO-$d_6$) 12.92 (s, 1H), 8.24 (s, 1H), 8.16 (d, 2H), 7.84-7.64 (m, 2H), 7.48 (d, 1H), 7.14 (d, 2H), 4.67 (bs, 1H), 3.86 (s, 3H), 3.58 (bs, 5H), 2.10-1.97 (m, 7H), 1.50-1.45 (2H).

EXAMPLE 11

This example was prepared by substituting 3,4-dichlorobenzaldehyde for benzaldehyde in EXAMPLE 7B. $^1$H NMR (300 MHz, DMSO-$d_6$) 13.19 (s, 1H), 8.44 (d, 1H), 8.25 (bs, 1H), 8.19 (dd, 1H), 7.89-7.74 (m, 3H), 7.55 (d, 1H), 4.66 (bs, 1H), 3.58 (bs, 4H), 2.41-2.34 (m, 1H), 2.09-1.97 (m, 6H), 1.50-1.44 (m, 2H).

EXAMPLE 12

This example was prepared by substituting phenylacetaldehyde for benzaldehyde in EXAMPLE 7B. $^1$H NMR (300 MHz, DMSO-$d_6$) 12.45 (bs, 1H), 8.22 (s, 1H), 7.76-7.56 (m, 2H), 7.44-7.31 (m, 5H), 7.27-7.22 (m, 1H), 4.65 (bs, 1H), 4.21 (s, 2H), 4.13 (m, 4H), 2.43-2.32 (m, 1H), 2.08-1.95 (m, 6H), 1.52-1.41 (m, 2H).

EXAMPLE 13

This example was prepared by substituting 3-phenyl-propionaldehyde for benzaldehyde in EXAMPLE 7B. $^1$H NMR (300 MHz, DMSO-$d_6$) 12.43 (d, 1H), 8.23 (s, 1H), 7.76-7.56

(m, 2H), 7.45-7.40 (m, 1H), 7.29 (d, 4H), 7.22-7.17 (m, 1H), 4.65 (bs, 1H), 3.59-3.57 (m, 4H), 3.22-3.11 (m, 7H), 2.39-2.28 (m, 2H), 2.08-1.96 (m, 6H), 1.54-1.40 (m, 2H).

EXAMPLE 14

This example was prepared by substituting thiophen-2-ylacetaldehyde (E. Winterfeldt et al., Chem. Berichte 1963, 96, 3349-3358) for benzaldehyde in EXAMPLE 7B. $^1$H NMR (300 MHz, DMSO-$d_6$) 12.50 (d, 1H), 8.22 (s, 1H), 7.78-7.57 (m, 2H), 7.45-7.39 (m, 2H), 7.06-7.03 (m, 1H), 7.01-6.97 (m, 1H), 4.65 (bs, 1H), 4.44 (s, 2H), 3.58 (bs, 5H), 2.44-2.30 (m, 1H), 2.12-1.93 (m, 6H), 1.54-1.40 (m, 2H).

EXAMPLE 15

This example was prepared by substituting (3-chlorophenyl)acetaldehyde, prepared as described in Chem. Res. Toxicol. 1996, 9, 268-276, for benzaldehyde in EXAMPLE 7B.
$^1$H NMR (300 MHz, DMSO-$d_6$) 12.48 (d, 1H), 8.22 (s, 1H), 7.77-7.57 (m, 2H), 7.46-7.30 (m, 5H), 4.65 (bs, 1H), 4.24 (s, 2H), 3.59-3.57 (m, 4H), 2.43-2.32 (m, 1H), 2.09-1.94 (m, 6H), 1.54-1.39 (m, 2H).

EXAMPLE 16

This example was prepared by substituting 4-(chlorophenyl)acetaldehyde, prepared as described in Chem. Res. Toxicol. 1996, 9, 268-276, for benzaldehyde in EXAMPLE 7B.
$^1$H NMR (300 MHz, DMSO-$d_6$) 12.45 (bs, 1H), 8.23 (s, 1H), 7.76-7.56 (m, 2H), 7.44-7.39 (m, 5H), 4.66 (bs, 1H), 4.22 (s, 2H), 3.61-3.57 (m, 4H), 2.41-2.35 (m, 1H), 2.08-1.96 (m, 6H), 1.51-1.44 (m, 2H).

EXAMPLE 17

This example was prepared by substituting 2-phenylpropionaldehyde for benzaldehyde in EXAMPLE 7B. $^1$H NMR (300 MHz, DMSO-$d_6$) 12.36 (d, 1H), 8.22 (s, 1H), 7.80-7.53 (m, 2H), 7.44-7.30 (m, 5H), 7.23 (t, 1H), 4.65 (bs, 1H), 4.42 (q, 1H), 3.58 (bs, 4H), 2.35 (t, 1H), 2.07-1.96 (m, 7H), 1.74-1.71 (m, 4H), 1.50-1.43 (m, 2H).

EXAMPLE 18

This example was prepared by substituting (2-chlorophenyl)acetaldehyde for benzaldehyde in EXAMPLE 7B. $^1$H NMR (300 MHz, DMSO-$d_6$) 12.47 (bs, 1H), 8.23 (s, 1H), 7.71-7.62 (m, 2H), 7.49-7.48 (m, 1H), 7.44-7.42 (m, 2H), 7.85-7.81 (m, 2H), 4.69-4.61 (m, 1H), 4.35 (s, 2H), 3.58 (bs, 4H), 2.38-2.33 (m, 1H), 2.07-1.95 (m, 6H), 1.50-1.42 (m, 2H).

EXAMPLE 19

This example was prepared by substituting (2-fluorophenyl)acetaldehyde for benzaldehyde in EXAMPLE 7B. $^1$H NMR (300 MHz, DMSO-$d_6$) 12.49 (d, 1H), 8.22 (s, 1H), 7.75-7.56 (m, 2H), 7.45-7.39 (m, 2H), 7.35-7.30 (m, 1H), 7.20 (m, 2H), 4.70-4.60 (m, 1H), 4.26 (s, 2H), 3.58 (bs, 4H), 2.40-2.30 (m, 1H), 2.10-1.94 (m, 6H), 1.54-1.39 (m, 2H).

EXAMPLE 20

This example was prepared by substituting (2-methylphenyl)acetaldehyde for benzaldehyde in EXAMPLE 7B. $^1$H NMR (300 MHz, DMSO-$d_6$) 12.35 (bs, 1H), 8.22 (s, 1H), 7.75-7.55 (m, 2H), 7.44-7.39 (m, 1H), 7.27-7.23 (m, 1H), 7.19-7.14 (m, 3H), 4.69-4.60 (m, 1H), 4.20 (s, 2H), 3.58 (bs, 4H), 2.36-2.32 (bs, 4H), 2.08-1.93 (m, 6H), 1.52-1.40 (m, 2H).

EXAMPLE 21

This example was prepared by substituting (3-fluorophenyl)acetaldehyde for benzaldehyde in EXAMPLE 7B. $^1$H NMR (300 MHz, DMSO-$d_6$) 12.48 (bs, 1H), 8.22 (s, 1H), 7.73-7.60 (m, 2H), 7.45-7.34 (m, 2H), 7.23-7.18 (m, 2H), 7.12-7.05 (m, 1H), 4.69-4.60 (m, 1H), 4.25 (s, 2H), 3.58 (bs, 4H), 2.37-2.26 (m, 1H), 2.08-1.94 (m, 6H), 1.54-1.40 (m, 2H).

EXAMPLE 22

This example was prepared by substituting (3-methylphenyl)acetaldehyde for benzaldehyde in EXAMPLE 7B. $^1$H NMR (300 MHz, DMSO-$d_6$) 12.43 (bs, 1H), 8.22 (s, 1H), 7.76-7.41 (m, 3H), 7.24-7.13 (m, 3H), 7.06 (d, 1H), 4.71-4.59 (m, 1H), 4.17 (s, 2H), 3.58 (bs, 4H), 2.40-2.31 (m, 1H), 2.28 (s, 3H), 2.08-1.94 (m, 7H), 1.54-1.40 (m, 2H).

EXAMPLE 23

This example was prepared by substituting (4-fluorophenyl)acetaldehyde for benzaldehyde in EXAMPLE 7B. $^1$H NMR (300 MHz, DMSO-$d_6$) 12.47 (bs, 1H), 8.22 (s, 1H), 7.73-7.58 (m, 2H), 7.44-7.38 (m, 3H), 7.18-7.15 (m, 2H), 4.68-4.62 (m, 1H), 4.21 (s, 2H), 3.58 (bs, 4H), 2.38-2.33 (m, 1H), 2.09-1.95 (m, 6H), 1.51-1.41 (m, 2H).

EXAMPLE 24

This example was prepared by substituting (4-methylphenyl)acetaldehyde for benzaldehyde in EXAMPLE 7B. $^1$H NMR (300 MHz, DMSO-$d_6$) 12.40 (d, 1H), 8.22 (s, 1H), 7.75-7.54 (m, 2H), 7.44-7.40 (m, 1H), 7.24 (d, 2H), 7.13 (d, 2H), 4.69-4.60 (m, 1H), 4.16 (s, 2H), 2.39-2.32 (m, 1H), 2.27 (s, 3H), 2.07-1.95 (m, 6H), 1.53-1.42 (m, 2H).

EXAMPLE 25

This example was prepared by substituting [3,4-dichlorophenyl)acetaldehyde for benzaldehyde in EXAMPLE 7B.
$^1$H NMR (400 MHz, DMSO-$d_6$) δ 12.47 (d, 1H), 8.22 (s, 1H), 7.77-7.66 (m, 3H), 7.62-7.57 (m, 1H), 7.46-7.42 (m, 1H), 7.39-7.35 (m, 1H), 4.68-4.61 (m, 1H), 4.26 (s, 2H), 3.58 (bs, 4H), 2.40-2.32 (m, 1H), 2.07-1.95 (m, 7H), 1.51-1.41 (m, 2H).

EXAMPLE 26

This example was prepared by substituting (2,6-dichlorophenyl)acetaldehyde for benzaldehyde in EXAMPLE 7B.
$^1$H NMR (300 MHz, DMSO-$d_6$) 12.46 (s, 1H), 8.22 (s, 1H), 7.69 (bs, 1H), 7.61-7.53 (m, 3H), 7.44-7.37 (m, 2H), 4.71-4.58 (m, 1H), 4.52 (s, 2H), 3.58 (bs, 4H), 2.40-2.27 (m, 1H), 2.08-1.94 (m, 6H), 1.53-1.41 (m, 2H).

EXAMPLE 27A

A mixture of 2-(2,3-dichlorophenyl)ethanol (0.50 g), NaHCO$_3$ (0.438 g) and Dess-Martin periodinane (1.22 g) in dichloromethane (10 mL) and water (46 mL) was stirred for 1 hour. The mixture was quenched with aqueous NaHCO$_3$ and saturated aqueous Na₂S₂O₃ and extracted with dichloromethane. The extract was dried (Na₂SO₄), filtered and concentrated. The concentrate was purified on silica gel with an Intelliflash-280 purification system with hexanes/ethyl acetate.

EXAMPLE 27B

This example was prepared by substituting EXAMPLE 27A for benzaldehyde in EXAMPLE 7B. $^1$H NMR (300 MHz, DMSO-d$_6$) 12.48 (bs, 1H), 8.22 (s, 1H), 7.74-7.59 (m, 3H), 7.47-7.36 (m, 3H), 4.70-4.60 (m, 1H), 4.42 (s, 2H), 3.58 (bs, 4H), 2.41-2.28 (m, 1H), 2.08-1.93 (m, 6H), 1.54-1.39 (m, 2H).

EXAMPLE 28

A mixture of A mixture of EXAMPLE 7A (0.2 g) and 10% Pd/C (0.04 g) in methanol (20 mL) at 50° C. in a Parr hydrogenation apparatus was shaken under hydrogen (60 psi) for 1.5 hour. The reaction was filtered through diatomaceous earth (Celite®), and concentrated. The concentrate was purified on silica gel with an Intelliflash-280 purification system with ethyl acetate/methanol/NH₄OH. The product (0.13 g) and 1-fluoro-3-isothiocyanatobenzene (0.051 g) in THF (4 mL) was stirred for 3 hours at ambient temperature and at 50° C. for 2 hours, treated N-(3-dimethylaminopropyl)-N'-ethylcarbodiimide (0.091 g), stirred for 2 hours, cooled and diluted with water and ethyl acetate. The extract was dried (MgSO₄), filtered and concentrated. The concentrate was purified on silica gel with an Intelliflash-280 purification system with ethyl acetate/methanol/NH₄OH. $^1$H NMR (300 MHz, DMSO-d$_6$) 11.18 (d, 1H), 9.84 (d, 1H), 8.23 (s, 1H), 7.95-7.88 (m, 1H), 7.63-7.51 (m, 2H), 7.46-7.29 (m, 4H), 6.75 (t, 1H), 4.72-4.59 (m, 1H), 3.58 (bs, 5H), 2.44-2.27 (m, 1H), 2.10-1.94 (m, 7H), 1.53-1.39 (m, 2H).

EXAMPLE 29A

This example was prepared by substituting 4-bromo-2-methyl-6-nitrophenylamine for 4-bromo-2-nitrophenylamine in EXAMPLE 2A.

EXAMPLE 29B

This example was prepared by substituting trans-3-iodo-1-(4-morpholin-4-yl-cyclohexyl)-1H-pyrazolo[3,4-d]pyrimidin-4-ylamine, prepared as described in Bioorg Med. Chem. Lett. 2002, 12, 1687-1690, and EXAMPLE 29A for cis-4-(4-(4-amino-3-iodopyrazolo[3,4-d]pyrimidin-1-yl)cyclohexyl)-1-methylpiperazdin-2-one and EXAMPLE 2A, respectively, in EXAMPLE 2B.

EXAMPLE 29C

This example was prepared by substituting EXAMPLE 29B and phenylacetaldehyde for EXAMPLE 7A and benzaldehyde, respectively, in EXAMPLE 7B. $^1$H NMR (400 MHz, DMSO-d$_6$) 12.42 (d, 1H), 8.21 (s, 1H), 7.52 (d, 1H), 7.38-7.31 (m, 4H), 7.27-7.22 (m, 2H), 4.69-4.60 (m, 1H), 4.21 (s, 2H), 3.58 (bs, 4H), 2.40-2.30 (m, 1H), 2.09-1.94 (m, 6H), 1.52-1.41 (m, 2H).

EXAMPLE 30A

This example was prepared by substituting (4-bromo-2-nitrophenyl)methylamine, prepared as described in J. Chem. Soc., Perkin Trans 1, 1974, 903-908, for 4-bromo-2-nitrophenylamine in EXAMPLE 2A.

EXAMPLE 30B

This example was prepared by substituting trans-3-iodo-1-(4-morpholin-4-ylcyclohexyl)-1H-pyrazolo[3,4-d]pyrimidin-4-ylamine, prepared as described in Bioorg Med. Chem. Lett. 2002, 12, 1687-1690, and EXAMPLE 30A for cis-4-(4-(4-amino-3-iodopyrazolo[3,4-d]pyrimidin-1-yl)cyclohexyl)-1-methylpiperazdin-2-one and EXAMPLE 2A, respectively, in EXAMPLE 2B.

EXAMPLE 30C

This example was prepared by substituting EXAMPLE 30B and phenylacetaldehyde for EXAMPLE 7A and benzaldehyde, respectively, in EXAMPLE 7B. $^1$H NMR (300 MHz, DMSO-d$_6$) 8.23 (s, 1H), 7.80 (bs, 1H), 7.65 (d, 1H), 7.50 (dd, 1H), 7.36-7.29 (m, 4H), 7.28-7.21 (m, 1H), 4.70-4.60 (m, 1H), 4.35 (s, 2H), 3.76 (s, 3H), 3.58 (bs, 4H), 2.40-2.31 (m, 1H), 2.09-1.95 (m, 6H), 1.55-1.39 (m, 2H).

EXAMPLE 31A

This example was prepared by substituting 3-iodo-1-(4-oxocyclohexyl)-1H-pyrazolo[3,4-d]pyrimidin-4-ylamine prepared as described in Bioorg. Med. Chem. Lett. 2002, 12, 1687-1690, for cis-4-(4-(4-amino-3-iodopyrazolo[3,4-d]pyrimidin-1-yl)cyclohexyl)-1-methylpiperazin-2-one in EXAMPLE 2B.

EXAMPLE 31B

This example was prepared by substituting EXAMPLE 31A and phenylacetaldehyde for EXAMPLE 7A and benzaldehyde, respectively, in EXAMPLE 7B.

EXAMPLE 31C

A mixture of EXAMPLE 31B (0.0437 g), 3-hydroxypyrrolidine (0.087 g) and NaCNBH₃ (0.031 g) in 10:1 methanol/acetic acid (3 mL) was stirred at 70° C. for 2.5 hours and concentrated. The concentrate was purified by reverse phase HPLC with a Shimadzu LC10 HPLC system with a Phenominex Luna 10 micron C18(2) 100 150×30 mm column with a 5-45% acetonitrile in water with 0.15% TFA over 25 minutes at a flow rate of 20 mL/min. The earlier eluting diastereomer was isolated. $^1$H NMR (300 MHz, DMSO-d$_6$) δ 9.62 & 9.71 (brs, 1H), 8.28 (s, 1H), 7.84 (s, 1H), 7.79 (d, 1H), 7.62 (d, 1H), 7.41-7.30 (m, 5H), 4.73 (m, 1H), 4.48 (m, 1H), 4.43 (s, 2H), 4.39 (m, 1H), 3.31 (m, 5H), 2.24 (m, 4H), 2.08 (m, 4H), 1.91 (m, 2H), 1.70 (m, 2H).

EXAMPLE 32

This example was the slower eluting diastereomer in EXAMPLE 31. $^1$H NMR (300 MHz, DMSO-d$_6$) 9.85 and 9.53 (brs, 1H), 8.31 (s, 1H), 7.92 and 7.89 (s, 1H), 7.81 (m, 1H), 7.71 (m, 1H), 7.43-7.31 (m, 5H), 4.94 (m, 1H), 4.47 (m, 1H), 4.44 (s, 2H), 4.38 (m, 1H), 3.69 (m, 1H), 3.60 (m, 1H), 3.34 (m, 1H), 3.22 (m, 1H), 3.06 (m, 1H), 2.42 (m, 1H), 2.22 (m, 1H), 2.07-1.91 (m, 8H).

EXAMPLE 33

This example was the faster eluting diastereomer, prepared by substituting 4-ethanesulfonylpiperazine for 3-hydroxypyrrolidine in EXAMPLE 31C. $^1$H NMR (300 MHz, DMSO-d$_6$) 9.83 (brs, 1H), 8.32 (s, 1H), 7.91-7.84 (m, 2H), 7.70 (m, 1H), 7.45-7.33 (m, 5H), 4.79 (m, 1H), 4.49 (s, 2H), 3.8 (m, 1H), 3.55 (m, 4H), 3.22 (m, 6H), 2.20 (m, 1H), 2.14 (m, 4H), 1.95 (m, 2H), 1.80 (m, 1H), 1.24 (t, 3H).

EXAMPLE 34

This example was the slower eluting diastereomer, prepared by substituting 4-ethanesulfonylpiperazine for 3-hydroxypyrrolidine in EXAMPLE 31C. $^1$H NMR (300 MHz, DMSO-$d_6$) 9.50 (brs, 1H), 8.31 (s, 1H), 7.90 (s, 1H), 7.81 (d, 1H), 7.70 (d, 1H), 7.42-7.30 (m, 5H), 4.98 (m, 1H), 4.44 (s, 2H), 3.78 (m, 1H), 3.64 (m, 4H), 3.19 (m, 6H), 2.42 (m, 2H), 2.13-1.99 (m, 6H), 1.22 (t, 3H).

EXAMPLE 35

This example was the faster eluting diastereomer prepared by substituting 4-(2-methoxyethyl)piperazine for 3-hydroxypyrrolidine in EXAMPLE 31C. $^1$H NMR (300 MHz, DMSO-$d_6$) 8.30 (s, 1H), 7.86 (s, 1H), 7.81 (d, 1H), 7.65 (d, 1H), 7.42-7.32 (m, 5H), 4.75 (m, 1H), 4.45 (s, 2H), 3.59 (m, 6H), 3.40 (m, 1H), 3.30 (s, 3H), 3.06 (m, 6H), 2.11 (m, 6H), 1.70 (m, 2H).

EXAMPLE 36

This example was the slower eluting diastereomer, prepared by substituting 4-(2-methoxyethyl)piperazine for 3-hydroxypyrrolidine in EXAMPLE 31C. $^1$H NMR (300 MHz, DMSO-$d_6$) 8.35 (s, 1H), 7.91 (s, 1H), 7.85 (d, 1H), 7.72 (d, 1H), 7.45-7.33 (m, 5H), 4.94 (m, 1H), 4.50 (s, 2H), 3.61 (m, 3H), 3.48 (m, 4H), 3.29 (s, 3H), 3.19 (m, 4H), 3.05 (m, 2H), 2.37 (m, 2H), 2.07 (m, 3H), 1.91 (m, 3H).

EXAMPLE 37

This example was the faster eluting diastereomer, prepared by substituting (2R,6S)-2,6-dimethylpiperazine for 3-hydroxypyrrolidine in EXAMPLE 31C. $^1$H NMR (300 MHz, DMSO-$d_6$) 9.20 (brs, 1H), 8.62 (brs, 1H), 8.31 (s, 1H), 7.86 (s, 1H), 7.83 (d, 1H), 7.67 (d, 1H), 7.44-7.25 (m, 5H), 4.76 (m, 1H), 4.47 (s, 2H), 3.0 (m, 1H), 2.89 (m, 2H), 2.73 (m, 2H), 2.11 (m, 6H), 1.73 (m, 2H), 1.26 (d, 6H).

EXAMPLE 38

This example was the slower eluting diastereomer, prepared by substituting (2R,6S)-2,6-dimethylpiperazine for 3-hydroxypyrrolidine in EXAMPLE 31C. $^1$H NMR (300 MHz, DMSO-$d_6$) 9.10 (brs, 1H), 8.31 (s, 1H), 7.86 (s, 1H), 7.78 (d, 1H), 7.65 (d, 1H), 7.42-7.31 (m, 5H), 4.92 (m, 1H), 4.43 (s, 2H), 3.41 (m, 5H), 2.33 (m, 2H), 2.10 (m, 4H), 1.87 (m, 2H).

EXAMPLE 39

This example was the faster eluting diastereomer, prepared by substituting 4-acetylpiperazine for 3-hydroxypyrrolidine in EXAMPLE 31C. $^1$H NMR (300 MHz, DMSO-$d_6$) 9.65 (brs, 1H), 8.30 (s, 1H), 7.86 (s, 1H), 7.82 (d, 1H), 7.65 (d, 1H), 7.42-7.32 (m, 5H), 4.68 (m, 1H), 4.51 (m, 1H), 4.45 (s, 2H), 4.06 (m, 1H), 3.20 (m, 3H), 2.97 (m, 4H), 2.13 (m, 6H), 2.06 (s, 3H), 1.80 (m, 2H).

EXAMPLE 40

This example was the slower eluting diastereomer, prepared by substituting 4-acetylpiperazine for 3-hydroxypyrrolidine in EXAMPLE 31C. $^1$H NMR (300 MHz, DMSO-$d_6$) 9.45 (brs, 1H), 8.30 (s, 1H), 7.89 (s, 1H), 7.81 (d, 1H), 7.69 (d, 1H), 7.41-7.31 (m, 5H), 4.97 (m, 1H), 4.46 (m, 1H), 4.43 (s, 2H), 4.01 (m, 1H), 3.46 (m, 2H), 3.13 (m, 1H), 2.85 (m, 4H), 2.42 (m, 2H), 2.06 (m, 6H), 2.04 (s, 3H).

EXAMPLE 41

This example was the faster eluting diastereomer, prepared by substituting 3-trifluoromethyl-5,6,7,8-tetrahydro-(1,2,4)triazolo-[4,3-a]pyrizine, prepared as described in J. Med. Chem., 2005, 48, 141-151, for 3-hydroxypyrrolidine in EXAMPLE 31C. $^1$H NMR (300 MHz, DMSO-$d_6$) 8.31 (s, 1H), 7.89 (s, 1H), 7.84 (d, 1H), 7.70 (d, 1H), 7.43-7.34 (m, 5H), 4.76 (m, 1H), 4.48 (s, 2H), 4.19 (m, 2H), 4.14 (m, 2H), 3.18 (m, 2H), 2.92 (m, 1H), 2.06 (m, 6H), 1.68 (m, 2H).

EXAMPLE 42

This example was the slower eluting diastereomer, prepared by substituting 3-trifluoromethyl-5,6,7,8-tetrahydro(1,2,4)triazolo-(4,3-a)pyrizine for 3-hydroxypyrrolidine, prepared as described in J. Med. Chem., 2005, 48, 141-151, in EXAMPLE 31C. $^1$H NMR (300 MHz, DMSO-$d_6$) 8.31 (s, 1H), 7.88 (s, 1H), 7.82 (d, 1H), 7.68 (d, 1H), 7.42-7.33 (m, 5H), 4.90 (m, 1H), 4.48 (s, 2H), 4.18 (m, 2H), 4.04 (m, 2H), 3.11 (m, 2H), 2.70 (m, 1H), 2.27 (m, 2H), 2.18 (m, 2H), 1.79 (m, 4H).

EXAMPLE 43A

To a solution of 3-iodo-1H-pyrazolo[3,4-d]pyrimidin-4-ylamine, prepared as described in Bioorg Med. Chem. Lett. 2002, 12, 1687-1690, (1.044 g) 4-hydroxypiperidine-1-carboxylic acid, tert-butyl ester (2.42 g) and triphenylphosphine (2.1 g) in THF (40 mL) was added DIAD (1.6 mL). The mixture was stirred for 18 hours, then partitioned between ethyl acetate and brine. The extract was dried, filtered and concentrated. The concentrate was eluted through silica gel plug with 30-50% ethyl acetate/hexanes then 5% methanol/ethyl acetate. The eluant was concentrated, and the concentrate was recrystallized from dichloromethane/ether.

EXAMPLE 43B

EXAMPLE 43A (0.56 g) in 4M HCl in dioxane 10 mL was stirred at room temperature for 1.5 hours and filtered.

EXAMPLE 43C

EXAMPLE 43B (0.17 g), iodoacetamide (0.1 g), $K_2CO_3$ (0.35 g) and tetrabutylammonium iodide (0.01 g) in DMF (5 mL) was stirred ofor 18 hours. The reaction mixture was diluted with ethyl acetate and washed with water and brine. The or concentrate was dried, filtered and concentrated.

EXAMPLE 43D

This example was prepared by substituting EXAMPLE 43C for cis-4-(4-(4-amino-3-iodopyrazolo[3,4-d]pyrimidin-1-yl)cyclohexyl)-1-methylpiperazin-2-one in EXAMPLE 2B.

EXAMPLE 43E

A mixture of EXAMPLE 43D (0.11 g), phenylacetaldehyde (0.02 mL) and $Na_2S_2O_4$ (0.09 g) in ethanol (2 mL) and water (2 mL) was stirred at 120° C. for 20 minutes in a microwave reactor and concentrated. The concentrate was purified by reverse phase HPLC with a Shimadzu LC10 HPLC system with a Phenominex Luna 10 micron C18(2) 100 150×30 mm column with a 5-45% acetonitrile in water with 0.15% TFA over 25 minutes at a flow rate of 20 mL/min. $^1$H NMR (300 MHz, DMSO-$d_6$) 9.84 (brs, 1H), 8.31 (s, 1H), 7.96 (m, 1H), 7.87 (s, 1H), 7.82 (d, 1H), 7.69 (d, 1H), 7.64 (m, 1H), 7.42-7.31 (m, 5H), 5.03 (m, 1H), 4.45 (s, 2H), 3.95 (s, 2H), 3.37 (m, 4H), 2.44 (m, 2H), 2.18 (m, 2H).

EXAMPLE 44

This example was the faster eluting diastereomer, prepared by substituting piperidine-3-carboxamide for 3-hydroxypyrrolidine in EXAMPLE 31C. $^1$H NMR (300 MHz, DMSO-$d_6$) 9.21 (brs, 1H), 8.32 (s, 1H), 7.89 (s, 1H), 7.85 (d, 1H), 7.69 (d, 1H), 7.57 (s, 1H), 7.45-7.29 (m, 5H), 7.12 (s, 1H), 4.80 (m, 1H), 4.49 (s, 2H), 3.45 (m, 2H), 3.17 (m, 1H), 3.01 (m, 2H), 2.66 (m, 1H), 2.13 (m, 6H), 1.93 (m, 2H), 1.81 (m, 3H), 1.51 (m, 1H).

EXAMPLE 45

This example was the slower eluting diastereomer, prepared by substituting piperidine-3-carboxamide for 3-hydroxypyrrolidine in EXAMPLE 31C. $^1$H NMR (300 MHz, DMSO-$d_6$) 9.15 (brs, 1H), 8.34 (s, 1H), 7.93 (s, 1H), 7.86 (d, 1H), 7.76 (d, 1H), 7.60 (s, 1H), 7.45-7.29 (m, 5H), 7.12 (s, 1H), 5.03 (m, 1H), 4.50(s, 2H), 3.51 (m, 2H), 3.24 (m, 1H), 3.00 (m, 2H), 2.66 (m, 1H), 2.36 (m, 2H), 2.18 (m, 2H), 1.97 (m, 5H), 1.76 (m, 2H), 1.48 (m, 1H).

EXAMPLE 46

This example was the faster eluting diastereomer, prepared by substituting piperidine-4-carboxamide for 3-hydroxypyrrolidine in EXAMPLE 31C. $^1$H NMR (300 MHz, DMSO-$d_6$) 9.07 (brs, 1H), 8.31 (s, 1H), 7.88 (s, 1H), 7.83 (d, 1H), 7.67 (d, 1H), 7.42-7.29 (m, 6H), 6.95 (s, 1H), 4.79 (m, 1H), 4.48 (s, 2H), 3.31 (m, 2H), 3.01 (m, 4H), 2.40 (m, 2H), 2.12 (m, 6H), 2.0 (m, 2H), 1.80(m, 2H).

EXAMPLE 47

This example was the slower eluting diastereomer, prepared by substituting piperidine-4-carboxamide for 3-hydroxypyrrolidine in EXAMPLE 31C. $^1$H NMR (300 MHz, DMSO-$d_6$) 8.98 (brs, 1H), 8.35 (s, 1H), 7.94 (s, 1H), 7.87 (d, 1H), 7.75 (d, 1H), 7.45-7.29 (m, 6H), 6.93 (s, 1H), 5.0 (m, 1H), 4.50(s, 2H), 3.52 (m, 2H), 3.34 (m, 2H), 2.99 (m, 2H), 2.38 (m, 2H), 2.12 (m, 2H), 1.99 (m, 6H), 1.82 (m, 2H).

EXAMPLE 48A

A mixture of 3-iodo-1H-pyrazolo[3,4-d]pyrimidin-4-ylamine, prepared as described in Bioorg Med. Chem. Lett. 2002, 12, 1687-1690, (1 g) and NaH (0.17 g) in DMF (17 mL) was stirred for 1 hour, treated with 4-fluorobenzaldehyde (0.45 mL), stirred at 100° C. for 18 hours, cooled, diluted with water and filtered.

EXAMPLE 48B

A mixture of EXAMPLE 48A (0.18 g), morpholine (0.44 mL) and NaCNBH$_3$ (0.16 g) in methanol/acetic acid (5/0.5 mL) was stirred at 70° C. for 2.5 hours and partitioned between ethyl acetate and brine. The extract was dried, filtered and concentrated. The concentrate was triturated with ether.

EXAMPLE 48C

This example was prepared 2 by substituting EXAMPLE 48B for cis-4-(4-(4-amino-3-iodopyrazolo[3,4-d]pyrimidin-1-yl)cyclohexyl)-1-methylpiperazin-2-one in EXAMPLE 2B.

EXAMPLE 48D

A mixture of EXAMPLE 48C (0.074 g), phenylacetaldehyde (0.02 mL), and Na$_2$S$_2$O$_4$ (0.09 g) in ethanol (2 mL) and water (2 mL) was stirred at 120° C. for 20 minutes in a microwave reactor and concentrated. The concentrate was purified by reverse phase HPLC with a Shimadzu LC10 HPLC system with a Phenominex Luna 10 micron C18(2) 100 150×30 mm column with a 5-45% acetonitrile in water with 0.15% TFA over 25 minutes at a flow rate of 20 mL/min. $^1$H NMR (300 MHz, DMSO-$d_6$) 10.02 (brs, 1H), 8.43 (s, 1H), 8.37 (d, 2H), 8.0 (s, 1H), 7.89 (d, 1H), 7.78 (d, 1H), 7.70 (d, 2H), 7.43-7.34 (m, 5H), 4.49 (s, 2H), 4.43 (s, 2H), 3.99 (m, 4H), 3.64 (m, 2H), 3.30 (m, 1H), 3.18 (m, 1H).

EXAMPLE 49

This example was the faster eluting diastereomer, prepared by substituting 4-methanesulfonylpiperazine for 3-hydroxypyrrolidine in EXAMPLE 3° C. $^1$H NMR (300 MHz, DMSO-$d_6$) 9.68 (brs, 1H), 8.30 (s, 1H), 7.86 (s, 1H), 7.81 (d, 1H), 7.65 (d, 1H), 7.42-7.32 (m, 5H), 4.79 (m, 1H), 4.45 (s, 2H), 3.74 (m, 4H), 3.17 (m, 5H), 3.05 (s, 3H), 2.24 (m, 2H), 2.13 (m, 4H), 1.78 (m, 2H).

EXAMPLE 50

This example was the slower eluting diastereomer, prepared by substituting 4-methanesulfonylpiperazine for 3-hydroxypyrrolidine in EXAMPLE 3° C. $^1$H NMR (300 MHz, DMSO-$d_6$) 9.40 (brs, 1H), 8.30 (s, 1H), 7.88 (s, 1H), 7.79 (d, 1H), 7.67 (d, 1H), 7.43-7.30 (m, 5H), 4.98 (m, 1H), 4.42 (s, 2H), 3.70 (m, 4H), 3.15 (m, 5H), 3.02 (s, 3H), 2.43 (m, 2H), 2.03 (m, 6H).

EXAMPLE 51A

EXAMPLE 43B (0.12 g), 4-morpholinecarbonylchloride (0.06 mL) and DIPEA (0.26 mL) in CH$_3$CN (10 mL) was stirred for 18 hours and partitioned between ethyl acetate and NaHCO$_3$. The extract washed with brine, dried, filtered and concentrated. The concentrate was recrystallized from diethyl ether.

EXAMPLE 51B

This example was prepared by substituting EXAMPLE 51A for cis-4-(4-(4-amino-3-iodopyrazolo[3,4-d]pyrimidin-1-yl)cyclohexyl)-1-methylpiperazin-2-one in EXAMPLE 2B.

EXAMPLE 51C

A mixture of EXAMPLE 51B (0.075 g), phenylacetaldehyde (0.02 mL), and Na$_2$S$_2$O$_4$ (0.09 g) in ethanol (2 mL) and water (2 mL) was stirred at 120° C. for 20 minutes in a microwave reactor and concentrated. The concentrate was purified by reverse phase HPLC with a Shimadzu LC10 HPLC system with a Phenominex Luna 10 micron C18(2) 100 150×30 mm column with a 5-45% acetonitrile in water with 0.15% TFA over 25 minutes at a flow rate of 20 mL/min. $^1$H NMR (300 MHz, DMSO-d$_6$) 8.32 (s, 1H), 7.91 (s, 1H), 7.85 (d, 1H), 7.72 (d, 1H), 7.43-7.33 (m, 5H), 4.94 (m, 1H), 4.50 (s, 2H), 3.72 (m, 4H), 3.17 (m, 4H), 3.02 (m, 4H), 2.12 (m, 2H), 1.95 (m, 2H).

EXAMPLE 52A

To a solution of 3-iodo-1H-pyrazolo[3,4-d]pyrimidin-4-ylamine, prepared as described in Bioorg Med. Chem. Lett. 2002, 12, 1687-1690, (0.82 g), 3-hydroxy-pyrrolidine-1-carboxylic acid, tert-butyl ester (1.17 g) and triphenylphosphine (1.65 g) in THF (40 mL) was added DIAD (1.2 mL). The mixture was stirred for 18 hours and partitioned between ethyl acetate and brine. The extract was dried, filtered and concentrated. The concentrate was eluted through silica gel plug with 30-50% ethyl acetate/anesnd then 5% methanol/ethyl acetate. The eluant was concentrated, and the concentrate was recrystallized from dichloromethane/ether.

EXAMPLE 52B

EXAMPLE 52A (0.54 g) in 4 M HCl in dioxane (10 mL) was stirred at room temperature for 1.5 hours and filtered.

EXAMPLE 52C

A mixture of EXAMPLE 52B (0.18 g), iodoacetamide (0.1 g), K$_2$CO$_3$ (0.35 g) and tetrabutylammonium iodide (0.01 g) in DMF (5 mL) was stirred at room temperature for 18 hours. The reaction mixture was diluted with ethyl acetate, washed with water and brine and dried, filtered and concentrated. The concentrate was recrystallized from diethylether.

EXAMPLE 52D

This example was prepared by substituting EXAMPLE 52C for cis-4-(4-(4-amino-3-iodopyrazolo[3,4-d]pyrimidin-1-yl)cyclohexyl)-1-methylpiperazin-2-one in EXAMPLE 2B.

EXAMPLE 52E

A mixture of EXAMPLE 52D (0.11 g), phenylacetaldehyde (0.02 mL), and Na$_2$S$_2$O$_4$ (0.09 g) in ethanol (2 mL) and water (2 mL) was stirred at 120° C. for 20 minutes in a microwave reactor and concentrated. The concentrate was purified by reverse phase HPLC with a Shimadzu LC10 HPLC system with a Phenominex Luna 10 micron C18(2) 100 150×30 mm column with a 5-45% acetonitrile in water with 0.15% TFA over 25 minutes at a flow rate of 20 mL/min. $^1$H NMR (300 MHz, DMSO-d$_6$) 10.38 (brs, 1H), 8.32 (s, 1H), 7.93 (s, 1H), 7.90 (s, 1H), 7.83 (d, 1H), 7.71 (d, 1H), 7.66 (s, 1H), 7.42-7.31 (m, 5H), 5.70 (m, 1H), 4.45 (s, 2H), 4.13 (m, 6H), 2.53 (m, 2H).

EXAMPLE 53

This example was the faster eluting diastereomer, prepared by substituting 4-(2-hydroxyethyl)piperazine for 3-hydroxypyrrolidine in EXAMPLE 31C. $^1$H NMR (300 MHz, DMSO-d$_6$) 8.29 (s, 1H), 7.85 (s, 1H), 7.80 (d, 1H), 7.65 (d, 1H), 7.41-7.31 (m, 5H), 4.75 (m, 1H), 4.44 (s, 2H), 3.70 (m, 8H), 3.08 (m, 6H), 2.10 (m, 6H), 1.68 (m, 2H).

EXAMPLE 54

This example was the slower eluting diastereomer, prepared by substituting 4-(2-hydroxyethyl)piperazine for 3-hydroxypyrrolidine in EXAMPLE 31C. $^1$H NMR (300 MHz, DMSO-d$_6$) 8.31 (s, 1H), 7.87 (s, 1H), 7.81 (d, 1H), 7.66 (d, 1H), 7.42-7.32 (m, 5H), 4.92 (m, 1H), 4.44 (s, 2H), 3.70 (m, 4H), 3.51 (m, 4H), 3.12 (m, 6H), 2.35 (m, 1H), 2.07 (m, 3H), 1.87 (m, 4H).

EXAMPLE 55

A mixture of EXAMPLE 31B (43.7 mg) and NaBH$_4$ (0.019 g) in methanol (3 mL) was stirred for 2.5 hours and concentrated. The concentrate was purified by reverse phase HPLC with a Shimadzu LC10 HPLC system with a Phenominex Luna 10 micron C18(2) 100 150×30 mm column with 5-45% acetonitrile in water with 0.15% TFA over 25 minutes at a flow rate of 20 mL/min $^1$H NMR (300 MHz, DMSO-d$_6$) 8.31 (s, 1H), 7.89 (s, 1H), 7.84 (d, 1H), 7.70 (d, 1H), 7.43-7.33 (m, 5H), 4.68 (m, 1H), 4.48 (s, 2H), 4.07 (m, 1H), 3.55 (m, 1H), 1.95 (m, 6H), 1.42 (m, 2H).

EXAMPLE 56A

This example was prepared by substituting cis-4-chloro-5-iodo-7-(4-(4-methylpiperazin-1-yl)cyclohexyl)-7H-pyrrolo[2,3-d]pyrimidine, prepared as described in WO 05/074603, for cis-4-(4-(4-amino-3-iodopyrazolo[3,4-d]pyrimidin-1-yl)cyclohexyl)-1-methylpiperazin-2-one in EXAMPLE 1B.

EXAMPLE 56B

A mixture of EXAMPLE 56A (0.048 g) and 30% NH$_4$OH (5 mL) in dioxane (5 mL) was stirred at 120° C. in a sealed tube for 24 hours, cooled and concentrated. The concentrate was purified by reverse phase HPLC.

EXAMPLE 57A

A mixture of 4-bromo-benzene-1,2-diamine (3 g) and 3-phenylpropionic acid (3.61 g) in 4N HCl (15 mL) was stirred at reflux for 3 hours, cooled and filtered. The filtrate was shaken in a seperatory funnel with dichloromethane and water. The water was adjusted to pH 7 with 30% NH$_4$OH and extracted with ethyl acetate. The extract was dried, filtered and concentrated. The concentrate was flash chromatographed on silica gel with 2:1 hexanes/ethyl acetate.

EXAMPLE 57B

A mixture of EXAMPLE 57A (1.128 g), bis(pinacolato)diboron (2.86 g), potassium acetate (2.2 g) and dichloro(1,1'-bis(diphenylphosphino)ferrocene)-palladium(II).dichloromethane (0.367 g) in DMF (24 mL) was stirred at 85° C. for 20 hours, cooled, filtered through diatomaceous earth (Celite®) and concentrated. The concentrate was flash chromatographed on silica gel with 1:1 hexanes/ethyl acetate. The eluant was concentrated, and the concentrate was triturated with heptane.

EXAMPLE 57C

A mixture of EXAMPLE 57B (0.435 g), cis-4-chloro-5-iodo-7-(4-(4-methylpiperazin-1-yl)cyclohexyl)-7H-pyrrolo

[2,3-d]pyrimidine, prepared as described in WO 05/074603 (0.383 g), $Na_2CO_3 \cdot H_2O$, (0.258 g) and tetrakis(triphenylphosphine) palladium(0) (0.116 g) in DME (8 mL) and water (4 mL) was heated to 80° C. for 18 hours, cooled and concentrated. The concentrate was treated with water and extracted with ethyl acetate. The extract washed with brine and dried, filtered and concentrated. The concentrate was flash chromatographed on silica gel with 10% methanol/dichloromethane.

EXAMPLE 57D

This example was prepared by substituting EXAMPLE 57C for cis-4-chloro-7-(4-(4-methylpiperazin-1-yl)cyclohexyl)-5-(2-phenyl-1H-benzoimidazol-5-yl)-7H-pyrrolo[2,3-d]pyrimidine in EXAMPLE 56B.

EXAMPLE 58A

To $H_2SO_4$ (28.9 mL) at 0° C. was added a solution of sodium nitrite (22.4 g) in water (57 mL) while maintaining the internal temperature below 25° C. 3-bromophenol (25 g) in ethanol was then added to the mixture while maintaining the internal temperature below 25° C. The mixture warmed to room temperature and was stirred for 2 hours, treated with water and extracted with dichloromethane. The extract was dried ($MgSO_4$) filtered and concentrated. The concentrate was flash chromatographed on silica gel with 5% ethyl acetate/hexanes.

EXAMPLE 58B

A mixture of EXAMPLE 58A (1 g) in ethanol (23 mL) was treated with a Raney Nickel suspension in water (0.1 mL), stirred for 3 hours under hydrogen (1 atm), filtered through diatomaceous earth (Celite®) and concentrated. The concentrate was flash chromatographed on silica gel with 20% ethyl acetate/hexanes.

EXAMPLE 58C

EXAMPLE 58B (0.42 g) in THF (25 mL) was treated with phenyl isothiocyanate (0.4 mL) and stirred for 18 hours. The mixture was treated with $CuSO_4$ (3.2 g), silica gel (3 g) and TEA (0.31 mL), stirred for 18 hours and concentrated. The concentrate was flash chromatographed on silica gel with 15% ethyl acetate/hexanes).

EXAMPLE 58D

This example was prepared by substituting EXAMPLE 58C for 4-bromo-2-nitrophenylamine in EXAMPLE 2A.

EXAMPLE 58E

This example was prepared by substituting EXAMPLE 58D and cis-3-iodo-1-(4-(4-methylpiperazin-1-yl)cyclohexyl)-1H-pyrazolo[3,4-d]pyrimidin-4-ylamine, prepared as described in Bioorg Med. Chem. Lett. 2002, 12, 1687-1690, for EXAMPLE 2A and cis-4-(4-(4-amino-3-iodopyrazolo[3,4-d]pyrimidin-1-yl)cyclohexyl)-1-methylpiperazin-2-one, respectively, in EXAMPLE 2B. $^1$H NMR (300 MHz, DMSO-$d_6$) 8.22 (s, 1H), 7.73-7.70 (m, 2H), 7.55 (m, 1H), 7.45-7.38 (m, 2H), 7.34-7.29 (m, 2H), 6.96-6.91 (m, 1H), 4.88-4.78 (m, 1H), 2.45 (bs, 3H), 2.37-2.32 (m, 4H), 2.28 (bs, 1H), 2.25 (bs, 1H), 2.21 (bs, 1H), 2.14 (s, 3H), 2.11-2.05 (m, 2H), 1.76-1.66 (m, 2H), 1.65-1.52 (m, 3H).

EXAMPLE 59

This example was prepared by substituting EXAMPLE 58D and trans-3-iodo-1-(4-(4-methylpiperazin-1-yl)cyclohexyl)-1H-pyrazolo[3,4-d]pyrimidin-4-ylamine, prepared as described in Bioorg Med. Chem. Lett. 2002, 12, 1687-1690, for EXAMPLE 2A and cis-4-(4-(4-amino-3-iodopyrazolo[3,4-d]pyrimidin-1-yl)cyclohexyl)-1-methylpiperazin-2-one, respectively, in EXAMPLE 2B. $^1$H NMR (300 MHz, DMSO-$d_6$) 10.79 (bs, 1H), 8.23 (s, 1H), 7.79 (d, 2H), 7.70 (s, 1H), 7.60-7.55 (m, 1H), 7.53-7.47 (m, 1H), 7.39 (t, 2H), 7.05 (t, 1H) 4.73-4.59 (m, 1H), 2.40-2.25 (m, 6H), 2.14 (s, 3H), 2.09-1.90 (m, 7H), 1.74 (s, 1H), 1.55-1.39 (m, 3H).

EXAMPLE 60

This example was prepared by substituting EXAMPLE 58D and trans-3-iodo-1-(4-morpholin-4-yl-cyclohexyl)-1H-pyrazolo[3,4-d]pyrimidin-4-ylamine, prepared as described in WO 05/074603 for EXAMPLE 2A, and cis-4-(4-(4-amino-3-iodopyrazolo[3,4-d]pyrimidin-1-yl)cyclohexyl)-1-methylpiperazin-2-one, respectively, in EXAMPLE 2B. $^1$H NMR (300 MHz, DMSO-$d_6$) 10.76 (bs, 1H), 8.24 (s, 1H), 7.79 (d, 2H), 7.71 (s, 1H), 7.62-7.55 (m, 1H), 7.53-7.47 (m, 1H), 7.44-7.36 (m, 2H), 7.06 (t, 1H) 4.73-4.59 (m, 1H), 3.61-3.54 (m, 5H), 2.43-2.29 (m, 1H), 2.14-1.95 (m, 7H), 1.55-1.39 (m, 3H).

EXAMPLE 61

This example was prepared by substituting EXAMPLE 58D and trans-3-iodo-1-(4-(2-methoxyethoxy)cyclohexyl)-1H-pyrazolo[3,4-d]pyrimidin-4-ylamine, prepared as described in WO 05/074603, for EXAMPLE 2A and cis-4-(4-(4-amino-3-iodopyrazolo[3,4-d]pyrimidin-1-yl)cyclohexyl)-1-methylpiperazin-2-one, respectively, in EXAMPLE 2B. $^1$H NMR (300 MHz, DMSO-$d_6$) 10.76 (bs, 1H), 8.24 (s, 1H), 7.79 (d, 2H), 7.71 (s, 1H), 7.61-7.56 (m, 1H), 7.53-7.48 (m, 1H), 7.40 (t, 2H), 7.06 (t, 1H) 4.76-4.63 (m, 1H), 3.61-3.54 (m, 2H), 3.48-3.43 (m, 2H), 3.26 (s, 3H), 2.20-1.91 (m, 6H), 1.50-1.34 (m, 3H).

EXAMPLE 62

This example was prepared by substituting 2-choro-6-fluorophenylacetaldehyde for benzaldehyde in EXAMPLE 7B. $^1$H NMR (300 MHz, DMSO-$d_6$) 12.51 (bs, 1H), 8.22 (s, 1H), 7.73-7.55 (m, 3H), 7.48-7.36 (m, 4H), 7.35-7.26 (m, 1H), 4.72-4.58 (m, 1H), 4.40-4.35 (m, 2H), 3.62-3.53 (m, 5H), 2.42-2.29 (m, 1H), 2.11-1.92 (m, 6H), 1.57-1.37 (m, 3H).

EXAMPLE 63A

To 4-bromoindole (400 mg) in DMF (5 mL) at 0° C. was added 60% oily sodium hydride (88 mg). The mixture was stirred for 5 minutes, warmed to ambient temperature, stirred for 10 minutes, cooled in an ice bath, treated with 2-chlorobenzylbromide, stirred at ambient temperature for 16 hours and partitioned between ethyl acetate and brine. The extract was washed with brine and dried ($Na_2SO_4$), filtered and concentrated.

EXAMPLE 63B

A mixture of EXAMPLE 63A (640 mg), dichloro(1,1'-bis(diphenylphosphino)-ferrocene) palladium(II).dichloromethane (44 mg), bis(pinacolato)diboron (1.52 g) and potassium acetate (980 mg) in DMF (8 mL) at 100° C. was stirred for 16 hours and partitioned between ethyl acetate and brine. The extract washed with brine and dried (MgSO$_4$), filtered and concentrated. The concentrate was flash chromatographed on silica gel with 5% ethyl acetate/hexanes.

EXAMPLE 63C

A mixture of EXAMPLE 63B (138 mg), cis-3-iodo-1-(4-morpholin-4-yl-cylohexyl)-1H-pyrazolo[3,4-d]pyrimidin-4-ylamine, prepared as described in WO 05/074603 (0.11 g), sodium carbonate (53 mg) and teterakis(Ph$_3$P) palladium(0) (17 mg) in of 1:1 1,2-dimethoxyethane:water (2 mL) at 130° C. was stirred for 20 minutes in a microwave reactor and partitioned between ethyl acetate and brine. The extract washed with brine and dried (Na$_2$SO$_4$), filtered and concentrated. The concentrate was purified by HPLC (column: phenomenex, 00F-4253-U0, micron, C-18, 150×30 mm; solvent A: 100% water with 0.1% TFA, solvent B: 100% acetonitrile with 0.1% TFA; gradient 20-60% B over 25 minutes). Fractions with product were lyophilized. $^1$H NMR (300 MHz, DMSO-d$_6$) 9.63 (bs 1H), 8.33 (s, 1H), 7.52-7.58 (m, 3H), 7.22-7.36 (m, 4H), 6.76 (dd, 1H), 6.65 (d, 1H), 5.61 (s, 2H), 4.77-4.88 (m, 1H), 4.00-4.08 (m, 3H), 3.41-3.52 (m, 4H), 3.10-3.24 (m, 3H), 2.22-2.33 (m, 2H), 2.09-2.21 (m, 3H), 1.70-1.84 (m. 2H).

EXAMPLE 64

This example was prepared by substituting 6-bromoindole for 4-bromoindole in EXAMPLE 63A. $^1$H NMR (300 MHz, DMSO-d$_6$) 9.83 (bs. 1H), 8.36 (s, 1H), 7.78 (d, 1H), 7.65 (s, 1H), 7.59 (d, 1H), 7.51 (dd, 1H), 7.22-7.38 (m, 3H), 6.73 (dd, 1H), 6.66 (d, 1H), 5.59 (s, 2H), 4.73-4.82 (m, 1H), 4.00-4.08 (m, 3H), 3.66-3.75 (m, 2H), 3.37-3.50 (m, 3H), 3.17 (br.m, 2H), 2.22-2.28 (m, 2H), 2.07-2.16 (m, 3H), 1.70-1.81 (m. 2H).

EXAMPLE 65

This example was prepared by substituting 5-bromoindole for 4-bromoindole in EXAMPLE 63A $^1$H NMR (300 MHz, DMSO-d$_6$) 9.86 (bs. 1H), 8.38 (s, 1H), 7.88 (d, 1H), 7.56-7.63 (m, 2H), 7.54 (dd, 1H), 7.42 (dd, 1H), 7.31-7.36 (m, 1H), 7.24-7.28 (m, 1H), 6.81 (dd, 1H), 6.67 (d, 1H), 5.59 (s, 2H), 4.74-4.83 (m, 1H), 4.00-4.08 (m, 3H), 3.66-3.76 (m, 2H), 3.39-3.49 (m, 2H), 3.11-3.22 (br.m, 2H), 3.01-3.07 (t, 1H), 2.22-2.29 (m, 2H), 2.09-2.18 (m, 3H), 1.72-1.82 (m. 2H).

EXAMPLE 66

This example was prepared by substituting 5-bromoindole and 3-chlorobenzylbromide for 4-bromoindole and 2-chlorobenzylbromide, respectively, in EXAMPLE 53A. $^1$H NMR (300 MHz, DMSO-d$_6$) 9.71 (bs. 1H), 8.34 (s, 1H), 7.85 (d, 1H), 7.64-7.69 (m, 2H), 7.31-7.44 (m, 4H), 7.20-7.25 (m, 1H), 6.81 (dd, 1H), 6.65 (d, 1H), 5.51 (s, 2H), 4.72-4.83 (m, 1H), 4.00-4.08 (m, 3H), 3.70 (t, 2H), 3.38-3.49 (m, 2H), 3.10-3.22 (br.m, 2H), 3.01-3.07 (t, 1H), 2.22-2.29 (m, 2H), 2.06-2.17 (m, 3H), 1.69-1.82 (m. 2H).

EXAMPLE 67A

A mixture of 2-amino-4-chlorophenol (1.44 g), triethylamine (1.74 mL), and phenylacetyl chloride (1.32 mL) in of dichloromethane (30 mL) was stirred for 16 hours and treated with ethyl acetate and brine. The extract washed with water, brine, 10% sodium bicarbonate, brine, 10% potassium hydrogen sulfate and brine and dried (Na$_2$SO$_4$) filtered and concentrated. The concentrate was recrystallized from ethyl acetate.

EXAMPLE 67B

EXAMPLE 67A (0.65 g), triphenylphosphine (980 mg) and diethylazodicarboxylate (0.59 mL) in of THF (15 mL) were stirred for 16 hours and concentrated. The concentrate was flash chromatographed on silica gel with 20% ethyl acetate in hexanes.

EXAMPLE 67C

A mixture of EXAMPLE 67B (244 mg), bis(dibenzylideneacetone)palladium(0) (16.3 mg), tricyclohexylphosphine (20 mg), bis(pinacolato)diboron (383 mg) and potassium acetate (150 mg) in dioxane (4 mL) was heated twice at 130° C. for 50 minutes and partitioned between ethyl acetate and brine. The extract washed with brine and dried (Na$_2$SO$_4$), filtered and concentrated. The concentrate was flash chromatographed on silica gel with 5% ethyl acetate in hexanes.

EXAMPLE 67D

This example was prepared by substituting EXAMPLE 67C for N-(2-chlorobenzyl)-4-(4,4,5,5-tetramethyl(1,3,2)dioxaborolan-2-yl)indole in EXAMPLE 53C.

EXAMPLE 68A

A mixture of 6-bromo-1H-indazole (1 g), bis(pinacolato) diboron (3.87 g), potassium acetate (2.49 g), dichloro(1,1'-bis(diphenylphosphino)ferrocene) palladium(II) (112 mg) in DMF (20 mL) was stirred at 100° C. for 18 hours, cooled and extracted with ethyl acetate. The extract washed with brine, dried (Na$_2$SO$_4$), filtered and concentrated. The concentrate was flash chromatographed on silica gel twice with 15% ethyl acetate/hexanes.

EXAMPLE 68B

A mixture of EXAMPLE 68A (122 mg), potassium carbonate (415 mg), and 2-chlorobenzylbromide (0.136 mL) in acetone (10 mL) at reflux was stirred for 2 days and extracted with ethyl acetate. The extract washed with brine and dried (Na$_2$SO$_4$), filtered and concentrated. The concentrate was flash chromatographed on silica gel with 5% ethyl acetate/hexanes.

EXAMPLE 68C

This example was prepared by substituting EXAMPLE 68B for N-(2-chlorobenzyl)-4-(4,4,5,5-tetramethyl(1,3,2)dioxaborolan-2-yl)indole in EXAMPLE 63C. $^1$H NMR (300 MHz, DMSO-d$_6$) 9.70 (bs. 1H), 8.33 (s, 1H), 8.26 (d, 1H), 7.98 (d, 1H), 7.91 (s, 1H), 7.45-7.52 (m, 2H), 7.23-7.36 (m, 2H), 6.88 (dd, 1H), 5.80 (s, 2H), 4.74-4.84 (m, 1H), 4.00-4.08 (m, 3H), 3.70 (t, 2H), 3.39-3.49 (m, 2H), 3.10-3.22 (br.m, 2H), 2.20-2.29 (m, 2H), 2.08-2.17 (m, 3H), 1.792-1.82 (m. 2H).

EXAMPLE 69A

This example was prepared by substituting 3-chlorobenzylbromide for 2-chlorobenzylbromide in EXAMPLE 68B.

EXAMPLE 69B

This example was prepared by substituting EXAMPLE 69A for N-(2-chlorobenzyl)-4-(4,4,5,5-tetramethyl(1,3,2)dioxaborolan-2-yl)indole in EXAMPLE 63C. $^1$H NMR (300 MHz, DMSO-$d_6$) 9.68 (bs. 1H), 8.33 (s, 1H), 8.25 (d, 1H), 7.94-7.97 (m, 2H), 7.43 (dd, 1H), 7.32-7.37 (m, 3H), 7.17-7.23 (m, 1H), 5.74 (s, 2H), 4.74-4.84 (m, 1H), 4.00-4.08 (m, 3H), 3.66-3.76 (m, 2H), 3.39-3.50 (m, 2H), 3.11-3.22 (br.m, 2H), 2.22-2.29 (m, 2H), 2.08-2.18 (m, 3H), 1.69-1.82 (m. 2H).

EXAMPLE 70

This example was prepared by substituting 2-amino-5-chlorophenol for 2-amino-4-chlorophenol EXAMPLE 67A. $^1$H NMR (300 MHz, DMSO-$d_6$) 9.64 (bs. 1H), 8.29 (s, 1H), 7.82-7.87 (m, 1H), 7.25-7.32 (m, 5H), 7.15 (d, 1H), 7.05 (dd, 1H), 4.39 (s, 2H), 4.70-4.81 (m, 1H), 4.00-4.08 (m, 3H), 3.66-3.76 (m, 2H), 3.39-3.49 (m, 2H), 3.08-3.24 (br.m, 2H), 2.18-2.29 (m, 2H), 2.03-2.18 (m, 3H), 1.67-1.82 (m. 2H).

EXAMPLE 71A

A mixture of EXAMPLE 68A (73 mg), cis-3-iodo-1-(4-morpholin-4-yl-cylohexyl)-1H-pyrazolo[3,4-d]pyrimidin-4-ylamine, prepared as described in WO 05/074603 (0.11 g), sodium carbonate (53 mg) and teterakis(triphenylphosphine) palladium(0) (17 mg) in 1:1 1,2-dimethoxyethane:water (2 mL) at 130° C. was stirred for 20 minutes in a microwave reactor and partitioned between ethyl acetate and brine. The extract washed with brine and dried ($Na_2SO_4$), filtered and concentrated. The product was purified by HPLC (column: phenomenex, 00F-4253-U0, 10 micron, C-18, 150×30 mm; solvent A; 100% water with 0.1% TFA, solvent B; 100% acetonitrile with 0.1% TFA; gradient 0-50% B over 25 minutes). Fractions containing product were lyophilized. $^1$H NMR (300 MHz, DMSO-$d_6$) 13.24 (br. 1H), 9.66 (bs 1H), 8.32 (s, 1H), 8.17 (d, 1H), 7.93 (dd, 1H), 7.77 (d, 1H), 7.43 (dd, 1H), 4.73-4.84 (m, 1H), 4.00-4.08 (m, 3H), 3.70 (t, 2H), 3.40-3.52 (m, 3H), 3.07-3.23 (m, 2H), 2.21-2.27 (m, 2H), 2.09-2.19 (m, 3H), 1.70-1.84 (m. 2H).

EXAMPLE 71B

A mixture of EXAMPLE 71A (20 mg), 3-fluorobenzyl bromide (0.0072 mL) and potassium carbonate (27 mg) in of acetone (5 mL) at reflux was stirred for 2 days and partitioned between ethyl acetate and brine. The extract washed with brine, and dried ($Na_2SO_4$), filtered and concentrated. The concentrate was purified by HPLC (column: phenomenex, 00F-4253-U0, micron, C-18, 150×30 mm; solvent A; 100% water with 0.1% TFA, solvent B; 100% acetonitrile with 0.1% TFA; gradient 15-70% B over 25 minutes). Fractions containing product were lyophilized.

EXAMPLE 72A

EXAMPLE 43B (0.057 g), methanesulfonyl chloride (0.015 mL) and diisopropylethylamine (0.13 mL) in dichloromethane (3 mL) was stirred for 16 hours, diluted with ethyl acetate and washed with water and brine. The extract was dried, filtered and concentrated. The concentrate was recrystallized from diethyl ether.

EXAMPLE 72B

This example was prepared by substituting EXAMPLE 72A for cis-4-(4-(4-amino-3-iodopyrazolo[3,4-d]pyrimidin-1-yl)cyclohexyl)-1-methylpiperazin-2-one in EXAMPLE 2B.

EXAMPLE 72C

This example was prepared by substituting EXAMPLE 72B for 2-(4-(4-amino-3-(4-amino-3-nitrophenyl)pyrazolo [3,4-d]pyrimidin-1-yl)piperidin-1-yl)acetamide in EXAMPLE 43E. $^1$H NMR (300 MHz, DMSO-$d_6$) 8.31 (s, 1H), 7.91 (s, 1H), 7.85 (d, 1H), 7.72 (d, 1H), 7.43-7.33 (m, 5H), 4.89 (m, 1H), 4.49 (s, 2H), 3.71 (m, 2H), 3.04 (m, 2H), 2.94 (s, 3H), 2.24 (m, 2H), 2.08 (m, 2H).

EXAMPLE 73A

A mixture of 3-iodo-1H-pyrazolo[3,4-d]pyrimidin-4-ylamine (0.12 g), prepared as described in Bioorg Med. Chem. Lett. 2002, 12, 1687-1690, and NaH (0.02 g) in DMF (5 mL) was stirred for 30 minutes at room temperature, treated with 4-nitro-benzenesulfonic acid oxiranylmethyl ester (0.11 g), stirred for stirring 16 hours, partitioned between ethyl acetate and brine and extracted with dichloromethane. The extract was dried o($Na_2SO_4$), filtered and concentrated. The concentrate was purified by reverse phase HPLC with a Shimadzu LC10 HPLC system with a Phenominex Luna 10 micron C18(2) 100 150×30 mm column with 5-45% acetonitrile in water with 0.15% TFA over 25 minutes at a flow rate of 20 mL/min.

EXAMPLE 73B

A mixture of EXAMPLE 73A (0.04 g) and morpholine (0.06 mL) in ethanol (3 mL) was stirred at 90° C. for 18 hours, cooled and partitioned between ethyl acetate and brine. The extract was dried ($Na_2SO_4$), filtered and concentrated.

EXAMPLE 73C

This example was prepared by substituting EXAMPLE 73B for cis-4-(4-(4-amino-3-iodopyrazolo[3,4-d]pyrimidin-1-yl)cyclohexyl)-1-methylpiperazin-2-one in EXAMPLE 2B.

EXAMPLE 73D

This example was prepared by substituting EXAMPLE 73C for 2-(4-(4-amino-3-(4-amino-3-nitrophenyl)pyrazolo [3,4-d]pyrimidin-1-yl)piperidin-1-yl)acetamide in EXAMPLE 43E. $^1$H NMR (300 MHz, DMSO-$d_6$) 9.73 (brs, 1H), 8.32 (s, 1H), 7.88 (s, 1H), 7.82 (d, 1H), 7.68 (d, 1H), 7.42-7.32 (m, 5H), 6.02 (brs, 1H), 4.49 (m, 2H), 4.45 (s, 2H), 4.38 (m, 1H), 3.91 (m, 4H), 3.76 (m, 1H), 3.31 (m, 4H), 3.16 (m, 1H).

EXAMPLE 74

This example was prepared by substituting (2,6-difluorophenyl)acetaldehyde for benzaldehyde in EXAMPLE 7B. $^1$H NMR (300 MHz, DMSO-$d_6$) 12.52 (d, 1H), 8.22 (s, 1H), 7.72-7.56 (m, 2H), 7.46-7.39 (m, 2H), 7.16 (t, 2H), 4.71-4.59 (m, 1H), 4.27 (s, 2H), 3.61-3.55 (brs, 4H), 2.44-2.46 (m, 1H), 2.10-1.94 (m, 6H), 1.54-1.37 (m, 2H).

EXAMPLE 75

This example was prepared by substituting (3-trifluoromethylphenyl)acetaldehyde for benzaldehyde in EXAMPLE 7B. $^1$H NMR (300 MHz, DMSO-$d_6$) 12.52 (bs, 1H), 8.22 (s, 1H), 7.78-7.75 (m, 21H), 7.71-7.55 (m, 5H), 7.46-7.41 (m, 1H), 4.71-4.59 (m, 1H), 4.35 (s, 2H), 3.59-3.56 (brs, 4H), 2.43-2.27 (m, 1H), 2.08-1.943 (m, 6H), 1.54-1.41 (m, 2H).

EXAMPLE 76A

A mixture of 2,4-dimethylaniline (0.51 g), pyridine (1 g), and 4-bromo-2-fluorobenzoylchloride (1 g) in dichloromethane (9 mL) was shaken for 18 hours, quenched with 1N HCl and concentrated. The concentrate was recrystallized from ethyl acetate/hexanes.

EXAMPLE 76B

To a Milestone Microsynth microwave vessel were added $PCl_5$ (0.92 g), EXAMPLE 76A (1.25 g) and toluene (21 mL). The vessel was sealed and heated at 150° C. with a 10 minute ramp time and a 15 minute hold time, cooled and concentrated. The concentrate was immediately dissolved in THF (20 mL) and added to a solution of hydrazine (1.35 g) in THF (20 mL). This mixture was stirred for three days, treated with ethyl acetate, washed with saturated aqueous sodium bicarbonate and brine and dried ($MgSO_4$), filtered and concentrated. The concentrate was flash chromatographed on silica gel with dichloromethane/methanol.

EXAMPLE 76C

A mixture of EXAMPLE 76B (1.3 g) and TEA (1.3 g, 12.6 mL) in acetonitrile (42 mL) in a microwave vessel was stirred in a Milestone Microsynth microwave with a 10 minute ramp time and a 30 minute hold time at 170° C., cooled and concentrated. The concentrate was purified by flash chromatography with dichloromethane/methanol. The soeluant was concentrated, and the concentrate was purified by reverse phase HPLC with $CH_3CN$/water/0.15% TFA.

EXAMPLE 76D

A mixture of bis(pinacolato)diboron (0.87 g), potassium acetate (0.84 g), $PdCl_2(dppf)$·dichloromethane (0.038 g), and EXAMPLE 76C (0.54 g) in DMF (3.5 mL) was stirred at 100° C. for 1-3 days. The mixture was filtered through a silica gel plug with ethyl acetate. The concentrate was flash chromatographed on silica gel with dichloromethane/methanol.

EXAMPLE 76E

A mixture of trans-3-iodo-1-(4-morpholin-4-yl-cyclohexyl)-1H-pyrazolo[3,4-d]pyrimidin-4-ylamine, prepared as described in WO 05/074603, (0.05 g), EXAMPLE 76D (0.055 g), $Na_2CO_3$ (0.025 g), $PdCl_2(PPh_3)_2$ (0.005 g), and DME/water (0.34 mL/0.17 mL). The mixture was sealed and stirred a Personal Chemistry Smith Synthesizer for 20 minutes at 150° C., cooled and concentrated. The concentrate was filtered through a of silica gel plug with ethyl acetate. The eluant was concentrated, and the concentrate was purified by reverse phase HPLC with $CH_3CN$/water/0.15% TFA. $^1$H NMR (300 MHz, DMSO-$d_6$) 12.16 (s, 1H), 9.64 (s, 1H), 8.30 (s, 1H), 7.88 (d, 1H), 7.60 (s, 1H), 7.58 (s, 1H), 7.47 (d, 1H), 7.28 (dd, 1H), 6.98 (s, 1H), 6.90 (dd, 1H), 4.72-4.87 (m, 1H), 4.04 (d, 2H), 3.64-3.76 (m, 2H), 3.46 (d, 3H), 3.09-3.24 (m, 2H), 2.30 (s, 3H), 2.27 (d, 2H), 2.23 (s, 3H), 2.14 (t, 4H), 1.66-1.85 (m, 2H).

EXAMPLE 77

This example was prepared by substituting 2-chloroaniline and 5-bromo-2-fluorobenzoylchloride for 2,4-dimethylaniline and 4-bromo-2-fluorobenzoylchloride, respectively, in EXAMPLE 76A. $^1$H NMR (300 MHz, DMSO-$d_6$) 12.58 (s, 1H), 9.76 (s, 1H), 8.32 (s, 1H), 8.03 (d, 2H), 7.83 (dd, 1H), 7.60-7.64 (m, 2H), 7.42 (dd, 1H), 7.16-7.28 (m, 1H), 6.86 (td, 1H), 4.78 (dt, 2H), 4.04 (d, 2H), 3.70 (t, 2H), 3.43 (t, 3H), 3.06-3.26 (m, 2H), 2.24 (d, 2H), 2.13 (t, 3H), 1.66-1.86 (m, 2H).

EXAMPLE 78

This example was prepared by substituting 3-chloroaniline and 5-bromo-2-fluorobenzoylchloride for 2,4-dimethylaniline and 4-bromo-2-fluorobenzoylchloride, respectively, in EXAMPLE 76A. $^1$H NMR (300 MHz, DMSO-$d_6$) 12.34 (s, 1H), 9.79 (s, 1H), 9.29 (s, 1H), 8.33 (s, 1H), 8.29 (s, 1H), 7.99 (t, 1H), 7.58-7.64 (m, 1H), 7.57 (s, 1H), 7.51-7.56 (m, 1H), 7.29 (t, 1H), 6.85 (dd, 1.70 Hz, 1H), 4.79 (dt, 1H), 4.04 (d, 2H), 3.64-3.76 (m, 2H), 3.47 (t, 3H), 3.09-3.26 (m, 2H), 2.20-2.32 (m, 2H), 2.09-2.20 (m, 4H), 1.64-1.89 (m, 2H).

EXAMPLE 79

This example was prepared by substituting 2-fluoroaniline and 5-bromo-2-fluorobenzoylchloride for 2,4-dimethylaniline and 4-bromo-2-fluorobenzoylchloride, respectively, in EXAMPLE 76A. $^1$H NMR (300 MHz, DMSO-$d_6$) 12.34 (s, 1H), 9.85 (s, 1H), 9.31 (s, 1H), 8.35 (s, 1H), 8.30 (s, 1H), 7.74 (ddd, 1H), 7.52-7.63 (m, 2H), 7.39 (dt, 1H), 7.22-7.34 (m, 1H), 6.53-6.68 (m, 1H), 4.71-4.87 (m, 1H), 4.04 (d, 2H), 3.71 (t, 2H), 3.35-3.54 (m, 3H), 3.07-3.28 (m, 2H), 2.26 (d, 2H), 2.08-2.20 (m, 4H), 1.69-1.86 (m, 2H).

EXAMPLE 80

This example was prepared by substituting 3-nitroaniline and 5-bromo-2-fluorobenzoylchloride for 2,4-dimethylaniline and 4-bromo-2-fluorobenzoylchloride, respectively, in EXAMPLE 76A. $^1$H NMR (300 MHz, DMSO-$d_6$) 12.47 (s, 1H), 9.67 (s, 2H), 8.81 (t, 1H), 8.31 (s, 1H), 8.29 (s, 1H), 8.03 (ddd, 1H), 7.51-7.72 (m, 4H), 4.71-4.86 (m, 1H), 4.05 (d, 2H), 3.69-3.76 (m, 2H), 3.39-3.48 (m, 3H), 3.12-3.25 (m, 2H), 2.25 (ddd, 2H), 2.15 (t, 4H), 1.69-1.86 (m, 2H).

EXAMPLE 81

This example was prepared by substituting ortho-anisidine and 5-bromo-2-fluorobenzoylchloride for 2,4-dimethylaniline and 4-bromo-2-fluorobenzoylchloride, respectively, in EXAMPLE 76A. $^1$H NMR (300 MHz, DMSO-$d_6$) 12.32 (s, 1H), 9.62 (s, 1H), 8.31 (s, 1H), 8.16 (s, 1H), 8.08 (dd, 1H), 7.79 (s, 1H), 7.60 (dd, 1H), 7.55 (d, 1H), 7.00 (dd, 1H), 6.90 (td, 1H), 6.82 (td, 1H), 4.70-4.87 (m, 1H), 4.04 (d, 2H), 3.90 (s, 3H), 3.63-3.75 (m, 2H), 3.44 (t, 3H), 3.16 (q, 2H), 2.19-2.31 (m, 2H), 2.15 (t, 4H), 1.66-1.86 (m, 2H).

EXAMPLE 82

This example was prepared by substituting 3-amino-6-(trifluoromethyl)pyridine and 5-bromo-2-fluorobenzoylchloride for 2,4-dimethylaniline and 4-bromo-2-fluorobenzoylchloride, respectively, in EXAMPLE 76A. $^1$H NMR (300 MHz, DMSO-$d_6$) 12.55 (s, 1H), 9.85 (s, 1H), 9.61 (s, 1H), 8.92 (d, 1H), 8.42-8.49 (m, 1H), 8.30 (s, 2H), 7.82 (d, 1H), 7.64 (dd, 1H), 7.59 (ddd, 1H), 4.79 (ddd, 1H), 4.04 (d, 2H), 3.65-3.75 (m, 2H), 3.46 (d, 3H), 3.12-3.25 (m, 2H), 2.20-2.30 (m, 2H), 2.08-2.20 (m, 4H), 1.69-1.85 (m, 2H).

EXAMPLE 83

This example was prepared by substituting benzylamine for 2,4-dimethylaniline in EXAMPLE 76A. $^1$H NMR (300 MHz, DMSO-$d_6$) 11.64 (s, 1H), 9.62 (s, 2H), 9.31 (s, 1H), 8.93 (d, 1H), 7.39-7.48 (m, 3H), 7.28-7.36 (m, 2H), 7.17-7.27 (m, 2H), 4.70-4.85 (m, 1H), 4.51 (s, 2H), 4.02 (d, 2H), 3.63-3.76 (m, 2H), 3.45 (d, 3H), 3.08-3.24 (m, 2H), 2.19-2.30 (m, 2H), 2.09-2.19 (m, 4H), 1.65-1.85 (m, 2H).

EXAMPLE 84

This example was prepared by substituting 4-(trifluoromethyl)aniline and 5-bromo-2-fluorobenzoylchloride for 2,4-dimethylaniline and 4-bromo-2-fluorobenzoylchloride, respectively, in EXAMPLE 76A. $^1$H NMR (300 MHz, DMSO-$d_6$) 12.43 (s, 1H), 9.72 (s, 2H), 9.52 (s, 1H), 8.30 (s, 1H), 8.29 (s, 1H), 7.86 (d, 2H), 7.57-7.65 (m, 4H), 4.72-4.86 (m, 1H), 4.04 (d, 2H), 3.64-3.78 (m, 2H), 3.39-3.47 (m, 3H), 3.08-3.26 (m, 2H), 2.21-2.31 (m, 2H), 2.09-2.21 (m, 4H), 1.66-1.87 (m, 2H).

EXAMPLE 85

This example was prepared by substituting 4-tert-butylaniline and 5-bromo-2-fluorobenzoylchloride for 2,4-dimethylaniline and 4-bromo-2-fluorobenzoylchloride, respectively, in EXAMPLE 76A. $^1$H NMR (300 MHz, DMSO-$d_6$) 12.14 (s, 1H), 9.68 (s, 1H), 8.90 (s, 1H), 8.31 (s, 1H), 8.29 (s, 1H), 7.60-7.68 (m, 2H), 7.54-7.60 (m, 1H), 7.48-7.54 (m, 1H), 7.25-7.34 (m, 2H), 4.79 (dt, 1H), 4.04 (d, 2H), 3.64-3.76 (m, 2H), 3.36-3.50 (m, 3H), 3.09-3.24 (m, 2H), 2.20-2.31 (m, 2H), 2.10-2.20 (m, 4H), 1.68-1.86 (m, 2H), 1.27 (s, 9H).

EXAMPLE 86

This example was prepared by substituting 3-aminophenol and 5-bromo-2-fluorobenzoylchloride for 2,4-dimethylaniline and 4-bromo-2-fluorobenzoylchloride, respectively, in EXAMPLE 76A. $^1$H NMR (300 MHz, DMSO-$d_6$) 12.16 (s, 1H), 9.63 (s, 1H), 9.16 (s, 1H), 8.85 (s, 1H), 8.28 (s, 2H), 7.54-7.62 (m, 1H), 7.48-7.54 (m, 1H), 7.27-7.31 (m, 1H), 7.00-7.05 (m, 1H), 6.23 (dt, 1H), 4.70-4.85 (m, 1H), 4.04 (d, 2H), 3.70 (t, 2H), 3.40-3.45 (m, 3H), 3.10-3.25 (m, 2H), 2.19-2.30 (m, 2H), 2.09-2.20 (m, 4H), 1.64-1.86 (m, 2H).

EXAMPLE 87

This example was prepared by substituting 2-fluoro-5-methylaniline for 2,4-dimethylaniline in EXAMPLE 76A. $^1$H NMR (300 MHz, DMSO-$d_6$) 12.34 (s, 1H), 9.63 (s, 1H), 8.44 (s, 1H), 8.31 (s, 1H), 8.14 (d, 1H), 7.93 (dd, 1H), 7.62 (s, 1H), 7.33 (dd, 1H), 7.08 (dd, 1H), 6.61-6.69 (m, 1H), 4.80 (dt, 1H), 4.04 (d, 2H), 3.63-3.80 (m, 2H), 3.46 (d, 3H), 3.08-3.26 (m, 2H), 2.26(2, 2H), 2.10-2.25 (m, 4H), 1.67-1.86 (m, 2H).

EXAMPLE 88

This example was prepared by substituting 2,5-dimethylaniline for 2,4-dimethylaniline in EXAMPLE 76A. $^1$H NMR (300 MHz, DMSO-$d_6$) 12.26 (s, 1H), 9.63 (s, 1H), 8.31 (s, 1H), 7.91 (d, 1H), 7.58-7.63 (m, 2H), 7.44 (d, 1H), 7.31 (dd, 1H), 7.03 (d, 1H), 6.63 (dd, 1H), 4.80 (ddd, 1H), 4.51 (s, 2H), 4.04 (dd, 2H), 3.64-3.77 (m, 2H), 3.46 (d, 3H), 3.09-3.27 (m, 2H), 2.30 (s, 3H), 2.22-2.39 (m, 2H), 2.20 (s, 3H), 2.07-2.19 (m, 4H), 1.66-1.85 (m, 2H).

EXAMPLE 89

This example was prepared by substituting 2,5-difluoroaniline for 2,4-dimethylaniline in EXAMPLE 76A. $^1$H NMR (300 MHz, DMSO-$d_6$) 12.50 (s, 1H), 9.63 (s, 1H), 8.89 (s, 1H), 8.31 (s, 1H), 8.21 (d, 1H), 8.06(ddd, 1H), 7.64 (s, 1H), 7.36 (dd, 1H), 7.25 (ddd, 1H), 6.59-6.69 (m, 1H), 4.72-4.88 (m, 1H), 4.04 (d, 2H), 3.65-3.76 (m, 2H), 3.46 (d, 3H), 3.08-3.25 (m, 2H), 2.25 (dd, 2H), 2.15 (t, 4H), 1.67-1.89 (m, 2H).

EXAMPLE 90

This example was prepared by substituting 4-fluoro-2-methylaniline for 2,4-dimethylaniline in EXAMPLE 76A. $^1$H NMR (300 MHz, DMSO-$d_6$) 12.18 (s, 1H), 9.65 (s, 1H), 8.31 (s, 1H), 7.91 (d, 1H), 7.72 (s, 1H), 7.56-7.64 (m, 2H), 7.30 (dd, 1H), 7.05 (dd, 1H), 6.94 (td, 1H), 4.71-4.89 (m, 1H), 4.04 (d, 2H), 3.69-3.84 (m, 2H), 3.48 (m, 3H), 3.08-3.25 (m, 2H), 2.35 (s, 3H), 2.20-2.31 (m, 2H), 2.07-2.20 (m, 4H), 1.67-1.89 (m, 2H).

EXAMPLE 91A

4-Bromo-ortho-phenylenediamine (1 g) and sodium carbonate (0.28 g) in ethyl acetate (5.5 mL) was treated with 1,1-dichloro-1,1-dipenoxymethane (1.44 g) in ethyl acetate (2.7 mL). The mixture was stirred for 5 hours and filtered. The filtrate was concentrated, and the concentrate was recystallized from ethyl acetate/hexanes.

EXAMPLE 91B

This example was prepared by substituting EXAMPLE 91A for 6-bromo-1H-indazol-3-yl-(2,4-dimethylphenyl)amine in EXAMPLE 76D. $^1$H NMR (300 MHz, DMSO-$d_6$) (s, 1H), 9.65 (s, 1H), 8.29 (s, 1H), 7.60 (d, 1H), 7.53 (d, 1H), 7.46-7.52 (m, 3H), 7.38-7.44 (m, 3H), 7.31 (tt, 1H), 4.77 (ddd, 1H), 4.04 (d, 2H), 3.64-3.75 (m, 2H), 3.44 (t, 3H), 3.08-3.24 (m, 2H), 2.19-2.32 (m, 2H), 2.08-2.18 (m, 4H), 1.65-1.84 (m, 2H).

EXAMPLE 92

3-(2-benzyl-1H-benzimidazol-5-yl)-1-(1-(methylsulfonyl)piperidin-4-yl)-1H-pyrazolo[3,4-d]pyrimidin-4-amine

EXAMPLE 92A

This compound was prepared by substituting methanesulfonyl chloride for iodoacetamide in EXAMPLE 43C.

EXAMPLE 92B

This compound was prepared by substituting EXAMPLE 92A for (cis)-4-(4-(-4-amino-3-iodo-pyrazolo[3,4-d]pyrimidin-1-yl)-cyclohexyl)-1 methyl-piperazin-2-one in EXAMPLE 2B.

EXAMPLE 92C

This compound was prepared by substituting EXAMPLE 92B for EXAMPLE 43D in EXAMPLE 43E. $^1$H NMR (300 MHz, DMSO-$d_6$) 8.31 (s, 1H), 7.91 (s, 1H), 7.85 (d, 1H), 7.72 (d, 1H), 7.43-7.33 (m, 5H), 4.89 (m, 1H), 4.49 (s, 2H), 3.71 (m, 2H), 3.04 (m, 2H), 2.94 (s, 3H), 2.24 (m, 2H), 2.08 (m, 2H).

EXAMPLE 93

(trans)-3-(1-(2-chlorobenzyl)-1H-indol-5-yl)-1-(4-morpholin-4-ylcyclohexyl)-1H-pyrazolo[3,4-d]pyrimidin-4-amine

EXAMPLE 93A

The desired product was synthesized as described in EXAMPLES 63A and 63B by substituting 5-bromo-indole for 4-bromoindole in EXAMPLE 63A. $^1$H NMR (300 MHz, DMSO-$d_6$) 7.99 (s, 1H), 7.17-7.52 (m, 6H), 6.59 (m, 2H), 5.53 (s, 2H), 1.30 (s, 12H).

EXAMPLE 93B trans-3-Iodo-1-(4-morpholin-4-yl-cyclohexyl)-1H-pyrazolo[3,4-d]pyrimidin-4-ylamine prepared as described in PTC Patent Application WO 2005/074603, 224 mg, 0.5 mmol), EXAMPLE 93A (220 mg, 0.5 mmol), sodium carbonate (106 mg, 1 mmol), and Pd((PPh$_3$)$_4$) (34 mg), were placed into microwave tube and 4 mL of DME:water (1:1) was added. It was microwaved at 130° C. for 20 minutes. After partitioning between ethyl acetate and brine, the ethyl acetate layer washed with brine (3×), dried and purified by HPLC to provide 360 mg of the title compound. $^1$H NMR (300 MHz, DMSO-$d_6$) 9.67 (br.s, 1H), 8.33 (s, 1H), 7.88 (br.s, 1H), 7.25-7.43 (m, 3H), 7.46 (dd, 1H), 7.23-7.36 (m, 2H), 6.79 (dd, 1H), 6.66 (d, 1H), 5.59 (s, 2H), 4.78 (br. m, 1H), 4.04 (br.d., 2H), 3.70 (br.t, 2H), 3.46 (s, 3H), 3.17 (br.m., 2H), 2.24 (m, 2H), 2.08-2.17 (br.m., 4H), 1.66-1.84 (br, m, 2H).

EXAMPLE 94

(trans)-3-(1-(2-chlorobenzyl)-1H-indazol-6-yl)-1-(4-morpholin-4-ylcyclohexyl)-1H-pyrazolo[3,4-d]pyrimidin-4-amine

EXAMPLE 94A

The desired product was synthesized by substituting 3-fluorobenzyl bromide for 2-chlorobenzyl bromide in EXAMPLE 121B.

EXAMPLE 94B

The desired product was synthesized by substituting EXAMPLE 94A for EXAMPLE 121B in EXAMPLE 121C. $^1$H NMR (300 MHz, DMSO-$d_6$) 9.76 (br.s, 1H), 8.38 (s., 1H), 8.27 (s, 1H), 8.05 (d., 1H), 7.93 (d., 1H), 7.69 (dd., 1H), 7.35-7.42 (m., 1H), 7.08-7.14 (m., 3H), 5.76 (s, 2H), 4.80 (m., 1H), 3.98-4.09 (m., 2H), 3.64-3.76 (br. t., 2H), 3.35-3.50 (m., 3H), 3.08-3.24 (m, 2H), 2.19-2.30 (m, 2H), 2.06-2.17 (br.m., 4H), 1.68-1.83 (br, m, 2H).

EXAMPLE 95

3-(2-benzyl-1H-benzimidazol-6-yl)-1-(2-morpholin-4-ylethyl)-1H-pyrazolo[3,4-d]pyrimidin-4-amine

EXAMPLE 95A

This compound was prepared by substituting N-(2-hydroxy-ethyl)morpholine for 3-hydroxy-pyrrolidine-1-carboxylic acid tert-butyl ester in EXAMPLE 52A. $^1$H NMR (400 MHz, DMSO-$d_6$) 8.20 (s, 1H); 4.38 (t, 2H); 3.47 (m, 4H); 2.72 (t, 2H); 2.40 (m, 4H).

EXAMPLE 95B 3-(2-benzyl-1H-benzimidazol-6-yl)-1-(2-morpholin-4-ylethyl)-1H-pyrazolo[3,4-d]pyrimidin-4-amine EXAMPLE 95A (93 mg, 0.25 mmole), EXAMPLE 188C (85 mg, 0.15 mmole) and CsF (113 mg, 0.75 mmole) were mixed with DME (3 mL) and MeOH (2 mL). The mixture was purged with argon and Pd(PPh$_3$)$_4$ (15 mg) was added. The sealed vessel was heated at 150° C. for 5 minutes on a Personal Chemistry microwave instrument. To the reaction mixture was added water (10 mL) and the mixture was then extracted with EtOAc. The EtOAc solution was dried, filtered and concentrated. The residue was taken up in 1 N HCl (20 mL) and washed with EtOAc. The aqueous solution was then neutralized to pH ~13 with saturated aq. NaOH, then extracted with EtOAc. The EtOAc solution was dried, filtered and evaporated to give the title compound as a white solid. $^1$H NMR (400 MHz, DMSO-$d_6$) 12.45 (s, 1H); 8.23 (s, 1 h); 7.66 (d, 1 h); 7.44 (d, 1H); 7.29-7.36 (m, 6 h); 4.45 (t, 2H); 4.20 (s, 2H), 3.49 (m, 4H); 2.80 (t, 2H); 2.44 (m, 4H).

EXAMPLE 96

3-(2-benzyl-1H-benzimidazol-6-yl)-1-(1-pyrimidin-2-ylpiperidin-4-yl)-1H-pyrazolo[3,4-d]pyrimidin-4-amine

EXAMPLE 96A

This compound was prepared by substituting N-(2-pyrimidinyl)-4-hydroxy-piperidine for 3-hydroxy-pyrrolidine-1-carboxylic acid tert-butyl ester in EXAMPLE 52A. $^1$H NMR (400 MHz, DMSO-$d_6$) 8.38 (d, 2H); 8.20 (s, 1H); 6.65 (t, 1H); 4.96 (m, 1H); 4.77 (m, 2H), 3.14 (m, 2H); 1.94-1.99 (m, 4H).

EXAMPLE 96B 3-(2-benzyl-1H-benzimidazol-6-yl)-1-(1-pyrimidin-2-ylpiperidin-4-yl)-1H-pyrazolo[3,4-d]pyrimidin-4-amine EXAMPLE 96A (105 mg, 0.25 mmole), EXAMPLE 188C (85 mg, 0.15 mmole) and CsF (113 mg, 0.75 mmole) were mixed with DME (3 mL) and MeOH (2 mL). The mixture was purged with argon and Pd(PPh$_3$)$_4$ (15 mg) was added. The sealed vessel was heated at 150° C. for 5 minutes on a Personal Chemistry microwave instrument. The reaction mixture was subjected to aqueous work-up and the crude product was purified by reverse-phase HPLC using a TFA buffered mobile phase, giving the TFA salt of the title compound as a white solid. 111 mg, 85% yield. $^1$H NMR (400 MHz, DMSO-$d_6$) 8.42 (s, 1H); 8.40 (d, 2H); 7.94 (s, 1 h); 7.87 (d, 1H); 7.75 (dd, 1H); 7.40-7.45 (m, 5H); 5.09-5.15 (m, 1H); 4.82 (m, 2H); 3.16-3.23 (m, 2H); 2.05-2.11 (m, 4H).

EXAMPLE 97

(trans)-3-(2-(2,3-difluorobenzyl)-1H-benzimidazol-6-yl)-1-(4-morpholin-4-ylcyclohexyl)-1H-pyrazolo[3,4-d]pyrimidin-4-amine This example was prepared as described in EXAMPLE 7 by substituting 2,3-difluorophenylacetaldehyde for benzaldehyde in EXAMPLE 7B. $^1$H NMR (400 MHz, DMSO) (s, 1H), 8.23 (s, 1H), 7.67-7.19 (m, 8H), 4.65 (m, 1H), 4.32 (s, 2H), 3.60 (bs, 4H), 2.51 (bs, 4H), 2.00 (m, 7H), 1.50 (m, 2H).

EXAMPLE 98

(trans)-3-(2-[3,4-d]fluorobenzyl)-1H-benzimidazol-6-yl)-1-(4-morpholin-4-ylcyclohexyl)-1H-pyrazolo[3,4-d]pyrimidin-4-amine This example was prepared as described in EXAMPLE 7 by substituting 3,4-difluorophenylacetaldehyde for benzaldehyde in EXAMPLE 7B. MS ((+)-ESI) 545.3 m/z (M+H)$^{30}$; $^1$H NMR (400 MHz, DMSO) (s, 1H), 8.22 (s, 1H), 7.49-7.21 (m, 8H), 4.65 (m, 1H), 4.24 (s, 2H), 3.58 (bs, 4H), 1.99 (m, 7H), 1.47 (m, 2H).

EXAMPLE 99

(trans)-3-(2-(3,5-difluorobenzyl)-1H-benzimidazol-6-yl)-1-(4-morpholin-4-ylcyclohexyl)-1H-pyrazolo[3,4-d]pyrimidin-4-amine This example was prepared as described in EXAMPLE 7 by substituting 3,5-difluorophenylacetaldehyde for benzaldehyde in EXAMPLE 7B. MS ((+)-ESI) 545.4 m/z (M+H)$^+$; $^1$H NMR (400 MHz, DMSO) (bs, 1H), 8.23 (s, 1H), 7.72-7.10 (m, 8H), 4.65 (m, 1H), 4.28 (s, 2H), 3.58 (bs, 4H), 2.00 (m, 7H), 1.47 (m, 2H).

EXAMPLE 100

(trans)-3-(2-benzyl-1H-benzimidazol-5-yl)-1-(4-{(2-(methylsulfonyl)ethyl)amino}cyclohexyl)-1H-pyrazolo[3,4-d]pyrimidin-4-amine This example was prepared by substituting 2-(methanesulfonyl)ethylamine for 3-hydroxyproline in EXAMPLE 3° C. The earlier eluting isomer was isolated. MS (ESI) m/e 545 (M+H)$^-$; $^1$H NMR (300 MHz, DMSO-d$_6$) δ8.74 (bs, 2H), 8.29 (s, 1H), 7.85 (s, 1H), 7.81 (d, 1H), 7.64 (d, 1H), 7.41-7.33 (m, 5H), 4.76 (m, 1H), 4.44 (s, 2H), 3.51 (m, 2H), 3.42 (m, 2H), 3.32 (m, 1H), 3.16 (s, 3H), 2.22 (m, 2H), 2.10 (m, 4H), 1.64 (m, 2H).

EXAMPLE 101

(cis)-3-(2-benzyl-1H-benzimidazol-5-yl)-1-(4-{(2-(methylsulfonyl)ethyl)amino}cyclohexyl)-1H-pyrazolo[3,4-d]pyrimidin-4-amine This compound was obtained as the slower eluting diastereomer in EXAMPLE 100. MS (ESI) m/e 545 (M+H)$^-$; $^1$H NMR (300 MHz, DMSO-d$_6$) δ8.61 (bs, 2H), 8.29 (s, 1H), 7.86 (s, 1H), 7.78 (d, 1H), 7.64 (d, 1H), 7.40-7.32 (m, 5H), 4.90 (m, 1H), 4.39 (s, 2H), 3.50 (m, 2H), 3.41 (m, 3H), 3.13 (s, 3H), 2.33 (m, 3H), 1.98 (m, 5H).

EXAMPLE 102

3-(2-benzyl-1H-benzimidazol-5-yl)-1-(4-(1,1-dioxidothiomorpholin-4-yl)cyclohexyl)-1H-pyrazolo[3,4-d]pyrimidin-4-amine This example was prepared as a mixture of diastereomers by substituting dioxothiomorpholine for 3-hydroxyproline in EXAMPLE 31C. MS (ESI) m/e 557 (M+H)$^-$; $^1$H NMR (300 MHz, DMSO-d$_6$) δ8.32 (s, 1H), 7.91 (s, 1H), 7.86 (m, 1H), 7.71 (m, 1H), 7.43-7.33 (m, 5H), 4.95 & 4.73 (m, 1H), 4.49 (s, 2H), 3.37 (m, 9H), 2.32 (m, 2H), 2.07 (m, 3H), 1.85-1.71 (m, 3H).

EXAMPLE 103

3-(2-benzyl-1H-benzimidazol-5-yl)-1-(4-({(2-(methylsulfonyl)ethyl)amino}methyl)phenyl)-1H-pyrazolo[3,4-d]pyrimidin-4-amine

EXAMPLE 103A

This example was prepared by substituting 2-(methanesulfonyl)ethylamine for morpholine in EXAMPLE 48B.

EXAMPLE 103B

This example was prepared by substituting EXAMPLE 103A for (cis)-4-(4-(-4-amino-3-iodo-pyrazolo[3,4-d]pyrimidin-1-yl)-cyclohexyl)-1 methyl-piperazin-2-one in EXAMPLE 2B.

EXAMPLE 103C

This example was prepared by substituting EXAMPLE 103B for EXAMPLE 48C in EXAMPLE 48D. MS (ESI) m/e 553 (M+H)$^-$; $^1$H NMR (300 MHz, DMSO-d$_6$) δ9.06 (bs, 2H), 8.41 (s, 1H), 8.36 (d, 2H), 7.95 (s, 1H), 7.82 (d, 1H), 7.71 (m, 3H), 7.41-7.33 (m, 5H), 4.42 (s, 2H), 4.30 (m, 2H), 3.43 (m, 4H), 3.15 (s, 3H).

EXAMPLE 104

(trans)-2-(4-(4-{4-amino-3-(2-(2-fluorobenzyl)-1H-benzimidazol-5-yl)-1H-pyrazolo[3,4-d]pyrimidin-1-yl}cyclohexyl)piperazin-1-yl)ethanol

EXAMPLE 104A

This example was prepared by substituting EXAMPLE 31A and 2-fluorophenyl acetaldehyde for EXAMPLE 7A and benzaldehyde, respectively, in EXAMPLE 7B.

EXAMPLE 104B

This example was prepared by substituting EXAMPLE 104A and 1-(2-hydroxyethyl)piperazine for EXAMPLE 31B and 3-hydroxypyrrolidine, respectively, in EXAMPLE 31C. The faster eluting diastereomer was isolated. MS (ESI) m/e 570 (M+H)$^-$; $^1$H NMR (300 MHz, DMSO-d$_6$) δ8.30 (s, 1H), 7.82 (s, 1H), 7.76 (d, 1H), 7.60 (d, 1H), 7.49 (m, 1H), 7.39 (m, 1H), 7.26 (m, 2H), 4.77 (m, 1H), 4.45 (s, 2H), 3.71-3.61 (m, 8H), 3.11 (m, 5H), 2.11 (m, 6H), 1.70 (m, 2H).

EXAMPLE 105

(cis)-2-(4-(4-{4-amino-3-(2-(2-fluorobenzyl)-1H-benzimidazol-5-yl)-1H-pyrazolo[3,4-d]pyrimidin-1-yl}cyclohexyl)piperazin-1-yl)ethanol This example is the slower eluting isomer in EXAMPLE 104. MS (ESI) m/e 570 (M+H)$^-$;

$^1$H NMR (300 MHz, DMSO-d$_6$) δ8.30 (s, 1H), 7.81 (s, 1H), 7.74 (d, 1H), 7.58 (d, 1H), 7.47 (m, 1H), 7.39 (m, 1H), 7.25 (m, 2H), 4.91 (m, 1H), 4.41 (s, 2H), 3.71-3.56 (m, 8H), 3.10 (m, 5H), 2.35 (m, 2H), 2.07 (m, 3H), 1.85 (m, 3H).

EXAMPLE 106

(trans)-3-(2-(2-chloro-3-fluorophenyl)-1H-benzimidazol-6-yl)-1-(4-morpholin-4-ylcyclohexyl)-1H-pyrazolo[3,4-d]pyrimidin-4-amine This example was prepared as described in EXAMPLE 7 by substituting 2-chloro-3-fluorobenzaldehye for benzaldehyde in EXAMPLE 7B. (ESI(+)) m/e 547 (M+H)$^+$; $^1$H NMR (300 MHz, DMSO-d$_6$) 12.98 (bs, 1H); 8.24 (s, 1H); 7.88-7.85 (bm, 1H); 7.83-7.78 (m, 2H); 7.63-7.54 (m, 3H); 4.67 (m, 1H); 3.60-3.57 (bm, 5H); 2.45-2.34 (m, 2H); 2.09-1.96 (m, 8H) 1.53-1.44 (m, 2H).

EXAMPLE 107

(trans)-1-(4-morpholin-4-ylcyclohexyl)-3-{2-(3-(trifluoromethyl)benzyl)-1H-benzimidazol-6-yl}-1H-pyrazolo[3,4-d]pyrimidin-4-amine This example was prepared as described in EXAMPLE 7 by substituting 2-(3-(trifluoromethyl)phenyl)acetaldehyde for benzaldehyde in EXAMPLE 7B. (ESI(+)) m/e 577 (M+H)$^+$; $^1$H NMR (300 MHz, DMSO-d$_6$) 12.52 (s, 1H); 8.22 (s, 1H); 7.76 (s, 1H); 7.70-7.56 (m, 5H); 7.43 (d, 1H); 4.65 (m, 1H); 4.35 (s, 2H); 3.57 (m, 4H); 2.43-2.31 (m, 2H); 2.08-1.95 (m, 7H); 1.50-1.41 (m, 2H).

EXAMPLE 108

N-{4-(4-amino-3-(2-benzyl-1H-benzimidazol-5-yl)-1H-pyrazolo[3,4-d]pyrimidin-1-yl)cyclohexyl}methanesulfonamide

EXAMPLE 108A

This compound was prepared by substituting EXAMPLE 31A for EXAMPLE 31B and ammonium acetate for 3-hydroxypyrrolidine in EXAMPLE 31C. MS (ESI) m/e 359 (M+H); $^1$H NMR (300 MHz, DMSO-d$_6$) 8.21 (s, 1H), 7.84 (m, 4H), 4.74 & 4.60 (m, 1H), 3.36 & 3.17 (m, 1H), 2.23 (m, 1H), 2.02 (m, 4H), 1.87 (m, 2H), 1.54 (m, 1H).

EXAMPLE 108B

This compound was prepared by substituting EXAMPLE 108A for EXAMPLE 43B in EXAMPLE 72A MS (ESI) m/e 437 (M+H); $^1$H NMR (300 MHz, DMSO-d$_6$) 8.19 (s, 1H), 7.08 (m, 1H), 4.68-4.52 (m, 1H), 3.35 & 3.25 (m, 1H), 2.93 & 2.94 (s, 3H), 2.25 (m, 1H), 2.02 (m, 2H), 1.91 (m, 2H), 1.72 (m, 1H), 1.46 (m, 1H), 1.16 (m, 1H).

EXAMPLE 108C

This example was prepared by substituting EXAMPLE 188C for EXAMPLE 63B and EXAMPLE 108B for (cis)-3-iodo-1-(4-morpholin-4-yl-cylohexyl)-1H-pyrazolo[3,4-d]pyrimidin-4-ylamine, respectively in EXAMPLE 63C. MS (ESI) m/e 517 (M+H)$^-$; $^1$H NMR (300 MHz, DMSO-d$_6$) δ8.30 (s, 1H), 7.89 (s, 1H), 7.84 (d, 1H), 7.70 (d, 1H), 7.43-7.33 (m, 5H), 7.11 (d, 1H), 4.68 (m, 1H), 4.48 (s, 2H), 3.17 (m, 1H), 2.95 (s, 3H), 2.15-1.95 (m, 6H), 1.51 (m, 2H).

EXAMPLE 109 ethyl 4-(4-amino-3-(2-benzyl-1H-benzimidazol-5-yl)-1H-pyrazolo[3,4-d]pyrimidin-1-yl)cyclohexylcarbamate

EXAMPLE 109A

This compound was prepared by substituting EXAMPLE 108A for EXAMPLE 43B and ethyl chloroformate for methanesulfonyl chloride in EXAMPLE 72A.

EXAMPLE 109B

This example was prepared by substituting EXAMPLE 188C for EXAMPLE 63B and EXAMPLE 109A for (cis)-3-iodo-1-(4-morpholin-4-yl-cylohexyl)-1H-pyrazolo[3,4-d]pyrimidin-4-ylamine, respectively in EXAMPLE 63C. MS (ESI) m/e 511 (M+H)$^-$; $^1$H NMR (300 MHz, DMSO-d$_6$) δ8.30 (s, 1H), 7.90 (s, 1H), 7.84 (d, 1H), 7.71 (m, 2H), 7.42-7.33 (m, 5H), 4.71 (m, 1H), 4.49 (s, 2H), 3.98 (m, 2H), 2.0 (m, 5H), 1.78 (m, 2H), 1.40 (m, 1H), 1.15 (m, 3H).

EXAMPLE 110

3-(2-benzyl-1H-benzimidazol-5-yl)-1-{1-(2-(methylsulfonyl)ethyl)pyrrolidin-3-yl}-1H-pyrazolo[3,4-d]pyrimidin-4-amine

EXAMPLE 110A

This compound was prepared by substituting methyl vinylsulfone for iodoacetamide in EXAMPLE 52C. MS (ESI) m/e 437 (M+H); $^1$H NMR (300 MHz, DMSO-d$_6$) δ8.20 (s, 1H), 5.31 (m, 1H), 3.28 (m, 2H), 3.06 (s, 3H), 2.98 (m, 1H), 2.85 (m, 4H), 2.68 (m, 1H), 2.34-2.19 (m, 2H).

EXAMPLE 110B

This compound was prepared by substituting EXAMPLE 110A for (cis)-4-(4-(-4-amino-3-iodo-pyrazolo[3,4-d]pyrimidin-1-yl)-cyclohexyl)-1 methyl-piperazin-2-one in EXAMPLE 2B.

EXAMPLE 110C

This compound was prepared by substituting EXAMPLE 110B for EXAMPLE 52D in EXAMPLE 52E. MS (ESI) m/e 517 (M+H)$^-$; $^1$H NMR (300 MHz, DMSO-d$_6$) δ8.32 (s, 1H), 7.89 (s, 1H), 7.84(d, 1H), 7.68 (d, 2H), 7.40-7.31 (m, 5H), 5.71 (m, 1H), 4.42 (s, 2H), 3.71-3.43 (m, 8H), 3.12 (s, 3H), 2.57 (m, 2H).

EXAMPLE 111

3-(2-(2-fluorobenzyl)-1H-benzimidazol-5-yl)-1-{1-(2-(methylsulfonyl)ethyl)pyrrolidin-3-yl}-1H-pyrazolo[3,4-d]pyrimidin-4-amine This compound was prepared by substituting EXAMPLE 110B for EXAMPLE 52D and 2-fluorophenylacetaldehyde for phenylacetaldehyde in EXAMPLE 52E. MS (ESI) m/e 535 (M+H)$^-$; $^1$H NMR (300 MHz, DMSO-d$_6$) δ8.32 (s, 1H), 7.85 (s, 1H), 7.75(d, 1H), 7.63 (d, 2H), 7.48 (m, 1H), 7.40 (m, 1H), 7.25 (m, 2H), 5.72 (m, 1H), 4.42 (s, 2H), 3.70-3.51 (m, 8H), 3.12 (s, 3H), 2.57 (m, 2H).

EXAMPLE 112

(trans)-3-(2-benzyl-1H-benzimidazol-5-yl)-1-{4-(4-(3-methoxypropyl)piperazin-1-yl)cyclohexyl}-1H-pyrazolo[3,4-d]pyrimidin-4-amine This example was the faster eluting diastereomer prepared as described in EXAMPLE 31 by substituting 4-(3-methoxypropyl)piperazine for 3-hydroxypyrrolidine in EXAMPLE 31C. MS (ESI) m/e 580 (M+H)$^-$; $^1$H NMR (300 MHz, DMSO-d$_6$) δ8.28 (s, 1H), 7.84 (s, 1H), 7.79 (d, 1H), 7.64 (d, 1H), 7.41-7.33 (m, 5H), 4.75 (m, 1H), 4.43 (s, 2H), 3.52-3.36 (m, 6H), 3.25 (s, 3H), 2.98-2.85 (m, 6H), 2.09 (m, 6H), 1.83 (m, 2H), 1.66 (m, 2H).

EXAMPLE 113

(cis)-3-(2-benzyl-1H-benzimidazol-5-yl)-1-{4-(4-(3-methoxypropyl)piperazin-1-yl)cyclohexyl}-1H-pyrazolo[3,4-d]pyrimidin-4-amine This example was the slower eluting diastereomer in EXAMPLE 112. MS (ESI) m/e 580 (M+H)$^-$; $^1$H NMR (300 MHz, DMSO-d$_6$) δ8.30 (s, 1H), 7.86 (s, 1H), 7.80 (d, 1H), 7.65 (d, 1H), 7.41-7.33 (m, 5H), 4.90 (m, 1H), 4.43 (s, 2H), 3.52-3.36 (m, 6H), 3.23 (s, 3H), 2.98-2.85 (m, 6H), 2.34 (m, 2H), 2.07 (m, 3H), 1.84 (m, 5H).

EXAMPLE 114

(trans)-3-(1-benzyl-1H-indol-5-yl)-1-(4-morpholin-4-ylcyclohexyl)-1H-pyrazolo[3,4-d]pyrimidin-4-amine

EXAMPLE 114A

The desired product was synthesized by substituting benzyl bromide for 2-fluorobenzyl bromide in EXAMPLE 210A.

EXAMPLE 114B trans-3-Iodo-1-(4-morpholin-4-yl-cyclohexyl)-1H-pyrazolo[3,4-d]pyrimidin-4-ylamine prepared as described in PTC Patent Application WO 2005/074603, 112 mg, 0.25 mmol), EXAMPLE 114A (126 mg, 0.3 mmol), sodium carbonate (53 mg, 0.5 mmol), and Pd((PPh$_3$)$_4$) (17 mg, 0.0007 mmol), were placed into microwave tube and 2 mL of DME:water (1:1) was added. It was microwaved at 130° C. for 20 minutes. After partitioned between ethyl acetate and brine, the ethyl acetate layer washed with brine (3×), dried and purified by HPLC method. 60 mg of the title compound was obtained. MS: ESI(+) m/e 508.3 (M+H)$^+$; $^1$H NMR (300 MHz, DMSO-d$_6$) 9.60 (br.s, 1H), 8.28 (s, 1H), 7.83 (br.s, 1H), 7.62-7.66 (m, 2H), 7.25-7.41 (m, 6H), 6.62 (d, 1H), 5.59 (s, 2H), 4.76 (br. m, 1H), 4.03 (br.d., 2H), 3.46 (br.m, 2H), 3.07-3.24 (m, 3H), 2.19-2.29 (m, 2H), 2.06-2.17 (br.m., 4H), 1.66-1.83 (br, m, 2H).

EXAMPLE 115

(trans)-3-(1-(2-methylbenzyl)-1H-indol-5-yl)-1-(4-morpholin-4-ylcyclohexyl)-1H-pyrazolo[3,4-d]pyrimidin-4-amine

EXAMPLE 115A

The desired product was synthesized by substituting 2-methylbenzyl bromide for 2-fluorobenzyl bromide in EXAMPLE 210A.

EXAMPLE 115B

The desired product was synthesized by substituting EXAMPLE 115A for EXAMPLE 114A in EXAMPLE 114B. MS: ESI(+) m/e 522.4 (M+H)$^+$; $^1$H NMR (300 MHz, DMSO-d$_6$) 9.68 (br.s, 1H), 8.30 (s, 1H), 7.54-7.67 (m, 3H), 7.45 (d, 1H), 7.40 (dd, 1H), 7.15-7.26 (m, 2H), 7.10(t, 1H), 6.65 (d, 1H), 6.61 (d, 1H), 5.44 (s, 2H), 4.78 (br. m, 1H), 4.04 (br.d., 2H), 3.70 (br.m, 2H), 3.45 (m, 3H), 3.16 (br. 2H), 2.36 (s, 3H), 2.19-2.30 (m,), 2.08-2.19 (br.m., 4H), 1.69-1.84 (br, m, 2H).

EXAMPLE 116

(trans)-3-(1-(3-methylbenzyl)-1H-indol-5-yl)-1-(4-morpholin-4-ylcyclohexyl)-1H-pyrazolo[3,4-d]pyrimidin-4-amine

EXAMPLE 116A

The desired product was synthesized by substituting 3-methylbenzyl bromide for 2-fluorobenzyl bromide in EXAMPLE 210A.

EXAMPLE 116B

The desired product was synthesized by substituting EXAMPLE 116A for EXAMPLE 114A in EXAMPLE 114B. MS: ESI(+) m/e 522.4 (M+H)$^+$; $^1$H NMR (300 MHz, DMSO-d$_6$) 9.69 (br.s, 1H), 8.30 (s, 1H), 7.84 (br.s, 1H), 7.61-7.66 (m, 2H), 7.40 (m, 1H), 7.21(t, 1H), 7.03-7.12 (m, 3H), 6.62 (d, 1H), 5.44 (s, 2H), 4.76 (br. m, 1H), 4.04 (br.d., 2H), 3.70 (br.m, 2H), 3.09-3.24 (m, 3H), 2.19-2.30 (m, 5H includes=2.26, s, 3H), 2.08-2.18 (br.m., 4H), 1.69-1.85 (br, m, 2H).

EXAMPLE 117

(trans)-3-(1-(2-fluorobenzyl)-1H-indol-5-yl)-1-(4-morpholin-4-ylcyclohexyl)-1H-pyrazolo[3,4-d]pyrimidin-4-amine The desired product was synthesized by substituting EXAMPLE 210A for EXAMPLE 114A in EXAMPLE 114B. MS: ESI(+) m/e 526.4 (M+H)$^+$; $^1$H NMR (300 MHz, DMSO-d$_6$) 9.61 (br.s, 1H), 8.29 (s, 1H), 7.84 (d, 1H), 7.67 (d, 1H), 7.58 (d, 1H), 7.42 (dd, 1H), 7.31-7.37 (m, 1H), 7.24 (m, 1H), 7.13-7.16(m, 2H), 6.62 (d, 1H), 5.54 (s, 2H), 4.76 (br. m, 1H), 4.04 (br.d., 2H), 3.69 (br.m, 2H), 3.09-3.25 (br. 2H), 2.36 (s, 3H), 2.19-2.29 (m,), 2.07-2.17 (br.m., 4H), 1.67-1.83 (br, m, 2H).

EXAMPLE 118

(trans)-3-(1-(3-fluorobenzyl)-1H-indol-5-yl)-1-(4-morpholin-4-ylcyclohexyl)-1H-pyrazolo[3,4-d]pyrimidin-4-amine

EXAMPLE 118A

The desired product was synthesized by substituting 3-fluorobenzyl bromide for 2-fluorobenzyl bromide in EXAMPLE 210A.

EXAMPLE 118B

The desired product was synthesized by substituting EXAMPLE 118A for EXAMPLE 114A in EXAMPLE 114B. MS: ESI(+) m/e 526.3 (M+H)+; $^1$H NMR (300 MHz, DMSO-d$_6$) 9.66 (br.s, 1H), 8.30 (s, 1H), 7.85 (d, 1H), 7.63-7.67 (m, 2H), 7.34-7.43 (m, 2H), 7.21(t, 1H), 7.06-7.13 (m, 3H), 6.64 (d, 1H), 5.52 (s, 2H), 4.76 (br. m, 1H), 4.04 (br.d., 2H), 3.69 (br.m, 2H), 3.08-3.24 (m, 3H), 2.19-2.30 (m, 2H), 2.07-2.18 (br.m., 4H), 1.67-1.84 (br, m, 2H).

EXAMPLE 119

(trans)-1-(4-morpholin-4-ylcyclohexyl)-3-{1-(2-(trifluoromethyl)benzyl)-1H-indol-5-yl}-1H-pyrazolo[3,4-d]pyrimidin-4-amine

EXAMPLE 119A

The desired product was synthesized by substituting 3-fluorobenzyl bromide for 2-fluorobenzyl bromide in EXAMPLE 210A.

EXAMPLE 119B

The desired product was synthesized by substituting EXAMPLE 119A for EXAMPLE 114A in EXAMPLE 114B. MS: ESI(+) m/e 576.3 (M+H)+; $^1$H NMR (300 MHz, DMSO-d$_6$) 9.66 (br.s, 1H), 8.31 (s, 1H), 7.90 (s, 1H), 7.82-7.85 (m, 1H), 7.59 (d, 1H), 7.51-7.54 (m, 2H), 7.24 (s, 2H), 6.71 (d, 1H), 6.59 (d, 1H), 5.71 (s, 2H), 4.77 (br. m, 1H), 4.04 (br.d., 2H), 3.69 (br.m, 2H), 3.36-3.51 (m, 3H), 3.08-3.24 (m, 2H), 2.19-2.29 (m, 2H), 2.07-2.17 (br.m., 4H), 1.69-1.83 (br, m, 2H).

EXAMPLE 120

(trans)-3-(1-(2-fluorobenzyl)-1H-indazol-5-yl)-1-(4-morpholin-4-ylcyclohexyl)-1H-pyrazolo[3,4-d]pyrimidin-4-amine

EXAMPLE 120A

The desired product was synthesized by substituting 2-fluorobenzyl bromide for 2-chlorobenzyl bromide in EXAMPLE 121B.

EXAMPLE 120B

The desired product was synthesized by substituting EXAMPLE 120A for EXAMPLE 121B in EXAMPLE 121C. MS: ESI(+) m/e 527.4 (M+H)$^{30}$; ESI(+) m/e 525.6 (M–H); $^1$H NMR (300 MHz, DMSO-d$_6$) 9.69 (br.s, 1H), 8.33 (s., 1H), 8.24 (s, 1H), 8.03 (d., 1H), 7.89 (d., 1H), 7.70 (dd., 1H), 7.55-7.66 (m., 1H), 7.34-7.41 (m, 1H), 6.93 (dd, 1H), 5.77 (s, 2H), 4.79 (m., 1H), 3.35-3.50 (m., 4H), 3.07-3.24 (m, 2H), 2.19-2.30 (m, 2H), 2.06-2.17 (br.m., 4H), 1.68-1.83 (br, m, 2H).

EXAMPLE 121

(trans)-3-(1-(2-chlorobenzyl)-1H-indazol-5-yl)-1-(4-morpholin-4-ylcyclohexyl)-1H-pyrazolo[3,4-d]pyrimidin-4-amine

EXAMPLE 121A

A solution of 5-bromo-1H-indazole (1.00 g, 5.08 mmol), bis(pinacolato)diboron (3.87 g, 15.24 mmol), potassium acetate (KOAC, 2.49 g, 25.40 mmol), and PdCl$_2$(dppf) (112 mg, 0.152 mmol) in 20 mL of DMF was stirred at 100° C. for 16 h. EtOAc was added and the organic layer washed with brine (×4), dried over MgSO$_4$. After evaporation to dryness, the residue was purified by silica gel column, eluting with 10% EtOAc in hexane to yield 1.2 g. MS: DCI(+) m/e 245.0 (M+H)+; m/e 262.1 (M+NH$_4$)+

EXAMPLE 121B

EXAMPLE 121A (122 mg, 0.5 mmol) and potassium carbonate (415 mg. 3 mmol) were added to 10 mL of acetone. 2-Chlorobenzyl bromide (130 L, 1 mmol) was added, and the mixture was stirred at 60° C. for 3 days. After filtration, the filtrate was concentrated in vacuo and the residue was dried.

EXAMPLE 121C

The desired product was synthesized by substituting EXAMPLE 121B for EXAMPLE 114A in EXAMPLE 114B. MS: ESI(+) m/e 543.3 (M+H)+; $^1$H NMR (300 MHz, DMSO-d$_6$) 9.69 (br.s, 1H), 8.34 (s., 1H), 8.28 (s, 1H), 8.05 (d., 1H), 7.87 (d., 1H), 7.70 (dd., 1H), 7.52 (dd., 1H), 7.25-7.38 (m, 2H), 6.93 (dd, 1H), 5.81 (s, 2H), 4.79 (m., 1H), 3.64-3.77 (br.t, 4H), 3.35-3.50 (m., 4H), 3.07-3.24 (m, 2H), 2.19-2.30 (m, 2H), 2.06-2.17 (br.m., 4H), 1.67-1.83 (br, m, 2H).

EXAMPLE 122

(trans)-3-(1-(3-chlorobenzyl)-1H-indazol-5-yl)-1-(4-morpholin-4-ylcyclohexyl)-1H-pyrazolo[3,4-d]pyrimidin-4-amine

EXAMPLE 122A

The desired product was synthesized by substituting 3-chlorobenzyl bromide for 2-chlorobenzyl bromide in EXAMPLE 121B.

EXAMPLE 122B

The desired product was synthesized by substituting EXAMPLE 122A for EXAMPLE 121B in EXAMPLE 121C. MS: ESI(+) m/e 543.3 (M+H)+; ESI(–) m/e 541.5 (M–H); $^1$H NMR (300 MHz, DMSO-d$_6$) 9.70 (br.s, 1H), 8.35 (s., 1H), 8.27 (s, 1H), 8.04 (d., 1H), 7.94 (d., 1H), 7.69 (dd., 1H), 7.36-7.37 (m., 3H), 7.22-7.27 (m., 1H), 5.75 (s, 2H), 4.79 (m., 1H), 4.00-4.09 (m., 2H), 3.64-3.76 (br. t., 2H), 3.35-3.50 (m., 3H), 3.08-3.24 (m, 2H), 2.19-2.30 (m, 2H), 2.06-2.17 (br.m., 4H), 1.68-1.83 (br, m, 2H).

EXAMPLE 123

(trans)-3-(1-benzyl-1H-indazol-5-yl)-1-(4-morpholin-4-ylcyclohexyl)-1H-pyrazolo[3,4-d]pyrimidin-4-amine

EXAMPLE 123A

The desired product was synthesized by substituting benzyl bromide for 2-chlorobenzyl bromide in EXAMPLE 121B.

EXAMPLE 123B

The desired product was synthesized by substituting EXAMPLE 123A for EXAMPLE 121B in EXAMPLE 121C. MS: ESI(+) m/e 509.3 (M+H)+; ESI(+) m/e 507.5 (M–H); $^1$H NMR (300 MHz, DMSO-d$_6$) 9.64 (br.s, 1H), 8.32 (s., 1H), 8.24 (s, 1H), 8.03 (d., 1H), 7.90 (d., 1H), 7.68 (dd., 1H), 7.55-7.64 (m., 1H), 7.21-7.36 (m., 4H), 5.72 (s, 2H), 4.79 (m., 1H), 4.00-4.08 (m., 2H), 3.37-3.50 (m., 3H), 3.10-3.24 (m, 2H), 2.19-2.30 (m, 2H), 2.06-2.17 (br.m., 4H), 1.68-1.83 (br, m, 2H).

EXAMPLE 124

3-(2-benzyl-1H-benzimidazol-5-yl)-1-{1-(2-(methylsulfonyl)ethyl)piperidin-4-yl}-1H-pyrazolo[3,4-d]pyrimidin-4-amine

EXAMPLE 124A

This compound was prepared by substituting methyl vinylsulfone for iodoacetamide in EXAMPLE 43C. MS (ESI) m/e 451 (M+H); $^1$H NMR (300 MHz, DMSO-$d_6$) δ8.19 (s, 1H), 4.60 (m, 1H), 3.28 (m, 2H), 3.06 (s, 3H), 3.01 (m, 2H), 2.76 (t, 2H), 2.21-2.02 (m, 4H), 1.86 (m, 2H).

EXAMPLE 124B

This compound was prepared by substituting EXAMPLE 124A for (cis)-4-(4-(-4-amino-3-iodo-pyrazolo[3,4-d]pyrimidin-1-yl)-cyclohexyl)-1 methyl-piperazin-2-one in EXAMPLE 2B.

EXAMPLE 124C

This compound was prepared by substituting EXAMPLE 92B for EXAMPLE 43D in EXAMPLE 43E. MS (ESI) m/e 531 (M+H)$^-$; $^1$H NMR (300 MHz, DMSO-$d_6$) δ9.65 (m, 1H), 8.30 (s, 1H), 7.82 (s, 1H), 7.77 (d, 1H), 7.60 (d, 1H), 7.40-7.31 (m, 5H), 5.04 (m, 1H), 4.38 (s, 2H), 3.68 (m, 4H), 3.39 (m, 4H), 3.14 (s, 3H), 2.25 (m, 4H).

EXAMPLE 125

3-(2-(2-fluorobenzyl)-1H-benzimidazol-5-yl)-1-{1-(2-(methylsulfonyl)ethyl)piperidin-4-yl}-1H-pyrazolo[3,4-d]pyrimidin-4-amine This compound was prepared by substituting EXAMPLE 92B for EXAMPLE 43D and 2-fluorophenylacetaldehyde for phenylacetaldehyde in EXAMPLE 43E. MS (ESI) m/e 549 (M+H)$^-$; $^1$H NMR (300 MHz, DMSO-$d_6$) δ9.67 (m, 1H), 8.30 (s, 1H), 7.81 (s, 1H), 7.75 (d, 1H), 7.59 (d, 1H), 7.48 (m, 1H), 7.39 (m, 1H), 7.23 (m, 2H), 5.05 (m, 1H), 4.42 (s, 2H), 3.68 (m, 4H), 3.39 (m, 4H), 3.14 (s, 3H), 2.25 (m, 4H).

EXAMPLE 126

(trans)-3-(1-(cyclohexylmethyl)-1H-indol-5-yl)-1-(4-morpholin-4-ylcyclohexyl)-1H-pyrazolo[3,4-d]pyrimidin-4-amine

EXAMPLE 126A

The desired product was synthesized by substituting bromomethylcyclohexane for 2-fluorobenzyl bromide in EXAMPLE 210A.

EXAMPLE 126B

The desired product was synthesized by substituting EXAMPLE 126A for EXAMPLE 114A in EXAMPLE 114B. MS: ESI(+) m/e 514.4 (M+H)$^+$; ESI(−) m/e 512.4 (M−H); $^1$H NMR (300 MHz, DMSO-$d_6$) 9.66 (br.s, 1H), 8.32 (s, 1H), 7.82 (d, 1H), 7.66 (d, 1H), 7.35-7.52 (m, 4H), 6.71 (d, 1H), 6.54 (d, 1H), 4.77 (br. m, 1H), 4.02-4.08 (m., 4H), 3.05-3.26 (m, 3H), 2.20-2.30 (m, 2H), 2.07-2.18 (br.m., 4H), 1.51-1.89 (m, 7H), 0.97-1.22 (m, 4H).

EXAMPLE 127

(trans)-3-(1-cyclopentyl-1H-indol-5-yl)-1-(4-morpholin-4-ylcyclohexyl)-1H-pyrazolo[3,4-d]pyrimidin-4-amine

EXAMPLE 127A

The desired product was synthesized by substituting bromocyclopentane for 2-fluorobenzyl bromide in EXAMPLE 210A.

EXAMPLE 127B

The desired product was synthesized by substituting EXAMPLE 127A for EXAMPLE 114A in EXAMPLE 114B. MS: ESI(+) m/e 486.3 (M+H)$^+$; $^1$H NMR (300 MHz, DMSO-$d_6$) 9.66 (br.s, 1H), 8.32 (s, 1H), 7.82 (d, 1H), 7.71 (d, 1H), 7.57 (d, 1H), 7.42 (dd, 1H), 6.58 (d, 1H), 4.96 (m., 1H), 4.78 (m, 1H), 4.04 (m., 2H), 3.07-3.25 (m, 2H), 2.08-2.31 (m, 8H), 1.67-1.95 (m, 8H).

EXAMPLE 128

(trans)-3-(1-(2,3-difluorobenzyl)-1H-indol-5-yl)-1-(4-morpholin-4-ylcyclohexyl)-1H-pyrazolo[3,4-d]pyrimidin-4-amine

EXAMPLE 128A

The desired product was synthesized by substituting 2,3-difluorobenzyl bromide for 2-fluorobenzyl bromide in EXAMPLE 210A.

EXAMPLE 128B

The desired product was synthesized by substituting EXAMPLE 128A for EXAMPLE 114A in EXAMPLE 114B. MS: ESI(+) m/e 544.4 (M+H)$^+$; ESI(−) m/e 542.3 (M−H); $^1$H NMR (300 MHz, DMSO-$d_6$) 9.69 (br.s, 1H), 8.32 (s, 1H), 7.85 (d, 1H), 7.68 (d, 1H), 7.59 (d, 1H), 7.43 (dd, 1H), 7.34-7.40 (m, 1H), 7.12-7.20 (m, 1H), 6.91-6.97 (m, 1H), 6.64 (d, 1H), 5.61 (s, 2H), 4.77 (m, 1H), 4.04 (m., 2H), 3.46 (m, 3H), 3.09-3.24 (m, 2H), 2.19-2.29 (m, 2H), 2.07-2.18 (m., 4H), 1.67-1.84 (m, 2H).

EXAMPLE 129

(trans)-3-(1-(2,5-difluorobenzyl)-1H-indol-5-yl)-1-(4-morpholin-4-ylcyclohexyl)-1H-pyrazolo[3,4-d]pyrimidin-4-amine

EXAMPLE 129A

The desired product was synthesized by substituting 2,5-difluorobenzyl bromide for 2-fluorobenzyl bromide in EXAMPLE 210A.

EXAMPLE 129B

The desired product was synthesized by substituting EXAMPLE 129A for EXAMPLE 114A in EXAMPLE 114B. MS: ESI(+) m/e 544.4 (M+H)⁺; ESI(−) m/e 542.3 (M−H); $^1$H NMR (300 MHz, DMSO-$d_6$) 9.74 (br.s, 1H), 8.34 (s, 1H), 7.86 (d, 1H), 7.69 (d, 1H), 7.59 (d, 1H), 7.44 (dd, 1H), 7.29-7.36 (m, 1H), 7.16-7.24 (m, 1H), 6.93-6.99 (m, 1H), 6.64 (d, 1H), 5.64 (s, 2H), 4.78 (m, 1H), 4.04 (m.), 3.70 (m., 2H), 3.46 (m, 3H), 3.08-3.24 (m, 2H), 2.20-2.29 (m, 2H), 2.07-2.18 (m., 4H), 1.67-1.84 (m, 2H).

EXAMPLE 130

(trans)-3-(1-(2,6-difluorobenzyl)-1H-indol-5-yl)-1-(4-morpholin-4-ylcyclohexyl)-1H-pyrazolo[3,4-d]pyrimidin-4-amine

EXAMPLE 130A

The desired product was synthesized by substituting 2,6-difluorobenzyl bromide for 2-fluorobenzyl bromide in EXAMPLE 210A.

EXAMPLE 130B

The desired product was synthesized by substituting EXAMPLE 130A for EXAMPLE 114A in EXAMPLE 114B. MS: ESI(+) m/e 544.4 (M+H)⁺; ESI(−) m/e 542.4 (M−H); $^1$H NMR (300 MHz, DMSO-$d_6$) 9.69 (br.s, 1H), 8.32 (s, 1H), 7.82 (d, 1H), 7.68 (d, 1H), 7.42-7.52 (m, 3H), 7.13-7.22 (m, 2H), 6.59 (d, 1H), 5.53 (s, 2H), 4.77 (m, 1H), 4.04 (m.), 3.70 (m., 2H), 3.46 (m, 3H), 3.08-3.26(m, 2H), 2.19-2.29 (m, 2H), 2.07-2.18 (m., 4H), 1.70-1.84 (m, 2H).

EXAMPLE 131

(trans)-3-(1-(2,5-dichlorobenzyl)-1H-indol-5-yl)-1-(4-morpholin-4-ylcyclohexyl)-1H-pyrazolo[3,4-d]pyrimidin-4-amine

EXAMPLE 131A

The desired product was synthesized by substituting 2,5-dichlorobenzyl bromide for 2-fluorobenzyl bromide in EXAMPLE 210A.

EXAMPLE 131B

The desired product was synthesized by substituting EXAMPLE 131A for EXAMPLE 114A in EXAMPLE 114B. MS: ESI(+) m/e 576.4 (M+H)⁺; ESI(−) m/e 574.4 (M−H); $^1$H NMR (300 MHz, DMSO-$d_6$) 9.70 (br.s, 1H), 8.33 (s, 1H), 7.89 (d, 1H), 7.58-7.63 (m, 2H), 7.34-7.53 (m, 3H), 6.77 (d, 1H), 6.68 (d, 1H), 5.59 (s, 2H), 4.78 (m, 1H), 4.04 (m.), 3.70 (m., 2H), 3.46 (m, 3H), 3.08-3.76(m, 2H), 2.19-2.30 (m, 2H), 2.06-2.18 (m., 4H), 1.69-1.84 (m, 2H).

EXAMPLE 132

(trans)-3-(1-(2,6-dichlorobenzyl)-1H-indol-5-yl)-1-(4-morpholin-4-ylcyclohexyl)-1H-pyrazolo[3,4-d]pyrimidin-4-amine

EXAMPLE 132A

The desired product was synthesized by substituting 2,6-dichlorobenzyl bromide for 2-fluorobenzyl bromide in EXAMPLE 210A.

EXAMPLE 132B

The desired product was synthesized by substituting EXAMPLE 132A for EXAMPLE 114A in EXAMPLE 114B. MS: ESI(+) m/e 576.3 (M+H)⁺; $^1$H NMR (300 MHz, DMSO-$d_6$) 9.67 (br.s, 1H), 8.32 (s, 1H), 7.84 (s, 1H), 7.77 (d, 1H), 7.61-7.64 (m, 2H), 7.46-7.53 (m, 2H), 7.11 (d, 1H), 6.58 (d, 1H), 5.63 (s, 2H), 4.78 (m, 1H), 4.04 (m.), 3.70 (m.), 3.46 (m, 3H), 3.09-3.26(m, 2H), 2.19-2.31 (m, 2H), 2.07-2.18 (m., 4H), 1.66-1.84 (m, 2H).

EXAMPLE 133

(trans)-1-(4-morpholin-4-ylcyclohexyl)-3-(2-(phenylsulfonyl)-1H-benzimidazol-5-yl)-1H-pyrazolo[3,4-d]pyrimidin-4-amine

EXAMPLE 133A 5-bromo-2-chloro-1H-benzo(d)imidazole

To a 1 liter flask was added 2-chlorobenzimidizole (25.7 g, 0.169 mol) and DMF (0.8 L). To the stirring solution was slowly added N-bromosuccinimide (33.0 g, 0.185 mol) and the reaction was allowed to stir overnight. To the reaction mixture was added 1 L of ethyl acetate and the organics were washed 2 times with 0.5 liters of water. The organic fraction washed 0.5 L of brine, dried over magnesium sulfate, filtered, and reduced in vacuo to afford the desired product as a white solid. (DCI(+)) m/e 231, 233 (M+H)⁺; $^1$H NMR (300 MHz, DMSO-$d_6$) 13.47 (bs, 1H), 7.73 (s, 1H), 7.48 (d, 1H), 7.37 (dd, 1H).

EXAMPLE 133B 5-bromo-2-(phenylsulfonyl)-1H-benzo(d)imidazole

EXAMPLE 133A (0.5 g, 2.16 mmol), benzenesulfinic acid sodium salt (0.71 g, 4.32 mmol), and DMF (2.2 mL) was heated to 170° C. for 20 min in a microwave reactor. To the reaction mixture was added ethyl acetate and the organics were washed 2× with water and brine. The organic fraction over magnesium sulfate, filtered, and reduced in vacuo. The residue was purified using reverse phase HPLC and freeze dried to afford the desired product as a white solid. (ESI(+)) m/e 337, 339 (M+H)⁺; (ESI(−)) m/e 335, 337 (M−H)⁻; $^1$H NMR (300 MHz, DMSO-$d_6$) 14.36 (bs, 1H), 8.11-8.00 (m, 2H), 7.85-7.65 (m, 4H), 7.63 (bs, 1H), 7.51 (d, 1H).

EXAMPLE 133C 2-(phenylsulfonyl)-5-(4,4,5,5-tetramethyl-1,3,2-dioxaborolan-2-yl)-1H-benzo(d)imidazole In a 20 ml vial was placed EXAMPLE 133B (0.328 g, 0.97 mmol), bis(pinacolato)diboron (0.493 g, 1.94 mmol), potassium acetate (0.476 g, 4.85 mmol), dichloro(1,1'-bis(diphenylphosphino)ferrocene)palladium(II)dichloromethane adduct (0.042 g, 0.058 mmol), and DMF (2 ml). Reaction was heated at 100° C. overnight until reaction was complete by LCMS. The reaction mixture was diluted with ethyl acetate and the resulting organics were washed with water then brine. The organics were dried over magnesium sulfate, filtered, and reduced in vacuo. The residue was purified using reverse phase HPLC and freeze dried to afford the desired product as a white solid. (ESI(+)) m/e 385 (M+H)⁺.

EXAMPLE 133D 1-((1r,4r)-4-morpholinocyclohexyl)-3-(2-(phenylsulfonyl)-1H-benzo(d)imidazol-6-yl)-1H-pyrazolo[3,4-d]pyrimidin-4-amine To a microwave vial was placed 3-iodo-1-((1r,4r)-4-morpholinocyclohexyl)-1H-pyrazolo[3,4-d]pyrimidin-4-amine (0.075 g, 0.175 mmol), EXAMPLE 133C (0.037 g, 0.35 mmol), dichlorobis(triphenylphosphine)palladium(II) (0.006 g, 0.009 mmol), DME 11.4 ml), and water (0.7 ml). The mixture was irradiated at 130° C. for 20 minutes in a microwave oven then allowed to cool. The solvent was reduced in vacuo and residue was using reverse phase HPLC and freeze dried to afford the desired product as a white solid. (ESI(+)) m/e 559 (M+H)$^+$; (ESI(−)) m/e 557 (M−H)$^-$; $^1$H NMR (300 MHz, DMSO-d$_6$) 9.62 (bs, 1H), 8.29 (d, 1H), 8.12-8.06 (m, 2H), 7.89-7.77 (m, 3H), 7.76-7.69 (m, 2H), 7.64 (d, 1H), 4.85-4.70 (m, 1H), 4.03 (dd, 2H), 3.76-3.67 (m, 2H), 3.45 (d, 2H), 3.24-3.08 (m, 3H), 2.29-2.18 (m, 2H), 2.13 (m, 4H), 1.75 (s, 2H).

EXAMPLE 134

(trans)-2-(4-(4-{4-amino-3-(1-(2-chlorobenzyl)-1H-indol-5-yl)-1H-pyrazolo[3,4-d]pyrimidin-1-yl}cyclohexyl)piperazin-1-yl)ethanol

EXAMPLE 134A

3-Iodo-1-(4-oxo-cyclohexyl)-1H-pyrazolo[3,4-d]pyrimidin-4-ylamine prepared as described in A. F. Burchat et al. Bioorg Med. Chem. Lett. 2002, 12, 1687-1690 (178.5 mg, 0.5 mmol), EXAMPLE 93A (220 mg, 0.6 mmol), sodium carbonate (106 mg, 1 mmol), and Pd(PPh$_3$)$_4$ (34 mg, 0.0015 mmol) were mixed in 4 mL of DME:water (1:1) and subjected to microwave heating at 130° C. for 20 minutes. After partitioning between EtOAc and brine, the ethyl acetate layer was washed with brine (×3), dried over MgSO$_4$. After filtration, the filtrate was evaporated to dryness to yield 140 mg of the title compound.

EXAMPLE 134B

EXAMPLE 134A (47 mg, 01 mmol) and 1-(2-hydroxyethyl)piperazine (123 L, 1 mmol) were stirred in 2 mL of methanol and 0.2 mL of acetic acid at room temperature for 30 minutes. Sodium cyanoborohydride (31 mg, 0.5 mmol) was then added and stirred at 70° C. for 1 hour. After partitioned between EtOAc and saturated sodium bicarbonate, the ethyl acetate layer washed with brine (×3), dried over MgSO$_4$. After filtration, the filtrate was evaporated to dryness and purified by HPLC. The faster eluting diastereomer was isolated, providing 4 mg of the title compound. MS: ESI(+) m/e 585.4 (M+H)$^+$; $^1$H NMR (300 MHz, DMSO-d$_6$) 8.27 (s, 1H), 7.87 (s, 1H), 7.52-7.60 (m, 3H), 7.41 (dd, 1H), 7.31-7.38 (dt, 1H), 7.23-7.28 (m, 1H), 6.78 (dd, 1H), 6.67 (dd, 1H), 5.59 (s, 2H), 4.74 (m, 1H), 4.04 (m.), 2.73 (m., 2H), 2.57-2.61 (m, 2H), 2.41-2.25 (m, 1H), 2.25-2.28 (m, 1H), 2.02-2.15 (m, 8H).

EXAMPLE 135

(trans)-3-(1-(2-fluorobenzyl)-1H-indazol-6-yl)-1-(4-morpholin-4-ylcyclohexyl)-1H-pyrazolo[3,4-d]pyrimidin-4-amine

EXAMPLE 135A

The desired product was synthesized by substituting 6-bromo-1H-indazole for 5-bromo-1H-indazole in EXAMPLE 121A.

EXAMPLE 135B

The desired product was synthesized by substituting EXAMPLE 135A for EXAMPLE 121A and 2-fluorobenzyl bromide for 2-chlorobenzyl bromide in EXAMPLE 121B.

EXAMPLE 135C

The desired product was synthesized by substituting EXAMPLE 135A for EXAMPLE 114A in EXAMPLE 114B. $^1$H NMR (300 MHz, DMSO-d$_6$) 9.53 (br.s, 1H), 8.57 (s., 1H), 8.27 (s, 1H), 7.86 (m., 1H), 7.59 (m., 1H), 7.40-7.35 (m., 3H), 7.24 (m, 1H), 5.75 (s, 2H), 4.79 (m., 1H), 3.35-3.50 (m., 4H), 3.07-3.24 (m, 2H), 2.19-2.30 (m, 2H), 2.06-2.17 (br.m., 4H), 1.68-1.83 (br, m, 2H).

941297 EXAMPLE 136 MEGUMI KAWAI 3-(1-(2-chlorobenzyl)-1H-indol-5-yl)-1-{4-(4-(2-ethoxyethyl)piperazin-1-yl)cyclohexyl}-1H-pyrazolo[3,4-d]pyrimidin-4-amine The desired product was synthesized as a mixture of diastereomers by substituting 1-(2-ethoxyethyl)piperazine for 1-(2-hydroxyethyl)piperazine in EXAMPLE 134B. MS: ESI (+) m/e 613.4 (M+H)$^+$; ESI(−) m/e 611.4 (M−H)$^+$; $^1$H NMR (300 MHz, DMSO-d$_6$) 8.29 (s, 0.6H), 8.28 (s, 0.4H), 7.84-7.89 (m, 1H), 7.51-7.60 (m, 3H), 7.38-7.44 (m, 1H), 7.30-7.36 (dt, 1H), 7.22-7.28 (m, 1H), 6.78 (d, 1H), 6.66 (d, 1H), 5.59 (s, 2H), 4.91 (m, 0.6H), 4.73 (m, 0.4H), 3.76 (t, 3H), 3.07-3.17 (m), 2.73 (m., 2H), 2.57-2.61 (m, 2H), 2.41-2.25 (m, 1H), 2.25-2.28 (m, 1H), 2.02-2.15 (m, 6H), 1.62-1.95 (m, 2H), 1.09-1.17 (m, 3H).

941303 EXAMPLE 137 MEGUMI KAWAI (cis)-2-(4-(4-{4-amino-3-(1-(2-chlorobenzyl)-1H-indol-5-yl)-1H-pyrazolo[3,4-d]pyrimidin-1-yl}cyclohexyl)piperazin-1-yl)ethanol This example was the slower eluting diastereomer in EXAMPLE 134B. MS: ESI(+) m/e 585.4 (M+H)$^+$; $^1$H NMR (300 MHz, DMSO-d$_6$) 8.29 (s, 1H), 7.87 (s, 1H), 7.52-7.60 (m, 3H), 7.41 (dd, 1H), 7.31-7.38 (dt, 1H), 7.23-7.28 (m, 1H), 6.78 (dd, 1H), 6.67 (dd, 1H), 5.59 (s, 2H), 4.91 (m, 1H), 3.68 (m.), 2.73 (m., 2H), 2.25-2.40 (m, 4H), 2.02-2.15 (m, 2H), 1.71-1.95 (m, 6H).

EXAMPLE 138

4-{4-amino-3-(1-(2-chlorobenzyl)-1H-indol-5-yl)-1H-pyrazolo[3,4-d]pyrimidin-1-yl}cyclohexanol EXAMPLE 134A (47 mg, 0.1 mmol) and Sodium cyanoborohydride (31 mg, 0.5 mmol) is stirred in 2 mL of methanol and 0.2 mL of acetic acid at 70° C. for 1 hour. After partitioning between EtOAc and saturated sodium bicarbonate, the ethyl acetate layer is washed with brine (×3), dried over MgSO$_4$. After filtration, the filtrate is then evaporated to dryness and purified by HPLC. MS: ESI (+) m/e 473.2 (M+H)$^+$; $^1$H NMR (300 MHz, DMSO-d$_6$) 8.31 (s, 1H), 7.87 (s, 1H), 7.52-7.59 (m, 3H), 7.41 (dd, 1H), 7.31-7.38 (dt, 1H), 7.23-7.28 (m, 1H), 6.77 (dd, 1H), 6.66 (dd, 1H), 5.59 (s, 2H), 4.69 (m, 1H), 1.92-2.08 (m, 6H).

EXAMPLE 139

3-(2-benzyl-1H-benzimidazol-6-yl)-1-(3-pyridin-3-ylpropyl)-1H-pyrazolo[3,4-d]pyrimidin-4-amine

EXAMPLE 139A 3-iodo-1-(3-(pyridine-3-yl)propyl)-1H-pyrazolo[3,4-d]pyrimidin-4-amine A suspension of 3-Iodo-1H-pyrazolo[3,4-d]pyrimidin-4-ylamine, prepared as described in A. F. Burchat et al. Bioorg Med. Chem. Lett. 2002, 12, 1687-1690, (0.392 g, 1.5 mmol), 3-(pyridine-3-yl)propan-1-ol (0.388 ml, 3 mmol), and triphenylphosphine (0.983 g, 3.75 mmol) in THF (10 ml) under inert atmosphere was cooled in an ice bath and diisopropyl azodicarboxylate (0.581 ml, 3 mmol) was added dropwise and the reaction was then stirred for 72 hrs at ambient temperature. The reaction was concentrated and the residue was acidified with 1M HCl and washed with EtOAc. The aqueous layer was basified with solid Na$_2$CO$_3$ and extracted with EtOAc. The EtOAc was dried over Na$_2$SO$_4$, filtered and concentrated. The residue was purified on silica gel using an ISCO Companion chromatography system eluted with 0-20% MeOH/CH$_2$Cl$_2$ to give the title compound as an off-white solid (310 mg, 54%). MS (ESI(+)) m/e 381 (M+H)$^+$, (ESI(−)) m/e 379 (M−H)$^-$; $^1$H NMR (300 MHz, DMSO-d$_6$) 8.39 (m, 2H), 8.20 (s, 1H), 7.61 (dd, 1H), 7.28 (m, 1H), 4.19 (t, 2H), 2.60 (m, 2H), 2.17 (m, 2H).

EXAMPLE 139B 3-(2-benzyl-1H-benzimidazol-6-yl)-1-(3-pyridin-3-ylpropyl)-1H-pyrazolo[3,4-d]pyrimidin-4-amine A suspension of EXAMPLE 139A (57 mg, 0.15 mmol), EXAMPLE 188C (55 mg, 0.165 mmol), cesium fluoride (68 mg, 0.45 mmol) and tetrakis(triphenylphosphine) palladium (0) (9 mg, 0.0075 mmol) in a mixture of DME (3 ml) and MeOH (1.5 ml) was sealed in a microwave vial under argon and microwave heated at 150° C. for six min. The reaction mixture was partitioned between brine and EtOAc. The EtOAc was dried (Na$_2$SO$_4$), filtered and concentrated. The residue was purified by reverse phase preparative HPLC to give the title compound as a white solid (54 mg, 78%). MS (ESI(+)) m/e 461 (M+H)$^+$, (ESI(−)) m/e 459 (M−H)$^-$; $^1$H NMR (300 MHz, DMSO-d$_6$) 8.65 (d, 1H), 8.54 (dd, 1H), 8.33 (s, 1H), 8.14 (d, 1H), 7.90 (s, 1H), 7.86 (d, 1H), 7.71 (d, 1H), 7.67 (m, 1H), 7.42 (m, 4H), 7.34 (m, 1H), 4.50 (s, 2H), 4.43 (t, 2H), 3.95 (vbr s, 3H), 2.79 (t, 2H), 2.27 (dt, 2H).

EXAMPLE 140

3-(2-benzyl-1H-benzimidazol-6-yl)-1-(1-benzylpiperidin-4-yl)-1H-pyrazolo[3,4-d]pyrimidin-4-amine The title compound, as a white solid, was prepared as described in EXAMPLE 139 substituting 1-benzylpiperidin-4-ol for 3-(pyridine-3-yl)propan-1-ol in EXAMPLE 139A. MS (ESI(+)) m/e 515 (M+H)$^+$, (ESI(−)) m/e 513 (M−H)$^-$; $^1$H NMR (300 MHz, DMSO-d$_6$) 9.78 (br s, 1H), 8.31 (s, 1H), 7.85 (d, 1H), 7.82 (d, 1H), 7.64 (d, 1H), 7.52 (m, 5H), 7.41 (m, 4H), 7.35 (m, 1H), 5.06 (m, 1H), 4.52 (s, 2H), 4.45 (s, 2H), 4.37 (m, 2H), 4.02 (v br s, 2H), 3.54 (m, 2H), 3.30 (m, 2H), 2.20 (m, 2H).

EXAMPLE 141I 3-(2-benzyl-1H-benzimidazol-6-yl)-1-(2-(4-methyl-1,3-thiazol-5-yl)ethyl)-1H-pyrazolo[3,4-d]pyrimidin-4-amine The title compound, as a white solid, was prepared as described in EXAMPLE 139 substituting 2-(4-methylthiazol-5-yl)ethanol for 3-(pyridine-3-yl)propan-1-ol in EXAMPLE 139A. MS (ESI(+)) m/e 467 (M+H)$^+$, (ESI(−)) m/e 465 (M−H)$^-$; $^1$H NMR (300 MHz, DMSO-d$_6$) 8.75 (s, 1H), 8.26 (s, 1H), 7.89 (m, 1H), 7.87 (d, 1H), 7.70 (d, 1H), 7.42 (m, 4H), 7.35 (m, 1H), 4.58 (t, 2H), 4.51 (s, 2H), 4.22 (v br s, 3H), 3.41 (t, 2H), 2.15 (s, 3H).

EXAMPLE 142

3-(2-benzyl-1H-benzimidazol-6-yl)-1-(1-(6-chloropyridazin-3-yl)piperidin-4-yl)-1H-pyrazolo[3,4-d]pyrimidin-4-amine The title compound, as a yellow solid, was prepared as described in EXAMPLE 139 substituting 1-(6-chloropyridazin-3-yl)piperidin-4-ol for 3-(pyridine-3-yl)propan-1-ol in EXAMPLE 139A. MS (ESI(+)) m/e 537 (M+H)$^+$; $^1$H NMR (300 MHz, DMSO-d$_6$) 8.37 (s, 1H), 7.92 (s, 1H), 7.86 (d, 1H), 7.73 (d, 1H), 7.56 (d, 1H), 7.49 (d, 1H), 7.41 (m, 4H), 7.35 (m, 1H), 5.18 (m, 1H), 4.53 (s, 2H), 4.50 (m, 2H), 3.85 (v br s, 3H), 3.27 (t, 2H), 2.16 (m, 2H), 2.07 (m, 2H).

EXAMPLE 143

3-(2-benzyl-1H-benzimidazol-6-yl)-1-(4-morpholin-4-ylbut-2-ynyl)-1H-pyrazolo[3,4-d]pyrimidin-4-amine

EXAMPLE 143A 1-(4-chlorobut-2-ynyl)-3-iodo-1H-pyrazolo[3,4-d]pyridine-4-amine

The title compound was prepared as described in EXAMPLE 52A, substituting 4-chloro-but-2-yn-1-ol for 3-hydroxy-pyrrolidine-1-carboxylic acid tert-butyl ester. The title compound was obtained as a mixture with triphenyl phosphine oxide in ~70% purity. $^1$H NMR (400 MHz, DMSO-d$_6$) 8.24 (s, 1H); 5.24 (s, 2H); 4.47 (s, 2H).

EXAMPLE 143B 3-iodo-1-(4-morpholinobut-2-ynyl)-1H-pyrazolo[3,4-d]pymidin-4-amine A solution of EXAMPLE 143A (0.4 g) and morpholine (0.4 mL, excess) in anhydrous DMF (5 mL) was stirred at 70° C. for 5 hr. The mixture was evaporated to dryness and the residue was taken up in 1 N HCl (25 mL) and washed with EtOAc. The aqueous solution was then basified (~pH 13) and extracted with EtOAc. The EtOAc solution was dried, filtered and evaporated to give the title compound as a white solid. (140 mg). MS (DCI) m/e 399 (M+H)+. ¹H NMR (400 MHz, DMSO-d₆) 8.30 (s, 1H); 5.23 (s, 2H); 3.61 (m, 4H); 3.31 (s, 2H); 2.44 (m, 4H).

EXAMPLE 143C 3-(2-benzyl-1H-benzimidazol-6-yl)-1-(4-morpholin-4-ylbut-2-ynyl)-1H-pyrazolo[3,4-d]pyrimidin-4-amine The title compound, as a tan solid, was prepared as described in EXAMPLE 139B substituting EXAMPLE 143B for EXAMPLE 139A. MS (ESI(+)) m/e 479 (M+H)+; (ESI (−)) m/e 477 (M−H)−; ¹H NMR (300 MHz, DMSO-d₆) 8.33 (s, 1H), 7.89 (s, 1H), 7.84 (d, 1H), 7.68 (d, 1H), 7.41 (m, 4H), 7.33 (m, 1H), 5.39 (s, 2H), 4.47 (s, 2H), 4.11 (s, 2H), 3.99 (br s, 3H), 3.77 (m, 4H), 3.19 (m, 4H).

EXAMPLE 144

3-(2-benzyl-1H-benzimidazol-6-yl)-1-{4-(4-(ethylsulfonyl)piperazin-1-yl)but-2-ynyl}-1H-pyrazolo[3,4-d]pyrimidin-4-amine The title compound, as a tan solid, was prepared as described in EXAMPLE 143, substituting 4-ethylsulfonyl-piperizine for morpholine in EXAMPLE 143B. MS (ESI+) m/e 570 (M+H)+; (ESI(−)) m/e 568 (M−H)−; ¹H NMR (300 MHz, DMSO-d₆) 8.34 (s, 1H), 7.91 (s, 1H), 7.86 (d, 1H), 7.71 (d, 1H), 7.41 (m, 4H), 7.34 (m, 1H), 5.36 (s, 2H), 4.47 (s, 2H), 4.09 (br s, 3H), 3.96 (s, 2H), 3.89 (m, 2H), 3.32 (m, 4H), 3.10 (q, 2H), 3.00 (m, 2H), 1.19 (t, 3H).

EXAMPLE 145

(cis)-5-(2-(2-chlorobenzyl)-1H-benzimidazol-6-yl)-7-(4-(4-methylpiperazin-1-yl)cyclohexyl)-7H-pyrrolo[2,3-d]pyrimidin-4-amine This example was prepared as described in EXAMPLE 6 by substituting 2-chlorophenylacetaldehyde for benzaldehyde in EXAMPLE 6B. MS ((+)-ESI) 555.4 m/z (M+H)+; ¹H NMR (400 MHz, DMSO) 8.13 (s, 1H), 7.55-6.53 (m, 9H), 6.05 (bs, 1H), 4.67 (m, 1H), 4.33 (s, 2H), 2.37-1.99 (m, 16H), 1.74-1.48 (m, 4H).

EXAMPLE 146

(trans)-3-(4-{4-(4-amino-3-(2-benzyl-1H-benzimidazol-5-yl)-1H-pyrazolo[3,4-d]pyrimidin-1-yl) cyclohexyl}piperazin-1-yl)propan-1-ol This example was the faster eluting diastereomer prepared as described in EXAMPLE 31 by substituting 1-(3-hydroxypropyl)piperazine for 3-hydroxypyrrolidine in EXAMPLE 31C. MS (ESI) m/e 566 (M+H)−; ¹H NMR (300 MHz, DMSO-d₆) δ8.29 (s, 1H), 7.85 (s, 1H), 7.80 (d, 1H), 7.64 (d, 1H), 7.41-7.33 (m, 5H), 4.74 (m, 1H), 4.44 (s, 2H), 3.52-3.36 (m, 6H), 3.05-2.85 (m, 6H), 2.09 (6H), 1.80-1.60 (m, 4H).

EXAMPLE 147

(cis)-3-(4-{4-(4-amino-3-(2-benzyl-1H-benzimidazol-5-yl)-1H-pyrazolo[3,4-d]pyrimidin-1-yl) cyclohexyl}piperazin-1-yl)propan-1-ol This example was the slower eluting diastereomer prepared as described in EXAMPLE 31 by substituting 1-(3-hydroxypropyl)piperazine for 3-hydroxypyrrolidine in EXAMPLE 31C. MS (ESI) m/e 566 (M+H)−; ¹H NMR (300 MHz, DMSO-d₆) δ8.31 (s, 1H), 7.87 (s, 1H), 7.81 (d, 1H), 7.65 (d, 1H), 7.42-7.33 (m, 5H), 4.86 (m, 1H), 4.44 (s, 2H), 3.84 (m, 6H), 3.47 (t, 2H), 3.10-2.90 (m, 5H), 2.35 (m, 2H), 2.07 (m, 4H), 1.85 (m, 2H), 1.75 (m, 2H).

EXAMPLE 148

(cis)-3-(4-(4-{4-amino-3-(1-(2-chlorobenzyl)-1H-indol-5-yl)-1H-pyrazolo[3,4-d]pyrimidin-1-yl}cyclohexyl)piperazin-1-yl)propan-1-ol The desired product was synthesized by substituting hydroxypropylpiperazine for 1-(2-hydroxyethyl)piperazine in EXAMPLE 134B. The faster eluting diastereomer was isolated. MS: ESI(+) m/e 599.4 (M+H)+; ¹H NMR (300 MHz, DMSO-d₆) 8.31 (s, 1H), 7.87 (d, 1H), 7.52-7.59 (m, 3H), 7.42 (dd, 1H), 7.34 (dt., 1H), 7.25 (dt., 1H), 6.77 (dd., 1H), 6.67 (d., 1H), 5.59 (s., 1H), 4.90 (m., 1H), 3.42-3.53 (m, 4H, includes=3.46, t, 2H), 2.90-3.16 (m, 4H), 2.24-2.43 (m, 2H), 2.01-2.15 (m, 2H), 1.67-1.94 (m, 4H).

EXAMPLE 149

(trans)-3-(4-(4-{4-amino-3-(1-(2-chlorobenzyl)-1H-indol-5-yl)-1H-pyrazolo[3,4-d]pyrimidin-1-yl}cyclohexyl)piperazin-1-yl)propan-1-ol This example was the slower eluting diastereomer in EXAMPLE 148. MS: ESI(+) m/e 599.4 (M+H)+; ¹H NMR (300 MHz, DMSO-d₆) 8.29 (s, 1H), 7.87 (d, 1H), 7.52-7.59 (m, 3H), 7.42 (dd, 1H), 7.34 (dt., 1H), 7.25 (dt., 1H), 6.78 (dd., 1H), 6.67 (d., 1H), 5.59 (s., 1H), 4.73 (m., 1H), 3.42-3.53 (m, 4H, includes=3.48, t, 2H), 2.90-3.16 (m, 4H), 2.02-2.17 (m, 6H), 1.61-1.84 (m, 4H).

EXAMPLE 150

(cis)-2-(1-(4-{4-amino-3-(1-(2-chlorobenzyl)-1H-indol-5-yl)-1H-pyrazolo[3,4-d]pyrimidin-1-yl}cyclohexyl)piperidin-4-yl)ethanol This example was the unresolved mixture of diastereomers produced in EXAMPLE 148.

EXAMPLE 151

(trans)-2-(1-(4-{4-amino-3-(1-(2-chlorobenzyl)-1H-indol-5-yl)-1H-pyrazolo[3,4-d]pyrimidin-1-yl}cyclohexyl)piperidin-4-yl)ethanol The desired product was synthesized by substituting 4-piperidinylethanol for 1-(2-hydroxyethyl)piperazine in EXAMPLE 134B. The faster eluting diastereomer was isolated. MS: ESI(+) m/e 584.4 (M+H)+; ¹H NMR (300 MHz, DMSO-d₆) 8.27 (s, 1H), 7.87 (d, 1H), 7.52-7.60 (m, 3H), 7.39 (dt, 1H), 7.32 (dt., 1H), 7.25 (dt., 1H), 6.75 (dd., 1H), 6.65

(dd., 1H), 5.58 (s., 1H), 4.75 (m, 1H), 2.98-3.08 (m, 4H), 2.06-2.20 (m, 4H), 1.63-2.00 (m), 1.32-1.43 (m, 2H).

EXAMPLE 152

(cis)-(1-(4-{4-amino-3-(1-(2-chlorobenzyl)-1H-indol-5-yl)-1H-pyrazolo[3,4-d]pyrimidin-1-yl}cyclohexyl)piperidin-4-yl)methanol The desired product was synthesized by substituting 4-piperidinylmethanol for 1-(2-hydroxyethyl)piperazine in EXAMPLE 134B. The faster eluting diastereomer was isolated. MS: ESI(+) m/e 584.4 (M+H)$^+$; $^1$H NMR (300 MHz, DMSO-$d_6$) 8.75 (br. 1H), 8.28 (s, 1H), 7.90 (d, 1H), 7.52-7.60 (m, 3H), 7.43 (dt, 1H), 7.33 (dt., 1H), 7.25 (dt., 1H), 6.80 (dd., 1H), 6.66 (dd., 1H), 5.58 (s., 1H), 4.96 (m, 1H).

EXAMPLE 153

(trans)-(1-(4-{4-amino-3-(1-(2-chlorobenzyl)-1H-indol-5-yl)-1H-pyrazolo[3,4-d]pyrimidin-1-yl}cyclohexyl)piperidin-4-yl)methanol This example was the slower eluting diastereomer in EXAMPLE 152. MS: ESI(+) m/e 570.4 (M+H)$^+$.

EXAMPLE 154

(cis)-3-(1-(2-chlorobenzyl)-1H-indol-5-yl)-1-{4-(4-(3-methoxypropyl)piperazin-1-yl)cyclohexyl}-1H-pyrazolo[3,4-d]pyrimidin-4-amine The desired product was synthesized by substituting 1-(3-methoxypropyl)piperazine for 1-(2-hydroxyethyl)piperazine in EXAMPLE 134B. The faster eluting diastereomer was isolated. MS: ESI (+) m/e 613.5 (M+H); $^1$H NMR (300 MHz, DMSO-$d_6$) 8.30 (s, 1H), 7.88 (s, 1H), 7.52-7.59 (m, 3H), 7.42 (dd, 1H), 7.34 (dt., 1H), 7.25 (dt., 1H), 6.76 (dd., 1H), 6.66 (d., 1H), 5.59 (s., 1H), 4.90 (m., 1H), 3.42-3.53 (m, 4H, includes=3.36, t, 2H), 3.23 (s, 3H), 2.90-3.16 (m, 4H), 2.25-2.45 (m, 2H), 2.01-2.14 (m, 2H), 1.67-1.92 (m, 4H).

EXAMPLE 155

(trans)-3-(1-(2-chlorobenzyl)-1H-indol-5-yl)-1-{4-(4-(3-methoxypropyl)piperazin-1-yl)cyclohexyl}-1H-pyrazolo[3,4-d]pyrimidin-4-amine This example was the slower eluting diastereomer in EXAMPLE 154. MS: ESI(+) m/e 613.5 (M+H)$^+$; $^1$H NMR (300 MHz, DMSO-$d_6$) 8.30 (s, 1H), 7.87 (d, 1H), 7.52-7.60 (m, 3H), 7.41 (dd, 1H), 7.33 (dt., 1H), 7.25 (dt., 1H), 6.78 (dd., 1H), 6.66 (d., 1H), 5.59 (s., 1H), 4.74 (m., 1H), 3.42-3.53 (m, 4H, includes=3.39, t, 2H), 3.25 (s, 3H), 2.90-3.16 (m, 4H), 2.04-2.17 (m, 6H), 1.78-1.90 (m, 2H), 1.60-1.74 (m, 2H).

EXAMPLE 156

3-(1-(2-chlorobenzyl)-1H-indol-5-yl)-1-(4-pyrrolidin-1-ylcyclohexyl)-1H-pyrazolo[3,4-d]pyrimidin-4-amine The desired product was synthesized as a mixture of diastereomers by substituting pyrrolidine for 1-(2-hydroxyethyl) piperazine in EXAMPLE 134B. MS: ESI(+) m/e 526.3 (M+H)$^+$; $^1$H NMR (300 MHz, DMSO-$d_6$) 9.59 (br., 0.4H), 9.33 (br. 0.6H), 8.32 (s, 0.6H), 8.31 (s., 0.4H), 7.88 (dd, 1H), 7.52-7.60 (m, 3H), 7.43 (dt, 1H), 7.34 (dt., 1H), 7.25 (dt., 1H), 6.77 (dd., 1H), 6.66-6.67 (m., 1H), 5.59 (s., 1H), 4.94 (m., 0.6H), 4.77 (m, 0.4H), 3.50-3.67 (m, 2H), 3.25-3.36 (m, 1H), 3.01-3.20 (m, 2H), 2.31-2.46 (m, 1H), 2.19-2.30 (m, 1H), 1.93-2.16 (m, 6H), 1.80-1.93 (m, 3H), 1.61-1.76 (m, 1H).

EXAMPLE 157

3-(4-(4-{4-amino-3-(1-(2-chlorobenzyl)-1H-indol-5-yl)-1H-pyrazolo[3,4-d]pyrimidin-1-yl}cyclohexyl)piperazin-1-yl)propanenitrile The desired product was synthesized by substituting 3-piperazinepropionitrile for 1-(2-hydroxyethyl)piperazine in EXAMPLE 134B. The title compound was obtained as a mixture of diastereomers. MS: ESI(+) m/e 594.4 (M+H)$^+$; $^1$H NMR (300 MHz, DMSO-$d_6$) 9.28 (br., 0.4H), 9.06 (br. 0.6H), 8.33 (s, 0.6H), 8.33 (s., 0.4H), 7.88 (dd, 1H), 7.52-7.60 (m, 3H), 7.43 (dt, 1H), 7.34 (dt., 1H), 7.26 (dt., 1H), 6.78 (dd., 1H), 6.66-6.67 (m., 1H), 5.59 (s., 1H), 4.98 (m., 0.6H), 4.74 (m, 0.4H), 3.48-3.61 (m, 2H), 3.25-3.36 (m, 1H), 3.32-3.45 (m, 1H), 2.98-3.18 (m, 4H), 2.63-2.77 (m, 4H), 2.34-2.44 (m, 2H), 2.19-2.30 (m, 1H), 1.90-2.16 (m, 4H), 1.69-1.84 (m, 1H).

EXAMPLE 158

3-(1-(2-fluorobenzyl)-1H-indol-5-yl)-1-{4-(4-(3-methoxypropyl)piperazin-1-yl)cyclohexyl}-1H-pyrazolo[3,4-d]pyrimidin-4-amine The desired product was synthesized by substituting 1-(3-methoxypropyl)piperazine for 3-aminobenzyl alcohol in EXAMPLE 210C. $^1$H NMR (300 MHz, DMSO-$d_6$) 8.31 (s., 0.6H), 8.30 (s., 0.4H), 7.84 (br., 1H), 7.66 (d., 1H), 7.57-7.59 (m., 1H), 7.33-7.44 (m., 2H), 7.26 (d., 1H), 7.14-7.17 (m., 2H), 6.63 (s., 1H), 5.55 (s., 2H), 4.90 (br.m., 0.5H), 4.74 (br.m., 0.5H), 4.14 (s., 2H), 3.42-3.53 (m, 4H, includes=3.38, t, 2H), 3.25 (s., 1.5H), 3.23 (s., 1.5H), 2.80-3.16 (m, 4H), 2.02-2.18 (m, 4H), 1.60-1.94 (m, 4H).

EXAMPLE 159

1-{4-(4-(2-ethoxyethyl)piperazin-1-yl)cyclohexyl}-3-(1-(2-fluorobenzyl)-1H-indol-5-yl)-1H-pyrazolo[3,4-d]pyrimidin-4-amine The desired product was synthesized by substituting 1-(2-ethoxyethyl)piperazine for 3-aminobenzyl alcohol in EXAMPLE 210C. MS: ESI(+) m/e 597.5 (M+H)$^+$; $^1$H NMR (300 MHz, DMSO-$d_6$) 8.32 (s., 0.6H), 8.31 (s., 0.4H), 7.84-7.85 (br., 1H), 7.66 (d., 1H), 7.54-7.67 (m., 3H), 7.40-7.45 (m., 1H), 7.32-7.37 (m., 1H), 7.26 (d., 1H), 7.12-7.16 (m., 2H), 6.63 (s., 0.4H), 6.62 (s., 0.6H), 5.55 (s., 2H), 4.92 (br.m., 0.6H), 4.75 (br.m., 0.4H), 3.42-3.53 (m, 4H,), 3.00-3.20 (m., 3H), 2.28-2.40 (m., 2H), 2.02-2.18 (m, 4H), 1.78-1.94 (m, 2H), 1.60-1.76 (m., 2H), 1.10-1.17 (m, 3H).

EXAMPLE 160

(cis)-2-(4-(4-{4-amino-3-(1-(2-fluorobenzyl)-1H-indol-5-yl)-1H-pyrazolo[3,4-d]pyrimidin-1-yl}cyclohexyl)piperazin-1-yl)ethanol The desired product was synthesized by substituting 1-(2-hydroxyethyl)piperazine for 3-aminobenzyl alcohol in EXAMPLE 210C. The earlier eluting diastereomer was isolated. MS: ESI(+) m/e 569.4 (M+H)+; 1H NMR (300 MHz, DMSO-d6) 8.32 (s., 1H), 7.85 (d., 1H), 7.66 (d., 1H), 7.60 (d., 1H), 7.43 (dd., 1H), 7.32-7.38 (m., 1H), 7.26 (d., 1H), 7.13-7.16 (m., 2H), 6.63 (d., 1H), 5.55 (s., 2H), 4.91 (br.m., 1H), 3.68-3.71 (m., 2H), 3.42-3.6 (m, 2H,), 2.95-3.20 (m., 4H), 2.26-2.40 (m., 2H), 2.02-2.18 (m, 2H), 1.77-1.96 (m, 4H).

EXAMPLE 161

(trans)-2-(4-(4-{4-amino-3-(1-(2-fluorobenzyl)-1H-indol-5-yl)-1H-pyrazolo[3,4-d]pyrimidin-1-yl}cyclohexyl)piperazin-1-yl)ethanol This example was the slower eluting diastereomer in EXAMPLE 160. MS: ESI(+) m/e 569.4 (M+H)+; 1H NMR (300 MHz, DMSO-d6) 8.30 (s., 1H), 7.84 (d., 1H), 7.66 (d., 1H), 7.58 (d., 1H), 7.43 (dd., 1H), 7.32-7.38 (m., 1H), 7.24 (m., 1H), 7.13-7.16 (m., 2H), 6.63 (d., 1H), 5.55 (s., 2H), 4.74 (br.m., 1H), 3.68-3.73 (m., 2H), 3.42-3.6 (m, 2H,), 2.95-3.20 (m., 4H), 2.26-2.40 (m., 2H), 2.04-2.20 (m, 4H), 1.60-1.78 (m, 2H).

EXAMPLE 162

(cis)-3-(4-(4-{4-amino-3-(1-(2-fluorobenzyl)-1H-indol-5-yl)-1H-pyrazolo[3,4-d]pyrimidin-1-yl}cyclohexyl)piperazin-1-yl)propan-1-ol The desired product was synthesized by substituting 1-(3-hydroxypropyl)piperazine for 3-aminobenzyl alcohol in EXAMPLE 210C. The earlier eluting diastereomer was isolated. MS: ESI(+) m/e 583.4 (M+H)+; 1H NMR (300 MHz, DMSO-d6) 8.32 (s., 1H), 7.85 (d., 1H), 7.66 (d., 1H), 7.60 (d., 1H), 7.43 (dd., 1H), 7.32-7.38 (m., 1H), 7.26 (d., 1H), 7.13-7.16 (m., 2H), 6.63 (d., 1H), 5.55 (s., 2H), 4.91 (br.m., 1H), 3.36-3.58 (m, 4H,), 2.84-3.12 (m., 4H), 2.26-2.40 (m., 2H), 2.00-2.15 (m, 2H), 1.68-1.95 (m, 4H).

EXAMPLE 163

(trans)-3-(4-(4-{4-amino-3-(1-(2-fluorobenzyl)-1H-indol-5-yl)-1H-pyrazolo[3,4-d]pyrimidin-1-yl}cyclohexyl)piperazin-1-yl)propan-1-ol This example was the slower eluting diastereomer in EXAMPLE 162. MS: ESI(+) m/e 583.5 (M+H); 1H NMR (300 MHz, DMSO-d6) 8.30 (s., 1H), 7.84 (d., 1H), 7.66 (d., 1H), 7.58 (d., 1H), 7.43 (dd., 1H), 7.32-7.38 (m., 1H), 7.24 (m., 1H), 7.13-7.16 (m., 2H), 6.63 (d., 1H), 5.54 (s., 2H), 4.74 (br.m., 1H), 3.68-3.73 (m., 2H), 3.42-3.6 (m, 2H,), 2.85-3.15 (m., 4H), 2.02-2.18 (m, 6H), 1.60-1.78 (m, 4H).

EXAMPLE 164

3-(4-(4-{4-amino-3-(1-(2-fluorobenzyl)-1H-indol-5-yl)-1H-pyrazolo[3,4-d]pyrimidin-1-yl}cyclohexyl)piperazin-1-yl)propanenitrile The desired product was synthesized by substituting 1-(2-cyanoethyl)piperazine for 3-aminobenzyl alcohol in EXAMPLE 210C. MS: ESI(+) m/e 578.4 (M+H); 1H NMR (300 MHz, DMSO-d6) 8.33 (s., 0.6H), 8.33 (s., 0.4H), 7.86 (dd., 1H), 7.67 (d., 1H), 7.57-7.60 (m., 1H), 7.41-7.48 (m., 1H), 7.32-7.38 (m., 1H), 7.22-7.28 (m., 1H), 7.14-7.17 (m., 2H), 6.62-6.64 (d., 1H), 5.55 (s., 2H), 4.96 (br.m., 0.6H), 4.76 (m., 0.4H), 3.326-3.60 (m, 4H,), 2.95-3.17 (m., 2H), 2.62-2.78 (m., 2H), 2.33-2.48 (m., 2H), 2.19-2.29 (m., 2H), 2.20-2.29 (m, 1H), 1.88-2.16 (m., 3H), 1.68-1.55 (m, 1H).

EXAMPLE 165I 3-(2-benzyl-1H-benzimidazol-6-yl)-1-((2-pyridin-3-yl-1,3-thiazol-4-yl)methyl)-1H-pyrazolo[3,4-d]pyrimidin-4-amine The title compound, as an off-white solid, was prepared as described in EXAMPLE 139 substituting (2-(pyridin-3-yl) thiazol-4-yl)methanol for 3-(pyridine-3-yl)propan-1-ol in EXAMPLE 139A. MS (ESI+) m/e 516 (M+H)+; (ESI(−)) m/e 514 (M−H)−; 1H NMR (300 MHz, DMSO-d6) 9.08 (d, 1H), 8.66 (dd, 1H), 8.37 (s, 1H), 8.25 (m, 1H), 7.94 (s, 1H), 7.86 (d, 1H), 7.74 (dd, 1H), 7.59 (s, 1H), 7.53 (dd, 1H), 7.41 (m, 4H), 7.33 (m, 1H), 5.77 (s, 2H), 4.50 (s, 2H), 3.88 (br s, 3H).

EXAMPLE 166

3-(2-benzyl-1H-benzimidazol-6-yl)-1-((4-benzyl-morpholin-2-yl)methyl)-1H-pyrazolo[3,4-d]pyrimidin-4-amine The title compound, as a white solid, was prepared as described in EXAMPLE 139 substituting (4-benzylmorpholin-2-yl)methanol for 3-(pyridine-3-yl)propan-1-ol in EXAMPLE 139A. MS (ESI(+)) m/e 531 (M+H)+;)+; (ESI(−)) m/e 529 (M−H)−; 1H NMR (300 MHz, DMSO-d6) 8.36 (s, 1H), 7.87 (s, 1H), 7.85 (d, 1H), 7.64 (d, 1H), 7.46 (m, 5H), 7.42 (m, 4H), 7.34 (m, 1H), 4.51 (s, 2H), 4.47 (s, 2H), 4.36 (s, 2H), 4.25 (v br s, 3H), 3.99 (m, 2H), 3.66 (m, 1H), 3.41 (m, 1H), 3.16 (m, 1H), 3.06 (m, 2H).

EXAMPLE 167

3-(1-(2-chlorobenzyl)-1H-indol-5-yl)-1-(3-(1,1-di-oxidothiomorpholin-4-yl)propyl)-1H-pyrazolo[3,4-d]pyrimidin-4-amine The title compound, as a red tinted white solid, was prepared as described in EXAMPLE 139 substituting 3-(1,1-dioxothiomorpholino)-1-propanol for 3-(pyridine-3-yl)propan-1-ol in EXAMPLE 139A and EXAMPLE 63B for EXAMPLE 188C in EXAMPLE 139B. MS (ESI+) m/e 550 (M+H)+; (ESI(−)) m/e 548 (M−H)−; 1H NMR (300 MHz, DMSO-d6) 8.37 (s, 1H), 7.89 (d, 1H), 7.58 (m, 2H), 7.53 (d, 1H), 7.43 (d, 1H), 7.34 (m, 1H), 7.25 (m, 1H), 6.79 (dd, 1H), 6.67 (d, 1H), 5.59 (s, 2H), 4.86 (vbr s, 2H), 4.44 (t, 2H), 3.28 (br s, 8H), 2.97 (m, 2H), 2.18 (m, 2H).

EXAMPLE 168

1-(4-(4-acetylpiperazin-1-yl)but-2-ynyl)-3-(2-benzyl-1H-benzimidazol-6-yl)-1H-pyrazolo[3,4-d]pyrimidin-4-amine The title compound, as a white solid, was prepared as described in EXAMPLE 143 substituting 1-(piperazin-1-yl) ethanone for morpholine in EXAMPLE 143B. MS (ESI+) m/e 520 (M+H)+; (ESI(−)) m/e 518 (M−H)−; 1H NMR (300 MHz, DMSO-d6) 8.34 (s, 1H), 7.91 (s, 1H), 7.86 (d, 1H), 7.69

(d, 1H), 7.42 (m, 4H), 7.38 (m, 1H), 5.38 (s, 2H), 4.48 (s, 2H), 4.06 (s, 2H), 3.97 (br s, 3H), 3.62 (m, 4H), 3.17 (m, 4H), 2.01 (s, 3H).

EXAMPLE 169

3-(2-benzyl-1H-benzimidazol-6-yl)-1-{4-(4-(2-methoxyethyl)piperazin-1-yl)but-2-ynyl}-1H-pyrazolo[3,4-d]pyrimidin-4-amine The title compound, as a yellow-tan solid, was prepared as described in EXAMPLE 143 substituting 1-(2-methoxyethyl)piperazine for morpholine in EXAMPLE 143B. MS (ESI+) m/e 536 (M+H)$^+$; (ESI(−)) m/e 534 (M−H)$^-$; $^1$H NMR (300 MHz, DMSO-d$_6$) 8.34 (s, 1H), 7.91 (s, 1H), 7.86 (d, 1H), 7.70 (d, 1H), 7.42 (m, 4H), 7.34 (m, 1H), 5.29 (s, 2H), 4.66 (br s, 3H), 4.49 (s, 2H), 3.62 (t, 2H), 3.44 (s, 4H), 3.29 (s, 3H), 3.24 (m, 2H), 3.02 (m, 2H), 2.88 (m, 2H), 2.57 (m, 2H).

EXAMPLE 170

3-(1-(2-chlorobenzyl)-1H-indol-5-yl)-1-(4-(1,1-dioxidothiomorpholin-4-yl)but-2-ynyl)-1H-pyrazolo[3,4-d]pyrimidin-4-amine

EXAMPLE 170A 3-iodo-1-(4-(1,1-dioxidothiomorpholin-4-yl)but-2-ynyl)-1H-pyrazolo[3,4-d]pyrimidin-4-amine The title compound, as a white solid, was prepared as described in EXAMPLE 143 substituting thiomorpholine 1,1-dioxide for morpholine in EXAMPLE 143B. MS (ESI(+)) m/e 447 (M+H)$^+$; $^1$H NMR (300 MHz, DMSO-d$_6$) 8.24 (s, 1H), 6.85 (vbr s, 2H), 5.19 (s, 2H), 3.45 (s, 2H), 3.11 (m, 4H), 2.89 (m, 4H).

EXAMPLE 170B 3-(1-(2-chlorobenzyl)-1H-indol-5-yl)-1-(4-(1,1-dioxidothiomorpholin-4-yl)but-2-ynyl)-1H-pyrazolo[3,4-d]pyrimidin-4-amine The title compound, as a white solid, was prepared as described in EXAMPLE 139B substituting EXAMPLE 170A for EXAMPLE 139A and EXAMPLE 63B for EXAMPLE 188C. MS (ESI+) m/e 560 (M+H)$^+$; (ESI(−)) m/e 558 (M−H)$^-$; $^1$H NMR (300 MHz, DMSO-d$_6$) 8.34 (s, 1H), 7.91 (s, 1H), 7.57 (m, 3H), 7.44 (d, 1H), 7.33 (m, 1H), 7.25 (m, 1H), 6.78 (d, 2H), 6.67 (d, 1H), 5.60 (s, 2H), 5.27 (s, 2H), 2.59 (br s, 2H), 2.50 (s, 2H), 3.10 (m, 4H), 2.91 (m, 4H).

EXAMPLE 171

1-(4-(4-acetylpiperazin-1-yl)but-2-ynyl)-3-(1-(2-chlorobenzyl)-1H-indol-5-yl)-1H-pyrazolo[3,4-d]pyrimidin-4-amine

EXAMPLE 171A 1-(4-(4-(4-amino-3-iodo-1H-pyrazolo[3,4-d]pyrimidin-1-yl)but-2-ynyl)piperazin-1-yl)ethanone The title compound, as a white solid, was prepared as described in EXAMPLE 143 substituting 1-(piperazin-1-yl)ethanone for morpholine in EXAMPLE 143B. MS (ESI(+)) m/e 440 (M+H)$^+$; $^1$H NMR (300 MHz, DMSO-d$_6$) 8.23 (s, 1H), 6.95 (vbr s, 2H), 5.16 (s, 2H), 3.40 (m, 4H), 3.28 (s, 2H), 2.39 (m, 2H), 2.33 (m, 2H), 1.97 (s, 3H).

EXAMPLE 171B 1-(4-(4-acetylpiperazin-1-yl)but-2-ynyl)-3-(1-(2-chlorobenzyl)-1H-indol-5-yl)-1H-pyrazolo[3,4-d]pyrimidin-4-amine The title compound, as a yellow tan solid, was prepared as described in EXAMPLE 139B substituting EXAMPLE 171A for EXAMPLE 139A and EXAMPLE 63B for EXAMPLE 188C. MS (ESI+) m/e 553 (M+H)$^+$; (ESI(−)) m/e 551 (M−H)$^-$; $^1$H NMR (300 MHz, DMSO-d$_6$) 8.33 (s, 1H), 7.89 (s, 1H), 7.60 (m, 2H), 7.54 (d, 1H), 7.44 (d, 1H), 7.34 (m, 1H), 7.26 (m, 1H), 6.79 (d, 1H), 6.68 (d, 1H), 5.60 (s, 2H), 5.37 (s, 2H), 4.10 (s, 2H), 3.99 (br s, 2H), 3.64 (m, 4H), 3.16 (m, 4H), 2.00 (s, 3H).

EXAMPLE 172

3-(1-(2-chlorobenzyl)-1H-indol-5-yl)-1-{4-(4-(2-methoxyethyl)piperazin-1-yl)but-2-ynyl}-1H-pyrazolo[3,4-d]pyrimidin-4-amine

EXAMPLE 172A 3-iodo-1-(4-(4-(2-methoxyethyl)piperazin-1-yl)but-2-ynyl)-1H-pyrazolo[3,4-d]pyrimidin-4-amine The title compound, as a tan solid, was prepared as described in EXAMPLE 143 substituting 1-(2-methoxyethyl)piperazine for morpholine in EXAMPLE 143B. MS (ESI(+)) m/e 456 (M+H)$^+$; $^1$H NMR (300 MHz, DMSO-d$_6$) 8.23 (s, 1H), 6.56 (vbr s, 2H), 5.16 (s, 2H), 3.40 (t, 2H), 3.23 (s, 2H), 3.21 (s, 3H), 2.48-2.24 (m, 10H).

EXAMPLE 172B 3-(1-(2-chlorobenzyl)-1H-indol-5-yl)-1-{4-(4-(2-methoxyethyl)piperazin-1-yl)but-2-ynyl}-1H-pyrazolo[3,4-d]pyrimidin-4-amine The title compound, as an off white solid, was prepared as described in EXAMPLE 139B substituting EXAMPLE 172A for EXAMPLE 139A and EXAMPLE 63B for EXAMPLE 188C. MS (ESI+) m/e 569 (M+H)$^+$; (ESI(−)) m/e 567 (M−H)$^-$; $^1$H NMR (300 MHz, DMSO-d$_6$) 8.33 (s, 1H), 7.89 (s, 1H), 7.58 (m, 2H), 7.54 (d, 1H), 7.43 (d, 1H), 7.33 (m, 1H), 7.25 (m, 1H), 6.79 (d, 1H), 6.68 (d, 1H), 5.59 (s, 2H), 5.28 (s, 2H), 4.00 (vbr s, 2H), 3.62(t, 2H), 3.44 (s, 2H), 3.41 (m, 2H), 3.28 (s, 3H), 3.24 (m, 2H), 3.02 (m, 2H), 2.89 (m, 2H), 2.57 (m, 2H).

EXAMPLE 173

1-((4-benzylmorpholin-2-yl)methyl)-3-(1-(2-chlorobenzyl)-1H-indol-5-yl)-1H-pyrazolo[3,4-d]pyrimidin-4-amine The title compound, as a red tinted white solid, was prepared as described in EXAMPLE 139 substituting (4-benzylmorpholin-2-yl)methanol for 3-(pyridine-3-yl)propan-1-ol in EXAMPLE 139A and EXAMPLE 63B for EXAMPLE 188C in EXAMPLE 139B. MS (ESI+) m/e 564 (M+H)$^+$; (ESI(−)) m/e 562 (M−H)$^-$; $^1$H NMR (300 MHz, DMSO-d$_6$) 8.31 (s, 1H), 7.86 (d, 1H), 7.59 (m, 2H), 7.54 (d, 1H), 7.45 (m, 5H), 7.39 (d, 1H), 7.34 (m, 1H), 7.26 (m, 1H), 6.81 (dd, 1H), 6.68 (d, 1H), 5.59 (s, 2H), 4.48 (m, 1H), 4.37 (s, 2H), 4.14 (vbr s, 2H), 4.00 (m, 2H), 3.66 (m, 2H), 3.43 (m, 1H), 3.27 (m, 1H), 3.07 (m, 2H).

EXAMPLE 174

(trans)-3-(2-(2-chlorobenzyl)-1H-benzimidazol-6-yl)-1-{4-(4-(3-methoxypropyl)piperazin-1-yl)cyclohexyl}-1H-pyrazolo[3,4-d]pyrimidin-4-amine

EXAMPLE 174A 3-iodo-1-(4-(4-(3-methoxypropyl)piperazin-1-yl)cyclohexyl)-1H-pyrazolo[3,4-d]pyrimidin-4-amine The desired product was synthesized as a mixture of diastereomers by substituting 1-(3-methoxypropyl)piperazine for 1-(tert-butoxycarbonyl)piperazine in EXAMPLE 318A.

EXAMPLE 174B 3-(4-amino-3-nitrophenyl)-1-(4-(4-(3-methoxypropyl)piperazin-1-yl)cyclohexyl)-1H-pyrazolo[3,4-d]pyrimidin-4-amine A mixture of EXAMPLE 174A (0.3 g, 0.6 mmol), EXAMPLE 2A (0.32 g, 1.24 mmol) (Ph$_3$P)$_2$PdCl$_2$ (0.021 g, 0.03 mmol), and 2 M aqueous Na$_2$CO$_3$ (0.62 mL, 1.24 mmol). The slurry was heated to 130° C. for 20 min in a microwave reactor. The reaction was filtered over a pad of Celite®, washed with CH$_2$Cl$_2$. The organics were reduced in vacuo directly onto silica. The reaction was purified via an Intelliflash-280 purification system (CH$_2$Cl$_2$/MeOH/NH$_4$OH) to afford the desired trans-diastereomeric product.

EXAMPLE 174C

A slurry of EXAMPLE 174B(?) (0.12 g, 0.23 mmol), 2-(2-chlorophenyl)acetaldehyde (0.036 g, 0.23 mmol), 1M Na$_2$S$_2$O$_4$ (0.7 mL, 0.70 mmol) and EtOH (1 mL), was placed in a microwave reactor, and heated to 130° C. for 20 min. The reaction was quenched by addition of 5 M NH$_4$OH, diluted with CH$_2$Cl$_2$/IPA (4/1 v/v). The organics were extracted with CH$_2$Cl$_2$ (3×10 mL). The organic extracts were pooled, dried over MgSO$_4$, filtered, and reduced in vacuo. The material was purified via reverse phase HPLC using the following column conditions: 0.15% TFA in CH$_3$CN/0.15% in H$_2$O to afford the desired product. (ESI(+)) m/e 614 (M+H)$^+$; $^1$H NMR (300 MHz, DMSO-d$_6$) 8.30 (s, 1H); 7.82 (s, 1H); 7.77 (d, 1H); 7.60 (d, 1H); 7.55-7.51 (m, 2H); 7.42-7.39 (m, 2H); 4.75 (m, 1H); 4.54 (s, 2H); 3.39 (m, 2H); 3.25 (s, 3H); 2.58 (m, 1H); 2.14-2.06 (m, 5H); 1.88-1.80 (m, 2H); 1.175-1.62 (m, 2H).

EXAMPLE 175

3-(2-benzyl-1H-benzimidazol-5-yl)-1-(1-(3-methoxypropyl)pyrrolidin-3-yl)-1H-pyrazolo[3,4-d]pyrimidin-4-amine

EXAMPLE 175A

A mixture of EXAMPLE 52B (0.3 g, 0.82 mmol), 1-bromo-3-methoxypropane (0.25 g, 1.64 mmol) and K$_2$CO$_3$ (0.56 g, 4.1 mmol) in CH$_3$CN 10 mL was stirred at room temperature overnight. The reaction mixture was diluted with EtOAc, washed with brine. The crude was recrystallized from ether to give 0.22 g of material in 68% yield. MS (ESI) m/e 403 (M+H); $^1$H NMR (300 MHz, DMSO-d$_6$) 8.19 (s, 1H), 5.28 (m, 1H), 3.35 (m, 2H), 3.22 (s, 3H), 3.03 (m, 1H), 2.68 (m, 4H), 2.30-2.16 (m, 3H), 1.67 (m, 2H).

EXAMPLE 175B

This compound was prepared by substituting EXAMPLE 175A for (cis)-4-(4-(-4-amino-3-iodo-pyrazolo[3,4-d]pyrimidin-1-yl)-cyclohexyl)-1 methyl-piperazin-2-one in EXAMPLE 2B.

EXAMPLE 175C

This compound was prepared by substituting EXAMPLE 175B for EXAMPLE 52D in EXAMPLE 52E. MS (ESI) m/e 483 (M+H)$^-$; $^1$H NMR (300 MHz, DMSO-d$_6$) δ9.86 (br, 1H), 8.32 (s, 1H), 7.88 (s, 1H), 7.80 (d, 1H), 7.67 (d, 2H), 7.41-7.33 (m, 5H), 5.71 (m, 1H), 4.42 (s, 2H), 4.14-4.02 (m, 2H), 3.42-3.32 (m, 6H), 3.23 (d, 3H), 2.45 (m, 2H), 1.92 (m, 2H).

EXAMPLE 176

(trans)-3-(2-benzyl-1H-benzimidazol-5-yl)-1-(4-{4-(2-(1,3-dioxolan-2-yl)ethyl)piperazin-1-yl}cyclohexyl)-1H-pyrazolo[3,4-d]pyrimidin-4-amine This example was the faster eluting diastereomer prepared as described in EXAMPLE 31 by substituting 1-(2-(1,3-dioxalan-2-yl)ethyl)piperazine for 3-hydroxypyrrolidine in EXAMPLE 31C. MS (ESI) m/e 608 (M+H)$^-$; $^1$H NMR (300 MHz, DMSO-d$_6$) δ8.29 (s, 1H), 7.85 (s, 1H), 7.81 (d, 1H), 7.65 (d, 1H), 7.42-7.33 (m, 5H), 4.88 (t, 1H), 4.74 (m, 1H), 4.45 (s, 2H), 3.91 (m, 2H), 3.79 (m, 2H), 3.39 (m, 5H), 2.89 (m, 6H), 2.10 (m, 6H), 1.92 (m, 2H), 1.69 (m, 2H).

EXAMPLE 177

(cis)-3-(2-benzyl-1H-benzimidazol-5-yl)-1-(4-{4-(2-(1,3-dioxolan-2-yl)ethyl)piperazin-1-yl}cyclohexyl)-1H-pyrazolo[3,4-d]pyrimidin-4-amine This example was the slower eluting diastereomer prepared as described in EXAMPLE 31 by substituting 1-(2-(1,3-dioxalan-2-yl)ethyl)piperazine for 3-hydroxypyrrolidine in EXAMPLE 31C. MS (ESI) m/e 608 (M+H)$^-$; $^1$H NMR (300 MHz, DMSO-d$_6$) δ8.31 (s, 1H), 7.88 (s, 1H), 7.82 (d, 1H), 7.68 (d, 1H), 7.42-7.33 (m, 5H), 4.92 (m, 1H), 4.87 (t, 1H), 4.46 (s, 2H), 3.90 (m, 2H), 3.79 (m, 2H), 3.41 (m, 5H), 2.98 (m, 6H), 2.35 (m, 2H), 2.06 (m, 2H), 1.91 (m, 6H).

EXAMPLE 178

(trans)-1-(4-morpholin-4-ylcyclohexyl)-3-(1-(tetrahydro-2H-pyran-2-ylmethyl)-1H-indol-5-yl)-1H-pyrazolo[3,4-d]pyrimidin-4-amine

EXAMPLE 178A

The desired product was synthesized by substituting 2-(bromomethyl)tetrahydro-2H-pyran for 2-fluorobenzyl bromide in EXAMPLE 210A.

EXAMPLE 178B

The desired product was synthesized by substituting EXAMPLE 178A for EXAMPLE 93A in EXAMPLE 93B.

MS: ESI(+) m/e 516.4 (M+H)$^+$; $^1$H NMR (300 MHz, DMSO-d$_6$) 9.64 (br.s, 1H), 8.31 (s, 1H), 7.81 (d, 1H), 7.67 (d, 1H), 7.39-7.44 (m, 2H), 6.55 (d, 1H), 4.78 (br. m, 1H), 4.23 (t., 2H), 4.04 (br.d., 2H), 3.46 (br.m, 2H), 3.10-3.32 (m, 4H), 2.19-2.30 (m, 2H), 2.06-2.18 (br.m., 4H), 1.70-1.84 (br, m, 3H), 1.57-1.64 (m., 1H), 1.38-1.50 (m., 3H), 1.15-1.30 (m., 1H).

EXAMPLE 179

(trans)-1-(4-morpholin-4-ylcyclohexyl)-3-(1-(pyridin-3-ylmethyl)-1H-indol-5-yl)-1H-pyrazolo[3,4-d]pyrimidin-4-amine

EXAMPLE 179A

The desired product was synthesized by substituting 3-(bromomethyl)pyridine for 2-fluorobenzyl bromide in EXAMPLE 210A.

EXAMPLE 179B

The desired product was synthesized by substituting EXAMPLE 179A for EXAMPLE 93A in EXAMPLE 93B. MS: ESI(+) m/e 509.3 (M+H)$^+$; $^1$H NMR (300 MHz, DMSO-d$_6$) 9.74 (br.s, 1H), 8.65 (d., 1H), 8.54-8.58 (m., 2H), 8.37 (s, 1H), 7.86 (d, 1H), 7.76-7.82 (d, 1H), 7.69-7.71 (m., 1H), 7.47-7.51 (m., 1H), 7.39-7.44 (m, 1H), 6.55 (d, 1H), 5.59 (s., 2H), 4.78 (br. m, 1H), 3.99-4.09 (m., 2H), 3.65-3.77 (m., 2H), 3.37-3.51 (m., 3H), 3.11-3.24 (m., 2H), 2.19-2.30 (m., 2H), 2.06-2.18 (m., 4H), 1.68-1.84 (m., 2H).

EXAMPLE 180

(trans)-1-(4-morpholin-4-ylcyclohexyl)-3-(1-(pyridin-2-ylmethyl)-1H-indol-5-yl)-1H-pyrazolo[3,4-d]pyrimidin-4-amine

EXAMPLE 180A

The desired product was synthesized by substituting 2-(bromomethyl)pyridine for 2-fluorobenzyl bromide in EXAMPLE 210A.

EXAMPLE 180B

The desired product was synthesized by substituting EXAMPLE 180A for EXAMPLE 93A in EXAMPLE 93B. MS: ESI(+) m/e 509.3 (M+H)$^+$; $^1$H NMR (300 MHz, DMSO-d$_6$) 9.72 (br.s, 1H), 8.56 (m., 1H), 8.36 (s, 1H), 7.85 (d, 1H), 7.76 (dt, 1H), 7.62-7.65 (m., 2H), 7.40 (dd., 1H), 7.29-7.33 (m, 1H), 7.11 (d., 1H), 6.64 (d, 1H), 5.58 (s., 2H), 4.78 (br. m, 1H), 4.00-4.09 (m., 2H), 3.645-3.76 (m., 2H), 3.37-3.51 (m., 3H), 3.11-3.24 (m., 2H), 2.19-2.30 (m., 2H), 2.06-2.18 (m., 4H), 1.70-1.84 (m., 2H).

EXAMPLE 181

3-(2-benzyl-1H-benzimidazol-5-yl)-1-tert-butyl-1H-pyrazolo[3,4-d]pyrimidin-4-amine To microwave reaction vessel were added 3-bromo-1-tert-butyl-1H-pyrazolo[3,4-d]pyrimidin-4-ylamine prepared as described in US Patent Application US20060025383 (0.047 g, 0.18 mmol), EXAMPLE 188C (0.063 g, 0.19 mmol), K$_2$CO$_3$ (0.069 g, 0.50 mmol), Pd(PPh$_3$)$_4$ (0.005 g, 0.004 mmol), and 2:1 DME:H$_2$O (3.3 ml:1.7 ml). The reaction vessel was sealed and heated under temperature control on a Personal Chemistry Smith Synthesizer for 20 minutes total at a target temperature of 150° C. The reaction mixture was diluted with CH$_2$Cl$_2$, and the organics washed sequentially with aqueous NaHCO$_3$, brine, then dried over MgSO$_4$. The solvent was removed under reduced pressure, and the residue purified by reverse-phase HPLC using CH$_3$CN/water/0.15% TFA to provide the TFA-salt of the title compound as a white solid (0.030 g). MS (ESI(+)) m/e 398 (M+H)$^+$; (ESI(−)) m/e 396 (M−H)$^−$; $^1$H NMR (300 MHz, DMSO-d$_6$) 8.31 (s, 1H); 7.88 (d, 1H); 7.83 (s, 1H); 7.70 (m, 1H); 7.42 (m, 3H); 7.36 (m, 2H); 4.49 (s, 2H); 1.77 (s, 9H).

EXAMPLE 182

5-(2-benzyl-1H-benzimidazol-5-yl)-7-tert-butyl-7H-pyrrolo[2,3-d]pyrimidin-4-amine The desired product was prepared by substituting 7-tert-butyl-5iodo-7H-pyrrolo[3,4-d]pyrimidin-4-ylamine prepared as described in US Patent Application US20060025383 for 3-bromo-1-tert-butyl-1H-pyrazolo[3,4-d]pyrimidin-4-ylamine in EXAMPLE 181. $^1$H NMR (300 MHz, DMSO-d$_6$) δ8.39 (s, 1H); 7.76 (d, 1H); 7.72 (m, 1H); 7.64 (s, 1H); 7.52 (m, 1H); 7.41 (m, 3H); 7.34 (m, 2H); 4.44 (s, 2H); 1.77 (s, 9H).

EXAMPLE 183

5-(2-benzyl-1H-benzimidazol-5-yl)-7-(4-(4-methylpiperazin-1-yl)cyclohexyl)-7H-pyrrolo[2,3-d]pyrimidin-4-amine The desired product was prepared by substituting 3-iodo-1-(4-(4-methyl-piperazin-1-yl)-cyclohexyl)-1H-pyrazolo[3,4-d]pyrimidin-4-ylamine prepared as described in A. F. Burchat et al. Bioorg Med. Chem. Lett. 2002, 12, 1687-1690 for 3-bromo-1-tert-butyl-1H-pyrazolo[3,4-d]pyrimidin-4-ylamine in EXAMPLE 181. $^1$H NMR (300 MHz, DMSO-d$_6$) δ8.40 (s, 1H); 7.78 (m, 2H); 7.71 (s, 1H); 7.62 (s, 1H); 7.48 (m, 1H); 7.41 (m, 3H); 7.35 (m, 1H); 4.86-4.79 (m, 1H); 4.44 (s, 2H); 2.48-2.20 (m, 8H); 2.14 (s, 3H); 2.09-2.04 (m, 1H); 1.76-1.56 (m, 4H).

EXAMPLE 184

(trans)-3-(1-benzyl-1H-benzimidazol-5-yl)-1-(4-morpholin-4-ylcyclohexyl)-1H-pyrazolo[3,4-d]pyrimidin-4-amine

EXAMPLE 184A

4-Bromo-1-fluoro-2-nitrobenzene (2.46 mL, 20 mmol) was dissolved in 20 mL of acetonitrile at room temperature. Benzylamine (2.28 mL, 21 mmol) and triethylamine (4.18 mL, mmol) were added to the mixture, and stirred at 50° C. for 16 h. EtOAc, followed by water were added and the organic layer washed with brine (×4), dried over Na$_2$SO$_4$ and evaporated to dryness. 6.16 g of the title compound was obtained.

EXAMPLE 184B

The desired compound was synthesized by substituting EXAMPLE 184A for EXAMPLE 185A in EXAMPLE 185B.

EXAMPLE 184C

The desired compound was synthesized by substituting EXAMPLE 184B for EXAMPLE 185B in EXAMPLE 185C.

EXAMPLE 184D

The desired compound was synthesized by substituting EXAMPLE 184C for EXAMPLE 185C in EXAMPLE 185D. MS: DCI(+) m/e 335.4 (M+H)$^+$;

EXAMPLE 184E

The desired compound was synthesized by substituting EXAMPLE 184D for EXAMPLE 185D in EXAMPLE 185E. MS: ESI(+) m/e 509.3 (M+H)$^+$; ESI(−) m/e 507.3 (M−H); $^1$H NMR (300 MHz, DMSO-d$_6$) 9.62 (br. 1H), 8.88 (s. 1H), 8.30 (s, 1H), 7.94 (d, 1H), 7.82 (d., 1H), 7.61 (dd., 1H), 7.32-7.44 (m., 5H), 5.63 (s., 2H), 4.77 (m., 1H), 4.04(m.), 3.36-3.49 (m., 3H), 3.09-3.23 (m., 2H), 2.19-2.29 (m., 2H), 2.07-2.18 (m., 4H), 1.67-1.83 (m., 2H).

EXAMPLE 185

(trans)-3-(1-(2-chlorobenzyl)-1H-benzimidazol-5-yl)-1-(4-morpholin-4-ylcyclohexyl)-1H-pyrazolo[3,4-d]pyrimidin-4-amine

EXAMPLE 185A

4-Bromo-2-nitroaniline (2.17 g, 10 mmol) was dissolved in DMF at room temperature. Sodium hydride (0.44 g, 11 mmol) was added. After stirring at room temperature for 30 minutes, 2-chlorobenzyl bromide (1.43 mL, 11 mmol) was added and stirred at 50° C. for 16 h. EtOAc, followed by brine were added and the EtOAc layer washed with brine (×4), dried over MgSO$_4$ and evaporated to dryness. The crude product was purified by silica gel column, eluting with 5% EtOAc in hexane to yield 1.54 g. $^1$H NMR (300 MHz, DMSO-d$_6$) 8.70 (t. 1H), 8.21 (d, 1H), 7.61 (dd, 1H), 7.50 (m, 1H), 7.27-7.34 (m, 3H), 6.77 (d, 1H), 4.69 (d, 2H).

EXAMPLE 185B

EXAMPLE 185A (680 mg, 2 mmol) was suspended in 15 mL of EtOH:water (4:1) and Iron (680 mg) was added. It was gently refluxed at 90° C. for 2.5 hours. EtOAc, followed by brine were added and the EtOAc layer washed with brine (×4), dried over MgSO$_4$ and evaporated to dryness, giving 620 mg of the title compound. MS: DCI (+) m/e 312.6 (M+H)$^+$;
$^1$H NMR (300 MHz, DMSO-d$_6$) 7.43-7.46 (m, 1H), 7.26-7.38 (m, 3H), 6.72 (d, 1H), 6.51 (dd., 1H), 6.11 (d, 1H), 5.32 (t., 1H), 4.93 (s., 2H), 4.34 (d, 2H).

EXAMPLE 185C

EXAMPLE 185B (620 mg, 2 mmol) was dissolved in 2 mL of methylene chloride. Triethyl orthoformate (1.66 mL, 10 mmol), followed by trifluoroacetic acid (77 L, 1 mmol) were added. It was stirred for 2 hours at room temperature. EtOAc, followed by 10% sodium bicarbonate were added and the organic layer washed with brine (×4), dried over MgSO$_4$ and evaporated to dryness, giving 620 mg of the title compound. MS: DCI(+) m/e 288.9 (M+H)$^+$; $^1$H NMR (300 MHz, DMSO-d$_6$) 8.47 (s., 1H), 7.86 (d., 1H), 7.49 (s, 1H), 7.26-7.38 (m, 5H), 6.72 (d, 1H), 5.51 (s, 2H).

EXAMPLE 185D

EXAMPLE 185C (610 mg, 1.9 mmol), potassium acetate (0.56 g, 5.7 mmol), bis(pinacolato)diboron (0.58 g, 2.28 mmol), dppf (31 mg, 0.057 mmol) and PdCl$_2$(dppf).CH$_2$Cl$_2$ complex (47 mg, 0.057 mmol) were added to 10 mL of dioxane. The mixture was stirred at 95° C. for 4 hours. Solvent was removed and the residue was directly purified by silica gel column chromatography, eluting with 2% methanol in methylene chloride. 610 mg of the compound was obtained. MS: DCI(+) m/e 369.4 (M+H)$^+$;

EXAMPLE 185E trans-3-iodo-1-(4-morpholin-4-yl-cyclohexyl)-1H-pyrazolo[3,4-d]pyrimidin-4-ylamine prepared as described in PTC Patent Application WO 2005/074603, (86 mg, 0.2 mmol), EXAMPLE 185D (88.5 mg, 0.24 mmol), sodium carbonate (42 mg, 0.4 mmol), and Pd(PPh$_3$)$_4$ (14 mg, 0.0006 mmol) were dissolved in 2 mL of DME:water (1:1) and microwaved at 13° C. for 20 minutes. After partitioning between ethyl acetate and brine, the ethyl acetate layer was washed with brine (3×), dried and the crude product purified by HPLC to yield 60 mg of the title compound. MS: ESI(+) m/e 543.3 (M+H)$^+$; ESI(−) m/e 541.3 (M−H); $^1$H NMR (300 MHz, DMSO-d$_6$) 9.66 (br. 1H), 8.74 (s. 1H), 8.32 (s, 1H), 7.95 (d, 1H), 7.75 (d., 1H), 7.55-7.61 (m., 2H), 7.32-7.43 (m, 2H), 7.21 (dd., 1H), 5.72 (s., 2H), 4.78 (m., 1H), 4.04 (m.), 3.70 (m., 3H), 3.36-3.49 (m., 3H), 3.09-3.23 (m., 2H), 2.19-2.29 (m., 2H), 2.05-2.17 (m., 4H), 1.68-1.82 (m., 2H).

EXAMPLE 186

(trans)-3-(1-(2-fluorobenzyl)-1H-benzimidazol-5-yl)-1-(4-morpholin-4-ylcyclohexyl)-1H-pyrazolo[3,4-d]pyrimidin-4-amine

EXAMPLE 186A

4-Bromo-1-fluoro-2-nitrobenzene (2.46 mL, 20 mmol) was dissolved in 20 mL of acetonitrile at room temperature. 2-Fluorobenzylamine (2.40 mL, 2 mmol) and triethylamine (4.18 mL, 30 mmol) were added to the mixture, and stirred at 50° C. for 16 h. EtOAc, followed by water were added and the EtOAc layer washed with brine (×4), dried over Na$_2$SO$_4$ and evaporated to dryness. 6.48 g of the title compound was obtained.

EXAMPLE 186B

The desired compound was synthesized by substituting EXAMPLE 186A for EXAMPLE 185A in EXAMPLE 185B.

EXAMPLE 186C

The desired compound was synthesized by substituting EXAMPLE 186B for EXAMPLE 185B in EXAMPLE 185C

EXAMPLE 186D

The desired compound was synthesized by substituting EXAMPLE 186C for EXAMPLE 185C in EXAMPLE 185D. MS: DCI(+) m/e 353.2 $(M+H)^+$;

EXAMPLE 186E

Trans-3-Iodo-1-(4-morpholin-4-yl-cyclohexyl)-1H-pyrazolo[3,4-d]pyrimidin-4-ylamine prepared as described in PTC Patent Application WO 2005/074603, (86 mg, 0.2 mmol), EXAMPLE 186D (100 mg, 0.24 mmol), sodium carbonate (42 mg, 0.4 mmol), and $Pd(PPh_3)_4$ (14 mg, 0.0006 mmol) were dissolved in 2 mL of DME:water (1:1) and microwaved at 130° C. for 20 minutes. After partitioning between ethyl acetate and brine, the ethyl acetate layer was washed with brine (3×), dried and the crude product purified by HPLC to yield 55 mg of the title compound. MS: ESI(+) m/e 527.4 $(M+H)^+$; ESI(−) m/e 525.3 (M−H); $^1$H NMR (300 MHz, DMSO-$d_6$) 9.65 (br. 1H), 8.74 (s. 1H), 8.31 (s, 1H), 7.93 (d, 1H), 7.78 (d., 1H), 7.60 (dd., 1H), 7.38-7.46 (m., 2H), 7.20-7.38 (m, 2H), 5.68 (s., 2H), 4.78 (m., 1H), 4.03(m.), 3.70 (m., 3H), 3.36-3.48 (m., 3H), 3.09-3.23 (m., 2H), 2.19-2.29 (m., 2H), 2.07-2.17 (m., 4H), 1.68-1.83 (m., 2H).

EXAMPLE 187

3-(1-(2-chlorobenzyl)-1H-indol-5-yl)-1-tetrahydro-2H-pyran-4-yl-1H-pyrazolo[3,4-d]pyrimidin-4-amine The desired product was prepared by substituting EXAMPLE 190A for (cis)-3-iodo-1-(4-morpholin-4-yl-cylohexyl)-1H-pyrazolo[3,4-d]pyrimidin-4-ylamine in EXAMPLE 63C. (ESI(+)) m/e 459 $(M+H)^+$; $^1$H NMR (300 MHz, DMSO-$d_6$) 8.39 (s, 1H), 7.90 (d, 1H), 7.60 (d, 1H), 7.57 (d, 1H), 7.53 (dd, 1H), 7.43 (dd, 1H), 7.33 (td, 1H), 7.25 (td, 1H), 6.79 (dd, 1H), 6.67 (d, 1H), 5.59 (s, 2H), 4.98 (m, 1H), 4.01 (dd, 2H), 3.56 (td, 2H), 2.22 (m, 2H), 1.92 (dd, 2H).

EXAMPLE 188

3-(2-benzyl-1H-benzimidazol-5-yl)-1-(3-methoxypropyl)-1H-pyrazolo[3,4-d]pyrimidin-4-amine

EXAMPLE 188A

To a solution of 3-Iodo-1H-pyrazolo[3,4-d]pyrimidin-4-ylamine prepared as described in A. F. Burchat et al. Bioorg Med. Chem. Lett. 2002, 12, 1687-1690 (0.500 g, 1.9 mmol), 3-methoxypropanol (0.55 mL, 5.7 mmol) and triphenylphosphine (1.01 g, 3.8 mmol) in 24 mL THF was slowly added DIAD (0.75 mL, 3.8 mmol). The reaction mixture was stirred at room temperature overnight. Additional triphenylphosphine (0.500 g) and DIAD (0.37 mL) were added, and the reaction mixture stirred overnight. The solvent was then removed under reduced pressure, and the residue purified over silica via a Flashmaster Solo purification system ($CH_2Cl_2$/MeOH) to give 492.3 mg of the title compound.

EXAMPLE 188B

A solution of 2-phenylacetonitrile (40 g, 341 mmol) in EtOH (22 mL) was cooled to 0° C., then HCl gas was bubbled through the reaction mixture for 10 minutes. The reaction was then allowed to warm to room temperature and stand overnight. Ether was then added, and the solvent removed under reduced pressure. The resulting solid was treated with ether and filtered. The filter cake washed with ether and dried over NaOH/$P_2O_5$ overnight under vacuum to afford 58 g of the desired compound as a white solid.

EXAMPLE 188C

To a solution of EXAMPLE 280A (6.9 g, 29.6 mmol) in MeOH (150 mL) was added EXAMPLE 188B (6.40 g, 32.5 mmol), and the resulting reaction stirred for 1.5 h. The reaction was concentrated under reduced pressure, and $CH_2Cl_2$ was added. The resulting mixture was filtered, and the filtrate concentrated onto silica gel. The reaction was purified on silica via an Intelliflash-280 purification system (EtOAc/hexanes) to afford the desired product (6.50 g) as a white solid.

EXAMPLE 188D

The desired product was prepared by substituting EXAMPLE 188C for EXAMPLE 63B and EXAMPLE 188A for (cis)-3-iodo-1-(4-morpholin-4-yl-cylohexyl)-1H-pyrazolo[3,4-d]pyrimidin-4-ylamine, respectively in EXAMPLE 63C. (ESI(+)) m/e 414 $(M+H)^+$; $^1$H NMR (300 MHz, DMSO-$d_6$) 8.34 (s, 1H), 7.92 (s, 1H), 7.86 (d, 1H), 7.72 (m, 1H), 7.42 (m, 4H), 7.34 (m, 1H), 4.50 (s, 2H), 4.43 (t, 2H), 3.36 (t, 2H), 3.22 (s, 3H), 2.08 (m, 2H).

EXAMPLE 189

3-(1-(2-chlorobenzyl)-1H-indol-5-yl)-1-(3-methoxypropyl)-1H-pyrazolo[3,4-d]pyrimidin-4-amine The desired product was prepared by substituting EXAMPLE 93C for EXAMPLE 63B and EXAMPLE 188A for (cis)-3-iodo-1-(4-morpholin-4-yl-cylohexyl)-1H-pyrazolo[3,4-d]pyrimidin-4-ylamine, respectively in EXAMPLE 63C. (ESI(+)) m/e 414 $(M+H)^+$; $^1$H NMR (300 MHz, DMSO-$d_6$) 8.38 (s, 1H), 7.89 (s, 1H), 7.58 (m, 2H), 7.54 (d, 1H), 7.44 (d, 1H), 7.33 (m, 1H), 7.25 (m, 1H), 6.80 (m, 1H), 6.66 (m, 1H), 5.59 (s, 2H), 4.43 (t, 2H), 3.37 (t, 2H), 3.22 (s, 3H), 2.09 (m, 2H).

EXAMPLE 190

3-(2-benzyl-1H-benzimidazol-5-yl)-1-tetrahydro-2H-pyran-4-yl-1H-pyrazolo[3,4-d]pyrimidin-4-amine

EXAMPLE 190A

This example was prepared by substituting tetrahydro-2H-pyran-4-ol for 3-methoxypropanol in EXAMPLE 188A.

EXAMPLE 190B

This example was prepared by substituting EXAMPLE 188C for EXAMPLE 63B and EXAMPLE 190A for (cis)-3-iodo-1-(4-morpholin-4-yl-cylohexyl)-1H-pyrazolo[3,4-d]pyrimidin-4-ylamine, respectively in EXAMPLE 63C. (ESI(+)) m/e 426 $(M+H)^+$; $^1$H NMR (300 MHz, DMSO-$d_6$) 8.30 (s, 1H), 7.90 (s, 1H), 7.84 (d, 1H), 7.71 (d, 1H), 7.42 (m, 4H), 7.35 (m, 1H), 4.97 (m, 1H), 4.48 (s, 2H), 4.01 (m, 2H), 3.56 (m, 2H), 2.22 (m, 2H), 1.91 (m, 2H).

EXAMPLE 191

3-(2-benzyl-1H-benzimidazol-5-yl)-1-(1-methylpiperidin-4-yl)-1H-pyrazolo[3,4-d]pyrimidin-4-amine

EXAMPLE 191A

This example was prepared by substituting 1-methylpiperidin-4-ol for 3-methoxypropanol in EXAMPLE 188A.

EXAMPLE 191B

This example was prepared by substituting EXAMPLE 188C for EXAMPLE 63B and EXAMPLE 191A for (cis)-3-iodo-1-(4-morpholin-4-yl-cylohexyl)-1H-pyrazolo[3,4-d]pyrimidin-4-ylamine, respectively in EXAMPLE 63C. (ESI (+)) m/e 439 (M+H)$^+$; $^1$H NMR (300 MHz, DMSO-d$_6$) 8.30 (s, 1H), 7.84 (s, 1H), 7.80 (d, 1H), 7.62 (d, 1H), 7.40 (m, 4H), 7.32 (m, 1H), 5.03 (m, 1H), 4.42 (s, 2H), 3.60 (m, 2H), 3.28 (m, 2H), 2.84 (d, 2H), 2.44 (m, 2H), 2.21 (m, 2H)

EXAMPLE 192

3-(1-(2-chlorobenzyl)-1H-indol-5-yl)-1-(1-methylpiperidin-4-yl)-1H-pyrazolo[3,4-d]pyrimidin-4-amine This example was prepared by substituting EXAMPLE 192A for (cis)-3-iodo-1-(4-morpholin-4-yl-cylohexyl)-1H-pyrazolo[3,4-d]pyrimidin-4-ylamine in EXAMPLE 63C. (ESI(+)) m/e 472 (M+H)$^+$; $^1$H NMR (300 MHz, DMSO-d$_6$) 9.45 (br s, 1H), 8.30 (s, 1H), 7.87 (d, 1H), 7.59 (d, 1H), 7.57 (d, 1H), 7.52 (dd, 1H), 7.41 (dd, 1H), 7.33 (td, 1H), 7.25 (td, 1H), 6.78 (d, 1H), 6.67 (d, 1H), 5.59 (s, 2H), 5.02 (m, 1H), 3.61 (m, 2H), 3.28 (m, 2H) 2.84 (d, 2H), 2.42 (m, 2H), 2.20 (m, 2H).

EXAMPLE 193

3-(2-benzyl-1H-benzimidazol-5-yl)-1-(3-(dimethylamino)propyl)-1H-pyrazolo[3,4-d]pyrimidin-4-amine

EXAMPLE 193A

This example was prepared by substituting 3-(dimethylamino)propan-1-ol for 3-methoxypropanol in EXAMPLE 188A.

EXAMPLE 193B

This example was prepared by substituting EXAMPLE 188C for EXAMPLE 63B and EXAMPLE 193A for (cis)-3-iodo-1-(4-morpholin-4-yl-cylohexyl)-1H-pyrazolo[3,4-d]pyrimidin-4-ylamine, respectively in EXAMPLE 63C. (ESI (+)) m/e 427 (M+H)$^+$; (ESI(−)) m/e 425 (M−H)$^+$; $^1$H NMR (300 MHz, DMSO-d$_6$) 9.37 (br s, 1H), 8.32 (s, 1H), 7.87 (s, 1H), 7.82 (d, 1H), 7.68 (d, 1H), 7.41 (m, 4H), 7.33 (m, 1H), 4.45 (m, 4H), 3.14 (m, 2H), 2.78 (s, 3H), 2.77 (s, 3H), 2.24 (m, 2H).

EXAMPLE 194

3-(1-(2-chlorobenzyl)-1H-indol-5-yl)-1-(3-(dimethylamino)propyl)-1H-pyrazolo[3,4-d]pyrimidin-4-amine This example was prepared by substituting EXAMPLE 193A for (cis)-3-iodo-1-(4-morpholin-4-yl-cylohexyl)-1H-pyrazolo[3,4-d]pyrimidin-4-ylamine in EXAMPLE 63C. (ESI(+)) m/e 460 (M+H)$^+$; $^1$H NMR (300 MHz, DMSO-d$_6$) 9.32 (br s, 1H), 8.31 (s, 1H), 7.89 (d, 1H), 7.59 (d, 1H), 7.57 (d, 1H), 7.53 (dd, 1H), 7.43 (dd, 1H), 7.33 (td, 1H), 7.25 (td, 1H), 6.80 (dd, 1H), 6.66 (d, 1H), 5.59 (s, 2H), 4.44 (t, 2H), 3.14 (m, 2H), 2.78 (s, 3H), 2.77 (s, 3H), 2.24 (m, 2H).

EXAMPLE 195

(trans)-3-(2-(2-bromobenzyl)-1H-benzimidazol-5-yl)-1-(4-morpholin-4-ylcyclohexyl)-1H-pyrazolo[3,4-d]pyrimidin-4-amine This example was prepared as described in EXAMPLE 7 by substituting (2-bromo-phenyl)-acetaldehyde for benzaldehyde in EXAMPLE 7B. MS (ESI) m/e 587 (M+H)$^-$; $^1$H NMR (300 MHz, DMSO-d$_6$) δ9.63 (bs, 1H), 8.29 (s, 1H), 7.81 (s, 1H), 7.75 (d, 1H), 7.70 (d, 1H), 7.61 (d, 1H), 7.48 (m, 2H), 7.32 (m, 1H), 4.79 (m, 1H), 4.53 (s, 2H), 4.04 (m, 2H), 3.69 (m, 2H), 3.46 (m, 2H), 3.18 (m, 2H), 2.27(m, 2H), 2.13 (m, 4H), 1.76 (m, 2H).

EXAMPLE 196

(trans)-3-(2-(2-methoxybenzyl)-1H-benzimidazol-5-yl)-1-(4-morpholin-4-ylcyclohexyl)-1H-pyrazolo[3,4-d]pyrimidin-4-amine This example was prepared as described in EXAMPLE 7 by substituting (2-methoxy-phenyl)-acetaldehyde for benzaldehyde in EXAMPLE 7B. MS (ESI) m/e 539 (M+H)$^-$; $^1$H NMR (300 MHz, DMSO-d$_6$) δ9.74 (bs, 1H), 8.31 (s, 1H), 7.88 (s, 1H), 7.84 (d, 1H), 7.71 (d, 1H), 7.38 (m, 2H), 7.08 (d, 1H), 7.02 (t, 1H), 4.79 (m, 1H), 4.45 (s, 2H), 4.04 (m, 2H), 3.70 (m, 2H), 3.46 (m, 2H), 3.18 (m, 2H), 2.26 (m, 2H), 2.13 (m, 4H), 1.76 (m, 2H).

EXAMPLE 197

(cis)-3-(2-(2-methoxybenzyl)-1H-benzimidazol-5-yl)-1-{4-(4-(3-methoxypropyl)piperazin-1-yl)cyclohexyl}-1H-pyrazolo[3,4-d]pyrimidin-4-amine This compound is the slower eluting isomer in EXAMPLE 198. MS (ESI) m/e 610 (M+H)$^-$; $^1$H NMR (300 MHz, DMSO-d$_6$) δ8.31 (s, 1H), 7.88 (s, 1H), 7.83 (d, 1H), 7.72 (d, 1H), 7.38 (m, 2H), 7.08 (d, 1H), 7.02 (t, 1H), 4.92 (m, 1H), 4.44 (s, 2H), 3.78 (s, 3H), 3.47 (m, 5H), 3.37 (t, 2H), 3.24 (s, 3H), 3.00 (m, 5H), 2.34 (m, 3H), 2.06 (m, 3H), 1.86 (m, 4H).

EXAMPLE 198

(trans)-3-(2-(2-methoxybenzyl)-1H-benzimidazol-5-yl)-1-{4-(4-(3-methoxypropyl)piperazin-1-yl)cyclohexyl}-1H-pyrazolo[3,4-d]pyrimidin-4-amine The desired product was prepared by substituting 1-(3-methoxypropyl)piperazine for 2-(trifluoromethyl)-5,6,7,8-tetrahydroimidazo[1,2-a]pyrazine in EXAMPLE 338. The faster eluting isomer was isolated: MS (ESI) m/e 610 (M+H)$^-$; $^1$H NMR (300 MHz, DMSO-d$_6$) δ8.29 (s, 1H), 7.86 (s, 1H), 7.82 (d, 1H), 7.71 (d, 1H), 7.38 (m, 2H), 7.08 (d, 1H), 7.02 (t, 1H), 4.75 (m, 1H), 4.44 (s, 2H), 3.78 (s, 3H), 3.65 (m, 5H), 3.39 (t, 2H), 3.25 (s, 3H), 2.95 (m, 5H), 2.09 (m, 6H), 1.83 (m, 2H), 1.67 (m, 4H).

EXAMPLE 199

(trans)-3-(2-(2-bromobenzyl)-1H-benzimidazol-5-yl)-1-{4-(4-(3-methoxypropyl)piperazin-1-yl)cyclohexyl}-1H-pyrazolo[3,4-d]pyrimidin-4-amine

EXAMPLE 199A

The desired product was prepared by substituting EXAMPLE 31A and 2-bromophenyl acetaldehyde for EXAMPLE 7A and benzaldehyde, respectively, in EXAMPLE 7B.

EXAMPLE 199B

The desired product was prepared by substituting EXAMPLE 199A and 1-(3-methoxypropyl)piperazine for EXAMPLE 31B and 3-hydroxypyrrolidine, respectively, in EXAMPLE 3° C. The faster eluting diastereomer was isolated. MS (ESI) m/e 660 (M+H)$^-$; $^1$H NMR (300 MHz, DMSO-d$_6$) δ8.30 (s, 1H), 7.82 (s, 1H), 7.76 (d, 1H), 7.71 (d, 1H), 7.61 (d, 1H), 7.48 (m, 2H), 7.32 (t, 1H), 4.75 (m, 1H), 4.55 (s, 2H), 3.45 (m, 5H), 3.39 (t, 2H), 3.25 (s, 3H), 2.98 (m, 5H), 2.10 (m, 6H), 1.84 (m, 2H), 1.67 (m, 2H).

EXAMPLE 200

(cis)-3-(2-(2-bromobenzyl)-1H-benzimidazol-5-yl)-1-{4-(4-(3-methoxypropyl)piperazin-1-yl)cyclohexyl}-1H-pyrazolo[3,4-d]pyrimidin-4-amine The desired product was the slower eluting isomer in EXAMPLE 199B. MS (ESI) m/e 660 (M+H)$^-$; $^1$H NMR (300 MHz, DMSO-d$_6$) δ8.29 (s, 1H), 7.81 (s, 1H), 7.74 (d, 1H), 7.70 (d, 1H), 7.59 (d, 1H), 7.45 (m, 2H), 7.31 (t, 1H), 4.90 (m, 1H), 4.50 (s, 2H), 3.62 (m, 5H), 3.37 (t, 2H), 3.23 (s, 3H), 2.98 (m, 5H), 2.33 (m, 2H), 2.06 (m, 3H), 1.84 (m, 5H).

EXAMPLE 201

3-(1-(2-chlorobenzyl)-1H-indol-5-yl)-1-(1'-methyl-1,4'-bipiperidin-4-yl)-1H-pyrazolo[3,4-d]pyrimidin-4-amine

EXAMPLE 201A tert-butyl 4-(4-amino-3-iodo-1H-pyrazolo[3,4-d]pyrimidin-1-yl)piperidine-1-carboxylate The title compound, as an off-white solid, was prepared as described in EXAMPLE 139A substituting tert-butyl 4-hydroxypiperidine-1-carboxylate for 3-(pyridine-3-yl)propan-1-ol. MS (ESI+) m/e 445 (M+H)$^+$; (ESI(−)) m/e 443 (M−H)$^-$; $^1$H NMR (300 MHz, DMSO-d$_6$) 8.20 (s, 1H), 7.77 (vbr s, 2H), 4.80 (m, 1H), 4.06 (m, 2H), 2.94 (m, 2H), 1.89 (m, 2H), 1.67 (m, 2H), 1.43 (s, 9H).

EXAMPLE 201B tert-butyl 4-(4-amino-3-(1-(2-chlorobenzyl)-1H-indol-5-yl)-1H-pyrazolo[3,4-d]pyrimidin-1-yl)piperidine-1-carboxylate The title compound, as a yellow solid foam, was prepared as described in EXAMPLE 139B substituting EXAMPLE 201A for EXAMPLE 139A and EXAMPLE 63B for EXAMPLE 188C except the purification was done on normal phase silica gel. MS (ESI+) m/e 558 (M+H)$^+$; (ESI(−)) m/e 556 (M−H)$^-$; $^1$H NMR (300 MHz, DMSO-d$_6$) 8.24 (s, 1H), 7.88 (s, 1H), 7.56 (m, 3H), 7.42 (d, 1H), 7.37 (m, 1H), 7.24 (m, 1H), 6.75 (dd, 1H), 6.66 (d, 1H), 6.28 (vbr s, 2H), 5.58 (s, 2H), 4.90 (m, 1H), 4.10 (m, 2H), 2.97 (m, 2H), 2.05 (m, 2H), 1.95 (m, 2H), 1.42 (s, 9H).

EXAMPLE 201C 3-(1-(2-chlorobenzyl)-1H-indol-5-yl)-1-(piperidin-4-yl)-1H-pyrazolo[3,4-d]pyrimidin-4-amine A solution of EXAMPLE 201B (1.28 g, 2.3 mmol) in anhydrous CH$_2$Cl$_2$ (30 ml) was cooled in an ice bath and TFA (7.5 ml) was added dropwise under inert atmosphere. After stirring 15 min the ice bath was removed and the reaction allowed to warm to ambient temperature while stirring 1 hr. The reaction was concentrated and the residue dissolved in 1M-HCl. The solution washed with EtOAc, basified with 1M-Na$_2$CO$_3$ (pH 9-10) and extracted with 5% MeOH/CH$_2$Cl$_2$ (3×100 ml). The combined extracts were dried over Na$_2$SO$_4$, filtered, concentrated and dried to give the title compound as a tan foam (70%). MS (ESI+) m/e 458 (M+H)$^+$; $^1$H NMR (300 MHz, DMSO-d$_6$) 8.22 (s, 1H), 7.88 (s, 1H), 7.55 (m, 3H), 7.42 (d, 1H), 7.33 (m, 1H), 7.25 (m, 1H), 6.74 (dd, 1H), 6.67 (d, 1H), 6.24 (vbr s, 3H), 5.59 (s, 2H), 4.73 (m, 1H), 3.07 (m, 2H), 2.63 (m, 2H), 2.04 (m, 2H), 1.82 (m, 2H).

EXAMPLE 201D 3-(1-(2-chlorobenzyl)-1H-indol-5-yl)-1-(1'-methyl-1,4'-bipiperidin-4-yl)-1H-pyrazolo[3,4-d]pyrimidin-4-amine A 20 ml vial was charged with EXAMPLE 201C (79 mg, 0.17 mmol), DMF (5 ml), ClCH$_2$CH$_2$Cl (5 ml), acetic acid (40 1, 0.7 mmol) and 1-methylpiperidin-4-one (80 1, 0.7 mmol). The vial was purged with argon and sodium triacetoxyborohydride (110 mg, 0.5 mmol) was added portionwise over 5 min. The vial was sealed and the mixture stirred 18 hr. The reaction was concentrated and the residue was purified by reverse phase preparative HPLC to give the title compound as a tan solid (89%). MS (ESI+) m/e 555 (M+H)$^+$; (ESI(−)) m/e 553 (M−H)$^-$; $^1$H NMR (300 MHz, DMSO-d$_6$) 9.80 (br s, 2H), 8.30 (s, 1H), 7.88 (s, 1H), 7.57 (m, 3H), 7.43 (d, 1H), 7.34 (m, 1H), 7.26 (m, 1H), 6.81 (dd, 1H), 6.66 (d, 1H), 5.59 (s, 2H), 5.11 (m, 1H), 3.63 (m, 4H), 3.45 (m, 1H), 3.34 (m, 2H), 3.02 (m, 2H), 2.78 (s, 3H), 2.51 (m, 2H), 2.27 (m, 4H), 1.90 (m, 2H).

EXAMPLE 202

3-(1-(2-chlorobenzyl)-1H-indol-5-yl)-1-(1'-ethyl-1,4'-bipiperidin-4-yl)-1H-pyrazolo[3,4-d]pyrimidin-4-amine The title compound, as an off-white solid, was prepared as described in EXAMPLE 201 substituting 1-ethylpiperidin-4-one for 1-methylpiperidin-4-one in EXAMPLE 201D. MS (ESI+) m/e 569 (M+H)$^+$; (ESI(−)) m/e 567 (M−H)$^-$; $^1$H NMR (300 MHz, DMSO-d$_6$) 9.82 (br s, 1H), 9.58 (br s, 1H), 8.30 (s, 1H), 7.88 (s, 1H), 7.57 (m, 3H), 7.43 (d, 1H), 7.34 (m, 1H), 7.25 (m, 1H), 6.80 (dd, 1H), 6.67 (d, 1H), 5.59 (s, 2H), 5.11

(m, 1H), 3.66 (m, 4H), 3.48 (m, 1H), 3.35 (m, 2H), 3.12 (m, 2H), 2.96 (m, 2H), 2.54 (m, 2H), 2.29 (m, 4H), 1.93 (m, 2H), 1.23 (t, 3H).

EXAMPLE 203

3-(1-(2-chlorobenzyl)-1H-indol-5-yl)-1-(1'-propyl-1,4'-bipiperidin-4-yl)-1H-pyrazolo[3,4-d]pyrimidin-4-amine The title compound, as an off-white solid, was prepared as described in EXAMPLE 201 substituting 1-propylpiperidin-4-one for 1-methylpiperidin-4-one in EXAMPLE 201D. MS (ESI+) m/e 583 (M+H)$^+$; (ESI(–)) m/e 581 (M–H)$^-$; $^1$H NMR (300 MHz, DMSO-d$_6$) 9.78 (br s, 1H), 9.57 (br s, 1H), 8.30 (s, 1H), 7.89 (s, 1H), 7.57 (m, 3H), 7.43 (d, 1H), 7.34 (m, 1H), 7.26 (m, 1H), 6.80 (dd, 1H), 6.67 (d, 1H), 5.59 (s, 2H), 5.12 (m, 1H), 3.64 (m, 4H), 3.49 (m, 1H), 3.35 (m, 2H), 3.00 (m, 4H), 2.55 (m, 2H), 2.28 (m, 4H), 1.94 (m, 2H), 1.67 (m, 2H), 0.91 (t, 3H).

EXAMPLE 204

3-(1-(2-chlorobenzyl)-1H-indol-5-yl)-1-(1'-isopropyl-1,4'-bipiperidin-4-yl)-1H-pyrazolo[3,4-d]pyrimidin-4-amine The title compound, as a tan solid, was prepared as described in EXAMPLE 201 substituting 1-isopropylpiperidin-4-one for 1-methylpiperidin-4-one in EXAMPLE 201D. MS (ESI+) m/e 583 (M+H)$^+$; (ESI(–)) m/e 581 (M–H)$^-$; $^1$H NMR (300 MHz, DMSO-d$_6$) 9.83 (br s, 1H), 9.42 (br s, 1H), 8.30 (s, 1H), 7.89 (s, 1H), 7.57 (m, 3H), 7.43 (d, 1H), 7.34 (m, 1H), 7.25 (m, 1H), 6.80 (dd, 1H), 6.66 (d, 1H), 5.58 (s, 2H), 5.13 (m, 1H), 3.56 (m, 6H), 3.36 (m, 2H), 3.04 (m, 2H), 2.54 (m, 2H), 2.29 (m, 4H), 1.97 (m, 2H), 1.25 (d, 6H).

EXAMPLE 205

3-(1-(2-chlorobenzyl)-1H-indol-5-yl)-1-(1'-isobutyl-1,4'-bipiperidin-4-yl)-1H-pyrazolo[3,4-d]pyrimidin-4-amine The title compound, as an off-white solid, was prepared as described in EXAMPLE 201 substituting 1-isobutylpiperidin-4-one for 1-methylpiperidin-4-one in EXAMPLE 201D. MS (ESI+) m/e 597 (M+H)$^+$; (ESI(–)) m/e 595 (M–H)$^-$; $^1$H NMR (300 MHz, DMSO-d$_6$) 9.82 (br s, 1H), 9.22 (br s, 1H), 8.29 (s, 1H), 7.88 (s, 1H), 7.57 (m, 3H), 7.43 (d, 1H), 7.35 (m, 1H), 7.25 (m, 1H), 6.80 (dd, 1H), 6.67 (d, 1H), 5.58 (s, 2H), 5.12 (m, 1H), 3.65 (m, 4H), 3.38 (m, 2H), 2.92 (m, 4H), 2.53 (m, 2H), 2.25 (m, 4H), 2.05 (m, 4H), 0.96 (d, 6H).

EXAMPLE 206

(trans)-3-(2-benzyl-1H-indol-5-yl)-1-(4-morpholin-4-ylcyclohexyl)-1H-pyrazolo[3,4-d]pyrimidin-4-amine

EXAMPLE 206A

5-Bromoindole (1.96 g, 10 mmol) was dissolved in 20 mL of DMF and 60%-sodium hydride (440 mg, 11 mmol) was added. It was stirred at room temperature for 30 minutes. After benzyl bromide (1.31 mL, 11 mmol) was added, it was stirred at 50° C. for over night. EtOAc, followed by brine were added. The EtOAc layer washed with water (×2), brine (×3), dried over Na$_2$SO$_4$, and then evaporated to dryness to yield 2.82 g of the title compound. MS: DCI(+) m/e 287.9 (M+H)$^+$; ESI(–) m/e 285.9 (M–H); $^1$H NMR (300 MHz, DMSO-d$_6$) 7.74 (d., 1H), 7.56 (d., 1H), 7.42 (d., 1H), 7.15-7.32 (m., 6H), 6.48 (dd., 1H), 5.43 (s., 2H)

EXAMPLE 206B

EXAMPLE 206A (140 mg, 0.5 mmol) was added to 10 mL of polyphosphoric acid (PPA) and stirred at 90° C. for 16 h. The mixture was poured into ice-water. The product was extracted by tert-butylmethyl ether (×3) and the organic layer washed with 10%-sodium bicarbonate (×3), brine (×3) and dried over Na$_2$SO$_4$. It was evaporated to dryness to yield 120 mg of the title compound. MS: DCI(+) m/e 287.9 (M+H); ESI(–) m/e 285.9 (M–H); $^1$H NMR (300 MHz, DMSO-d$_6$) 11.14 (br. 1H), 7.59 (d., 1H), 7.22-7.34 (m., 7H), 7.09 (dd., 1H), 6.13 (d., 1H), 4.06 (s., 2H).

EXAMPLE 206C

The desired product was synthesized by substituting EXAMPLE 206B for 4-bromo2-nitro-phenylamine in EXAMPLE 2A. MS: DCI(+) m/e 333.7 (M+H)$^+$

EXAMPLE 206D

The desired product was synthesized by substituting trans-3-iodo-1-(4-morpholin-4-yl-cyclohexyl)-1H-pyrazolo[3,4-d]pyrimidin-4-ylamine prepared as described in PTC Patent Application WO 2005/074603 for EXAMPLE 318A and EXAMPLE 206C for EXAMPLE 217C, respectively, in EXAMPLE 318B. MS: ESI(+) m/e 508.3 (M+H)$^+$; ESI(–) m/e 506.3 (M–H); $^1$H NMR (300 MHz, DMSO-d$_6$) 11.24 (s., 1H), 9.64 (br., 1H), 8.30 (s., 1H), 7.69 (d., 1H), 7.44 (d., 1H), 7.21-7.33 (m., 6H), 6.28 (d., 1H), 4.76 (m., 1H), 4.11 (s., 2H), 4.03 (m., 2H), 3.64-3.75 (m., 2H), 3.32-3.49 (m., 3H), 3.10-3.23 (m., 2H), 2.20-2.29 (m., 2H), 2.07-2.19 (m., 4H), 1.70-1.83 (m., 2H).

EXAMPLE 207

(trans)-3-(2-benzyl-1H-indol-6-yl)-1-(4-morpholin-4-ylcyclohexyl)-1H-pyrazolo[3,4-d]pyrimidin-4-amine

EXAMPLE 207A

The desired product was synthesized by substituting 6-bromoindole for 5-bromoindole in EXAMPLE 206A.

EXAMPLE 207B

The desired product was synthesized by substituting EXAMPLE 207A for EXAMPLE 206A in EXAMPLE 206B. MS: DCI(+) m/e 287.8 (M+H)$^+$; ESI(–) m/e 285.8 (M–H); $^1$H NMR (300 MHz, DMSO-d$_6$) 11.13 (br. 1H), 7.44 (d., 1H), 7.36 (d., 1H), 7.19-7.34 (m., 5H), 7.04 (dd., 1H), 6.16 (d., 1H), 4.06 (s., 2H).

EXAMPLE 207C

The desired product was synthesized by substituting EXAMPLE 207B for EXAMPLE 206B in EXAMPLE 206C. MS: DCI(+) m/e 334.3 (M+H)$^+$

EXAMPLE 207D

The desired product was synthesized by substituting trans-3-iodo-1-(4-morpholin-4-yl-cyclohexyl)-1H-pyrazolo[3,4- d]pyrimidin-4-ylamine prepared as described in PTC Patent Application WO 2005/074603 for EXAMPLE 318A and EXAMPLE 207C for EXAMPLE 217C, respectively, in EXAMPLE 318B. MS: ESI(+) m/e 508.3 (M+H)$^+$; ESI(−) m/e 506.2 (M−H); $^1$H NMR (300 MHz, DMSO-d$_6$) 11.24 (s., 1H), 9.63 (br., 1H), 8.30 (s., 1H), 7.54-7.60 (m., 2H), 7.32-7.33 (m., 4H), 7.22-7.27 (m., 2H), 6.25 (d., 1H), 4.77 (m., 1H), 4.11 (s., 2H), 4.03 (m., 2H), 3.64-3.75 (m., 2H), 3.40-3.50 (m., 3H), 3.10-3.23 (m., 2H), 2.19-2.29 (m., 2H), 2.07-2.18 (m., 4H), 1.70-1.83 (m., 2H).

EXAMPLE 208

3-(1-(2-chlorobenzyl)-1H-indol-5-yl)-1-(4-{(4-(3-methoxypropyl)piperazin-1-yl)methyl}phenyl)-1H-pyrazolo[3,4-d]pyrimidin-4-amine

EXAMPLE 208A 4-(4-amino-3-iodo-1H-pyrazolo[3,4-d]pyrimidin-1-yl)benzaldehyde To a slurry of NaH (1.68 g, 42.1 mmol, 60% in oil) in 300 mL of DMF at RT, was added 3-iodo-1H-pyrazolo[3,4-d]pyrimidin-4-amine (10 g, 38.3 mmol) via a solid addition funnel over 45 min. After addition of the amine was complete, 4-fluorobenzaldehyde (5.0 g, 40.2 mmol) was added dropwise to the reaction mixture. The reaction was heated to 100° C. for 24 hr, an additional NaH (0.25 equivalents) was added and the mixture stirred at 100° C. for another 24 hr. The reaction was cooled to RT for 2 hr, a precipitate formed upon cooling. The reaction mixture was filtered, washed sequentially with water, then Et$_2$O to afford a tan solid, 6.5 g, 47% yield.

EXAMPLE 208B

3-Iodo-1-(4-((4-(3-methoxypropyl)piperazin-1-yl)methyl)phenyl)-1H-pyrazolo[3,4-d]pyrimidin-4-amine A solution of 1-(3-methoxypropyl)piperazine (1.30 g, 8.22 mmol) and EXAMPLE 208A (1.0 g, 2.74 mmol) was slurried into 14 mL of a CH$_3$OH/AcOH solution (9/1 v/v) and heated to 70° C. for 3 hr. The reaction was cooled to RT, diluted with a mixture of CH$_2$Cl$_2$/IPA (4/1 v/v) and washed with saturated aqueous NaHCO$_3$. The layers were separated, and the organic layer was dried over MgSO$_4$, filtered and reduced in vacuo directly onto silica. The reaction was purified via an Intelliflash-280 purification system (CH$_2$Cl$_2$/MeOH) to afford a white solid, 0.45 g, 33% yield.

EXAMPLE 208C

EXAMPLE 208B (0.2 g, 0.39 mmol) and EXAMPLE 93A (0.22 g, 0.59 mmol) were mixed into a 0.3 M solution of DME/H$_2$O (2/1 v/v), added 2 M aqueous Na$_2$CO$_3$ (0.39 mL, 0.39 mmol) and heated the reaction mixture to 130° C. for 20 min in a microwave reactor. The crude reaction mixture was filtered over Celite®. The pad washed with CH$_2$Cl$_2$ and MeOH, the filtrate was dried over MgSO$_4$, filtered, reduced in vacuo. The material was purified via an Intelliflash-280 purification system (CH$_2$Cl$_2$/MeOH) to afford the desired product. (ESI(+)) m/e 621 (M+H)$^+$; $^1$H NMR (300 MHz, DMSO-d$_6$) 8.37 (s, 1H); 8.18 (d, 2H); 7.98 (s, 1H); 7.62-7.45 (m, 6H); 7.34-7.24 (m 2H); 6.78 (d, 1H); 6.70 (d, 1H); 5.61 (s, 2H); 3.51 (s, 2H); 3.20 (s, 3H); 2.39 (bs, 6H); 2.29 (t, 3H); 1.63 (m, 2H).

EXAMPLE 209

(trans)-3-(2-(2-chlorobenzyl)-1H-indol-6-yl)-1-(4-morpholin-4-ylcyclohexyl)-1H-pyrazolo[3,4-d]pyrimidin-4-amine

EXAMPLE 209A

The desired product was synthesized by substituting 6-bromoindole for 5-bromoindole and 2-chlorobenzylbromide for benzyl bromide in EXAMPLE 206A.

EXAMPLE 209B

The desired product was synthesized by substituting EXAMPLE 209A for EXAMPLE 206A in EXAMPLE 206B. MS: DCI(+) m/e 319.9 (M+H)$^+$; ESI(−) m/e 317.9 (M−H);

EXAMPLE 209C

The desired product was synthesized by substituting EXAMPLE 209B for 4-bromo2-nitro-phenylamine in EXAMPLE 2A. MS: DCI(+) m/e 368.3 (M+H)$^+$

EXAMPLE 209D

The desired product was synthesized by substituting trans-3-iodo-1-(4-morpholin-4-yl-cyclohexyl)-1H-pyrazolo[3,4-d]pyrimidin-4-ylamine prepared as described in PTC Patent Application WO 2005/074603 for EXAMPLE 318A and EXAMPLE 209C for EXAMPLE 217C in EXAMPLE 318B. MS: ESI(+) m/e 542.3 (M+H)$^+$; ESI(−) m/e 540.3 (M−H); $^1$H NMR (300 MHz, DMSO-d$_6$) 11.29 (s., 1H), 9.72 (br., 1H), 8.33 (s., 1H), 7.57-7.60 (m., 2H), 7.47-7.75 (m., 2H), 7.25-7.41 (m., 4H), 6.16 (s., 1H), 4.78(m., 1H), 4.24s., 2H), 4.04 (m., 2H), 3.64-3.75 (m., 2H), 3.40-3.50 (m., 3H), 3.10-3.23 (m., 2H), 2.19-2.29 (m., 2H), 2.07-2.18 (m., 4H), 1.70-1.83 (m., 2H).

EXAMPLE 210

{3-((4-{4-amino-3-(1-(2-fluorobenzyl)-1H-indol-5-yl)-1H-pyrazolo[3,4-d]pyrimidin-1-yl}cyclohexyl)amino)phenyl}methanol

EXAMPLE 210A

5-Bromoindole (1.96 g, 10 mmol) was dissolved in 20 mL of DMF, 60%-NaH (0.44 g, 11 mmol) was added. It was stirred for 30 minutes, then 2-fluorobenzyl bromide (1.33 mL, 11 mmol) was added. Stirring continued at 50° C. for 5 hours. After dilution with EtOAc, the organic layer washed with brine (5×), dried over MgSO$_4$. After evaporation to dryness, it was then dried under high vacuum to yield N-2-Fluorobenzyl-5-bromoindole in quantitative yield. The title compound was prepared by substituting N-2-Fluorobenzyl-5-bromoindole (3.04 g, 10 mmol) for 4-bromo-2-nitrophenylamine in EXAMPLE 2A. Crude material was purified by silica gel column chromatography, eluting with 2.5% EtOAc in hexane. 2.18 g of the title compound was obtained. MS: ESI(+) m/e 352.1 (M+H)$^+$.

EXAMPLE 210B

3-Iodo-1-(4-oxo-cyclohexyl)-1H-pyrazolo[3,4-d]pyrimidin-4-ylamine prepared as described in A. F. Burchat et al. Bioorg Med. Chem. Lett. 2002, 12, 1687-1690 (1.192 g, 3.34 mmol), EXAMPLE 210A (1.29 g, 3.67 mmol), $Na_2CO_3$ (708 mg, 6.68 mmol) and $Pd(PPh_3)_4$ (227 mg, 0.1 mmol) were placed into microwave reaction tube and 30 mL of DME:water (1:1) was added. The mixture was microwaved at 130° C. for 20 minutes. 50 mL of EtOAc and 20 mL of water were added. The precipitated solid was collected by filtration, washed with water and dried to yield 600 mg of the title compound. MS: DCI(+) m/e 455.07 (M+H)$^+$;

EXAMPLE 210C

EXAMPLE 210B (45 mg, 0.1 mmol) and 3-aminobenzyl alcohol (123 mg, 1 mmol) was dissolved in 2 mL of methanol and 0.2 mL of acetic acid. After stirring at room temperature for 30 minutes, sodium cyanoborohydride (31 mg, 0.5 mmol) was added and the mixture stirred at 70° C. for 16 h. The mixture was partitioned between EtOAc and brine, the EtOAc layer washed with brine (3×), dried over $MgSO_4$. The crude product was purified by high pressure liquid chromatography (HPLC) to yield 46 mg of the title compound as a mixture of diastereomers. MS: ESI(+) m/e 562.4 (M+H)$^+$; ESI(−) m/e 560.3 (M−H); $^1$H NMR (300 MHz, DMSO-$d_6$) 8.40 (s, 0.6H), 8.38 (s, 0.4H), 7.87 (m, 1H), 7.68 (d, 1H), 7.59 (t, 1H), 7.45 (m, 1H), 7.34 (m, 1H), 7.26 (m, 1H), 7.07-7.19 (m, 3H), 6.64 (m, 1H), 5.56 (s, 2H), 4.44 (s, 0.4H), 4.41 (s, 0.6H), 3.62 (br. 0.6H0, 3.40-3.51 (m, 0.4H), 2.26-2.43 (m, 1H), 1.95-2.18 (m, 3H), 1.77-1.91 (m, 2H).

EXAMPLE 211

4-((4-{4-amino-3-(1-(2-fluorobenzyl)-1H-indol-5-yl)-1H-pyrazolo[3,4-d]pyrimidin-1-yl}cyclohexyl)amino)-3-methylphenol The desired product was prepared as a mixture of diastereomers by substituting 4-amino-m-cresol for 3-aminobenzyl alcohol in EXAMPLE 210C. MS: ESI(+) m/e 562.3 (M+H)$^+$; ESI(−) m/e 560.3 (M−H); $^1$H NMR (300 MHz, DMSO-$d_6$) 8.32 (s, 1H), 7.91 (m, 1H), 7.22-7.71 (m, 5H), 7.07-7.18 (m, 3H), 6.61-6.76 (m, 3H), 5.57 (s, 2H), 4.92 (br. 1H), 3.52 (br. 1H), 2.31 (s, 3H), 1.92-2.13 (m, 6H).

EXAMPLE 212

3-((4-{4-amino-3-(1-(2-fluorobenzyl)-1H-indol-5-yl)-1H-pyrazolo[3,4-d]pyrimidin-1-yl}cyclohexyl)amino)phenol The desired product was prepared as a mixture of diastereomers by substituting 3-aminophenol for 3-aminobenzyl alcohol in EXAMPLE 210C. MS: ESI(+) m/e 548.3 (M+H)$^+$; ESI(−) m/e 546.3 (M−H); $^1$H NMR (300 MHz, DMSO-$d_6$) 8.39 (s, 0.6H), 8.37 (s, 0.4H), 7.88 (m, 1H), 7.68 (d, 1H), 7.58 (dd, 1H), 7.42-7.47 (m, 1H), 7.32-7.38 (m, 1H), 7.22-7.28 (m, 1H), 7.14-7.17 (m, 2H), 6.86-7.06 (br. m., 1H), 6.63-6.65 (m, 1H), 6.07-6.42 (br. 2H), 5.55 (s, 2H), 4.70-4.90 (br. 1H), 2.25-2.41 (m, 1H), 1.92-2.19 (m, 4H), 1.75-1.92 (m, 2H), 1.42-1.60 (m, 1H).

EXAMPLE 213 ethyl 4-((4-{4-amino-3-(1-(2-fluorobenzyl)-1H-indol-5-yl)-1H-pyrazolo[3,4-d]pyrimidin-1-yl}cyclohexyl)amino)benzoate The desired product was prepared as a mixture of diastereomers by substituting 4-aminophenylactic acid ethyl ester for 3-aminobenzyl alcohol in EXAMPLE 210C. MS: ESI(+) m/e 618.4 (M+H)$^+$; ESI(−) m/e 616.6 (M−H); $^1$H NMR (300 MHz, DMSO-$d_6$) 8.40 (s, 0.6H), 8.39 (s, 0.4H), 7.88 (m, 1H), 7.68 (d, 1H), 7.58 (d, 1H), 7.43-7.47 (m, 1H), 7.32-7.39 (m, 1H), 7.22-7.28 (m, 1H), 7.14-7.17 (m, 2H), 7.02-7.04 (br., 1H), 6.74 (br., 1H), 6.64 (d. 1H), 5.55 (s, 2H), 4.78-4.89 (br. 1H), 4.01-4.09 (m, 2H), 3.42-3.61 (m, 3H), 2.26-2.43 (m, 1H), 1.92-2.21 (m, 4H), 1.76-1.91 (m, 3H), 1.15-1.20 (m, 3H).

EXAMPLE 214

(trans)-3-((4-{4-amino-3-(1-(2-fluorobenzyl)-1H-indol-5-yl)-1H-pyrazolo[3,4-d]pyrimidin-1-yl}cyclohexyl)amino)benzoic acid The desired product was prepared by substituting 4-aminobenzoic acid for 3-aminobenzyl alcohol in EXAMPLE 210C. The earlier eluting diastereomer was isolated. MS: ESI(+) m/e 618.4 (M+H)$^+$; ESI(−) m/e 616.6 (M−H); $^1$H NMR (300 MHz, DMSO-$d_6$) 8.40 (s, 0.6H), 8.39 (s, 0.4H), 7.88 (m, 1H), 7.68 (d, 1H), 7.58 (d, 1H), 7.43-7.47 (m, 1H), 7.32-7.39 (m, 1H), 7.22-7.28 (m, 1H), 7.14-7.17 (m, 2H), 7.02-7.04 (br., 1H), 6.74 (br., 1H), 6.64 (d. 1H), 5.55 (s, 2H), 4.78-4.89 (br. 1H), 4.01-4.09 (m, 2H), 3.42-3.61 (m, 3H), 2.26-2.43 (m, 1H), 1.92-2.21 (m, 4H), 1.76-1.91 (m, 3H), 1.15-1.20 (m, 3H).

EXAMPLE 215

(cis)-3-((4-{4-amino-3-(1-(2-fluorobenzyl)-1H-indol-5-yl)-1H-pyrazolo[3,4-d]pyrimidin-1-yl}cyclohexyl)amino)benzoic acid The desired product was the slower eluting diastereomer in EXAMPLE 214. MS: ESI(+) m/e 576.3 (M+H)$^+$; ESI(−) m/e 574.3 (M−H); $^1$H NMR (300 MHz, DMSO-$d_6$) 8.42 (s, 1H) 7.88 (d, 1H), 7.69 (d, 1H), 7.58 (d, 1H), 7.46 (dd, 1H), 7.32-7.38 (m, 1H), 7.09-7.28 (m, 6H), 6.89 (dd., 1H), 6.64 (dd. 1H), 5.55 (s, 2H), 4.84 (br. 1H), 3.62 (m, 1H), 2.28-2.42 (m, 2H), 1.93-2.05 (m, 2H), 1.78-1.92 (m, 4H).

EXAMPLE 216

(trans)-3-(2-(2-chlorobenzyl)-1H-indol-5-yl)-1-(4-morpholin-4-ylcyclohexyl)-1H-pyrazolo[3,4-d]pyrimidin-4-amine

EXAMPLE 216A

The desired product was synthesized by substituting 2-chlorobenzylbromide for benzyl bromide in EXAMPLE 206A.

EXAMPLE 216B

The desired product was synthesized by substituting EXAMPLE 216A for EXAMPLE 206A in EXAMPLE 206B.

EXAMPLE 216C

The desired product was synthesized by substituting EXAMPLE 216B for 4-bromo2-nitro-phenylamine in EXAMPLE 2A.

EXAMPLE 216D

The desired product was synthesized by substituting trans-3-iodo-1-(4-morpholin-4-yl-cyclohexyl)-1H-pyrazolo[3,4-d]pyrimidin-4-ylamine prepared as described in PTC Patent Application WO 2005/074603 for EXAMPLE 318A and EXAMPLE 216C for EXAMPLE 217C in EXAMPLE 318B. $^1$H NMR (300 MHz, DMSO-$d_6$) 11.30 (s., 1H), 9.64 (br., 1H), 8.30 (s., 1H), 7.68 (d., 1H), 7.46 (d., 1H), 7.32 (m., 3H), 7.29 (m., 2H), 6.19 (s., 1H), 4.76 (m., 1H), 4.23 (s., 2H), 4.02 (m., 2H), 3.44 (m., 3H), 3.17 (m., 2H), 2.26 (m., 2H), 2.13 (m., 4H), 1.75 (m., 2H).

EXAMPLE 217

(trans)-3-(2-(2-fluorobenzyl)-1H-indol-5-yl)-1-(4-morpholin-4-ylcyclohexyl)-1H-pyrazolo[3,4-d]pyrimidin-4-amine

EXAMPLE 217A

The desired product was synthesized by substituting 2-fluorobenzylbromide for benzyl bromide in EXAMPLE 206A.

EXAMPLE 217B

The desired product was synthesized by substituting EXAMPLE 217A for EXAMPLE 206A in EXAMPLE 206B.

EXAMPLE 217C

The desired product was synthesized by substituting EXAMPLE 217B for 4-bromo-2-nitro-phenylamine in EXAMPLE 2A. MS: DCI(+) m/e 352.4 (M+H)$^+$

EXAMPLE 217D

The desired product was synthesized by substituting trans-3-iodo-1-(4-morpholin-4-yl-cyclohexyl)-1H-pyrazolo[3,4-d]pyrimidin-4-ylamine prepared as described in PTC Patent Application WO 2005/074603 for EXAMPLE 318A and EXAMPLE 217C for EXAMPLE 217C in EXAMPLE 318B. It was then purified by HPLC to yield 30 mg of the title compound. MS: ESI(+) m/e 526.4 (M+H)$^+$; ESI(−) m/e 524.4 (M−H); $^1$H NMR (300 MHz, DMSO-$d_6$) 11.28 (s., 1H), 9.61 (br., 1H), 8.29 (s., 1H), 7.68 (d., 1H), 7.46 (d., 1H), 7.28-7.38 (m., 3H), 7.15-7.24 (m., 2H), 6.22 (s., 1H), 4.76 (m., 1H), 4.14 (s., 2H), 4.03 (m., 2H), 3.40-3.50 (m., 3H), 3.10-3.24 (m., 2H), 2.20-2.29 (m., 2H), 2.07-2.18 (m., 4H), 1.68-1.83 (m., 2H).

EXAMPLE 218

3-((4-{4-amino-3-(1-(2-fluorobenzyl)-1H-indol-5-yl)-1H-pyrazolo[3,4-d]pyrimidin-1-yl}cyclohexyl)amino)-4-chlorobenzoic acid The desired product was prepared by substituting 3-amino-4-chlorobenzoic acid for 3-aminobenzyl alcohol in EXAMPLE 210C. MS: ESI(+) m/e 610.5 (M+H)$^+$; ESI(−) m/e 608.5 (M−H); $^1$H NMR (300 MHz, DMSO-$d_6$) 8.38 (s, 0.4H), 8.37 (s, 0.6H), 7.88 (m, 1H), 7.69 (d, 1H), 7.13-7.48 (m, 10H), 6.64 (d. 1H), 5.55 (s, 2H), 4.78-4.89 (br. 1H), 4.01-4.09 (m, 2H), 2.22-2.34 (m, 2H), 2.01-2.19 (m, 4H), 1.84-1.97 (m, 2H).

EXAMPLE 219

(trans)-3-(2-(4-methylphenoxy)-1H-benzimidazol-6-yl)-1-(4-morpholin-4-ylcyclohexyl)-1H-pyrazolo[3,4-d]pyrimidin-4-amine

EXAMPLE 219A 5-bromo-2-(p-tolyloxy)-1H-benzo(d)imidazole

To a microwave vial was added p-cresol (0.326 g, 3.02 mmol), sodium hydride 60% dispersion (0.12 g, 3.02 mmol), DMF (2.2 mL) and the solution was allowed to stir at room temperature for 30 minutes. To the reaction mixture was added EXAMPLE 133A (0.5 g, 2.16 mmol) and heated to 170° C. for 20 minutes in a microwave reactor. To the reaction mixture was added ethyl acetate and the organics were washed 2× with water and brine. The organic fraction over magnesium sulfate, filtered, and reduced in vacuo. The residue was purified using LC with hexane/ethyl acetate gradient solvent was reduced in vacuo to afford the desired product as a white solid. (ESI(+)) m/e 303, 305 (M+H)$^+$.

EXAMPLE 219B 5-(4,4,5,5-tetramethyl-1,3,2-dioxaborolan-2-yl)-2-(p-tolyloxy)-1H-benzo(d)imidazole The desired product was prepared by substituting EXAMPLE 219A for EXAMPLE 133B in EXAMPLE 133C. (ESI(+)) m/e 351 (M+H)$^+$.

EXAMPLE 219C 1-((1r,4r)-4-morpholinocyclohexyl)-3-(2-(p-tolyloxy)-1H-benzo(d)imidazol-6-yl)-1H-pyrazolo[3,4-d]pyrimidin-4-amine The desired product was prepared by substituting EXAMPLE 219B for EXAMPLE 133C in EXAMPLE 133D. (ESI(+)) m/e 525 (M+H)$^+$; (ESI(−)) m/e 523 (M−H)$^-$; $^1$H NMR (500 MHz, ACETONE-$d_6$) 10.96 (bs, 1H), 8.46 (s, 1H), 7.71 (s, 1H), 7.57-7.47 (m, 2H), 7.34-7.23 (m, 4H), 5.34 (bs, 2H), 4.93 (ddd, 1H), 4.03 (bs, 4H), 3.65-3.55 (m, 2H), 3.50 (t, 2H), 3.28 (s, 2H), 2.49 (d, 2H), 2.35 (s, 3H), 2.32-2.26 (m, 4H), 2.07 (m 2H).

EXAMPLE 220

(trans)-3-(2-(3-methylphenoxy)-1H-benzimidazol-6-yl)-1-(4-morpholin-4-ylcyclohexyl)-1H-pyrazolo[3,4-d]pyrimidin-4-amine

EXAMPLE 220A 5-bromo-2-(m-tolyloxy)-1H-benzo(d)imidazole

The desired product was prepared by substituting 5-bromo-2-(m-tolyloxy)-1H-benzo(d)imidazole for 5-bromo-2-(phenylsulfonyl)-1H-benzo(d)imidazole in EXAMPLE 219A. (ESI(+)) m/e 351 (M+H)$^+$.

EXAMPLE 220B 5-(4,4,5,5-tetramethyl-1,3,2-dioxaborolan-2-yl)-2-(m-tolyloxy)-1H-benzo(d)imidazole The desired product was prepared by substituting EXAMPLE 220A for EXAMPLE 133B in EXAMPLE 133C. (ESI(+)) m/e 351 (M+H)$^+$.

EXAMPLE 220C 1-((1r,4r)-4-morpholinocyclohexyl)-3-(2-(m-tolyloxy)-1H-benzo(d)imidazol-6-yl)-1H-pyrazolo[3,4-d]pyrimidin-4-amine The desired product was prepared by substituting EXAMPLE 220B for EXAMPLE 133C in EXAMPLE 133D. (ESI(+)) m/e 525 (M+H)$^+$; (ESI(−)) m/e 523 (M−H)$^−$; $^1$H NMR (500 MHz, ACETONE-d$_6$) 10.93 (bs, 1H), 8.47 (s, 1H), 7.74 (d, 1H), 7.58-7.55 (m, 1H), 7.53-7.49 (m, 1H), 7.35(t, 1H), 7.27-7.23 (m, 2H), 7.12 (d, 1H), 4.98-4.88 (m, 1H), 4.03 (bs, 4H), 3.66-3.55 (m, 2H), 3.54-3.45 (m, 2H), 3.28 (s, 2H), 2.49 (d, 2H), 2.38 (s, 3H), 2.33-2.25 (m, 4H), 2.07 (m, 2H).

EXAMPLE 221

3-(4-(4-{4-amino-3-(3-(2-fluorobenzyl)-1H-indol-5-yl)-1H-pyrazolo[3,4-d]pyrimidin-1-yl}cyclohexyl)piperazin-1-yl)propan-1-ol The title product was isolated as by-product in EXAMPLE 223. MS: ESI(+) m/e 583.4 (M+H)$^+$; ESI(−) m/e 581.5 (M−H); $^1$H NMR (300 MHz, DMSO-d$_6$) 11.33-11.36 (m., 1H), 8.31 (s, 1H includes 8.30), 7.43-7.47 (m, 1H), 7.26-7.34 (m., 2H), 7.11-7.23 (m., 3H), 6.20 (d., 1H), 4.92 (m., 0.6H), 4.75 (m., 0.4H), 4.12 (s., 2H), 3.42-3.53 (m, 4H), 2.82-3.16 (m, 4H), 2.24-2.41 (m., 2H), 2.02-2.15 (m, 4H), 1.60-1.95 (m, 4H).

EXAMPLE 222

(cis)-3-(4-(4-{4-amino-3-(2-(2-fluorobenzyl)-1H-indol-5-yl)-1H-pyrazolo[3,4-d]pyrimidin-1-yl}cyclohexyl)piperazin-1-yl)propan-1-ol The desired product was the slower eluting diastereomer in EXAMPLE 223. MS: ESI(+) m/e 583.4 (M+H)$^+$; ESI(−) m/e 581.5 (M−H); $^1$H NMR (300 MHz, DMSO-d$_6$) 11.30 (s., 1H), 8.31 (s, 1H), 7.70 (s, 1H), 7.48 (d., 1H), 7.28-7.38 (m., 3H), 7.15-7.24 (m., 2H), 6.22 (d., 1H), 4.94 (m., 1H), 4.15 (s., 2H), 3.42-3.53 (m, 4H, includes=3.46, t, 2H), 2.89-3.16 (m, 4H), 2.24-2.41 (m., 2H), 2.02-2.14 (m, 2H), 1.68-1.94 (m, 4H).

EXAMPLE 223

(trans)-3-(4-(4-{4-amino-3-(2-(2-fluorobenzyl)-1H-indol-5-yl)-1H-pyrazolo[3,4-d]pyrimidin-1-yl}cyclohexyl)piperazin-1-yl)propan-1-ol

EXAMPLE 223A

The desired product was synthesized by substituting 3-Iodo-1-(4-oxo-cyclohexyl)-1H-pyrazolo[3,4-d]pyrimidin-4-ylamine prepared as described in A. F. Burchat et al. Bioorg Med. Chem. Lett. 2002, 12, 1687-1690 for EXAMPLE 318A in EXAMPLE 318B. MS: ESI(+) m/e 455.5 (M+H)$^+$.

EXAMPLE 223B

The desired product was synthesized by substituting 1-(3-hydroxypropyl)piperazine for 1-(2-hydroxyethyl)piperazine in EXAMPLE 134B. The earlier eluting diastereomer was isolated. MS: ESI(+) m/e 583.5 (M+H)$^+$; ESI(−) m/e 581.6 (M−H); $^1$H NMR (300 MHz, DMSO-d$_6$) 11.25 (s., 1H), 8.27 (s, 1H), 7.68 (d, 1H), 7.47 (d., 1H), 7.28-7.38 (m., 3H), 7.16-7.25 (m., 2H), 6.22 (d., 1H), 4.72 (m., 1H), 4.14 (s., 2H), 3.42-3.53 (m, 4H, includes=3.48, t, 2H), 2.90-3.16 (m, 4H), 2.02-2.17 (m, 6H), 1.61-1.84 (m, 4H).

EXAMPLE 224

3-(3-(2-fluorobenzyl)-1H-indol-5-yl)-1-{4-(4-(3-methoxypropyl)piperazin-1-yl)cyclohexyl}-1H-pyrazolo[3,4-d]pyrimidin-4-amine The title product was isolated as by-product in EXAMPLE 225. MS: ESI(+) m/e 597.5 (M+H)$^+$; ESI(−) m/e 595.4 (M−H); $^1$H NMR (300 MHz, DMSO-d$_6$) 11.31-11.36 (m., 1H), 8.30 (s, 0.6H), 8.29 (s., 0.4H), 7.43-7.47 (m, 1H), 7.25-7.34 (m., 2H), 7.13-7.22 (m., 3H), 6.20 (d., 1H), 4.92 (m., 0.6H), 4.78(m., 0.4H), 4.12 (s., 2H), 3.33-3.41 (m, 4H), 3.25 (s., 1.3H), 3.22 (s., 1.7H), 2.82-3.16 (m, 4H), 2.24-2.41 (m., 2H), 2.02-2.15 (m, 4H), 1.60-1.95 (m, 4H).

EXAMPLE 225

3-(2-(2-fluorobenzyl)-1H-indol-5-yl)-1-{4-(4-(3-methoxypropyl)piperazin-1-yl)cyclohexyl}-1H-pyrazolo[3,4-d]pyrimidin-4-amine The desired product was synthesized as a mixture of diastereomers by substituting 1-(3-methoxypropyl)-piperazine for 1-(2-hydroxyethyl)piperazine in EXAMPLE 134B. MS: ESI(+) m/e 597.4 (M+H)$^+$; ESI(−) m/e 595.5 (M−H); $^1$H NMR (300 MHz, DMSO-d$_6$) 11.29 (s., 1H), 8.29 (s, 1H includes 8.30, s), 7.69 (br.d, 1H), 7.47 (dd., 1H), 7.28-7.38 (m., 3H), 7.15-7.24 (m., 2H), 6.22 (s., 1H), 4.94 (br.m., 0.5H), 4.73 (br.m., 0.5H), 4.14 (s., 2H), 3.42-3.53 (m, 4H, includes=3.37, t, 2H), 3.25 (s., 1.5H), 3.23 (s., 1.5H), 2.90-3.16 (m, 4H), 2.02-2.18 (m, 4H), 1.60-1.94 (m, 4H).

EXAMPLE 226

2-(4-(4-{4-amino-3-(3-(2-fluorobenzyl)-1H-indol-5-yl)-1H-pyrazolo[3,4-d]pyrimidin-1-yl}cyclohexyl)piperazin-1-yl)ethanol The title product was isolated as a byproduct in EXAMPLE 227. MS: ESI(+) m/e 569.4 (M+H)$^+$; ESI(−) m/e 567.4 (M−H); $^1$H NMR (300 MHz, DMSO-d$_6$) 11.33-11.38 (m., 1H), 8.31 (s, 0.6H), 8.30 (s., 0.4H), 7.43-7.47 (m, 1H), 7.25-7.33 (m., 2H), 7.12-7.23 (m., 3H), 6.19 (d., 1H), 4.94 (m., 0.6H), 4.77(m., 0.4H), 4.13 (s., 2H), 3.38-3.54 (m, 4H), 2.92-3.20 (m, 4H), 2.24-2.40 (m., 2H), 1.98-2.17 (m, 4H), 1.65-1.95 (m, 2H).

EXAMPLE 227

(cis)-2-(4-(4-{4-amino-3-(2-(2-fluorobenzyl)-1H-indol-5-yl)-1H-pyrazolo[3,4-d]pyrimidin-1-yl}cyclohexyl)piperazin-1-yl)ethanol The desired product was synthesized by substituting EXAMPLE 223A for EXAMPLE 134A in EXAMPLE 134B. The earlier eluting diastereomer was isolated. MS: ESI(+) m/e 569.4 (M+H)$^+$; ESI(−) m/e 567.4 (M−H); $^1$H NMR (300 MHz, DMSO-d$_6$) 11.29 (s., 1H), 8.30 (s, 1H), 7.69 (br.d, 1H), 7.47 (dd., 1H), 7.29-7.37 (m., 3H), 7.15-7.24 (m., 2H), 6.22 (s., 1H), 4.89 (br.m., 1H), 4.15 (s., 2H), 3.42-3.53 (m, 4H, includes=3.69, t, 2H), 3.3.34-3.59 (m., 3H), 2.98-3.18 (m, 4H), 2.26-2.40 (m., 2H), 2.02-2.18 (m, 4H), 1.74-1.94 (m, 4H).

EXAMPLE 228

(trans)-2-(4-(4-{4-amino-3-(2-(2-fluorobenzyl)-1H-indol-5-yl)-1H-pyrazolo[3,4-d]pyrimidin-1-yl}cyclohexyl)piperazin-1-yl)ethanol The desired product was the slower eluting diastereomer in EXAMPLE 227. MS: ESI(+) m/e 569.4 (M+H)$^+$; ESI(−) m/e 567.4 (M−H); $^1$H NMR (300 MHz, DMSO-d$_6$) 11.30 (s., 1H), 8.32 (s, 1H), 7.68 (d, 1H), 7.47 (d., 1H), 7.28-7.39 (m., 3H), 7.15-7.24 (m., 2H), 6.22 (d., 1H), 4.75 (m., 1H), 4.15 (s., 2H), 3.42-3.53 (m, 4H, includes=3.72, t, 2H), 3.01-3.19 (m, 4H), 2.04-2.20 (m, 4H), 1.52-1.64 (m, 2H).

EXAMPLE 229

(cis)-3-(4-{4-(4-amino-3-(2-benzyl-1H-indol-5-yl)-1H-pyrazolo[3,4-d]pyrimidin-1-yl)cyclohexyl}piperazin-1-yl)propan-1-ol

EXAMPLE 229A

The desired product was synthesized by substituting 3-Iodo-1-(4-oxo-cyclohexyl)-1H-pyrazolo[3,4-d]pyrimidin-4-ylamine prepared as described in A. F. Burchat et al. Bioorg Med. Chem. Lett. 2002, 12, 1687-1690 for EXAMPLE 318A and EXAMPLE 207C for EXAMPLE 217C in EXAMPLE 318B. MS: ESI(+) m/e 437.2

EXAMPLE 229B

The desired product was synthesized by substituting EXAMPLE 229A for EXAMPLE 223A in EXAMPLE 134B. The earlier eluting diastereomer was isolated. MS: ESI(+) m/e 565.4 (M+H)$^+$; ESI(−) m/e 563.4 (M−H); $^1$H NMR (300 MHz, DMSO-d$_6$) 11.26 (s., 1H), 8.32 (s, 1H), 7.70 (s, 1H), 7.45 (d., 1H), 7.22-7.33 (m, 6H), 6.23 (d., 1H), 4.90 (m., 1H), 4.11 (s., 2H), 3.40-3.58 (m, 4H, includes=3.47, t, 2H), 2.26-2.40 (m., 1H), 2.09-3.13 (m, 3H), 2.24-2.41 (m., 1H), 2.03-2.16 (m, 2H), 1.68-1.94 (m, 4H).

EXAMPLE 230

(trans)-3-(4-{4-(4-amino-3-(2-benzyl-1H-indol-5-yl)-1H-pyrazolo[3,4-d]pyrimidin-1-yl)cyclohexyl}piperazin-1-yl)propan-1-ol This example was the slower eluting diastereomer in EXAMPLE 229. MS: ESI(+) m/e 565.5 (M+H)$^+$; ESI(−) m/e 563.4 (M−H); $^1$H NMR (300 MHz, DMSO-d$_6$) 11.26 (s., 1H), 8.34 (s, 1H), 7.69 (d, 1H), 7.46 (d., 1H), 7.21-7.33 (m., 6H), 6.28 (d., 1H), 4.76 (m., 1H), 4.11 (s., 2H), 3.41-3.65 (m, 4H, includes=3.49, t, 2H), 3.01-3.18 (m, 4H), 2.04-2.18 (m, 4H), 1.64-1.83 (m, 2H).

EXAMPLE 231

3-(2-benzyl-1H-indol-5-yl)-1-{4-(4-(3-methoxypropyl)piperazin-1-yl)cyclohexyl}-1H-pyrazolo[3,4-d]pyrimidin-4-amine The desired product was synthesized as a mixture of diastereomers by substituting 1-(3-methoxypropyl)piperazine for 1-(3-hydroxypropyl)piperazine and EXAMPLE 229A for EXAMPLE 223A in EXAMPLE 134B. MS: ESI(+) m/e 579.5 (M+H)$^+$; ESI(−) m/e 577.4 (M−H);
$^1$H NMR (300 MHz, DMSO-d$_6$) 11.26 (s., 1H), 8.31 (s, 0.6H), 8.30 (s., 0.4), 7.43-7.47 (m., 1H), 7.21-7.33 (m., 7H), 6.28 (s., 1H), 4.90 (br.m., 0.6H), 4.74 (br.m., 0.4H), 4.11 (s., 2H), 3.42-3.53 (m, 4H, includes=3.38, q, 2H), 3.25 (s., 1.5H), 3.23 (s., 1.5H), 2.82-3.12 (m, 4H), 2.26-2.40 (m., 2H), 2.02-2.18 (m, 4H), 1.60-1.94 (m, 4H).

EXAMPLE 232

(cis)-2-(4-{4-(4-amino-3-(2-benzyl-1H-indol-5-yl)-1H-pyrazolo[3,4-d]pyrimidin-1-yl)cyclohexyl}piperazin-1-yl)ethanol The desired product was synthesized by substituting EXAMPLE 229A for EXAMPLE 134A in EXAMPLE 134B. The earlier eluting diastereomer was isolated. MS: ESI(+) m/e 551.5 (M+H)$^+$; ESI(−) m/e 549.4 (M−H); $^1$H NMR (300 MHz, DMSO-d$_6$) 11.27 (s., 1H), 8.33 (s, 1H), 7.71 (br.d, 1H), 7.46 (dd., 1H), 7.22-7.33 (m., 6H), 6.28 (s., 1H), 4.92 (br.m., 1H), 4.11 (s., 2H), 3.70 (t, 2H), 3.42-3.61 (m., 2H), 3.05-3.20 (m, 4H), 2.30-2.41(m., 1H), 2.02-2.18 (m, 2H), 1.80-1.94 (m, 2H).

EXAMPLE 233

(trans)-2-(4-{4-(4-amino-3-(2-benzyl-1H-indol-5-yl)-1H-pyrazolo[3,4-d]pyrimidin-1-yl)cyclohexyl}piperazin-1-yl)ethanol This example was the slower eluting diastereomer in EXAMPLE 232. MS: ESI(+) m/e 551.4 (M+H)$^+$; ESI(−) m/e 549.5 (M−H); $^1$H NMR (300 MHz, DMSO-d$_6$) 11.25 (s., 1H), 8.30 (s, 1H), 7.69 (d, 1H), 7.54-7.65 (m., 2H), 7.45 (d., 1H), 7.21-7.33 (m., 4H), 6.28 (d., 1H), 4.74 (m., 1H), 4.11 (s., 2H), 3.71 (t, 2H), 3.42-3.61 (m., 2H), 3.00-3.20 (m, 4H), 2.02-2.18 (m, 4H), 1.60-1.77 (m, 2H).

EXAMPLE 234

(cis)-4-(4-{4-amino-5-(1-(2-fluorobenzyl)-1H-indol-5-yl)-7H-pyrrolo[2,3-d]pyrimidin-7-yl}cyclohexyl)-1-isopropylpiperazin-2-one The desired product was synthesized by substituting (cis)-4-(4-(-4-amino-3-iodo-pyrazolo[3,4-d]pyrimidin-1-yl)-cyclohexyl)-1-isopropyl-piperazin-2-one prepared as described in WO 2005/074603 for 3-iodo-1-(4-oxo-cyclohexyl)-1H-pyrazolo[3,4-d]pyrimidin-4-ylamine in EXAMPLE 210B. MS (ESI) m/e 580 (M+H)$^−$; $^1$H NMR (300 MHz, DMSO-d$_6$) δ8.39 (s, 1H), 7.68 (s, 1H), 7.62 (d, 1H), 7.56 (m, 2H), 7.34 (m, 1H), 7.28 (s, 1H), 7.24 (m, 1H), 7.15 (m, 2H), 6.56 (d, 1H), 5.53 (s, 2H), 4.84 (m, 1H), 4.62 (m, 1H), 3.44 (m, 6H), 2.18 (m, 4H), 1.91 (m, 4H), 1.10 (d, 6H).

EXAMPLE 235

(cis)-4-(4-{4-amino-5-(1-(2-chlorobenzyl)-1H-indol-5-yl)-7H-pyrrolo[2,3-d]pyrimidin-7-yl}cyclohexyl)-1-isopropylpiperazin-2-one The desired product was synthesized by substituting (cis)-4-(4-(-4-amino-3-iodo-pyrazolo[3,4-d]pyrimidin-1-yl)-cyclohexyl)-1-isopropyl-piperazin-2-one prepared as described in WO 2005/074603 for trans-3-iodo-1-(4-morpholin-4-yl-cyclohexyl)-1H-pyrazolo[3,4-d]pyrimidin-4-ylamine in EXAMPLE 93B. MS (ESI) m/e 596 (M+H)$^-$; $^1$H NMR (300 MHz, DMSO-d$_6$) δ8.40 (s, 1H), 7.71 (s, 1H), 7.56 (m, 4H), 7.33 (t, 1H), 7.26 (m, 2H), 6.77 (d, 1H), 6.59 (d, 1H), 5.57 (s, 2H), 4.85 (m, 1H), 4.62 (m, 1H), 3.45 (m, 6H), 2.18 (m, 4H), 1.91 (m, 4H), 1.10 (d, 6H).

EXAMPLE 236

(cis)-4-(4-{4-amino-5-(1-(2-fluorobenzyl)-1H-indol-5-yl)-7H-pyrrolo[2,3-d]pyrimidin-7-yl}cyclohexyl)-1-ethylpiperazin-2-one The desired product was synthesized by substituting (cis)-4-(4-(-4-amino-3-iodo-pyrazolo[3,4-d]pyrimidin-1-yl)-cyclohexyl)-1-ethyl-piperazin-2-one prepared as described in WO 2005/074603 for 3-iodo-1-(4-oxo-cyclohexyl)-1H-pyrazolo[3,4-d]pyrimidin-4-ylamine in EXAMPLE 210B. MS (ESI) m/e 566 (M+H)$^-$; $^1$H NMR (300 MHz, DMSO-d$_6$) δ8.39 (s, 1H), 7.68 (s, 1H), 7.62 (d, 1H), 7.56 (m, 2H), 7.35 (m, 1H), 7.28 (s, 1H), 7.24 (m, 1H), 7.15 (m, 2H), 6.56 (d, 1H), 5.53 (s, 2H), 4.84 (m, 1H), 3.66 (m, 6H), 3.39 (q, 2H), 2.17 (m, 4H), 1.91 (m, 4H), 1.07 (t, 3H).

EXAMPLE 237

(cis)-4-(4-{4-amino-5-(1-(2-chlorobenzyl)-1H-indol-5-yl)-7H-pyrrolo[2,3-d]pyrimidin-7-yl}cyclohexyl)-1-ethylpiperazin-2-one The desired product was synthesized by substituting (cis)-4-(4-(-4-amino-3-iodo-pyrazolo[3,4-d]pyrimidin-1-yl)-cyclohexyl)-1-ethyl-piperazin-2-one prepared as described in WO 2005/074603 for trans-3-iodo-1-(4-morpholin-4-yl-cyclohexyl)-1H-pyrazolo[3,4-d]pyrimidin-4-ylamine in EXAMPLE 93B. MS (ESI) m/e 582 (M+H)$^-$; $^1$H NMR (300 MHz, DMSO-d$_6$) δ8.39 (s, 1H), 7.71 (s, 1H), 7.54 (m, 4H), 7.34 (t, 1H), 7.27 (m, 2H), 6.78 (d, 1H), 6.59 (d, 1H), 5.57 (s, 2H), 4.85 (m, 1H), 3.66 (m, 6H), 3.39 (q, 2H), 2.17 (m, 4H), 1.91 (m, 4H), 1.07 (t, 3H).

EXAMPLE 238

5-(1-(2-fluorobenzyl)-1H-indol-5-yl)-7-(4-(4-methylpiperazin-1-yl)cyclohexyl)-7H-pyrrolo[2,3-d]pyrimidin-4-amine The desired product was synthesized by substituting 3-iodo-1-(4-(4-methyl-piperazin-1-yl)-cyclohexyl)-1H-pyrazolo[3,4-d]pyrimidin-4-ylamine prepared as described in A. F. Burchat et al. Bioorg Med. Chem. Lett. 2002, 12, 1687-1690 for 3-iodo-1-(4-oxo-cyclohexyl)-1H-pyrazolo[3,4-d]pyrimidin-4-ylamine in EXAMPLE 210B. MS (ESI) m/e 538 (M+H)$^-$; $^1$H NMR (300 MHz, DMSO-d$_6$) δ8.42, 8.41 (s, 1H), 7.67, 7.68 (s, 1H), 7.62 (d, 1H), 7.56 (m, 2H), 7.35 (m, 1H), 7.27 (m, 2H), 7.15 (m, 2H), 6.56 (d, 1H), 5.53 (s, 2H), 4.80, 4.67 (m, 1H), 3.42 (m, 4H), 3.25, 3.07 (m, 4H), 2.77 (s, 3H), 2.04 (m, 4H), 1.91-1.59 (m, 4H).

EXAMPLE 239

5-(1-(2-chlorobenzyl)-1H-indol-5-yl)-7-(4-(4-methylpiperazin-1-yl)cyclohexyl)-7H-pyrrolo[2,3-d]pyrimidin-4-amine The desired product was synthesized by substituting 3-iodo-1-(4-(4-methyl-piperazin-1-yl)-cyclohexyl)-1H-pyrazolo[3,4-d]pyrimidin-4-ylamine prepared as described in A. F. Burchat et al. Bioorg Med. Chem. Lett. 2002, 12, 1687-1690 for trans-3-iodo-1-(4-morpholin-4-yl-cyclohexyl)-1H-pyrazolo[3,4-d]pyrimidin-4-ylamine in EXAMPLE 93B. MS (ESI) m/e 554 (M+H)$^-$; $^1$H NMR (300 MHz, DMSO-d$_6$) δ8.41, 8.40 (s, 1H), 7.70 (m, 2H), 7.56 (m, 3H), 7.34 (m, 1H), 7.25 (m, 2H), 6.78 (m, 1H), 6.60 (d, 1H), 5.57 (s, 2H), 4.80, 4.67 (m, 1H), 3.42 (m, 4H), 3.24, 3.06 (m, 4H), 2.77 (s, 3H), 2.04 (m, 4H), 1.91-1.59 (m, 4H).

EXAMPLE 240

7-tert-butyl-5-(1-(2-fluorobenzyl)-1H-indol-5-yl)-7H-pyrrolo[2,3-d]pyrimidin-4-amine The desired product was synthesized by substituting 7-tert-butyl-5-iodo-7H-pyrrolo[3,4-d]pyrimidin-4-ylamine prepared as described in US Patent Application US20060025383 for 3-iodo-1-(4-oxo-cyclohexyl)-1H-pyrazolo[3,4-d]pyrimidin-4-ylamine in EXAMPLE 210B. MS (ESI) m/e 414 (M+H)$^-$; $^1$H NMR (300 MHz, DMSO-d$_6$) δ8.40 (s, 1H), 7.68 (s, 1H), 7.62 (d, 1H), 7.55 (m, 2H), 7.35 (m, 1H), 7.26 (m, 2H), 7.15 (m, 2H), 6.56 (d, 1H), 5.53 (s, 2H), 1.76 (s, 9H).

EXAMPLE 241

7-tert-butyl-5-(1-(2-chlorobenzyl)-1H-indol-5-yl)-7H-pyrrolo[2,3-d]pyrimidin-4-amine The desired product was synthesized by substituting 7-tert-butyl-5-iodo-7H-pyrrolo[3,4-d]pyrimidin-4-ylamine prepared as described in US Patent Application US20060025383 for trans-3-iodo-1-(4-morpholin-4-yl-cyclohexyl)-1H-pyrazolo[3,4-d]pyrimidin-4-ylamine in EXAMPLE 93B. MS (ESI) m/e 430 (M+H)$^-$; $^1$H NMR (300 MHz, DMSO-d$_6$) δ8.40 (s, 1H), 7.71 (s, 1H), 7.54 (m, 3H), 7.33 (m, 1H), 7.25 (m, 2H), 6.78 (m, 1H), 6.60 (d, 1H), 5.57 (s, 1H), 1.77 (s, 9H).

EXAMPLE 242

3-(1-(2-fluorobenzyl)-1H-indol-5-yl)-1-(4-(morpholin-4-ylmethyl)phenyl)-1H-pyrazolo[3,4-d]pyrimidin-4-amine The desired product was synthesized by substituting EXAMPLE 48B for 3-iodo-1-(4-oxo-cyclohexyl)-1H-pyrazolo[3,4-d]pyrimidin-4-ylamine in EXAMPLE 210B. MS (ESI) m/e 534 (M+H)$^-$; $^1$H NMR (300 MHz, DMSO-d$_6$) δ9.83 (bs, 1H), 8.41 (m, 3H), 7.79 (s, 1H), 7.71 (m, 3H), 7.61 (d, 1H), 7.53 (d, 1H), 7.35 (m, 1H), 7.25 (m, 1H), 7.16 (m, 2H), 6.66 (d, 1H), 5.57 (s, 1H), 4.42 (s, 2H), 3.97 (m, 2H), 3.64 (m, 2H), 3.31 (m, 2H), 3.17 (m, 2H).

EXAMPLE 243

(trans)-4-((4-{4-amino-3-(1-(2-fluorobenzyl)-1H-indol-5-yl)-1H-pyrazolo[3,4-d]pyrimidin-1-yl}cyclohexyl)amino)benzoic acid The desired product was prepared by substituting 4-aminobenzoic acid for 3-aminobenzyl alcohol in EXAMPLE 210C. The earlier eluting diastereomer was isolated. MS: ESI(+) m/e 576.4 (M+H)$^+$; ESI(−) m/e 574.4 (M−H); $^1$H NMR (300 MHz, DMSO-$d_6$) 8.39 (s, 1H) 7.88 (d, 1H), 7.65-7.71(m, 3H), 7.59 (d, 1H), 7.46 (dd, 1H), 7.31-7.40 (m, 1H), 7.22-7.28 (m, 1H), 7.12-7.20 (m, 2H), 6.62-6.65 (m, 3H), 5.55 (s, 2H), 4.78 (br. 1H), 3.46 (m, 1H), 2.10-2.28 (m, 4H), 1.97-2.08 (m, 2H), 1.39-1.55 (m, 2H).

EXAMPLE 244

(cis)-4-((4-{4-amino-3-(1-(2-fluorobenzyl)-1H-indol-5-yl)-1H-pyrazolo[3,4-d]pyrimidin-1-yl}cyclohexyl)amino)benzoic acid The desired product was the slower eluting diastereomer in EXAMPLE 243. MS: ESI(+) m/e 576.4 (M+H)$^+$; ESI(−) m/e 574.4 (M−H); $^1$H NMR (300 MHz, DMSO-$d_6$) 8.40 (s, 1H), 7.88 (d, 1H), 7.65-7.70(m, 3H), 7.59 (d, 1H), 7.45 (dd, 1H), 7.32-7.40 (m, 1H), 7.22-7.28 (m, 1H), 7.12-7.20 (m, 2H), 6.62-6.69 (m, 3H), 5.55 (s, 2H), 4.85 (br. 1H), 3.67 (m, 1H), 2.24-2.41 (m, 2H), 1.93-2.09 (m, 2H), 1.80-1.93 (m, 4H).

EXAMPLE 245

3-(2-(2-chlorobenzyl)-1H-benzimidazol-5-yl)-1-(4-(morpholin-4-ylmethyl)phenyl)-1H-pyrazolo[3,4-d]pyrimidin-4-amine The desired product was prepared as described in EXAMPLE 48 by substituting 2-chlorophenylacetaldehyde for phenylacetaldehyde in EXAMPLE 48D. MS (ESI) m/e 551 (M+H)$^-$; $^1$H NMR (300 MHz, DMSO-$d_6$) 9.85 (bs, 1H), 8.41 (m, 3H), 7.92 (s, 1H), 7.78 (d, 1H), 7.69 (m, 3H), 7.53 (m, 2H), 7.40 (m, 2H), 4.51 (s, 2H), 4.43 (s, 2H), 4.00 (m, 2H), 3.64 (m, 2H), 3.32 (m, 2H), 3.18 (m, 2H).

EXAMPLE 246

3-(2-(3-methylbenzyl)-1H-benzimidazol-5-yl)-1-(4-(morpholin-4-ylmethyl)phenyl)-1H-pyrazolo[3,4-d]pyrimidin-4-amine The desired product was prepared as described in EXAMPLE 48 by substituting 3-methylphenylacetaldehyde for phenylacetaldehyde in EXAMPLE 48D. MS (ESI) m/e 531 (M+H)$^-$; $^1$H NMR (300 MHz, DMSO-$d_6$) 9.91 (bs, 1H), 8.42 (s, 1H), 8.38 (d, 2H), 7.97 (s, 1H), 7.86 (d, 1H), 7.75 (d, 1H), 7.70 (d, 2H), 7.24(m, 3H), 7.14 (d, 1H), 4.43 (s, 2H), 4.40 (s, 2H), 3.98 (m, 2H), 3.64 (m, 2H), 3.32 (m, 2H), 3.17 (m, 2H).

EXAMPLE 247

3-(2-(2-bromobenzyl)-1H-benzimidazol-5-yl)-1-(4-(morpholin-4-ylmethyl)phenyl)-1H-pyrazolo[3,4-d]pyrimidin-4-amine The desired product was prepared as described in EXAMPLE 48 by substituting 2-bromophenylacetaldehyde for phenylacetaldehyde in EXAMPLE 48D. MS (ESI) m/e 597 (M+H)$^-$; $^1$H NMR (300 MHz, DMSO-$d_6$) 9.92 (bs, 1H), 8.42 (s, 1H), 8.38 (d, 2H), 7.95 (s, 1H), 7.81 (d, 1H), 7.72 (m, 4H), 7.50 (m, 2H), 7.32(m, 1H), 4.56 (s, 2H), 4.43 (s, 2H), 3.98 (m, 2H), 3.64 (m, 2H), 3.32 (m, 2H), 3.17 (m, 2H).

EXAMPLE 248

3-(2-(2-methoxybenzyl)-1H-benzimidazol-5-yl)-1-(4-(morpholin-4-ylmethyl)phenyl)-1H-pyrazolo[3,4-d]pyrimidin-4-amine The desired product was prepared as described in EXAMPLE 48 by substituting 2-methoxyphenylacetaldehyde for phenylacetaldehyde in EXAMPLE 48D. MS (ESI) m/e 547 (M+H)$^-$; $^1$H NMR (300 MHz, DMSO-$d_6$) 9.86 (bs, 1H), 8.42 (s, 1H), 8.38 (d, 2H), 7.96 (s, 1H), 7.85 (d, 1H), 7.76 (m, 1H), 7.70 (d, 2H), 7.36(m, 2H), 7.00 (m, 1H), 4.43 (s, 2H), 4.40 (s, 2H), 3.98 (m, 2H), 3.64 (m, 2H), 3.32 (m, 2H), 3.17 (m, 2H).

EXAMPLE 249

(trans)-4-(4-{4-(4-amino-3-(2-benzyl-1H-benzimidazol-5-yl)-1H-pyrazolo[3,4-d]pyrimidin-1-yl)cyclohexyl}piperazin-1-yl)-2-methylbutan-2-ol The desired product was the faster eluting diastereomer prepared as described in EXAMPLE 31 by substituting 1-(3-hydroxy-3-methylbutyl)piperazine for 3-hydroxypyrrolidine in EXAMPLE 31C. MS (ESI) m/e 594 (M+H)$^-$; $^1$H NMR (300 MHz, DMSO-$d_6$) 8.30 (s, 1H), 7.86 (s, 1H), 7.81 (d, 1H), 7.67 (d, 1H), 7.42-7.34 (m, 5H), 4.75 (m, 1H), 4.45 (s, 2H), 3.56-3.36 (m, 4H), 3.11-2.97 (m, 6H), 2.10 (m, 6H), 1.69 (m, 4H), 1.15 (s, 6H).

EXAMPLE 250

(cis)-4-(4-{4-(4-amino-3-(2-benzyl-1H-benzimidazol-5-yl)-1H-pyrazolo[3,4-d]pyrimidin-1-yl)cyclohexyl}piperazin-1-yl)-2-methylbutan-2-ol The desired product was the slower eluting diastereomer prepared as described in EXAMPLE 31 by substituting 1-(3-hydroxy-3-methylbutyl)piperazine for 3-hydroxypyrrolidine in EXAMPLE 31C. MS (ESI) m/e 594 (M+H)$^-$; $^1$H NMR (300 MHz, DMSO-$d_6$) 8.33 (s, 1H), 7.89 (s, 1H), 7.83 (d, 1H), 7.68 (d, 1H), 7.42-7.31 (m, 5H), 4.92 (m, 1H), 4.47 (s, 2H), 3.56 (m, 5H), 3.14 (m, 5H), 2.35 (m, 2H), 2.07 (m, 3H), 1.87 (m, 3H), 1.70 (m, 2H), 1.13 (s, 6H).

EXAMPLE 251

(cis)-3-((4-{4-amino-3-(1-(2-fluorobenzyl)-1H-indol-5-yl)-1H-pyrazolo[3,4-d]pyrimidin-1-yl}cyclohexyl)amino)propan-1-ol The desired product was the slower eluting diastereomer in EXAMPLE 252. MS: ESI(+) m/e 514.3 (M+H)$^+$; ESI(−) m/e 512.4 (M−H); $^1$H NMR (300 MHz, DMSO-d$_6$) 8.32 (s, 1H), 8.30 (br. 1H), 7.88 (d, 1H), 7.67 (d, 1H), 7.58 (d, 1H), 7.46 (dd, 1H), 7.33-7.38 (m, 1H), 7.22-7.28 (m, 1H), 7.13-7.18 (m, 2H), 6.63 (d, 1H), 5.55 (s, 2H), 4.91 (br. 1H), 3.49 (t, 1H), 3.29 (br. 1H), 3.03 (br. 2H), 2.28-2.40 (m, 2H), 2.18-2.24 (m, 6H), 1.71-1.81 (m, 2H).

EXAMPLE 252

(trans)-3-((4-{4-amino-3-(1-(2-fluorobenzyl)-1H-indol-5-yl)-1H-pyrazolo[3,4-d]pyrimidin-1-yl}cyclohexyl)amino)propan-1-ol The desired product was prepared by substituting 3-amino-1-propanol for 3-aminobenzyl alcohol in EXAMPLE 210C. The earlier eluting diastereomer was isolated. MS: ESI(+) m/e 514.3 (M+H)$^+$; ESI(−) m/e 512.3 (M−H); $^1$H NMR (300 MHz, DMSO-d$_6$) 8.38 (br. 1H), 8.30 (s, 1H) 7.84 (d, 1H), 7.67 (d, 1H), 7.58 (d, 1H), 7.42 (dd, 1H), 7.32-7.38 (m, 1H), 7.21-7.28 (m, 1H), 7.13-7.16 (m, 2H), 6.62 (d, 1H), 5.54 (s, 2H), 4.73 (br. 1H), 3.51 (t, 1H), 3.24 (br. 1H), 3.03 (br. 2H), 2.18-2.20 (m, 2H), 2.02-2.16 (m, 3H), 1.90-2.01 (br. 1H), 1.70-1.81 (m, 2H), 1.53-1.67 (br. m., 2H).

EXAMPLE 253

2-((4-{4-amino-3-(1-(2-fluorobenzyl)-1H-indol-5-yl)-1H-pyrazolo[3,4-d]pyrimidin-1-yl}cyclohexyl)amino)ethanol The desired product was prepared by substituting 2-amino-1-ethanol for 3-aminobenzyl alcohol in EXAMPLE 210C. MS: ESI(+) m/e 500.3 (M+H)$^+$; ESI(−) m/e 498.3 (M−H); $^1$H NMR (300 MHz, DMSO-d$_6$) 8.50 (br. 1H), 8.40 (br. 1H), 8.33 (s, 1H), 7.86 (d, 1H), 7.67 (d, 1H), 7.58 (t, 1H), 7.32-7.49 (m, 2H), 7.22-7.28 (m, 1H), 7.14-7.18 (m, 2H), 6.63 (m, 1H), 5.55 (s, 2H), 4.91 (br. 0.5H), 4.71 (br. 0.5H), 3.28 (br. 1H), 3.05 (br. 2H), 2.31-2.41 (m, 1H), 2.16-2.27 (m, 1H), 1.89-2.12 (m, 6H), 1.56-1.70 (br. m., 2H).

EXAMPLE 254

2-{2-((4-{4-amino-3-(1-(2-fluorobenzyl)-1H-indol-5-yl)-1H-pyrazolo[3,4-d]pyrimidin-1-yl}cyclohexyl)amino)ethoxy}ethanol The desired product was prepared by substituting 2-(2-aminoethoxy)ethanol for 3-aminobenzyl alcohol in EXAMPLE 210C. MS: ESI(+) m/e 544.4 (M+H)$^+$; ESI(−) m/e 542.4 (M−H); $^1$H NMR (300 MHz, DMSO-d$_6$) 8.50 (br. 0.7H), 8.40 (br. 0.3H), 8.32 (s, 1H), 7.84-7.89 (m, 1H), 7.67 (d, 1H), 7.55-7.60 (m, 1H), 7.40-7.49 (m, 1H), 7.34-7.38 (m, 1H), 7.22-7.28 (m, 1H), 7.13-7.18 (m, 2H), 6.62 (m, 1H), 5.55 (s, 2H), 4.91 (br. 0.3H), 4.71 (br. 0.7H), 3.66-3.71 (m, 2H), 3.49-3.59 (m, 4H), 3.14-3.34 (m, 2H), 2.17-2.28 (m, 1H), 1.88-2.15 (m, 6H), 1.41-1.72 (br. m., 2H).

EXAMPLE 255

(cis)-(2R)-3-((4-{4-amino-3-(1-(2-fluorobenzyl)-1H-indol-5-yl)-1H-pyrazolo[3,4-d]pyrimidin-1-yl}cyclohexyl)amino)propane-1,2-diol The desired product was prepared by substituting S-(−)-3-amino-1,2-propanediol for 3-aminobenzyl alcohol in EXAMPLE 210C. The earlier eluting diastereomer was isolated. MS: ESI(+) m/e 530.4 (M+H)$^+$; ESI(−) m/e 528.4 (M−H); $^1$H NMR (300 MHz, DMSO-d$_6$) 8.40 (br. 1H), 8.31 (s, 1H), 7.89 (d, 1H), 7.67 (d, 1H), 7.59 (d, 1H), 7.47 (dd, 1H), 7.32-7.38 (m, 1H), 7.22-7.28 (m, 1H), 7.13-7.16 (m, 2H), 6.62 (m, 1H), 5.55 (s, 2H), 4.90 (br. 1H), 3.41-3.47 (m, 1H), 3.24-3.36 (m, 2H), 3.07-3.19 (br. 1H), 2.77-2.90 (br. 1H), 2.30-2.46 (br. 2H), 1.87-2.14 (m, 6H).

EXAMPLE 256

(trans)-(2R)-3-((4-{4-amino-3-(1-(2-fluorobenzyl)-1H-indol-5-yl)-1H-pyrazolo[3,4-d]pyrimidin-1-yl}cyclohexyl)amino)propane-1,2-diol The desired product was the slower eluting diastereomer in EXAMPLE 255. MS: ESI(+) m/e 530.4 (M+H)$^+$; ESI(−) m/e 528.4 (M−H); $^1$H NMR (300 MHz, DMSO-d$_6$) 8.47 (br. 1H), 8.33 (s, 1H), 7.84 (d, 1H), 7.67 (d, 1H), 7.57 (d, 1H), 7.42 (dd, 1H), 7.32-7.38 (m, 1H), 7.22-7.28 (m, 1H), 7.13-7.16 (m, 2H), 6.62 (m, 1H), 5.55 (s, 2H), 4.70 (br. 1H), 3.80 (br. 1H), 3.43-3.49 (m, 1H), 3.31-3.37 (m, 1H), 3.19-3.29 (br. 1H), 3.06-3.17 (br. 1H), 2.81-2.94 (br. 1H), 2.14-2.30 (br. 2H), 1.89-2.13 (m, 5H), 1.54-1.77 (br.m., 2H).

EXAMPLE 257

2,2'-(4-(4-amino-3-(1-(2-fluorobenzyl)-1H-indol-5-yl)-1H-pyrazolo[3,4-d]pyrimidin-1-yl)cyclohexylazanediyl)diethanol The desired product was prepared by substituting diethanolamine for 3-aminobenzyl alcohol in EXAMPLE 210C. MS: ESI(+) m/e 544.4 (M+H)$^+$; ESI(−) m/e 542.4 (M−H); $^1$H NMR (300 MHz, DMSO-d$_6$) 8.68-8.83 (br. 1H), 8.32 (s, 1H), 7.87 (d, 1H), 7.67 (d, 1H), 7.57-7.59 (m, 1H), 7.41-7.49 (m, 1H), 7.32-7.38 (m, 1H), 7.22-7.28 (m, 1H), 7.14-7.18 (m, 2H), 6.62 (m, 1H), 5.55 (s, 2H), 5.04 (br., 0.6H), 4.91 (br. 0.4H), 3.76-3.80 (m, 4H), 3.28-3.36 (m, 4H), 1.81-2.35 (m, 8H).

EXAMPLE 258

(cis)-N-(4-{4-amino-3-(1-(2-fluorobenzyl)-1H-indol-5-yl)-1H-pyrazolo[3,4-d]pyrimidin-1-yl}cyclohexyl)-beta-alanine The desired product was prepared by substituting-alanine for 3-aminobenzyl alcohol in EXAMPLE 210C. The earlier eluting diastereomer was isolated. MS: ESI(+) m/e 528.4 (M+H)$^+$; ESI(−) m/e 526.4 (M−H); $^1$H NMR (300 MHz, DMSO-d$_6$) 8.34 (br. 1H), 8.30 (s, 1H), 7.87 (s, 1H), 7.67 (d, 1H), 7.58 (d, 1H), 7.46 (dd, 1H), 7.32-7.38 (m, 1H), 7.22-7.28 (m, 1H), 7.13-7.16 (m, 2H), 6.62 (m, 1H), 5.55 (s, 2H), 4.90 (br. 1H), 3.15-3.24 (br. 3H), 2.64 (t, 2H), 2.24-2.39 (m, 2H), 1.88-2.08 (m, 6H).

EXAMPLE 259

(trans)-N-(4-{4-amino-3-(1-(2-fluorobenzyl)-1H-indol-5-yl)-1H-pyrazolo[3,4-d]pyrimidin-1-yl}cyclohexyl)-beta-alanine The desired product was the slower eluting diastereomer in EXAMPLE 258. MS: ESI(+) m/e 528.3 (M+H)$^+$; ESI(−) m/e 526.4 (M−H); $^1$H NMR (300 MHz, DMSO-d$_6$) 8.45 (br. 1H), 8.29 (s, 1H), 7.84 (d, 1H), 7.67 (d, 1H), 7.58 (d, 1H), 7.42 (dd, 1H), 7.32-7.38 (m, 1H), 7.22-7.28 (m, 1H), 7.13-7.16 (m, 2H), 6.62 (m, 1H), 5.55 (s, 2H), 4.66-4.71 (br. 1H), 3.14-3.29 (br. 3H), 2.67 (t, 2H), 1.91-2.33 (m, 6H), 1.54-1.69 (m, 2H).

EXAMPLE 260

(trans)-4-{4-amino-3-(2-(2-methoxybenzyl)-1H-benzimidazol-5-yl)-1H-pyrazolo[3,4-d]pyrimidin-1-yl}cyclohexanol To EXAMPLE 339C (0.13 g, 0.28 mmol) in a 0.2 M solution of MeOH/AcOH (9/1 v/v). is added NaCNBH$_3$ (0.035, 0.558 mmol). The reaction is stirred at RT for 1.5 hr, diluted with CH$_2$Cl$_2$, and washed with saturated aqueous NaHCO$_3$. The organic layer is dried over MgSO$_4$, filtered, reduced in vacuo, and purified via reverse phase HPLC. MS (ESI) m/e 470 (M+H)$^-$; $^1$H NMR (300 MHz, DMSO-d$_6$) δ8.31 (s, 1H), 7.89 (s, 1H), 7.84 (d, 1H), 7.75 (d, 1H), 7.39 (m, 2H), 7.09 (d, 1H), 7.03 (t, 1H), 4.69 (m, 1H), 4.46 (s, 2H), 3.78 (s, 3H), 2.06-1.91(m, 6H), 1.42 (m, 2H).

EXAMPLE 261

N-(4-{4-amino-3-(1-(2-fluorobenzyl)-1H-indol-5-yl)-1H-pyrazolo[3,4-d]pyrimidin-1-yl}cyclohexyl)-L-alanine The desired product was prepared by substituting L-alanine for 3-aminobenzyl alcohol in EXAMPLE 210C. MS: ESI(+) m/e 528.4 (M+H)$^+$; ESI(−) m/e 526.4 (M−H); $^1$H NMR (300 MHz, DMSO-d$_6$) 8.93 (br. 1H), 8.81 (br. 1H), 8.34 (br. 1H), 8.30 (s, 1H), 7.86 (s, 1H), 7.67 (d, 1H), 7.57-7.59 (m, 1H), 7.41-7.49 (m, 1H), 7.32-7.38 (m, 1H), 7.22-7.28 (m, 1H), 7.13-7.16 (m, 2H), 6.62 (m, 1H), 5.55 (s, 2H), 4.89 (br. 0.4H), 4.69 (m, 0.6H), 4.17 (m, 1H), 3.30 (br. 2H), 2.35-2.46 (br.m., 1H), 1.90-2.28 (m, 6H), 1.67-1.77 (br.m., 1H), 1.47 (m, 3H).

EXAMPLE 262

(cis)-N-(4-{4-amino-3-(1-(2-fluorobenzyl)-1H-indol-5-yl)-1H-pyrazolo[3,4-d]pyrimidin-1-yl}cyclohexyl)-D-alanine The desired product was prepared by substituting D-alanine for 3-aminobenzyl alcohol in EXAMPLE 101C. The earlier eluting diastereomer was isolated. MS: ESI(+) m/e 528.4 (M+H)$^+$; ESI(−) m/e 526.4 (M−H); $^1$H NMR (300 MHz, DMSO-d$_6$) 8.82 (br. 2H), 8.30 (s, 1H), 7.88 (s, 1H), 7.67 (d, 1H), 7.58 (d, 1H), 7.48 (dd, 1H), 7.32-7.38 (m, 1H), 7.22-7.28 (m, 1H), 7.13-7.15 (m, 2H), 6.62 (m, 1H), 5.55 (s, 2H), 4.89 (br. 1H), 4.16 (m, 1H), 3.31 (br. 2H), 2.33-2.47 (br.m., 2H), 1.90-2.09 (m, 6H), 1.46 (d, 3H).

EXAMPLE 263

(trans)-N-(4-{4-amino-3-(1-(2-fluorobenzyl)-1H-indol-5-yl)-1H-pyrazolo[3,4-d]pyrimidin-1-yl}cyclohexyl)-D-alanine The desired product was the slower eluting diastereomer in EXAMPLE 258. MS: ESI(+) m/e 528.4 (M+H)$^+$; ESI(−) m/e 526.4 (M−H); $^1$H NMR (300 MHz, DMSO-d$_6$) 8.92 (br. 2H), 8.29 (s, 1H), 7.84 (s, 1H), 7.67 (d, 1H), 7.56 (d, 1H), 7.44 (dd, 1H), 7.32-7.38 (m, 1H), 7.21-7.28 (m, 1H), 7.13-7.16 (m, 2H), 6.62 (m, 1H), 5.55 (s, 2H), 4.69 (br. 1H), 4.18 (m, 1H), 1.89-2.27(m, 8H), 1.55-1.75 (m, 2H), 1.48 (d, 3H).

EXAMPLE 264

N-(4-{4-amino-3-(1-(2-fluorobenzyl)-1H-indol-5-yl)-1H-pyrazolo[3,4-d]pyrimidin-1-yl}cyclohexyl)-N-methylglycine The desired product was prepared by substituting sarcosine for 3-aminobenzyl alcohol in EXAMPLE 210C. MS: ESI(+) m/e 528.4 (M+H)$^+$; ESI(−) m/e 526.4 (M−H); $^1$H NMR (300 MHz, DMSO-d$_6$) 9.63 (br. 1H), 8.30 (s, 1H), 7.87 (dd, 1H), 7.67 (d, 1H), 7.57-7.59 (m, 1H), 7.40-7.49 (m, 1H), 7.32-7.38 (m, 1H), 7.21-7.28 (m, 1H), 7.12-7.18 (m, 2H), 6.62 (m, 1H), 5.55 (s, 2H), 5.00 (br. 0.4H), 4.78 (m, 0.6H), 4.15 (m, 1H), 3.49 (br. 2H), 2.85 (s, includes 2.82, s., 3H), 2.30-2.38 (br.m., 1H), 2.06-2.22 (m, 4H), 1.91-2.04 (m, 2H), 1.76-1.90 (br.m., 1H).

EXAMPLE 265

(trans)-1-{4-(4-(3-methoxypropyl)piperazin-1-yl)cyclohexyl}-3-(2-(thien-2-ylmethyl)-1H-benzimidazol-6-yl)-1H-pyrazolo[3,4-d]pyrimidin-4-amine

EXAMPLE 265A 4-(4-amino-3-(2-(thiophen-2-ylmethyl)-1H-benzo(d)imidazol-6-yl)-1H-pyrazolo[3,4-d]pyrimidin-1-yl)cyclohexanone A slurry of EXAMPLE 31A (0.88 g, 2.4 mmol), 2-(thiophen-2-yl)acetaldehyde (0.32 g, 2.5 mmol), 1M Na$_2$S$_2$O$_4$ (7.2 mL, 7.2 mmol) in EtOH (8 mL) was placed in a microwave reactor, and heated to 130° C. for 20 min. The reaction was quenched by addition of 5 M NH$_4$OH, diluted with CH$_2$Cl$_2$/IPA (4/1 v/v). The resulting layers were separated, the organics were dried over MgSO$_4$, filtered, reduced in vacuo to afford the desired product as a tan solid (0.2 g, 20% yield).

EXAMPLE 265B

To a mixture of EXAMPLE 265A (0.22 g, 0.5 mmol) and 1-(3-methoxypropyl)piperazine (0.39 g, 2.48 mmol) in 0.3 M solution of MeOH/AcOH (9/1 v/v) added NaCNBH$_3$ (0.094 g, 1.5 mmol). The reaction was heated to 80° C. After 2 hr of heating, the reaction was cooled to RT, purified directly via reverse phase HPLC, using the following column conditions: 0.15% TFA in CH$_3$CN/0.15% in H$_2$O to afford 55 mg of the desired material. (ESI(+)) m/e 586 (M+H)$^+$; $^1$H NMR (300 MHz, DMSO-d$_6$) 8.32 (s, 1H); 7.85 (s, 1H); 7.80 (d, 1H); 7.63 (d, 1H); 7.49 (d, 1H); 7.13 (m, 1H); 7.05 (dd, 1H); 4.76 (m, 2H); 4.66 (s, 2H); 3.39 (t, 2H); 3.25 (s, 3H); 3.01 (bm, 3H); 2.11 (bm, 5H); 1.89-182 (m, 2H); 1.75-1.65 (m, 2H).

EXAMPLE 266

3-(2-benzyl-1H-benzimidazol-6-yl)-1-(1'-(3-methoxypropyl)-1,4'-bipiperidin-4-yl)-1H-pyrazolo[3,4-d]pyrimidin-4-amine

EXAMPLE 266A

The title compound, as a tan solid, was prepared as described in EXAMPLE 139B substituting EXAMPLE 201A for EXAMPLE 139A except the purification was done on normal phase silica gel. MS (ESI+) m/e 525 (M+H)$^+$; (ESI(−)) m/e 523 (M−H)$^-$; $^1$H NMR (300 MHz, DMSO-d$_6$)

12 45 (br s, 1H), 8.24 (s, 1H), 7.70 (m, 2H), 7.33 (m, 6H), 4.90 (m, 1H), 4.21 (s, 2H), 4.09 (m, 2H), 3.00 (m, 2H), 1.96 (m, 4H), 1.43 (s, 9H), 1.25 (m, 2H).

EXAMPLE 266B 3-(2-benzyl-1H-benzo(d)imidazol-6-yl)-1-(piperidin-4-yl)-1H-pyrazolo[3,4-d]pyrimidin-4-amine The title compound, as a tan foam, was prepared as described in EXAMPLE 201C substituting EXAMPLE 266A for EXAMPLE 201B. MS (ESI+) m/e 425 (M+H)$^+$; (ESI(−)) m/e 423 (M−H)$^−$; $^1$H NMR (300 MHz, DMSO-d$_6$) 8.78 (m, 1H), 8.47 (m, 1H), 8.34 (s, 1H), 7.91 (s, 1H), 7.87 (d, 1H), 7.70 (d, 1H), 7.42 (m, 4H), 7.33 (m, 1H), 5.09 (m, 1H), 4.87 (vbr s, 2H), 4.51 (s, 2H), 3.45 (m, 2H), 3.22 (m, 2H), 2.35 (m, 2H), 2.15 (m, 2H).

EXAMPLE 266C 3-(2-benzyl-1H-benzimidazol-6-yl)-1-(1'-(3-methoxypropyl)-1,4'-bipiperidin-4-yl)-1H-pyrazolo[3,4-d]pyrimidin-4-amine The title compound, as a tan solid, was prepared as described in EXAMPLE 201D substituting EXAMPLE 266B for EXAMPLE 201C and 1-(3-methoxypropyl)piperidin-4-one for 1-methylpiperidin-4-one. MS (ESI+) m/e 580 (M+H)$^+$; (ESI(−)) m/e 578 (M−H)$^−$; $^1$H NMR (300 MHz, DMSO-d$_6$) 9.79 (br s, 1H), 9.48 (br s, 1H), 8.29 (s, 1H), 7.80 (s, 1H), 7.74 (d, 1H), 7.56 (d, 1H), 7.37 (m, 4H), 7.28 (m, 1H), 5.12 (m, 1H), 4.36 (s, 2H), 3.65 (m, 3H), 3.40 (vbr s, 1H), 3.25 (s, 3H), 3.12 (m, 4H), 2.99 (m, 4H), 2.28 (m, 6H), 1.90 (m, 6H).

EXAMPLE 267

(cis)-2-{4-(4-(4-amino-3-{1-(2-(difluoromethoxy)benzyl)-1H-indol-5-yl}-1H-pyrazolo[3,4-d]pyrimidin-1-yl)cyclohexyl)piperazin-1-yl}ethanol

EXAMPLE 267A

The desired product was synthesized by substituting 2-(difluoromethoxy)benzyl bromide for 2-fluorobenzyl bromide in EXAMPLE 210A.

EXAMPLE 267B

The desired product was synthesized by substituting EXAMPLE 267A for EXAMPLE 210A in EXAMPLE 210B.

EXAMPLE 267C

EXAMPLE 267B (75 mg, 0.15 mmol) was dissolved in 3 mL of methanol and 0.3 mL of acetic acid at room temperature. 1-(2-Hydroxyethyl)piperazine (184 L, 1.5 mmol) was added and stirred for an additional 30 minutes. (Polystyrylmethyl)trimethylammonium cyanoborohydride (4.2 mmol/g, 180 mg, 0.75 mmol) was added, and the mixture stirred for 16 h. After insoluble material was removed, the filtrate was concentrated in vacuo and the residue was purified by HPLC. The earlier eluting diastereomer was isolated, giving 19 mg of the title product. MS: ESI(+) m/e 617.4 (M+H)$^+$; $^1$H NMR (300 MHz, DMSO-d$_6$) 8.32 (s, 1H), 7.86 (d, 1H), 7.57-7.61 (m., 2H), 7.35-7.43 (m., 2H), 7.25 (dd., 1H), 7.16 (dt., 1H), 6.93 (dd., 1H), 6.64 (d., 1H), 5.52 (s., 1H), 4.91 (m., 1H), 3.69 (t, 2H), 3.42-3.59 (m, 4H), 3.00-3.20 (m, 4H), 2.26-2.40 (m., 2H), 2.00-2.14 (m, 2H), 1.75-1.93 (m, 2H).

EXAMPLE 268

(trans)-2-{4-(4-(4-amino-3-{1-(2-(difluoromethoxy)benzyl)-1H-indol-5-yl}-1H-pyrazolo[3,4-d]pyrimidin-1-yl)cyclohexyl)piperazin-1-yl}ethanol The desired product was the slower eluting diastereomer in EXAMPLE 267. MS: ESI(+) m/e 617.4 (M+H)$^+$; ESI(−) m/e 615.4 (M−H); $^1$H NMR (300 MHz, DMSO-d$_6$) 8.31 (s, 1H), 7.85 (d, 1H), 7.55-7.62 (m., 2H), 7.34-7.43 (m., 2H), 7.26 (d., 1H), 7.16 (dt., 1H), 6.96 (dd., 1H), 6.64 (d., 1H), 5.51 (s., 1H), 4.75 (m., 1H), 3.72 (t, 2H), 3.42-3.59 (m, 4H), 3.00-3.20 (m, 4H), 2.04-2.20 (m, 6H), 1.60-1.78 (m, 2H).

EXAMPLE 269

(cis)-3-{4-(4-(4-amino-3-{1-(2-(difluoromethoxy)benzyl)-1H-indol-5-yl}-1H-pyrazolo[3,4-d]pyrimidin-1-yl)cyclohexyl)piperazin-1-yl}propan-1-ol The desired product was synthesized by substituting 1-(3-hydroxypropyl)piperazine for hydroxyethylpiperazine in EXAMPLE 268C. The earlier eluting diastereomer was isolated. MS: ESI(+) m/e 631.5 (M+H)$^+$; $^1$H NMR (300 MHz, DMSO-d$_6$) 8.32 (s, 1H), 7.86 (d, 1H), 7.57-7.61 (m., 2H), 7.35-7.43 (m., 2H), 7.26 (dd., 1H), 7.16 (dt., 1H), 6.95 (dd., 1H), 6.64 (d., 1H), 5.52 (s., 1H), 4.91 (m., 1H), 3.42-3.57 (m., 4H, includes 3.47, t, 2H), 3.00-3.20 (m, 4H), 2.26-2.40 (m., 2H), 2.00-2.14 (m, 2H), 1.75-1.96 (m, 4H).

EXAMPLE 270

(trans)-3-{4-(4-(4-amino-3-{1-(2-(difluoromethoxy)benzyl)-1H-indol-5-yl}-1H-pyrazolo[3,4-d]pyrimidin-1-yl)cyclohexyl)piperazin-1-yl}propan-1-ol The desired product was the slower eluting diastereomer in EXAMPLE 269. MS: ESI(+) m/e 631.4 (M+H)$^+$; ESI(−) m/e 629.4 (M−H); $^1$H NMR (300 MHz, DMSO-d$_6$) 8.31 (s, 1H), 7.85 (d, 1H), 7.55-7.62 (m., 2H), 7.34-7.42 (m., 2H), 7.26 (d., 1H), 7.16 (dt., 1H), 6.96 (dd., 1H), 6.64 (d., 1H), 5.51 (s., 1H), 4.75 (m., 1H), 3.49 (t, 2H), 3.42-3.59 (m, 4H), 2.93-3.20 (m, 4H), 2.00-2.20 (m, 6H), 1.60-1.82 (m, 4H).

EXAMPLE 271

3-(2-(2,6-difluorobenzyl)-1H-benzimidazol-5-yl)-1-(4-(morpholin-4-ylmethyl)phenyl)-1H-pyrazolo[3,4-d]pyrimidin-4-amine The desired product was prepared as described in EXAMPLE 48 by substituting 2,6-difluorophenylacetaldehyde for phenylacetaldehyde in EXAMPLE 48D. MS (ESI) m/e 553 (M+H)$^−$; $^1$H NMR (300 MHz, DMSO-d$_6$) δ9.84 (bs, 1H), 8.41 (m, 3H), 7.87 (s, 1H), 7.71 (m, 3H), 7.61 (d, 1H), 7.45 (m, 1H), 7.18 (m, 2H), 4.42 (s, 2H), 4.38 (s, 2H), 3.99 (m, 2H), 3.62 (m, 2H), 3.32 (m, 2H), 3.16 (m, 2H).

EXAMPLE 272

2-{4-(4-amino-3-(2-benzyl-1H-benzimidazol-6-yl)-1H-pyrazolo[3,4-d]pyrimidin-1-yl)-1,4'-bipiperidin-1'-yl}ethanol The title compound, as a yellow orange solid, was prepared as described in EXAMPLE 266 substituting 1-(2-hydroxyethyl)piperidin-4-one for 1-(3-methoxypropyl)piperidin-4-one in EXAMPLE 266C. MS (ESI+) m/e 552 (M+H)$^+$; (ESI(−)) m/e 550 (M−H)$^−$; $^1$H NMR (300 MHz, DMSO-d$_6$) 9.79 (br s, 1H), 9.48 (br s, 1H), 8.28 (s, 1H), 7.78 (s, 1H), 7.71 (d, 1H), 7.52 (d, 1H), 7.36 (m, 4H), 7.28 (m, 1H), 5.42 (br s, 1H), 5.12 (m, 1H), 4.30 (s, 2H), 3.73 (m, 3H), 3.62 (m, 4H), 3.45 (vbr s, 3H), 3.17 (m, 4H), 3.03 (m, 4H), 2.26 (m, 4H), 2.00 (m, 2H).

EXAMPLE 273

3-{4-(4-amino-3-(2-benzyl-1H-benzimidazol-6-yl)-1H-pyrazolo[3,4-d]pyrimidin-1-yl)-1,4'-bipiperidin-1'-yl}propan-1-ol The title compound, as a yellow solid, was prepared as described in EXAMPLE 266 substituting 1-(3-hydroxypropyl)piperidin-4-one for 1-(3-methoxypropyl)piperidin-4-one in EXAMPLE 266C. MS (ESI+) m/e 566 (M+H)$^+$; (ESI(−)) m/e 564 (M−H)$^−$; $^1$H NMR (300 MHz, DMSO-d$_6$) 9.79 (br s, 1H), 9.48 (br s, 1H), 8.29 (s, 1H), 7.79 (s, 1H), 7.72 (d, 1H), 7.53 (d, 1H), 7.37 (m, 4H), 7.28 (m, 1H), 5.12 (m, 1H), 4.80 (vbr s, 1H), 4.32 (s, 2H), 3.65 (m, 6H), 3.49 (m, 3H), 3.39 (vbr s, 1H), 3.13 (m, 4H), 2.99 (m, 2H), 2.27 (m, 4H), 1.93 (m, 2H), 1.80 (m, 2H).

EXAMPLE 274

3-(2-benzyl-1H-benzimidazol-6-yl)-1-(1'-(2-methoxyethyl)-1,4'-bipiperidin-4-yl)-1H-pyrazolo[3,4-d]pyrimidin-4-amine The title compound, as an off-white solid, was prepared as described in EXAMPLE 266 substituting 1-(2-methoxyethyl)piperidin-4-one for 1-(3-methoxypropyl)piperidin-4-one in EXAMPLE 266C. MS (ESI+) m/e 566 (M+H)$^+$; (ESI(−)) m/e 564 (M−H)$^−$; $^1$H NMR (300 MHz, DMSO-d$_6$) 9.82 (br s, 1H), 9.67 (br s, 1H), 8.28 (s, 1H), 7.78 (s, 1H), 7.71 (d, 1H), 7.52 (d, 1H), 7.37 (m, 4H), 7.29 (m, 1H), 5.12 (m, 1H), 4.30 (s, 2H), 3.66 (m, 6H), 3.46 (vbr s, 4H), 3.32 (s, 3H), 3.28 (m, 4H), 3.03 (m, 2H), 2.26 (m, 4H), 1.98 (m, 2H).

EXAMPLE 275

2-(4-{4-amino-3-(1-(2-chlorobenzyl)-1H-indol-5-yl)-1H-pyrazolo[3,4-d]pyrimidin-1-yl}-1,4'-bipiperidin-1'-yl)ethanol The title compound, as a tan solid, was prepared as described in EXAMPLE 201 substituting 1-(2-hydroxyethyl)piperidin-4-one for 1-methylpiperidin-4-one in EXAMPLE 201D. MS (ESI+) m/e 585 (M+H)$^+$; (ESI(−)) m/e 583 (M−H)$^−$; $^1$H NMR (300 MHz, DMSO-d$_6$) 9.74 (br s, 1H), 9.45 (br s, 1H), 8.28 (s, 1H), 7.87 (s, 1H), 7.58 (m, 3H), 7.43 (d, 1H), 7.33 (m, 1H), 7.25 (m, 1H), 6.79 (dd, 1H), 6.66 (d, 1H), 5.58 (s, 2H), 5.40 (br s, 1H), 5.11 (m, 1H), 3.73 (m, 4H), 3.64 (m, 2H), 3.56 (m, 2H), 3.47 (m, 3H), 3.16 (m 2H), 3.03 (m, 2H), 2.27 (m, 4H), 2.00 (m, 2H).

EXAMPLE 276

3-(1-(2-chlorobenzyl)-1H-indol-5-yl)-1-(1'-(2-methoxyethyl)-1,4'-bipiperidin-4-yl)-1H-pyrazolo[3,4-d]pyrimidin-4-amine The title compound, as a tan solid, was prepared as described in EXAMPLE 201 substituting 1-(2-methoxyethyl)piperidin-4-one for 1-methylpiperidin-4-one in EXAMPLE 201D. MS (ESI+) m/e 599 (M+H)$^+$; (ESI(−)) m/e 597 (M−H)$^−$; $^1$H NMR (300 MHz, DMSO-d$_6$) 9.80 (br s, 1H), 9.65 (br s, 1H), 8.28 (s, 1H), 7.88 (s, 1H), 7.57 (m, 3H), 7.43 (d, 1H), 7.33 (m, 1H), 7.25 (m, 1H), 6.80 (dd, 1H), 6.66 (d, 1H), 5.58 (s, 2H), 5.11 (m, 1H), 3.65 (m, 4H), 3.59 (m, 2H), 3.49 (m, 3H), 3.33 (s, 3H), 3.28 (m 2H), 3.02 (m, 2H), 2.54 (m, 2H), 2.26 (m, 4H), 1.98 (m, 2H).

EXAMPLE 277

3-(1-(2-fluorobenzyl)-1H-indol-5-yl)-1-(4-(4-pyridin-2-ylpiperazin-1-yl)cyclohexyl)-1H-pyrazolo[3,4-d]pyrimidin-4-amine The desired product was prepared by substituting 1-(2-pyridyl)piperazine for 3-aminobenzylalcohol in EXAMPLE 210C. MS ((+)-ESI) 602.4 m/z (M+H)$^+$; $^1$H NMR (400 MHz, DMSO) 8.23 (s, 1H), 8.10 (m, 1H), 7.84 (s, 1H), 7.66-7.09 (m, 8H), 6.80 (m, 1H), 6.62 (m, 2H), 4.84-4.65 (m, 1H), 3.48 (bs, 4H), 2.70-2.60 (m, 3H), 2.32-1.52 (m, 10H).

EXAMPLE 278

(trans)-3-(2-benzyl-1H-benzimidazol-5-yl)-1-(4-(4-pyridin-2-ylpiperazin-1-yl)cyclohexyl)-1H-pyrazolo[3,4-d]pyrimidin-4-amine The desired product was prepared by substituting 1-(2-pyridyl)piperazine for 3-hydroxyproline in EXAMPLE 3° C. The faster eluting diastereomer was isolated. MS ((+)-ESI) 585.4 m/z (M+H)$^+$; $^1$H NMR (400 MHz, DMSO) 8.23 (s, 1H), 8.11 (m, 1H), 7.71-7.23 (m, 11H), 6.81 (m, 1H), 6.62 (m, 1H), 4.67 (m, 1H), 4.22 (s, 2H), 3.46 (m, 4H), 2.63 (m, 4H), 2.09-1.99 (m, 6H), 1.53 (m, 2H).

EXAMPLE 279

(cis)-3-(2-benzyl-1H-benzimidazol-5-yl)-1-(4-(4-pyridin-2-ylpiperazin-1-yl)cyclohexyl)-1H-pyrazolo[3,4-d]pyrimidin-4-amine This is the slower eluting diastereomer of EXAMPLE 278. MS ((+)-ESI) 585.4 m/z (M+H)$^+$; $^1$H NMR (400 MHz, DMSO) 8.24 (s, 1H), 8.11 (m, 1H), 7.82-7.55 (m, 11H), 6.79 (m, 1H), 6.61 (m, 1H), 4.83 (m, 1H), 4.21 (s, 2H), 3.51 (m, 4H), 2.58 (m, 4H), 2.31 (m, 3H), 2.09 (m, 2H), 1.82-1.58 (m, 4H).

EXAMPLE 280

(trans)-1-(4-morpholin-4-ylcyclohexyl)-3-(2-(pyridin-2-ylmethyl)-1H-benzimidazol-6-yl)-1H-pyrazolo[3,4-d]pyrimidin-4-amine

EXAMPLE 280A 4-(4,4,5,5-tetramethyl-1,3,2-dioxaborolan-2-yl)benzene-1,2-diamine EXAMPLE 2A (5 g, 18.5 mmol) was dissolved into 100 mL of EtOAc, treated with 10% Pd/C (2 g, 1.89 mmol). The mixture was place in a Parr hydrogenation apparatus under 60 psi of $H_2$ at RT for 18 hr. The reaction was filtered, and reduced in vacuo. The product was triturated with $Et_2O$/hexanes, and carried on without further purification.

EXAMPLE 280B 2-(Pyridin-2-yl)acetic acid hydrochloride (0.81 g, 4.7 mmol) was slurried into THF (7 mL) at RT, and $Et_3N$ (0.47 mL, 4.7 mmol) was added. After 10 min, CDI (0.7 g, 4.48 mmol), was added, and the mixture heated to 50° C. After 30 min, EXAMPLE 280A (1 g, 4.2 mmol) was added and the reaction was stirred for 1 hr at 50° C. The reaction was cooled, quenched with water and diluted with EtOAc. The organics were separated, extracted the organics with EtOAc (2×30 mL). The organics were pooled, dried over $MgSO_4$, filtered, reduced in vacuo onto silica. The reaction was purified via an Intelliflash-280 purification system (hexanes/EtOAc) to afford a mixture of the desired amide products.

EXAMPLE 280C

To a slurry of 3-iodo-1-(4-morpholin-4-yl-cyclohexyl)-1H-pyrazolo[3,4-d]pyrimidin-4-ylamine (0.27 g, 0.63 mmol, prepared as described in WO 2005/074603), EXAMPLE 280B (0.45 g, 1.27 mmol), dichloro(1,1'-bis(diphenylphosphino)ferrocene) palladium(II)dichloromethane adduct (0.022 g, 0.03 mmol) in 0.3 M DME/water (2/1, v/v) was added 2 M aqueous $Na_2CO_3$ (0.63 mL, 1.27 mmol). The reaction was heated in a microwave reactor for 20 min at 130° C. The reaction was filtered over Celite, washed pad with $CH_2Cl_2$. The filtrate was dried over $MgSO_4$, filtered, reduced in vacuo onto silica. The reaction was purified via an Intelliflash-280 purification system ($CH_2Cl_2$/MeOH) to afford a mixture of the desired products.

EXAMPLE 280D

EXAMPLE 280C (0.25 g, 0.47 mmol) was slurred into AcOH (2 mL), and heated to 100 C for 1.5 hr. The contents were cooled to RT, diluted with $CH_2Cl_2$/IPA (4/1), and washed with saturated aqueous $NaHCO_3$. The organics were separated, dried over $MgSO_4$, filtered and reduced in vacuo. The material was purified via reverse phase HPLC using the following column conditions: 0.15% TFA in $CH_3CN$/0.15% in $H_2O$ to afford the desired product. (ESI(+)) m/e 510 (M+H)$^+$; $^1H$ NMR (300 MHz, DMSO-$d_6$) 12.49 (s, 1H); 8.53-8.51 (m, 1H); 8.22 (s, 1H); 7.80-7.75 (m, 2H); 7.68-7.75 (m, 1H); 7.45-7.40 (m, 3H); 7.30-7.26 (m, 1H); 4.70-4.60 (m, 1H); 4.39 (s, 2H); 5.39-3.56 (m, 5H); 2.41-2.31 (m, 2H); 2.08-1.96 (m, 8H); 1.53-1.40 (m, 3H).

EXAMPLE 281

3-(2-benzyl-1H-benzimidazol-6-yl)-1-(1'-isobutyl-1,4'-bipiperidin-4-yl)-1H-pyrazolo[3,4-d]pyrimidin-4-amine The title compound, as a white solid, was prepared as described in EXAMPLE 266 substituting 1-isobutylpiperidin-4-one for 1-(3-methoxypropyl)piperidin-4-one in EXAMPLE 266C. MS (ESI+) m/e 564 (M+H)$^+$; (ESI(−)) m/e 562 (M−H)$^−$; $^1H$ NMR (300 MHz, DMSO-$d_6$) 9.85 (br s, 1H), 9.20 (br s, 1H), 8.31 (s, 1H), 7.89 (s, 1H), 7.79 (d, 1H), 7.62 (d, 1H), 7.40 (m, 4H), 7.30 (m, 1H), 5.14 (m, 1H), 4.42 (s, 2H), 3.83 (vbr s, 2H), 3.63 (m, 4H), 3.39 (m, 2H), 2.97 (m, 4H), 2.54 (m, 2H), 2.26 (m, 4H), 2.06 (m, 2H), 0.97 (d, 6H).

EXAMPLE 282

(trans)-1-(4-morpholin-4-ylcyclohexyl)-3-(2-(pyridin-3-ylmethyl)-1H-benzimidazol-6-yl)-1H-pyrazolo[3,4-d]pyrimidin-4-amine

EXAMPLE 282A

The desired product was prepared by substituting 2-(pyridin-3-yl)acetic acid hydrochloride for 2-(pyridin-2-yl)acetic acid hydrochloride in EXAMPLE 280B.

EXAMPLE 282B

The desired product was prepared by substituting EXAMPLE 282A for EXAMPLE 280B in EXAMPLE 280C.

EXAMPLE 282D

The desired product was prepared by substituting EXAMPLE 282B for EXAMPLE 280C in EXAMPLE 280D. (ESI(+)) m/e 510 (M+H)$^+$; $^1H$ NMR (300 MHz, DMSO-$d_6$) 9.84 (bs, 1H); 8.77 (m, 1H); 8.66-8.64 (m, 1H); 8.37 (s, 1H); 8.07-8.04 (m, 1H); 7.87-7.81 (m, 2H); 7.66.7.60 (m, 2H); 4.85-4.74 (m, 1H); 4.57 (s, 2H); 4.06-4.02 (m, 2H); 3.75-3.67 (t, 2H); 3.48-3.38 (m, 3H); 3.22-3.11 (m, 2H); 2.30-2.20 (m, 2H); 2.16-2.07 (m, 2H); 1.83-1.70 (m, 2H).

EXAMPLE 283

(cis)-1-(1-(2-chlorobenzyl)-1H-indol-5-yl)-3-(3-(4-methylpiperazin-1-yl)cyclobutyl)imidazo[1,5-a]pyrazin-8-amine

EXAMPLE 283A (3-chloropyrazin-2-yl)methanamine dihydrochloride

To a solution of (3-chloropyrazin-2-yl)methanol (B. Klein et al. J. Org. Chem. 1963, 28, 1682.) (10.78 g, 74.6 mmol), phthalimide (13.18 g, 89.7 mmol) and triphenylphosphine (23.78 g, 90.8 mmol) in THF (350 mL) was added DIAD (17.8 mL, 90.8 mmol) and the mixture stirred at ambient temp for 16 h. The mixture was concentrated by rotary evaporation. The intermediate 2-((3-chloropyrazin-2-yl)methyl)isoindoline-1,3-dione was taken up in $CH_2Cl_2$ (300 mL) and methanol (450 mL) and treated with anhydrous hydrazine (6.0 mL, 190 mmol) at ambient temperature for 18 h. The mixture was filtered and the precipitate discarded. The filtrate was concentrated by rotary evaporation, then taken up in EtOAc and refiltered. The filtrate was concentrated to dryness, dissolved in 600 mL EtOAc, then treated with 40 mL of 4N HCL in dioxane. The precipitated solids were collected, washed with ether and vacuum dried to give 12.53 g tan solid.

EXAMPLE 283B

N-((3-chloropyrazin-2-yl)methyl)-3-methylenecyclobutanecarboxamide

EDCI (13.47 g, 70 mmol), DMAP (1.19 g, 9.8 mmol) and EXAMPLE 283A (12.5 g, 58 mmol) in $CH_2Cl_2$ (300 mL) were treated with ethyldiisopropyl amine (20 mL, 170 mmol) and 3-methylene-cyclobutanecarboxylic acid (Caserio et al. J. Am. Chem. Soc. 1958, 80, 5507)(6.59 g, 59 mmol). After 8 h at ambient temperature, an additional 2.88 g of EDCI was added, and the mixture stirred at ambient temperature for 16 h. The mixture was concentrated by rotary evaporator, diluted with EtOAc (600 mL), then washed sequentially with water (2×), aqueous $NaHCO_3$ (2×) and brine (2×) and dried ($Na_2SO_4$). Solvent removal gave a red-brown oil which was purified by column chromatography on silica gel, eluting with 0-70% EtOAc/hexanes to provide 6.55 g of product.

EXAMPLE 283C 8-chloro-3-(3-methylenecyclobutyl)imidazo[1,5-a]pyrazine

EXAMPLE 283B (6.55 g, 27.6 mmol) in acetonitrile (130 mL) was treated with DMF (0.3 mL) and $POCl_3$ (13 mL, 138 mmol), and the mixture stirred in a 55° C. oil bath for 30 min. The mixture was cooled and concentrated by rotary evaporation, and the residues treated with aq. $Na_2CO_3$, then extracted twice with $CH_2Cl_2$. The combined organics were washed with, dried ($Na_2SO_4$). The crude product was adsorbed on Celite and chromatographed on silica gel eluting with 0-50% EtOAc/hexanes to give the product as an off-white solid (4.36 g).

EXAMPLE 283D 3-(8-chloroimidazo[1,5-a]pyrazin-3-yl)-1-(hydroxymethyl)cyclobutanol EXAMPLE 283C (4.36 g, 19.8 mmol) in THF (240 mL) and water (25 mL) was treated with NMMO (4.8 mL, 20 mmol) and potassium osmate dihydrate (0.290 g, 0.87 mmol), and the mixture stirred vigorously at ambient temperature for 24 h. Sodium sulfite (11.5 g) was added, and the mixture stirred vigorously for 30 min then concentrated by rotary evaporation. The residues were partitioned between EtOAc (400 mL) and water (250 ml), and the organics were washed with brine. The combined aqueous washes were back extracted with 4×100 mL EtOAc, and the combined EtOAc layers dried over $Na_2SO_4$. Solvent removal gave the product as a white foam (2.55 g).

EXAMPLE 283E 3-(8-chloro-1-iodoimidazo[1,5-a]pyrazin-3-yl)-1-(hydroxymethyl)cyclobutanol EXAMPLE 283D (2.55 g, 10.1 mmol) and N-iodo-succinimide (2.87 g, 12.8 mmol) in DMF (25 ml) were stirred at 60° C. for 4.5 h. The mixture was vacuum dried, and the residues adsorbed on Celite and chromatographed on silica gel, eluting with 0-5% $CH_3OH/CH_2Cl_2$ to give the product as a light brown gum (3.60 g).

EXAMPLE 283F 3-(8-chloro-1-iodoimidazo[1,5-a]pyrazin-3-yl)cyclobutanone

A solution of EXAMPLE 283E (3.60 g, 9.5 mmol) in THF (100 mL) and water (25 mL) was cooled to 0° C. in an ice bath and treated with sodium periodate (2.42 g, 11.3 mmol). The ice bath was removed, and the mixture stirred for 3.5 h. The mixture was diluted with EtOAc (200 mL), washed with brine (3×), then dried ($MgSO_4$). Solvent removal and drying under vacuum provided the product as a tan solid (2.68 g).

EXAMPLE 283G 8-chloro-1-iodo-3-((1s,3s)-3-(4-methylpiperazin-1-yl)cyclobutyl)imidazo[1,5-a]pyrazine EXAMPLE 283F (2.68 g, 7.7 mmol), N-methyl-morpholine (0.90 mL, 8.1 mmol) and $NaBH(OAc)_3$ (3.34 g, 15.8 mmol) in 1,2-dichloroethane (150 mL) were stirred at ambient temperature for 4 h. The mixture was concentrated by rotary evaporation, and the residues partitioned between $CH_2Cl_2$ and aqueous $NaHCO_3$. The organics were washed with brine, dried over $Na_2SO_4$. Solvent removal gave the product as a light yellow solid (2.94 g).

EXAMPLE 283H 1-iodo-3-((1s,3s)-3-(4-methylpiperazin-1-yl)cyclobutyl)imidazo[1,5-a]pyrazin-8-amine A pressure bomb was charged with EXAMPLE 283G (2.94 g, 6.8 mmol), 2N ammonia in isopropanol (50 mL) and anhydrous ammonia (20 mL), and heated to 110° C. for 48 h. After solvent removal, the residues were purified by chromatography on silica gel with a mixture of 7% ammonia saturated methanol/$CH_2Cl_2$ to give the product as a yellow solid (1.85 g).

EXAMPLE 283I (cis)-1-(1-(2-chlorobenzyl)-1H-indol-5-yl)-3-(3-(4-methylpiperazin-1-yl)cyclobutyl)imidazo[1,5-a]pyrazin-8-amine To microwave reaction vessel were added EXAMPLE 283H (0.049 g, 0.12 mmol), EXAMPLE 93A (0.096 g, 0.26 mmol), $K_2CO_3$ (0.078 g, 0.56 mmol), $Pd(PPh_3)_4$ (0.015 g, 0.012 mmol), and 2:1 DME:$H_2O$ (2 ml:1 ml). The reaction vessel was sealed and heated under temperature control on a Personal Chemistry Smith Synthesizer for 20 minutes total at a target temperature of 150° C. The reaction mixture was diluted with EtOAc and the organics washed sequentially with aqueous $Na_2CO_3$ (2×), brine, then dried over $MgSO_4$. The solvent was removed under reduced pressure, and the residue purified by reverse-phase HPLC using $CH_3CN$/water/0.15% TFA to provide the TFA-salt of the title compound as a white solid (0.040 g). $^1$H NMR (300 MHz, DMSO-$d_6$) δ7.88 (d, 1H); 7.75 (d, 1H); 7.60 (d, 1H); 7.59 (s, 1H); 7.54 (m, 1H); 7.42 (dd, 1H); 7.34 (td, 1H); 7.26 (td, 1H); 7.07 (d, 1H), 6.81 (d, 1H); 6.66 (d, 1H); 5.60 (s, 2H); 3.80-3.60 (m, 8H); 3.46 (m, 1H); 3.00 (m, 1H); 2.76 (s, 3H); 2.65-2.58 (m, 2H); 2.29-2.25 (m, 2H).

EXAMPLE 284

(cis)-1-(2-benzyl-1H-indol-5-yl)-3-(3-(4-methylpiperazin-1-yl)cyclobutyl)imidazo[1,5-a]pyrazin-8-amine The desired product was prepared by substituting EXAMPLE 206C for EXAMPLE 93A in EXAMPLE 283I. $^1$H NMR (300 MHz, DMSO-$d_6$) δ11.31 (s, 1H); 7.74 (d, 1H); 7.70 (s, 1H); 7.45 (d, 1H); 7.34 (s, 2H); 7.32 (m, 2H); 7.28 (dd, 1H); 7.23 (m, 1H), 7.06 (d, 1H); 6.28 (s, 1H); 4.11 (s, 2H); 3.80-3.60 (m, 8H); 3.46 (m, 1H); 3.00 (m, 1H); 2.76 (s, 3H); 2.65-2.58 (m, 2H); 2.29-2.25 (m, 2H).

EXAMPLE 285

(cis)-1-(2-benzyl-1H-benzimidazol-5-yl)-3-(3-(4-methylpiperazin-1-yl)cyclobutyl)imidazo[1,5-a]pyrazin-8-amine The desired product was prepared by substituting EXAMPLE 188C for EXAMPLE 93A in EXAMPLE 283I. $^1$H NMR (300 MHz, DMSO-$d_6$) δ7.86 (d, 1H); 7.81 (d, 1H); 7.78 (d, 1H); 7.61 (dd, 1H); 7.45-7.36 (m, 4H); 7.32 (m, 1H); 7.13 (d, 1H); 4.11 (s, 2H); 3.80-3.60 (m, 8H); 3.46 (m, 1H); 3.00 (m, 1H); 2.77 (s, 3H); 2.65-2.58 (m, 2H); 2.29-2.25 (m, 2H).

EXAMPLE 286

(trans)-1-(4-morpholin-4-ylcyclohexyl)-3-(2-(thien-3-ylmethyl)-1H-benzimidazol-6-yl)-1H-pyrazolo[3,4-d]pyrimidin-4-amine

EXAMPLE 286A

To a slurry of EXAMPLE 7A (2.9 g, 6.62 mmol) in THF/MeOH (30 mL/30 mL), was added Pd/C (0.6 g, 0.05% by weight Pd). The sample was purged with $H_2$, then evacuated (3 times). The reaction was placed on a Parr hydrogenator under 60 psi of $H_2$ for 1.5 hr. The reaction was filtered over a Teflon filter, washed with THF. The organic washes were combined, reduced in vacuo onto silica. Purified via an Intelliflash-280 purification system ($CH_2Cl_2$/MeOH/$NH_4OH$) to afford a tan solid of the desired intermediate (2 g, 75% yield).

EXAMPLE 286B 2-(Thiophen-3-yl)acetic acid (0.057 g, 0.4 mmol) and CDI (0.062 g, 0.38 mmol) was dissolved into 1 mL of NMP and the reaction was immediately warmed to 50° C. for 30 min. EXAMPLE 286A (0.15 g, 0.36 mmol), was added, and the mixture was stirred at 50° C. for 1.5 hr. To the crude reaction mixture was added AcOH (1 mL), and the reaction was heated to 90° C. for 12 hr. The reaction was cooled to RT, diluted with $CH_2Cl_2$/IPA (4/1 v/v) and quenched with 1 M NaOH. The resulting layers were separated, extracted the aqueous layer with $CH_2Cl_2$/IPA (2×25 mL). The organic extracts were pooled, dried over $MgSO_4$, filtered, and reduced in vacuo. The crude reaction mixture was purified via reverse phase HPLC using the following conditions: 0.15% TFA in $CH_3CN$/0.15% in $H_2O$ to afford the desired product. (ESI(+)) m/e 515 (M+H)$^+$;

$^1$H NMR (300 MHz, DMSO-$d_6$) 12.42 (bs, 1H); 8.22 (s, 1H); 7.73-7.68 (m, 1H); 7.67-7.60 (m, 1H); 7.51-7.49 (m, 1H); 7.44-7.41 (dd, 1H); 7.44 (d, 1H); 7.11 (dd, 1H); 4.65 (m, 1H); 4.22 (s, 2H); 3.59-3.56 (m, 5H); 2.40-2.32 (bm, 1H); 2.08-1.96 (m, 8H); 1.53-1.41 (m, 3H).

EXAMPLE 287

(trans)-3-(2-(1,3-benzodioxol-5-ylmethyl)-1H-benzimidazol-6-yl)-1-(4-morpholin-4-ylcyclohexyl)-1H-pyrazolo[3,4-d]pyrimidin-4-amine The desired product was prepared by substituting 2-(benzo(d)(1,3)dioxol-5-yl)acetic acid for 2-(thiophen-3-yl)acetic acid in EXAMPLE 286B. (ESI(+)) m/e 553 (M+H)$^+$; $^1$H NMR (300 MHz, DMSO-$d_6$) 12.38 (d, 1H); 8.22 (s, 1H); 7.68-7.64 (m, 1H); 7.42 (m, 1H); 6.93 (m, 1H); 6.88-6.83 (m, 3H); 5.98 (s, 2H); 4.65 (m, 1H); 2.48 (s, 2H); 3.58 (m, 5H); 2.41-2.29 (m, 2H); 2.08-1.93 (m, 8H); 1.53-1.40 (m, 3H).

EXAMPLE 288

(trans)-3-(2-(2-fluorobenzyl)-1H-indol-5-yl)-1-{4-(4-(3-methoxypropyl)piperazin-1-yl)cyclohexyl}-1H-pyrazolo[3,4-d]pyrimidin-4-amine The desired product was prepared by substituting 1-bromo-3-methoxypropane for 2-(2-ethoxyethoxy)ethyl bromide in EXAMPLE 318D. MS: ESI(+) m/e 613.5 (M+H)$^+$; $^1$H NMR (300 MHz, DMSO-$d_6$) 11.29 (s, 1H), 8.31 (s, 1H), 7.68 (br.s, 1H), 7.46 (d, 1H), 7.28-7.38 (m, 3H), 7.15-7.24 (m, 2H), 6.22 (s, 1H), 4.74 (br. m, 1H), 4.14 (s, 2H), 3.39 (br.m, 2H), 3.25 (s, 3H), 3.01 (br.m., 4H), 2.05-2.16 (m, 6H), 1.77-1.90 (br.m., 2H), 1.60-1.78 (br, m, 2H).

EXAMPLE 289

(cis)-3-(2-(2-fluorobenzyl)-1H-indol-5-yl)-1-{4-(4-(3-methoxypropyl)piperazin-1-yl)cyclohexyl}-1H-pyrazolo[3,4-d]pyrimidin-4-amine

EXAMPLE 289A

The cis isomer formed in EXAMPLE 318A (1.25 g, 2.37 mmol), EXAMPLE 217C, (1.0 g, 2.84 mmol), sodium carbonate (0.5 g, 4.71 mmol), palladium tetrakis triphenylphosphine (82 mg, 0.07 mmol) was suspended in 30 mL of DME:water (1:1). This was microwaved at 130° C. for 20 minutes. After partitioning between ethyl acetate and brine, the ethyl acetate layer was washed with brine (3×), dried and purified by silica gel column chromatography, eluting with 7% methanol in ethyl acetate.

EXAMPLE 289B

The desired product was synthesized by substituting EXAMPLE 289A for EXAMPLE 382B in EXAMPLE 382C. MS: ESI(+) m/e 597.5 (M+H); ESI(−) m/e 595.5 (M−H)$^+$; $^1$H NMR (300 MHz, DMSO-$d_6$) 11.31 (s, 1H), 8.33 (s, 1H), 7.70 (br.s, 1H), 7.47 (d, 1H), 7.28-7.38 (m, 3H), 7.15-7.24 (m, 2H), 6.21 (s, 1H), 4.91 (br. m, 1H), 4.15(s, 2H), 3.40-3.60 (br.m., 4H), 3.24 (s., 3H), 2.90-3.10 (m., 4H), 2.28-2.41 (m., 2H), 2.00-2.15 (m., 2H), 1.79-1.95 (m., 4H). 2.19-2.07 (m, 6H), 1.79-1.64 (br, m, 2H).

EXAMPLE 290

(trans)-4-(4-amino-3-{2-(2-(trifluoromethoxy)benzyl}-1H-benzimidazol-5-yl}-1H-pyrazolo[3,4-d]pyrimidin-1-yl)cyclohexanol

EXAMPLE 290A

The desired product was prepared by substituting 2-trifluoromethoxyphenylacetonitrile for phenylmethylacetonitrile in EXAMPLE 118B.

EXAMPLE 290B

The desired product was prepared by substituting EXAMPLE 290A for EXAMPLE 339A in EXAMPLE 339B.

EXAMPLE 290C

The desired product was prepared by substituting EXAMPLE 290B for EXAMPLE 339B in EXAMPLE 339C.

EXAMPLE 290D

The desired product was prepared by substituting EXAMPLE 290C for EXAMPLE 339C in EXAMPLE 260. MS (ESI) m/e 524 (M+H)$^-$; $^1$H NMR (300 MHz, DMSO-d$_6$) δ8.32 (s, 1H), 7.84 (s, 1H), 7.78 (d, 1H), 7.64 (d, 1H), 7.54 (m, 1H), 7.46 (m, 3H), 4.68 (m, 1H), 4.50 (s, 2H), 2.08-1.91(m, 6H), 1.42 (m, 2H).

EXAMPLE 291

(trans)-1-{4-(4-(3-methoxypropyl)piperazin-1-yl)cyclohexyl}-3-{2-(2-(trifluoromethoxy)benzyl)-1H-benzimidazol-5-yl}-1H-pyrazolo[3,4-d]pyrimidin-4-amine The desired product was prepared by substituting EXAMPLE 290C for EXAMPLE 265A in EXAMPLE 265B. The faster eluting diastereomer was isolated. MS (ESI) m/e 664 (M+H)$^-$;

$^1$H NMR (300 MHz, DMSO-d$_6$) δ8.30 (s, 1H), 7.80 (s, 1H), 7.74 (d, 1H), 7.57 (d, 1H), 7.53 (d, 1H), 7.45 (m, 3H), 4.75 (m, 1H), 4.45 (s, 2H), 3.66 (m, 5H), 3.39 (t, 2H), 3.25 (s, 3H), 2.98 (m, 5H), 2.09 (m, 6H), 1.84 (m, 2H), 1.67 (m, 2H).

EXAMPLE 292

(cis)-1-{4-(4-(3-methoxypropyl)piperazin-1-yl)cyclohexyl}-3-{2-(2-(trifluoromethoxy)benzyl)-1H-benzimidazol-5-yl}-1H-pyrazolo[3,4-d]pyrimidin-4-amine This compound is the slower eluting diastereomer in EXAMPLE 291. MS (ESI) m/e 664 (M+H)$^-$; $^1$H NMR (300 MHz, DMSO-d$_6$) δ8.31 (s, 1H), 7.82 (s, 1H), 7.74 (d, 1H), 7.58 (d, 1H), 7.54 (d, 1H), 7.46 (m, 3H), 4.91 (m, 1H), 4.44 (s, 2H), 3.47 (m, 5H), 3.39 (t, 2H), 3.24 (s, 3H), 3.00 (m, 5H), 2.35 (m, 3H), 2.05 (m, 3H), 1.85 (m, 4H).

EXAMPLE 293

(trans)-1-(4-morpholin-4-ylcyclohexyl)-3-(2-(2-naphthylmethyl)-1H-benzimidazol-6-yl)-1H-pyrazolo[3,4-d]pyrimidin-4-amine The desired product was prepared by substituting 2-(naphthalen-2-yl)acetic acid for 2-(thiophen-3-yl)acetic acid in EXAMPLE 286B. (ESI(+)) m/e 559 (M+H)$^+$; $^1$H NMR (300 MHz, DMSO-d$_6$) 12.48 (s, 1H); 8.22 (s, 1H); 7.90-7.87 (m, 4H); 7.67-7.65 (m, 1H); 7.55-7.41 (m, 5H); 4.65 (m, 1H); 4.40 (s, 2H); 3.59-3.56 (m, 5H); 2.40-2.20 (m, 2H); 1.99-1.96 (m, 8H); 1.56-1.48 (m 2H).

EXAMPLE 294

(trans)-3-(2-(2,6-difluorobenzyl)-1H-benzimidazol-5-yl)-1-{4-(4-(3-methoxypropyl)piperazin-1-yl)cyclohexyl}-1H-pyrazolo[3,4-d]pyrimidin-4-amine

EXAMPLE 294A

The desired product was prepared by substituting 2,6-difluorophenylacetonitrile for phenylmethylacetonitrile in EXAMPLE 118B.

EXAMPLE 294B

The desired product was prepared by substituting EXAMPLE 294A for EXAMPLE 339A in EXAMPLE 339B.

EXAMPLE 294C

The desired product was prepared by substituting EXAMPLE 294B for EXAMPLE 339B in EXAMPLE 339C.

EXAMPLE 294D

The desired product was prepared by substituting EXAMPLE 294C for EXAMPLE 265A in EXAMPLE 265B. The faster eluting diastereomer was isolated. MS (ESI) m/e 616 (M+H)$^-$; $^1$H NMR (300 MHz, DMSO-d$_6$) δ8.30 (s, 1H), 7.77 (s, 1H), 7.71 (d, 1H), 7.54 (d, 1H), 7.47 (m, 1H), 7.19 (m, 2H), 4.76 (m, 1H), 4.40 (s, 2H), 3.42 (m, 5H), 3.39 (t, 2H), 3.25 (s, 3H), 2.98 (m, 5H), 2.10 (m, 6H), 1.84 (m, 2H), 1.68 (m, 2H).

EXAMPLE 295

(cis)-3-(2-(2,6-difluorobenzyl)-1H-benzimidazol-5-yl)-1-{4-(4-(3-methoxypropyl)piperazin-1-yl)cyclohexyl}-1H-pyrazolo[3,4-d]pyrimidin-4-amine This compound is the slower eluting diastereomer in EXAMPLE 294. MS (ESI) m/e 616 (M+H)$^-$; $^1$H NMR (300 MHz, DMSO-d$_6$) δ8.31 (s, 1H), 7.78 (s, 1H), 7.70 (d, 1H), 7.53 (d, 1H), 7.46 (m, 1H), 7.18 (m, 2H), 4.92 (m, 1H), 4.38 (s, 2H), 3.70 (m, 5H), 3.37 (t, 2H), 3.24 (s, 3H), 3.00 (m, 5H), 2.34 (m, 2H), 2.07 (m, 3H), 1.86 (m, 5H).

EXAMPLE 296

(trans)-2-({6-(4-amino-1-(4-morpholin-4-ylcyclohexyl)-1H-pyrazolo[3,4-d]pyrimidin-3-yl)-1H-benzimidazol-2-yl}methyl)phenol The desired product was prepared by substituting 2-(2-hydroxyphenyl)acetic acid for 2-(thiophen-3-yl)acetic acid in EXAMPLE 286B. (ESI(+)) m/e 525 (M+H)$^+$; $^1$H NMR (300 MHz, DMSO-d$_6$) 8.28 (s, 1H); 7.85-7.79 (m, 2H); 7.70-7.63 (m, 1H); 7.31-7.28 (m, 1H); 7.22-7.17 (m, 1H); 6.90-6.84 (m. 2H); 4.77 (m, 1H); 4.38 (s, 2H); 4.08-3.99 (m, 2H); 3.74-3.64 (m, 1H); 2.28-2.20 (m, 3H); 2.16-2.08 (m, 7H); 1.81-1.68 (m, 3H).

EXAMPLE 297

3-(2-(2-methoxybenzyl)-1H-benzimidazol-5-yl)-1-(4-{(4-(3-methoxypropyl)piperazin-1-yl)methyl}phenyl)-1H-pyrazolo[3,4-d]pyrimidin-4-amine

EXAMPLE 297A

The desired product was prepared by substituting 1-(3-methoxypropyl)piperazine for morpholine in EXAMPLE 48B.

EXAMPLE 297B

The desired product was prepared by substituting EXAMPLE 297A for (cis)-4-(4-(-4-amino-3-iodo-pyrazolo[3,4-d]pyrimidin-1-yl)-cyclohexyl)-1 methyl-piperazin-2-one in EXAMPLE 2B.

EXAMPLE 297C

The desired product was prepared by substituting EXAMPLE 297B for EXAMPLE 48C and 2-methoxyphenylacetaldehyde for phenylacetaldehyde in EXAMPLE 48D. MS (ESI) m/e 618 (M+H)$^-$; $^1$H NMR (300 MHz, DMSO-d$_6$) δ8.40 (s, 1H), 8.21(d, 2H), 7.98 (s, 1H), 7.88 (d, 1H), 7.81 (d, 1H), 7.54 (d, 2H), 7.39(m, 2H), 7.09 (d, 1H), 7.03 (t, 1H), 4.45 (s, 2H), 3.79 (s, 3H), 3.46 (m, 4H), 3.38 (m, 2H), 3.24 (s, 3H), 3.06 (m, 8H), 1.85 (m, 2H).

EXAMPLE 298

1-(4-({4-(2-(1,3-dioxolan-2-yl)ethyl)piperazin-1-yl}methyl)phenyl)-3-(2-(2-methoxybenzyl)-1H-benzimidazol-5-yl)-1H-pyrazolo[3,4-d]pyrimidin-4-amine

EXAMPLE 298A

The desired product was prepared by substituting 1-(2-(1,3-dioxolan-2-yl)ethyl)piperazine for morpholine in EXAMPLE 48B.

EXAMPLE 298B

The desired product was prepared by substituting EXAMPLE 298A for (cis)-4-(4-(-4-amino-3-iodo-pyrazolo[3,4-d]pyrimidin-1-yl)-cyclohexyl)-1 methyl-piperazin-2-one in EXAMPLE 2B.

EXAMPLE 298C

The desired product was prepared by substituting EXAMPLE 298B for EXAMPLE 48C and 2-methoxyphenylacetaldehyde for phenylacetaldehyde in EXAMPLE 48D. MS (ESI) m/e 646 (M+H)$^-$; $^1$H NMR (300 MHz, DMSO-d$_6$) δ8.41 (s, 1H), 8.23 (d, 2H), 8.00 (s, 1H), 7.87 (m, 2H), 7.56 (d, 2H), 7.40 (m, 2H), 7.09 (d, 1H), 7.03 (t, 1H), 4.89 (t, 1H), 4.48 (s, 2H), 3.90 (m, 4H), 3.80 (m, 2H), 3.79 (s, 3H), 3.10 (m, 10H), 1.99 (m, 2H).

EXAMPLE 299

(trans)-3-{2-((2-methyl-1,3-thiazol-4-yl)methyl)-1H-benzimidazol-6-yl}-1-(4-morpholin-4-ylcyclohexyl)-1H-pyrazolo[3,4-d]pyrimidin-4-amine The desired product was prepared by substituting 2-(2-methylthiazol-4-yl)acetic acid for 2-(thiophen-3-yl)acetic acid in EXAMPLE 286B. (ESI(+)) m/e 530 (M+H)$^+$; $^1$H NMR (300 MHz, DMSO-d$_6$) 12.44 (s, 1H); 8.23 (s, 1H); 7.73-7.61 (m, 2H); 7.45-7.41 (m, 1H); 7.31 (s, 1H); 4.70-4.61 (m, 1H); 4.30 (s, 2H); 3.59-3.56 (m, 5H); 2.40-2.31 (m, 1H); 2.07-1.96 (m, 6H); 1.53-1.42 (m, 2H).

EXAMPLE 300

3-(2-(2-methoxybenzyl)-1H-benzimidazol-5-yl)-1-(4-{(4-(methylsulfonyl)piperazin-1-yl)methyl}phenyl)-1H-pyrazolo[3,4-d]pyrimidin-4-amine

EXAMPLE 300A

The desired product was prepared by substituting 1-(methanesulfonyl)piperazine for morpholine in EXAMPLE 48B.

EXAMPLE 300B

The desired product was prepared by substituting EXAMPLE 300A for (cis)-4-(4-(-4-amino-3-iodo-pyrazolo[3,4-d]pyrimidin-1-yl)-cyclohexyl)-1 methyl-piperazin-2-one in EXAMPLE 2B.

EXAMPLE 300C

The desired product was prepared by substituting EXAMPLE 300B for EXAMPLE 48C and 2-methoxyphenylacetaldehyde for phenylacetaldehyde in EXAMPLE 48D. MS (ESI) m/e 624 (M+H)$^-$; $^1$H NMR (300 MHz, DMSO-d$_6$) δ8.43 (s, 1H), 8.37(d, 2H), 8.01 (s, 1H), 7.86 (m, 2H), 7.69 (d, 2H), 7.40 (m, 2H), 7.09 (d, 1H), 7.03 (t, 1H), 4.48 (s, 2H), 4.45 (s, 2H), 3.79 (s, 3H), 3.24 (m, 8H), 3.02 (s, 3H).

EXAMPLE 301

2-(4-{4-amino-3-(2-(2-fluorobenzyl)-1H-indol-5-yl)-1H-pyrazolo[3,4-d]pyrimidin-1-yl}-1,4'-bipiperidin-1'-yl)ethanol

EXAMPLE 301A tert-butyl 4-(4-amino-3-(2-(2-fluorobenzyl)-1H-indol-5-yl)-1H-pyrazolo[3,4-d]pyrimidin-1-yl)piperidine-1-carboxylate The title compound, as a tan solid foam, was prepared as described in EXAMPLE 139B substituting EXAMPLE 201A for EXAMPLE 139A and EXAMPLE 217C for EXAMPLE 188C except the purification was done on normal phase silica gel. MS (ESI+) m/e 542 (M+H)$^+$; (ESI(−)) m/e 540 (M−H)⁻; ¹H NMR (300 MHz, DMSO-d₆) 11.26 (s, 1H), 8.22 (s, 1H), 7.68 (s, 1H), 7.45 (d, 1H), 7.32 (m, 3H), 7.19 (m, 2H), 6.21 (s, 1H), 4.89 (m, 1H), 4.13 (s, 2H), 4.10 (m, 2H), 3.32 (s, 2H), 3.00 (m, 2H), 2.04 (m, 2H), 1.94 (m, 2H), 1.43 (s, 9H).

EXAMPLE 301B 3-(2-(2-fluorobenzyl)-1H-indol-5-yl)-1-(piperidin-4-yl)-1H-pyrazolo[3,4-d]pyrimidin-4-amine The title compound, as a purple tint white solid, was prepared as described in EXAMPLE 201C substituting EXAMPLE 301A for EXAMPLE 201B. MS (ESI+) m/e 442 (M+H)⁺; (ESI(−)) m/e 440 (M−H)⁻; ¹H NMR (300 MHz, DMSO-d₆) 11.32 (s, 1H), 8.77 (m, 1H), 8.43 (m, 1H), 8.14 (s. 1H), 7.70 (s, 1H), 7.48 (d, 1H), 7.32 (m, 3H), 7.19 (m, 2H), 6.23 (s, 1H), 5.08 (m, 1H), 4.24 (vbr s, 1H), 4.15 (s, 2H), 3.47 (m, 2H), 3.22 (m, 2H), 2.37 (m, 2H), 2.14 (m, 2H).

EXAMPLE 301C 2-(4-{4-amino-3-(2-(2-fluorobenzyl)-1H-indol-5-yl)-1H-pyrazolo[3,4-d]pyrimidin-1-yl}-1,4'-bipiperidin-1'-yl)ethanol The title compound, as a brown solid, was prepared as described in EXAMPLE 201D substituting EXAMPLE 301B for EXAMPLE 201C and 1-(2-hydroxyethyl)-piperidin-4-one for 1-methylpiperidin-4-one. MS (ESI+) m/e 569 (M+H)⁺; (ESI(−)) m/e 567 (M−H)⁻; ¹H NMR (300 MHz, DMSO-d₆) 11.32 (s, 1H), 9.75 (m, 1H), 9.46 (m, 1H), 8.31 (s. 1H), 7.70 (s, 1H), 7.48 (d, 1H), 7.34 (m, 3H), 7.19 (m, 2H), 6.22 (s, 1H), 5.12 (m, 1H), 4.15 (s, 2H), 3.75 (m, 4H), 3.56 (vbr s, 2H), 3.36 (m, 4H), 3.28 (m, 2H), 3.03 (m, 2H), 2.56 (m, 2H), 2.28 (m, 4H), 2.00 (m, 2H).

EXAMPLE 302

3-(4-{4-amino-3-(2-(2-fluorobenzyl)-1H-indol-5-yl)-1H-pyrazolo[3,4-d]pyrimidin-1-yl}-1,4'-bipiperidin-1'-yl)propan-1-ol The title compound, as a brown solid, was prepared as described in EXAMPLE 301 substituting 1-(3-hydroxypropyl)piperidin-4-one for 1-(2-hydroxyethyl)-piperidin-4-one in EXAMPLE 301C. MS (ESI+) m/e 583 (M+H)⁺; (ESI(−)) m/e 581 (M−H)⁻; ¹H NMR (300 MHz, DMSO-d₆) 11.32 (s, 1H), 9.74 (m, 1H), 9.43 (m, 1H), 8.32 (s. 1H), 7.70 (s, 1H), 7.47 (d, 1H), 7.33 (m, 3H), 7.19 (m, 2H), 6.22 (s, 1H), 5.12 (m, 1H), 4.14 (s, 2H), 3.75 (m, 4H), 3.60 (vbr s, 2H), 3.34 (m, 4H), 3.13 (m, 2H), 3.00 (m, 2H), 2.53 (m, 2H), 2.29 (m, 4H), 1.93 (m, 2H), 1.80 (m, 2H).

EXAMPLE 303

3-(2-(2-fluorobenzyl)-1H-indol-5-yl)-1-(1'-(2-methoxyethyl)-1,4'-bipiperidin-4-yl)-1H-pyrazolo[3,4-d]pyrimidin-4-amine The title compound, as a brown solid, was prepared as described in EXAMPLE 301 substituting 1-(2-methoxyethyl)piperidin-4-one for 1-(2-hydroxyethyl)-piperidin-4-one in EXAMPLE 301C. MS (ESI+) m/e 583 (M+H)⁺; (ESI(−)) m/e 581 (M−H)⁻; ¹H NMR (300 MHz, DMSO-d₆) 11.32 (s, 1H), 9.78 (m, 1H), 9.62 (m, 1H), 8.32 (s. 1H), 7.69 (s, 1H), 7.47 (d, 1H), 7.32 (m, 3H), 7.19 (m, 2H), 6.21 (s, 1H), 5.12 (m, 1H), 4.14 (s, 2H), 4.00 (vbr s, 5H), 3.65 (m, 4H), 3.33 (s, 3H), 3.30 (m, 2H), 3.03 (m, 2H), 2.53 (m, 2H), 2.27 (m, 4H), 2.00 (m, 2H).

EXAMPLE 304

3-(2-(2-fluorobenzyl)-1H-indol-5-yl)-1-(1'-(3-methoxypropyl)-1,4'-bipiperidin-4-yl)-1H-pyrazolo[3,4-d]pyrimidin-4-amine The title compound, as a brown solid, was prepared as described in EXAMPLE 301 substituting 1-(3-methoxypropyl)piperidin-4-one for 1-(2-hydroxyethyl)-piperidin-4-one in EXAMPLE 301C. MS (ESI+) m/e 597 (M+H)⁺; (ESI(−)) m/e 595 (M−H)⁻; ¹H NMR (300 MHz, DMSO-d₆) 11.30 (s, 1H), 9.74 (m, 1H), 9.53 (m, 1H), 8.31 (s. 1H), 7.69 (s, 1H), 7.47 (d, 1H), 7.31 (m, 3H), 7.19 (m, 2H), 6.21 (s, 1H), 5.12 (m, 1H), 4.14 (s, 2H), 3.86 (vbr s, 3H), 3.66 (m, 4H), 3.39 (m, 2H), 3.24 (s, 3H), 3.13 (m, 2H), 3.00 (m, 2H), 2.55 (m, 2H), 2.26 (m, 4H), 1.89 (m, 4H).

EXAMPLE 305

3-(2-(2-fluorobenzyl)-1H-indol-5-yl)-1-(1'-isobutyl-1,4'-bipiperidin-4-yl)-1H-pyrazolo[3,4-d]pyrimidin-4-amine The title compound, as a brown solid, was prepared as described in EXAMPLE 301 substituting 1-isobutylpiperidin-4-one for 1-(2-hydroxyethyl)-piperidin-4-one in EXAMPLE 301C. MS (ESI+) m/e 581 (M+H)⁺; (ESI(−)) m/e 579 (M−H)⁻; ¹H NMR (300 MHz, DMSO-d₆) 11.30 (s, 1H), 9.76 (m, 1H), 9.15 (m, 1H), 8.37 (s. 1H), 7.70 (s, 1H), 7.47 (d, 1H), 7.33 (m, 3H), 7.20 (m, 2H), 6.22 (s, 1H), 5.12 (m, 1H), 4.15 (s, 2H), 3.80 (vbr s, 2H), 3.65 (m, 4H), 3.37 (m, 2H), 2.93 (m, 2H), 2.56 (m, 2H), 2.25 (m, 4H), 2.06 (m, 4H), 0.96 (d, 6H).

EXAMPLE 306

2-(4-(4-{4-amino-3-(2-(2,5-difluorobenzyl)-1H-indol-5-yl)-1H-pyrazolo[3,4-d]pyrimidin-1-yl}cyclohexyl)piperazin-1-yl)ethanol

EXAMPLE 306A

The desired product was synthesized by substituting 2,5-difluorobenzylbromide for benzyl bromide in EXAMPLE 206A.

EXAMPLE 306B

The desired product was synthesized by substituting EXAMPLE 306A for EXAMPLE 206A in EXAMPLE 206B.

EXAMPLE 306C

The desired product was synthesized by substituting EXAMPLE 306B for 4-bromo2-nitro-phenylamine in EXAMPLE 2A.

EXAMPLE 306D

The desired product was synthesized by substituting 3-Iodo-1-(4-oxo-cyclohexyl)-1H-pyrazolo[3,4-d]pyrimidin-4-ylamine prepared as described in A. F. Burchat et al. Bioorg Med. Chem. Lett. 2002, 12, 1687-1690 for EXAMPLE 318A and EXAMPLE 306C for EXAMPLE 217C in EXAMPLE 318B.

EXAMPLE 306E

The desired product was synthesized by substituting EXAMPLE 306D for EXAMPLE 267B in EXAMPLE 267C. $^1$H NMR (300 MHz, DMSO-$d_6$) 11.37 (s., 1H), 8.35 (s, 1H), 7.47 (m., 1H), 7.28-7.10 (m., 5H), 6.23 (d., 1H), 4.95 (m., 1H), 4.13 (s., 2H), 3.42-3.58 (m, 4H), 2.89-3.19 (m, 4H), 2.24-2.41 (m., 2H), 2.02-2.14 (m, 2H), 1.68-1.94 (m, 4H).

EXAMPLE 307

3-(4-(4-{4-amino-3-(2-(2-fluorobenzyl)-1H-indol-5-yl)-1H-pyrazolo[3,4-d]pyrimidin-1-yl}cyclohexyl)piperazin-1-yl)propan-1-ol The desired product was the mixture of diastereomers generated in EXAMPLE 223. MS: ESI(+) m/e 583.4 (M+H)$^+$; ESI(−) m/e 581.5 (M−H); $^1$H NMR (300 MHz, DMSO-$d_6$) 11.29 (s., 1H), 8.32 (s, 1H), 7.69 (s, 1H), 7.46 (d., 1H), 7.28-7.38 (m., 3H), 7.15-7.24 (m., 2H), 6.22 (d., 1H), 4.90 (m., 1H), 4.15 (s., 2H), 3.42-3.53 (m, 4H, includes=3.46, t, 2H), 2.89-3.16 (m, 4H), 2.24-2.41 (m., 2H), 2.02-2.14 (m, 2H), 1.68-1.94 (m, 4H).

EXAMPLE 308

(cis)-1-(4-({2-(2-(2-aminoethoxy)ethoxy)ethyl}amino)cyclohexyl)-3-(2-(2-fluorobenzyl)-1H-indol-5-yl)-1H-pyrazolo[3,4-d]pyrimidin-4-amine The desired product was synthesized by substituting 2,2'-(ethylenedioxy)bis(ethylamine) for 1-(3-hydroxypropyl)piperazine in EXAMPLE 223B. The earlier eluting diastereomer was isolated. MS: ESI(+) m/e 587.4 (M+H)$^+$; ESI(−) m/e 585.5 (M−H); $^1$H NMR (300 MHz, DMSO-$d_6$) 11.30 (s, 1H), 8.51 (br., 1H), 8.31 (s, 1H), 7.80 (br., 2H), 7.73 (br.s, 1H), 7.47 (d, 1H), 7.28-7.38 (m, 3H), 7.15-7.24 (m, 2H), 6.22 (s, 1H), 4.90 (br. m, 1H), 4.14 (s, 2H), 3.68 (t., 2H), 3.58 ((t., 2H), 3.26-3.36 (br.m., 1H), 3.12-3.21 (m., 2H), 2.93-3.02 (m., 2H), 2.32-2.44 (m., 2H), 1.87-2.13 (m., 6H).

EXAMPLE 309

1-(4-({2-(2-(2-aminoethoxy)ethoxy)ethyl}amino)cyclohexyl)-3-(2-(2-fluorobenzyl)-1H-indol-5-yl)-1H-pyrazolo[3,4-d]pyrimidin-4-amine The desired product was the unresolved mixture of diastereomers generated in EXAMPLE 308. $^1$H NMR (300 MHz, DMSO-$d_6$) 11.29 (s, 1H), 8.57-8.48 (br., 1H), 8.29 (s, 1H), 7.78-7.70 (br., 2H), 7.67 (br.s, 1H), 7.46 (d, 1H), 7.27-7.37 (m, 3H), 7.14-7.23 (m, 2H), 6.22 (s, 1H), 4.89-4.70 (br. m, 1H), 4.14 (s, 2H), 3.24-3.36 (br.m., 3H), 2.94-3.04 (m., 2H), 2.17-2.28 (m., 2H), 2.03-2.16 (m., 6H), 1.57-1.73 (m, 2H).

EXAMPLE 310

(trans)-1-(4-({2-(2-(2-aminoethoxy)ethoxy)ethyl}amino)cyclohexyl)-3-(2-(2-fluorobenzyl)-1H-indol-5-yl)-1H-pyrazolo[3,4-d]pyrimidin-4-amine The desired product was the slower eluting diastereomer in EXAMPLE 308. MS: ESI(+) m/e 587.4 (M+H)$^+$; $^1$H NMR (300 MHz, DMSO-$d_6$) 11.28 (s, 1H), 8.57 (br., 1H), 8.28 (s, 1H), 7.78 (br., 2H), 7.67 (br.s, 1H), 7.46 (d, 1H), 7.27-7.37 (m, 3H), 7.14-7.23 (m, 2H), 6.21 (s, 1H), 4.70 (br. m, 1H), 4.14 (s, 2H), 3.24-3.36 (br.m., 3H), 2.94-3.04 (m., 2H), 2.17-2.28 (m., 2H), 2.03-2.16 (m., 6H), 1.57-1.73 (m, 2H).

EXAMPLE 311

2-{2-((4-{4-amino-3-(2-(2-fluorobenzyl)-1H-indol-5-yl)-1H-pyrazolo[3,4-d]pyrimidin-1-yl}cyclohexyl)amino)ethoxy}ethanol The desired product was synthesized by substituting 2-(2-hydroxyethoxy)ethylamine for 1-(3-hydroxypropyl)piperazine in EXAMPLE 223B. MS: ESI(+) m/e 544.4 (M+H)$^+$; $^1$H NMR (300 MHz, DMSO-$d_6$) 11.31 (s, 1H), 8.53 (br., 1H), 8.44 (br., 1H), 8.34 (s, 1H), 7.74 (d., 0.5H), 7.69 (s., 0.5H), 7.54-7.65 (m., 1H), 7.45-7.49 (m., 1H), 7.28-7.38 (m, 3H), 7.15-7.24 (m, 2H), 6.22 (s, 1H), 4.90 (br. m, 0.5H), 4.71 (m., 0.5H), 4.14 (s, 2H), 3.66-3.71 (m., 2H), 3.48-3.59 (m., 4H), 3.12-3.36 (m., 3H), 2.31-2.41 (m., 1H), 2.16-2.28 (m., 2H), 1.87-2.14 (m., 6H), 1.55-1.70 (m., 1H).

EXAMPLE 312

2-(1-(4-{4-amino-3-(2-(2-fluorobenzyl)-1H-indol-5-yl)-1H-pyrazolo[3,4-d]pyrimidin-1-yl}cyclohexyl)piperidin-4-yl)ethanol The desired product was synthesized by substituting 4-(2-hydroxyethyl)piperidine for 1-(2-hydroxyethyl)piperazine in EXAMPLE 267C. MS: ESI(+) m/e 568.4 (M+H)$^+$; $^1$H NMR (300 MHz, DMSO-$d_6$) 11.31 (s, 1H), 8.99 (br., 0.5H), 8.84 (br., 0.5H), 8.33 (s, 1H), 7.73 (d., 0.5H), 7.68 (s., 0.5H), 7.45-7.50 (m., 1H), 7.28-7.38 (m, 3H), 7.15-7.24 (m, 2H), 6.22 (s, 1H), 4.98 (br. m, 0.5H), 4.76 (m., 0.5H), 4.14 (s, 2H), 3.37-3.52 (m., 3H), 3.15-3.36 (m., 3H), 2.89-3.05 (m., 2H), 2.31-2.43 (m., 1H), 2.15-2.22 (m., 3H), 1.58-2.44 (m., 6H), 130-1.45(m., 3H).

EXAMPLE 313

(1-(4-{4-amino-3-(2-(2-fluorobenzyl)-1H-indol-5-yl)-1H-pyrazolo[3,4-d]pyrimidin-1-yl}cyclohexyl)piperidin-4-yl)methanol The desired product was synthesized by substituting 4-hydroxymethylpiperidine for 1-(2-hydroxyethyl)piperazine in EXAMPLE 267C. MS: ESI(+) m/e 554.4 (M+H)$^+$; $^1$H NMR (300 MHz, DMSO-$d_6$) 11.33 (s, 1H), 8.95 (br., 0.5H), 8.82 (br., 0.5H), 8.33 (s, 1H), 7.73 (d., 0.5H), 7.69 (s., 0.5H), 7.45-7.50 (m., 1H), 7.28-7.38 (m, 3H), 7.15-7.24 (m, 2H), 6.22 (s, 1H), 4.98 (br. m, 0.5H), 4.76 (m., 0.5H), 4.15 (s, 2H), 3.22-3.54 (m., 8H), 2.90-3.07 (m., 2H), 2.07-2.23 (m., 2H), 1.78-2.05 (m., 6H), 1.56-1.71 (m., 1H), 1.33-1.52 (m., 1H).

EXAMPLE 314

(trans)-3-(2-(2-fluorobenzyl)-1H-indol-5-yl)-1-(4-{4-(2-(2-methoxyethoxy)ethyl)piperazin-1-yl}cyclohexyl)-1H-pyrazolo[3,4-d]pyrimidin-4-amine The desired product was prepared by substituting 1-bromo-2-(2-methoxyethyoxy)ethane for 2-(2-ethoxyethoxy)ethyl bromide in EXAMPLE 318D. MS: ESI(+) m/e 627.5 (M+H)$^+$; ESI(−) m/e 625.6 (M−H); $^1$H NMR (300

MHz, DMSO-d$_6$) 11.30 (s, 1H), 8.33 (s, 1H), 7.68 (br.s, 1H), 7.46 (d, 1H), 7.39-7.28 (m, 3H), 7.24-7.15 (m, 2H), 6.22 (s, 1H), 4.79-4.67 (br. m, 1H), 4.61 (s, 3H), 4.14 (s, 2H), 3.69 (br.t, 2H), 3.59-3.55 (m, 2H), 3.50-3.46 (m, 2H), 3.15 (br.m., 1H), 2.19-2.07 (m, 6H), 1.79-1.64 (br, m, 2H).

EXAMPLE 315

(trans)-3-(2-(2-fluorobenzyl)-1H-indol-5-yl)-1-(4-{4-(2-(methoxymethoxy)ethyl)piperazin-1-yl}cyclohexyl)-1H-pyrazolo[3,4-d]pyrimidin-4-amine The desired product was prepared by substituting 2-bromoethylmethoxymethyl ether for 2-(2-ethoxyethoxy)ethyl bromide in EXAMPLE 318D. MS: ESI(+) m/e 613.5 (M+H)$^+$; $^1$H NMR (300 MHz, DMSO-d$_6$) 11.28 (s, 1H), 8.31 (s, 1H), 7.68 (br.s, 1H), 7.46 (d, 1H), 7.38-7.28 (m, 3H), 7.24-7.15 (m, 2H), 6.22 (s, 1H), 4.79-4.67 (br. m, 1H), 4.61 (s, 3H), 4.14 (s, 2H), 3.75 (br.m), 3.15-3.00 (br.m., 1H), 2.19-2.05 (m, 6H), 1.79-1.62 (br, m, 2H).

EXAMPLE 316

3-(4-(4-{4-amino-3-(2-(2,5-difluorobenzyl)-1H-indol-5-yl)-1H-pyrazolo[3,4-d]pyrimidin-1-yl}cyclohexyl)piperazin-1-yl)propan-1-ol The desired product was synthesized by substituting EXAMPLE 306D for EXAMPLE 267B and 1-(3-hydroxypropyl)piperazine for 1-(2-hydroxyethyl)piperazine in EXAMPLE 267C. $^1$H NMR (300 MHz, DMSO-d$_6$) 11.37 (s., 1H), 8.36 (s, 1H), 7.47 (m., 1H), 7.28-7.10 (m., 5H), 6.24 (d., 1H), 4.95 (m., 1H), 4.13 (s., 2H), 3.42-3.53 (m, 4H, includes=3.46, t, 2H), 3.01-3.17 (m, 4H), 2.24-2.41 (m., 2H), 2.02-2.14 (m, 2H), 1.68-1.94 (m, 4H).

EXAMPLE 317

2-(4-(4-{4-amino-3-(2-(2-fluorobenzyl)-1H-indol-5-yl)-1H-pyrazolo[3,4-d]pyrimidin-1-yl}cyclohexyl)piperazin-1-yl)ethanol The desired product was the mixture of diastereomers generated in EXAMPLE 227. $^1$H NMR (300 MHz, DMSO-d$_6$) 11.29 (s., 1H), 8.33 (s, 1H), 7.70 (s, 1H), 7.46 (d., 1H), 7.28-7.38 (m., 3H), 7.15-7.24 (m., 2H), 6.22 (d., 1H), 4.91 (m., 1H), 4.14 (s., 2H), 3.42-3.58 (m, 4H), 2.89-3.19 (m, 4H), 2.24-2.41 (m., 2H), 2.02-2.14 (m, 2H), 1.68-1.94 (m, 4H).

EXAMPLE 318

(trans)-1-(4-{4-(2-(2-ethoxyethoxy)ethyl)piperazin-1-yl}cyclohexyl)-3-(2-(2-fluorobenzyl)-1H-indol-5-yl)-1H-pyrazolo[3,4-d]pyrimidin-4-amine

EXAMPLE 318A

3-Iodo-1-(4-oxo-cyclohexyl)-1H-pyrazolo[3,4-d]pyrimidin-4-ylamine prepared as described in A. F. Burchat et al. Bioorg Med. Chem. Lett. 2002, 12, 1687-1690 (1.785 g, 5 mmol) and tert-butyl 1-piperazine carboxylate (4.65 g, 25 mmol) were suspended in 70 mL of methanol and 7 mL of acetic acid and stirred at room temperature for 20 min. (Polystyryl)trimethylammonium cyanoborohydride resin (4.2 mmol/g, 4.5 g) was added, the mixture was stirred at 70° C. for 16 h. The resin was removed by filtration, the filtrate was concentrated in vacuo and the residue was purified by silica gel column, eluting with 7% methanol in ethyl acetate to yield the trans diastereomer (1.08 g).

EXAMPLE 318B

EXAMPLE 318A (1.25 g, 2.37 mmol), EXAMPLE 217C, (1.0 g, 2.84 mmol), sodium carbonate (0.5 g, 4.71 mmol), palladium tetrakis triphenylphosphine (82 mg, 0.07 mmol) was suspended in 30 mL of DME:water (1:1). This was microwaved at 130° C. for 20 minutes. After partitioning between ethyl acetate and brine, the ethyl acetate layer washed with brine (3×), dried and purified by silica gel column chromatography, eluting with 7% methanol in ethyl acetate, providing 720 mg of the title compound.

EXAMPLE 318C

EXAMPLE 318B (312 mg, 0.5 mmol) was treated with 1.25 mL of trifluoroacetic acid (TFA) and 5 mL of methylene chloride for 1 hour. Solvent was removed and the residue was triturated with ether, and dried under high vacuum to yield the title compound in quantitative yield.

EXAMPLE 318D

EXAMPLE 318C (94 mg, 0.15 mmol), 2-(2-ethoxyethoxy)ethyl bromide (44 mg, 0.225 mmol), sodium iodide (56 mg, 0.375 mmol) and potassium carbonate (104 mg, 0.75 mmol) were mixed in 5 mL of acetonitrile. The solution was stirred at 65° C. for 16 h. Insoluble material was filtered off and was purified by HPLC. 54 mg was obtained. MS: ESI(+) m/e 641.5 (M+H)$^+$; ESI(−) m/e 639.6 (M−H); $^1$H NMR (300 MHz, DMSO-d$_6$) 11.28 (s, 1H), 8.30 (s, 1H), 7.68 (br.s, 1H), 7.46 (d, 1H), 7.38-7.28 (m, 3H), 7.24-7.15 (m, 2H), 6.22 (s, 1H), 4.80-4.67 (br. m, 1H), 4.14 (s, 2H), 3.58-3.49 (m, 8H), 3.45 (q, 2H), 3.15-3.00 (br.m., 1H), 2.18-2.05 (m, 6H), 1.76-1.61 (br, m, 2H), 1.11 (t, 3H).

EXAMPLE 319

1-(4-{4-amino-3-(2-(2-methoxybenzyl)-1H-benzimidazol-5-yl)-1H-pyrazolo[3,4-d]pyrimidin-1-yl}cyclohexyl)piperidin-4-ol The desired product was prepared by substituting 4-hydroxypiperidine for 2-(trifluoromethyl)-5,6,7,8-tetrahydroimidazo[1,2-a]pyrazine in EXAMPLE 338. MS (ESI) m/e 553 (M+H)$^−$; $^1$H NMR (300 MHz, DMSO-d$_6$) δ9.0 (bs, 1H), 8.32 (s, 1H), 7.92 (s, 1H), 7.85 (d, 1H), 7.77 (d, 1H), 7.39 (m, 2H), 7.08 (d, 1H), 7.02 (t, 1H), 5.00 (m, 1H), 4.45 (s, 2H), 3.78 (s, 3H), 3.42 (m, 2H), 3.30 (m, 1H), 3.18 (m, 1H), 3.04 (m, 1H), 2.40 (m, 2H), 2.11-1.96 (m, 7H), 1.79 (m, 2H), 1.58 (m, 1H).

EXAMPLE 320

(trans)-3-(2-(2-methoxybenzyl)-1H-benzimidazol-5-yl)-1-{4-(4-(4-methoxyphenyl)piperazin-1-yl)cyclohexyl}-1H-pyrazolo[3,4-d]pyrimidin-4-amine The desired product was prepared by substituting 1-(4-methoxyphenyl)piperazine for 2-(trifluoromethyl)-5,6,7,8-tetrahydroimidazo[1,2-a]pyrazine in EXAMPLE 338. The faster eluting isomer was isolated: MS (ESI) m/e 644 (M+H)$^−$; $^1$H NMR (300 MHz, DMSO-d$_6$) δ9.46 (bs, 1H), 8.30 (s, 1H), 7.87 (s, 1H), 7.83 (d, 1H), 7.72 (d, 1H), 7.38 (m, 2H), 7.08 (d, 1H), 7.00 (m, 3H), 6.87 (d, 2H), 4.80 (m, 1H), 4.44 (s, 2H), 3.78 (s, 3H), 3.70 (s, 3H), 3.28 (m, 4H), 2.92 (m, 4H), 2.27 (m, 2H), 2.14 (m, 4H), 1.82 (m, 2H).

EXAMPLE 321

(cis)-3-(2-(2-methoxybenzyl)-1H-benzimidazol-5-yl)-1-{4-(4-(4-methoxyphenyl)piperazin-1-yl)cyclohexyl}-1H-pyrazolo[3,4-d]pyrimidin-4-amine This compound is the slower eluting diastereomer in EXAMPLE 320. MS (ESI) m/e 644 (M+H)⁻; ¹H NMR (300 MHz, DMSO-d₆) δ9.30 (bs, 1H), 8.32 (s, 1H), 7.91 (s, 1H), 7.84 (d, 1H), 7.77 (d, 1H), 7.38 (m, 2H), 7.08 (d, 1H), 7.02 (t, 1H), 6.95 (d, 2H), 6.86 (d, 2H), 5.00 (m, 1H), 4.43 (s, 2H), 3.78 (s, 3H), 3.70 (s, 3H), 3.23 (m, 4H), 2.90 (m, 4H), 2.08 (m, 8H).

EXAMPLE 322

(trans)-4-(4-{4-amino-3-(2-(2-methoxybenzyl)-1H-benzimidazol-5-yl)-1H-pyrazolo[3,4-d]pyrimidin-1-yl}cyclohexyl)piperazin-2-one The desired product was prepared by substituting 2-oxopiperazine for 2-(trifluoromethyl)-5,6,7,8-tetrahydroimidazo[1,2-a]pyrazine in EXAMPLE 338. The faster eluting isomer was isolated: MS (ESI) m/e 552 (M+H)⁻; ¹H NMR (300 MHz, DMSO-d₆) δ8.49 (bs, 1H), 8.31 (s, 1H), 7.88 (s, 1H), 7.84 (d, 1H), 7.72 (d, 1H), 7.38 (m, 2H), 7.08 (d, 1H), 7.02 (t, 1H), 4.80 (m, 1H), 4.45 (s, 2H), 3.87 (m, 2H), 3.78 (s, 3H), 3.45 (m, 4H), 2.12 (m, 6H), 1.83 (m, 2H).

EXAMPLE 323

(cis)-4-(4-{4-amino-3-(2-(2-methoxybenzyl)-1H-benzimidazol-5-yl)-1H-pyrazolo[3,4-d]pyrimidin-1-yl}cyclohexyl)piperazin-2-one This compound is the slower eluting diastereomer in EXAMPLE 322. MS (ESI) m/e 552 (M+H)⁻; ¹H NMR (300 MHz, DMSO-d₆) δ8.46 (bs, 1H), 8.31 (s, 1H), 7.90 (s, 1H), 7.82 (d, 1H), 7.75 (d, 1H), 7.38 (m, 2H), 7.08 (d, 1H), 7.02 (t, 1H), 4.97 (m, 1H), 4.43 (s, 2H), 3.84 (m, 2H), 3.78 (s, 3H), 3.40 (m, 4H), 2.36 (m, 2H), 2.12 (m, 3H), 1.97 (m, 3H).

EXAMPLE 324

(trans)-5-(2-(2-methoxybenzyl)-1H-benzimidazol-5-yl)-7-{4-(4-(3-methoxypropyl)piperazin-1-yl)cyclohexyl}-7H-pyrrolo[2,3-d]pyrimidin-4-amine

EXAMPLE 324A

The desired product was prepared by substituting 4-(4-amino-5-iodo-pyrrolo[2,3-d]pyrimidin-7-yl)-cyclohexanone prepared as described in WO 2005/074603 for 4-(4-amino-3-iodo-1H-pyrazolo[3,4-d]pyrimidin-1-yl)cyclohexanone in EXAMPLE 339C. MS (ESI) m/e 467 (M+H); ¹H NMR (300 MHz, DMSO-d₆) 12.17 (bs, 1H), 8.16 (s, 1H), 7.57 (m, 1H), 7.43 (m, 2H), 7.23 (m, 3H), 7.02 (m, 1H), 6.91 (m, 1H), 5.18 (m, 1H), 4.14 (s, 2H), 3.81 (s, 3H), 2.76 (m, 2H), 2.34 (m, 4H), 2.22 (m, 2H).

EXAMPLE 324B

The desired product was prepared by substituting 1-(3-methoxypropyl)piperazine for 2-(trifluoromethyl)-5,6,7,8-tetrahydroimidazo[1,2-a]pyrazine and EXAMPLE 324A for EXAMPLE 339C in EXAMPLE 338. The faster eluting isomer was isolated: MS (ESI) m/e 609 (M+H)⁻; ¹H NMR (300 MHz, DMSO-d₆) δ8.40 (s, 1H), 7.79 (m, 2H), 7.72 (s, 1H), 7.54 (d, 1H), 7.38 (m, 2H), 7.08 (d, 1H), 7.02 (t, 1H), 4.68 (m, 1H), 4.44 (s, 2H), 3.78 (s, 3H), 3.67 (m, 5H), 3.39 (t, 2H), 3.25 (s, 3H), 2.99 (m, 5H), 2.07 (m, 6H), 1.85 (m, 2H), 1.67 (m, 2H).

EXAMPLE 325

(cis)-5-(2-(2-methoxybenzyl)-1H-benzimidazol-5-yl)-7-{4-(4-(3-methoxypropyl)piperazin-1-yl)cyclohexyl}-7H-pyrrolo[2,3-d]pyrimidin-4-amine The desired product is the slower eluting isomer in EXAMPLE 324B: MS (ESI) m/e 609 (M+H)⁻; ¹H NMR (300 MHz, DMSO-d₆) δ8.42 (s, 1H), 7.78 (d, 1H), 7.72 (s, 1H), 7.65 (s, 1H), 7.54 (d, 1H), 7.38 (m, 2H), 7.08 (d, 1H), 7.02 (t, 1H), 4.80 (m, 1H), 4.44 (s, 2H), 3.78 (s, 3H), 3.68 (m, 5H), 3.38 (t, 2H), 3.24 (s, 3H), 3.06 (m, 5H), 2.18-2.07 (m, 4H), 1.86-1.76 (m, 6H).

EXAMPLE 326

(trans)-3-(2-(2-methoxybenzyl)-1H-benzimidazol-5-yl)-1-{4-(4-(tetrahydrofuran-2-ylmethyl)piperazin-1-yl)cyclohexyl}-1H-pyrazolo[3,4-d]pyrimidin-4-amine The desired product was prepared by substituting 1-(cyclopent-2-ylmethyl)piperazine for 2-(trifluoromethyl)-5,6,7,8-tetrahydroimidazo[1,2-a]pyrazine in EXAMPLE 338. The faster eluting isomer was isolated: MS (ESI) m/e 622 (M+H)⁻; ¹H NMR (300 MHz, DMSO-d₆) δ8.29 (s, 1H), 7.87 (s, 1H), 7.81 (d, 1H), 7.70 (d, 1H), 7.38 (m, 2H), 7.08 (d, 1H), 7.02 (t, 1H), 4.77 (m, 1H), 4.44 (s, 2H), 4.12 (m, 1H), 3.80 (m, 2H), 3.78 (s, 3H), 3.71 (m, 6H), 3.02 (m, 5H), 2.11 (m, 6H), 2.01 (m, 1H), 1.84 (m, 2H), 1.70 (m, 2H) 1.50 (m, 1H).

EXAMPLE 327

(cis)-3-(2-(2-methoxybenzyl)-1H-benzimidazol-5-yl)-1-{4-(4-(tetrahydrofuran-2-ylmethyl)piperazin-1-yl)cyclohexyl}-1H-pyrazolo[3,4-d]pyrimidin-4-amine This compound is the slower eluting diastereomer in EXAMPLE 326. MS (ESI) m/e 622 (M+H)⁻; ¹H NMR (300 MHz, DMSO-d₆) δ8.33 (s, 1H), 7.90 (s, 1H), 7.84 (d, 1H), 7.75 (d, 1H), 7.38 (m, 2H), 7.08 (d, 1H), 7.02 (t, 1H), 4.93 (m, 1H), 4.45 (s, 2H), 4.15 (m, 1H), 3.81 (m, 2H), 3.78 (s, 3H), 3.71 (m, 2H), 3.48 (m, 4H), 3.05 (m, 4H), 2.37 (m, 2H), 2.02 (m, 4H), 1.86 (m, 5H), 1.49 (m, 1H).

EXAMPLE 328

(trans)-3-(2-(2-methoxybenzyl)-1H-benzimidazol-5-yl)-1-{4-(4-(tetrahydrofuran-2-ylcarbonyl)piperazin-1-yl)cyclohexyl}-1H-pyrazolo[3,4-d]pyrimidin-4-amine The desired product was prepared by substituting 1-(cyclopent-2-oyl)piperazine for 2-(trifluoromethyl)-5,6,7,8-tetrahydroimidazo[1,2-a]pyrazine in EXAMPLE 338. The faster eluting isomer was isolated: MS (ESI) m/e 636 (M+H)⁻; ¹H NMR (300 MHz, DMSO-d₆) δ9.80 (bs, 1H), 8.31 (s, 1H), 7.88 (s, 1H), 7.84 (d, 1H), 7.72 (d, 1H), 7.38 (m, 2H), 7.08 (d, 1H), 7.02 (t, 1H), 4.79 (m, 1H), 4.72 (m, 2H), 4.45 (s, 2H), 4.23 (m, 2H), 3.78 (s, 3H), 3.74 (m, 2H), 3.49 (m, 4H), 3.04 (m, 2H), 2.19 (m, 2H), 2.13 (m, 4H), 2.02 (m, 2H), 1.84 (m, 2H) 1.79 (m, 2H).

EXAMPLE 329

(cis)-3-(2-(2-methoxybenzyl)-1H-benzimidazol-5-yl)-1-{4-(4-(tetrahydrofuran-2-ylcarbonyl)piperazin-1-yl)cyclohexyl}-1H-pyrazolo[3,4-d]pyrimidin-4-amine This compound is the slower eluting diastereomer in EXAMPLE 328. MS (ESI) m/e 636 (M+H)$^-$; $^1$H NMR (300 MHz, DMSO-d$_6$) δ9.60 (bs, 1H), 8.32 (s, 1H), 7.91 (s, 1H), 7.84 (d, 1H), 7.77 (d, 1H), 7.38 (m, 2H), 7.08 (d, 1H), 7.02 (t, 1H), 4.98 (m, 1H), 4.69 (m, 2H), 4.45 (s, 2H), 4.18 (m, 2H), 3.78 (s, 3H), 3.74 (m, 2H), 3.54 (m, 2H), 3.42 (m, 2H), 3.01 (m, 2H), 2.42 (m, 2H), 2.03 (m, 8H), 1.83 (m, 2H).

EXAMPLE 330

(cis)-2-{2-((4-{4-amino-3-(1-(2-fluorobenzyl)-1H-indol-5-yl)-1H-pyrazolo[3,4-d]pyrimidin-1-yl}cyclohexyl)amino)ethoxy}ethanol The desired product was synthesized by substituting 2-(2-hydroxyethoxy)ethylamine for 3-aminobenzyl alcohol in EXAMPLE 210C. The earlier eluting diastereomer was isolated. MS: ESI(+) m/e 544.3 (M+H)$^+$; $^1$H NMR (300 MHz, DMSO-d$_6$) 8.41(br., 1H), 8.32 (s, 1H), 7.78 (d., 1H), 7.67 (d., 1H), 7.58 (d., 1H), 7.47 (dd., 1H), 7.31-7.38 (m, 1H), 7.21-7.28 (m, 1H), 7.13-7.16 (m., 2H), 6.63 (s, 1H), 5.55 (s., 2H), 4.91 (br. m, 1H), 4.15 (s, 2H), 3.48-3.56 (m., 6H), 3.24-3.36 (m., 2H), 3.13-3.23 (m., 2H), 2.28-2.43 (m., 3H), 1.86-2.09 (m., 6H).

EXAMPLE 331

(trans)-2-{2-((4-{4-amino-3-(1-(2-fluorobenzyl)-1H-indol-5-yl)-1H-pyrazolo[3,4-d]pyrimidin-1-yl}cyclohexyl)amino)ethoxy}ethanol The desired product was the slower eluting diastereomer in EXAMPLE 330. MS: ESI(+) m/e 544.3 (M+H)$^+$; $^1$H NMR (300 MHz, DMSO-d$_6$) 8.52(br., 1H), 8.33 (s, 1H), 7.84 (d., 1H), 7.67 (d., 1H), 7.58 (d., 1H), 7.42 (dd., 1H), 7.31-7.38 (m, 1H), 7.22-7.28 (m, 1H), 7.13-7.16 (m., 2H), 6.63 (s, 1H), 5.55 (s., 2H), 4.71 (br. m, 1H), 3.69 (t., 2H), 3.51-3.58 (m., 4H), 3.13-3.23 (m., 4H), 2.13-2.28 (m., 2H), 2.03-2.14 (m., 4H), 1.56-1.71 (m., 2H).

EXAMPLE 332

(trans)-3-(4-(4-{4-amino-3-(2-(2-fluorobenzyl)-1H-indol-6-yl)-1H-pyrazolo[3,4-d]pyrimidin-1-yl}cyclohexyl)piperazin-1-yl)propan-1-ol The desired product was prepared by substituting 3-bromo-1-propanol for 2-(2-ethoxyethoxy)ethyl bromide in EXAMPLE 318D. MS: ESI(+) m/e 583.4 (M+H)$^+$; $^1$H NMR (300 MHz, DMSO-d$_6$) 11.28 (s, 1H), 8.30 (s, 1H), 7.58 (d., 1H), 7.56 (s., 1H), 7.28-7.38 (m, 2H), 7.15-7.27 (m, 3H), 6.19 (s, 1H), 4.75 (br. m, 1H), 4.15 (s, 2H), 2.90-3.17 (m, 3H), 2.02-2.20 (br.m, 6H), 1.58-1.83 (br.m., 4H).

EXAMPLE 333

(trans)-3-(2-(2-fluorobenzyl)-1H-indol-6-yl)-1-{4-(4-(3-methoxypropyl)piperazin-1-yl)cyclohexyl}-1H-pyrazolo[3,4-d]pyrimidin-4-amine The desired product was prepared by substituting 1-bromo-3-methoxypropane for 2-(2-ethoxyethoxy)ethyl bromide in EXAMPLE 318D. MS: ESI(+) m/e 597.5 (M+H)$^+$; $^1$H NMR (300 MHz, DMSO-d$_6$) 11.27 (s, 1H), 8.30 (s, 1H), 7.58 (d., 1H), 7.56 (s., 1H), 7.28-7.38 (m, 2H), 7.15-7.27 (m, 3H), 6.19 (s, 1H), 4.74 (br. m, 1H), 4.15 (s, 2H), 3.25 (s., 3H), 2.90-3.17 (m, 3H), 2.02-2.20 (br.m, 6H), 1.78-1.90 (m., 2H), 1.58-1.75(br.m., 2H).

EXAMPLE 334

(trans)-2-(4-(4-{4-amino-3-(2-(2-fluorobenzyl)-1H-indol-6-yl)-1H-pyrazolo[3,4-d]pyrimidin-1-yl}cyclohexyl)piperazin-1-yl)ethanol

EXAMPLE 334A

The desired product was prepared by substituting 6-bromoindole for 5-bromoindole and 2-fluorobenzyl bromide for 2-methoxybenzyl bromide in EXAMPLE 341A.

EXAMPLE 334B

The title product was prepared by substituting EXAMPLE 334A for EXAMPLE 341A in EXAMPLE 341B.

EXAMPLE 334C

The desired product was prepared by substituting EXAMPLE 334B for EXAMPLE 382A in EXAMPLE 382B.

EXAMPLE 334D

The desired product was prepared by substituting EXAMPLE 334C for EXAMPLE 341C in EXAMPLE 341D. MS: ESI(+) m/e 569.4 (M+H)$^+$; ESI(−) m/e 567.4 (M−H); $^1$H NMR (300 MHz, DMSO-d$_6$) 11.29 (s, 1H), 8.32 (s, 1H), 7.58 (d., 1H), 7.56 (s., 1H), 7.28-7.38 (m, 2H), 7.15-7.27 (m, 3H), 6.19 (s, 1H), 4.76 (br. m, 1H), 4.15 (s, 2H), 3.72 (br. t, 2H), 3.10-3.20 (m, 3H), 2.07-2.22 (br., 4H), 1.64-1.82 (br.m., 2H).

EXAMPLE 335

(trans)-1-(4-{4-amino-3-(2-(2-fluorobenzyl)-1H-indol-5-yl)-1H-pyrazolo[3,4-d]pyrimidin-1-yl}cyclohexyl)piperidin-4-ol The desired product was synthesized by substituting 4-hydroxypiperidine for 1-(2-hydroxyethyl)piperazine in EXAMPLE 267C. MS: ESI(+) m/e 540.4 (M+H)$^+$; $^1$H NMR (300 MHz, DMSO-d$_6$) 11.28 (s, 1H), 9.00 (br., 0.4H), 8.84 (br., 0.6H), 8.29 (s, 0.4H), 8.28 (s., 0.6H), 7.72 (d, 0.6H), 7.68 (s, 0.4H), 7.45-7.49 (m, 1H), 7.28-7.38 (m, 3H), 7.14-7.24 (m, 2H), 6.22 (s, 1H), 4.97 (br. m, 0.6H), 4.76 (m., 0.4H), 4.14 (s, 2H), 3.00-3.14 (m., 2H), 2.34-2.45 (m., 1H), 2.06-2.23 (m., 3H), 1.92-2.04 (m., 3H), 1.72-1.89 (m., 3H), 1.72-1.88 (m., 2H), 1.50-1.48 (m., 1H).

EXAMPLE 336

(trans)-1-(4-{4-(2-(1,3-dioxolan-2-yl)ethyl)piperazin-1-yl}cyclohexyl)-3-(2-(2-methoxybenzyl)-1H-benzimidazol-5-yl)-1H-pyrazolo[3,4-d]pyrimidin-4-amine The desired product was prepared by substituting 1-(2-(1,3-dioxolan-2-yl)ethyl)piperazine for 2-(trifluoromethyl)-5,6,7,8-tetrahydroimidazo[1,2-a]pyrazine in EXAMPLE 338. The faster eluting isomer was isolated: MS (ESI) m/e 638 (M+H)$^-$; $^1$H NMR (300 MHz, DMSO-d$_6$) δ8.29 (s, 1H), 7.87 (s, 1H), 7.82 (d, 1H), 7.70 (d, 1H), 7.38 (m, 2H), 7.08 (d, 1H), 7.02 (t, 1H), 4.89 (t, 1H), 4.75 (m, 1H), 4.44 (s, 2H), 3.91 (m, 2H), 3.80 (m, 2H), 3.78 (s, 3H), 2.92 (m, 10H), 2.10 (m, 6H), 1.91 (m, 2H), 1.68 (m, 2H).

EXAMPLE 337

(cis)-1-(4-{4-(2-(1,3-dioxolan-2-yl)ethyl)piperazin-1-yl}cyclohexyl)-3-(2-(2-methoxybenzyl)-1H-benzimidazol-5-yl)-1H-pyrazolo[3,4-d]pyrimidin-4-amine This compound is the slower eluting diastereomer in EXAMPLE 336. MS (ESI) m/e 638 (M+H)$^-$; $^1$H NMR (300 MHz, DMSO-d$_6$) δ8.32 (s, 1H), 7.89 (s, 1H), 7.84 (d, 1H), 7.73 (d, 1H), 7.38 (m, 2H), 7.09 (d, 1H), 7.02 (t, 1H), 4.92 (m, 1H), 4.88 (t, 1H), 4.45 (s, 2H), 3.91 (m, 2H), 3.80 (m, 2H), 3.78 (s, 3H), 2.98 (m, 10H), 2.36 (m, 2H), 2.06 (m, 2H), 1.93 (m, 6H).

EXAMPLE 338

(trans)-3-(2-(2-methoxybenzyl)-1H-benzimidazol-6-yl)-1-{4-(2-(trifluoromethyl)-5,6-dihydroimidazo[1,2-a]pyrazin-7(8H)-yl)cyclohexyl}-1H-pyrazolo[3,4-d]pyrimidin-4-amine To a mixture of EXAMPLE 339C (0.13 g, 0.28 mmol) and 2-(trifluoromethyl)-5,6,7,8-tetrahydroimidazo[1,2-a]pyrazine (0.16 g, 0.83 mmol) was added 0.2 M solution of MeOH/AcOH (9/1 v/v). The mixture stirred for 15 min, added NaCNBH$_3$ (0.035, 0.558 mmol). The reaction was stirred at RT for 1.5 hr. The reaction was diluted with CH$_2$Cl$_2$, washed with saturated aqueous NaHCO$_3$. The organic layer was dried over MgSO$_4$, filtered, reduced in vacuo, and purified via reverse phase HPLC. The faster eluting isomer was isolated. (ESI(+)) m/e 643 (M+H)$^+$; $^1$H NMR (300 MHz, DMSO-d$_6$) 12.26 (bs, 1H); 8.23 (s, 1H); 7.70 (s, 2H); 7.64-7.61 (m, 1H); 7.41 (m, 1H); 7.29-7.24 (m, 1H); 7.20-7.18 (1H, m); 7.02 (d, 1H); 6.91 (t, 1H); 4.71 (bm, 1H); 4.17 (s, 2H); 4.01 (bm, 2H); 3.81 (bs, 5H); 3.00 (m, 2H); 2.73 (m, 1H); 2.05 (m, 6H); 1.67-1.55 (m, 2H).

EXAMPLE 339

4-{4-amino-3-(2-(2-methoxybenzyl)-1H-benzimidazol-6-yl)-1H-pyrazolo[3,4-d]pyrimidin-1-yl}cyclohexanone

EXAMPLE 339A

The desired product was synthesized by substituting 2-methoxyphenylacetonitrile for phenylacetonitrile in EXAMPLE 118B.

EXAMPLE 339B

To a mixture of EXAMPLE 280A (3.0 g, 12.76 mmol) and EXAMPLE 339A (3.21 g, 14.04 mmol) was added MeOH (63 mL), the resulting solution was stirred at RT for 2 hr. The reaction was reduced in vacuo, redissolved into EtOAc, and washed with saturated aqueous NaHCO$_3$. The resulting organics were dried over MgSO$_4$, filtered, and reduced in vacuo onto silica. The reaction was purified via an Intelliflash-280 purification system (hexanes/EtOAc) to afford the desired product as a white solid, 2.7 g.

EXAMPLE 339C

To a slurry of EXAMPLE 339B (2 g, 5.49 mmol) and 4-(4-amino-3-iodo-1H-pyrazolo[3,4-d]pyrimidin-1-yl)cyclohexanone prepared as described in A. F. Burchat et al. Bioorg Med. Chem. Lett. 2002, 12, 1687-1690 (1.63 g, 4.57 mmol), and (Ph$_3$P)$_2$PdCl$_2$ (0.16 g, 0.228 mmol) in 0.3 M solution of DME/H$_2$O (2/1, v/v) was added 2M Na$_2$CO$_3$ (4.5 mL, 9.14 mmol). The reaction was heated in a microwave reactor for 20 min at 130° C. The reaction was filtered over Celite, washed pad with CH$_2$Cl$_2$. The filtrate was dried over MgSO$_4$, filtered, reduced in vacuo onto silica. The reaction was purified via an Intelliflash-280 purification system (EtOAc/MeOH) to afford the desired product was a white solid, 1.7 g, 80% yield. (ESI(+)) m/e 468 (M+H)$^+$; $^1$H NMR (300 MHz, DMSO-d$_6$) 12.35 (bs, 1H); 8.26 (s, 1H); 7.76-7.55 (bm, 2H); 7.44-7.41 (m, 1H); 7.29-7.17 (m, 2H); 7.04-7.00 (m, 1H); 6.94-6.88 (m, 1H); 5.25 (m, 1H); 4.17 (s, 2H); 3.81 (s, 3H); 2.72-2.70 (m, 2H); 2.45-2.36 (m, 4H); 2.29-2.24 (m, 2H).

EXAMPLE 340

(cis)-3-(2-(2-methoxybenzyl)-1H-benzimidazol-6-yl)-1-{4-(2-(trifluoromethyl)-5,6-dihydroimidazo[1,2-a]pyrazin-7(8H)-yl)cyclohexyl}-1H-pyrazolo[3,4-d]pyrimidin-4-amine The desired product is the slower eluting isomer in EXAMPLE 338: (ESI(+)) m/e 643 (M+H)$^+$; $^1$H NMR (300 MHz, DMSO-d$_6$) 12.19 (bs, 1H); 8.23 (s, 1H); 7.70 (s, 2H); 7.67-7.63 (m, 1H); 7.40 (d, 1H); 7.24 (d, 1H); 7.18 (m, 1H); 7.01 (m, 1H); 6.90 (t, 1H); 4.85 (m, 1H); 4.16 (s, 2H); 4.04 (m, 2H); 3.80 (s, 3H); 3.75 (m, 2H); 2.98-2.96 (m, 2H); 2.74-2.72 (m, 2H); 2.28-2.26 (m, 2H); 2.22-2.13 (m, 2H); 1.81-1.66 (m, 3H).

EXAMPLE 341

(trans)-2-(4-(4-{4-amino-3-(2-(2-methoxybenzyl)-1H-indol-5-yl)-1H-pyrazolo[3,4-d]pyrimidin-1-yl}cyclohexyl)piperazin-1-yl)ethanol

EXAMPLE 341A

5-Bromoindole (1.96 g, 10 mmol) and 2-methoxybenzyl chloride (1.53 mL, 11 mmol) were dissolved in 20 mL of DMF. 60% sodium hydride (0.44 g, 11 mmol) was added to the mixture. It was stirred at 60° C. for 16 h. 150 mL of EtOAc and 50 mL of brine were added, and the EtOAc layer washed with brine (3×), dried over MgSO$_4$ and evaporated to dryness to yield N-(2-methoxy)benzyl indole in quantitative yield. This was suspended in 50 mL of polyphosphoric acid at 93° C. for 16 h. After cooling to room temperature, the mixture was poured into ice water. The product was extracted with tert-butyl methyl ether (TBME). The organic layer washed with 10%-NaHCO$_3$ (3×), dried over MgSO$_4$ and evaporated to dryness to yield 3.12 g of the title compound.

EXAMPLE 341B

The title product was prepared by substituting EXAMPLE 341A (3.16 g, 10.0 mmol) for 4-bromo-2-nitro-phenylamine in EXAMPLE 2A. MS: DCI(+) m/e 364.44 (M+H)$^+$; $^1$H NMR (300 MHz, DMSO-d$_6$) 10.99 (s, 1H), 7.79 (s, 1H), 7.19-34 (m, 3H), 7.09 (dd, 1H), 7.00 (dd, 1H), 6.87 (dt, 1H), 6.09 (s, 1H), 4.01 (s, 2H), 3.81 (s, 3H), 1.30 (s, 12H)

EXAMPLE 341C

The desired product was prepared by substituting EXAMPLE 341B for EXAMPLE 382A in EXAMPLE 382B. MS: DCI(+) m/e 637.50 (M+H)$^+$;

EXAMPLE 341D

EXAMPLE 341C (90 mg, 0.15 mmol) was treated with 2 mL of CH$_2$Cl$_2$ and 0.6 mL of TFA at room temperature for 1 hours. It was evaporated to dryness. The obtained was dissolved in 5 mL of MeCN. Sodium iodide (56 mg, 0.375 mmol), K$_2$CO$_3$ (104 mg, 0.75 mmol) and bromoethanol (32 L, 0.45 mmol) were added and the mixture was stirred at 50° C. for 16 h. The reaction mixture was partitioned between EtOAc and brine, the EtOAc layer washed with brine (3×), and dried over MgSO$_4$. The crude product was purified by high pressure liquid chromatography (HPLC) to yield 48.3 mg of the title compound. MS: ESI(+) m/e 581.4 (M+H)$^+$; ESI(−) m/e 579.4 (M−H); $^1$H NMR (300 MHz, DMSO-d$_6$) 11.16 (s, 1H), 8.32 (s, 1H), 7.67 (s, 1H), 7.46 (d, 1H), 7.28 (dd, 1H), 7.23 (dd, 1H), 7.14 (dd, 1H), 7.02 (d, 1H), 6.89 (dt, 1H), 6.18 (s, 1H), 4.75 (br. m, 1H), 4.06 (s, 2H), 3.83 (s, 3H), 3.72 (m, 2H), 3.14 (br.m., 2H), 2.11 (br., 6H), 1.71 (m, 2H).

EXAMPLE 342

(trans)-3-(4-(4-{4-amino-3-(2-(2-methoxybenzyl)-1H-indol-5-yl)-1H-pyrazolo[3,4-d]pyrimidin-1-yl}cyclohexyl)piperazin-1-yl)propan-1-ol The desired product was prepared by substituting 3-bromo-1-propanol for bromoethanol in EXAMPLE 341D. MS: ESI(+) m/e 581.4 (M+H)$^+$; ESI(−) m/e 579.4 (M−H); $^1$H NMR (300 MHz, DMSO-d$_6$) 11.16 (s, 1H), 8.32 (s, 1H), 7.67 (s, 1H), 7.46 (d, 1H), 7.28 (dd, 1H), 7.23 (dd, 1H), 7.14 (dd, 1H), 7.02 (d, 1H), 6.89 (dt, 1H), 6.19 (s, 1H), 4.75 (br. m, 1H), 4.06 (s, 21H), 3.83 (s, 3H), 3.49 (t, 2H), 3.7 (br.m., 2H), 2.11 (br., 6H), 1.69-1.82 (m, 4H).

EXAMPLE 343

(trans)-3-(2-(2-methoxybenzyl)-1H-indol-5-yl)-1-{4-(4-(3-methoxypropyl)piperazin-1-yl)cyclohexyl}-1H-pyrazolo[3,4-d]pyrimidin-4-amine The desired product was prepared by substituting 1-bromo-3-methoxypropane for bromoethanol in EXAMPLE 341D. MS: ESI (+) m/e 609.4 (M+H)$^+$; $^1$H NMR (300 MHz, DMSO-d$_6$) 11.16 (s, 1H), 8.31 (s, 1H), 7.67 (s, 1H), 7.46 (d, 1H), 7.28 (dd, 1H), 7.23 (dd, 1H), 7.14 (dd, 1H), 7.02 (d, 1H), 6.89 (dt, 1H), 6.18 (s, 1H), 4.74 (br. m, 1H), 4.06 (s, 2H), 3.83 (s, 3H), 3.39 (t, 2H), 3.25 (s, 3H), 2.10 (br., 6H), 1.84 (br.m, 2H), 1.69 (br. 2H).

EXAMPLE 344

(trans)-2-(4-(4-{4-amino-3-(2-(2-methoxybenzyl)-1H-indol-6-yl)-1H-pyrazolo[3,4-d]pyrimidin-1-yl}cyclohexyl)piperazin-1-yl)ethanol

EXAMPLE 344A

The desired product was prepared by substituting 6-bromoindole for 5-bromoindole in EXAMPLE 341A. MS: DCI (+) m/e 317.43 (M+H)$^+$;

EXAMPLE 344B

The title product was prepared by substituting EXAMPLE 344A for EXAMPLE 341A in EXAMPLE 341B. MS: DCI (+) m/e 364.44 (M+H)$^+$; $^1$H NMR (300 MHz, DMSO-d$_6$) 10.97 (s, 1H), 7.65 (s, 1H), 7.37 (d, 1H), 7.20-7.26 (m, 2H), 7.09 (dd, 1H), 7.00 (dd, 1H), 6.87 (dt, 1H), 6.05 (s, 1H), 4.04 (s, 2H), 3.81 (s, 3H), 1.29 (s, 12H).

EXAMPLE 344C

The desired product was prepared by substituting EXAMPLE 344B for EXAMPLE 382A in EXAMPLE 382B. MS: DCI(+) m/e 637.13 (M+H)$^+$.

EXAMPLE 344D

The desired product was prepared by substituting EXAMPLE 344C for EXAMPLE 341C in EXAMPLE 341D. MS: ESI(+) m/e 581.4 (M+H)$^+$; ESI(−) m/e 579.4 (M−H); $^1$H NMR (300 MHz, DMSO-d$_6$) 11.14 (s, 1H), 8.33 (s, 1H), 7.55-7.58 (m, 2H), 7.22-7.27 (m, 2H), 7.15 (dd, 1H), 7.02 (d, 1H), 6.89 (dt, 1H), 6.15 (s, 1H), 4.75 (br. m, 1H), 4.06 (s, 2H), 3.82 (s, 3H), 3.73 (br. t. 2H), 3.17 (m, 2H), 2.07-2.19 (br., 4H), 1.66-1.78 (br.m., 2H).

EXAMPLE 345

(trans)-3-(4-(4-{4-amino-3-(2-(2-methoxybenzyl)-1H-indol-6-yl)-1H-pyrazolo[3,4-d]pyrimidin-1-yl}cyclohexyl)piperazin-1-yl)propan-1-ol The desired product was prepared by substituting 3-bromo-1-propanol for bromoethanol and EXAMPLE 344C for EXAMPLE 341C, respectively, in EXAMPLE 341D. MS: ESI(+) m/e 595.4 (M+H)$^+$; ESI(−) m/e 593.5 (M−H); $^1$H NMR (300 MHz, DMSO-d$_6$) 11.14 (s, 1H), 8.30 (s, 1H), 7.55-7.57 (m, 2H), 7.22-7.27 (m, 2H), 7.15 (dd, 1H), 7.02 (d, 1H), 6.90 (dt, 1H), 6.15 (s, 1H), 4.75 (br. m, 1H), 4.06 (s, 2H), 3.83 (s, 3H), 3.49 (m, 2H), 2.05-2.16 (br., 6H), 1.61-1.81 (br. m., 4H).

EXAMPLE 346

(trans)-3-(2-(2-methoxybenzyl)-1H-indol-6-yl)-1-{4-(4-(3-methoxypropyl)piperazin-1-yl)cyclohexyl}-1H-pyrazolo[3,4-d]pyrimidin-4-amine The desired product was prepared by substituting 1-bromo-3-methoxypropane for bromoethanol and EXAMPLE 344C for EXAMPLE 341C, respectively, in EXAMPLE 341D. MS: ESI(+) m/e 609.5 (M+H)$^+$; ESI(−) m/e 607.5 (M−H); $^1$H NMR (300 MHz, DMSO-d$_6$) 11.14 (s, 1H), 8.31 (s, 1H), 7.55-7.57 (m, 2H), 7.22-7.27 (m, 2H), 7.15 (dd, 1H), 7.02 (d, 1H), 6.90 (dt, 1H), 6.15 (s, 1H), 4.75 (br. m, 1H), 4.06 (s, 2H), 3.82 (s, 3H), 3.39 (t, 2H), 3.25 (s, 3H), 2.05-2.16 (br., 6H), 1.84 (br.m, 2H), 1.69 (br. 2H).

EXAMPLE 347

(trans)-3-(2-(2-methoxybenzyl)-1H-benzimidazol-5-yl)-1-(4-piperazin-1-ylcyclohexyl)-1H-pyrazolo[3,4-d]pyrimidin-4-amine

EXAMPLE 347A

EXAMPLE 318A (2.91 g, 5.52 mmol) was dissolved into CH$_2$Cl$_2$ (60 mL), and cooled to 0° C. for 15 min. Added TFA (23 g, 201 mmol) dropwise at 0° C., after addition was finished the reaction was promptly warmed to RT. The reaction stirred at RT for 3 hr. Once the reaction had consumed starting material, the reaction was partitioned between CH$_2$Cl$_2$/IPA (4/1 v/v) and 3 M NaOH. The organics were separated, extracted the aqueous layer with CH$_2$Cl$_2$/IPA (3×50 mL). The organics were combined, dried over MgSO$_4$, filtered, reduced in vacuo to afford the desired product as a white solid, 1.97 g, which was used without further purification.

EXAMPLE 347B

To a mixture of EXAMPLE 347A (0.1 g, 0.23 mmol), EXAMPLE 339B (0.10 g, 0.28 mmol), (Ph$_3$P)$_2$PdCl$_2$ (0.008 g, 0.011 mmol) in 0.3 M solution of DME/H$_2$O (2/1 v/v) was added 2M aqueous Na$_2$CO$_3$ (0.23 mL, 0.46 mmol). The contents were heated in a microwave reactor at 130° C. for 20 min. The reaction was filtered over Celite, washed pad with CH$_2$Cl$_2$ and MeOH. The filtrate was reduced in vacuo, and purified directly via reverse phase HPLC (CH$_3$CN/0.05% NH$_4$OH in water) to afford the desired product. (ESI(+)) m/e 538 (M+H)$^+$; $^1$H NMR (300 MHz, DMSO-d$_6$) 12.25 (d, 1H); 8.22 (s, 1H); 7.74 (m, 0.5H); 7.65-7.63 (m, 1H); 7.57 (d, 0.5H); 7.43-7.39 (m, 1H); 7.29-7.24 (m, 1H); 7.21-7.17 (m, 1H); 7.02 (d, 1H); 6.91 (t, 1H); 4.64 (m, 1H); 4.17 (s, 2H); 3.81 (s, 3H); 2.73 (bm, 5H); 2.06-1.90 (m, 7H); 1.54-1.45 (m, 2H).

EXAMPLE 348

(trans)-3-(2-(2-methoxybenzyl)-1H-benzimidazol-5-yl)-1-(4-(4-methylpiperazin-1-yl)cyclohexyl)-1H-pyrazolo[3,4-d]pyrimidin-4-amine To a mixture of (trans)-3-iodo-1-(4-(4-methyl-piperazin-1-yl)-cyclohexyl)-1H-pyrazolo[3,4-d]pyrimidin-4-ylamine prepared as described in A. F. Burchat et al. Bioorg Med. Chem. Lett. 2002, 12, 1687-1690 (0.1 g, 0.23 mmol), EXAMPLE 339B (0.098 g, 0.27 mmol), (Ph$_3$P)$_2$PdCl$_2$ (0.008 g, 0.011 mmol) in 0.3 M solution of DME/H$_2$O (2/1 v/v) was added 2M aqueous Na$_2$CO$_3$ (0.23 mL, 0.46 mmol). The contents were heated in a microwave reactor at 130° C. for 20 min. The reaction was filtered over Celite, washed pad with CH$_2$Cl$_2$ and MeOH. The filtrate was reduced in vacuo, and purified directly via reverse phase HPLC (CH$_3$CN/0.05% NH$_4$OH in water) to afford the desired product. (ESI(+)) m/e 551 (M+H)$^+$; $^1$H NMR (300 MHz, DMSO-d$_6$) 12.15 (d, 1H); 8.12 (s, 1H); 7.60-7.58 (m, 1H); 7.51-7.46 (m, 1H); 7.28-7.16 (m, 5H); 7.04-7.01 (m, 1H); 6.93-6.88 (m, 1H); 6.05-5.97 (m, 2H); 4.69 (m, 1H); 4.15 (s, 2H); 3.81 (s, 4H); 2.45-2.32 (m, 7H); 2.18 (m, 1H); 2.14 (s, 3H); 2.11-2.03 (m, 4H); 1.75-1.67 (m, 2H); 1.63-1.51 (m, 2H).

EXAMPLE 349

(trans)-{5-(4-amino-1-(4-morpholin-4-ylcyclohexyl)-1H-pyrazolo[3,4-d]pyrimidin-3-yl)-1-benzofuran-2-yl}(phenyl)methanone

EXAMPLE 349A phenyl(5-(4,4,5,5-tetramethyl-1,3,2-dioxaborolan-2-yl)benzofuran-2-yl)methanone A mixture of 5-bromo-2-benzoyl-benzofuran purchased from Indofine Chemicals (0.251 g, 0.83 mmol), bis(pinacolato)diboron (0.33 g, 1.3 mmol), potassium acetate (0.26 g, 2.7 mmol), 1,3-bis(diisopropylphenyl)imidazolium chloride (0.032 g, 0.075 mmol) and palladium(II)acetate (0.011 g, 0.05 mmol) in THF (4 mL) was heated to 125° C. for 20 min in a microwave reactor. The reaction mixture was diluted with EtOAc and the organics washed sequentially with brine, then dried over MgSO$_4$. The solvent was removed under reduced pressure, and the residue purified by silica gel chromatography eluting with 10-50% EtOAc/hexanes to provide the title compound as a white solid.

EXAMPLE 349B (trans)-{5-(4-amino-1-(4-morpholin-4-ylcyclohexyl)-1H-pyrazolo[3,4-d]pyrimidin-3-yl)-1-benzofuran-2-yl}(phenyl)methanone The desired product was prepared by substituting (trans)-3-iodo-1-(4-morpholin-4-yl-cyclohexyl)-1H-pyrazolo[3,4-d]pyrimidin-4-ylamine prepared as described in WO 2005/074603 for 3-bromo-1-tert-butyl-1H-pyrazolo[3,4-d]pyrimidin-4-ylamine and EXAMPLE 349A for EXAMPLE 188C in EXAMPLE 181. $^1$H NMR (300 MHz, methanol-d$_4$) 8.38 (s, 1H), 8.14 (s, 1H), 8.09 (m, 2H), 7.88 (s, 2H); 7.80 (s, 1H); 7.72 (m, 1H); 7.61 (m, 2H); 4.95 (m, 1H); 4.12 (m, 2H), 3.80 (m, 2H); 3.58-3.38 (m, 4H); 2.44-2.38 (m, 2H); 2.38-2.25 (m, 4H); 1.94-1.82 (m, 2H).

EXAMPLE 350

(trans)-3-(2-benzyl-1,3-benzothiazol-5-yl)-1-(4-morpholin-4-ylcyclohexyl)-1H-pyrazolo[3,4-d]pyrimidin-4-amine

EXAMPLE 350A

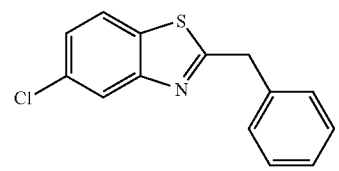

2-benzyl-5-chlorobenzo(d)thiazole

A round bottom flask fitted with a Dean-Stark trap was charged with 4-Chloro-2-aminobenzenethiol (3.47 g, 21.7 mmol) and phenacyl chloride (3.0 mL, 22.7 mmol) in benzene (40 mL), and the mixture heated 18 h in an 80° C. oil bath. The reaction mixture was diluted with CH$_2$Cl$_2$, and the organics washed sequentially with aqueous Na$_2$CO$_3$, brine, then dried over MgSO$_4$. The solvent was removed under reduced pressure, and the residue purified by silica gel chromatography eluting with 35-100% CH$_2$Cl$_2$/hexanes to provide the title compound as a white solid (1.94 g).

EXAMPLE 350B 2-benzyl-5-(4,4,5,5-tetramethyl-1,3,2-dioxaborolan-2-yl)benzo(d)thiazole The desired product was prepared by substituting EXAMPLE 350A for 5-bromo-2-benzoyl-benzofuran in EXAMPLE 349B.

EXAMPLE 350C (trans)-3-(2-benzyl-1,3-benzothiazol-5-yl)-1-(4-morpholin-4-ylcyclohexyl)-1H-pyrazolo[3,4-d]pyrimidin-4-amine The desired product was prepared by substituting (trans)-3-iodo-1-(4-morpholin-4-yl-cyclohexyl)-1H-pyrazolo[3,4-d]pyrimidin-4-ylamine prepared as described in WO 2005/074603 for 3-bromo-1-tert-butyl-1H-pyrazolo[3,4-d]pyrimidin-4-ylamine and EXAMPLE 350B for EXAMPLE 188C in EXAMPLE 181. $^1$H NMR (300 MHz, methanol-d$_4$) 8.40 (s, 1H), 8.23 (d, 1H), 8.12 (d, 1H), 7.72 (dd, 1H); 7.43-7.30 (m, 5H); 4.95 (m, 1H); 4.51 (s, 2H); 4.12 (m, 2H); 3.80 (m, 2H); 3.58-3.38 (m, 4H); 2.44-2.38 (m, 2H); 2.38-2.25 (m, 4H); 1.94-1.82 (m, 2H).

EXAMPLE 351

(trans)-3-dibenzo(b,d)thien-3-yl-1-(4-morpholin-4-ylcyclohexyl)-1H-pyrazolo[3,4-d]pyrimidin-4-amine The desired product was prepared by substituting (trans)-3-iodo-1-(4-morpholin-4-yl-cyclohexyl)-1H-pyrazolo[3,4-d]pyrimidin-4-ylamine prepared as described in WO 2005/074603 for 3-bromo-1-tert-butyl-1H-pyrazolo[3,4-d]pyrimidin-4-ylamine and dibenzo(b,d)thiophen-3-ylboronic acid (purchased from Maybridge Chemicals) for EXAMPLE 188C in EXAMPLE 181. $^1$H NMR (300 MHz, methanol-d$_4$) 8.56 (d, 1H), 8.40 (s, 1H), 8.34 (m, 1H), 8.12 (d, 1H); 7.96 (m, 1H); 7.80 (d, 1H); 7.54 (m, 2H); 4.95 (m, 1H); 4.12 (m, 2H); 3.80 (m, 2H); 3.58-3.38 (m, 4H); 2.44-2.38 (m, 2H); 2.38-2.25 (m, 4H); 1.94-1.82 (m, 2H).

EXAMPLE 352

(trans)-1-(4-(4-ethylpiperazin-1-yl)cyclohexyl)-3-(2-(2-methoxybenzyl)-1H-benzimidazol-6-yl)-1H-pyrazolo[3,4-d]pyrimidin-4-amine The desired product was prepared by substituting 1-ethylpiperazine for 2-(trifluoromethyl)-5,6,7,8-tetrahydroimidazo[1,2-a]pyrazine in EXAMPLE 338. The faster eluting isomer was isolated: (ESI(+)) m/e 566 (M+H)$^+$; $^1$H NMR (300 MHz, DMSO-d$_6$) 8.31 (s, 1H); 7.88-7.83 (m, 2H); 7.73-7.70 (m, 1H); 7.40-7.36 (m, 2H); 7.10-7.07 (m, 1H); 7.02 (t, 1H); 4.76 (m, 1H); 4.45 (s, 2H); 3.78 (s, 3H); 3.14-3.05 (m, 5H); 2.14-2.05 (m, 7H); 1.74-1.63 (m, 3H); 1.21 (t, 3H).

EXAMPLE 353

(cis)-1-(4-(4-ethylpiperazin-1-yl)cyclohexyl)-3-(2-(2-methoxybenzyl)-1H-benzimidazol-6-yl)-1H-pyrazolo[3,4-d]pyrimidin-4-amine The desired product is the slower eluting isomer in EXAMPLE 352: (ESI(+)) m/e 566 (M+H)$^+$; $^1$H NMR (300 MHz, DMSO-d$_6$) 8.31 (s, 1H): 7.88-7.81 (m, 2H); 7.73-7.70 (m, 1H); 7.40-7.35 (m, 2H); 7.10-7.07 (m, 1H); 7.04-6.99 (m, 1H); 4.91 (m, 1H); 4.43 (s, 2H); 3.78 (s, 3H); 3.14-3.04 (m, 3H); 2.40-2.25 (m, 2H); 2.14-1.99 (m, 2H); 1.94-1.76 (m, 3H); 1.19 (t, 3H).

EXAMPLE 354

(trans)-5-(2-(2-methoxybenzyl)-1H-benzimidazol-5-yl)-7-(4-(2-methoxyethoxy)cyclohexyl)-7H-pyrrolo[2,3-d]pyrimidin-4-amine The desired product was prepared by substituting (trans)-3-iodo-1-(4-(2-methoxy-ethoxy)-cyclohexyl)-1H-pyrazolo[3,4-d]pyrimidin-4-ylamine prepared as described in WO 2005/074603 for 4-(4-amino-3-iodo-1H-pyrazolo[3,4-d]pyrimidin-1-yl)cyclohexanone in EXAMPLE 339C. MS (ESI) m/e 527 (M+H)$^-$; $^1$H NMR (300 MHz, DMSO-d$_6$) δ8.39 (s, 1H), 7.80 (d, 1H), 7.77 (s, 1H), 7.71 (s, 1H), 7.54 (d, 1H), 7.38 (m, 2H), 7.08 (d, 1H), 7.01 (t, 1H), 4.66 (m, 1H), 4.43 (s, 2H), 3.78 (s, 3H), 3.58 (m, 2H), 3.45 (m, 2H), 3.26 (s, 3H), 2.12 (m, 2H), 1.97 (m, 4H), 1.40 (m, 2H).

EXAMPLE 355

(trans)-1-(4-(4-acetylpiperazin-1-yl)cyclohexyl)-3-(2-(3-methoxybenzyl)-1H-benzimidazol-6-yl)-1H-pyrazolo[3,4-d]pyrimidin-4-amine The desired product was prepared by substituting 1-acetylpiperazine for 2-(trifluoromethyl)-5,6,7,8-tetrahydroimidazo[1,2-a]pyrazine in EXAMPLE 338. The faster eluting isomer was isolated: MS: (ESI(+)) m/e 580 (M+H)$^+$; $^1$H NMR (300 MHz, DMSO-d$_6$) 9.67 (bs, 1H); 8.30 (s, 1H); 7.87-7.82 (m, 2H); 7.72-7.69 (m, 1H); 7.40-7.36 (m, 2H); 7.10-6.99 (m, 2H); 4.79 (m, 1H); 4.53-4.48 (m, 1H); 4.44 (m, 2H); 4.10-4.01 (m, 1H); 3.78 (s, 3H); 3.20-3.14 (m, 3H); 3.05-2.87 (m, 3H); 2.26-2.09 (m, 7H); 2.06 (m, 3H); 1.87-1.73 (m, 2H).

EXAMPLE 356

(trans)-4-(4-(4-{4-amino-3-(2-(2-methoxybenzyl)-1H-benzimidazol-6-yl)-1H-pyrazolo[3,4-d]pyrimidin-1-yl}cyclohexyl)piperazin-1-yl)-2-methylbutan-2-ol The desired product was prepared by substituting 2-methyl-4-(piperazin-1-yl)butan-2-ol for 2-(trifluoromethyl)-5,6,7,8-tetrahydroimidazo[1,2-a]pyrazine in EXAMPLE 338. The faster eluting isomer was isolated: MS (ESI(+)) m/e 624 (M+H)$^+$; $^1$H NMR (300 MHz, DMSO-d$_6$) 8.29 (s, 1H); 7.86-7.81 (m, 2H); 7.72-7.69 (m, 1H); 7.40-7.35 (m, 2H); 7.10-7.07 (m, 1H); 7.01 (t, 1H); 4.75 (m, 1H); 4.44 (s, 2H); 3.78 (s, 3H); 3.13-3.08 (m, 3H); 2.97-2.88 (m, 2H); 2.12-2.04 (m, 5H); 1.74-1.68 (m, 4H); 1.15 (s, 6H).

EXAMPLE 357

(cis)-4-(4-(4-{4-amino-3-(2-(3-methoxybenzyl)-1H-benzimidazol-6-yl)-1H-pyrazolo[3,4-d]pyrimidin-1-yl}cyclohexyl)piperazin-1-yl)-2-methylbutan-2-ol The desired product is the slower eluting isomer in EXAMPLE 356. (ESI(+)) m/e 624 (M+H)$^+$; $^1$H NMR (300 MHz, DMSO-d$_6$) 8.31 (s, 1H); 7.88-7.81 (m, 2H); 7.73-7.70 (m, 1H); 7.40-7.35 (m, 2H); 7.10-7.07 (m, 1H); 7.01 (t, 1H); 4.91 (m, 1H); 4.43 (s, 2H); 3.78 (s, 3H); 3.15-3.09 (m, 3H); 3.02-2.91 (m, 2H); 2.35 (m, 1H); 2.11-2.02 (m, 2H); 1.90-1.81 (m, 3H); 1.73-1.67 (m, 2H); 1.13 (s, 6H).

EXAMPLE 358

(cis)-3-(2-(2-methoxybenzyl)-1H-benzimidazol-6-yl)-1-(4-(4-pyrazin-2-ylpiperazin-1-yl)cyclohexyl)-1H-pyrazolo[3,4-d]pyrimidin-4-amine The desired product was prepared by substituting 1-(2-pyrizinyl)piperazine for 2-(trifluoromethyl)-5,6,7,8-tetrahydroimidazo[1,2-a]pyrazine in EXAMPLE 338. The slower eluting isomer was isolated: $^1$H NMR (300 MHz, DMSO-d$_6$) δ8.31 (s, 1H), 8.23 (s, 1H), 7.91 (s, 1H), 7.84 (d, 1H), 7.65 (d, 1H), 7.40 (d, 1H), 7.25 (d, 1H), 7.17 (d, 1H), 7.03 (t, 1H), 6.90 (d, 2H), 5.00 (m, 1H), 4.43 (s, 2H), 3.78 (s, 3H), 3.23 (m, 4H), 2.90 (m, 4H), 2.08 (m, 8H).

EXAMPLE 359

(cis)-2-(4-(4-{4-amino-3-(2-(2-methoxybenzyl)-1H-benzimidazol-6-yl)-1H-pyrazolo[3,4-d]pyrimidin-1-yl}cyclohexyl)piperazin-1-yl)ethanol The desired product is the slower eluting isomer in EXAMPLE 360. MS (ESI(+)) m/e 582 (M+H)$^+$; $^1$H NMR (300 MHz, DMSO-d$_6$) 8.31 (s, 1H); 7.88 (s, 1H); 7.82 (d, 1H); 7.72 (d, 1H); 7.40-7.35 (m, 2H); 7.08 (d, 1H); 7.01 (t, 1H); 4.92 (bm, 1H); 4.43 (s, 2H); 3.78 (s, 3H); 3.70 (m, 5H); 3.06 (m, 3H); 2.41-2.29 (m, 2H); 2.14-2.00 (m, 2H); 1.95-1.81 (m, 3H).

EXAMPLE 360

(trans)-2-(4-(4-{4-amino-3-(2-(2-methoxybenzyl)-1H-benzimidazol-6-yl)-1H-pyrazolo[3,4-d]pyrimidin-1-yl}cyclohexyl)piperazin-1-yl)ethanol The desired product was prepared by substituting 1-hydroxyethylpiperazine for 2-(trifluoromethyl)-5,6,7,8-tetrahydroimidazo[1,2-a]pyrazine in EXAMPLE 338. The faster eluting isomer was isolated: MS (ESI(+)) m/e 582 (M+H)$^+$; $^1$H NMR (300 MHz, DMSO-d$_6$) 12.23 (s, 1H); 8.22 (s, 1H); 7.73-7.54 (m, 2H); 7.43-7.40 (m, 1H); 7.30-7.24 (m, 1H); 7.21-7.18 (m, 1H); 7.04-7.01 (m, 1H); 6.91 (t, 1H); 4.64 (bm, 1H); 4.33 (t, 1H); 4.14 (s, 2H); 3.81 (s, 3H); 3.51-3.45 (m, 2H); 2.41-2.33 (m, 8H); 2.07-1.93 (m, 6H); 1.53-1.39 (m, 2H).

EXAMPLE 361

(trans)-4-(4-{4-amino-3-(2-(2-methoxybenzyl)-1H-benzimidazol-6-yl)-1H-pyrazolo[3,4-d]pyrimidin-1-yl}cyclohexyl)-N,N-dimethylpiperazine-1-carboxamide The desired product was prepared by substituting N,N-dimethylpiperazine-1-carboxamide for 2-(trifluoromethyl)-5,6,7,8-tetrahydroimidazo[1,2-a]pyrazine in EXAMPLE 338. The faster eluting isomer was isolated: MS (ESI(+)) m/e 609 (M+H)$^+$; $^1$H NMR (300 MHz, DMSO-d$_6$) 9.53 (bs, 1H); 8.29 (s, 1H); 7.86-7.81 (m, 2H); 7.72-7.69 (m, 1H); 7.41-7.36 (m, 2H); 7.10 (d, 1H); 7.02 (t, 1H); 4.78 (m, 1H); 4.44 (s, 2H); 3.78 (s, 3H); 3.13-3.03 (m, 5H); 2.80 (m, 7H); 2.27 (m, 2H); 2.16-2.07 (m, 4H); 1.85-1.71 (m, 2H).

EXAMPLE 362

(cis)-4-(4-{4-amino-3-(2-(2-methoxybenzyl)-1H-benzimidazol-6-yl)-1H-pyrazolo[3,4-d]pyrimidin-1-yl}cyclohexyl)-N,N-dimethylpiperazine-1-carboxamide The desired product is the slower eluting isomer in EXAMPLE 361. MS (ESI(+)) m/e 609 (M+H)$^+$; $^1$H NMR (300 MHz, DMSO-d$_6$) 9.38 (m, 1H); 8.31 (s, 1H); 7.90 (s, 1H); 7.82-7.85 (m, 1H); 7.75 (d, 1H); 7.41-7.35 (m, 2H); 7.08 (d, 1H); 7.02 (t, 1H); 4.98 (m, 1H); 4.44 (s, 2H); 3.78 (s, 3H); 3.11-3.00 (m, 5H); 2.77 (m, 7H); 2.14-1.96 (m, 6H).

EXAMPLE 363

(trans)-ethyl 4-(4-{4-amino-3-(2-(2-methoxybenzyl)-1H-benzimidazol-6-yl)-1H-pyrazolo[3,4-d]pyrimidin-1-yl}cyclohexyl)piperazine-1-carboxylate The desired product was prepared by substituting ethyl piperazine-1-carboxylate for 2-(trifluoromethyl)-5,6,7,8-tetrahydroimidazo[1,2-a]pyrazine in EXAMPLE 338. The faster eluting isomer was isolated: MS (ESI(+)) m/e 610 (M+H)$^+$; $^1$H NMR (300 MHz, DMSO-d$_6$) 12.24 (bs, 1H); 8.22 (s, 1H); 7.70-7.56 (m, 2H); 7.42-7.39 (m, 1H); 7.29-7.24 (m, 1H); 7.20-7.17 (m, 1H); 7.02 (d, 1H); 6.91 (t, 1H); 4.64 (m, 1H); 4.17 (s, 2H); 4.03 (q, 2H); 3.81 (s, 3H); 3.36-3.34 (m, 5H); 2.09-1.90 (m, 6H); 1.55-1.41 (m, 2H); 1.18 (t, 3H).

EXAMPLE 364

(cis)-ethyl 4-(4-{4-amino-3-(2-(2-methoxybenzyl)-1H-benzimidazol-6-yl)-1H-pyrazolo[3,4-d]pyrimidin-1-yl}cyclohexyl)piperazine-1-carboxylate The desired product is the slower eluting isomer in EXAMPLE 363. MS (ESI(+)) m/e 610 (M+H)$^+$; $^1$H NMR (300 MHz, DMSO-d$_6$) 12.24 (m, 1H); 8.22 (s, 1H); 7.70-7.59 (m, 2H); 7.41-7.39 (m, 1H); 7.29-7.24 (m, 1H); 7.20-7.17 (m, 1H); 7.04-7.01 (m, 1H); 6.90 (t, 1H); 4.82 (m, 1H); 4.17 (s, 2H); 4.02 (q, 2H); 3.81 (s, 3H); 3.40-3.35 (m, 4H); 2.46-2.40 (m, 6H); 2.31-2.21 (m, 4H); 2.13-2.02 (m, 2H); 1.78-1.68 (m, 2H); 1.67-1.55 (m, 2H); 1.17 (t, 3H).

EXAMPLE 365

(cis)-3-(7-chloro-2-(2-methoxybenzyl)-1H-benzimidazol-5-yl)-1-{4-(4-(3-methoxypropyl)piperazin-1-yl)cyclohexyl}-1H-pyrazolo[3,4-d]pyrimidin-4-amine

EXAMPLE 365A

A mixture of EXAMPLE 31A (0.3 g, 0.8 mmol), and NCS (0.11 g 0.8 mmol) in DMF (3 mL) was stirred at room temperature overnight. The reaction mixture was diluted with EtOAc, washed with water and then brine. The crude was purified by silica gel column chromatography eluting with EtOAc to give the title compound (0.15 g). MS (ESI) m/e 402 (M+H); $^1$H NMR (300 MHz, DMSO-d$_6$) 11.90 (s, 2H), 9.11

(s, 1H), 8.48 (s, 1H), 7.94 (s, 1H), 7.48 (s, 2H), 5.19 (m, 1H), 2.69 (m, 2H), 2.38 (m, 4H), 2.24 (m, 2H).

EXAMPLE 365B

The desired product was prepared as described in EXAMPLE 7 by substituting EXAMPLE 365A and 2-methoxyphenylacetaldehyde for EXAMPLE 7A and benzaldehyde, respectively, in EXAMPLE 7B.

EXAMPLE 365C

The desired product was prepared by substituting 1-(3-methoxypropyl)piperazine for 2-(trifluoromethyl)-5,6,7,8-tetrahydroimidazo[1,2-a]pyrazine and EXAMPLE 365B for EXAMPLE 339C in EXAMPLE 338. The slower eluting isomer was isolated: MS (ESI) m/e 644 (M+H)$^-$; $^1$H NMR (300 MHz, DMSO-d$_6$) δ8.35 (s, 1H), 7.67 (s, 1H), 7.52 (s, 1H), 7.29 (t, 1H), 7.21 (d, 1H), 7.04 (d, 1H), 6.93 (t, 1H), 4.93 (m, 1H), 4.24 (s, 2H), 3.81 (s, 3H), 3.56 (m, 5H), 3.38 (t, 2H), 3.24 (s, 3H), 3.06 (m, 5H), 2.35 (m, 2H), 2.07 (m, 3H), 1.86 (m, 5H).

EXAMPLE 366

(trans)-1-{4-(4-(ethylsulfonyl)piperazin-1-yl)cyclohexyl}-3-(2-(2-methoxybenzyl)-1H-benzimidazol-6-yl)-1H-pyrazolo[3,4-d]pyrimidin-4-amine The desired product was prepared by substituting 1-ethanesulfonylpiperazine for 2-(trifluoromethyl)-5,6,7,8-tetrahydroimidazo[1,2-a]pyrazine in EXAMPLE 338. The faster eluting isomer was isolated: MS (ESI(+)) m/e 630 (M+H)$^+$; $^1$H NMR (300 MHz, DMSO-d$_6$) 12.25 (m, 1H); 8.22 (s, 1H); 7.74-7.55 (m, 2H); 7.43-7.40 (m, 1H); 7.30-7.24 (m, 1H); 7.21-7.18 (m, 1H); 7.04-7.02 (m, 1H); 6.91 (m, 1H); 4.66 (bm, 1H); 4.17 (s, 2H); 3.81 (s, 3H); 3.19-3.15 (m, 6H); 2.64-2.56 (m, 4H); 2.10-1.89 (m, 7H); 1.57-1.44 (m, 2H); 1.22 (t, 3H).

EXAMPLE 367

(cis)-1-{4-(4-(ethylsulfonyl)piperazin-1-yl)cyclohexyl}-3-(2-(2-methoxybenzyl)-1H-benzimidazol-6-yl)-1H-pyrazolo[3,4-d]pyrimidin-4-amine The desired product is the slower eluting isomer in EXAMPLE 366. MS (ESI(+)) m/e 610 (M+H)$^+$; $^1$H NMR (300 MHz, DMSO-d$_6$) 12.27 (m, 1H); 8.23 (s, 1H); 7.73-7.57 (m, 2H); 7.43-7.39 (m, 1H); 7.29-7.25 (m, 1H); 7.20-7.18 (m, 1H); 7.04-7.02 (m, 1H); 6.94-6.89 (m, 1H); 4.82 (m, 1H); 4.17 (s, 2H); 3.81 (s, 3H); 3.22-3.17 (m, 6H); 3.03 (q, 2H); 2.73-2.71 (m, 1H); 2.34-2.24 (m, 4H); 2.15-2.04 (m, 2H); 1.79-1.59 (m, 4H); 1.20 (t, 3H).

EXAMPLE 368

(trans)-3-(7-chloro-2-(2-methoxybenzyl)-1H-benzimidazol-5-yl)-1-{4-(4-(3-methoxypropyl)piperazin-1-yl)cyclohexyl}-1H-pyrazolo[3,4-d]pyrimidin-4-amine The desired product was prepared by substituting 1-(3-methoxypropyl)piperazine for 2-(trifluoromethyl)-5,6,7,8-tetrahydroimidazo[1,2-a]pyrazine and EXAMPLE 365B for EXAMPLE 339C in EXAMPLE 338. The faster eluting isomer was isolated: MS (ESI) m/e 644 (M+H)$^-$; $^1$H NMR (300 MHz, DMSO-d$_6$) δ8.29 (s, 1H), 7.65 (s, 1H), 7.50 (s, 1H), 7.30 (t, 1H), 7.21 (d, 1H), 7.05 (d, 1H), 6.94 (t, 1H), 4.76 (m, 1H), 4.23 (s, 2H), 3.81 (s, 3H), 3.73 (m, 5H), 3.39 (t, 2H), 3.25 (s, 3H), 2.98 (m, 5H), 2.11 (m, 6H), 1.85 (m, 2H), 1.69 (m, 2H).

EXAMPLE 369

(trans)-1-(4-(4-{2-(2-(2-aminoethoxy)ethoxy)ethyl}piperazin-1-yl)cyclohexyl)-3-(2-(2-methoxybenzyl)-1H-benzimidazol-6-yl)-1H-pyrazolo[3,4-d]pyrimidin-4-amine The desired product was prepared by substituting 1-(2-(2-(2-aminoethyl)ethoxy)ethoxy)piperazine for 2-(trifluoromethyl)-5,6,7,8-tetrahydroimidazo[1,2-a]pyrazine in EXAMPLE 338. The faster eluting isomer was isolated: $^1$H NMR (300 MHz, DMSO-d$_6$) δ8.34 (s, 1H), 7.90 (s, 1H), 7.85 (s, 1H), 7.38 (m, 2H), 7.08 (d, 1H), 7.02 (t, 1H), 4.78 (m, 1H), 4.47 (s, 2H), 3.78 (s, 3H), 3.70 (m, 6H), 3.59 (m, 6H), 3.12 (m, 4H), 2.98 (m, 3H), 2.12 (m, 6H), 1.74 (m, 4H).

EXAMPLE 370

(trans)-1-{4-(4-(cyclopropylmethyl)piperazin-1-yl)cyclohexyl}-3-(2-(2-methoxybenzyl)-1H-benzimidazol-6-yl)-1H-pyrazolo[3,4-d]pyrimidin-4-amine The desired product was prepared by substituting 1-cyclopropylmethylpiperazine for 2-(trifluoromethyl)-5,6,7,8-tetrahydroimidazo[1,2-a]pyrazine in EXAMPLE 338. The faster eluting isomer was isolated: MS (ESI(+)) m/e 592 (M+H)$^+$; $^1$H NMR (300 MHz, DMSO-d$_6$) 8.32 (s, 1H); 7.89-7.84 (m, 2H); 7.74-7.72 (m, 1H); 7.41-7.36 (m, 2H); 7.10-7.07 (m, 1H); 7.05-7.00 (m, 1H); 4.78 (m, 1H); 4.47 (s, 2H); 3.78 (s, 3H); 3.69-3.45 (m, 6H); 3.05-2.97 (m, 4H); 2.17-2.07 (m, 7H); 1.79-1.62 (m, 2H); 1.09-1.02 (m, 1H); 0.68-0.62 (m, 2H); 0.38-0.34 (m, 2H).

EXAMPLE 371

(cis)-1-{4-(4-(cyclopropylmethyl)piperazin-1-yl)cyclohexyl}-3-(2-(2-methoxybenzyl)-1H-benzimidazol-6-yl)-1H-pyrazolo[3,4-d]pyrimidin-4-amine The desired product is the slower eluting isomer in EXAMPLE 370. MS (ESI(+)) m/e 592 (M+H)$^+$; $^1$H NMR (300 MHz, DMSO-d$_6$) 8.34 (s, 1H); 7.90-7.83 (m, 2H); 7.76-7.73 (m, 1H); 7.41-7.36 (m, 2H); 7.10-7.04 (m, 1H); 7.02-7.00 (m, 1H); 4.93 (m, 1H); 4.46 (m, 2H); 3.78 (s, 3H); 3.67-3.43 (m, 3H); 3.01-2.99 (m, 2H); 2.41-2.30 (m, 2H); 2.14-2.03 (m, 2H); 1.96-1.82 (m, 3H); 1.03 (m, 1H); 0.66-0.60 (m, 2H); 0.36-0.32 (m, 2H).

EXAMPLE 372

(trans)-4-(4-(4-{4-amino-3-(2-(2,6-difluorobenzyl)-1H-benzimidazol-5-yl)-1H-pyrazolo[3,4-d]pyrimidin-1-yl}cyclohexyl)piperazin-1-yl)-2-methylbutan-2-ol The desired product was prepared by substituting EXAMPLE 294C for EXAMPLE 265A and 1-(3-hydroxy-3-methylbutyl)piperazine for 1-(3-methoxypropyl)piperazine in EXAMPLE 265B. The faster eluting diastereomer was isolated. MS (ESI) m/e 630 (M+H)$^-$; $^1$H NMR (300 MHz, DMSO-d$_6$) δ 8.33 (s, 1H), 7.78 (s, 1H), 7.72 (d, 1H), 7.57 (d, 1H), 7.48 (m, 1H), 7.19 (m, 2H), 4.77 (m, 1H), 4.43 (s, 2H), 3.63 (m, 6H), 3.17 (m, 4H), 2.11 (m, 6H), 1.72 (m, 4H), 1.15 (s, 6H).

EXAMPLE 373

(cis)-4-(4-{4-amino-3-(2-(2,6-difluorobenzyl)-1H-benzimidazol-5-yl)-1H-pyrazolo[3,4-d]pyrimidin-1-yl}cyclohexyl)piperazin-1-yl)-2-methylbutan-2-ol This product was the slower eluting diastereomer in EXAMPLE 372. MS (ESI) m/e 630 (M+H)$^-$; $^1$H NMR (300 MHz, DMSO-d$_6$) δ 8.33 (s, 1H), 7.80 (s, 1H), 7.71 (d, 1H), 7.57 (d, 1H), 7.47 (m, 1H), 7.18 (m, 2H), 4.92 (m, 1H), 4.41 (s, 2H), 3.56 (m, 6H), 3.15 (m, 4H), 2.36 (m, sH), 2.07 (m, 2H), 1.88 (m, 4H), 1.71 (m, 2H), 1.13 (s, 6H).

EXAMPLE 374

(trans)-2-(4-(4-{4-amino-3-(2-(2,6-difluorobenzyl)-1H-benzimidazol-5-yl)-1H-pyrazolo[3,4-d]pyrimidin-1-yl}cyclohexyl)piperazin-1-yl)ethanol The desired product was prepared by substituting EXAMPLE 294C for EXAMPLE 265A and 1-(2-hydroxyethyl)piperazine for 1-(3-methoxypropyl)piperazine in EXAMPLE 265B. The faster eluting diastereomer was isolated. MS (ESI) m/e 588 (M+H)$^-$; $^1$H NMR (300 MHz, DMSO-d$_6$) δ 8.34 (s, 1H), 7.80 (s, 1H), 7.74 (d, 1H), 7.58 (d, 1H), 7.48 (m, 1H), 7.19 (m, 2H), 4.78 (m, 1H), 4.45 (s, 2H), 3.75 (t, 2H), 3.5-3.3 (m, 6H), 3.19 (m, 4H), 2.12 (m, 6H), 1.74 (m, 2H).

EXAMPLE 375

(cis)-2-(4-(4-{4-amino-3-(2-(2,6-difluorobenzyl)-1H-benzimidazol-5-yl)-1H-pyrazolo[3,4-d]pyrimidin-1-yl}cyclohexyl)piperazin-1-yl)ethanol This product was the slower eluting diastereomer in EXAMPLE 374. MS (ESI) m/e 588 (M+H)$^-$; $^1$H NMR (300 MHz, DMSO-d$_6$) δ 8.34 (s, 1H), 7.81 (s, 1H), 7.72 (d, 1H), 7.57 (d, 1H), 7.47 (m, 1H), 7.19 (m, 2H), 4.93 (m, 1H), 4.41 (s, 2H), 3.71 (t, 2H), 3.56 (m, 6H), 3.17 (m, 4H), 2.36 (m, 2H), 2.07 (m, 2H), 1.91 (m, 4H).

EXAMPLE 376

(trans)-3-(2-(2,6-difluorobenzyl)-1H-benzimidazol-5-yl)-1-(4-(4-ethylpiperazin-1-yl)cyclohexyl)-1H-pyrazolo[3,4-d]pyrimidin-4-amine The desired product was prepared by substituting EXAMPLE 294C for EXAMPLE 265A and 1-ethylpiperazine for 1-(3-methoxypropyl)piperazine in EXAMPLE 265B. The faster eluting diastereomer was isolated. MS (ESI) m/e 572 (M+H)$^-$; $^1$H NMR (300 MHz, DMSO-d$_6$) δ 8.33 (s, 1H), 7.79 (s, 1H), 7.73 (d, 1H), 7.56 (d, 1H), 7.48 (m, 1H), 7.19 (m, 2H), 4.77 (m, 1H), 4.43 (s, 2H), 3.61 (m, 6H), 3.12 (m, 4H), 2.11 (m, 6H), 1.71 (m, 2H), 1.22 (t, 3H).

EXAMPLE 377

(cis)-3-(2-(2,6-difluorobenzyl)-1H-benzimidazol-5-yl)-1-(4-(4-ethylpiperazin-1-yl)cyclohexyl)-1H-pyrazolo[3,4-d]pyrimidin-4-amine This product was the slower eluting diastereomer in EXAMPLE 376. MS (ESI) m/e 572 (M+H)$^-$; $^1$H NMR (300 MHz, DMSO-d$_6$) δ 8.35 (s, 1H), 7.81 (s, 1H), 7.73 (d, 1H), 7.58 (d, 1H), 7.48 (m, 1H), 7.19 (m, 2H), 4.93 (m, 1H), 4.42 (s, 2H), 3.55 (m, 6H), 3.12 (m, 4H), 2.34 (m, 2H), 2.07 (m, 2H), 1.89 (m, 4H), 1.20 (t, 3H).

EXAMPLE 378

(trans)-3-(2-(2-methoxybenzyl)-1H-benzimidazol-6-yl)-1-{4-(4-(2-methoxyethyl)piperazin-1-yl)cyclohexyl}-1H-pyrazolo[3,4-d]pyrimidin-4-amine The desired product was prepared by substituting 1-(2-methoxyethyl)piperazine for 2-(trifluoromethyl)-5,6,7,8-tetrahydroimidazo[1,2-a]pyrazine in EXAMPLE 338. The faster eluting isomer was isolated: MS (ESI(+)) m/e 596 (M+H)$^+$; $^1$H NMR (300 MHz, DMSO-d$_6$) 8.31 (s, 1H); 7.88-7.83 (m, 1H); 7.74-7.71 (m, 1H); 7.41-7.35 (m, 1H); 7.10-7.07 (m, 1H); 7.05-6.99 (m, 1H); 4.77 (m, 1H); 4.46 (s, 2H); 3.78 (s, 3H); 3.63-3.60 (m, 2H); 3.30 (s, 3H); 3.18-3.11 (m, 2H); 2.19-2.06 (m, 4H); 1.78-1.66 (m, 1H).

EXAMPLE 379

(cis)-3-(2-(2-methoxybenzyl)-1H-benzimidazol-6-yl)-1-{4-(4-(2-methoxyethyl)piperazin-1-yl)cyclohexyl}-1H-pyrazolo[3,4-d]pyrimidin-4-amine The desired product is the slower eluting isomer in EXAMPLE 378. $^1$H NMR (300 MHz, DMSO-d$_6$) 8.33 (s, 1H); 7.90-7.83 (m, 2H); 7.77-7.74 (m, 1H); 7.40-7.35 (m, 2H); 7.10-7.07 (m, 1H); 7.02-6.99 (m, 1H); 4.93 (m, 1H); 4.45 (m, 2H); 3.78 (s, 3H); 3.62-3.59 (m, 2H); 3.52-3.37 (m, 3H); 3.21-3.13 (m, 2H); 2.40-2.31 (m, 2H); 2.13-1.98 (m, 2H); 1.95-1.85 (m, 3H).

EXAMPLE 380

(trans)-1-(4-(4-isopropylpiperazin-1-yl)cyclohexyl)-3-(2-(2-methoxybenzyl)-1H-benzimidazol-6-yl)-1H-pyrazolo[3,4-d]pyrimidin-4-amine The desired product was prepared by substituting 1-(isopropyl)piperazine for 2-(trifluoromethyl)-5,6,7,8-tetrahydroimidazo[1,2-a]pyrazine in EXAMPLE 338. The faster eluting isomer was isolated: $^1$H NMR (300 MHz, DMSO-d$_6$) 8.31 (s, 1H); 7.88-7.83 (m, 2H); 7.73-7.70 (m, 1H); 7.41-7.36 (m, 2H); 7.10-7.04 (m, 1H); 7.04-7.00 (m, 1H); 4.77 (m, 1H); 4.45 (m, 2H); 3.78 (s, 3H); 3.59-3.42 (m, 5H); 3.28-2.98 (m, 5H); 2.19-2.06 (m, 6H); 1.78-1.64 (m, 2H); 1.25 (d, 6H).

EXAMPLE 381

(cis)-1-(4-(4-isopropylpiperazin-1-yl)cyclohexyl)-3-(2-(2-methoxybenzyl)-1H-benzimidazol-6-yl)-1H-pyrazolo[3,4-d]pyrimidin-4-amine The desired product is the slower eluting isomer in EXAMPLE 380. $^1$H NMR (300 MHz, DMSO-d$_6$) 8.32 (s, 1H); 7.89-7.82 (m, 2H); 7.75-7.72 (m, 1H); 7.40-7.36 (m, 2H); 7.10-7.07 (m, 1H); 7.04-6.99 (m, 1H); 4.93 (m, 1H); 4.45 (s, 2H); 3.78 (s, 3H); 3.54-3.40 (m, 5H); 3.16-3.00 (m, 3H); 2.39-2.28 (m, 2H); 2.12-2.03 (m, 2H); 1.95-1.82 (m, 4H); 1.23 (d, 6H).

EXAMPLE 382

EXAMPLE 382A

Cyclohexylactic acid (313 mg, 2.2 mmol) was dissolved in THF (3 mL) and N,N'-carbonyldiimidazole (340 mg, 2.1 mmol) was added. It was stirred at 50° C. for 30 min. EXAMPLE 280A (470 mg, 2 mmol) was then added and mixture was continuously stirred at 50° C. After 2 hours, 3 mL of acetic acid glacial was added to the reaction mixture, it was heated at 90° C. with stirring for over night. Mixture was diluted with EtOAc, and the organic layer was washed with saturated sodium bicarbonate solution (3×), brine (2×), and dried over magnesium sulfate anhydrous ($MgSO_4$). Obtained crude product was purified by silica gel column, eluting with 40% EtOAc in hexane to yield 270 mg of the title compound.

EXAMPLE 382B

EXAMPLE 382A (100 mg, 0.3 mmol), EXAMPLE 318A (132 mg, 0.25 mmol) sodium carbonate (53 mg, 0.5 mmol), and palladium tetrakistriphenylphosphine (15 mg, 0.0125 mmol) were mixed in 4 mL of dimethoxyethane:water (1:1) and microwaved at 130° C. for 20 minutes. After partitioning between ethyl acetate and brine, the ethyl acetate layer washed with brine (3×), dried and purified by silica gel column chromatography, eluting with 7% methanol in ethyl acetate to yield 150 mg of the title compound.

EXAMPLE 382C

EXAMPLE 382B (150 mg, 0.244 mmol) was treated with 5 mL of 25% trifluoroacetic acid (TFA) in methylene chloride ($CH_2Cl_2$) for 1 hour, and evaporated to dryness. The residue was dissolved in 5 mL of acetonitrile (MeCN). Sodium Iodide (NaI, 93 mg, 0.625 mmol), potassium carbonate ($K_2CO_3$, 173 mg, 1.25 mmol) and (methoxy)propyl bromide (57 L, 0.375 mmol) were added to the above solution. Mixture was stirred at 50° C. for 16 h. Partitioned between EtOAc and brine, the EtOAc layer washed with brine, dried over $MgSO_4$. Crude product was purified by high pressure liquid chromatography (HPLC). 81 mg of the title compound was obtained. $^1$H NMR (300 MHz, DMSO-$d_6$) 8.33 (s, 1H), 7.89-7.93 (m, 2H), 7.75 (dd, 1H), 4.76 (br. m, 1H), 3.39 (t, 2H), 3.25 (s, 3H), 3.04 (br, 4H), 2.11 (br., 6H), 1.81-1.95 (m, 3H), 1.60-1.76 (br.m., 6H), 1.01-1.30 (m, 4H).

EXAMPLE 383

EXAMPLE 383A

The desired product was prepared by substituting cyclopentyl acetic acid for cyclohexyl acetic acid in EXAMPLE 382A.

EXAMPLE 383B

The desired product was prepared by substituting EXAMPLE 383A for EXAMPLE 382A in EXAMPLE 382B.

EXAMPLE 383C

The desired product was prepared by substituting EXAMPLE 383B for EXAMPLE 382B in EXAMPLE 382C. $^1$H NMR (300 MHz, DMSO-$d_6$) 8.31 (s, 1H), 7.88-7.93 (m, 2H), 7.75 (dd, 1H), 4.77 (br. m, 1H), 3.39 (t, 2H), 3.26 (s, 3H), 3.13 (d, 2H), 3.00 (br, 2H), 2.39-2.44 (m, 2H), 2.11 (br., 6H), 1.54-1.88 (m, 6H), 1.26-1.34 (m, 2H).

EXAMPLE 384

EXAMPLE 384A

The desired product was synthesized by substituting 3-fluorobenzyl bromide for 2-chlorobenzyl bromide in EXAMPLE 121B.

EXAMPLE 384B

The desired product was synthesized by substituting EXAMPLE 384A for EXAMPLE 121B in EXAMPLE 121C. $^1$H NMR (300 MHz, DMSO-$d_6$) 9.76 (br.s, 1H), 8.38 (s., 1H), 8.27 (s, 1H), 8.05 (d., 1H), 7.93 (d., 1H), 7.69 (dd., 1H), 7.35-7.42 (m., 1H), 7.08-7.14 (m., 3H), 5.76 (s, 2H), 4.80 (m., 1H), 3.98-4.09 (m., 2H), 3.64-3.76 (br. t., 2H), 3.35-3.50 (m., 3H), 3.08-3.24 (m, 2H), 2.19-2.30 (m, 2H), 2.06-2.17 (br.m., 4H), 1.68-1.83 (br, m, 2H).

EXAMPLE 385

EXAMPLE 385A

The desired product was synthesized by substituting 2-methylbenzyl bromide for 2-chlorobenzyl bromide in EXAMPLE 121B.

EXAMPLE 385B

The desired product was synthesized by substituting EXAMPLE 385A for EXAMPLE 121B in EXAMPLE 121C. $^1$H NMR (300 MHz, DMSO-$d_6$) 9.67 (br.s, 1H), 8.34 (s., 1H), 8.25 (s, 1H), 8.05 (d., 1H), 7.83 (d., 1H), 7.67 (dd., 1H), 7.55-7.64 (m., 3H), 7.22-7.27 (m., 1H), 5.72 (s, 2H), 4.79 (m., 1H), 3.64-3.76 (br. t., 2H), 3.35-3.50 (m., 3H), 3.08-3.24 (m, 2H), 2.39 (s., 3H), 2.19-2.30 (m, 2H), 2.06-2.17 (br.m., 4H), 1.68-1.84 (br, m, 2H).

EXAMPLE 386

EXAMPLE 386A

The desired product was synthesized by substituting 3-methylbenzyl bromide for 2-chlorobenzyl bromide in EXAMPLE 121B.

EXAMPLE 386B

The desired product was synthesized by substituting EXAMPLE 386A for EXAMPLE 121B in EXAMPLE 121C. $^1$H NMR (300 MHz, DMSO-$d_6$) 9.66 (br.s, 1H), 8.33 (s., 1H), 8.23 (s, 1H), 8.02 (d., 1H), 7.89 (d., 1H), 7.67 (dd., 1H), 7.07-7.21 (m., 4H), 5.67 (s, 2H), 4.78 (m., 1H), 3.64-3.75 (br. t., 2H), 3.35-3.50 (m., 3H), 3.08-3.24 (m, 2H), 2.19-2.30 (m, 5H includes 2.26, S., 3H), 2.06-2.17 (br.m., 4H), 1.68-1.84 (br, m, 2H).

EXAMPLE 387

(trans)-1-(4-(4-phenylpiperazin-1-yl)cyclohexyl)-3-(2-(2-methoxybenzyl)-1H-benzimidazol-6-yl)-1H-pyrazolo[3,4-d]pyrimidin-4-amine The desired product was prepared by substituting 1-phenylpiperazine for 2-(trifluoromethyl)-5,6,7,8-tetrahydroimidazo[1,2-a]pyrazine in EXAMPLE 338. The faster eluting isomer was isolated. $^1$H NMR (300 MHz, DMSO-$d_6$) 12.25 (bm, 1H); 8.23 (s, 1H); 7.73-7.56 (m, 2H); 7.43-7.41 (m, 1H); 7.30-7.18 (m, 5H); 7.04-7.01 (m, 1H); 6.95-6.89 (m, 4H); 6.79-6.74 (m, 1H); 4.67 (m, 1H); 4.17 (s, 2H); 3.81 (m, 3H); 3.14-3.11 (m, 4H); 2.70-2.67 (m, 4H); 2.07-1.97 (m, 5H); 1.60-1.47 (m, 2H).

EXAMPLE 388

(cis)-1-(4-(4-phenylpiperazin-1-yl)cyclohexyl)-3-(2-(2-methoxybenzyl)-1H-benzimidazol-6-yl)-1H-pyrazolo[3,4-d]pyrimidin-4-amine The desired product is the slower eluting isomer in EXAMPLE 387. $^1$H NMR (300 MHz, DMSO-$d_6$) 12.23 (m, 1H); 8.23 (s, 1H); 7.73-7.54 (m, 2H); 7.42-7.39 (m, 1H); 7.26-7.16 (m, 5H); 7.03-7.00 (m, 1H); 6.93-6.88 (m, 4H); 6.75 (t, 1H); 4.83 (m, 1H); 4.16 (s, 2H); 3.79 s, 3H); 3.17-3.14 (m, 4H); 2.63-2.59 (m, 3H); 2.33-2.26 (m, 3H); 2.17-2.07 (m, 2H); 1.76-1.60 (m, 3H).

EXAMPLE 389

(trans)-1-(4-(4-ethylpiperazin-1-yl)cyclohexyl)-3-(2-(2-methoxybenzyl)-1H-benzimidazol-6-yl)-1H-pyrazolo[3,4-d]pyrimidin-4-amine

EXAMPLE 389A

The desired product was prepared by substituting 2-chlorophenylacetonitrile for phenylmethylacetonitrile in EXAMPLE 118B.

EXAMPLE 389B

The desired product was prepared by substituting EXAMPLE 389A for EXAMPLE 339A in EXAMPLE 339B.

EXAMPLE 389C

The desired product was prepared by substituting EXAMPLE 389B for EXAMPLE 339B in EXAMPLE 339C.

EXAMPLE 389D

To a mixture of EXAMPLE 389C (0.10 g, 0.21 mmol) and N-ethylpiperazine (0.12 g, 1.06 mmol) was added 0.2 M solution of MeOH/AcOH (9/1 v/v). The mixture was stirred for 15 min, then NaCNBH$_3$ (0.040, 0.639 mmol) was added and the reaction was stirred at RT for 1.5 hr. The reaction was diluted with CH$_2$Cl$_2$, and washed with saturated aqueous NaHCO$_3$. The organic layer was dried over MgSO$_4$, filtered, reduced in vacuo, and purified via reverse phase HPLC. The faster eluting isomer was isolated. $^1$H NMR (300 MHz, DMSO-$d_6$) 8.31 (s, 1H); 7.83-7.77 (m, 2H); 7.64-7.61 (m, 1H); 7.56-7.52 (m, 2H); 7.43-7.40 (m, 2H); 4.76 (m, 1H); 4.56 (s, 2H); 3.64-3.50 (m, 4H); 3.14-3.05 (m, 3H); 3.03-2.90 (m, 3H); 2.15-2.05 (m, 6H); 1.74-1.61 (m, 2H); 1.21 (t, 3H).

EXAMPLE 390

(cis)-1-(4-(4-ethylpiperazin-1-yl)cyclohexyl)-3-(2-(2-methoxybenzyl)-1H-benzimidazol-6-yl)-1H-pyrazolo[3,4-d]pyrimidin-4-amine The desired product is the slower eluting isomer in EXAMPLE 389. $^1$H NMR (300 MHz, DMSO-$d_6$) 8.32 (s, 1H); 7.84 (bm, 1H); 7.76 (d, 1H); 7.62 (dd, 1H); 7.55-7.51 (m, 2H); 7.42-7.39 (m, 2H); 4.92 (m, 1H); 4.54 (bs, 2H); 3.59-3.40 (bm, 5H); 3.14-3.05 (m, 3H); 2.40-2.26 (m, 2H); 2.12-2.01 (m, 2H); 1.91-1.78 (m, 3H); 1.19 (t, 3H).

EXAMPLE 391

(trans)-1-(4-(4-(2-hydroxyethyl)piperazin-1-yl)cyclohexyl)-3-(2-(2-methoxybenzyl)-1H-benzimidazol-6-yl)-1H-pyrazolo[3,4-d]pyrimidin-4-amine The desired product was prepared by substituting 1-(2-hydroxyethyl)piperazine for 1-ethylpiperazine in EXAMPLE 389D. The faster eluting isomer was isolated: $^1$H NMR (300 MHz, DMSO-$d_6$) 8.30 (s, 1H); 7.82 (bm, 1H); 7.76 (d, 1H); 7.63 (dd, 1H); 7.55-7.51(m, 2H); 7.42-7.39 (m, 2H); 4.76 (m, 1H); 4.55 (bs, 2H); 3.75 (m, 7H); 3.16-3.07 (m, 6H); 2.17-2.04 (m, 7H); 1.29-1.62 (m, 2H).

EXAMPLE 392

(cis)-1-(4-(4-(2-hydroxyethyl)piperazin-1-yl)cyclohexyl)-3-(2-(2-methoxybenzyl)-1H-benzimidazol-6-yl)-1H-pyrazolo[3,4-d]pyrimidin-4-amine The desired product is the slower eluting isomer in EXAMPLE 391. NMR (300 MHz, DMSO-$d_6$) 8.34 (s, 1H); 7.85 (bs, 1H); 7.78 (d, 1H); 7.66-7.63 (dd, 1H); 7.56-7.52 (m, 2H); 7.43-7.40 (m, 2H); 4.93 (m, 1H); 4.56 (bs, 2H); 3.71 (m, 3H); 3.61-3.46 (m, 4H); 3.19-3.13 (m, 3H); 2.42-2.31 (m, 2H); 2.13-2.02 (m, 2H); 1.97-1.85 (m, 3H).

The foregoing is meant to illustrate the invention but not to limit it. Variations and changes obvious to one skilled in the art are intended to be within the scope of the invention as defined in the claims.

We claim:

1. A compound having formula (25)

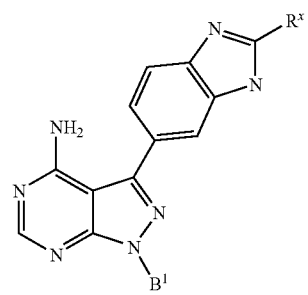

(25)

or a salt thereof, wherein
R$^x$ and the moiety to which it is attached form A$^1$;
A$^1$ is R$^2$;
R$^2$ is 1H-benzo[d]imidazol-6-yl;

B¹ is R³, R⁴, R⁵ or W¹;

R³ is phenyl which is unfused or fused with benzene, heteroarene or R³ᴬ; R³ᴬ is cycloalkane, cycloalkene, heterocycloalkane or heterocycloalkene;

R⁴ is heteroaryl which is unfused or fused with benzene, heteroarene or R⁴ᴬ; R⁴ᴬ is cycloalkane, cycloalkene, heterocycloalkane or heterocycloalkene;

R⁵ is cycloalkyl, cycloalkenyl, heterocycloalkyl or heterocycloalkenyl, each of which is unfused or fused with benzene, heteroarene or R⁵ᴬ; R⁵ᴬ is cycloalkane, cycloalkene, heterocycloalkane or heterocycloalkene;

W¹ is alkyl, alkenyl or alkynyl, each of which is unsubstituted or substituted with one or two of independently selected W², W³, W⁴, OH, OW⁵, SW⁵, S(O)W⁵, SO₂W⁵, NH₂, NHW⁵, N(W⁵)₂, C(O)NH₂, C(O)NHW⁵, C(O)N(W⁵)₂, NHC(O)W⁵ or NW⁵C(O)W⁵;

W² is phenyl which is unfused or fused with benzene, heteroarene or W²ᴬ; W²ᴬ is cycloalkane, cycloalkene, heterocycloalkane or heterocycloalkene;

W³ is heteroaryl which is unfused or fused with benzene, heteroarene or W³ᴬ; W³ᴬ is cycloalkane, cycloalkene, heterocycloalkane or heterocycloalkene;

W⁴ is cycloalkyl, cycloalkenyl, heterocycloalkyl or heterocycloalkenyl, each of which is unfused or fused with benzene, heteroarene or W⁵ᴬ; W⁵ᴬ is cycloalkane, cycloalkene, heterocycloalkane or heterocycloalkene;

W⁵ is alkyl, alkenyl or alkynyl;

wherein the moieties represented by A¹, B¹, W², W³ and W⁴ are independently unsubstituted or substituted with one or two or three or four of independently selected R⁶, OR⁶, SR⁶, S(O)R⁶, SO₂R⁶, NH₂, NHR⁶, N(R⁶)₂, C(O)R⁶, C(O)OR⁶, C(O)NH₂, C(O)NHR⁶, C(O)N(R⁶)₂, NHC(O)R⁶, NR⁶C(O)R⁶, NHSO₂R⁶, NR⁶SO₂R⁶, NHC(O)OR⁶, NR⁶C(O)OR⁶, SO₂NH₂, SO₂NHR⁶, SO₂N(R⁶)₂, NHC(O)NH₂, NHC(O)NHR⁶, NHC(O)N(R⁶)₂, NR⁶C(O)N(R⁶)₂C(NH)NH₂, C(NH)NHR⁶, C(NH)N(R⁶)₂, NHC(NH)NH2, NHC(NH)NHR⁶, NHC(NH)N(R⁶)₂, OH, (O), C(O)H, C(O)OH, NO₂, CN, CF₃, OCF₃, CF₂CF₃, F, Cl, Br or I;

R⁶ is R⁷, R⁸, R⁹ or R¹⁰;

R⁷ is phenyl which is unfused or fused with benzene, heteroarene or R⁷ᴬ; R⁷ᴬ is cycloalkane, cycloalkene, heterocycloalkane or heterocycloalkene;

R⁸ is heteroaryl which is unfused or fused with benzene, heteroarene or R⁸ᴬ; R⁸ᴬ is cycloalkane, cycloalkene, heterocycloalkane or heterocycloalkene;

R⁹ is cycloalkyl, cycloalkenyl, heterocycloalkyl or heterocycloalkenyl, each of which is unfused or fused with benzene, heteroarene or R⁹ᴬ; R⁹ᴬ is cycloalkane, cycloalkene, heterocycloalkane or heterocycloalkene;

R¹⁰ is alkyl, alkenyl or alkynyl, each of which is unsubstituted or substituted with one or two of independently selected R¹¹, OR¹¹, SR¹¹, S(O)R¹¹, SO₂R¹¹, NH₂, NHR¹¹, N(R¹¹)₂, C(O)R¹¹, C(O)NH₂, C(O)NHR¹¹, C(O)N(R¹¹)₂, NHC(O)R¹¹, NR¹¹C(O)R¹¹, NHSO₂R¹¹, NR¹¹SO₂R¹¹, NHC(O)OR¹¹, NR¹¹C(O)OR¹¹, SO₂NH₂, SO₂NHR¹¹, SO₂N(R¹¹)₂, NHC(O)NH₂, NHC(O)NHR¹¹, NHC(O)N(R¹¹)₂, NR¹¹C(O)N(R¹¹)₂, OH, (O), C(O)OH, CN, CF₃, OCF₃, CF₂CF₃, F, Cl, Br or I;

R¹¹ is alkyl, alkenyl, alkynyl, R¹², R¹³, R¹⁴;

R¹² is phenyl which is unfused or fused with benzene, heteroarene or R¹²ᴬ; R¹²ᴬ is cycloalkane, cycloalkene, heterocycloalkane or heterocycloalkene;

R¹³ is heteroaryl which is unfused or fused with benzene, heteroarene or R¹³ᴬ; R¹³ᴬ is cycloalkane, cycloalkene, heterocycloalkane or heterocycloalkene; and R¹⁴ is cycloalkyl, cycloalkenyl, heterocycloalkyl or heterocycloalkenyl, each of which is unfused or fused with benzene, heteroarene or R¹⁴ᴬ; R¹⁴ᴬ is cycloalkane, cycloalkene, heterocycloalkane or heterocycloalkene;

wherein the moieties represented by R⁷, R⁸, R⁹ and R¹¹ are independently unsubstituted or substituted with one or two or three or four of independently selected R¹⁵, OR¹⁵, SR¹⁵, S(O)R¹⁵, SO₂R¹⁵, C(O)R¹⁵, C(O)NH₂, C(O)NHR¹⁵, C(O)N(R¹⁵)₂, OH, (O), C(O)OH, CN, CF₃, OCF₃, CF₂CF₃, F, Cl, Br or I, wherein R¹⁵ is alkyl, alkenyl, alkynyl, each of which is unsubstituted or substituted with OH, OR¹⁶, C(O)NH₂, C(O)NHR¹⁶, C(O)N(R¹⁶)₂, wherein R¹⁶ is alkyl, alkenyl or alkynyl.

2. A composition comprising an excipient and a therapeutically effective amount of a compound of claim 1.

3. The compound or a salt thereof according to claim 1 selected from cis-4-(4-(4-amino-3-(2-phenyl-1H-benzimidazol-6-yl)-1H-pyrazolo[3,4-d]pyrimidin-1-yl)cyclohexyl)-1-methylpiperazin-2-one;

cis-4-(4-(4-amino-3-(2-(4-fluorophenyl)-1H-benzimidazol-6-yl)-1H-pyrazolo[3,4-d]pyrimidin-1-yl)cyclohexyl)-1-methylpiperazin-2-one;

cis-4-(4-(4-amino-3-(2-cyclopropyl-1H-benzimidazol-6-yl)-1H-pyrazolo[3,4-d]pyrimidin-1-yl) cyclohexyl)-1-methylpiperazin-2-one;

cis-4-(4-(4-amino-3-(2-pyridin-2-yl-1H-benzimidazol-6-yl)-1H-pyrazolo[3,4-d]pyrimidin-1-yl)cyclohexyl)-1-methylpiperazin-2-one;

trans-1-(4-(2-methoxylthoxy)cyclohexyl)-3-(2-phenyl-1H-benzimidazol-5-yl)-1H-pyrazolo [3,4-d]pyrimidin-4-amine;

cis-1-(4-(4-methylpiperazin-1-yl)cyclohexyl)-3-(2-phenyl-1H-benzimidazol-5-yl)-1H-pyrazolo [3,4-d]pyrimidin-4-amine;

trans-1-(4-morpholin-4-ylcyclohexyl)-3-(2-phenyl-1H-benzimidazol-5-yl)-1H-pyrazolo[3,4-d]pyrimidin-4-amine;

trans-3-(2-(4-methylphenyl)-1H-benzimidazol-6-yl)-1-(4-morpholin-4-ylcyclohexyl)-1H-pyrazolo[3,4-d]pyrimidin-4-amine;

trans-3-(2-(4-chlorophenyl)-1H-benzimidazol-6-yl)-1-(4-morpholin-4-ylcyclohexyl)-1H-pyrazolo [3,4-d]pyrimidin-4-amine;

trans-3-(2-(4-methoxyphenyl)-1H-benzimidazol-6-yl)-1-(4-morpholin-4-ylcyclohexyl)-1H-pyrazolo[3,4-d]pyrimidin-4-amine;

trans-3-(2-(3,4-dichlorophenyl)-1H-benzimidazol-6-yl)-1-(4-morpholin-4-ylcyclohexyl)-1H-pyrazolo [3,4-d]pyrimidin-4-amine;

trans-3-(2-benzyl-1H-benzimidazol-6-yl)-1-(4-morpholin-4-ylcyclohexyl)-1H-pyrazolo[3,4-d]pyrimidin-4-amine;

trans-1-(4-morpholin-4-ylcyclohexyl)-3-(2-(2-phenyl ethyl)-1H-benzimidazol-6-yl)-1H-pyrazolo[3,4-d]pyrimidin-4-amine;

trans-1-(4-morpholin-4-ylcyclohexyl)-3-(2-(thien-2-ylmethyl)-1H-benzimidazol-6-yl)-1H-pyrazolo [3,4-d]pyrimidin-4-amine;

trans-3-(2-(3-chlorobenzyl)-1H-benzimidazol-6-yl)-1-(4-morpholin-4-ylcyclohexyl)-1H-pyrazolo [3,4-d]pyrimidin-4-amine;

trans-3-(2-(4-chlorobenzyl)-1H-benzimidazol-6-yl)-1-(4-morpholin-4-ylcyclohexyl)-1H-pyrazolo[3,4-d]pyrimidin-4-amine;

trans-1-(4-morpholin-4-ylcyclohexyl)-3-(2-(1-phenylethyl)-1H-benzimidazol-6-yl)-1H-pyrazolo [3,4-d]pyrimidin-4-amine;

trans-3-(2-(2-chlorobenzyl)-1H-benzimidazol-6-yl)-1-(4-morpholin-4-ylcyclohexyl)-1H-pyrazolo [3,4-d]pyrimidin-4-amine;

trans-3-(2-(2-fluorobenzyl)-1H-benzimidazol-6-yl)-1-(4-morpholin-4-ylcyclohexyl)-1H-pyrazolo [3,4-d]pyrimidin-4-amine;

trans-3-(2-(2-methylbenzyl)-1H-benzimidazol-6-yl)-1-(4-morpholin-4-ylcyclohexyl)-1H-pyrazolo [3,4-d]pyrimidin-4-amine.

4. The compound or a salt thereof according to claim 1 selected from trans-3-(2-(3-fluorobenzyl)-1H-benzimidazol-6-yl)-1-(4-morpholin-4-ylcyclohexyl)-1H-pyrazolo[3,4-d]pyrimidin-4-amine;

trans-3-(2-(3-methylbenzyl)-1H-benzimidazol-6-yl)-1-(4-morpholin-4-ylcyclohexyl)-1H-pyrazolo[3,4-d]pyrimidin-4-amine;

trans-3-(2-(4-fluorobenzyl)-1H-benzimidazol-6-yl)-1-(4-morpholin-4-ylcyclohexyl)-1H-pyrazolo [3,4-d]pyrimidin-4-amine;

trans-3-(2-(4-methlybenzyl)-1H-benzimidazol-6-yl)-1-(4-morpholin-4-ylcyclohexyl)-1H-pyrazolo[3,4-d]pyrimidin-4-amine;

trans-3-(2-(3,4-dichlorobenzyl)-1H-benzimidazol-6-yl)-1-(4-morpholin-4-ylcyclohexyl)-1H-pyrazolo[3,4-d]pyrimidin-4-amine;

trans-3-(2-(2,6-dichlorobenzyl)-1H-benzimidazol-5-yl)-1-(4-morpholin-4-ylcyclohexyl)-1H-pyrazolo[3,4-d]pyrimidin-4-amine;

trans-3-(2-(2,3-dichlorobenzyl)-1H-benzimidazol-5-yl)-1-(4-morpholin-4-ylcyclohexyl)-1H-pyrazolo[3,4-d]pyrimidin-4-amine;

trans-3-(2-((3-fluorobenzyl)amino)-1H-benzimidazol-6-yl)-1-(4-morpholin-4-ylcyclohexyl)-1H-pyrazolo[3,4-d]pyrimidin-4-amine;

trans-3-(2-benzly-4methly-1H-benzimidazol-6-yl)-1-(4-morpholin-4-ylcyclohexyl)-1H-pyrazolo[3,4-d]pyrimidin-4-amine;

trans-3-(2-benzly-1methly-1H-benzimidazol-5-yl)-1-(4-morpholin-4-ylcyclohexyl)-1H-pyrazolo[3,4-d]pyrimidin-4-amine;

trans-1-(4-(4-amino-3-(2-benzyl-1H-benzimidazol-5-yl)-1H-pyrazolo[3,4-d]pyrimidin-1-yl)cyclohexyl)pyrrolidin-3-ol;

cis-1-(4-(4-amino-3-(2-benzyl-1H-benzimidazol-5-yl)-1H-pyrazolo[3,4-d]pyrimidin-1-yl)cyclohexyl)pyrrolidin-3-ol;

trans-3-(2-benzyl-1H-benzimidazol-5-yl)-1-(4-(4-(ethylsulfonyl)piperazin-1-yl)cyclohexyl)-1H-pyrazolo[3,4-d]pyrimidin-4-amine;

cis-3-(2-benzyl-1H-benzimidazol-5-yl)-1-(4-(4-(ethylsulfonyl)piperazin-1-yl)cyclohexyl)-1H-pyrazolo[3,4-d]pyrimidin-4-amine;

trans-3-(2-benzyl-1H-benzimidazol-5-yl)-1-(4-(4-(ethylsulfonyl)piperazin-1-yl)cyclohexyl)-1H-pyrazolo[3,4-d]pyrimidin-4-amine;

cis-3-(2-benzyl-1H-benzimidazol-5-yl)-1-(4-(4-(ethylsulfonyl)piperazin-1-yl)cyclohexyl)-1H-pyrazolo[3,4-d]pyrimidin-4-amine;

trans-3-(2-benzyl-1H-benzimidazol-5-yl)-1-(4-((3R,5S)-3,5-dimethylpiperazin-1-yl)cyclohexyl)-1H-pyrazolo[3,4-d]pyrimidin-4-amine;

cis-3-(2-benzyl-1H-benzimidazol-5-yl)-1-(4-((3R,5S)-3,5-dimethylpiperazin-1-yl)cyclohexyl)-1H-pyrazolo[3,4-d]pyrimidin-4-amine;

trans-1-(4-(4-acetylpiperazin-1-yl)cyclohexyl)-3-(2-benzyl-1H-benzimidazol-5-yl)-1H-pyrazolo[3,4-d]pyrimidin-4-amine; or cis-1-(4-(4-acetylpiperazin-1-yl)cyclohexyl)-3-(2-benzyl-1H-benzimidazol-5-yl)-1H-pyrazolo[3,4-d]pyrimidin-4-amine.

5. The compound or a salt thereof according to claim 1 selected from trans-3-(2-benzyl-1H-benzimidazol-5-yl)-1-(4-(3-(trifluoromethyl)-5,6-dihydro[1,2,4]triazolo[4,3-a]pyrazin-7(8H)-yl)cyclohexyl)-1H-pyrazolo[3,4-d]pyrimidin-4-amine;

cis-3-(2-benzyl-1H-benzimidazol-5-yl)-1-(4-(3-(trifluoromethyl)-5,6-dihydro[1,2,4]triazolo[4,3-a]pyrazin-7(8H)-yl)cyclohexyl)-1H-pyrazolo[3,4-d]pyrimidin-4-amine;

2-(4-(4-amino-3-(2-benzyl-1H-benzimidazol-5-yl)-1H-pyrazolo[3,4-d]pyrimidin-1-yl)piperidin-1-yl)acetamide;

trans-1-(4-(4-amino-3-(2-benzyl-1H-benzimidazol-5-yl)-1H-pyrazolo[3,4-d]pyrimidin-1-yl)cyclohexyl)piperidine-3-carboxamide;

cis-1-(4-(4-amino-3-(2-benzyl-1H-benzimidazol-5-yl)-1H-pyrazolo[3,4-d]pyrimidin-1-yl)cyclohexyl)piperidine-3-carboxamide;

trans-1-(4-(4-amino-3-(2-benzyl-1H-benzimidazol-5-yl)-1H-pyrazolo[3,4-d]pyrimidin-1-yl)cyclohexyl)piperidine-4-carboxamide;

cis-1-(4-(4-amino-3-(2-benzyl-1H-benzimidazol-5-yl)-1H-pyrazolo[3,4-d]pyrimidin-1-yl)cyclohexyl)piperidine-4-carboxamide;

3-(2-benzyl-1H-benzimidazol-5-yl)-1-(4-(morpholin-4-ylmethyl)phenyl)-1H-pyrazolo[3,4-d]pyrimidin-4-amine;

trans-3-(2-benzyl-1H-benzimidazol-5-yl)-1-(4-(4-(methylsulfonyl)piperazin-1-yl)cyclohexyl)-1H-pyrazolo[3,4-d]pyrimidin-4-amine;

cis-3-(2-benzyl-1H-benzimidazol-5-yl)-1-(4-(4-(methylsulfonyl)piperazin-1-yl)cyclohexyl)-1H-pyrazolo[3,4-d]pyrimidin-4-amine;

3-(2-benzyl-1H-benzimidazol-5-yl)-1-(1-(morpholin-4-yl)carbonyl)pipridin-4-yl)-1H-pyrazolo[3,4-d]pyrimidin-4-amine;

2-(3-(4-amino-3-(2-benzyl-1H-benzimidazol-5-yl)-1H-pyrazolo[3,4-d]pyrimidin-1-yl)pyrrolidin-1-yl)acetamide;

trans-2-(4-(4-(4-amino-3-(2-benzyl-1H-benzimidazol-5-yl)-1H-pyrazolo[3,4-d]pyrimidin-1-yl)cyclohexyl)piperazin-1-yl)ethanol;

cis-2-(4-(4-(4-amino-3-(2-benzyl-1H-benzimidazol-5-yl)-1H-pyrazolo[3,4-d]pyrimidin-1-yl)cyclohexyl)piperazin-1-yl)ethanol;

4-(4-amino-3-(2-benzyl-1H-benzimidazol-5-yl)-1H-pyrazolo[3,4-d]pyrimidin-1-yl)cyclohexanol;

trans-3-(2-(2-chloro-6-fluorobenzyl)-1H-benzimidazol-5-yl)-1-(4-morpholin-4-ylcyclohexyl)-1H-pyrazolo[3,4-d]pyrimidin-4-amine;

3-(2-benzyl-1H-benzimidazol-5-yl)-1-(1-(methylsulfonyl)piperidin-4-yl)-1H-pyrazolo[3,4-d]pyrimidin-4-amine;

(2S)-1-(4-amino-3-(2-benzyl-1H-benzimidazol-5-yl)-1H-pyrazolo[3,4-d]pyrimidin-1-yl)-3-morpholin-4-ylpropan-2-ol; or trans-3-(2-(2,6-difluorobenzyl)-1H-benzimidazol-6-yl)-1-(4-morpholin-4-ylcyclohexyl)-1H-pyrazolo[3,4-d]pyrimidin-4-amine.

6. The compound or a salt thereof according to claim 1 selected from trans-3-(2-(3-trifluorobenzyl)-1H-benzimidazol-6-yl-1-4-morpholin-4-ylcyclohexyl)-1H-pyrazolo[3,4-d]pyrimidin-4-amine;

3-(2-benzyl-1H-benzimidazol-5-yl)-1-(1-(methylsulfonyl)piperidin-4-yl)-1H-pyrazolo[3,4-d]pyrimidin-4-amine;

3-(2-benzyl-1H-benzimidazol-6-yl)-1-(2-morpholin-4-ylethyl)-1H-pyrazolo[3,4-d]pyrimidin-4-amine;

3-(2-benzyl-1H-benzimidazol-6-yl)-1-(1-pyrimidin-2-ylpiperidin-4-yl)-1H-pyrazolo[3,4-d]pyrimidin-4-amine;

(trans)-3-(2-(2,3-difluorobenzyl)-1H-benzimidazol-6-yl)-1-(4-morpholin-4-ylcyclohexyl)-1H-pyrazolo[3,4-d]pyrimidin-4-amine;

(trans)-3-(2-(3,4-difluorobenzyl)-1H-benzimidazol-6-yl)-1-(4-morpholin-4-ylcyclohexyl)-1H-pyrazolo[3,4-d]pyrimidin-4-amine;

(trans)-3-(2-(3,5-difluorobenzyl)-1H-benzimidazol-6-yl)-1-(4-morpholin-4-ylcyclohexyl)-1H-pyrazolo[3,4-d]pyrimidin-4-amine;

(trans)-3-(2-benzyl-1H-benzimidazol-5-yl)-1-(4-((2-(methylsulfonyl)ethyl)amino)cyclohexyl)-1H-pyrazolo[3,4-d]pyrimidin-4-amine;

(cis)-3-(2-benzyl-1H-benzimidazol-5-yl)-1-(4-((2-(methylsulfonyl)ethyl)amino)cyclohexyl)-1H-pyrazolo[3,4-d]pyrimidin-4-amine;

3-(2-benzyl-1H-benzimidazol-5-yl)-1-(4-(1,1-dioxidothiomorpholin-4-yl)cyclohexyl)-1H-pyrazolo[3,4-d]pyrimidin-4-amine;

3-(2-benzyl-1H-benzimidazol-5-yl)-1-(4-((2-(methylsulfonyl)ethyll)amino)methyl)phenyl)-1H-pyrazolo[3,4-d]pyrimidin-4-amine;

(trans)-2-(4-(4-(4-amino-3-(2-(2-fluorobenzyl)-1H-benzimidazol-5-yl)-1H-pyrazolo[3,4-d]pyrimidin-1-yl)cyclohexyl)piperazin-1-yl)ethanol;

(cis)-2-(4-(4-(4-amino-3-(2-(2-fluorobenzyl)-1H-benzimidazol-5-yl)-1H-pyrazolo[3,4-d]pyrimidin-1-yl)cyclohexyl)piperazin-1-yl)ethanol;

(trans)-3-(2-(2-chloro-3-fluorophenyl)-1H-benzimidazol-6-yl)-1-(4-morpholin-4-ylcyclohexyl)-1H-pyrazolo[3,4-d]pyrimidin-4-amine;

(trans)-1-(4-morpholin-4-ylcyclohexyl)-3-(2-(3-(trifluoromethyl)benzyl)-1H-benzimidazol-6-yl)-1H-pyrazolo[3,4-d]pyrimidin-4-amine;

N-(4-(4-amino-3-(2-benzyl-1H-benzimidazol-5-yl)-1H-pyrazolo[3,4-d]pyrimidin-1-yl)cyclohexyl)methanesulfonamide;

ethyl4-(4-amino-3-(2-benzyl-1H-benzimidazol-5-yl)-1H-pyrazolo[3,4-d]pyrimidin-1-yl)cyclohexylcarbamate;

3-(2-benzyl-1H-benzimidazol-5-yl)-1-(1-(2-(methylsulfonyl)ethyl)pyrrolidin-3-yl)-1H-pyrazolo[3,4-d]pyrimidin-4-amine;

3-(2-(2-fluorobenzyl)-1H-benzimidazol-5-yl)-1-(1-(2-(methylsulfonylethyl)pyrrolidin-3-yl)-1H-pyrazolo[3,4-d]pyrimidin-4-amine; or (trans)-3-(2-benzyl-1H-benzimidazol-5-yl)-1-(4-(4-(3-methoxypropyl)piperazin-1-yl)cyclohexyl)-1H-pyrazolo[3,4-d]pyrimidin-4-amine.

7. The compound or a salt thereof according to claim 1 selected from (cis)-3-(2-benzyl-1H-benzimidazol-5-yl)-1-(4-(4-(3-methoxypropyl)piperazin-1-yl)cyclohexyl)-1H-pyrazolo[3,4-d]pyrimidin-4-amine;

3-(2-benzyl-1H-benzimidazol-5-yl)-1-(1-(2-(methylsulfonyl)ethyl)piperidin-4-yl)-1H-pyrazolo[3,4-d]pyrimidin-4-amine;

3-(2-(2-fluorobenzyl)-1H-benzimidazol-5-yl)-1-(1-(2-(methylsulfonyl)ethyl)piperidin-4-yl)-1H-pyrazolo[3,4-d]pyrimidin-4-amine;

(trans)-1-(4-morpholin-4-ylcyclohexyl)-3-(2-(phenylsulfonyl)-1H-benzimidazol-5-yl)-1H-pyrazolo[3,4-d]pyrimidin-4-amine;

3-(2-benzyl-1H-benzimidazol-6-yl)-1-(3-pyridin-3-ylpropyl)-1H-pyrazolo[3,4-d]pyrimidin-4-amine;

3-(2-benzyl-1H-benzimidazol-6-yl)-1-(1-benzylpiperidin-4-yl)-1H-pyrazolo[3,4-d]pyrimidin-4-amine;

3-(2-benzyl-1H-benzimidazol-6-yl)-1-(2-(4methyl-1,3-thiazol-5-yl)ethyl)1H-pyrazolo [3,4-d]pyrimidin-4-amine;

3-(2-benzyl-1H-benzimidazol-6-yl)-1-(1-(6-chloropyridazin-3-yl)piperidin-4-yl)-1H-pyrazolo[3,4-d]pyrimidin-4-amine;

3-(2-benzyl-1H-benzimidazol-6-yl)-1-(4-morpholin-4-yl-but-2ynly)-1H-pyrazolo[3,4-d]pyrimidin-4-amine;

3-(2-benzyl-1H-benzimidazol-6-yl)-1-(4-(4-(ethylsulfonyl)piperazin-1-yl)but-2-ynyl)-1H-pyrazolo[3,4-d]pyrimidin-4-amine;

(trans)-3-(4-(4-(4-amino-3-(2-benzyl-1H-benzimidazol-5-yl)-1H-pyrazolo[3,4-d]pyrimidin-1-yl)cyclohexyl)piperazin-1-yl)propan-1-ol;

(cis)-3-(4-(4-(4-amino-3-(2-benzyl-1H-benzimidazol-5-yl)-1H-pyrazolo[3,4-d]pyrimidin-1-yl)cyclohexyl)piperazin-1-yl)propan-1-ol;

3-(2-benzyl-1H-benzimidazol-6-yl)-1-((2-pyridin-3-yl-1,3-thiazol-4-yl)methyl)-1H-pyrazolo[3,4-d]pyrimidin-4-amine;

3-(2-benzyl-1H-benzimidazol-6-yl)-1-((4-benzylmorpholin-2-yl)methyl)-1H-pyrazolo[3,4-d]pyrimidin-4-amine;

1-(4-(4-acetylpiperazin-1-yl)but-2-ynyl)-3-(2-benzyl-1H-benzimidazol-6-yl)-1H-pyrazolo[3,4-d]pyrimidin-4-amine;

3-(2-benzyl-1H-benzimidazol-6-yl)-1-(4-(4-(2-methoxylthyl)piperazin-1-yl)but-2-ynyl)-1H-pyrazolo[3,4-d]pyrimidin-4-amine;

(trans)-3-(2-(2-chlorobenzyl)-1H-benzimidazol-6-yl)-1-(4-(4-(3-methoxypropyl)piperazin-1-yl)cyclohexyl)-1H-pyrazolo[3,4-d]pyrimidin-4-amine;

3-(2-benzyl-1-H-benzimidazol-5-yl)-1-(1-(3-methoxypropyl)pyrrolidin-3-yl)-1H-pyrazolo[3,4-d]pyrimidin-4-amine;

3-(2-benzyl-1H-benzimidazol-5-yl)-1-tert-butyl-1H-pyrazolo[3,4-d]pyrimidin-4-amine.

8. The compound or a salt thereof according to claim 1 selected from (trans)-3-(1-benzyl-1H-benzimidazol-5-yl)-1-(4-morpholin-4-ylcyclohexyl)-1H-pyrazolo[3,4-d]pyrimidin-4-amine;

(trans)-3-(1-(2-chlorobenzyl)-1H-benzimidazol-5-yl)-1-(4-morpholin-4-ylcyclohexyl)-1H-pyrazolo[3,4-d]pyrimidin-4-amine;

(trans)-3-(1-(2-fluorobenzyl)-1H-benzimidazol-5-yl)-1-(4-morpholin-4-ylcyclohexyl)-1H-pyrazolo[3,4-d]pyrimidin-4-amine;

3-(2-benzyl-1H-benzimidazol-5-yl)-1-(3-methoxypropyl)-1H-pyrazolo[3,4-d]pyrimidin-4-amine;

3-(2-benzyl-1H-benzimidazol-5-yl)-1-tetrahydro-2H-pyran-4-yl-1H-pyrazolo[3,4-d]pyrimidin-4-amine;
3-(2-benzyl-1H-benzimidazol-5-yl)-1-(1-methylpiperidin-4-yl)-1H-pyrazolo[3,4-d]pyrimidin-4-amine;
3-(2-benzyl-1H-benzimidazol-5-yl)-1-(3-(dimethylamino)propyl)-1H-pyrazolo[3,4-d]pyrimidin-4-amine;
(trans)-3-(2-(2-bromobenzyl)-1H-benzimidazol-5-yl)-1-(4-morpholin-4-ylcyclohexyl)-1H-pyrazolo[3,4-d]pyrimidin-4-amine;
(trans)-3-(2-(2-methoxybenzyl)-1H-benzimidazol-5-yl)-1-(4-morpholin-4-ylcyclohexyl)-1H-pyrazolo[3,4-d]pyrimidin-4-amine;
(cis)-3-(2-(2-methoxybenzyl)-1H-benzimidazol-5-yl)-1-(4-(4-(3-methoxypropyl)piperazin-1-yl)cyclohexyl)-1H-pyrazolo[3,4-d]pyrimidin-4-amine;
(trans)-3-(2-(2-methoxybenzyl)-1H-benzimidazol-5-yl)-1-(4-(4-(3-methoxypropyl)piperazin-1-yl)cyclohexyl)-1H-pyrazolo[3,4-d]pyrimidin-4-amine;
(trans)-3-(2-(2-bromobenzyl)-1H-benzimidazol-5-yl)-1-(4-(4-(3-methoxypropyl)piperazin-1-yl)cyclohexyl)-1H-pyrazolo[3,4-d]pyrimidin-4-amine;
(cis)-3-(2-(2-bromobenzyl)-1H-benzimidazol-5-yl)-1-(4-(4-(3-methoxypropyl)piperazin-1-yl)cyclohexyl)-1H-pyrazolo[3,4-d]pyrimidin-4-amine;
(trans)-3-(2-(4-methylphenoxy)-1H-benzimidazol-6-yl)-1-(4-morpholin-4-ylcyclohexyl)-1H-pyrazolo[3,4-d]pyrimidin-4-amine;
(trans)-3-(2-(3-methylphenoxy)-1H-benzimidazol-6-yl)-1-(4-morpholin-4-ylcyclohexyl)-1H-pyrazolo[3,4-d]pyrimidin-4-amine;
3-(2-(2-chlorobenzyl)-1H-benzimidazol-5-yl)-1-(4-(morpholin-4-ylmethyl)phenyl)-1H-pyrazolo[3,4-d]pyrimidin-4-amine;
3-(2-(3-methylbenzyl)-1H-benzimidazol-5-yl)-1-(4-(morpholin-4-ylmethyl)phenyl)-1H-pyrazolo[3,4-d]pyrimidin-4-amine;
3-(2-(2-bromobenzyl)-1H-benzimidazol-5-yl)-1-(4-(morpholin-4-ylmethyl)phenyl)-1H-pyrazolo[3,4-d]pyrimidin-4-amine;
3-(2-(2-methoxybenzyl)-1H-benzimidazol-5-yl)-1-(4-(morpholin-4-ylmethyl)phenyl)-1H-pyrazolo[3,4-d]pyrimidin-4-amine;
(trans)-4-(4-(4-(4-amino-3-(2-benzyl-1H-benzimidazol-5-yl)-1H-pyrazolo[3,4-d]pyrimidin-1-yl)cyclohexyl)piperazin-1-yl)-2-methylbutan-2-ol; or
(cis)-4-(4-(4-(4-amino-3-(2-benzyl-1H-benzimidazol-5-yl)-1H-pyrazolo[3,4-d]pyrimidin-1-yl)cyclohexyl)piperazin-1-yl)-2-methylbutan-2-ol.

9. The compound or a salt thereof according to claim 1 selected from
(trans)-4-(4-amino-3-(2-(2-methoxybenzyl)-1H-benzimidazol-5-yl)-1H-pyrazolo[3,4-d]pyrimidin-1-yl)cyclohexanol;
(trans)-1-(4-(4-(3-methoxypropyl)piperazin-1-yl)cyclohexyl)-3-(2-(thien-2-ylmethyl)-1H-benzimidazol-6-yl)-1H-pyrazolo[3,4-d]pyrimidin-4-amine;
3-(2-benzyl-1H-benzimidazol-6-yl)-1-(1'-(3-methoxypropyl)-1,4'-bipiperidin-4-yl)-1H-pyrazolo[3,4-d]pyrimidin-4-amine;
3-(2-(2,6-difluorobenzyl)-1H-benzimidazol-5-yl)-1-(4-(morpholin-4-ylmethyl)phenyl)-1H-pyrazolo[3,4-d]pyrimidin-4-amine;
2-(4-(4-amino-3-(2-benzyl-1H-benzimidazol-6-yl)-1H-pyrazolo[3,4-d]pyrimidin-1-yl)-1,4'-bipiperidin-1'-yl)ethanol;
3-(4-(4-amino-3-(2-benzyl-1H-benzimidazol-6-yl)-1H-pyrazolo[3,4-d]pyrimidin-1-yl)-1,4'-bipiperidin-1'-yl)propan-1-ol;
3-(2-benzyl-1H-benzimidazol-6-yl)-1-(1'-(2-methoxylthyl)-1,4'-bipiperidin-4-yl)-1H-pyrazolo[3,4-d]pyrimidin-4-amine;
(trans)-1-(4-morpholin-4-ylcyclohexyl)-3-(2-(pyridin-2-ylmethyl)-1H-benzimidazol-6-yl)-1H-pyrazolo[3,4-d]pyrimidin-4-amine;
3-(2-benzyl-1H-benzimidazol-6-yl)-1-(1'-isobutyl-1,4'-bipiperidin-4-yl)-1H-pyrazolo[3,4-d]pyrimidin-4-amine;
(trans)-1-(4-morpholin-4-ylcyclohexyl)-3-(2-(pyridin-3-ylmethyl)-1H-benzimidazol-6-yl)-1H-pyrazolo[3,4-d]pyrimidin-4-amine;
(trans)-1-(4-morpholin-4-ylcyclohexyl)-3-(2-(thien-3-ylmethyl)-1H-benzimidazol-6-yl)-1H-pyrazolo[3,4-d]pyrimidin-4-amine;
(trans)-3-(2-(1,3-benzodioxol-5-ylmethyl)-1H-benzimidazol-6-yl)-1-(4-morpholin-4-ylcyclohexyl)-1H-pyrazolo[3,4-d]pyrimidin-4-amine;
(trans)-4-(4-amino-3-(2-(2-(trifluoromethoxy)benzyl)-1H-benzimidazol-5-yl)-1H-pyrazolo[3,4-d]pyrimidin-1-yl)cyclohexanol;
(trans)-1-(4-(4-(3-methoxypropyl)piperazin-1-yl)cyclohexyl)-3-(2-(2-(trifluoromethoxy)benzyl)-1H-benzimidazol-5-yl)-1H-pyrazolo[3,4-d]pyrimidin-4-amine;
(cis)-1-(4-(4-(3-methoxypropyl)piperazin-1-yl)cyclohexyl)-3-(2(2-(trifluoromethoxy)benzyl)-1H-benzimidazol-5-yl)-1H-pyrazolo[3,4-d]pyrimidin-4-amine;
(trans)-1-(4-morpholin-4-ylcyclohexyl)-3-(2-(2-naphthylmethyl)-1H-benzimidazol-6-yl)-1H-pyrazolo[3,4-d]pyrimidin-4-amine;
(trans)-3-(2(2,6-difluorobenzyl)-1H-benzimidazol-5-yl)-1-(4-(4-(3-methoxypropyl)piperazin-1-yl)cyclohexyl)-1H-pyrazolo[3,4-d]pyrimidin-4-amine; or
(cis)-3-(2-(2,6-difluorobenzyl)-1H-benzimidazol-5-yl)-1-(4-(4-(3-methoxypropyl)piperazin-1-yl)cyclohexyl)-1H-pyrazolo[3,4-d]pyrimidin-4-amine.

10. The compound or a salt thereof according to claim 1 selected from
(trans)-2-((6-(4-amino-1-(4-morpholin-4-ylcyclohexyl)-1H-pyrazolo[3,4-d]pyrimidin-3-yl)-1H-benzimidazol-2-yl)methyl)phenol;
3-(2-(2-methoxybenzyl)-1H-benzimidazol-5-yl)-1-(4-((4-(3-methoxypropyl)piperazin-1-yl)methyl)phenyl)-1H-pyrazolo[3,4-d]pyrimidin-4-amine;
(trans)-3-(2-((2-methyl-1,3-thiazol-4-yl)methyl)-1H-benzimidazol-6-yl)-1-(4-morpholin-4-ylcyclohexyl)-1H-pyrazolo[3,4-d]pyrimidin-4-amine;
3-(2-(2-methoxybenzyl)-1H-benzimidazol-5-yl)-1-(4-((4-(methylsulfonyl)piperazin-1-yl)methyl)phenyl)-1H-pyrazolo[3,4-d]pyrimidin-4-amine;
1-(4-(4-amino-3-(2-(2-methoxybenzyl)-1H-benzimidazol-5-yl)-1H-pyrazolo[3,4-d]pyrimidin-1-yl)cyclohexyl)piperidin-4-ol;
(trans)-4-(4-(4-amino-3-(2-(2-methoxybenzyl)-1H-benzimidazol-5-yl)-1H-pyrazolo[3,4-d]pyrimidin-1-yl)cyclohexyl)piperazin-2-one;
(cis)-4-(4-(4-amino-3-(2-(2-methoxybenzyl)-1H-benzimidazol-5-yl)-1H-pyrazolo[3,4-d]pyrimidin-1-yl)cyclohexyl)piperazin-2-one;
(trans)-3-(2-(2-methoxybenzyl)-1H-benzimidazol-6-yl)-1-(4-(2-(trifluoromethyl)-5,6-dihydroimidazo(1,2-a)pyrazin-7(8H)-yl)cyclohexyl)-1H-pyrazolo[3,4-d]pyrimidin-4-amine;

4-(4-amino-3-(2-(2-methoxybenzyl)-1H-benzimidazol-6-yl)-1H-pyrazolo[3,4-d]pyrimidin-1-yl)cyclohexanone; or (cis)-3-(2-(2-methoxybenzyl)-1H-benzimidazol-6-yl)-1-(4-(2-(trifluoromethyl)-5,6-dihydroimidazo(1,2-a)pyrazin-7(8H)-yl)cyclohexyl)-1H-pyrazolo[3,4-d]pyrimidin-4-amine.

11. The compound or a salt thereof according to claim 1 selected from (trans)-3-(2-(2-methoxybenzyl)-1H-benzimidazol-5-yl)-1-(4-piperazin-1-ylcyclohexyl)-1H-pyrazolo[3,4-d]pyrimidin-4-amine;

(trans)-3-(2-(2-methoxybenzyl)-1H-benzimidazol-5-yl)-1-(4-(4-methylpiperazin-1-yl)cyclohexyl)-1H-pyrazolo[3,4-d]pyrimidin-4-amine;

(trans)-1-(4-(4-ethylpiperazin-1-yl)cyclohexyl)-3-(2-(2-methoxybenzyl)-1H-benzimidazol-6-yl)-1H-pyrazolo[3,4-d]pyrimidin-4-amine;

(cis)-1-(4-(4-ethylpiperazin-1-yl)cyclohexyl)-3-(2-(2-methoxybenzyl)-1H-benzimidazol-6-yl)-1H-pyrazolo[3,4-d]pyrimidin-4-amine;

(trans)-1-(4-(4-ac etylpiperazin-1-yl)cyclohexyl)-3-(2-(3-methoxybenzyl)-1H-benzimidazol-6-yl)-1H-pyrazolo[3,4-d]pyrimidin-4-amine;

(trans)-4-(4-(4-(4-amino-3-(2-(2-methoxybenzyl)-1H-benzimidazol-6-yl)-1H-pyrazolo[3,4-d]pyrimidin-1-yl)cyclohexyl)piperazin-1-yl)-2-methylbutan-2-ol;

(cis)-4-(4-(4-(4-amino-3-(2-(3-methoxybenzyl)-1H-benzimidazol-6-yl)-1H-pyrazolo[3,4-d]pyrimidin-1-yl)cyclohexyl)piperazin-1-yl)-2-methylbutan-2-ol;

(cis)-2-(4-(4-(4-amino-3-(2-(2-methoxybenzyl)-1H-benzimidazol-6-yl)-1H-pyrazolo[3,4-d]pyrimidin-1-yl)cyclohexyl)piperazin-1-yl)ethanol;

(trans)-2-(4-(4-(4-amino-3-(2-(2-methoxybenzyl)-1H-benzimidazol-6-yl)-1H-pyrazolo[3,4-d]pyrimidin-1-yl)cyclohexyl)piperazin-1-yl)ethanol;

(trans)-4-(4-(4-amino-3-(2-(2-methoxybenzyl)-1H-benzimidazol-6-yl)-1H-pyrazolo[3,4-d]pyrimidin-1-yl)cyclohexyl)-N,N-dimethylpiperazine-1-carboxamide;

(cis)-4-(4-(4-amino-3-(2-(2-methoxybenzyl)-1H-benzimidazol-6-yl)-1H-pyrazolo[3,4-d]pyrimidin-1-yl)cyclohexyl)-N,N-dimethylpiperazine-1-carboxamide;

(trans)-ethyl 4-(4-(4-amino-3-(2-(2-methoxybenzyl)-1H-benzimidazol-6-yl)-1H-pyrazolo[3,4-d]pyrimidin-1-yl)cyclohexyl)piperazine-1-carboxylate;

(cis)-ethyl 4-(4-(4-amino-3-(2-(2-methoxybenzyl)-1H-benzimidazol-6-yl)-1H-pyrazolo[3,4-d]pyrimidin-1-yl)cyclohexyl)piperazine-1-carboxylate;

(cis)-3-(7-chloro-2-(2-methoxybenzyl)-1H-benzimidazol-5-yl)-1-(4-(4-(3-methoxypropyl)piperazin-1-yl)cyclohexyl)-1H-pyrazolo[3,4-d]pyrimidin-4-amine;

(trans)-1-(4-(4-(ethylsulfonyl)piperazin-1-yl)cyclohexyl)-3-(2-(2-methoxybenzyl)-1H-benzimidazol-6-yl)-1H-pyrazolo[3,4-d]pyrimidin-4-amine;

(cis)-1-(4-(4-(ethylsulfonyl)piperazin-1-yl)cyclohexyl)-3-(2-(2-methoxybenzyl)-1H-benzimidazol-6-yl)-1H-pyrazolo[3,4-d]pyrimidin-4-amine; or (trans)-3-(7-chloro-2-(2-methoxybenzyl)-1H-benzimidazol-5-yl)-1-(4-(4-(3-methoxypropyl)piperazin-1-yl)cyclohexyl)-1H-pyrazolo[3,4-d]pyrimidin-4-amine.

12. The compound or a salt thereof according to claim 1 selected from (trans)-4-(4-(4-(4-amino-3-(2-(2,6-difluorobenzyl)-1H-benzimidazol-5-yl)-1H-pyrazolo[3,4-d]pyrimidin-1-yl)cyclohexyl)piperazin-1-yl)-2-methylbutan-2-ol;

(cis)-4-(4-(4-(4-amino-3-(2-(2,6-difluorobenzyl)-1H-benzimidazol-5-yl)-1H-pyrazolo[3,4-d]pyrimidin-1-yl)cyclohexyl)piperazin-1-yl)-2-methylbutan-2-ol;

(trans)-2-(4-(4-(4-amino-3-(2-(2,6-difluorobenzyl)-1H-benzimidazol-5-yl)-1H-pyrazolo[3,4-d]pyrimidin-1-yl)cyclohexyl)piperazin-1-yl)ethanol;

(cis)-2-(4-(4-(4-amino-3-(2-(2,6-difluorobenzyl)-1H-benzimidazol-5-yl)-1H-pyrazolo[3,4-d]pyrimidin-1-yl)cyclohexyl)piperazin-1-yl)ethanol;

(trans)-3-(2-(2,6-difluorobenzyl)-1H-benzimidazol-5-yl)-1-(4-(4-ethylpiperazin-1-yl)cyclohexyl)-1H-pyrazolo[3,4-d]pyrimidin-4-amine;

(cis)-3-(2-(2,6-difluorobenzyl)-1H-benzimidazol-5-yl)-1-(4-(4-ethylpiperazin-1-yl)cyclohexyl)-1H-pyrazolo[3,4-d]pyrimidin-4-amine;

(trans)-3-(2-(2-methoxybenzyl)-1H-benzimidazol-6-yl)-1-(4-(4-(2-methoxylthyl)piperazin-1-yl)cyclohexyl)-1H-pyrazolo[3,4-d]pyrimidin-4-amine;

(cis)-3-(2-(2-methoxybenzyl)-1H-benzimidazol-6-yl)-1-(4-(4-(2-methoxylthyl)piperazin-1-yl)cyclohexyl)-1H-pyrazolo[3,4-d]pyrimidin-4-amine;

(trans)-1-(4-(4-isopropylpiperazin-1-yl)cyclohexyl)-3-(2-(2-methoxybenzyl)-1H-benzimidazol-6-yl)-1H-pyrazolo[3,4-d]pyrimidin-4-amine;

(cis)-1-(4-(4-isopropylpiperazin-1-yl)cyclohexyl)-3-(2-(2-methoxybenzyl)-1H-benzimidazol-6-yl)-1H-pyrazolo[3,4-d]pyrimidin-4-amine;

(trans)-3-(2-(cyclohexylmethyl)-1H-benzimidazol-6-yl)-1-(4-(4-(3-methoxypropyl)piperazin-1-yl)cyclohexyl)-1H-pyrazolo[3,4-d]pyrimidin-4-amine;

(trans)-3-(2-(cyclopentylmethyl)-1H-benzimidazol-6-yl)-1-(4-(4-(3-methoxypropyl)piperazin-1-yl)cyclohexyl)-1H-pyrazolo[3,4-d]pyrimidin-4-amine;

(trans)-3-(2-(2-methoxybenzyl)-1H-benzimidazol-6-yl)-1-(4-(4-phenylpiperazin-1-yl)cyclohexyl)-1H-pyrazolo[3,4-d]pyrimidin-4-amine;

(cis)-3-(2-(2-methoxybenzyl)-1H-benzimidazol-6-yl)-1-(4-(4-phenylpiperazin-1-yl)cyclohexyl)-1H-pyrazolo[3,4-d]pyrimidin-4-amine;

(trans)-3-(2-(2-chlorobenzyl)-1H-benzimidazol-6-yl)-1-(4-(4-ethylpiperazin-1-yl)cyclohexyl)-1H-pyrazolo[3,4-d]pyrimidin-4-amine;

(cis)-3-(2-(2-chlorobenzyl)-1H-benzimidazol-6-yl)-1-(4-(4-ethylpiperazin-1-yl)cyclohexyl)-1H-pyrazolo[3,4-d]pyrimidin-4-amine;

(trans)-2-(4-(4-(4-amino-3-(2-(2-chlorobenzyl)-1H-benzimidazol-6-yl)-1H-pyrazolo[3,4-d]pyrimidin-1-yl)cyclohexyl)piperazin-1-yl)ethanol; or (cis)-2-(4-(4-(4-amino-3-(2-(2-chlorobenzyl)-1H-benzimidazol-6-yl)-1H-pyrazolo[3,4-d]pyrimidin-1-yl)cyclohexyl)piperazin-1-yl)ethanol.

13. A compound having formula (6)

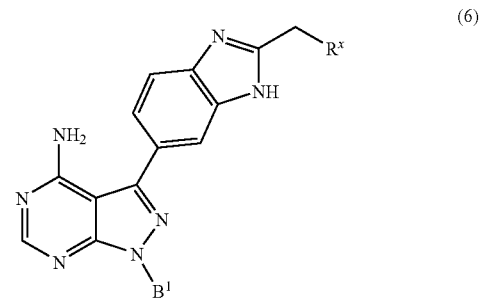

or a salt thereof, wherein
R$^x$ and the moiety to which it is attached form A$^1$;
A$^1$ is R$^2$; wherein R$^2$ is 2-substituted with R$^6$, wherein R$^6$ is R$^{10}$, and further wherein R$^{10}$ is methyl which is unsubstituted or substituted with one or two of independently selected R$^{11}$, OR$^{11}$, SR$^{11}$, S(O)R$^{11}$, SO$_2$R$^{11}$, NH$_2$, NHR$^{11}$, N(R$^{11}$)$_2$, C(O)R$^{11}$, C(O)NH$_2$, C(O)NHR$^{11}$, C(O)N(R$^{11}$)$_2$, NHC(O)R$^{11}$, NR$^{11}$C(O)R$^{11}$, NHSO$_2$R$^{11}$, NR$^{11}$SO$_2$R$^{11}$, NHC(O)OR$^{11}$, NR$^{11}$C(O)OR$^{11}$, SO$_2$NH$_2$, SO$_2$NHR$^{11}$, SO$_2$N(R$^{11}$)$_2$, NHC(O)NH$_2$, NHC(O)NHR$^{11}$, NHC(O)N(R$^{11}$)$_2$, NR$^{11}$C(O)N(R$^{11}$)$_2$, OH, (O), C(O)OH, CN, CF$_3$, OCF$_3$, CF$_2$CF$_3$, F, Cl, Br or I;
R$^2$ is 1H-benzo[d]imidazol-6-yl;
B$^1$ is R$^3$, R$^4$, R$^5$ or W$^1$;
R$^3$ is phenyl which is unfused or fused with benzene, heteroarene or R$^{3.4}$; R$^{3.4}$ is cycloalkane, cycloalkene, heterocycloalkane or heterocycloalkene;
R$^4$ is heteroaryl which is unfused or fused with benzene, heteroarene or R$^{4.4}$; R$^{4.4}$ is cycloalkane, cycloalkene, heterocycloalkane or heterocycloalkene;
R$^5$ is cycloalkyl, cycloalkenyl, heterocycloalkyl or heterocycloalkenyl, each of which is unfused or fused with benzene, heteroarene or R$^{5.4}$; R$^{5.4}$ is cycloalkane, cycloalkene, heterocycloalkane or heterocycloalkene;
W$^1$ is alkyl, alkenyl or alkynyl, each of which is unsubstituted or substituted with one or two of independently selected W$^2$, W$^3$, W$^4$, OH, OW$^5$, SW$^5$, S(O)W$^5$, SO$_2$W$^5$, NH$_2$, NHW$^5$, N(W$^5$)$_2$, C(O)NH$_2$, C(O)NHW$^5$, C(O)N(W$^5$)$_2$, NHC(O)W$^5$ or NW$^5$C(O)W$^5$;
W$^2$ is phenyl which is unfused or fused with benzene, heteroarene or W$^{2.4}$; W$^{2.4}$ is cycloalkane, cycloalkene, heterocycloalkane or heterocycloalkene;
W$^3$ is heteroaryl which is unfused or fused with benzene, heteroarene or W$^{3.4}$; W$^{3.4}$ is cycloalkane, cycloalkene, heterocycloalkane or heterocycloalkene;
W$^4$ is cycloalkyl, cycloalkenyl, heterocycloalkyl or heterocycloalkenyl, each of which is unfused or fused with benzene, heteroarene or W$^{5.4}$; W$^{5.4}$ is cycloalkane, cycloalkene, heterocycloalkane or heterocycloalkene;
W$^5$ is alkyl, alkenyl or alkynyl;
wherein the moieties represented by B$^1$, W$^1$, W$^2$, W$^3$ and W$^4$ are independently unsubstituted or substituted with one or two or three or four of independently selected R$^6$, OR$^6$, SR$^6$, S(O)R$^6$, SO$_2$R$^6$, NH$_2$, NHR$^6$, N(R$^6$)$_2$, C(O)R$^6$, C(O)OR$^6$, C(O)NH$_2$, C(O)NHR$^6$, C(O)N(R$^6$)$_2$, NHC(O)R$^6$, NR$^6$C(O)R$^6$, NHSO$_2$R$^6$, NR$^6$SO$_2$R$^6$, NHC(O)OR$^6$, NR$^6$C(O)OR$^6$, SO$_2$NH$_2$, SO$_2$NHR$^6$, SO$_2$N(R$^6$)$_2$, NHC(O)NH$_2$, NHC(O)NHR$^6$, NHC(O)N(R$^6$)$_2$, NR$^6$C(O)N(R$^6$)$_2$, C(NH)NH$_2$, C(NH)NHR$^6$, C(NH)N(R$^6$)$_2$, NHC(NH)NH$_2$, NHC(NH)NHR$^6$, NHC(NH)N(R$^6$)$_2$, OH, (O), C(O)H, C(O)OH, NO$_2$, CN, CF$_3$, OCF$_3$, CF$_2$CF$_3$, F, Cl, Br or I;
R$^6$ is R$^7$, R$^8$, R$^9$ or R$^{10}$;
R$^7$ is phenyl which is unfused or fused with benzene, heteroarene or R$^{7.4}$; R$^{7.4}$ is cycloalkane, cycloalkene, heterocycloalkane or heterocycloalkene;
R$^8$ is heteroaryl which is unfused or fused with benzene, heteroarene or R$^{8.4}$; R$^{8.4}$ is cycloalkane, cycloalkene, heterocycloalkane or heterocycloalkene;
R$^9$ is cycloalkyl, cycloalkenyl, heterocycloalkyl or heterocycloalkenyl, each of which is unfused or fused with benzene, heteroarene or R$^{9.4}$; R$^{9.4}$ is cycloalkane, cycloalkene, heterocycloalkane or heterocycloalkene;
R$^{10}$ is alkyl, alkenyl or alkynyl, each of which is unsubstituted or substituted with one or two of independently selected R$^{11}$, OR$^{11}$, SR$^{11}$, S(O)R$^{11}$, SO$_2$R$^{11}$, NH$_2$, NHR$^{11}$, N(R$^{11}$)$_2$, C(O)R$^{11}$, C(O)NH$_2$, C(O)NHR$^{11}$, C(O)N(R$^{11}$)$_2$, NHC(O)R$^{11}$, NR$^{11}$C(O)R$^{11}$, NHSO$_2$R$^{11}$, NR$^{11}$SO$_2$R$^{11}$, NHC(O)OR$^{11}$, NR$^{11}$C(O)OR$^{11}$, SO$_2$NH$_2$, SO$_2$NHR$^{11}$, SO$_2$N(R$^{11}$)$_2$, NHC(O)NH$_2$, NHC(O)NHR$^{11}$, NHC(O)N(R$^{11}$)$_2$, NR$^{11}$C(O)N(R$^{11}$)$_2$, OH, (O), C(O)OH, CN, CF$_3$, OCF$_3$, CF$_2$CF$_3$, F, Cl, Br or I;
R$^{11}$ is alkyl, alkenyl, alkynyl, R$^{12}$, R$^{13}$ or R$^{14}$;
R$^{12}$ is phenyl which is unfused or fused with benzene, heteroarene or R$^{12.4}$; R$^{12.4}$ is cycloalkane, cycloalkene, heterocycloalkane or heterocycloalkene;
R$^{13}$ is heteroaryl which is unfused or fused with benzene, heteroarene or R13A; R$^{13.4}$ is cycloalkane, cycloalkene, heterocycloalkane or heterocycloalkene; and
R$^{14}$ is cycloalkyl, cycloalkenyl, heterocycloalkyl or heterocycloalkenyl, each of which is unfused or fused with benzene, heteroarene or R$^{14.4}$; R$^{14.4}$ is cycloalkane, cycloalkene, heterocycloalkane or heterocycloalkene;
wherein the moieties represented by R$^7$, R$^8$, R$^9$ and R$^{11}$ are independently unsubstituted or substituted with one or two or three or four of independently selected R$^{15}$, OR$^{15}$, SR$^{15}$, S(O)R$^{15}$, SO$_2$R$^{15}$, C(O)R$^{15}$, C(O)NH$_2$, C(O)NHR$^{15}$, C(O)N(R$^{15}$)$_2$, OH, (O), C(O)OH, CN, CF$_3$, OCF$_3$, CF$_2$CF$_3$, F, Cl, Br or I, wherein
R$^{15}$ is alkyl, alkenyl, alkynyl, each of which is unsubstituted or substituted with OH, OR$^{16}$, C(O)NH$_2$, C(O)NHR$^{16}$, C(O)N(R$^{16}$)$_2$, wherein
R$^{16}$ is alkyl, alkenyl or alkynyl.

14. A compound or a salt thereof selected from
cis-3-(2-anilino-1,3-benzoxazol-6-yl)-1-(4-(4-methylpiperazin-1-yl)cyclohexyl)-1H-pyrazolo[3,4-d]pyrimidin-4-amine;
trans-3-(2-anilino-1,3-benzoxazol-6-yl)-1-(4-(4-methylpiperazin-1-yl)cyclohexyl)-1H-pyrazolo[3,4-d]pyrimidin-4-amine;
trans-3-(2-anilino-1,3-benzoxazol-6-yl)-1-(4-morpholin-4-ylcyclohexyl)-1H-pyrazolo[3,4-d]pyrimidin-4-amine;
trans-3-(2-anilino-1,3-benzoxazol-6-yl)-1-(4-(2-methoxylthoxy)cyclohexyl)-1H-pyrazolo[3,4-d]pyrimidin-4-amine;
trans-3-(1-(2-chlorobenzyl)-1H-indol-4-yl)-1-(4-morpholin-4-ylcyclohexyl)-1H-pyrazolo[3,4-d]pyrimidin-4-amine;
trans-3-(1-(2-chlorobenzyl)-1H-indol-6-yl)-1-(4-morpholin-4-ylcyclohexyl)-1H-pyrazolo[3,4-d]pyrimidin-4-amine;
trans-3-(1-(2-chlorobenzyl)-1H-indol-5-yl)-1-(4-morpholin-4-ylcyclohexyl)-1H-pyrazolo[3,4-d]pyrimidin-4-amine;
trans-3-(1-(3-chlorobenzyl)-1H-indol-5-yl)-1-(4-morpholin-4-ylcyclohexyl)-1H-pyrazolo[3,4-d]pyrimidin-4-amine;
trans-3-(2-benzyl-1,3-benzoxazol-5-yl)-1-(4-morpholin-4-ylcyclohexyl)-1H-pyrazolo[3,4-d]pyrimidin-4-amine;
trans-3-(1-(2-chlorobenzyl)-1H-indazol-6-yl)-1-(4-morpholin-4-ylcyclohexyl)-1H-pyrazolo[3,4-d]pyrimidin-4-amine;
trans-3-(1-(3-chlorobenzyl)-1H-indazol-6-yl)-1-(4-morpholin-4-ylcyclohexyl)-1H-pyrazolo[3,4-d]pyrimidin-4-amine;
trans-3-(2-benzyl-1,3-benzoxazol-6-yl)-1-(4-morpholin-4-ylcyclohexyl)-1H-pyrazolo[3,4-d]pyrimidin-4-amine;
trans-3-(1-(3-fluorobenzyl)-1H-indazol-6-yl)-1-(4-morpholin-4-ylcyclohexyl)-1H-pyrazolo[3,4-d]pyrimidin-4-amine;

trans-3-(3-((2,4-dimethylphenyl)amino)-1H-indazol-6-yl)-1-(4-morpholin-4-ylcyclohexyl)-1H-pyrazolo[3,4-d]pyrimidin-4-amine;
trans-3-(3-((2-chlorophenyl)amino)-1H-indazol-5-yl)-1-(4-morpholin-4-ylcyclohexyl)-1H-pyrazolo[3,4-d]pyrimidin-4-amine;
trans-3-(3-((3-chlorophenyl)amino)-1H-indazol-5-yl)-1-(4-morpholin-4-ylcyclohexyl)-1H-pyrazolo[3,4-d]pyrimidin-4-amine;
trans-3-(3-((3-fluorophenyl)amino)-1H-indazol-5-yl)-1-(4-morpholin-4-ylcyclohexyl)-1H-pyrazolo[3,4-d]pyrimidin-4-amine;
trans-1-(4-morpholin-4-ylcyclohexyl)-3-(3-((3-nitrophenyl)amino)-1H-indazol-5-yl)-1H-pyrazolo[3,4-d]pyrimidin-4-amine;
trans-3-(3-((2-methoxyphenyl)amino)-1H-indazol-5-yl)-1-(4-morpholin-4-ylcyclohexyl)-1H-pyrazolo[3,4-d]pyrimidin-4-amine;
trans-1-(4-morpholin-4-ylcyclohexyl)-3-(3-((6-(trifluoromethyl)pyridin-3-yl)amino)-1H-indazol-5-yl)-1H-pyrazolo[3,4-d]pyrimidin-4-amine;
trans-3-(3-(benzylamino)-1H-indazol-6-yl)-1-(4-morpholin-4-ylcyclohexyl)-1H-pyrazolo[3,4-d]pyrimidin-4-amine;
trans-1-(4-morpholin-4-ylcyclohexyl)-3-(3-((4-(trifluoromethyl)phenylamino)-1H-indazol-5-yl)-1H-pyrazolo[3,4-d]pyrimidin-4-amine;
trans-3-(3-((4-tert-butylphenyl)amino)-1H-indazol-5-yl)-1-(4-morpholin-4-ylcyclohexyl)-1H-pyrazolo[3,4-d]pyrimidin-4-amine;
trans-3-((5-(4-amino-1-(4-morpholin-4-ylcyclohexyl)-1H-pyrazolo[3,4-d]pyrimidin-3-yl)-1H-indazol-3-yl)amino)phenol;
trans-3-(3-((2-fluoro-5-methylphenyl)amino)-1H-indazol-6-yl)-1-(4-morpholin-4-ylcyclohexyl)-1H-pyrazolo[3,4-d]pyrimidin-4-amine;
trans-3-(3-((2,5-dimethylphenyl)amino)-1H-indazol-6-yl)-1-(4-morpholin-4-ylcyclohexyl)-1H-pyrazolo[3,4-d]pyrimidin-4-amine;
trans-3-(3-((2,5-difluorophenyl)amino)-1H-indazol-6-yl)-1-(4-morpholin-4-ylcyclohexyl)-1H-pyrazolo[3,4-d]pyrimidin-4-amine;
trans-3-(3-b[(4-fluoro-2-methylphenyl)amino]-1H-indazol-6-yl)-1-(4-morpholin-4-ylcyclohexyl)-1H-pyrazolo[3,4-d]pyrimidin-4-amine and
(trans)-3-(1-(2-chlorobenzyl)-1H-indol-5-yl)-1-(4-morpholin-4-ylcyclohexyl)-1H-pyrazolo[3,4-d]pyrimidin-4-amine;
(trans)-3-(1-(2-chlorobenzyl)-1H-indazol-6-yl)-1-(4-morpholin-4-ylcyclohexyl)-1H-pyrazolo[3,4-d]pyrimidin-4-amine;
(trans)-3-(1-benzyl-1H-indol-5-yl)-1-(4-morpholin-4-ylcyclohexyl)-1H-pyrazolo[3,4-d]pyrimidin-4-amine;
(trans)-3-(1-(2-methylbenzyl)-1H-indol-5-yl)-1-(4-morpholin-4-ylcyclohexyl)-1H-pyrazolo[3,4-d]pyrimidin-4-amine;
(trans)-3-(1-(3-methylbenzyl)-1H-indol-5-yl)-1-(4-morpholin-4-ylcyclohexyl)-1H-pyrazolo[3,4-d]pyrimidin-4-amine; or
(trans)-3-(1-(2-fluorobenzyl)-1H-indol-5-yl)-1-(4-morpholin-4-ylcyclohexyl)-1H-pyrazolo[3,4-d]pyrimidin-4-amine.

15. A compound or a salt thereof selected from
(trans)-3-(1-(3-fluorobenzyl)-1H-indol-5-yl)-1-(4-morpholin-4-ylcyclohexyl)-1H-pyrazolo[3,4-d]pyrimidin-4-amine;
(trans)-1-(4-morpholin-4-ylcyclohexyl)-3-(1-(2-(trifluoromethyl)benzyl)-1H-indol-5-yl)-1H-pyrazolo[3,4-d]pyrimidin-4-amine;
(trans)-3-(1-(2-fluorobenzyl)-1H-indazol-5-yl)-1-(4-morpholin-4-ylcyclohexyl)-1H-pyrazolo[3,4-d]pyrimidin-4-amine;
(trans)-3-(1-(2-chlorobenzyl)-1H-indazol-5-yl)-1-(4-morpholin-4-ylcyclohexyl)-1H-pyrazolo[3,4-d]pyrimidin-4-amine;
(trans)-3-(1-(3-chlorobenzyl)-1H-indazol-5-yl)-1-(4-morpholin-4-ylcyclohexyl)-1H-pyrazolo[3,4-d]pyrimidin-4-amine;
(trans)-3-(1-benzyl-1H-indazol-5-yl)-1-(4-morpholin-4-ylcyclohexyl)-1H-pyrazolo[3,4-d]pyrimidin-4-amine;
(trans)-3-(1-(cyclohexylmethyl)-1H-indol-5-yl)-1-(4-morpholin-4-ylcyclohexyl)-1H-pyrazolo[3,4-d]pyrimidin-4-amine;
(trans)-3-(1-cyclopenty1-1H-indol-5-yl)-1-(4-morpholin-4-ylcyclohexyl)-1H-pyrazolo[3,4-d]pyrimidin-4-amine;
(trans)-3-(1-(2,3-difluorobenzyl)-1H-indol-5-yl)-1-(4-morpholin-4-ylcyclohexyl)-1H-pyrazolo[3,4-d]pyrimidin-4-amine;
(trans)-3-(1-(2,5-difluorobenzyl)-1H-indol-5-yl)-1-(4-morpholin-4-ylcyclohexyl)-1H-pyrazolo[3,4-d]pyrimidin-4-amine;
(trans)-3-(1-(2,6-difluorobenzyl)-1H-indol-5-yl)-1-(4-morpholin-4-ylcyclohexyl)-1H-pyrazolo[3,4-d]pyrimidin-4-amine;
(trans)-3-(1-(2,5-dichlorobenzyl)-1H-indol-5-yl)-1-(4-morpholin-4-ylcyclohexyl)-1H-pyrazolo[3,4-d]pyrimidin-4-amine;
(trans)-3-(1-(2,6-dichlorobenzyl)-1H-indol-5-yl)-1-(4-morpholin-4-ylcyclohexyl)-1H-pyrazolo[3,4-d]pyrimidin-4-amine;
(trans)-2-(4-(4-(4-amino-3-(1-(2-chlorobenzyl)-1H-indol-5-yl)-1H-pyrazolo[3,4-d]pyrimidin-1-yl)cyclohexyl)piperazin-1-yl)ethanol;
(trans)-3-(1-(2-fluorobenzyl)-1H-indazol-6-yl)-1-(4-morpholin-4-ylcyclohexyl)-1H-pyrazolo[3,4-d]pyrimidin-4-amine;
3-(1-(2-chlorobenzyl)-1H-indol-5-yl)-1-(4-(4-(2-ethoxylthyl)piperazin-1-yl)cyclohexyl)-1H-pyrazolo[3,4-d]pyrimidin-4-amine;
(cis)-2-(4-(4-(4-amino-3-(1-(2-chlorobenzyl)-1H-indol-5-yl)-1H-pyrazolo[3,4-d]pyrimidin-1-yl)cyclohexyl)piperazin-1-yl)ethanol;
4-(4-amino-3-(1-(2-chlorobenzyl)-1H-indol-5-yl)-1H-pyrazolo[3,4-d]pyrimidin-1-yl)cyclohexanol;
(cis)-3-(4-(4-(4-amino-3-(1-(2-chlorobenzyl)-1H-indol-5-yl)-1H-pyrazolo[3,4-d]pyrimidin-1-yl)cyclohexyl)piperazin-1-yl)propan-1-ol;
(trans)-3-(4-(4-(4-amino-3-(1-(2-chlorobenzyl)-1H-indol-5-yl)-1H-pyrazolo[3,4-d]pyrimidin-1-yl)cyclohexyl)piperazin-1-yl)propan-1-ol;
2-(1-(4-(4-amino-3-(1-(2-chlorobenzyl)-1H-indol-5-yl)-1H-pyrazolo[3,4-d]pyrimidin-1-yl)cyclohexyl)piperidin-4-yl)ethanol;
(trans)-2-(1-(4-(4-amino-3-(1-(2-chlorobenzyl)-1H-indol-5-yl)-1H-pyrazolo[3,4-d]pyrimidin-1-yl)cyclohexyl)piperidin-4-yl)ethanol;
(cis)-(1-(4-(4-amino-3-(1-(2-chlorobenzyl)-1H-indol-5-yl)-1H-pyrazolo[3,4-d]pyrimidin-1-yl)cyclohexyl)piperidin-4-yl)methanol;
(trans)-(1-(4-(4-amino-3-(1-(2-chlorobenzyl)-1H-indol-5-yl)-1H-pyrazolo[3,4-d]pyrimidin-1-yl)cyclohexyl)piperidin-4-yl)methanol;

(cis)-3-(1-(2-chlorobenzyl)-1H-indol-5-yl)-1-(4-(4-(3-methoxypropyl)piperazin-1-yl)cyclohexyl)-1H-pyrazolo[3,4-d]pyrimidin-4-amine;
(trans)-3-(1-(2-chlorobenzyl)-1H-indol-5-yl)-1-(4-(4-(3-methoxypropyl)piperazin-1-yl)cyclohexyl)-1H-pyrazolo[3,4-d]pyrimidin-4-amine;
3-(1-(2-chlorobenzyl)-1H-indol-5-yl)-1-(4-pyrrolidin-1-ylcyclohexyl)-1H-pyrazolo[3,4-d]pyrimidin-4-amine;
3-(4-(4-(4-amino-3-(1-(2-chlorobenzyl)-1H-indol-5-yl)-1H-pyrazolo[3,4-d]pyrimidin-1-yl)cyclohexyl)piperazin-1-yl)propanenitrile;
3-(1-(2-fluorobenzyl)-1H-indol-5-yl)-1-(4-(4-(3-methoxypropyl)piperazin-1-yl)cyclohexyl)-1H-pyrazolo[3,4-d]pyrimidin-4-amine;
1-(4-(4-(2-ethoxylthyl)piperazin-1-yl)cyclohexyl)-3-(1-(2-fluorobenzyl)-1H-indol-5-yl)-1H-pyrazolo[3,4-d]pyrimidin-4-amine;
(cis)-2-(4-(4-(4-amino-3-(1-(2-fluorobenzyl)-1H-indol-5-yl)-1H-pyrazolo[3,4-d]pyrimidin-1-yl)cyclohexyl)piperazin-1-yl)ethanol;
(trans)-2-(4-(4-(4-amino-3-(1-(2-fluorobenzyl)-1H-indol-5-yl)-1H-pyrazolo[3,4-d]pyrimidin-1-yl)cyclohexyl)piperazin-1-yl)ethanol; or
(cis)-3-(4-(4-(4-amino-3-(1-(2-fluorobenzyl)-1H-indol-5-yl)-1H-pyrazolo[3,4-d]pyrimidin-1-yl)cyclohexyl)piperazin-1-yl)propan-1-ol.

16. A compound or a salt thereof selected from
(trans)-3-(4-(4-(4-amino-3-(1-(2-fluorobenzyl)-1H-indol-5-yl)-1H-pyrazolo[3,4-d]pyrimidin-1-yl)cyclohexyl)piperazin-1-yl)propan-1-ol;
3-(4-(4-(4-amino-3-(1-(2-fluorobenzyl)-1H-indol-5-yl)-1H-pyrazolo[3,4-d]pyrimidin-1-yl)cyclohexyl)piperazin-1-yl)propanenitrile;
3-(1-(2-chlorobenzyl)-1H-indol-5-yl)-1-(3-(1,1-dioxidothiomorpholin-4-yl)propyl)-1H-pyrazolo[3,4-d]pyrimidin-4-amine;
3-(1-(2-chlorobenzyl)-1H-indol-5-yl)-1-(4-(1,1-dioxidothiomorpholin-4-yl)but-2-ynyl)-1H-pyrazolo[3,4-d]pyrimidin-4-amine;
1-(4-(4-acetylpiperazin-1-yl)but-2-ynyl)-3-(1-(2-chlorobenzyl)-1H-indol-5-yl)-1H-pyrazolo[3,4-d]pyrimidin-4-amine;
3-(1-(2-chlorobenzyl)-1H-indol-5-yl)-1-(4-(4-(2-methoxylthyl)piperazin-1-yl)but-2-ynyl)-1H-pyrazolo[3,4-d]pyrimidin-4-amine;
1-((4-benzylmorpholin-2-yl)methyl)-3-(1-(2-chlorobenzyl)-1H-indol-5-yl)-1H-pyrazolo[3,4-d]pyrimidin-4-amine;
(trans)-1-(4-morpholin-4-ylcyclohexyl)-3-(1-(tetrahydro-2H-pyran-2-ylmethyl)-1H-indol-5-yl)-1H-pyrazolo[3,4-d]pyrimidin-4-amine;
(trans)-1-(4-morpholin-4-ylcyclohexyl)-3-(1-(pyridin-3-ylmethyl)-1H-indol-5-yl)-1H-pyrazolo[3,4-d]pyrimidin-4-amine;
(trans)-1-(4-morpholin-4-ylcyclohexyl)-3-(1-(pyridin-2-ylmethyl)-1H-indol-5-yl)-1H-pyrazolo[3,4-d]pyrimidin-4-amine;
3-(1-(2-chlorobenzyl)-1H-indol-5-yl)-1-tetrahydro-2H-pyran-4-yl-1H-pyrazolo[3,4-d]pyrimidin-4-amine;
3-(1-(2-chlorobenzyl)-1H-indol-5-yl)-1-(3-methoxypropyl)-1H-pyrazolo[3,4-d]pyrimidin-4-amine;
3-(1-(2-chlorobenzyl)-1H-indol-5-yl)-1-(1-methylpiperidin-4-yl)-1H-pyrazolo[3,4-d]pyrimidin-4-amine;
3-(1-(2-chlorobenzyl)-1H-indol-5-yl)-1-(3-(dimethylamino)propyl)-1H-pyrazolo[3,4-d]pyrimidin-4-amine;
3-(1-(2-chlorobenzyl)-1H-indol-5-yl)-1-(1'-methyl-1,4'-bipiperidin-4-yl)-1H-pyrazolo[3,4-d]pyrimidin-4-amine;
3-(1-(2-chlorobenzyl)-1H-indol-5-yl)-1-(1'-bethyl-1,4'-bipiperidin-4-yl)-1H-pyrazolo[3,4-d]pyrimidin-4-amine;
3-(1-(2-chlorobenzyl)-1H-indol-5-yl)-1-(1'-propyl-1,4'-bipiperidin-4-yl)-1H-pyrazolo[3,4-d]pyrimidin-4-amine;
3-(1-(2-chlorobenzyl)-1H-indol-5-yl)-1-(1'-isopropyl-1,4'-bipiperidin-4-yl)-1H-pyrazolo[3,4-d]pyrimidin-4-amine;
3-(1-(2-chlorobenzyl)-1H-indol-5-yl)-1-(1'-isobutyl-1,4'-bipiperidin-4-yl)-1H-pyrazolo[3,4-d]pyrimidin-4-amine;
(trans)-3-(2-benzyl-1H-indol-5-yl)-1-(4-morpholin-4-ylcyclohexyl)-1H-pyrazolo[3,4-d]pyrimidin-4-amine;
(trans)-3-(2-benzyl-1H-indol-6-yl)-1-(4-morpholin-4-ylcyclohexyl)-1H-pyrazolo[3,4-d]pyrimidin-4-amine;
3-(1-(2-chlorobenzyl)-1H-indol-5-yl)-1-(4-((4-(3-methoxypropyl)piperazin-1-yl)methyl)phenyl)-1H-pyrazolo[3,4-d]pyrimidin-4-amine;
(trans)-3-(2-(2-chlorobenzyl)-1H-indol-6-yl)-1-(4-morpholin-4-ylcyclohexyl)-1H-pyrazolo[3,4-d]pyrimidin-4-amine;
(3-((4-(4-amino-3-(1-(2-fluorobenzyl)-1H-indol-5-yl)-1H-pyrazolo[3,4-d]pyrimidin-1-yl)cyclohexyl)amino)phenyl)methanol;
4-((4-(4-amino-3-(1-(2-fluorobenzyl)-1H-indol-5-yl)-1H-pyrazolo[3,4-d]pyrimidin-1-yl)cyclohexyl)amino)-3-methylphenol;
3-((4-(4-amino-3-(1-(2-fluorobenzyl)-1H-indol-5-yl)-1H-pyrazolo[3,4-d]pyrimidin-1-yl)cyclohexyl)amino)phenol;
ethyl4-((4-(4-amino-3-(1-(2-fluorobenzyl)-1H-indol-5-yl)-1H-pyrazolo[3,4-d]pyrimidin-1-yl)cyclohexyl)amino)benzoate;
(trans)-3-((4-(4-amino-3-(1-(2-fluorobenzyl)-1H-indol-5-yl)-1H-pyrazolo[3,4-d]pyrimidin-1-yl)cyclohexyl)amino)benzoic acid;
(cis)-3-((4-(4-amino-3-(1-(2-fluorobenzyl)-1H-indol-5-yl)-1H-pyrazolo[3,4-d]pyrimidin-1-yl)cyclohexyl)amino)benzoic acid;
(trans)-3-(2-(2-chlorobenzyl)-1H-indol-5-yl)-1-(4-morpholin-4-ylcyclohexyl)-1H-pyrazolo[3,4-d]pyrimidin-4-amine;
(trans)-3-(2-(2-fluorobenzyl)-1H-indol-5-yl)-1-(4-morpholin-4-ylcyclohexyl)-1H-pyrazolo[3,4-d]pyrimidin-4-amine; or
3-((4-(4-amino-3-(1-(2-fluorobenzyl)-1H-indol-5-yl)-1H-pyrazolo[3,4-d]pyrimidin-1-yl)cyclohexyl)amino)-4-chlorobenzoic acid.

17. A compound or a salt thereof selected from
3-(4-(4-(4-amino-3-(3-(2-fluorobenzyl)-1H-indol-5-yl)-1H-pyrazolo[3,4-d]pyrimidin-1-yl)cyclohexyl)piperazin-1-yl)propan-1-ol;
(cis)-3-(4-(4-(4-amino-3-(2-(2-fluorobenzyl)-1H-indol-5-yl)-1H-pyrazolo[3,4-d]pyrimidin-1-yl)cyclohexyl)piperazin-1-yl)propan-1-ol;
(trans)-3-(4-(4-(4-amino-3-(2-(2-fluorobenzyl)-1H-indol-5-yl)-1H-pyrazolo[3,4-d]pyrimidin-1-yl)cyclohexyl)piperazin-1-yl)propan-1-ol;
3-(3-(2-fluorobenzyl)-1H-indol-5-yl)-1-(4-(4-(3-methoxypropyl)piperazin-1-yl)cyclohexyl)-1H-pyrazolo[3,4-d]pyrimidin-4-amine;

3-(2-(2-fluorobenzyl)-1H-indol-5-yl)-1-(4-(4-(3-methoxypropyl)piperazin-1-yl)cyclohexyl)-1H-pyrazolo[3,4-d]pyrimidin-4-amine;

2-(4-(4-(4-amino-3-(3-(2-fluorobenzyl)-1H-indol-5-yl)-1H-pyrazolo[3,4-d]pyrimidin-1-yl)cyclohexyl)piperazin-1-yl)ethanol;

(cis)-2-(4-(4-(4-amino-3-(2-(2-fluorobenzyl)-1H-indol-5-yl)-1H-pyrazolo[3,4-d]pyrimidin-1-yl)cyclohexyl)piperazin-1-yl)ethanol;

(trans)-2-(4-(4-(4-amino-3-(2-(2-fluorobenzyl)-1H-indol-5-yl)-1H-pyrazolo[3,4-d]pyrimidin-1-yl)cyclohexyl)piperazin-1-yl)ethanol;

(cis)-3-(4-(4-(4-amino-3-(2-benzyl-1H-indol-5-yl)-1H-pyrazolo[3,4-d]pyrimidin-1-yl)cyclohexyl)piperazin-1-yl)propan-1-ol;

(trans)-3-(4-(4-(4-amino-3-(2-benzyl-1H-indol-5-yl)-1H-pyrazolo[3,4-d]pyrimidin-1-yl)cyclohexyl)piperazin-1-yl)propan-1-ol;

3-(2-benzyl-1H-indol-5-yl)-1-(4-(4-(3-methoxypropyl)piperazin-1-yl)cyclohexyl)-1H-pyrazolo[3,4-d]pyrimidin-4-amine;

(cis)-2-(4-(4-(4-amino-3-(2-benzyl-1H-indol-5-yl)-1H-pyrazolo[3,4-d]pyrimidin-1-yl)cyclohexyl)piperazin-1-yl)ethanol;

(trans)-2-(4-(4-(4-amino-3-(2-benzyl-1H-indol-5-yl)-1H-pyrazolo[3,4-d]pyrimidin-1-yl)cyclohexyl)piperazin-1-yl)ethanol;

3-(1-(2-fluorobenzyl)-1H-indol-5-yl)-1-(4-(morpholin-4-ylmethyl)phenyl)-1H-pyrazolo[3,4-d]pyrimidin-4-amine;

(trans)-4-((4-(4-amino-3-(1-(2-fluorobenzyl)-1H-indol-5-yl)-1H-pyrazolo[3,4-d]pyrimidin-1-yl)cyclohexyl)amino)benzoic acid;

(cis)-4-((4-(4-amino-3-(1-(2-fluorobenzyl)-1H-indol-5-yl)-1H-pyrazolo[3,4-d]pyrimidin-1-yl)cyclohexyl)amino)benzoic acid;

(cis)-3-((4-(4-amino-3-(1-(2-fluorobenzyl)-1H-indol-5-yl)-1H-pyrazolo[3,4-d]pyrimidin-1-yl)cyclohexyl)amino)propan-1-ol;

(trans)-3-((4-(4-amino-3-(1-(2-fluorobenzyl)-1H-indol-5-yl)-1H-pyrazolo[3,4-d]pyrimidin-1-yl)cyclohexyl)amino)propan-1-ol;

2-((4-(4-amino-3-(1-(2-fluorobenzyl)-1H-indol-5-yl)-1H-pyrazolo[3,4-d]pyrimidin-1-yl)cyclohexyl)amino)ethanol;

2-(2-((4-(4-amino-3-(1-(2-fluorobenzyl)-1H-indol-5-yl)-1H-pyrazolo[3,4-d]pyrimidin-1-yl)cyclohexyl)amino)ethoxy)ethanol;

(cis)-(2S)-3-((4-(4-amino-3-(1-(2-fluorobenzyl)-1H-indol-5-yl)-1H-pyrazolo[3,4-d]pyrimidin-1-yl)cyclohexyl)amino)propane-1,2-diol;

(trans)-(2S)-3-((4-(4-amino-3-(1-(2-fluorobenzyl)-1H-indol-5-yl)-1H-pyrazolo[3,4-d]pyrimidin-1-yl)cyclohexyl)amino)propane-1,2-diol;

2,2'-(4-(4-amino-3-(1-(2-fluorobenzyl)-1H-indol-5-yl)-1H-pyrazolo[3,4-d]pyrimidin-1-yl)cyclohexylazanediyl)diethanol;

(cis)-N-(4-(4-amino-3-(1-(2-fluorobenzyl)-1H-indol-5-yl)-1H-pyrazolo[3,4-d]pyrimidin-1-yl)cyclohexyl)-beta-alanine;

(trans)-N-(4-(4-amino-3-(1-(2-fluorobenzyl)-1H-indol-5-yl)-1H-pyrazolo[3,4-d]pyrimidin-1-yl)cyclohexyl)-beta-alanine;

N-(4-(4-amino-3-(1-(2-fluorobenzyl)-1H-indol-5-yl)-1H-pyrazolo[3,4-d]pyrimidin-1-yl)cyclohexyl)-L-alanine;

(cis)-N-(4-(4-amino-3-(1-(2-fluorobenzyl)-1H-indol-5-yl)-1H-pyrazolo[3,4-d]pyrimidin-1-yl)cyclohexyl)-D-alanine;

(trans)-N-(4-(4-amino -3-(1-(2-fluorobenzyl)-1H-indol-5-yl)-1H-pyrazolo[3,4-d]pyrimidin-1-yl)cyclohexyl)-D-alanine;

N-(4-(4-amino-3-(1-(2-fluorobenzyl)-1H-indol-5-yl)-1H-pyrazolo[3,4-d]pyrimidin-1-yl)cyclohexyl)-N-methylglycine;

(cis)-2-(4-(4-(4-amino-3-(1-(2-(difluoromethoxy)benzyl)-1H-indol-5-yl)-1H-pyrazolo[3,4-d]pyrimidin-1-yl)cyclohexyl)piperazin-1-yl)ethanol;

(trans)-2-(4-(4-(4-amino -3-(1-(2-(difluoromethoxy)benzyl)-1H-indol-5-yl)-1H-pyrazolo[3,4-d]pyrimidin-1-yl)cyclohexyl)piperazin-1-yl)ethanol;

(cis)-3-(4-(4-(4-amino -3-(1-(2-(difluoromethoxy)benzyl)-1H-indol-5-yl)-1H-pyrazolo[3,4-d]pyrimidin-1-yl)cyclohexyl)piperazin-1-yl)propan-1-ol; or (trans)-3-(4-(4-(4-amino -3-(1-(2-(difluoromethoxy)benzyl)-1H-indol-5-yl)-1H-pyrazolo[3,4-d]pyrimidin-1-yl)cyclohexyl)piperazin-1-yl)propan-1-ol.

18. A compound or a salt thereof selected from 2-(4-(4-amino-3-(1-(2-chlorobenzyl)-1H-indol-5-yl)-1H-pyrazolo[3,4-d]pyrimidin-1-yl)-1,4'-bipiperidin-1'-yl)ethanol;

3-(1-(2-chlorobenzyl)-1H-indol-5-yl)-1-(1'-(2-methoxylthyl)-1,4'-bipiperidin-4-yl)-1H-pyrazolo[3,4-d]pyrimidin-4-amine;

3-(1-(2-fluorobenzyl)-1H-indol-5-yl)-1-(4-(4-pyridin-2-ylpiperazin-1-yl)cyclohexyl)-1H-pyrazolo[3,4-d]pyrimidin-4-amine;

(trans)-3-(2-(2-fluorobenzyl)-1H-indol-5-yl)-1-(4-(4-(3-methoxypropyl)piperazin-1-yl) cyclohexyl)-1H-pyrazolo[3,4-d]pyrimidin-4-amine;

(cis)-3-(2-(2-fluorobenzyl)-1H-indol-5-yl)-1-(4-(4-(3-methoxypropyl)piperazin-1-yl)cyclohexyl)-1H-pyrazolo[3,4-d]pyrimidin-4-amine;

2-(4-(4-amino-3-(2-(2-fluorobenzyl)-1H-indol-5-yl)-1H-pyrazolo[3,4-d]pyrimidin-1-yl)-1,4'-bipiperidin-1'-yl)ethanol;

3-(4-(4-amino-3-(2-(2-fluorobenzyl)-1H-indol-5-yl)-1H-pyrazolo[3,4-d]pyrimidin-1-yl)-1,4'-bipiperidin-1'-yl)propan-1-ol;

3-(2-(2-fluorobenzyl)-1H-indol-5-yl)-1-(1'-(2-methoxylthyl)-1,4'-bipiperidin-4-yl)-1H-pyrazolo[3,4-d]pyrimidin-4-amine;

3-(2-(2-fluorobenzyl)-1H-indol-5-yl)-1-(1'-(3-methoxypropyl)-1,4'-bipiperidin-4-yl)-1H-pyrazolo[3,4-d]pyrimidin-4-amine;

3-(2-(2-fluorobenzyl)-1H-indol-5-yl)-1-(1'-isobutyl-1,4'-bipiperidin-4-yl)-1H-pyrazolo[3,4-d]pyrimidin-4-amine;

2-(4-(4-(4-amino-3-(2-(2,5-difluorobenzyl)-1H-indol-5-yl)-1H-pyrazolo[3,4-d]pyrimidin-1-yl)cyclohexyl)piperazin-1-yl)ethanol;

3-(4-(4-(4-amino-3-(2-(2-fluorobenzyl)-1H-indol-5-yl)-1H-pyrazolo[3,4-d]pyrimidin-1-yl)cyclohexyl)piperazin-1-yl)propan-1-ol;

(cis)-1-(4((2-(2-(2-aminoethoxy)ethoxy)ethyl)amino)cyclohexyl)-3-(2-(2-fluorobenzyl)-1H-indol-5-yl)-1H-pyrazolo[3,4-d]pyrimidin-4-amine;

1-(4-((2-(2-(2-aminoethoxy)ethoxy)ethyl)amino)cyclohexyl)-3-(2-(2-fluorobenzyl)-1H-indol-5-yl)-1H-pyrazolo[3,4-d]pyrimidin-4-amine;

(trans)-1-(4(2-(2-(2-aminoethoxy)ethoxy)ethyl)amino)cyclohexyl)-3-(2-(2-fluorobenzyl)-1H-indol-5-yl)-1H-pyrazolo[3,4-d]pyrimidin-4-amine;

2-(2-((4-(4-amino-3-(2-(2-fluorobenzyl)-1H-indol-5-yl)-1H-pyrazolo[3,4-d]pyrimidin-1-yl)cyclohexyl)amino)ethoxy)ethanol;

2-(1-(4-(4-amino-3-(2-(2-fluorobenzyl)-1H-indol-5-yl)-1H-pyrazolo[3,4-d]pyrimidin-1-yl)cyclohexyl)piperidin-4-yl)ethanol;

(1-(4-(4-amino-3-(2-(2-fluorobenzyl)-1H-indol-5-yl)-1H-pyrazolo[3,4-d]pyrimidin-1-yl)cyclohexyl)piperidin-4-yl)methanol;

(trans)-3-(2-(2-fluorobenzyl)-1H-indol-5-yl)-1-(4-(4-(2-(2-methoxylthoxy)ethyl)piperazin-1-yl)cyclohexyl)-1H-pyrazolo[3,4-d]pyrimidin-4-amine;

(trans)-3-(2-(2-fluorobenzyl)-1H-indol-5-yl)-1-(4-(4-(2-(methoxymethoxy)ethyl)piperazin-1-yl)cyclohexyl)-1H-pyrazolo[3,4-d]pyrimidin-4-amine;

3-(4-(4-(4-amino-3-(2-(2,5-difluorobenzyl)-1H-indol-5-yl)-1H-pyrazolo[3,4-d]pyrimidin-1-yl)cyclohexyl)piperazin-1-yl)propan-1-ol;

2-(4-(4-(4-amino-3-(2-(2-fluorobenzyl)-1H-indol-5-yl)-1H-pyrazolo[3,4-d]pyrimidin-1-yl)cyclohexyl)piperazin-1-yl)ethanol;

(trans)-1-(4-(4-(2-(2-ethoxylthoxy)ethyl)piperazin-1-yl)cyclohexyl)-3-(2-(2-fluorobenzyl)-1H-indol-5-yl)-1H-pyrazolo[3,4-d]pyrimidin-4-amine;

(cis)-2-(2-((4-(4-amino-3-(1-(2-fluorobenzyl)-1H-indol-5-yl)-1H-pyrazolo[3,4-d]pyrimidin-1-yl)cyclohexyl)amino)ethoxy)ethanol;

(trans)-2-(2-((4-(4-amino-3-(1-(2-fluorobenzyl)-1H-indol-5-yl)-1H-pyrazolo[3,4-d]pyrimidin-1-yl)cyclohexyl)amino)ethoxy)ethanol;

(trans)-3-(4-(4-(4-amino-3-(2-(2-fluorobenzyl)-1H-indol-6-yl)-1H-pyrazolo[3,4-d]pyrimidin-1-yl)cyclohexyl)piperazin-1-yl)propan-1-ol;

(trans)-3-(2-(2-fluorobenzyl)-1H-indol-6-yl)-1-(4-(4-(3-methoxypropyl)piperazin-1-yl)cyclohexyl)-1H-pyrazolo[3,4-d]pyrimidin-4-amine;

(trans)-2-(4-(4-(4-amino-3-(2-(2-fluorobenzyl)-1H-indol-6-yl)-1H-pyrazolo[3,4-d]pyrimidin-1-yl)cyclohexyl)piperazin-1-yl)ethanol;

(trans)-1-(4-(4-amino-3-(2-(2-fluorobenzyl)-1H-indol-5-yl)-1H-pyrazolo[3,4-d]pyrimidin-1-yl)cyclohexyl)piperidin-4-ol;

(trans)-2-(4-(4-(4-amino-3-(2-(2-methoxybenzyl)-1H-indol-5-yl)-1H-pyrazolo[3,4-d]pyrimidin-1-yl)cyclohexyl)piperazin-1-yl)ethanol;

(trans)-3-(4-(4-(4-amino-3-(2-(2-methoxybenzyl)-1H-indol-5-yl)-1H-pyrazolo[3,4-d]pyrimidin-1-yl)cyclohexyl)piperazin-1-yl)propan-1-ol; or (trans)-3-(2-(2-methoxybenzyl)-1H-indol-5-yl)-1-(4-(4-(3-methoxypropyl)piperazin-1-yl)cyclohexyl)-1H-pyrazolo[3,4-d]pyrimidin-4-amine.

19. A compound or a salt thereof selected from 2-(4-(4-amino-3-(1-(2-chlorobenzyl)-1H-indol-5-yl)-1H-pyrazolo[3,4-d]pyrimidin-1-yl)-1,4'-bipiperidin-1'-yl)ethanol;

3-(1-(2-chlorobenzyl)-1H-indol-5-yl)-1-(1'-(2-methoxylthyl)-1,4'-bipiperidin-4-yl)-1H-pyrazolo[3,4-d]pyrimidin-4-amine;

3-(1-(2-fluorobenzyl)-1H-indol-5-yl)-1-(4-(4-pyridin-2-ylpiperazin-1-yl)cyclohexyl)-1H-pyrazolo[3,4-d]pyrimidin-4-amine;

(trans)-3-(2-(2-fluorobenzyl)-1H-indol-5-yl)-1-(4-(4-(3-methoxypropyl)piperazin-1-yl)cyclohexyl)-1H-pyrazolo[3,4-d]pyrimidin-4-amine;

(cis)-3-(2-(2-fluorobenzyl)-1H-indol-5-yl)-1-(4-(4-(3-methoxypropyl)piperazin-1-yl)cyclohexyl)-1H-pyrazolo[3,4-d]pyrimidin-4-amine;

2-(4-(4-amino-3-(2-(2-fluorobenzyl)-1H-indol-5-yl)-1H-pyrazolo[3,4-d]pyrimidin-1-yl)-1,4'-bipiperidin-1'-yl)ethanol;

3-(4-(4-amino-3-(2-(2-fluorobenzyl)-1H-indol-5-yl)-1H-pyrazolo[3,4-d]pyrimidin-1-yl)-1,4'-bipiperidin-1'-yl)propan-1-ol;

3-(2-(2-fluorobenzyl)-1H-indol-5-yl)-1-(1'-(2-methoxylthyl)-1,4'-bipiperidin-4-yl)-1H-pyrazolo[3,4-d]pyrimidin-4-amine;

3-(2-(2-fluorobenzyl)-1H-indol-5-yl)-1-(1'-(3-methoxypropyl)-1,4'-bipiperidin-4-yl)-1H-pyrazolo[3,4-d]pyrimidin-4-amine;

3-(2-(2-fluorobenzyl)-1H-indol-5-yl)-1-(1'-isobutyl-1,4'-bipiperidin-4-yl)-1H-pyrazolo[3,4-d]pyrimidin-4-amine;

2-(4-(4-(4-amino-3-(2-(2,5-difluorobenzyl)-1H-indol-5-yl)-1H-pyrazolo[3,4-d]pyrimidin-1-yl)cyclohexyl)piperazin-1-yl)ethanol;

3-(4-(4-(4-amino-3-(2-(2-fluorobenzyl)-1H-indol-5-yl)-1H-pyrazolo[3,4-d]pyrimidin-1-yl)cyclohexyl)piperazin-1-yl)propan-1-ol;

(cis)-1-(4((2-(2-(2-aminoethoxy)ethoxy)ethyl)amino)cyclohexyl)-3-(2-(2-fluorobenzyl)-1H-indol-5-yl)-1H-pyrazolo[3,4-d]pyrimidin-4-amine;

1-(4-((2-(2-(2-aminoethoxy)ethoxy)ethyl)amino)cyclohexyl)-3-(2-(2-fluorobenzyl)-1H-indol-5-yl)-1H-pyrazolo[3,4-d]pyrimidin-4-amine;

(trans)-1-(4-((2-(2-(2-aminoethoxy)ethoxy)ethyl)amino)cyclohexyl)-3-(2-(2-fluorobenzyl)-1H-indol-5-yl)-1H-pyrazolo[3,4-d]pyrimidin-4-amine;

2-(2-((4-(4-amino-3-(2-(2-fluorobenzyl)-1H-indol-5-yl)-1H-pyrazolo[3,4-d]pyrimidin-1-yl)cyclohexyl)amino)ethoxy)ethanol;

2-(1-(4-(4-amino-3-(2-(2-fluorobenzyl)-1H-indol-5-yl)-1H-pyrazolo[3,4-d]pyrimidin-1-yl)cyclohexyl)piperidin-4-yl)ethanol;

(1-(4-(4-amino-3-(2-(2-fluorobenzyl)-1H-indol-5-yl)-1H-pyrazolo[3,4-d]pyrimidin-1-yl)cyclohexyl)piperidin-4-yl)methanol;

(trans)-3-(2-(2-fluorobenzyl)-1H-indol-5-yl)-1-(4-(4-(2-(2-methoxylthoxy)ethyl)piperazin-1-yl)cyclohexyl)-1H-pyrazolo[3,4-d]pyrimidin-4-amine;

(trans)-3-(2-(2-fluorobenzyl)-1H-indol-5-yl)-1-(4-(4-(2-(methoxymethoxy)ethyl)piperazin-1-yl)cyclohexyl)-1H-pyrazolo[3,4-d]pyrimidin-4-amine;

3-(4-(4-(4-amino-3-(2-(2,5-difluorobenzyl)-1H-indol-5-yl)-1H-pyrazolo[3,4-d]pyrimidin-1-yl)cyclohexyl)piperazin-1-yl)propan-1-ol;

2-(4-(4-(4-amino-3-(2-(2-fluorobenzyl)-1H-indol-5-yl)-1H-pyrazolo[3,4-d]pyrimidin-1-yl)cyclohexyl)piperazin-1-yl)ethanol;

(trans)-1-(4-(4-(2-(2-ethoxylthoxy)ethyl)piperazin-1-yl)cyclohexyl)-3-(2-(2-fluorobenzyl)-1H-indol-5-yl)-1H-pyrazolo[3,4-d]pyrimidin-4-amine;

(cis)-2-(2-((4-(4-amino-3-(1-(2-fluorobenzyl)-1H-indol-5-yl)-1H-pyrazolo[3,4-d]pyrimidin-1-yl)cyclohexyl)amino)ethoxy)ethanol;

(trans)-2-(2-((4-(4-amino-3-(1-(2-fluorobenzyl)-1H-indol-5-yl)-1H-pyrazolo[3,4-d]pyrimidin-1-yl)cyclohexyl)amino)ethoxy)ethanol;

(trans)-3-(4-(4-(4-amino-3-(2-(2-fluorobenzyl)-1H-indol-6-yl)-1H-pyrazolo[3,4-d]pyrimidin-1-yl)cyclohexyl)piperazin-1-yl)propan-1-ol;

(trans)-3-(2-(2-fluorobenzyl)-1H-indol-6-yl)-1-(4-(4-(3-methoxypropyl)piperazin-1-yl)cyclohexyl)-1H-pyrazolo[3,4-d]pyrimidin-4-amine;

(trans)-2-(4-(4-(4-amino-3-(2-(2-fluorobenzyl)-1H-indol-6-yl)-1H-pyrazolo[3,4-d]pyrimidin-1-yl)cyclohexyl)piperazin-1-yl)ethanol;
(trans)-1-(4-(4-amino-3-(2-(2-fluorobenzyl)-1H-indol-5-yl)-1H-pyrazolo[3,4-d]pyrimidin-1-yl)cyclohexyl)piperidin-4-ol;
(trans)-2-(4-(4-(4-amino-3-(2-(2-methoxybenzyl)-1H-indol-5-yl)-1H-pyrazolo[3,4-d]pyrimidin-1-yl)cyclohexyl)piperazin-1-yl)ethanol;
(trans)-3-(4-(4-(4-amino-3-(2-(2-methoxybenzyl)-1H-indol-5-yl)-1H-pyrazolo[3,4-d]pyrimidin-1-yl)cyclohexyl)piperazin-1-yl)propan-1-ol; or
(trans)-3-(2-(2-methoxybenzyl)-1H-indol-5-yl)-1-(4-(4-(3-methoxypropyl)piperazin-1-yl)cyclohexyl)-1H-pyrazolo[3,4-d]pyrimidin-4-amine.

20. A compound or a salt thereof selected from
(trans)-3-(2-benzyl-1H-benzimidazol-5-yl)-1-(4-(4-(2-(1,3-dioxolan-2-yl)ethyl)piperazin-1-yl)cyclohexyl)-1H-pyrazolo[3,4-d]pyrimidin-4-amine;
(cis)-3-(2-benzyl-1H-benzimidazol-5-yl)-1-(4-(4-(2-(1,3-dioxolan-2-yl)ethyl)piperazin-1-yl)cyclohexyl)-1H-pyrazolo[3,4-d]pyrimidin-4-amine;
(trans)-3-(2-benzyl-1H-benzimidazol-5-yl)-1-(4-(4-pyridin-2-ylpiperazin-1-yl)cyclohexyl)-1H-pyrazolo[3,4-d]pyrimidin-4-amine;
(cis)-3-(2-benzyl-1H-benzimidazol-5-yl)-1-(4-(4-pyridin-2-ylpiperazin-1-yl)cyclohexyl)-1H-pyrazolo[3,4-d]pyrimidin-4-amine;
1-(4-((4-(2-(1,3-dioxolan-2-yl)ethyl)piperazin-1-yl)methyl)phenyl)-3-(2-(2-methoxybenzyl)-1H-benzimidazol-5-yl)-1H-pyrazolo[3,4-d]pyrimidin-4-amine;
(trans)-3-(2-(2-methoxybenzyl)-1H-benzimidazol-5-yl)-1-(4-(4-(4-methoxyphenyl)piperazin-1-yl)cyclohexyl)-1H-pyrazolo[3,4-d]pyrimidin-4-amine;
(cis)-3-(2-(2-methoxybenzyl)-1H-benzimidazol-5-yl)-1-(4-(4-(4-methoxyphenyl)piperazin-1-yl)cyclohexyl)-1H-pyrazolo[3,4-d]pyrimidin-4-amine;
(trans)-3-(2-(2-methoxybenzyl)-1H-benzimidazol-5-yl)-1-(4-(4-(tetrahydrofuran-2-ylmethyl)piperazin-1-yl)cyclohexyl)-1H-pyrazolo[3,4-d]pyrimidin-4-amine;
(cis)-3-(2-(2-methoxybenzyl)-1H-benzimidazol-5-yl)-1-(4-(4-(tetrahydrofuran-2-ylmethyl)piperazin-1-yl)cyclohexyl)-1H-pyrazolo[3,4-d]pyrimidin-4-amine;
(trans)-3-(2-(2-methoxybenzyl)-1H-benzimidazol-5-yl)-1-(4-(4-(tetrahydrofuran-2-ylcarbonyl)piperazin-1-yl)cyclohexyl)-1H-pyrazolo[3,4-d]pyrimidin-4-amine;
(cis)-3-(2-(2-methoxybenzyl)-1H-benzimidazol-5-yl)-1-(4-(4-(tetrahydrofuran-2-ylcarbonyl)piperazin-1-yl)cyclohexyl)-1H-pyrazolo[3,4-d]pyrimidin-4-amine;
(trans)-1-(4-(4-(2-(1,3-dioxolan-2-yl)ethyl)piperazin-1-yl)cyclohexyl)-3-(2-(2-methoxybenzyl)-1H-benzimidazol-5-yl)-1H-pyrazolo[3,4-d]pyrimidin-4-amine;
(cis)-1-(4-(4-(2-(1,3-dioxolan-2-yl)ethyl)piperazin-1-yl)cyclohexyl)-3-(2-(2-methoxybenzyl)-1H-benzimidazol-5-yl)-1H-pyrazolo[3,4-d]pyrimidin-4-amine;
(trans)-3-(2-benzyl-1,3-benzothiazol-5-yl)-1-(4-morpholin-4-ylcyclohexyl)-1H-pyrazolo[3,4-d]pyrimidin-4-amine;
(cis)-3-(2-(2-methoxybenzyl)-1H-benzimidazol-6-yl)-1-(4-(4-pyrazin-2-ylpiperazin-1-yl)cyclohexyl)-1H-pyrazolo[3,4-d]pyrimidin-4-amine;
(trans)-1-(4-(4-(2-(2-(2-aminoethoxy)ethoxy)ethyl)piperazin-1-yl)cyclohexyl)-3-(2-(2-methoxybenzyl)-1H-benzimidazol-6-yl)-1H-pyrazolo[3,4-d]pyrimidin-4-amine;
(trans)-1-(4-(4-(cyclopropylmethyl)piperazin-1-yl)cyclohexyl)-3-(2-(2-methoxybenzyl)-1H-benzimidazol-6-yl)-1H-pyrazolo[3,4-cl]pyrimidin-4-amine; or
(cis)-1-(4-(4-(cyclopropylmethyl)piperazin-1-yl)cyclohexyl)-3-(2-(2-methoxybenzyl)-1H-benzimidazol-6-yl)-1H-pyrazolo[3,4-d]pyrimidin-4-amine.

* * * * *

UNITED STATES PATENT AND TRADEMARK OFFICE
CERTIFICATE OF CORRECTION

| | |
|---|---|
| PATENT NO. | : 7,772,231 B2 |
| APPLICATION NO. | : 11/617398 |
| DATED | : August 10, 2010 |
| INVENTOR(S) | : George S. Sheppard |

It is certified that error appears in the above-identified patent and that said Letters Patent is hereby corrected as shown below:

Column 196 part of Claim 3, Line 31 revise – "trans-1-(4-(2-methoxylthoxy)cyclohexyl)" to read as --trans-1-(4-(2-methoxyethoxy)cyclohexyl)--

Column 197 part of Claim 3, Line 9 revise – "midin-4-amine;" to read as --midin-4-amine; or--

Column 197 part of Claim 4, Line 40 revise – "trans-3-(2-benzly-4methly-1H-benzimidazol-6-yl)" to read as --trans-3-(2-benzyl-4-methyl-1H-benzimidazol-6-yl)--

Column 197 part of Claim 4, Line 43 revise – "trans-3-(2-benzly-1methly-1H-benzimidazol-5-yl)" to read as --trans-3-(2-benzyl-1-methyl-1H-benzimidazol-5-yl)--

Column 197 part of Claim 4, line 59-60 revise – "trans-3-(2-benzyl-1H-benzimidazol-5-yl)-1-(4-(4-(ethyl-sulfonyl)piperazin" to read as
--trans-3-(2-benzyl-1H-benzimidazol-5-yl)-1-(4-(4-(2-methoxyethyl)piperazin--

Column 197 part of Claim 4, lines 62-63 revise – "cis-3-(2-benzyl-1H-benzimidazol-5-yl)-1-(4-(4-(ethylsulfonyl)piperazin" to read as --cis-3-(2-benzyl-1H-benzimidazol-5-yl)-1-(4-(4-(2-methoxyethyl)piperazin--

Column 198 part of claim 5, Line 45-46 revise – "3-(2-benzyl-1H-benzimidazol-5-yl)-1-(1-(morpholin-4-yl)carbonyl)pipridin-4-yl)" to read as --3-(2-benzyl-1H-benzimidazol-5-yl)-1-(1-(morpholin-4-ylcarbonyl)piperidin-4-yl)--

Column 199 Part of Claim 6, Lines 36-37 revise – "3-(2-benzyl-1H-benzimidazol-5-yl)-1-(4-((2-(methylsulfonyl)ethyll)amino)methyl)phenyl)" to read as --3-(2-benzyl-1H-benzimidazol-5-yl)-1-(4-(((2-(methylsulfonyl)ethyl)amino)methyl)phenyl)--

Column 199 Part of Claim 6, Line 55 revise – "ethyl4-(4-amino-3-(2-benzyl-1H-benzimidazol-5-yl)-1H-" to read as --ethyl 4-(4-amino-3-(2-benzyl-1H-benzimidazol-5-yl)-1H--

Signed and Sealed this
Twenty-fifth Day of December, 2012

David J. Kappos
*Director of the United States Patent and Trademark Office*

CERTIFICATE OF CORRECTION (continued)
U.S. Pat. No. 7,772,231 B2

Column 199 Part of Claim 6, Line 61 revise – "(methylsulfonylethyl)pyrrolidin-3-yl)" to read as --(methylsulfonyl)ethyl)pyrrolidin-3-yl)--

Column 200 Part of Claim 7, Line 17-18 revise – "3-(2-benzyl-1H-benzimidazol-6-yl)-1-(2-(4methyl-1,3-thiazol-5-yl)ethyl)1H-pyrazolo" to read as --3-(2-benzyl-1H-benzimidazol-6-yl)-1-(2-(4-methyl-1,3-thiazol-5-yl)ethyl)-1H-pyrazolo--

Column 200 Part of Claim 7, Line 24 revise – "but-2ynly)" to read as --but-2-ynyl)--

Column 200 Part of Claim 7, Line 45 revise – "lthyl)piperazin" to read as --ethyl)piperazin--

Column 200 Part of Claim 7, Line 50 revise – "3-(2-benzyl-1-H-benzimidazol-5-yl)" to read as --3-(2-benzyl-1H-benzimidazol-5-yl)--

Column 202 Part of Claim 9, Line 5 revise –"lthyl)" to read as --ethyl)--

Column 202 Part of Claim 9, Line 35 revise –"(trans)-3-(2(2,6-difluorobenzyl)" to read as --(trans)-3-(2-(2,6-difluorobenzyl)--

Column 203 Part of Claim 11, Line 23 revise – "(trans)-1-(4-(4-ac etylpiperazin-1-yl)" to read as --(trans)-1-(4-(4-acetylpiperazin-1-yl)--

Column 203 Part of Claim 11, Line 44 revise – "(trans)-ethyl4-" to read as --(trans)-ethyl 4--

Column 203 Part of Claim 11, Line 47 revise – "(cis)-ethyl4-" to read as --(cis)-ethyl 4--

Column 204 Part of Claim 12, Line 17 revise – "1-(4-(4-(2-methoxylthyl)" to read as --1-(4-(4-(2-methoxyethyl)--

Column 204 Part of Claim 12, Line 20 revise – "(4-(4-(2-methoxylthyl)piperazin-1-yl)" to read as --(4-(4-(2-methoxyethyl)piperazin-1-yl)--

Column 206 Part of Claim 13, Line 11 revise – "heteroarene or R13A; $R^{13A}$" to read as --heteroarene or $R^{13A}$; $R^{13A}$--

Column 206 Part of Claim 14, Lines 37-38 revise – "trans-3-(2-anilino-1,3-benzoxazol-6-yl)-1-(4-(2-methoxylthoxy)" to read as --trans-3-(2-anilino-1,3-benzoxazol-6-yl)-1-(4-(2-methoxyethoxy)--

Column 207 Part of Claim 14, Line 26 revise – "romethyl)phenylamino)" to read as --romethyl)phenyl)amino)--

Column 207 Part of Claim 14, Line 44 revise – "trans-3-(3-b[(4-fluoro-2-methylphenyl)" to read as --trans-3-(3-[(4-fluoro-2-methylphenyl )--

Column 208 Part of Claim 15, Line 37 remove space "pyrimidin -1-yl)" to read as --pyrimidin-1-yl)--

Column 208 Part of Claim 15, Line 42-43 revise – "3-(1-(2-chlorobenzyl)-1H-indol-5-yl)-1-(4-(4-(2-ethoxy-lthyl)" to read as --3-(1-(2-chlorobenzyl)-1H-indol-5-yl)-1-(4-(4-(2-ethoxyethyl)--

Column 209 Part of Claim 15, Line 15 revise – "1-(4-(4-(2-ethoxylthyl)" to read as --1-(4-(4-(2-ethoxyethyl)--

Column 209 Part of Claim 16, Lines 44-45 to revise – "3-(1-(2-chlorobenzyl)-1H-indol-5-yl)-1-(4-(4-(2-meth-oxylthyl)" to read as --3-(1-(2-chlorobenzyl)-1H-indol-5-yl)-1-(4-(4-(2-methoxyethyl)--

Column 210 Part of Claim 16, Line 4 revise – "3-(1-(2-chlorobenzyl)-1H-indol-5-yl)-1-(1′-bethyl-1,4′" to read as --3-(1-(2-chlorobenzyl)-1H-indol-5-yl)-1-(1′-ethyl-1,4′--

Column 210 Part of Claim 16, Line 36 add space "ethyl4-" to read as --ethyl 4- --

Column 212 Part of Claim 17, Line 4 remove space "(trans)-N-(4-(4-amino   -3-(1-(2" to read as --(trans)-N-(4-(4-amino-3-(1-(2--

Column 212 Part of Claim 17, Line 13 remove space "(trans)-2-(4-(4-(4-amino   -3-(1-(2" to read as --(trans)-2-(4-(4-(4-amino-3-(1-(2--

Column 212 Part of Claim 17, Line 16 remove space "(cis)-3-(4-(4-(4-amino   -3-(1-(2" to read as --(cis)-3-(4-(4-(4-amino-3-(1-(2--

Column 212 Part of Claim 17, Line 19 remove space "(trans)-3-(4-(4-(4-amino   -3-(1-(2" to read as --(trans)-3-(4-(4-(4-amino-3-(1-(2--

Column 212 Part of Claim 18, Lines 26-27 revise – "3-(1-(2-chlorobenzyl)-1H-indol-5-yl)-1-(1′-(2-methoxy-lthyl) to read as --3-(1-(2-chlorobenzyl)-1H-indol-5-yl)-1-(1′-(2-methoxyethyl)--

Column 212 Part of Claim 18, Line 33 remove space "methoxypropyl)piperazin-1-yl)   cyclohexyl)" to read as --methoxypropyl)piperazin-1-yl)cyclohexyl)--

Column 212 Part of Claim 18, Lines 44-45 revise – "3-(2-(2-fluorobenzyl)-1H-indol-5-yl)-1-(1′-(2-methoxy-lthyl) to read as --3-(2-(2-fluorobenzyl)-1H-indol-5-yl)-1-(1′-(2-methoxyethyl)--

Column 212 Part of Claim 18, Line 59 revise – "(cis)-1-(4((2-(2-(2-aminoethoxy)" to read as --(cis)-1-(4-((2-(2-(2-aminoethoxy)--

Column 212 Part of Claim 18, line 65 revise – "(trans)-1-(4(2-(2-(2-aminoethoxy)" to read as --(trans)-1-(4-((2-(2-(2-aminoethoxy)--

Column 213 Part of Claim 18, Line 11 revise – "(2-methoxylthoxy)ethyl)" to read as --(2-methoxyethoxy)ethyl)--

CERTIFICATE OF CORRECTION (continued)

U.S. Pat. No. 7,772,231 B2

Column 213 Part of Claim 18, Line 22 revise – "(trans)-1-(4-(4-(2-(2-ethoxylthoxy)" to read as --(trans)-1-(4-(4-(2-(2-ethoxyethoxy)--

Column 213 Part of Claim 19, Lines 56-57 revise – "3-(1-(2-chlorobenzyl)-1H-indol-5-yl)-1-(1'-(2-methoxy-lthyl)" to read as --3-(1-(2-chlorobenzyl)-1H-indol-5-yl)-1-(1'-(2-methoxyethyl)--

Column 214 Part of Claim 19, Lines 7-8 revise – "3-(2-(2-fluorobenzyl)-1H-indol-5-yl)-1-(1'-(2-methoxy-lthyl)" to read as --3-(2-(2-fluorobenzyl)-1H-indol-5-yl)-1-(1'-(2-methoxyethyl)--

Column 214 Part of Claim 19, Line 41 revise – "(2-methoxylthoxy)" to read as --(2-methoxyethoxy)--

Column 214 Part of Claim 19, Line 53 revise – "(trans)-1-(4-(4-(2-(2-ethoxylthoxy)" to read as --(trans)-1-(4-(4-(2-(2-ethoxyethoxy)--

Column 216 Part of Claim 20, Line 32 revise – "yl)-1H-pyrazolo[3,4-cl]pyrimidin" to read as --yl)-1H-pyrazolo[3,4-d]pyrimidin--